(12) United States Patent
Lin et al.

(10) Patent No.: US 12,145,947 B2
(45) Date of Patent: Nov. 19, 2024

(54) PYRIMIDINE BASED MODULATORS AND USES THEREOF

(71) Applicant: Quanta Therapeutics, Inc., South San Francisco, CA (US)

(72) Inventors: Hong Lin, Exton, PA (US); Juan Luengo, Phoenixville, PA (US); Neil Johnson, Downingtown, PA (US); Audrey Hospital, Robbinsville, NJ (US); Jin Zeng, Audubon, PA (US)

(73) Assignee: QUANTA THERAPEUTICS, INC., South San Francisco, CA (US)

( * ) Notice: Subject to any disclaimer, the term of this patent is extended or adjusted under 35 U.S.C. 154(b) by 0 days.

(21) Appl. No.: 18/503,626

(22) Filed: Nov. 7, 2023

(65) Prior Publication Data

US 2024/0199650 A1  Jun. 20, 2024

Related U.S. Application Data

(63) Continuation of application No. PCT/US2023/023445, filed on May 24, 2023.

(60) Provisional application No. 63/486,934, filed on Feb. 24, 2023, provisional application No. 63/380,544, filed on Oct. 21, 2022, provisional application No. 63/345,794, filed on May 25, 2022.

(51) Int. Cl.
| | | |
|---|---|---|
| C07D 519/00 | (2006.01) | |
| A61K 31/506 | (2006.01) | |
| A61K 31/5377 | (2006.01) | |
| A61K 31/5386 | (2006.01) | |
| A61K 31/55 | (2006.01) | |
| A61K 31/551 | (2006.01) | |
| A61K 31/553 | (2006.01) | |
| A61K 31/554 | (2006.01) | |
| C07D 487/08 | (2006.01) | |

(52) U.S. Cl.
CPC .......... *C07D 519/00* (2013.01); *A61K 31/506* (2013.01); *A61K 31/5377* (2013.01); *A61K 31/5386* (2013.01); *A61K 31/55* (2013.01); *A61K 31/551* (2013.01); *A61K 31/553* (2013.01); *A61K 31/554* (2013.01); *C07D 487/08* (2013.01)

(58) Field of Classification Search
CPC .. C07D 519/00; C07D 487/08; A61K 31/506; A61K 31/5377; A61K 31/5386; A61K 31/55; A61K 31/551; A61K 31/553; A61K 31/554
See application file for complete search history.

(56) References Cited

U.S. PATENT DOCUMENTS

| | | |
|---|---|---|
| 10,647,715 B2 | 5/2020 | Marx et al. |
| 10,822,312 B2 | 11/2020 | Li et al. |
| 11,267,812 B2 | 3/2022 | Fischer et al. |
| 11,312,724 B2 | 4/2022 | Li et al. |
| 2005/0234108 A1 | 10/2005 | Himmelsbach et al. |
| 2011/0166135 A1 | 7/2011 | Morimoto et al. |
| 2013/0012485 A1 | 1/2013 | Bäschlin et al. |
| 2016/0136180 A1 | 5/2016 | Himmelsbach et al. |
| 2020/0331911 A1 | 10/2020 | Marx et al. |
| 2021/0380574 A1 | 12/2021 | Abbott et al. |
| 2022/0402916 A1 | 12/2022 | Hoover et al. |
| 2023/0135152 A1 | 5/2023 | Smrcina et al. |

FOREIGN PATENT DOCUMENTS

| | | |
|---|---|---|
| CN | 112409331 A | 2/2021 |
| CN | 113396147 A | 9/2021 |
| CN | 114685460 A | 7/2022 |
| JP | 2020111571 A | 7/2020 |
| WO | WO-2005003099 A2 | 1/2005 |
| WO | WO-2010064705 A1 | 6/2010 |
| WO | WO-2010120996 A1 | 10/2010 |
| WO | WO-2014172639 A1 | 10/2014 |
| WO | WO-2016081679 A1 | 5/2016 |
| WO | WO-2017087528 A1 | 5/2017 |
| WO | WO-2017201161 A1 | 11/2017 |
| WO | WO-2018212774 A1 | 11/2018 |
| WO | WO-2019013311 A1 | 1/2019 |
| WO | WO-2020028706 A1 | 2/2020 |
| WO | WO-2020146613 A1 | 7/2020 |
| WO | WO-2020236940 A1 | 11/2020 |
| WO | WO-2021041671 A1 | 3/2021 |
| WO | WO-2021093758 A1 | 5/2021 |
| WO | WO-2021106231 A1 | 6/2021 |
| WO | WO-2021139748 A1 | 7/2021 |
| WO | WO-2022002102 A1 | 1/2022 |
| WO | WO-2022031678 A1 | 2/2022 |
| WO | WO-2022040469 A1 | 2/2022 |
| WO | WO-2022042630 A1 | 3/2022 |
| WO | WO-2022047260 A1 | 3/2022 |
| WO | WO-2022061251 A1 | 3/2022 |
| WO | WO-2022105857 A1 | 5/2022 |

(Continued)

OTHER PUBLICATIONS

CAS Registry Substances: 2443964-06-3. SciFinder. Accessed Nov. 9, 2023. 2 pages.
CAS Registry Substances: 2443964-21-2. SciFinder. Accessed Nov. 9, 2023. 2 pages.
CAS Registry Substances: 2445825-88-5. SciFinder. Accessed Nov. 9, 2023. 2 pages.
CAS Registry Substances: 2445851-64-7. SciFinder. Accessed Nov. 9, 2023. 2 pages.
CAS Registry Substances: 2448474-02-8. SciFinder. Accessed Nov. 9, 2023. 2 pages.
CAS Registry Substances: 2448613-12-3. SciFinder. Accessed Nov. 9, 2023. 2 pages.

(Continued)

*Primary Examiner* — Sarah Pihonak
*Assistant Examiner* — Padmaja S Rao
(74) *Attorney, Agent, or Firm* — Wilson Sonsini Goodrich & Rosati

(57) ABSTRACT

Provided herein are compounds, such as compounds of Formula (I), Formula (I-A), Formula (I-B), or pharmaceutically acceptable salts of any one there, useful for modulating KRAS GD12 and/or other G12 mutants.

22 Claims, No Drawings

Specification includes a Sequence Listing.

(56) References Cited

FOREIGN PATENT DOCUMENTS

| | | |
|---|---|---|
| WO | WO-2022105859 A1 | 5/2022 |
| WO | WO-2022109487 A1 | 5/2022 |
| WO | WO-2022115439 A1 | 6/2022 |
| WO | WO-2022127827 A1 | 6/2022 |
| WO | WO-2022132200 A1 | 6/2022 |
| WO | WO-2022133038 A1 | 6/2022 |
| WO | WO-2022135470 A1 | 6/2022 |
| WO | WO-2022135546 A1 | 6/2022 |
| WO | WO-2022148422 A1 | 7/2022 |
| WO | WO-2022156761 A1 | 7/2022 |
| WO | WO-2022170999 A1 | 8/2022 |
| WO | WO-2022173870 A1 | 8/2022 |
| WO | WO-2022177917 A2 | 8/2022 |
| WO | WO-2022184178 A1 | 9/2022 |
| WO | WO-2022187527 A1 | 9/2022 |
| WO | WO-2022187528 A1 | 9/2022 |
| WO | WO-2022188729 A1 | 9/2022 |
| WO | WO-2022192790 A1 | 9/2022 |
| WO | WO-2022192794 A1 | 9/2022 |
| WO | WO-2022193982 A1 | 9/2022 |
| WO | WO-2022194066 A1 | 9/2022 |
| WO | WO-2022194191 A1 | 9/2022 |
| WO | WO-2022194192 A1 | 9/2022 |
| WO | WO-2022194245 A1 | 9/2022 |
| WO | WO-2022214102 A1 | 10/2022 |
| WO | WO-2022217118 A1 | 10/2022 |
| WO | WO-2022221386 A1 | 10/2022 |
| WO | WO-2022221739 A1 | 10/2022 |
| WO | WO-2022228543 A1 | 11/2022 |
| WO | WO-2022232331 A1 | 11/2022 |
| WO | WO-2022232332 A1 | 11/2022 |
| WO | WO-2022247760 A1 | 12/2022 |
| WO | WO-2022251576 A1 | 12/2022 |
| WO | WO-2022256459 A1 | 12/2022 |
| WO | WO-2022261210 A1 | 12/2022 |
| WO | WO-2022266069 A1 | 12/2022 |
| WO | WO-2022266249 A1 | 12/2022 |
| WO | WO-2022268051 A1 | 12/2022 |
| WO | WO-2022269508 A1 | 12/2022 |
| WO | WO-2022269525 A1 | 12/2022 |
| WO | WO-2022271658 A1 | 12/2022 |
| WO | WO-2022271823 A1 | 12/2022 |
| WO | WO-2022271923 A1 | 12/2022 |
| WO | WO-2023001123 A1 | 1/2023 |
| WO | WO-2023001141 A1 | 1/2023 |
| WO | WO-2023274324 A1 | 1/2023 |
| WO | WO-2023274383 A1 | 1/2023 |
| WO | WO-2023278600 A1 | 1/2023 |
| WO | WO-2023280026 A1 | 1/2023 |
| WO | WO-2023280136 A1 | 1/2023 |
| WO | WO-2023280280 A1 | 1/2023 |
| WO | WO-2023283213 A1 | 1/2023 |
| WO | WO-2023060362 A1 | 4/2023 |
| WO | WO-2023061294 A1 | 4/2023 |
| WO | WO-2023061463 A1 | 4/2023 |
| WO | WO-2023064857 A1 | 4/2023 |
| WO | WO-2023066371 A1 | 4/2023 |
| WO | WO-2023067546 A1 | 4/2023 |
| WO | WO-2023072188 A1 | 5/2023 |
| WO | WO-2023072297 A1 | 5/2023 |
| WO | WO-2023077441 A1 | 5/2023 |
| WO | WO-2023081476 A1 | 5/2023 |
| WO | WO-2023081840 A1 | 5/2023 |
| WO | WO-2023086383 A1 | 5/2023 |
| WO | WO-2023097227 A1 | 6/2023 |
| WO | WO-2023098425 A1 | 6/2023 |
| WO | WO-2023098426 A1 | 6/2023 |
| WO | WO-2023098832 A1 | 6/2023 |
| WO | WO-2023099592 A1 | 6/2023 |
| WO | WO-2023099608 A1 | 6/2023 |
| WO | WO-2023099612 A1 | 6/2023 |
| WO | WO-2023099620 A1 | 6/2023 |
| WO | WO-2023099623 A1 | 6/2023 |
| WO | WO-2023099624 A1 | 6/2023 |
| WO | WO-2023101928 A1 | 6/2023 |
| WO | WO-2023103523 A1 | 6/2023 |
| WO | WO-2023103906 A1 | 6/2023 |
| WO | WO-2023104018 A1 | 6/2023 |
| WO | WO-2023105491 A1 | 6/2023 |
| WO | WO-2023114733 A1 | 6/2023 |
| WO | WO-2023116934 A1 | 6/2023 |
| WO | WO-2023117681 A1 | 6/2023 |
| WO | WO-2023119677 A1 | 6/2023 |
| WO | WO-2023120742 A1 | 6/2023 |
| WO | WO-2023125627 A1 | 7/2023 |
| WO | WO-2023125989 A1 | 7/2023 |
| WO | WO-2023130012 A1 | 7/2023 |
| WO | WO-2023133181 A1 | 7/2023 |
| WO | WO-2023133183 A1 | 7/2023 |
| WO | WO-2023134465 A1 | 7/2023 |
| WO | WO-2023137223 A1 | 7/2023 |
| WO | WO-2023138524 A1 | 7/2023 |
| WO | WO-2023138589 A1 | 7/2023 |
| WO | WO-2023141570 A2 | 7/2023 |
| WO | WO-2023143312 A1 | 8/2023 |
| WO | WO-2023150284 A2 | 8/2023 |
| WO | WO-2023151621 A1 | 8/2023 |
| WO | WO-2023152255 A1 | 8/2023 |
| WO | WO-2023154766 | 8/2023 |
| WO | WO-2023230190 A1 | 11/2023 |

OTHER PUBLICATIONS

Co-pending U.S. Appl. No. 18/362,576, inventor Lin; Hong, filed Jul. 31, 2023.
PCT/US2022/024111 International Search Report and Written Opinion dated Aug. 1, 2022.
PCT/US2022/031846 International Search Report and Written Opinion dated Oct. 5, 2022.
PCT/US2022/032680 International Search Report and Written Opinion dated Oct. 26, 2022.
PCT/US2022/081393 International Search Report and Written Opinion dated May 9, 2023.
PCT/US2023/062235 International Search Report and Written Opinion dated Aug. 17, 2023.
Pubchem-SID:325121534 Deposit Date: Jan. 25, 2017 (Jan. 25, 2017) pp. 1-7; p. 2.
U.S. Appl. No. 18/362,576 Notice of Allowance dated Dec. 6, 2023.
U.S. Appl. No. 18/362,576 Office Action dated Nov. 8, 2023.

PYRIMIDINE BASED MODULATORS AND USES THEREOF

CROSS-REFERENCE

This application is a continuation of International Patent Application No. PCT/US23/23445, filed on May 24, 2023, which claims the benefit of U.S. Provisional Patent Applications Nos. 63/345,794, filed on May 25, 2022; 63/380,544 filed on Oct. 21, 2022; and 63/486,934, filed on Feb. 24, 2023; each of which is incorporated by reference herein in its entirety.

SEQUENCE LISTING

The instant application contains a Sequence Listing which has been submitted electronically in XML format and is hereby incorporated by reference in its entirety. Said XML copy, created on Jan. 4, 2024, is named 55172-719_301_SL.xml and is 8,738 bytes in size.

BACKGROUND OF THE INVENTION

The small GTPase protein Kirsten Rat Sarcoma 2 Viral Oncogene Homolog (KRAS) is a member of the Ras family of cell signaling switches, regulating growth and survival of normal and cancerous cells (e.g., see Cully, M. and J. Downward, SnapShot: Ras Signaling. Cell, 2008. 133(7): p. 1292-1292 e1). KRAS mutations drive approximately 25% of human cancers by aberrant regulation of the mitogen-activated protein kinase (MAPK) signaling cascade and other effector pathways (e.g., see Stephen, A. G., et al., Dragging ras back in the ring. Cancer Cell, 2014. 25(3): p. 272-81). Though Ras has been recognized as a target in cancer for about 40 years, Ras-driven cancers remain among the most difficult to treat due to insensitivity to available targeted therapies. Ras, encoded by the three major genes KRAS, NRAS and HRAS, has the highest frequency of mutation of any oncogene. All oncogenic Ras mutations drive the switch to accumulate in the active GTP-bound state. The most common Ras mutation found across human tumor types is KRAS G12D (e.g., see The AACR Project GENIE Consortium. Cancer Discovery, 2017. 7(8): p. 818-831. Dataset Version 4). Activating mutations in codon 12 impair the small GTPases' ability to perform their role in hydrolyzing GTP. This regulatory impairment is fundamental for initiating and maintaining tumor progression.

Despite extensive efforts, small molecules have not been identified which block effector binding or restore GTPase activating protein (GAP) sensitivity, though some have been TES which activates Ras at the plasma membrane. KRAS G12C mutations, most common in lung adenocarcinoma, have been clinically shown to be susceptible to direct inhibition by covalent modification with small molecule inhibitors trapping the protein in the inactive GDP-bound state. KRAS G12D mutation confers a significantly slower intrinsic rate of GTP hydrolysis than G12C, resulting in more constitutive activation. Thus, pharmacological targeting the of inactive state is unlikely to achieve similar results against G12D, despite the existence of a similar binding pocket in the GDP-state. Additionally, a cysteine present at the site of the activating mutation yields itself to covalent chemistry, while aspartic acid does not provide typical medicinal chemistry approaches for selective covalent modification.

In order to potentially exploit the accumulation of KRAS G12D and other mutant variants in the GTP-bound state as a vulnerability to achieve selective inhibition of cancer cells while sparing normal Ras function, it is attractive for small molecule inhibitors to bind selectively to the GTP-state and stabilize a conformation that is incompetent for oncogenic signaling interactions with effector proteins. Furthermore, it has been shown that only constitutive activation of Raf, MEK and ERK kinases in the MAPK cascade downstream of Ras can bypass the requirement for Ras proteins in proliferative signaling (e.g., see Drosten, M., et al., Genetic analysis of Ras signalling pathways in cell proliferation, migration and survival. EMBO J, 2010. 29(6): p. 1091-104). As all evidence has indicated that MAPK signaling is essential for the growth effects of Ras in cancer, KRAS-mutant-selective inhibition in this pathway is considered the critical functional readout for potential clinical benefit of novel therapeutic approaches. Thus, there is a need to develop new inhibitors for KRAS-driven cancers that demonstrate inhibition of MAPK signals via a mechanism of action that is selective for binding to the active GTP-bound state over the inactive GDP-bound state.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY OF THE INVENTION

In certain aspects, the present disclosure provides a compound represented by the structure of Formula (I):

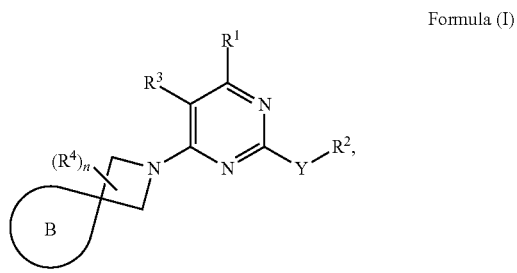

Formula (I)

or a pharmaceutically acceptable salt thereof wherein:

B is selected from a 7- to 15-membered heterocycle and $C_7$-$C_{15}$ carbocycle, wherein the 7- to 15-membered heterocycle and $C_7$-$C_{15}$ carbocycle are each optionally substituted with one or more substituents independently selected from halogen, —CN, —NO$_2$, =O, —N(R$^{21}$)$_2$, —B(OR$^{21}$)$_2$, —OR$^{21}$, —SR$^{21}$, —S(O)$_2$(R$^{21}$), —S(O)$_2$N(R$^{21}$)$_2$, —NR$^{21}$S(O)$_2$R$^{21}$, —C(O)N(R$^{21}$)$_2$, —C(O)NR$^{21}$OR$^{21}$, —N(R$^{21}$)C(O)R$^{21}$, —N(R$^{21}$)C(O)N(R$^{21}$)$_2$, —N(R$^{21}$)C(O)OR$^{21}$, —C(O)R$^{21}$, C(O)OR$^{21}$, —OC(O)R$^{21}$, —OC(O)N(R$^{21}$)$_2$, $C_{1-6}$ alkyl-N(R$^{20}$)$_2$, $C_{1-6}$ aminoalkyl, $C_{1-6}$ alkoxy, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, $C_3$-$C_{12}$ carbocycle and 5- to 12-membered heterocycle;

R$^1$ is selected from hydrogen and 5- to 15-membered heterocycle, wherein the 5- to 15-membered heterocycle is optionally substituted with one or more substituents independently selected from halogen, —B(OR$^{20}$)$_2$, —OR$^{20}$, —SR$^{20}$, —S(O)$_2$(R$^{20}$), —S(O)$_2$ N($R^{20}$)$_2$, —S(O)N($R^{20}$)$_2$, —S(O)$R^{20}$(=N$R^{20}$), —N$R^{20}$S(O)$_2R^{20}$, —C(O)N($R^{20}$)$_2$, —C(=N$R^{20}$)N($R^{20}$)$_2$, —$C_{1-6}$ alkyl(=NO$R^{20}$), —C(O)N$R^{20}$O$R^{20}$, —N($R^{20}$)C(O)O$R^{20}$, —N($R^{20}$)C(O)N($R^{20}$)$_2$, —N($R^{20}$)C(O)O$R^{20}$, —N($R^{20}$)$_2$, —C(O)$R^{20}$, —C(O)O$R^{20}$, —OC(O)$R^{20}$, —OC(O)N($R^{20}$)$_2$, —NO$_2$, =O, =N($R^{20}$), =NO($R^{20}$), —CN, —NHCN, $C_{1-6}$ alkyl-N($R^{20}$)$_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl-SO$_2R^{20}$, $C_{1-6}$ alkoxyalkyl, $C_{1-6}$ alkyl, $C_{2-6}$ alkenyl, $C_{2-6}$ alkynyl, $C_3$-$C_{12}$ carbocycle and 5- to 12-membered heterocycle, wherein the $C_3$-$C_{12}$ carbocycle and 5- to 12-membered heterocycle are each optionally substituted independently with one or more $R^{1*}$;

each $R^{1*}$ is independently selected from halogen, —B(O$R^{20}$)$_2$, —O$R^{20}$, —S$R^{20}$, —S(O)$_2$($R^{20}$), —S(O)$_2$N($R^{20}$)$_2$, —S(O)N($R^{20}$)$_2$, —S(O)$R^{20}$(=N$R^{20}$), —N$R^{20}$S(O)$_2R^{20}$, —C(O)N($R^{20}$)$_2$, —C(O)N$R^{20}$O$R^{20}$, —N($R^{20}$)C(O)$R^{20}$, —N($R^{20}$)C(O)N($R^{20}$)$_2$, —N($R^{20}$)C(O)O$R^{20}$, —N($R^{20}$)$_2$, —C(O)$R^{20}$, —C(O)O$R^{20}$, —OC(O)$R^{20}$, —OC(O)N($R^{20}$)$_2$, —NO$_2$, =O, =N($R^{20}$), =NO($R^{20}$), —CN, —NHCN, $C_{1-6}$ alkyl-N($R^{20}$)$_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, and $C_3$-$C_{12}$ carbocycle;

Y is selected from a bond, —O—, —S—, and —N($R^5$)—;

$R^2$ is selected from heterocycle, aryl, $C_1$-$C_6$ alkyl, -L-heterocycle, -L-N($R^{23}$)$_2$, -L-O$R^{23}$, -L-aryl, -L-heteroaryl, -L-cycloalkyl, -L-NHC(=NH)NH$_2$, -L-C(O)N($R^{23}$)$_2$, -L-$C_1$-$C_6$ haloalkyl, -L-O$R^{23}$, -L-N$R^{23}$C(O)-aryl, -L-COOH, -L-N$R^{23}$S(O)$_2$($R^{23}$), -L-S(O)$_2$N($R^{23}$)$_2$, -L-N($R^{23}$)C(O)(O$R^{23}$), -L-OC(O)N($R^{23}$)$_2$, and -L-C(=O)O$C_1$-$C_6$ alkyl, wherein the heterocycle, the heterocycle portion of -L-heterocycle, and the cycloalkyl portion of the -L-cycloalkyl are each optionally substituted with one or more $R^6$, and wherein the aryl, aryl portion of -L-N$R^{23}$C(O)-aryl, the aryl portion of -L-N$R^{23}$C(O)-aryl, the aryl of the -L-aryl, and the heteroaryl of -L-heteroaryl are each optionally substituted with one or more $R^7$;

$R^3$ is selected from hydrogen, halogen, —CN, —NO$_2$, —N($R^{20}$)$_2$, —O$R^{20}$, —S$R^{20}$, —S(O)$_2$($R^{20}$), —S(O)$_2$N($R^{20}$)$_2$, —S(O)N($R^{20}$)$_2$, —S(O)$R^{20}$(=N$R^{20}$), —N$R^{20}$S(O)$_2R^{20}$, —C(O)N($R^{20}$)$_2$, —N($R^{20}$)C(O)$R^{20}$, —N($R^{20}$)C(O)N($R^{20}$)$_2$, —N($R^{20}$)C(O)O$R^{20}$, —C(O)$R^{20}$, —C(O)O$R^{20}$, —OC(O)$R^{20}$, —OC(O)N($R^{20}$)$_2$, $C_{1-6}$ alkyl-N($R^{20}$)$_2$, $C_{1-6}$ aminoalkyl, $C_{1-6}$ alkoxy, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, $C_3$-$C_{12}$ carbocycle and 5- to 12-membered heterocycle;

each $R^4$ is independently selected from halogen, —NO$_2$, =O, =S, —CN, $C_{1-6}$ alkyl, $C_{2-6}$ alkynyl, $C_{1-6}$ alkyl-N($R^{20}$)$_2$, $C_{1-6}$ aminoalkyl, $C_{1-6}$ alkoxy, $C_{1-6}$ cyanoalkyl, $C_{1-6}$ hydroxyalkyl, and $C_{1-6}$ haloalkyl;

n is selected from 0, 1, 2, 3, and 4;

each $R^5$ is independently selected from hydrogen and $C_1$-$C_6$ alkyl;

each $R^6$ is independently selected from halogen, hydroxy, $C_1$-$C_3$ hydroxyalkyl, $C_1$-$C_3$ alkyl, oxo, $C_1$-$C_3$ haloalkyl, $C_1$-$C_3$ alkoxy, cyano, =CH$_2$, =NO—$C_1$-$C_3$ alkyl, $C_1$-$C_3$ aminoalkyl, —N($R^5$)S(O)$_2$($R^5$), -Q-phenyl, -Q-phenylSO$_2$F, —NHC(O)phenyl, —NHC(O)phenylSO$_2$F, $C_1$-$C_3$ alkyl substituted pyrazolyl, —$C_1$-$C_3$ alkyl-N($R^5$)$_2$, —C(O)N($R^5$)$_2$, tert-butyldimethylsilyloxyCH$_2$—, —N($R^5$)$_2$, ($C_1$-$C_3$ alkoxy)$C_1$-$C_3$ alkyl-, ($C_1$-$C_3$ alkyl)C(=O), oxo, ($C_1$-$C_3$ haloalkyl)C(=O)—, —SO$_2$F, ($C_1$-$C_3$ alkoxy)$C_1$-$C_3$ alkoxy, —CH$_2$OC(O)N($R^5$)$_2$, —CH$_2$NHC(O)O$C_1$-$C_6$ alkyl, —CH$_2$NHC(O)N($R^5$)$_2$, —CH$_2$NHC(O)$C_1$-$C_6$ alkyl, —CH$_2$(pyrazolyl), —CH$_2$NHSO$_2$$C_1$-$C_6$ alkyl, —CH$_2$OC(O)heterocycle, —OC(O)N($R^5$)$_2$, —OC(O)NH($C_1$-$C_3$ alkyl)O($C_1$-$C_3$ alkyl), —OC(O)NH($C_1$-$C_3$ alkyl)O($C_1$-$C_3$ alkyl)phenyl($C_1$-$C_3$ alkyl)N(CH$_3$)$_2$, —OC(O)NH($C_1$-$C_3$ alkyl)O($C_1$-$C_3$ alkyl)phenyl, —OC(O)heterocycle, —O—$C_1$-$C_3$ alkyl, —S(O)$_2$($R^{20}$), —S(O)$_2$N($R^{20}$)$_2$, —S(O)N($R^{20}$)$_2$, —S(O)$R^{20}$(=N$R^{20}$), —N$R^{20}$S(O)$_2R^{20}$, and —CH$_2$ heterocycle, wherein the phenyl of —NHC(O)phenyl and —OC(O)NH($C_1$-$C_3$ alkyl)($C_1$-$C_3$ alkyl)phenyl are optionally substituted with one or more substituents selected from —C(O)H and OH, and wherein the alkyl of —O—$C_1$-$C_3$ alkyl is optionally substituted with substituents selected from heterocycle, oxo and hydroxy; and wherein the heterocycle of —CH$_2$ heterocyclyl is optionally substituted with oxo;

each Q is selected from a bond, S, and O;

each $R^7$ is independently selected from halogen, hydroxy, HC(=O)—, $C_1$-$C_4$ alkyl, $C_1$-$C_4$ alkoxy, $C_1$-$C_4$ haloalkyl, $C_1$-$C_4$ hydroxyalkyl, —$C_1$-$C_3$ alkyl-N($R^5$)$_2$, —C(O)N($R^5$)$_2$, and —N($R^5$)$_2$;

each L is independently selected from a $C_1$-$C_4$ alkylene optionally substituted with one or more substituents independently selected from halogen, hydroxy, $C_{1-6}$ alkoxy, $C_1$-$C_4$ hydroxyalkyl, $C_1$-$C_4$ alkyl, $C_3$-$C_6$ carbocycle, and 3- to 8-membered heterocycle, wherein the $C_3$-$C_6$ carbocycle and 3- to 8-membered heterocycle are each optionally substituted with one or more substituents independently selected from halogen, —OH, —NO$_2$, =O, =S, —CN, $C_{1-6}$ alkyl-N($R^{20}$)$_2$, $C_{1-6}$ aminoalkyl, $C_{1-6}$ alkoxy, $C_{1-6}$ hydroxyalkyl, $C_{1-6}$ haloalkyl; and wherein optionally two substituents on the same carbon atom of L come together to form a $C_3$-$C_6$ carbocycle or 3- to 8-membered heterocycle, wherein the $C_3$-$C_6$ carbocycle and 3- to 8-membered heterocycle are each optionally substituted with one or more substituents independently selected from halogen, —OH, —NO$_2$, =O, =S, —CN, $C_{1-6}$ alkyl-N($R^{20}$)$_2$, $C_{1-6}$ aminoalkyl, $C_{1-6}$ alkoxy, $C_{1-6}$ hydroxyalkyl, and $C_{1-6}$ haloalkyl;

each $R^{20}$ is independently selected from hydrogen; and $C_{1-6}$ alkyl, $C_{2-6}$ alkenyl, $C_{2-6}$ alkynyl, $C_{3-12}$ carbocycle, and 3- to 12-membered heterocycle, each of which is optionally substituted with one or more substituents independently selected from halogen, —OH, —CN, —NO$_2$, —NH$_2$, —N($C_{1-6}$ alkyl)$_2$, $C_{1-10}$ alkyl, —$C_{1-10}$haloalkyl, —O—$C_{1-10}$ alkyl, oxo, $C_{3-12}$ carbocycle, and 3- to 12-membered heterocycle;

each $R^{21}$ is independently selected from hydrogen; and $C_{1-6}$ alkyl, $C_{2-6}$ alkenyl, $C_{2-6}$ alkynyl, $C_{3-12}$ carbocycle, and 3- to 12-membered heterocycle, each of which is optionally substituted with one or more substituents independently selected from halogen, —OH, —CN, —NO$_2$, —NH$_2$, —N($C_{1-6}$ alkyl)$_2$, $C_{1-10}$ alkyl, —$C_{1-10}$ haloalkyl, —O—$C_{1-10}$ alkyl, oxo, $C_{3-12}$ carbocycle, and 3- to 12-membered heterocycle; and each $R^{23}$ is independently selected from hydrogen; and $C_{1-6}$ alkyl, $C_{2-6}$ alkenyl, $C_{2-6}$ alkynyl, $C_{3-12}$ carbocycle, and 3- to 12-membered heterocycle, each of which is optionally substituted with one or more substituents independently selected from halogen, —OH, —CN, —NO$_2$, —NH$_2$, —N($C_{1-6}$ alkyl)$_2$, $C_{1-10}$ alkyl, —$C_{1-10}$ haloalkyl, —O—$C_{1-10}$ alkyl, oxo, $C_{3-12}$ carbocycle, and 3- to 12-membered heterocycle.

In an aspect, the present disclosure provides a compound of Formula (I-A)

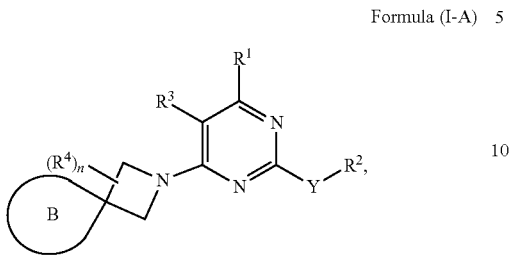

Formula (I-A)

or a pharmaceutically acceptable salt thereof wherein:
$R^1$ is selected from 8- to 10-membered heterocycle, wherein the 8- to 10-membered heterocycle is optionally substituted with one or more substituents independently selected from halogen, —$OR^{20}$, —$S(O)_2(R^{20})$, —$C(O)N(R^{20})_2$, —$C_{1-6}$ alkyl(=$NOR^{20}$), —$C(O)R^{20}$, =O, —CN, —NHCN, $C_{1-6}$ alkyl-$N(R^{20})_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl-$SO_2R^{20}$, $C_{1-6}$ alkoxyalkyl, $C_{1-6}$ alkyl, $C_{2-6}$ alkynyl, and 5- to 12-membered heterocycle, wherein the 5- to 12-membered heterocycle are each optionally substituted independently with one or more $R^{1*}$;
each $R^{1*}$ is independently selected from halogen, —$B(OR^{20})_2$, —$OR^{20}$, —$SR^{20}$, —$S(O)_2(R^{20})$, —$S(O)_2N(R^{20})_2$, —$S(O)N(R^{20})_2$, —$S(O)R^{20}$(=$NR^{20}$), —$NR^{20}S(O)_2R^{20}$, —$C(O)N(R^{20})_2$, —$C(O)NR^{20}OR^{20}$, —$N(R^{20})C(O)R^{20}$, —$N(R^{20})C(O)N(R^{20})_2$, —$N(R^{20})C(O)OR^{20}$, —$N(R^{20})_2$, —$C(O)R^{20}$, —$C(O)OR^{20}$, —$OC(O)R^{20}$, —$OC(O)N(R^{20})_2$, —$NO_2$, =O, =$N(R^{20})$, =$NO(R^{20})$, —CN, —NHCN, $C_{1-6}$ alkyl-$N(R^{20})_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, and $C_3$-$C_{12}$ carbocycle;
B is selected from a 7- to 15-membered heterocycle and $C_7$-$C_{15}$ carbocycle, wherein the 7- to 15-membered heterocycle and $C_7$-$C_{15}$ carbocycle are each optionally substituted with one or more substituents independently selected from halogen, —CN, —$NO_2$, =O, —$N(R^{21})_2$, —$B(OR^{21})_2$, —$OR^{21}$, —$SR^{21}$, —$S(O)_2(R^{21})$, —$S(O)_2N(R^{21})_2$, —$NR^{21}S(O)_2R^{21}$, —$C(O)N(R^{21})_2$, —$C(O)NR^{21}OR^{21}$, —$N(R^{21})C(O)R^{21}$, —$N(R^{21})C(O)N(R^{21})_2$, —$N(R^{21})C(O)OR^{21}$, —$C(O)R^{21}$, $C(O)OR^{21}$, —$OC(O)R^{21}$, —$OC(O)N(R^{21})_2$, $C_{1-6}$ alkyl-$N(R^{20})_2$, $C_{1-6}$ aminoalkyl, $C_{1-6}$ alkoxy, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, $C_3$-$C_{12}$ carbocycle and 5- to 12-membered heterocycle;
Y is selected from a bond, and —O—;
$R^2$ is selected from heterocycle, aryl, $C_1$-$C_6$ alkyl, -L-heterocycle, -L-$N(R^{23})_2$, -L-$OR^{23}$, -L-aryl, -L-heteroaryl, -L-cycloalkyl, -L-NHC(=NH)$NH_2$, -L-$C(O)N(R^{23})_2$, -L-$C_1$-$C_6$ haloalkyl, -L-$OR^{23}$, -L-$NR^{23}C(O)$-aryl, -L-COOH, -L-$NR^{23}S(O)_2(R^{23})$, -L-$S(O)_2N(R^{23})_2$, -L-$N(R^{23})C(O)(OR^{23})$, -L-$OC(O)N(R^{23})_2$, and -L-C(=O)$OC_1$-$C_6$ alkyl, wherein the heterocycle, the heterocycle portion of -L-heterocycle, and the cycloalkyl portion of the -L-cycloalkyl are each optionally substituted with one or more $R^6$, and wherein the aryl, aryl portion of -L-$NR^{23}C(O)$-aryl, the aryl portion of -L-$NR^{23}C(O)$-aryl, the aryl of the -L-aryl, and the heteroaryl of -L-heteroaryl are each optionally substituted with one or more $R^7$;
$R^3$ is selected from hydrogen, halogen, —CN, —$NO_2$, —$N(R^{20})_2$, —$OR^{20}$, —$SR^{20}$, —$S(O)_2(R^{20})$, —$S(O)_2N(R^{20})_2$, —$S(O)N(R^{20})_2$, —$S(O)R^{20}$(=$NR^{20}$), —$NR^{20}S(O)_2R^{20}$, —$C(O)N(R^{20})_2$, —$N(R^{20})C(O)R^{20}$, —$N(R^{20})C(O)N(R^{20})_2$, —$N(R^{20})C(O)OR^{20}$, —$C(O)R^{20}$, —$C(O)OR^{20}$, —$OC(O)R^{20}$, —$OC(O)N(R^{20})_2$, $C_{1-6}$ alkyl-$N(R^{20})_2$, $C_{1-6}$ aminoalkyl, $C_{1-6}$ alkoxy, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, $C_3$-$C_{12}$ carbocycle and 5- to 12-membered heterocycle;
each $R^4$ is independently selected from halogen, —$NO_2$, =O, =S, —CN, $C_{1-6}$ alkyl, $C_{2-6}$ alkynyl, $C_{1-6}$ alkyl-$N(R^{20})_2$, $C_{1-6}$ aminoalkyl, $C_{1-6}$ alkoxy, $C_{1-6}$ cyanoalkyl, $C_{1-6}$ hydroxyalkyl, and $C_{1-6}$ haloalkyl;
n is selected from 0, 1, 2, 3, and 4;
each $R^5$ is independently selected from hydrogen and $C_1$-$C_6$ alkyl;
each $R^6$ is independently selected from halogen, hydroxy, $C_1$-$C_3$ hydroxyalkyl, $C_1$-$C_3$ alkyl, oxo, $C_1$-$C_3$ haloalkyl, $C_1$-$C_3$ alkoxy, cyano, =$CH_2$, =NO—$C_1$-$C_3$ alkyl, $C_1$-$C_3$ aminoalkyl, —$N(R^5)S(O)_2(R^5)$, -Q-phenyl, -Q-phenyl$SO_2H$, —NHC(O)phenyl, —NHC(O)phenyl$SO_2F$, $C_1$-$C_3$ alkyl substituted pyrazolyl, —$C_1$-$C_3$ alkyl-$N(R^5)_2$, —$C(O)N(R^5)_2$, tert-butyldimethylsilyloxy$CH_2$—, —$N(R^5)_2$, ($C_1$-$C_3$ alkoxy)$C_1$-$C_3$ alkyl-, ($C_1$-$C_3$ alkyl)C(=O), oxo, ($C_1$-$C_3$ haloalkyl)C(=O)—, —$SO_2F$, ($C_1$-$C_3$ alkoxy)$C_1$-$C_3$ alkoxy, —$CH_2OC(O)N(R^5)_2$, —$CH_2NHC(O)OC_1$-$C_6$ alkyl, —$CH_2NHC(O)N(R^5)_2$, —$CH_2NHC(O)C_1$-$C_6$ alkyl, —$CH_2$(pyrazolyl), —$CH_2NHSO_2C_1$-$C_6$ alkyl, —$CH_2OC(O)$heterocycle, —$OC(O)N(R^5)_2$, —OC(O)NH($C_1$-$C_3$ alkyl)O($C_1$-$C_3$ alkyl), —OC(O)NH($C_1$-$C_3$ alkyl)O($C_1$-$C_3$ alkyl)phenyl($C_1$-$C_3$ alkyl)N($CH_3$)$_2$, —OC(O)NH($C_1$-$C_3$ alkyl)O($C_1$-$C_3$ alkyl)phenyl, —OC(O)heterocycle, —O—$C_1$-$C_3$ alkyl, —$S(O)_2(R^{20})$, —$S(O)_2N(R^{20})_2$, —$S(O)N(R^{20})_2$, —$S(O)R^{20}$(=$NR^{20}$), —$NR^{20}S(O)_2R^{20}$, and —$CH_2$ heterocycle, wherein the phenyl of —NHC(O)phenyl and —OC(O)NH($C_1$-$C_3$ alkyl)($C_1$-$C_3$ alkyl)phenyl are optionally substituted with one or more substituents selected from —C(O)H and OH, and wherein the alkyl of —O—$C_1$-$C_3$ alkyl is optionally substituted with substituents selected from heterocycle, oxo and hydroxy; and wherein the heterocycle of —$CH_2$ heterocyclyl is optionally substituted with oxo;
each Q is selected from a bond, S, and O;
each $R^7$ is independently selected from halogen, hydroxy, HC(=O)—, $C_1$-$C_4$ alkyl, $C_1$-$C_4$ alkoxy, $C_1$-$C_4$ haloalkyl, $C_1$-$C_4$ hydroxyalkyl, —$C_1$-$C_3$ alkyl-$N(R^5)_2$, —$C(O)N(R^5)_2$, and —$N(R^5)_2$;
each L is independently selected from a $C_1$-$C_4$ alkylene optionally substituted with one or more substituents independently selected from halogen, hydroxy, $C_{1-6}$ alkoxy, $C_1$-$C_4$ hydroxyalkyl, $C_1$-$C_4$ alkyl, $C_3$-$C_6$ carbocycle, and 3- to 8-membered heterocycle, wherein the $C_3$-$C_6$ carbocycle and 3- to 8-membered heterocycle are each optionally substituted with one or more substituents independently selected from halogen, —OH, —$NO_2$, =O, =S, —CN, $C_{1-6}$ alkyl-$N(R^{20})_2$, $C_{1-6}$ aminoalkyl, $C_{1-6}$ alkoxy, $C_{1-6}$ hydroxyalkyl, $C_{1-6}$ haloalkyl; and wherein optionally two substituents on the same carbon atom of L come together to form a $C_3$-$C_6$ carbocycle or 3- to 8-membered heterocycle, wherein the $C_3$-$C_6$ carbocycle and 3- to 8-membered heterocycle are each optionally substituted with one or more substituents independently selected from halogen, —OH, —NO$_2$, =O, =S, —CN, C$_{1-6}$ alkyl-N(R$^{20}$)$_2$, C$_{1-6}$ aminoalkyl, C$_{1-6}$ alkoxy, C$_{1-6}$ hydroxyalkyl, and C$_{1-6}$ haloalkyl;

each R$^{20}$ is independently selected from hydrogen; and C$_{1-6}$ alkyl, C$_{2-6}$ alkenyl, C$_{2-6}$ alkynyl, C$_{3-12}$ carbocycle, and 3- to 12-membered heterocycle, each of which is optionally substituted with one or more substituents independently selected from halogen, —OH, —CN, —NO$_2$, —NH$_2$, —N(C$_{1-6}$ alkyl)$_2$, C$_{1-10}$ alkyl, —C$_{1-10}$ haloalkyl, —O—C$_{1-10}$ alkyl, oxo, C$_{3-12}$ carbocycle, and 3- to 12-membered heterocycle;

each R$^{21}$ is independently selected from hydrogen; and C$_{1-6}$ alkyl, C$_{2-6}$ alkenyl, C$_{2-6}$ alkynyl, C$_{3-12}$ carbocycle, and 3- to 12-membered heterocycle, each of which is optionally substituted with one or more substituents independently selected from halogen, —OH, —CN, —NO$_2$, —NH$_2$, —N(C$_{1-6}$ alkyl)$_2$, C$_{1-10}$ alkyl, —C$_{1-10}$ haloalkyl, —O—C$_{1-10}$ alkyl, oxo, C$_{3-12}$ carbocycle, and 3- to 12-membered heterocycle;

each R$^{23}$ is independently selected from hydrogen; and C$_{1-6}$ alkyl, C$_{2-6}$ alkenyl, C$_{2-6}$ alkynyl, C$_{3-12}$ carbocycle, and 3- to 12-membered heterocycle, each of which is optionally substituted with one or more substituents independently selected from halogen, —OH, —CN, —NO$_2$, —NH$_2$, —N(C$_{1-6}$ alkyl)$_2$, C$_{1-10}$ alkyl, —C$_{1-10}$ haloalkyl, —O—C$_{1-10}$ alkyl, oxo, C$_{3-12}$ carbocycle, and 3- to 12-membered heterocycle.

In certain embodiments, Formula (I-A) is represented by Formula (I-B),

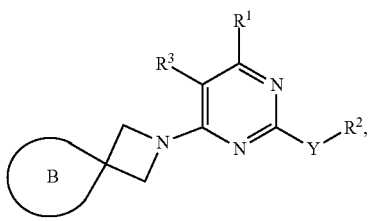

Formula (I-B)

or a pharmaceutically acceptable salt thereof wherein:
wherein R$^1$ is selected from

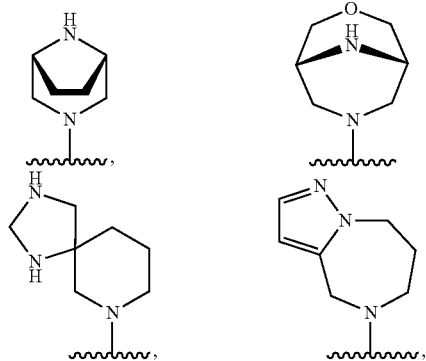

each of which is optionally substituted with one or more substituents independently selected from halogen, —S(O)$_2$(R$^{20}$), —C(O)N(R$^{20}$)$_2$, —C$_{1-6}$ alkyl (=NOR$^{20}$), —C(O)R$^{20}$, =O, and 5- to 12-membered heterocycle, wherein the 5- to 12-membered heterocycle are each optionally substituted independently with one or more R$^{1*}$;

each R$^{1*}$ is independently selected from halogen, —OR$^{20}$, —N(R$^{20}$)$_2$, —NO$_2$, =O, =N(R$^{20}$), =NO(R$^{20}$), —CN, —NHCN, C$_{1-6}$ alkyl-N(R$^{20}$)$_2$, C$_{1-6}$ aminoalkyl, C$_{1-6}$ alkoxy, C$_{1-6}$ hydroxyalkyl, C$_{1-6}$ cyanoalkyl, C$_{1-6}$ haloalkyl, and C$_{1-6}$ alkyl;

Y is —O—;

R$^2$ is selected from -L-heterocycle, and -L-N(R$^{23}$)$_2$, wherein the heterocycle portion of -L-heterocycle is optionally substituted with one or more R$^6$.

B is selected from a 7- to 15-membered heterocycle, wherein the 7- to 15-membered heterocycle is optionally substituted with one or more substituents independently selected from halogen, —CN, =O, —N(R$^{21}$)$_2$, —OR$^{21}$, C$_{1-6}$ alkyl-N(R$^{20}$)$_2$, C$_{1-6}$ aminoalkyl, C$_{1-6}$ alkoxy, C$_{1-6}$ alkoxyalkyl, C$_{1-6}$ hydroxyalkyl, C$_{1-6}$ cyanoalkyl, C$_{1-6}$ haloalkyl, C$_{1-6}$ alkyl, and C$_{2-6}$ alkynyl;

R$^3$ is selected from hydrogen, halogen, —CN, —N(R$^{20}$)$_2$, —OR$^{20}$, —C(O)R$^{20}$, C$_{1-6}$ alkyl-N(R$^{20}$)$_2$, C$_{1-6}$ aminoalkyl, C$_{1-6}$ alkoxy, C$_{1-6}$ alkoxyalkyl, C$_{1-6}$ hydroxyalkyl, C$_{1-6}$ cyanoalkyl, C$_{1-6}$ haloalkyl, and C$_{1-6}$ alkyl; and each R$^{20}$ is independently selected from hydrogen; and C$_{1-6}$ alkyl, and C$_{3-12}$ carbocycle, each of which is optionally substituted with one or more substituents independently selected from halogen, —OH, —CN, —NH$_2$, —N(C$_{1-6}$ alkyl)$_2$, C$_{1-10}$ alkyl, —C$_{1-10}$ haloalkyl, —O—C$_{1-10}$ alkyl, and oxo.

In certain embodiments, the disclosure provides a pharmaceutical composition comprising a compound or salt of Formula (I) and a pharmaceutically acceptable excipient. In certain embodiments, the disclosure provides a pharmaceutical composition comprising a compound or salt of Formula (I-A) and a pharmaceutically acceptable excipient. In certain embodiments, the disclosure provides a pharmaceutical composition comprising a compound or salt of Formula (I-B) and a pharmaceutically acceptable excipient.

In certain embodiments, the disclosure provides a method of treating a disease or disorder, using a compound or salt of Formula (I). In certain embodiments, the disclosure provides a method of treating a disease or disorder, using a compound or salt of Formula (I) and a pharmaceutically acceptable excipient. In certain embodiments, the disclosure provides a method of treating a disease or disorder, using a pharmaceutical composition compromising a compound or salt of Formula (I).

In certain embodiments, the disclosure provides a method of treating a disease or disorder, using a compound or salt of Formula (I-A). In certain embodiments, the disclosure provides a method of treating a disease or disorder, using a compound or salt of Formula (I-A) and a pharmaceutically acceptable excipient. In certain embodiments, the disclosure provides a method of treating a disease or disorder, using a pharmaceutical composition compromising a compound or salt of Formula (I-A).

In certain embodiments, the disclosure provides a method of inhibiting KRas G12D and/or other G12 mutants, using a compound or salt of Formula (I). In certain embodiments, the disclosure provides a method of inhibiting KRas G12D and/or other G12 mutants, using a compound or salt of Formula (I) and a pharmaceutically acceptable excipient. In certain embodiments, the disclosure provides a method of inhibiting KRas G12D and/or other G12 mutants, using a pharmaceutical composition compromising a compound or salt of Formula (I) and a pharmaceutically acceptable excipient.

In certain embodiments, the disclosure provides a method of inhibiting KRas G12D and/or other G12 mutants, using a compound or salt of Formula (I-A). In certain embodiments, the disclosure provides a method of inhibiting KRas G12D and/or other G12 mutants, using a compound or salt of Formula (I-A) and a pharmaceutically acceptable excipient. In certain embodiments, the disclosure provides a method of inhibiting KRas G12D and/or other G12 mutants, using a pharmaceutical composition compromising a compound or salt of Formula (I-A) and a pharmaceutically acceptable excipient.

DETAILED DESCRIPTION OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Definitions

Unless defined otherwise, all technical and scientific terms used herein have the same meaning as is commonly understood by one of skill in the art to which this invention belongs. All patents and publications referred to herein are incorporated by reference.

As used in the specification and claims, the singular form "a", "an" and "the" includes plural references unless the context clearly dictates otherwise.

The term "$C_{x-y}$" when used in conjunction with a chemical moiety, such as alkyl, alkenyl, or alkynyl is meant to include groups that contain from x to y carbons in the chain. For example, the term "$C_{1-6}$alkyl" refers to saturated hydrocarbon groups, including straight-chain alkyl and branched-chain alkyl groups that contain from 1 to 6 carbons. For example —$C_{1-6}$ alkyl- may be selected from methyl, ethyl, propyl, butyl, pentyl, and hexyl, any one of which is optionally substituted. The term —$C_{x-y}$ alkylene- refers to a substituted or unsubstituted alkylene chain with from x to y carbons in the alkylene chain. For example —$C_{1-6}$ alkylene- may be selected from methylene, ethylene, propylene, butylene, pentylene, and hexylene, any one of which is optionally substituted.

"Alkyl" as used herein refers to a straight or branched hydrocarbon chain radical consisting solely of carbon and hydrogen atoms, containing no unsaturation, and preferably having from one to fifteen carbon atoms (i.e., $C_1$-$C_{15}$ alkyl). In certain embodiments, an alkyl comprises one to thirteen carbon atoms (i.e., $C_1$-$C_{13}$ alkyl). In certain embodiments, an alkyl comprises one to eight carbon atoms (i.e., $C_1$-$C_8$ alkyl). In other embodiments, an alkyl comprises one to five carbon atoms (i.e., $C_1$-$C_5$ alkyl). In other embodiments, an alkyl comprises one to four carbon atoms (i.e., $C_1$-$C_4$ alkyl). In other embodiments, an alkyl comprises one to three carbon atoms (i.e., $C_1$-$C_3$ alkyl). In other embodiments, an alkyl comprises one to two carbon atoms (i.e., $C_1$-$C_2$ alkyl). In other embodiments, an alkyl comprises one carbon atom (i.e., $C_1$ alkyl). In other embodiments, an alkyl comprises five to fifteen carbon atoms (i.e., $C_5$-$C_{15}$ alkyl). In other embodiments, an alkyl comprises five to eight carbon atoms (i.e., $C_5$-$C_8$ alkyl). In other embodiments, an alkyl comprises two to five carbon atoms (i.e., $C_2$-$C_5$ alkyl). In other embodiments, an alkyl comprises three to five carbon atoms (i.e., $C_3$-$C_5$ alkyl). In certain embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond.

"Alkenyl" as used herein refers to a straight or branched hydrocarbon chain radical group consisting solely of carbon and hydrogen atoms, containing at least one carbon-carbon double bond, and preferably having from two to twelve carbon atoms (i.e., $C_2$-$C_{12}$ alkenyl). In certain embodiments, an alkenyl comprises two to eight carbon atoms (i.e., $C_2$-$C_8$ alkenyl). In certain embodiments, an alkenyl comprises two to six carbon atoms (i.e., $C_2$-$C_6$ alkenyl). In other embodiments, an alkenyl comprises two to four carbon atoms (i.e., $C_2$-$C_4$ alkenyl). The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like.

"Alkynyl" as used herein refers to a straight or branched hydrocarbon chain radical group consisting solely of carbon and hydrogen atoms, containing at least one carbon-carbon triple bond, and preferably having from two to twelve carbon atoms (i.e., $C_2$-$C_{12}$ alkynyl). In certain embodiments, an alkynyl comprises two to eight carbon atoms (i.e., $C_2$-$C_8$ alkynyl). In other embodiments, an alkynyl comprises two to six carbon atoms (i.e., $C_2$-$C_6$ alkynyl). In other embodiments, an alkynyl comprises two to four carbon atoms (i.e., $C_2$-$C_4$ alkynyl). The alkynyl is attached to the rest of the molecule by a single bond, for example, ethynyl, propynyl, butynyl, pentynyl, hexynyl, and the like.

The terms "$C_{x-y}$ alkenyl" and "$C_{x-y}$ alkynyl" as used herein refer to substituted or unsubstituted unsaturated aliphatic groups analogous in length and possible substitution to the alkyls described above, but that contain at least one double or triple bond, respectively. The term —$C_{x-y}$ alkenylene- refers to a substituted or unsubstituted alkenylene chain with from x to y carbons in the alkenylene chain. For example, —$C_{2-6}$ alkenylene- may be selected from ethenylene, propenylene, butenylene, pentenylene, and hexenylene, any one of which is optionally substituted. An alkenylene chain may have one double bond or more than one double bond in the alkenylene chain. The term —$C_{x-y}$ alkynylene- refers to a substituted or unsubstituted alkynylene chain with from x to y carbons in the alkenylene chain. For example, —$C_{2-6}$ alkenylene- may be selected from ethynylene, propynylene, butynylene, pentynylene, and hexynylene, any one of which is optionally substituted. An alkynylene chain may have one triple bond or more than one triple bond in the alkynylene chain.

"Alkylene" refers to a straight divalent hydrocarbon chain linking the rest of the molecule to a radical group, consisting solely of carbon and hydrogen, containing no unsaturation, and preferably having from one to twelve carbon atoms, for example, methylene, ethylene, propylene, butylene, and the like. The alkylene chain is attached to the rest of the molecule through a single bond and to the radical group through a single bond. The points of attachment of the alkylene chain to the rest of the molecule and to the radical group are through the terminal carbons respectively. In other embodiments, an alkylene comprises one to five carbon atoms (i.e., $C_1$-$C_5$ alkylene). In other embodiments, an alkylene comprises one to four carbon atoms (i.e., $C_1$-$C_4$ alkylene). In other embodiments, an alkylene comprises one to three carbon atoms (i.e., $C_1$-$C_3$ alkylene). In other embodiments, an alkylene comprises one to two carbon atoms (i.e., $C_1$-$C_2$ alkylene). In other embodiments, an alkylene comprises one carbon atom (i.e., $C_1$ alkylene). In other embodiments, an alkylene comprises five to eight carbon atoms (i.e., $C_5$-$C_8$ alkylene). In other embodiments, an alkylene comprises two to five carbon atoms (i.e., $C_2$-$C_5$ alkylene). In other embodiments, an alkylene comprises three to five carbon atoms (i.e., $C_3$-$C_5$ alkylene). Unless stated otherwise specifically in the specification, an alkylene chain is optionally substituted by one or more substituents such as those substituents described herein.

"Alkenylene" refers to a straight divalent hydrocarbon chain linking the rest of the molecule to a radical group, consisting solely of carbon and hydrogen, containing at least one carbon-carbon double bond, and preferably having from two to twelve carbon atoms. The alkenylene chain is attached to the rest of the molecule through a single bond and to the radical group through a single bond. The points of attachment of the alkenylene chain to the rest of the molecule and to the radical group are through the terminal carbons respectively. In other embodiments, an alkenylene comprises two to five carbon atoms (i.e., $C_2$-$C_5$ alkenylene). In other embodiments, an alkenylene comprises two to four carbon atoms (i.e., $C_2$-$C_4$ alkenylene). In other embodiments, an alkenylene comprises two to three carbon atoms (i.e., $C_2$-$C_3$ alkenylene). In other embodiments, an alkenylene comprises two carbon atom (i.e., $C_2$ alkenylene). In other embodiments, an alkenylene comprises five to eight carbon atoms (i.e., $C_5$-$C_8$ alkenylene). In other embodiments, an alkenylene comprises three to five carbon atoms (i.e., $C_3$-$C_5$ alkenylene). Unless stated otherwise specifically in the specification, an alkenylene chain is optionally substituted by one or more substituents such as those substituents described herein.

"Alkynylene" refers to a straight divalent hydrocarbon chain linking the rest of the molecule to a radical group, consisting solely of carbon and hydrogen, containing at least one carbon-carbon triple bond, and preferably having from two to twelve carbon atoms. The alkynylene chain is attached to the rest of the molecule through a single bond and to the radical group through a single bond. The points of attachment of the alkynylene chain to the rest of the molecule and to the radical group are through the terminal carbons respectively. In other embodiments, an alkynylene comprises two to five carbon atoms (i.e., $C_2$-$C_5$ alkynylene). In other embodiments, an alkynylene comprises two to four carbon atoms (i.e., $C_2$-$C_4$ alkynylene). In other embodiments, an alkynylene comprises two to three carbon atoms (i.e., $C_2$-$C_3$ alkynylene). In other embodiments, an alkynylene comprises two carbon atom (i.e., $C_2$ alkynylene). In other embodiments, an alkynylene comprises five to eight carbon atoms (i.e., $C_5$-$C_8$ alkynylene). In other embodiments, an alkynylene comprises three to five carbon atoms (i.e., $C_3$-$C_5$ alkynylene). Unless stated otherwise specifically in the specification, an alkynylene chain is optionally substituted by one or more substituents such as those substituents described herein.

"Halo" or "halogen" as used herein refers to halogen substituents such as bromo, chloro, fluoro and iodo substituents.

"Haloalkyl" as used herein refers to an alkyl radical, as defined above, that is substituted by one or more halogen radicals, for example, trifluoromethyl, dichloromethyl, bromomethyl, 2,2,2-trifluoroethyl, 1-fluoromethyl-2-fluoroethyl, and the like. Examples of halogen substituted alkanes ("haloalkanes") include halomethane (e.g., chloromethane, bromomethane, fluoromethane, iodomethane), di- and trihalomethane (e.g., trichloromethane, tribromomethane, trifluoromethane, triiodomethane), 1-haloethane, 2-haloethane, 1,2-dihaloethane, and any other suitable combinations of alkanes (or substituted alkanes) and halogens. When an alkyl group is substituted with more than one halogen radicals, each halogen may be independently selected, for example 1-chloro, 2-bromoethane.

"Alkoxy" refers to a radical bonded through an oxygen atom of the formula —O-alkyl, where alkyl is an alkyl chain as defined above.

"Fluoroalkyl" refers to an alkyl radical, as defined above, that is substituted by one or more fluoro radicals, for example, trifluoromethyl, difluoromethyl, fluoromethyl, 2,2,2-trifluoroethyl, 1-fluoromethyl-2-fluoroethyl, and the like.

"Aminoalkyl" refers to an alkyl radical, as defined above, that is substituted by one or more amine radicals, for example, propan-2-amine, butane-1,2-diamine, pentane-1,2,4-triamine and the like.

"Hydroxyalkyl" refers to an alkyl radical, as defined above, that is substituted by one or more hydroxy radicals, for example, propan-1-ol, butane-1,4-diol, pentane-1,2,4-triol, and the like.

"Alkoxyalkyl" refers to an alkyl radical, as defined above, that is substituted by one or more alkoxy radicals, for example, methoxymethane, 1,3-dimethoxybutane, 1-methoxypropane, 2-ethoxypentane, and the like.

"Cyanoalkyl" as used herein refers to an alkyl radical, as defined above, that is substituted by one or more cyano radicals, for example, acetonitrile, 2-ethyl-3-methylsuccinonitrile, butyronitrile, and the like.

The term "carbocycle" as used herein refers to a saturated, unsaturated or aromatic ring in which each atom of the ring is carbon atom. Carbocycle includes 3- to 10-membered monocyclic rings, 6- to 12-membered bicyclic rings, and 6- to 12-membered bridged rings. Each ring of a bicyclic carbocycle may be selected from saturated, unsaturated, and aromatic rings. In an exemplary embodiment, an aromatic ring, e.g., phenyl, may be fused to a saturated or unsaturated ring, e.g., cyclohexane, cyclopentane, or cyclohexene. A bicyclic carbocycle includes any combination of saturated, unsaturated and aromatic bicyclic rings, as valence permits. A bicyclic carbocycle includes any combination of ring sizes such as 4-5 fused ring systems, 5-5 fused ring systems, 5-6 fused ring systems, 6-6 fused ring systems, 5-7 fused ring systems, 6-7 fused ring systems, 5-8 fused ring systems, and 6-8 fused ring systems. Exemplary carbocycles include cyclopentyl, cyclohexyl, cyclohexenyl, adamantyl, phenyl, indanyl, and naphthyl. Bicyclic carbocycles may be fused, bridged, or spiro-ring systems. In some cases, spiro-ring carbocycles have at least two molecular rings with only one common atom.

"Aryl" as used herein refers to a radical derived from an aromatic monocyclic or aromatic multicyclic hydrocarbon ring system by removing a hydrogen atom from a ring carbon atom. The aromatic monocyclic or aromatic multicyclic hydrocarbon ring system contains only hydrogen and carbon and from five to eighteen carbon atoms, where at least one of the rings in the ring system is aromatic, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene.

The term "unsaturated carbocycle" refers to carbocycles with at least one degree of unsaturation and excluding aromatic carbocycles. Examples of unsaturated carbocycles include cyclohexadiene, cyclohexene, and cyclopentene.

"Cycloalkyl" refers to a fully saturated monocyclic or polycyclic hydrocarbon radical consisting solely of carbon and hydrogen atoms, which includes fused or bridged ring systems, and preferably having from three to twelve carbon atoms. In certain embodiments, a cycloalkyl comprises three to ten carbon atoms. In other embodiments, a cycloalkyl comprises five to seven carbon atoms. The cycloalkyl may be attached to the rest of the molecule by a single bond. Examples of monocyclic cycloalkyls include, e.g., cyclopropyl, cyclobutyl, cyclopentyl, cyclohexyl, cycloheptyl, and cyclooctyl. Polycyclic cycloalkyl radicals include, for example, adamantyl, norbornyl (i.e., bicyclo[2.2.1]heptanyl), norbomenyl, decalinyl, 7,7-dimethyl-bicyclo[2.2.1]heptanyl, and the like.

The term "$C_{x-y}$ carbocycle" is meant to include groups that contain from x to y carbons in the cycle. For example, the term "$C_{3-6}$ carbocycle" refers to a saturated, unsaturated, or aromatic ring comprising from 3 to 6 carbons. For example —$C_{3-6}$ carbocycle- may be selected from cyclopropyl, cyclobutyl, cyclopentyl, cyclohexyl, and phenyl, any one of which is optionally substituted.

The term "carbocyclene" refers to a divalent ring, linking the rest of the molecule to a radical group, consisting solely of carbon and hydrogen atoms. The carbocyclene is attached to the rest of the molecule through a single bond and to the radical group through a single bond. The points of attachment of the carbocyclene are to the rest of the molecule and to the radical group are through any two carbons respectively. Carbocyclene includes arylene and cycloalkylene. The term therefore distinguishes carbocyclene from heterocyclene in which the divalent ring comprises at least one atom that is different from a carbon atom. The heterocyclene is attached to the rest of the molecule through a single bond and to the radical group through a single bond. The points of attachment of the heterocyclene are to the rest of the molecule and to the radical group through any two atoms respectively, valency permitting. Heterocyclene includes heteroarylene and heterocycloalkylene. Carbocyclene and heterocyclene may each be optionally substituted by one or more substituents such as those substituents described herein.

The term "heterocycle" as used herein refers to a saturated, unsaturated or aromatic ring comprising one or more heteroatoms. Exemplary heteroatoms include N, O, Si, P, B, and S atoms. The heterocycle may be attached to the rest of the molecule through any atom of the heterocycle, valence permitting, such as a carbon or nitrogen atom of the heterocycle. Heterocycles include 3- to 10-membered monocyclic rings, 6- to 12-membered bicyclic rings, and 6- to 12-membered bridged rings. A bicyclic heterocycle includes any combination of saturated, unsaturated and aromatic bicyclic rings, as valence permits. In an exemplary embodiment, an aromatic ring, e.g., pyridyl, may be fused to a saturated or unsaturated ring, e.g., cyclohexane, cyclopentane, morpholine, piperidine or cyclohexene. A bicyclic heterocycle includes any combination of ring sizes such as 4-5 fused ring systems, 5-5 fused ring systems, 5-6 fused ring systems, 6-6 fused ring systems, 5-7 fused ring systems, 6-7 fused ring systems, 5-8 fused ring systems, and 6-8 fused ring systems. Bicyclic heterocycles may be fused, bridged, or spiro-ring systems. A spiro-ring system may be referred as a "spiro-heterocycle", "spiro heterocycle", or "spiro-heterocycle". In some cases, spiro-heterocycles, spiro heterocycles, or spiro-heterocycles have at least two molecular rings with only one common atom. The spiro-heterocycle, spiro heterocycle, or spiroheterocycle comprises one or more heteroatoms.

"Heteroaryl" or "aromatic heterocycle" refers to a radical derived from a heteroaromatic ring radical that comprises one to eleven carbon atoms and at least one heteroatom wherein each heteroatom may be selected from N, O, and S. As used herein, the heteroaryl ring may be selected from monocyclic or bicyclic and fused or bridged ring systems rings wherein at least one of the rings in the ring system is aromatic, i.e., it contains a cyclic, delocalized (4n+2) π-electron system in accordance with the Hückel theory. The heteroatom(s) in the heteroaryl radical may be optionally oxidized. One or more nitrogen atoms, if present, are optionally quaternized. The heteroaryl may be attached to the rest of the molecule through any atom of the heteroaryl, valence permitting, such as a carbon or nitrogen atom of the heteroaryl. Examples of heteroaryls include, but are not limited to, pyridine, pyrimidine, oxazole, furan, thiophene, benzthiazole, and imdazopyridine.

An "X-membered heteroaryl" refers to the number of endocylic atoms, i.e., X, in the ring. For example, a 5-membered heteroaryl ring or 5-membered aromatic heterocycle has 5 endocyclic atoms, e.g., triazole, oxazole, thiophene, etc.

The term "unsaturated heterocycle" refers to heterocycles with at least one degree of unsaturation and excluding aromatic heterocycles. Examples of unsaturated heterocycles include dihydropyrrole, dihydrofuran, oxazoline, pyrazoline, and dihydropyridine. Heterocycles may be optionally substituted by one or more substituents such as those substituents described herein.

"Substituted" refers to moieties having substituents replacing a hydrogen on one or more carbons or substitutable heteroatoms, e.g., an NH or $NH_2$ of a compound. It will be understood that "substitution" or "substituted with" includes the implicit proviso that such substitution is in accordance with permitted valence of the substituted atom and the substituent, and that the substitution results in a stable compound, i.e., a compound which does not spontaneously undergo transformation such as by rearrangement, cyclization, elimination, etc. In certain embodiments, substituted refers to moieties having substituents replacing two hydrogen atoms on the same carbon atom, such as substituting the two hydrogen atoms on a single carbon with an oxo, imino or thioxo group. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds.

As used herein, the term "optional" or "optionally" means that the subsequently described event of circumstances may or may not occur, and that the description includes instances where the event or circumstance occurs and instances in which it does not. For example, "optionally substituted aryl" means that the aryl group may or may not be substituted and that the description includes both substituted aryl groups and aryl groups having no substitution.

As used herein, the term "electrophile" or "electrophilic moiety" is any moiety capable of reacting with a nucleophile (e.g., a moiety having a lone pair of electrons, a negative charge, a partial negative charge and/or an excess of electrons, for example an —SH group). Electrophiles typically are electron poor or comprise atoms which are electron poor.

In certain embodiments, an electrophile contains a positive charge or partial positive charge, has a resonance structure which contains a positive charge or partial positive charge, or is a moiety in which delocalization or polarization of electrons results in one or more atoms which contains a positive charge or partial positive charge. In some embodiments, an electrophile comprises a conjugated double bond, for example an α,β-unsaturated carbonyl or α,β-unsaturated thiocarbonyl compound.

In some embodiments, substituents may include any substituents described herein, for example: halogen, hydroxy, oxo (=O), thioxo (=S), cyano (—CN), nitro (—NO$_2$), imino (=N—H), oximo (=N—OH), hydrazino (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$, —C(O)OR$^a$, —R$^b$—C(O)N(R$^a$)$_2$, —R$^b$—O—R$^a$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2), and —R$^b$—S(O)$_t$N(R$^a$)$_2$ (where t is 1 or 2); and alkyl, alkenyl, alkynyl, aryl, aralkyl, aralkenyl, aralkynyl, cycloalkyl, cycloalkylalkyl, heterocycloalkyl, heterocycloalkylalkyl, heteroaryl, and heteroarylalkyl any of which may be optionally substituted by alkyl, alkenyl, alkynyl, halogen, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$, —C(O)OR$^a$, —R$^b$—C(O)N(R$^a$)$_2$, —R$^b$—O—R$^a$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); wherein each R$^a$ is independently selected from hydrogen, alkyl, cycloalkyl, cycloalkylalkyl, aryl, aralkyl, heterocycloalkyl, heterocycloalkylalkyl, heteroaryl, or heteroarylalkyl, wherein each R$^a$, valence permitting, may be optionally substituted with alkyl, alkenyl, alkynyl, halogen, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$, —C(O)OR$^a$, —R$^b$—C(o)N(R$^a$)$_2$, —R$^b$—O—R$^a$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2) and —R$^b$—S(O)$_t$N(R$^a$)$_2$ (where t is 1 or 2); and wherein each R$^b$ is independently selected from a direct bond or a straight or branched alkylene, alkenylene, or alkynylene chain, and each R$^a$ is a straight or branched alkylene, alkenylene or alkynylene chain. It will be understood by those skilled in the art that substituents can themselves be substituted, if appropriate.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The terms "subject," "individual," and "patient" may be used interchangeably and refer to humans, the as well as non-human mammals (e.g., non-human primates, canines, equines, felines, porcines, bovines, ungulates, lagomorphs, and the like). In various embodiments, the subject can be a human (e.g., adult male, adult female, adolescent male, adolescent female, male child, female child) under the care of a physician or other health worker in a hospital, as an outpatient, or other clinical context. In certain embodiments, the subject may not be under the care or prescription of a physician or other health worker.

As used herein, the phrase "a subject in need thereof" refers to a subject, as described infra, that suffers from, or is at risk for, a pathology to be prophylactically or therapeutically treated with a compound or salt described herein.

The terms "administer", "administered", "administers" and "administering" are defined as providing a composition to a subject via a route known in the art, including but not limited to intravenous, intraarterial, oral, parenteral, buccal, topical, transdermal, rectal, intramuscular, subcutaneous, intraosseous, transmucosal, or intraperitoneal routes of administration. In certain embodiments, oral routes of administering a composition can be used. The terms "administer", "administered", "administers" and "administering" a compound should be understood to mean providing a compound of the invention or a prodrug of a compound of the invention to the individual in need.

The term "effective amount" or "therapeutically effective amount" refers to that amount of a compound or salt described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term can also apply to a dose that can induce a particular response in target cells, e.g., reduction of proliferation or down regulation of activity of a target protein. The specific dose can vary depending on the particular compounds chosen, the dosing regimen to be followed, whether it is administered in combination with other compounds, timing of administration, the tissue to which it is administered, and the physical delivery system in which it is carried.

As used herein, "treatment" or "treating" refers to an approach for obtaining beneficial or desired results with respect to a disease, disorder, or medical condition including, but not limited to, a therapeutic benefit and/or a prophylactic benefit. In certain embodiments, treatment or treating involves administering a compound or composition disclosed herein to a subject. A therapeutic benefit may include the eradication or amelioration of the underlying disorder being treated. Also, a therapeutic benefit may be achieved with the eradication or amelioration of one or more of the physiological symptoms associated with the underlying disorder, such as observing an improvement in the subject, notwithstanding that the subject may still be afflicted with the underlying disorder. In certain embodiments, for prophylactic benefit, the compositions are administered to a subject at risk of developing a particular disease, or to a subject reporting one or more of the physiological symptoms of a disease, even though a diagnosis of this disease may not have been made. Treating can include, for example, reducing, delaying or alleviating the severity of one or more symptoms of the disease or condition, or it can include reducing the frequency with which symptoms of a disease, defect, disorder, or adverse condition, and the like, are experienced by a patient. Treating can be used herein to refer to a method that results in some level of treatment or amelioration of the disease or condition, and can contemplate a range of results directed to that end, including but not restricted to prevention of the condition entirely.

In certain embodiments, the term "prevent" or "preventing" as related to a disease or disorder may refer to a compound that, in a statistical sample, reduces the occurrence of the disorder or condition in the treated sample relative to an untreated control sample, or delays the onset or reduces the severity of one or more symptoms of the disorder or condition relative to the untreated control sample.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

As used herein, "sum frequency generation" (SFG) is a nonlinear, optical technique whereby light at one frequency ($\Omega1$) is mixed with light at another frequency ($\Omega2$) to yield a response at the sum frequency ($\Omega1+\Omega2$) (Shen, 1984, 1989). For example, SFG is particularly useful for the detection of molecules at surfaces through their characteristic vibrational transitions and, in this case, is essentially a surface-selective infrared spectroscopy with $\Omega1$ and $\Omega2$ at visible and infrared frequencies. When the terms "SHG" or "second harmonic generation" are used herein, it is understood that SFG and "sum frequency generation" can substitute and be used in place of SHG with methods well known to one skilled in the art.

"Second harmonic-active moiety" or "second harmonic-active moiety," as used herein, refers to a nonlinear-active moiety, particle or molecule which can be attached (covalently or non-covalently) to a molecule (e.g., a protein, such as an enzyme), particle or phase (e.g., lipid bilayer) in order to render it more nonlinear optical active.

A "nonlinear active moiety," as used herein, is a substance which possesses a hyperpolarizability.

"Hyperpolarizability" or "Nonlinear Susceptibility" as used herein refer to the properties of a molecule, particle, interface, or phase which allow for generation of nonlinear light. The terms "hyperpolarizability," "second-order nonlinear polarizability," and "nonlinear susceptibility" are some-times used interchangeably.

"Allosteric", "allosteric modulator", or "allosteric candidate" as used herein, refers to a molecule, moiety or substance which binds predominantly to a site other than the active site and causes conformational change, which can be determined by SHG or SFG, and thus exert their effect via an allosteric mechanism of action.

The term "inhibit", "selective inhibition" or "selectively inhibit" as referred to a biologically active agent refers to the agent's ability to preferentially reduce the target signaling activity as compared to off-target signaling activity, via direct or interact interaction with the target.

The term "targeted agent" or "targeted therapy" as described herein referred to a therapy that uses specific drugs to target specific genes, protein, or active sites involved in the development, survival, and proliferation of cancer cells.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The section headings used herein are for organizational purposes only and are not to be construed as limiting the subject matter described.

Compounds

In certain aspects, the present disclosure provides a compound represented by the structure of Formula (I):

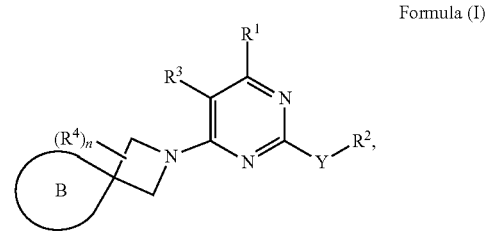

Formula (I)

or a pharmaceutically acceptable salt thereof wherein:
B is selected from a 7- to 15-membered heterocycle and $C_7$-$C_{15}$ carbocycle, wherein the 7- to 15-membered heterocycle and $C_7$-$C_{15}$ carbocycle are each optionally substituted with one or more substituents independently selected from halogen, —CN, —NO$_2$, =O, —N(R$^{21}$)$_2$, —B(OR$^{21}$)$_2$, —OR$^{21}$, —SR$^{21}$, —S(O)$_2$(R$^{21}$), —S(O)$_2$N(R$^{21}$)$_2$, —NR$^{21}$S(O)$_2$R$^{21}$, —C(O)N(R$^{21}$)$_2$, —C(O)NR$^{21}$OR$^{21}$, —N(R$^{21}$)C(O)R$^{21}$, —N(R$^{21}$)C(O)N(R$^{21}$)$_2$, —N(R$^{21}$)C(O)OR$^{21}$, —C(O)R$^{21}$, C(O)OR$^{21}$, —OC(O)R$^{21}$, —OC(O)N(R$^{21}$)$_2$, $C_{1-6}$ alkyl-N(R$^{20}$)$_2$, $C_{1-6}$ aminoalkyl, $C_{1-6}$ alkoxy, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, $C_3$-$C_{12}$ carbocycle and 5- to 12-membered heterocycle;

R$^1$ is selected from hydrogen and 5- to 15-membered heterocycle, wherein the 5- to 15-membered heterocycle is optionally substituted with one or more substituents independently selected from halogen, —B(OR$^{20}$)$_2$, —OR$^{20}$, —SR$^{20}$, —S(O)$_2$(R$^{20}$), —S(O)$_2$N(R$^{20}$)$_2$, —S(O)N(R$^{20}$)$_2$, —S(O)R$^{20}$(=NR$^{20}$), —$NR^{20}S(O)_2R^{20}$, —$C(O)N(R^{20})_2$, —$C(=NR^{20})N(R^{20})_2$, —$C_{1-6}$ alkyl(=$NOR^{20}$), —$C(O)NR^{20}OR^{20}$, —$N(R^{20})C(O)R^{20}$, —$N(R^{20})C(O)N(R^{20})_2$, —$N(R^{20})C(O)OR^{20}$, —$N(R^{20})_2$, —$C(O)R^{20}$, —$C(O)OR^{20}$, —$OC(O)R^{20}$, —$OC(O)N(R^{20})_2$, —$NO_2$, =O, =$N(R^{20})$, =$NO(R^{20})$, —CN, —NHCN, $C_{1-6}$ alkyl-$N(R^{20})_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl-$SO_2R^{20}$, $C_{1-6}$ alkoxyalkyl, $C_{1-6}$ alkyl, $C_{2-6}$ alkenyl, $C_{2-6}$ alkynyl, $C_3$-$C_{12}$ carbocycle and 5- to 12-membered heterocycle, wherein the $C_3$-$C_{12}$ carbocycle and 5- to 12-membered heterocycle are each optionally substituted independently with one or more $R^{1*}$;

each $R^{1*}$ is independently selected from halogen, —$B(OR^{20})_2$, —$OR^{20}$, —$SR^{20}$, —$S(O)_2(R^{20})$, —$S(O)_2N(R^{20})_2$, —$S(O)N(R^{20})_2$, —$S(O)R^{20}$(=$NR^{20}$), —$NR^{20}S(O)_2R^{20}$, —$C(O)N(R^{20})_2$, —$C(O)NR^{20}OR^{20}$, —$N(R^{20})C(O)R^{20}$, —$N(R^{20})C(O)N(R^{20})_2$, —$N(R^{20})C(O)OR^{20}$, —$N(R^{20})_2$, —$C(O)R^{20}$, —$C(O)OR^{20}$, —$OC(O)R^{20}$, —$OC(O)N(R^{20})_2$, —$NO_2$, =O, =$N(R^{20})$, =$NO(R^{20})$, —CN, —NHCN, $C_{1-6}$ alkyl-$N(R^{20})_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, and $C_3$-$C_{12}$ carbocycle;

Y is selected from a bond, —O—, —S—, and —$N(R^5)$—;

$R^2$ is selected from heterocycle, $C_1$-$C_6$ alkyl, -L-heterocycle, -L-$N(R^{23})_2$, -L-$OR^{23}$, -L-aryl, -L-heteroaryl, -L-cycloalkyl, -L-NHC(=NH)$NH_2$, -L-$C(O)N(R^{23})_2$, -L-$C_1$-$C_6$ haloalkyl, -L-$OR^{23}$, -L-$NR^{23}C(O)$-aryl, -L-COOH, -L-$NR^{23}S(O)_2(R^{23})$, -L-$S(O)_2N(R^{23})_2$, -L-$N(R^{23})C(O)(OR^{23})$, -L-$OC(O)N(R^{23})_2$, and -L-C(=O)$OC_1$-$C_6$ alkyl, wherein the heterocycle, the heterocycle portion of -L-heterocycle, and the cycloalkyl portion of the -L-cycloalkyl are each optionally substituted with one or more $R^6$, and wherein the aryl portion of -L-$NR^{23}C(O)$-aryl, the aryl portion of -L-$NR^{23}C(O)$-aryl, the aryl of the -L-aryl, and the heteroaryl of -L-heteroaryl are each optionally substituted with one or more $R^7$;

$R^3$ is selected from hydrogen, halogen, —CN, —$NO_2$, —$N(R^{20})_2$, —$OR^{20}$, —$SR^{20}$, —$S(O)_2(R^{20})$, —$S(O)_2N(R^{20})_2$, —$S(O)N(R^{20})_2$, —$S(O)R^{20}$(=$NR^{20}$), —$NR^{20}S(O)_2R^{20}$, —$C(O)N(R^{20})_2$, —$N(R^{20})C(O)R^{20}$, —$N(R^{20})C(O)N(R^{20})_2$, —$N(R^{20})C(O)OR^{20}$, —$C(O)R^{20}$, —$C(O)OR^{20}$, —$OC(O)R^{20}$, —$OC(O)N(R^{20})_2$, $C_{1-6}$ alkyl-$N(R^{20})_2$, $C_{1-6}$ aminoalkyl, $C_{1-6}$ alkoxy, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, $C_3$-$C_{12}$ carbocycle and 5- to 12-membered heterocycle;

each $R^4$ is independently selected from halogen, —$NO_2$, =O, =S, —CN, $C_{1-6}$ alkyl, $C_{2-6}$ alkynyl, $C_{1-6}$ alkyl-$N(R^{20})_2$, $C_{1-6}$ aminoalkyl, $C_{1-6}$ alkoxy, $C_{1-6}$ cyanoalkyl, $C_{1-6}$ hydroxyalkyl, and $C_{1-6}$ haloalkyl;

n is selected from 0, 1, 2, 3, and 4;

each $R^5$ is independently selected from hydrogen and $C_1$-$C_6$ alkyl;

each $R^6$ is independently selected from halogen, hydroxy, $C_1$-$C_3$ hydroxyalkyl, $C_1$-$C_3$ alkyl, oxo, $C_1$-$C_3$ haloalkyl, $C_1$-$C_3$ alkoxy, cyano, =$CH_2$, =NO—$C_1$-$C_3$ alkyl, $C_1$-$C_3$ aminoalkyl, —$N(R^5)S(O)_2(R^5)$, -Q-phenyl, -Q-phenyl$SO_2F$, —NHC(O)phenyl, —NHC(O)phenyl$SO_2F$, $C_1$-$C_3$ alkyl substituted pyrazolyl, tert-butyldimethylsilyloxy$CH_2$—, —$N(R^5)_2$, ($C_1$-$C_3$ alkoxy)$C_1$-$C_3$ alkyl-, ($C_1$-$C_3$ alkyl)C(=O), oxo, ($C_1$-$C_3$ haloalkyl)C(=O)—, —$SO_2F$, ($C_1$-$C_3$ alkoxy)$C_1$-$C_3$ alkoxy, —$CH_2OC(O)N(R^5)_2$, —$CH_2NHC(O)OC_1$-$C_6$ alkyl, —$CH_2NHC(O)N(R^5)_2$, —$CH_2NHC(O)C_1$-$C_6$ alkyl, —$CH_2$(pyrazolyl), —$CH_2NHSO_2C_1$-$C_6$ alkyl, —$CH_2OC(O)$heterocycle, —$OC(O)N(R^5)_2$, —$OC(O)NH(C_1$-$C_3$ alkyl)$O(C_1$-$C_3$ alkyl), —$OC(O)NH(C_1$-$C_3$ alkyl)$O(C_1$-$C_3$ alkyl)phenyl($C_1$-$C_3$ alkyl)$N(CH_3)_2$, —$OC(O)NH(C_1$-$C_3$ alkyl)$O(C_1$-$C_3$ alkyl)phenyl, —$OC(O)$heterocycle, —O—$C_1$-$C_3$ alkyl, —$S(O)_2(R^{20})$, —$S(O)_2N(R^{20})_2$, —$S(O)N(R^{20})_2$, —$S(O)R^{20}$(=$NR^{20}$), —$NR^{20}S(O)_2R^{20}$, and —$CH_2$ heterocycle, wherein the phenyl of —NHC(O)phenyl and —OC(O)NH($C_1$-$C_3$ alkyl)($C_1$-$C_3$ alkyl)phenyl are optionally substituted with one or more substituents selected from —C(O)H and OH, and wherein the alkyl of —O—$C_1$-$C_3$ alkyl is optionally substituted with substituents selected from heterocycle, oxo and hydroxy; and wherein the heterocycle of —$CH_2$ heterocyclyl is optionally substituted with oxo;

each Q is selected from a bond, S, and O;

each $R^7$ is independently selected from halogen, hydroxy, HC(=O)—, $C_1$-$C_4$ alkyl, $C_1$-$C_4$ alkoxy, $C_1$-$C_4$ haloalkyl, $C_1$-$C_4$ hydroxyalkyl, and —$N(R^5)_2$;

each L is independently selected from a $C_1$-$C_4$ alkylene optionally substituted with one or more substituents independently selected from halogen, hydroxy, $C_{1-6}$ alkoxy, $C_1$-$C_4$ hydroxyalkyl, $C_1$-$C_4$ alkyl, $C_3$-$C_6$ carbocycle, and 3- to 8-membered heterocycle, wherein the $C_3$-$C_6$ carbocycle and 3- to 8-membered heterocycle are each optionally substituted with one or more substituents independently selected from halogen, —OH, —$NO_2$, =O, =S, —CN, $C_{1-6}$ alkyl-$N(R^{20})_2$, $C_{1-6}$ aminoalkyl, $C_{1-6}$ alkoxy, $C_{1-6}$ hydroxyalkyl, $C_{1-6}$ haloalkyl; and wherein optionally two substituents on the same carbon atom of L come together to form a $C_3$-$C_6$ carbocycle or 3- to 8-membered heterocycle, wherein the $C_3$-$C_6$ carbocycle and 3- to 8-membered heterocycle are each optionally substituted with one or more substituents independently selected from halogen, —OH, —$NO_2$, =O, =S, —CN, $C_{1-6}$ alkyl-$N(R^{20})_2$, $C_{1-6}$ aminoalkyl, $C_{1-6}$ alkoxy, $C_{1-6}$ hydroxyalkyl, and $C_{1-6}$ haloalkyl;

each $R^{20}$ is independently selected from hydrogen; and $C_{1-6}$ alkyl, $C_{2-6}$ alkenyl, $C_{2-6}$ alkynyl, $C_{3-12}$ carbocycle, and 3- to 12-membered heterocycle, each of which is optionally substituted with one or more substituents independently selected from halogen, —OH, —CN, —$NO_2$, —$NH_2$, —$N(C_{1-6}$ alkyl)$_2$, $C_{1-10}$ alkyl, —$C_{1-10}$ haloalkyl, —O—$C_{1-10}$ alkyl, oxo, $C_{3-12}$ carbocycle, and 3- to 12-membered heterocycle;

each $R^{21}$ is independently selected from hydrogen; and $C_{1-6}$ alkyl, $C_{2-6}$ alkenyl, $C_{2-6}$ alkynyl, $C_{3-12}$ carbocycle, and 3- to 12-membered heterocycle, each of which is optionally substituted with one or more substituents independently selected from halogen, —OH, —CN, —$NO_2$, —$NH_2$, —$N(C_{1-6}$ alkyl)$_2$, $C_{1-10}$ alkyl, —$C_{1-10}$ haloalkyl, —O—$C_{1-10}$ alkyl, oxo, $C_{3-12}$ carbocycle, and 3- to 12-membered heterocycle;

each $R^{23}$ is independently selected from hydrogen; and $C_{1-6}$ alkyl, $C_{2-6}$ alkenyl, $C_{2-6}$ alkynyl, $C_{3-12}$ carbocycle, and 3- to 12-membered heterocycle, each of which is optionally substituted with one or more substituents independently selected from halogen, —OH, —CN, —$NO_2$, —$NH_2$, —$N(C_{1-6}$ alkyl)$_2$, $C_{1-10}$ alkyl, —$C_{1-10}$ haloalkyl, —O—$C_{1-10}$ alkyl, oxo, $C_{3-12}$ carbocycle, and 3- to 12-membered heterocycle.

In some embodiments, for a compound or salt for Formula (I), B is selected from an optionally substituted 7- to 15-membered fused heterocycle and optionally substituted $C_7$-$C_{15}$ fused carbocycle. In some cases, and optionally substituted C_7-C_15 fused carbocycle. In some cases, B is an optionally substituted 7- to 15-membered fused heterocycle. In some cases, B is an optionally substituted unsaturated 7- to 15-membered fused heterocycle. In some cases, B is an optionally substituted 7- to 15-membered fused heteroaryl. In some cases, B is selected from an optionally substituted 7- to 15-membered fused heteroaryl and optionally substituted C_7-C_15 fused aryl. In some cases, B is an optionally substituted unsaturated C_7-C_15 fused carbocycle. In some cases, B is an optionally substituted 7- to 15-membered fused heterocycle, wherein the fused heterocycle is partially unsaturated. In some cases, B is an optionally substituted 7- to 15-membered fused heterocycle, wherein the fused heterocycle is partially saturated.

In some embodiments, for a compound or salt for Formula (I), B is selected from an optionally substituted 8- to 15-membered fused heterocycle and optionally substituted C_8-C_15 fused carbocycle. In some cases, and optionally substituted C_5-C_15 fused carbocycle. In some cases, B is an optionally substituted 8- to 15-membered fused heterocycle. In some cases, B is an optionally substituted unsaturated 8- to 15-membered fused heterocycle. In some cases, B is an optionally substituted 8- to 15-membered fused heteroaryl. In some cases, B is selected from an optionally substituted 8- to 15-membered fused heteroaryl and optionally substituted C_8-C_15 fused aryl. In some cases, B is an optionally substituted unsaturated C_8-C_15 fused carbocycle. In some cases, B is an optionally substituted 8- to 15-membered fused heterocycle, wherein the fused heterocycle is partially unsaturated. In some cases, B is an optionally substituted 8- to 15-membered fused heterocycle, wherein the fused heterocycle is partially saturated.

In some embodiments, for a compound or salt for Formula (I), B is selected from an optionally substituted 8- to 15-membered fused heterocycle, wherein the fused heterocycle is formed by combining three rings (e.g., tricyclic). In some cases, B is selected from an optionally substituted 8- to 15-membered fused heterocycle, wherein the fused heterocycle is formed by combining two rings (e.g., bicyclic). In some cases, for B the optionally substituted 8- to 15-membered fused heterocycle and optionally substituted C_8-C_15 fused carbocycle are each independently bicyclic or tricyclic. In some cases, for B the optionally substituted 8- to 15-membered fused heterocycle is bicyclic. In some cases, for B the optionally substituted 8- to 15-membered fused heterocycle is tricyclic.

In some embodiments, for a compound or salt for Formula (I), the heterocycle or carbocycle of B is bicyclic. In some cases, the heterocycle or carbocycle of B is tricyclic. In some cases, the tricyclic heterocycle contains three interconnected rings of atoms.

In some embodiments, for a compound or salt for Formula (I), for B, the heterocycle and carbocycle are each independently selected from bicyclic and tricyclic. In some cases, for B, the heterocycle and carbocycle are each independently tricyclic. In some cases, for B, the heterocycle and carbocycle are each independently bicyclic.

In some embodiments, for a compound or salt for Formula (I), for B, the optionally substituted 8- to 15-membered fused heterocycle and optionally substituted C_8-C_15 fused carbocycle are selected from

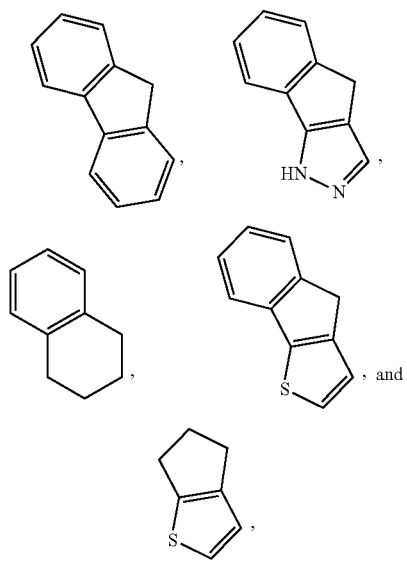

each of which is optionally substituted with one or more substituents. In some cases, for B, the optionally substituted 8- to 15-membered fused heterocycle and optionally substituted C_8-C_15 fused carbocycle are selected from

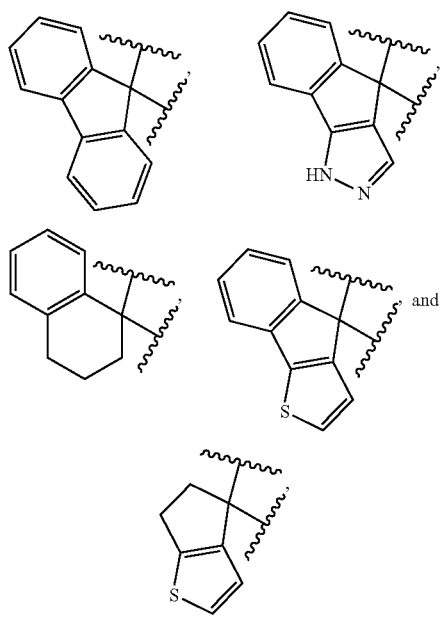

each of which is optionally substituted with one or more substituents. In some cases, B is selected from

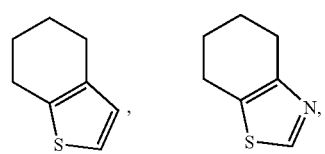

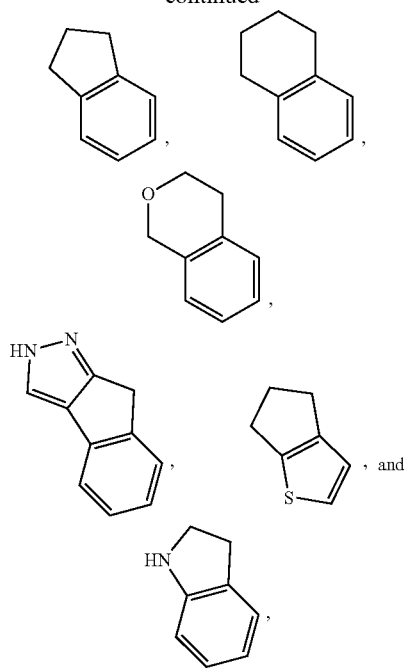
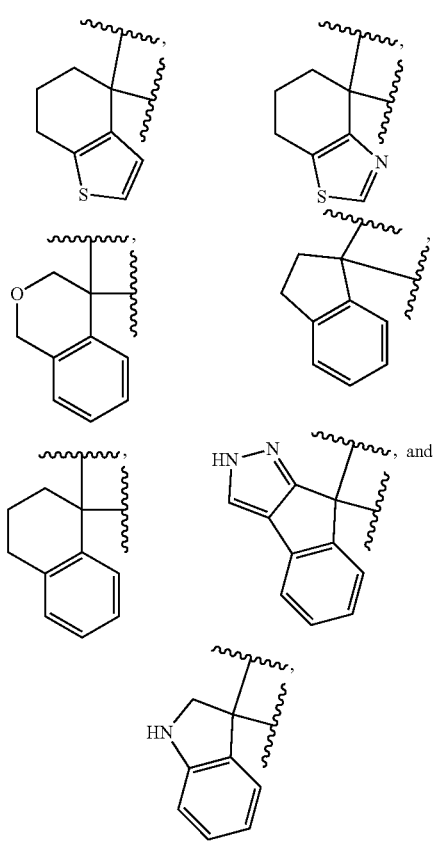
each of which is optionally substituted with one or more substituents. In some cases, B is selected from
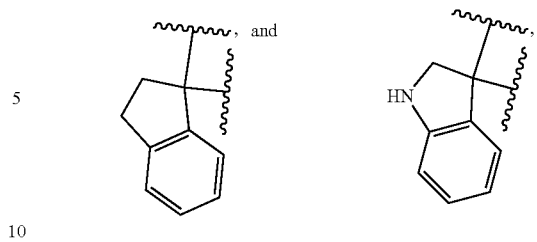
each of which is optionally substituted with one or more substituents.
In some embodiments, for a compound or salt for Formula (I), B is selected from
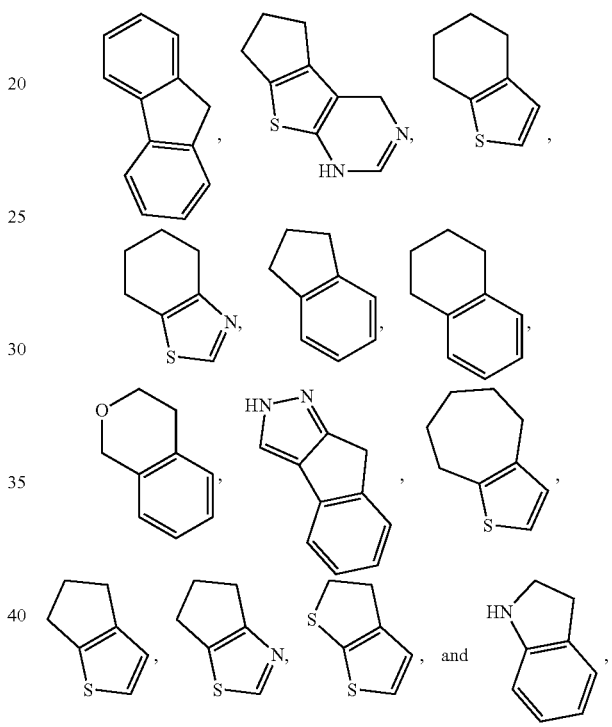
each of which is optionally substituted with one or more substituents. In some cases, B is selected from
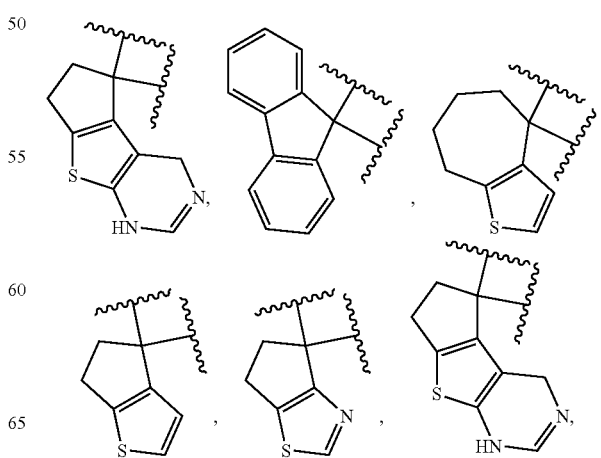

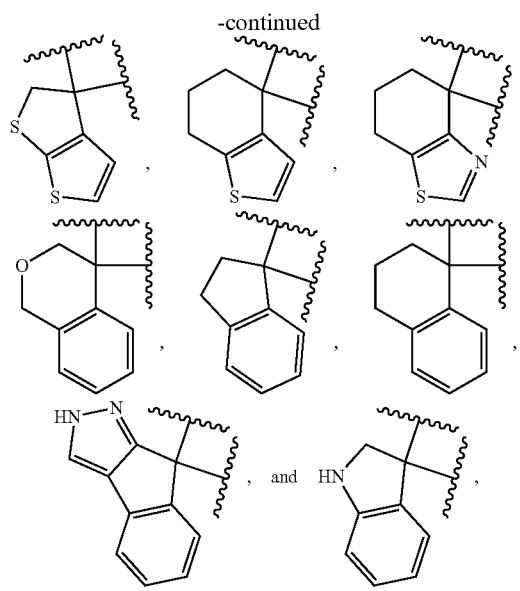

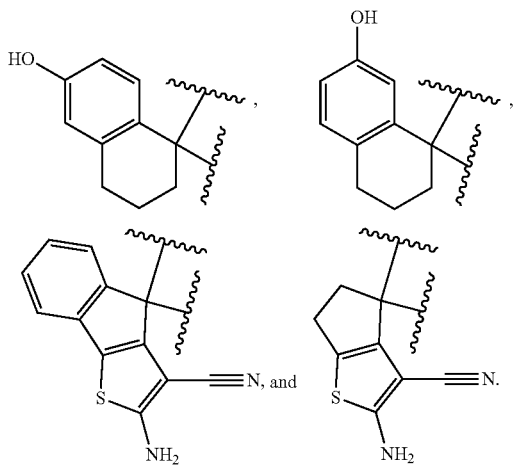

and each of which is optionally substituted with one or more substituents.

In some embodiments, for a compound or salt for Formula (I), for B, the optional substituents of the heterocycle and carbocycle are each independently selected from halogen, —CN, —NO$_2$, =O, —N(R$^{21}$)$_2$, —B(OR$^{21}$)$_2$, —OR$^{21}$, —SR$^{21}$, C$_{1-6}$ aminoalkyl, C$_{1-6}$ alkoxy, C$_{1-6}$ alkoxyalkyl, C$_{1-6}$ hydroxyalkyl, C$_{1-6}$ cyanoalkyl, C$_{1-6}$ haloalkyl, C$_{1-6}$ alkyl, C$_{2-6}$ alkenyl, C$_{2-6}$ alkynyl, C$_3$-C$_{12}$ carbocycle and 5- to 12-membered heterocycle. In some cases, the optional substituents of the heterocycle and carbocycle are each independently selected from halogen, —CN, —NO$_2$, =O, —N(R$^{21}$)$_2$, —B(OR$^{21}$)$_2$, —OH, —SR$^{21}$, C$_{1-6}$ aminoalkyl, C$_{1-6}$ alkoxy, C$_{1-6}$ alkoxyalkyl, C$_{1-6}$ hydroxyalkyl, C$_{1-6}$ cyanoalkyl, C$_{1-6}$ haloalkyl, C$_{1-6}$ alkyl, C$_{2-6}$ alkenyl, and C$_{2-6}$ alkynyl. In some cases, for B, the one or more optional substituents of the heterocycle and carbocycle are independently selected at each occurrence from halogen, oxo, —NH$_2$, C$_1$-C$_3$ alkyl, —B(OH)$_2$, —OH, —O—C$_1$-C$_3$ haloalkyl, —C(O)NH$_2$, —NH$_2$, =O, —CN, C$_{1-6}$ alkoxy, C$_{1-6}$ hydroxyalkyl, and C$_{2-6}$ alkynyl. In some cases, the optional substituents of the heterocycle and carbocycle are each independently selected from halogen, —CN, =O, —NH$_2$, —N(C$_{1-6}$ alkyl)H—N(C$_{1-6}$ alkyl)$_2$, —OH, C$_{1-6}$ aminoalkyl, C$_{1-6}$ alkoxy, C$_{1-6}$ alkoxyalkyl, C$_{1-6}$ hydroxyalkyl, C$_{1-6}$ cyanoalkyl, C$_{1-6}$ haloalkyl, C$_{1-6}$ alkyl, C$_{2-6}$ alkenyl, and C$_{2-6}$ alkynyl. In some cases, the one or more optional substituents of the heterocycle and carbocycle are each independently selected from oxo, —NH$_2$, halogen, C$_1$-C$_3$ alkyl. In some cases, for B, the optionally substituted 8- to 15-membered fused heterocycle and optionally substituted C$_8$-C$_{15}$ fused carbocycle are selected from

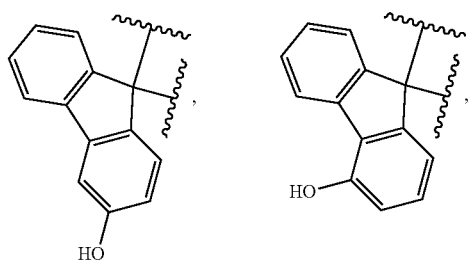

In some cases, B is selected from

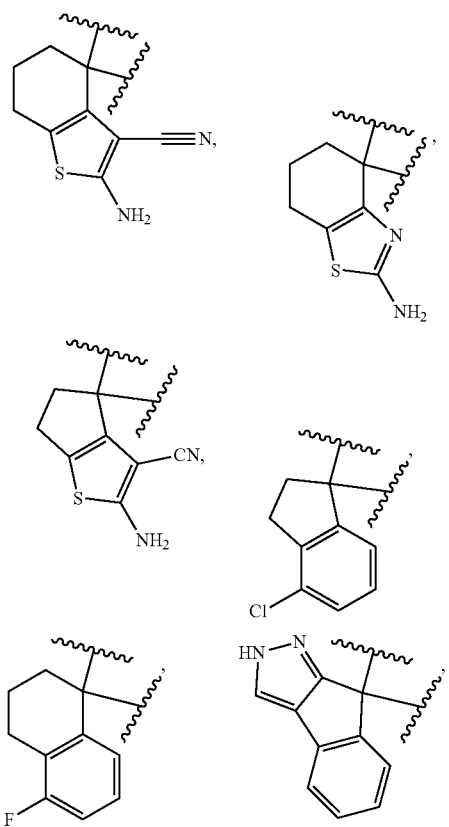

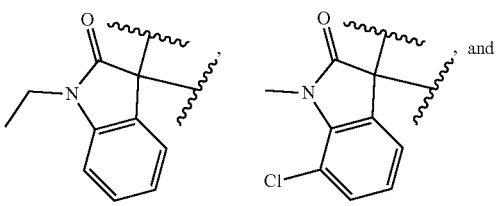

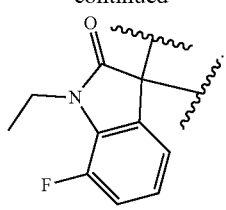
In some cases, B is selected from
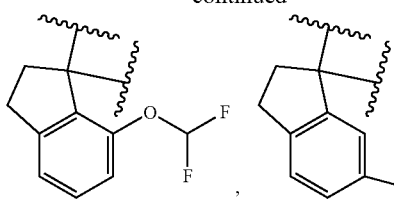
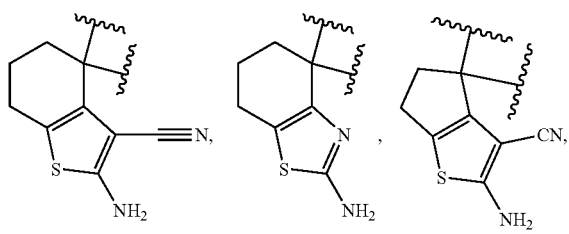
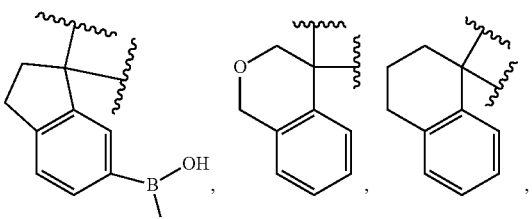
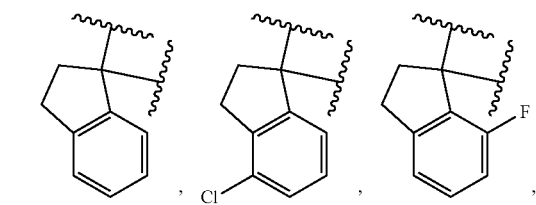
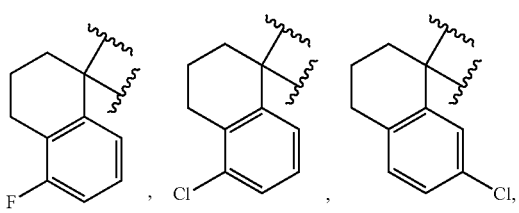
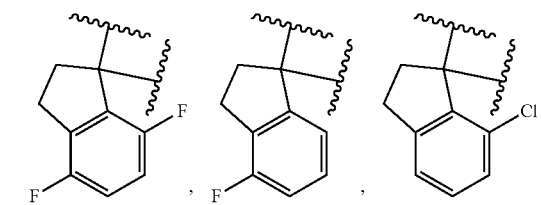
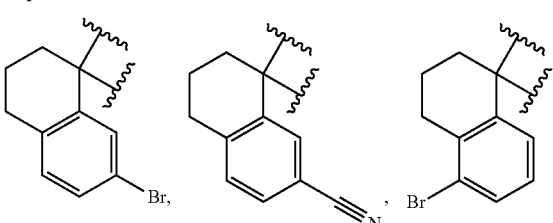
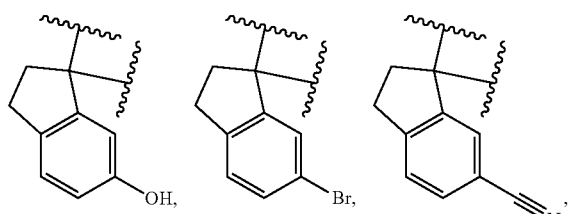
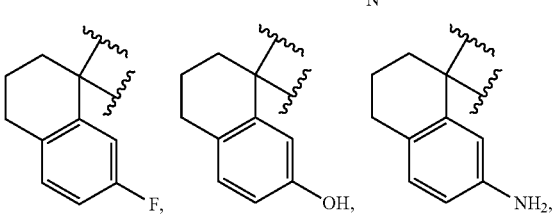
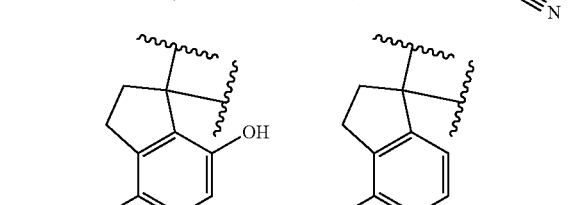
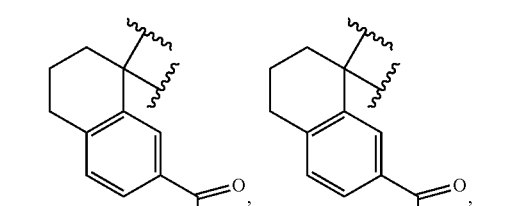
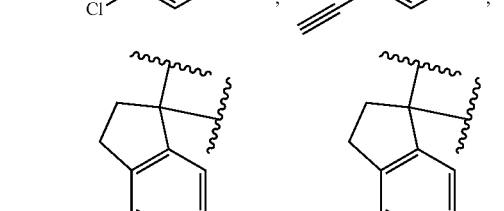
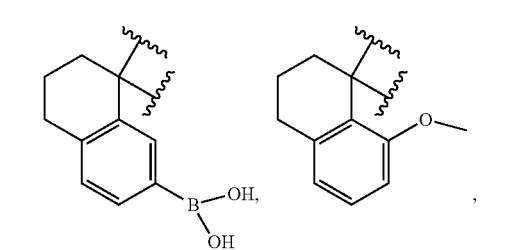

-continued

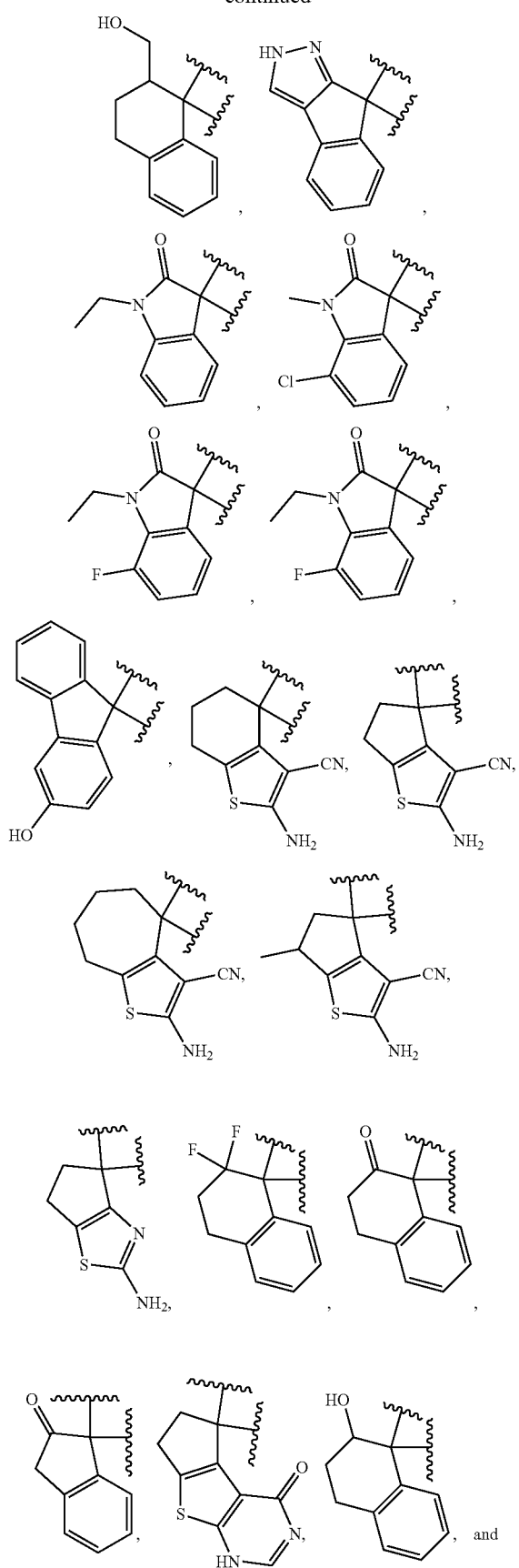

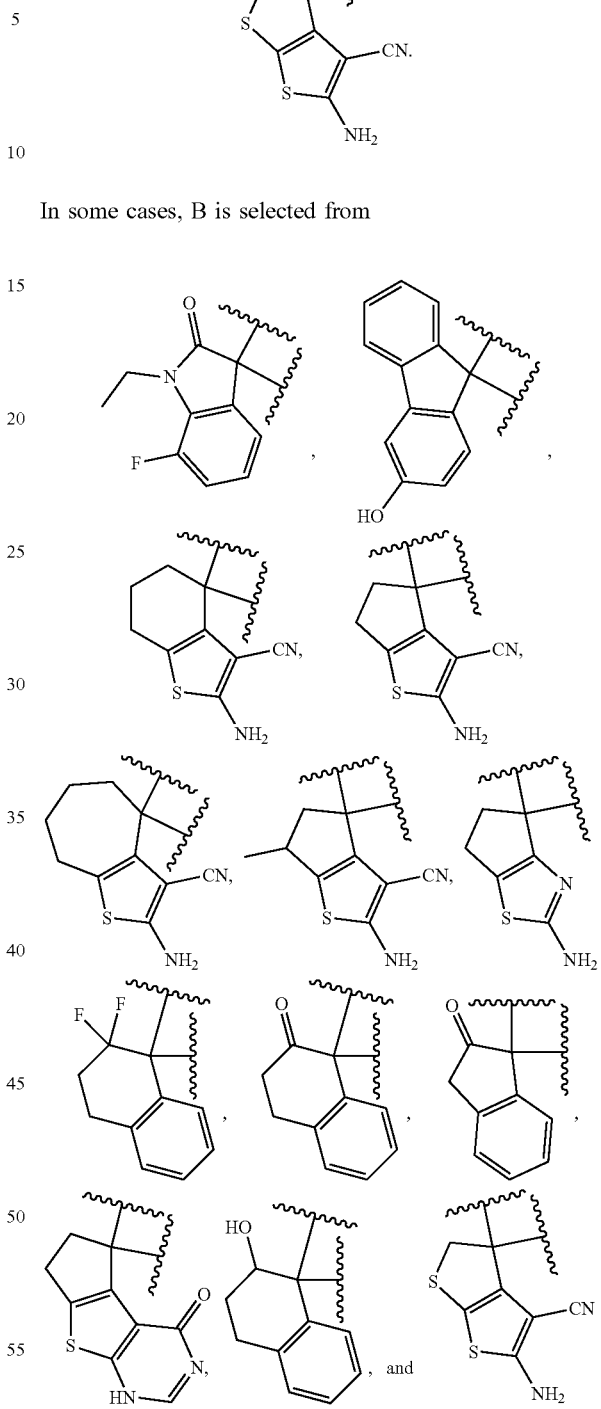

In some cases, B is selected from

In some embodiments, for a compound or salt for Formula (I), B is selected from an optionally substituted 7- to 12-membered fused heterocycle and optionally substituted $C_{9-10}$ fused carbocycle. In some cases, the heterocycle of B has at least one sulfur atom. In some cases, the heterocycle of B has one or sulfur atoms. In some cases, the heterocycle of B has at least one nitrogen atom. In some cases, B is selected from

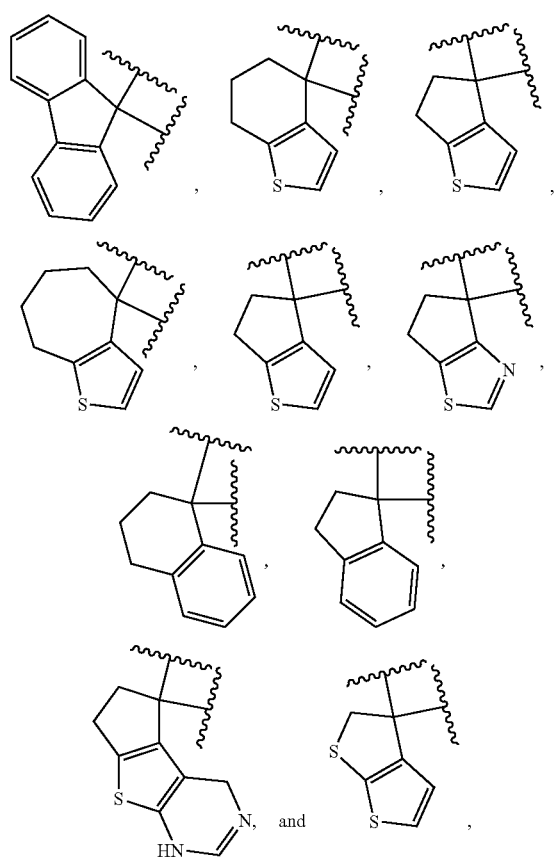

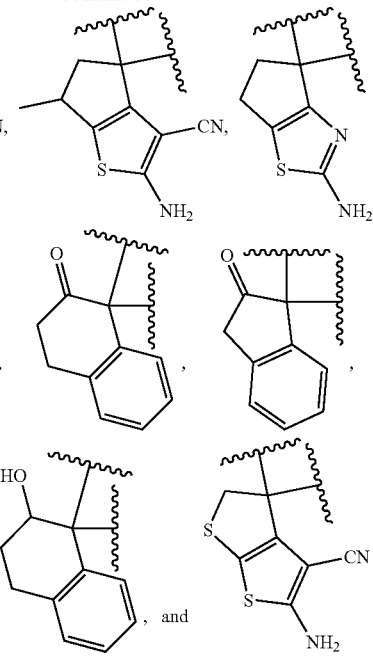

each of which is optionally substituted. In some cases, the one or more optional substituents of B are independently selected at each occurrence from halogen, $C_1$-$C_3$ alkyl, —B(OR$^{20}$)$_2$, —OR$^{20}$, —C(O)N(R$^{20}$)$_2$, —N(R$^{20}$)$_2$, =O, —CN, —NHCN, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{2-6}$ alkenyl, and $C_{2-6}$ alkynyl. In some cases, the one or more optional substituents of B are independently selected at each occurrence from halogen, $C_1$-$C_3$ alkyl, —OH, —NH$_2$, =O, and —CN. In some cases, B is selected from

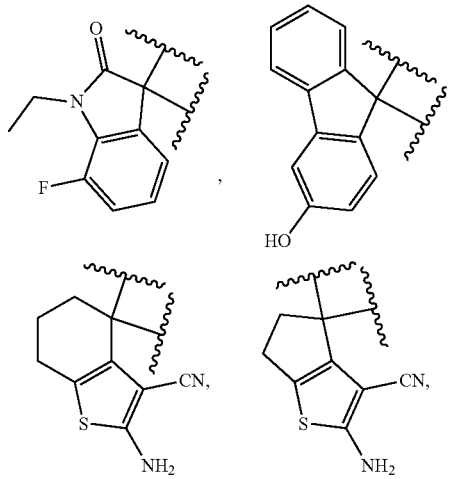

In some embodiments, for a compound or salt for Formula (I), B is selected from an optionally substituted 8- to 10-membered fused heterocycle having at least one sulfur atom. In some cases, B is selected from

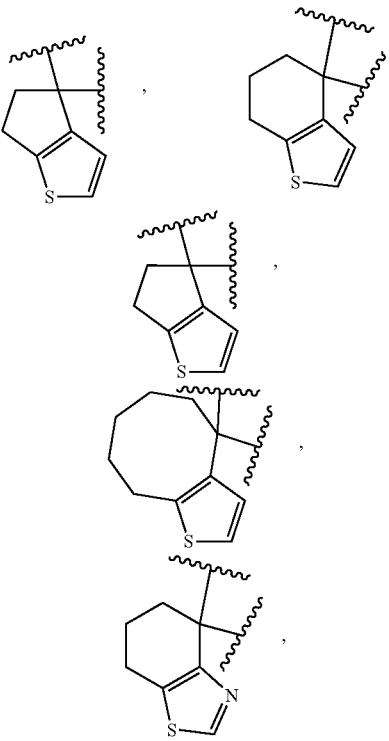

each of which is optionally substituted. In some cases, the one or more optional substituents of B are independently selected at each occurrence from halogen, $C_1$-$C_3$ alkyl, —OR$^{20}$, —C(O)N(R$^{20}$)$_2$, —N(R$^{20}$)$_2$, =O, —CN, —NHCN, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{2-6}$ alkenyl, and $C_{2-6}$ alkynyl. In some cases, the one or more optional substituents of B are independently selected at each occurrence from halogen, $C_1$-$C_3$ alkyl, —$NH_2$, and —CN. In some cases, B is substituted. In some cases, B is substituted with at least one —$NH_2$. In some cases, B is selected from

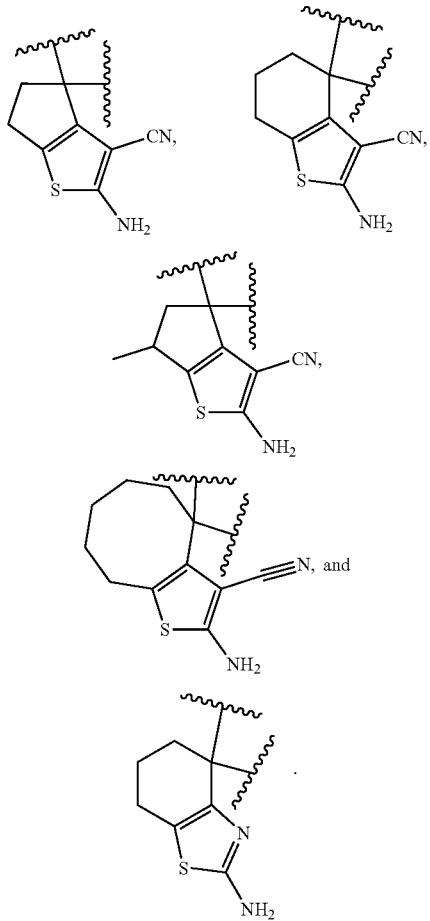

In some cases, B is substituted with at least one —$NH_2$ at least one —CN. In some cases, B is selected from

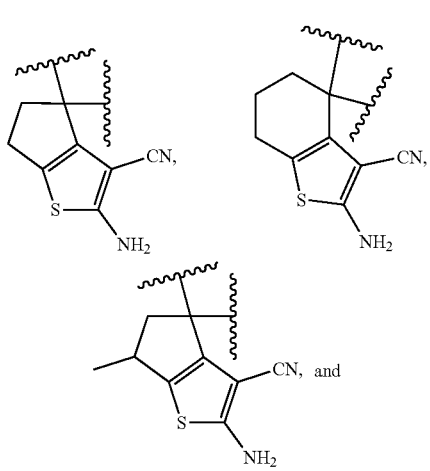

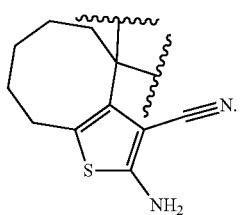

In some embodiments, for a compound or salt for Formula (I), B is an optionally substituted 7- to 11-membered fused heterocycle. In some cases, B is an optionally substituted 8- to 10-membered fused heterocycle. In some cases, B is an optionally substituted 7-membered fused heterocycle. In some cases, B is an optionally substituted 8-membered fused heterocycle. In some cases, B is an optionally substituted 9-membered fused heterocycle. In some cases, B is an optionally substituted 10-membered fused heterocycle. In some cases, the heterocycle of B is an unsaturated heterocycle. In some cases, the heterocycle of B is a non-aromatic heterocycle. In some cases, B has at least one sulfur atom. In some cases, B has at two sulfur atoms. In some cases, B has at least one sulfur atom and at least one nitrogen atom. In some cases, B has at least one sulfur atom and at least one oxygen atom. In some cases, B has only 1 heteroatom. In some cases, B has at least 2 heteroatoms. In some cases, B is selected from

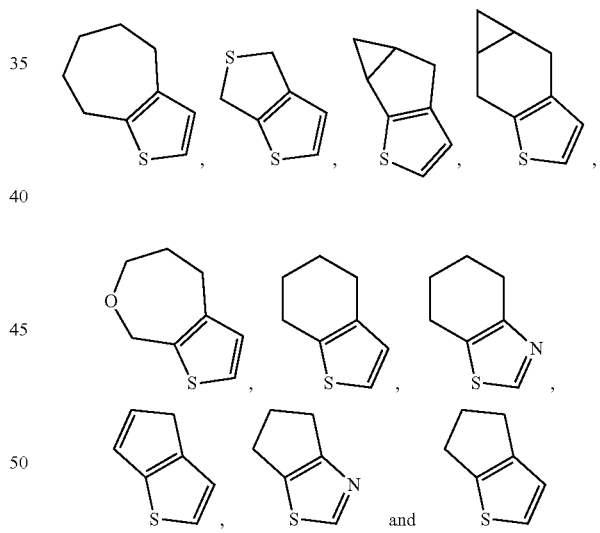

each of which is optionally substituted. In some cases, B is selected from

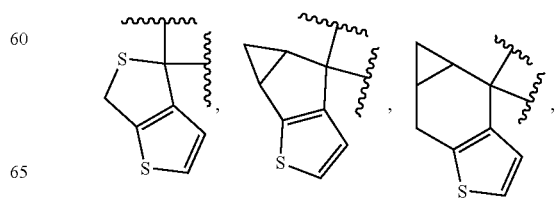

-continued

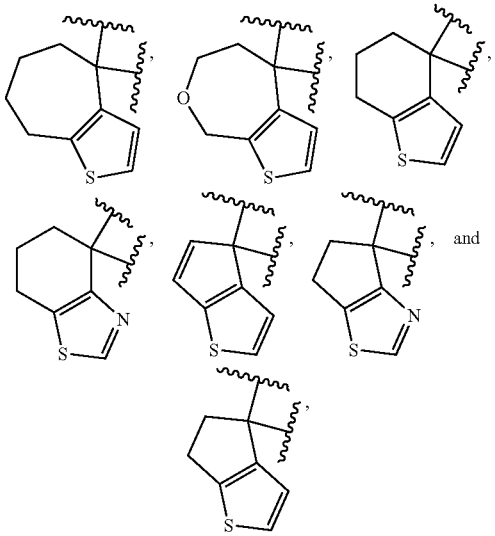

each of which is optionally substituted. In some cases, B is selected from

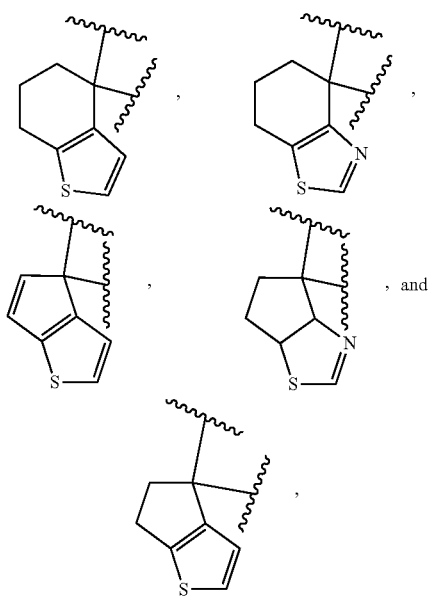

each of which is optionally substituted. In some cases, the one or more optional substituents of B, are independently selected at each occurrence from halogen, oxo, —$NH_2$, $C_1$-$C_3$ alkyl, —$B(OH)_2$, —OH, —O—$C_1$-$C_3$ haloalkyl, —$C(O)NH_2$, —$NH_2$, =O, —CN, $C_{1-6}$ alkoxy, $C_{1-6}$ hydroxyalkyl, and $C_{2-6}$ alkynyl. In some cases, the one or more optional substituents of B, are independently selected at each occurrence from halogen, $C_1$-$C_3$ alkyl, —$NH_2$, and —CN. In some cases, B is substituted with at least three substituents. In some cases, B is substituted with at least two substituents. In some cases, B is substituted with at least one substituent. In some cases, B is substituted with at least one substituent selected from halogen, $C_1$-$C_3$ alkyl, —$NH_2$, and —CN. In some cases, B is substituted with at least one substituent selected from halogen. In some cases, B is substituted with at least one substituent selected from —$NH_2$. In some cases, B is substituted with at least one substituent selected from —CN. In some cases, B is selected from

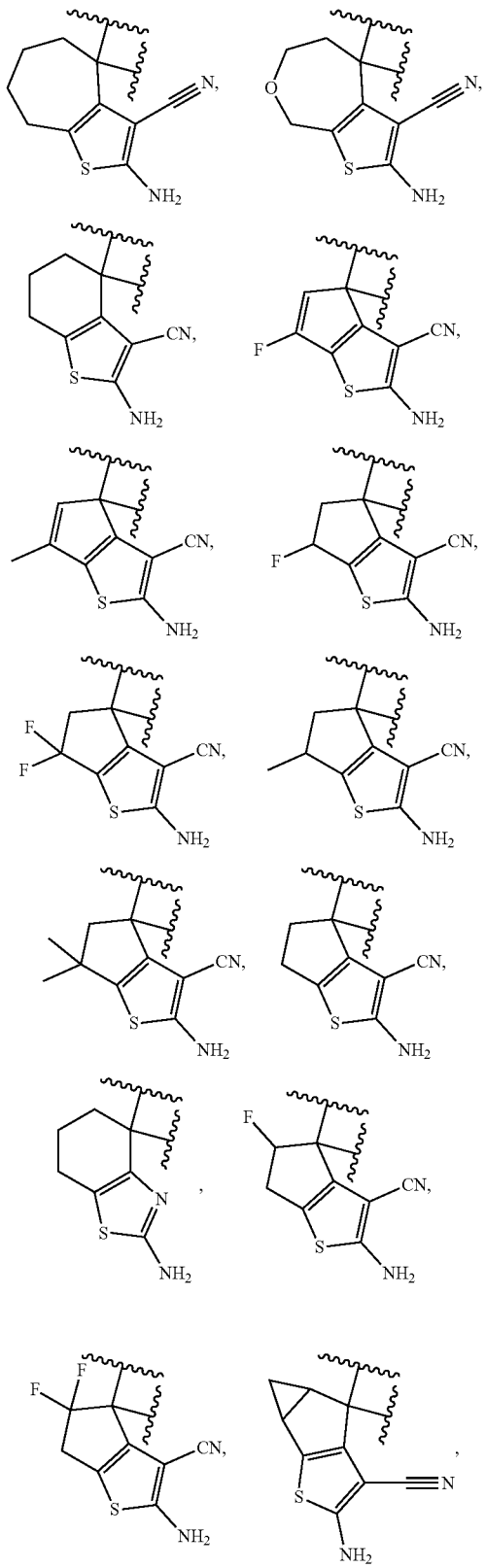

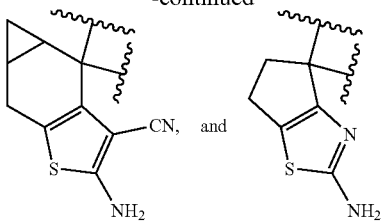

In some embodiments, for a compound or salt for Formula (I), $R^3$ is selected from hydrogen, halogen, —CN, —NO$_2$, —N(R$^{20}$)$_2$, —OR$^{20}$, —SR$^{20}$, —S(O)$_2$(R$^{20}$), —S(O)$_2$N(R$^{20}$)$_2$, —NR$^{20}$S(O)$_2$R$^{20}$, —C(O)N(R$^{20}$)$_2$, —N(R$^{20}$)C(O)R$^{20}$, —N(R$^{20}$)C(O)N(R$^{20}$)$_2$, —N(R$^{20}$)C(O)OR$^{20}$, —C(O)R$^{20}$, —C(O)OR$^{20}$, —OC(O)R$^{20}$, —OC(O)N(R$^{20}$)$_2$, $C_{1-6}$ aminoalkyl, $C_{1-6}$ alkoxy, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl. In some cases, $R^3$ is selected from hydrogen, halogen, —CN, —NO$_2$, —N(R$^{20}$)$_2$, —OR$^{20}$, —SR$^{20}$, —C(O)N(R$^{20}$)$_2$, —C(O)R$^{20}$, —C(O)OR$^{20}$, —OC(O)R$^{20}$, $C_{1-6}$ aminoalkyl, $C_{1-6}$ alkoxy, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl. In some cases, $R^3$ is selected from hydrogen, halogen, —CN, —NO$_2$, —NH$_2$, —N(C$_{1-6}$ alkyl)H, —N(C$_{1-6}$ alkyl)$_2$, —OH, —C(O)N(R$^{20}$)$_2$, —C(O)R$^{20}$, —C(O)OR$^{20}$, —OC(O)R$^{20}$, $C_{1-6}$ aminoalkyl, $C_{1-6}$ alkoxy, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkenyl, and $C_{2-6}$ alkynyl. In some cases, $R^3$ is selected from hydrogen, —CN, —C(O)R$^{20}$, $C_{1-6}$ aminoalkyl, $C_{1-6}$ alkoxy, $C_{1-6}$ alkoxyalkyl, $C_{1-6}$ hydroxyalkyl, $C_{1-6}$ cyanoalkyl, $C_{1-6}$ haloalkyl, and $C_{1-6}$ alkyl. In some cases, $R^3$ is selected from hydrogen, —CN, —C(O)R$^{20}$, $C_{1-6}$ hydroxyalkyl, and $C_{1-6}$ alkyl. In some cases, $R^3$ is selected from hydrogen, —CN, —C(O)H, $C_1$ hydroxyalkyl, and $C_{1-6}$ alkyl. In some cases, $R^3$ is selected from hydrogen, fluorine, and —CN. In some cases, $R^3$ is selected from fluorine. In some cases, $R^3$ is selected from hydrogen. In some cases, $R^3$ is selected from —CN.

In some embodiments, for a compound or salt for Formula (I), Y is —O—. In some cases, Y is a bond. In some cases, Y is —S—. In some cases, Y is —N(R$^5$)—.

In some embodiments, for a compound or salt for Formula (I), L is selected from $C_1$-$C_4$ alkylene. In some cases, L is selected from an unsubstituted $C_1$-$C_4$ alkylene. In some cases, L is selected from an unsubstituted $C_1$ alkylene. In some cases, two substituents on the same carbon atom of L come together to form a $C_3$-$C_6$ carbocycle or 3- to 8-membered heterocycle, wherein the $C_3$-$C_6$ carbocycle and 3- to 8-membered heterocycle are each optionally substituted with one or more substituents independently selected from halogen, —OH, —NO$_2$, =O, =S, —CN, $C_{1-6}$ aminoalkyl, $C_{1-6}$ alkoxy, $C_{1-6}$ hydroxyalkyl, $C_{1-6}$ haloalkyl. In some cases, two substituents on the same carbon atom of L come together to form a $C_3$-$C_6$ carbocycle or 3- to 8-membered heterocycle. In some cases, two substituents on the same carbon atom of L come together to form a $C_3$-$C_6$ carbocycle. In some embodiments, for a compound or salt for Formula (I), L is selected from $C_1$-$C_4$ alkylene. In some cases, L is selected from unsubstituted $C_1$-$C_4$ alkylene. In some cases, each L is independently selected from a $C_1$-$C_4$ alkylene optionally substituted; and wherein optionally two substituents on the same carbon atom of L come together to form a $C_3$-$C_6$ carbocycle or 3- to 8-membered heterocycle wherein the $C_3$-$C_6$ carbocycle and 3- to 8-membered heterocycle are each optionally substituted with one or more substituents selected from halogen, —OH, —NO$_2$, =O, =S, —CN, $C_{1-6}$ aminoalkyl, $C_{1-6}$ alkoxy, $C_{1-6}$ hydroxyalkyl, $C_{1-6}$ haloalkyl. In some cases, the optional substituents of L are selected from $C_1$-$C_4$ hydroxyalkyl, $C_1$-$C_4$ alkyl, $C_3$-$C_6$ carbocycle; and wherein optionally two substituents on the same carbon atom of L come together to form a $C_3$-$C_6$ carbocycle or 3- to 8-membered heterocycle wherein the $C_3$-$C_6$ carbocycle and 3- to 8-membered heterocycle are optionally substituted with one or more substituents selected from halogen and $C_{1-6}$ haloalkyl. In some cases, L is selected from

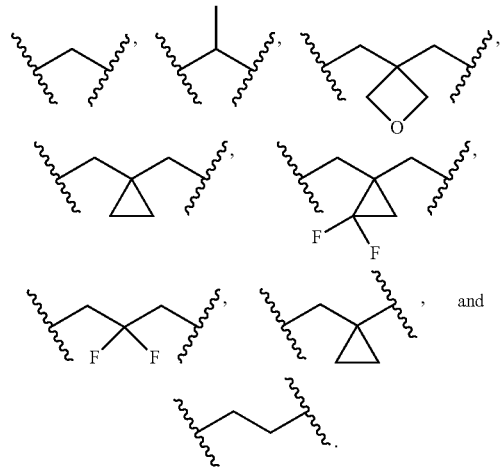

In some cases, L is selected from

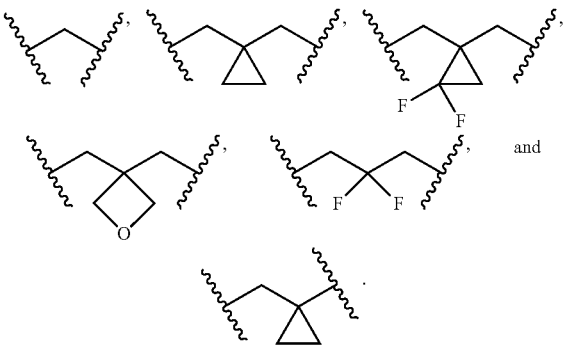

In some cases, each L is independently selected from a substituted $C_1$-$C_4$ alkylene, and wherein two substituents on the same carbon atom of L come together to form a $C_3$-$C_6$ carbocycle 3- to 5-membered heterocycle. In some cases, each L is independently selected from a substituted $C_{2-3}$ alkylene, and wherein two substituents on the same carbon atom of L come together to form a $C_3$ carbocycle or 4-membered heterocycle, wherein the $C_3$ carbocycle is optionally substituted with one or more substituents selected from halogen. In some cases, each L is independently selected from

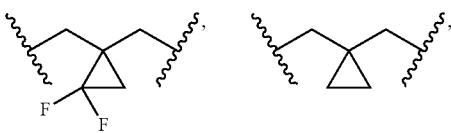

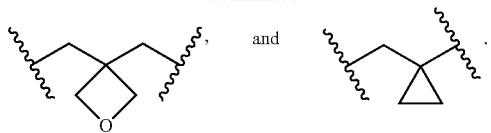

In some cases, each L is independently selected from

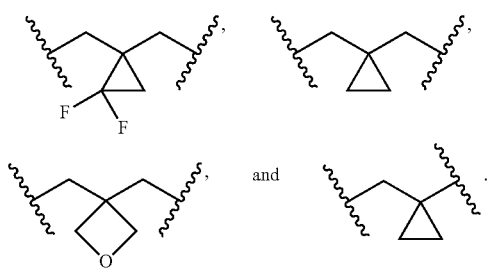

In some cases, each L is independently selected from

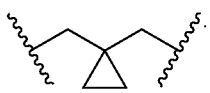 [SMILES: *CC1(C*)CC1]

In some cases, each L is independently selected from a $C_1$-$C_4$ alkylene optionally substituted with one or more substituents independently selected from halogen and $C_1$-$C_4$ alkyl. In some cases, L is selected from

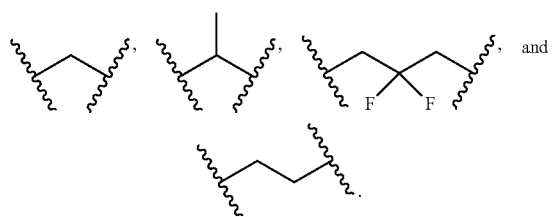

In some embodiments, for a compound or salt for Formula (I), each L is independently selected from an unsubstituted $C_1$-$C_4$ alkylene. In some cases, L is selected from

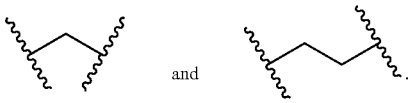

In some cases, L is selected from

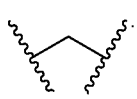

In some embodiments, for a compound or salt for Formula (I), $R^2$ is selected from heterocycle, $C_1$-$C_6$ alkyl, -L-heterocycle, -L-N($R^{23}$)$_2$, -L-O$R^{23}$, -L-aryl, -L-heteroaryl, -L-cycloalkyl, -L-N($R^{23}$)$_2$, -L-NHC(=NH)NH$_2$, -L-C(O)N($R^{23}$)$_2$, -L-$C_1$-$C_6$ haloalkyl, -L-O$R^{23}$, -L-N$R^{23}$C(O)-aryl, -L-COOH, -L-N$R^{23}$S(O)$_2$($R^{23}$), -L-S(O)$_2$N($R^{23}$)$_2$, -L-N($R^{23}$)C(O)(O$R^{23}$), -L-OC(O)N($R^{23}$)$_2$, and -L-C(=O)O$C_1$-$C_6$ alkyl, wherein the heterocycle, the heterocycle portion of -L-heterocycle, and the cycloalkyl portion of the -L-cycloalkyl are each optionally substituted with one or more $R^6$, and wherein the aryl portion of -L-N$R^{23}$C(O)-aryl, the aryl portion of -L-N$R^{23}$C(O)-aryl, the aryl of the -L-aryl, and the heteroaryl of -L-heteroaryl are each optionally substituted with one or more $R^7$.

In some embodiments, for a compound or salt for Formula (I), $R^2$ is selected from heterocycle, -L-heterocycle, -L-aryl, -L-heteroaryl, and -L-N($R^{23}$)$_2$, wherein the heterocycle, the heterocycle portion of -L-heterocycle, are each optionally substituted with one or more $R^6$, and wherein the aryl of the -L-aryl, and the heteroaryl of -L-heteroaryl are each optionally substituted with one or more $R^7$.

In some embodiments, for a compound or salt for Formula (I), $R^2$ is -L-heterocycle, wherein the heterocycle portion is optionally substituted. In some cases, $R^2$ is -L-heterocycle, wherein the heterocycle portion is a bicyclic heterocycle. In some cases, $R^2$ is -L-heterocycle, wherein the heterocycle portion is a monocyclic heterocycle. In some cases, $R^2$ is -L-heterocycle, wherein the heterocycle portion is a saturated heterocycle. In some cases, $R^2$ is selected from a -L-5- to 10-membered heterocycle. In some cases, $R^2$ is selected from a —($C_1$-$C_2$ alkylene)-5- to 10-membered heterocycle. In some cases, $R^2$ is selected from a -L-5- to 8-membered heterocycle. In some cases, $R^2$ is selected from a -L-5- to 8-membered saturated heterocycle. In some cases, $R^2$ is a -L-5-membered heterocycle. In some cases, $R^2$ is a -L-8-membered heterocycle. In some cases, the heterocycle contains at least 1 nitrogen atom. In some cases, the heterocycle contains at most 1 nitrogen atom. In some cases, the heterocycle contains 1 nitrogen atom. In some cases, the bicyclic heterocycle contains at least 1 nitrogen atom. In some cases, the bicyclic heterocycle contains at most 1 nitrogen atom. In some cases, the bicyclic heterocycle contains 1 nitrogen atom. In some cases, Y—$R^2$ is selected from

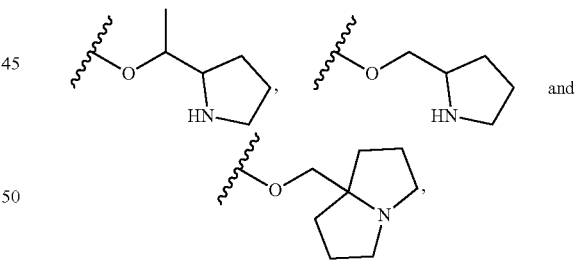

wherein the heterocycle portion is optionally substituted. In some cases, Y—$R^2$ is selected from

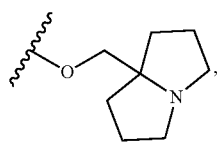 [SMILES: *OCC12CCCN1CCC2]

wherein the heterocycle portion is optionally substituted. In some cases, the heterocycle portion is optionally substituted with one or more substituents selected from halogen, hydroxy, $C_1$-$C_3$ hydroxyalkyl, $C_1$-$C_3$ alkyl, $C_1$-$C_3$ haloalkyl, $C_1$-$C_3$ alkoxy, —CN, and $C_1$-$C_3$ aminoalkyl. In some cases, the heterocycle portion is optionally substituted with one or more substituents selected from halogen, hydroxy, —CN, $C_1$-$C_3$ hydroxyalkyl, $C_1$-$C_3$ alkyl, $C_1$-$C_3$ haloalkyl, $C_1$-$C_3$ alkoxy, and $C_1$-$C_3$ aminoalkyl. In some cases, the heterocycle portion is optionally substituted with one or more substituents selected from $C_1$-$C_3$ alkyl and halogen. In some cases, Y—$R^2$ is selected from

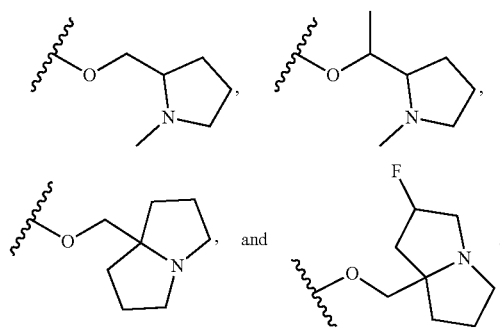

In some cases, Y—$R^2$ is selected from

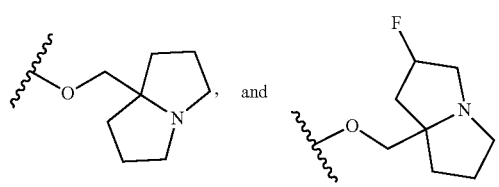

In some cases, Y—$R^2$ is selected from

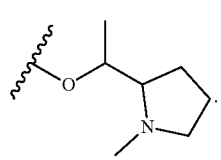 [SMILES: *OC(C)C1CCCN1C]

In some cases, Y—$R^2$ is

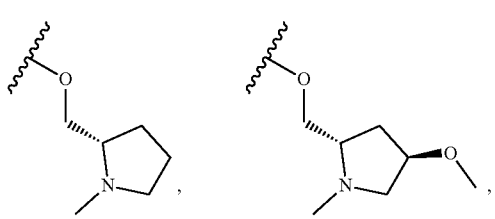

In some embodiments, for a compound or salt of Formula (I), $R^2$ is selected from optionally substituted -L-heterocycle. In some cases, the heterocycle is a bicyclic heterocycle. In some cases, the heterocycle is a monocyclic heterocycle. In some cases, the heterocycle has only 1 nitrogen atom. In some cases, the heterocycle has only 1 nitrogen atom and no other heteroatoms. In some cases, Y—$R^2$ is selected from

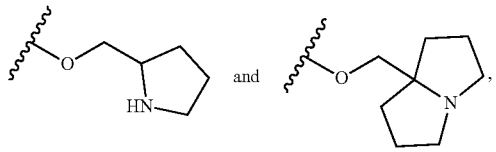 [SMILES: *OCC1CCCN1 ; *OCC12CCCN1CCC2]

wherein the heterocycle portion is optionally substituted. In some cases, Y—$R^2$ is selected from (second structure set)

wherein the heterocycle portion is optionally substituted. In some cases, Y—$R^2$ is selected from (third structure set)

wherein the heterocycle portion is optionally substituted. In some cases, Y—$R^2$ is selected from (fourth structure)

wherein the heterocycle portion is optionally substituted. In some cases, the heterocycle is optionally substituted with one or more substituent selected from halogen, hydroxy, $C_1$-$C_3$ alkyl, —N($R^5$)S(O)$_2$($R^5$), —OC(O)N($R^5$)$_2$, oxo, =CH$_2$, =NO—$C_1$-$C_3$ alkyl, —CH$_2$OC(O)heterocycle, —CH$_2$ heterocycle, —CH$_2$OC(O)N($R^5$)$_2$, and —O—$C_1$-$C_3$ alkyl, wherein the alkyl of —O—$C_1$-$C_3$ alkyl is optionally substituted with substituents selected from heterocycle, oxo, and hydroxy. In some cases, the heterocycle is substituted with at least one halogen. In some cases, the heterocycle is substituted with at least one =CH$_2$. In some cases, Y—$R^2$ is selected from

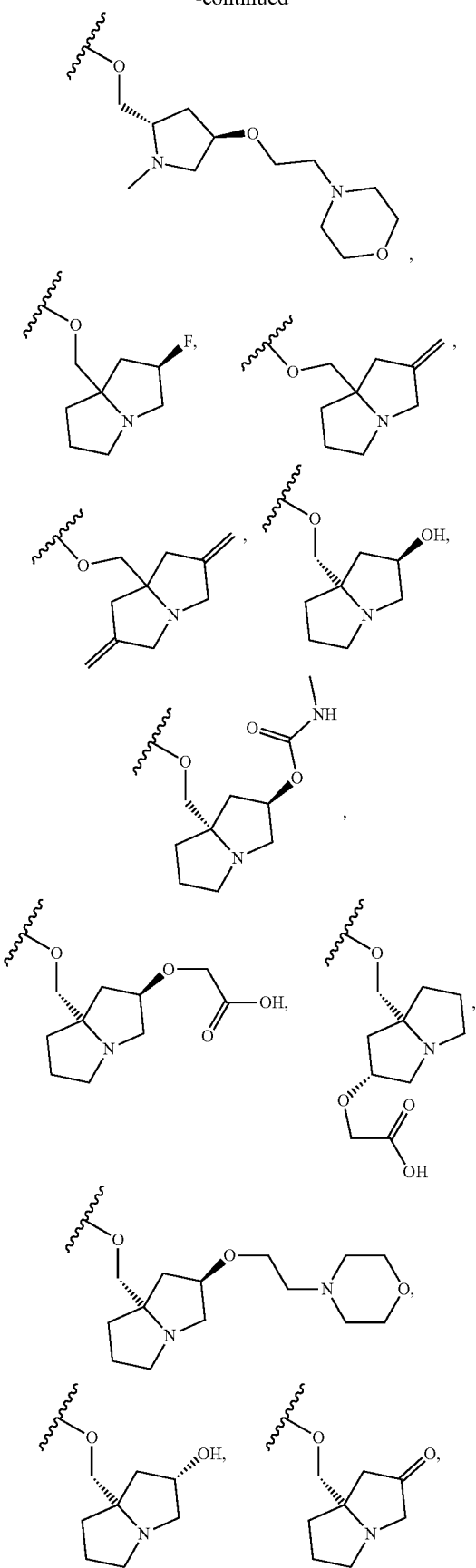
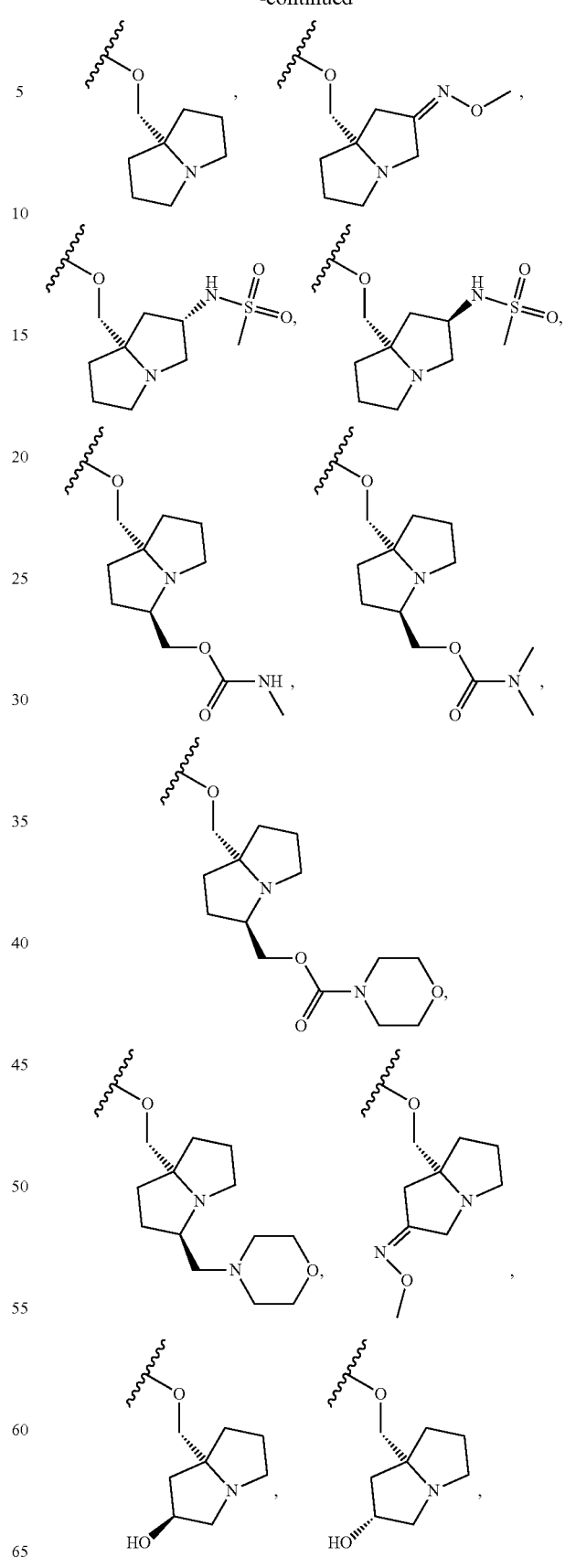

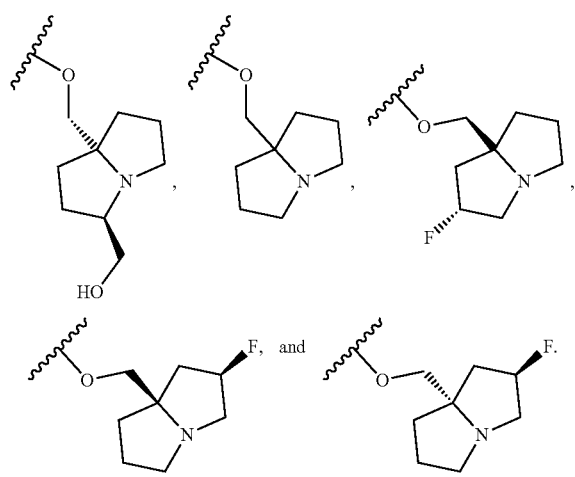
In some cases, Y—R² is selected from
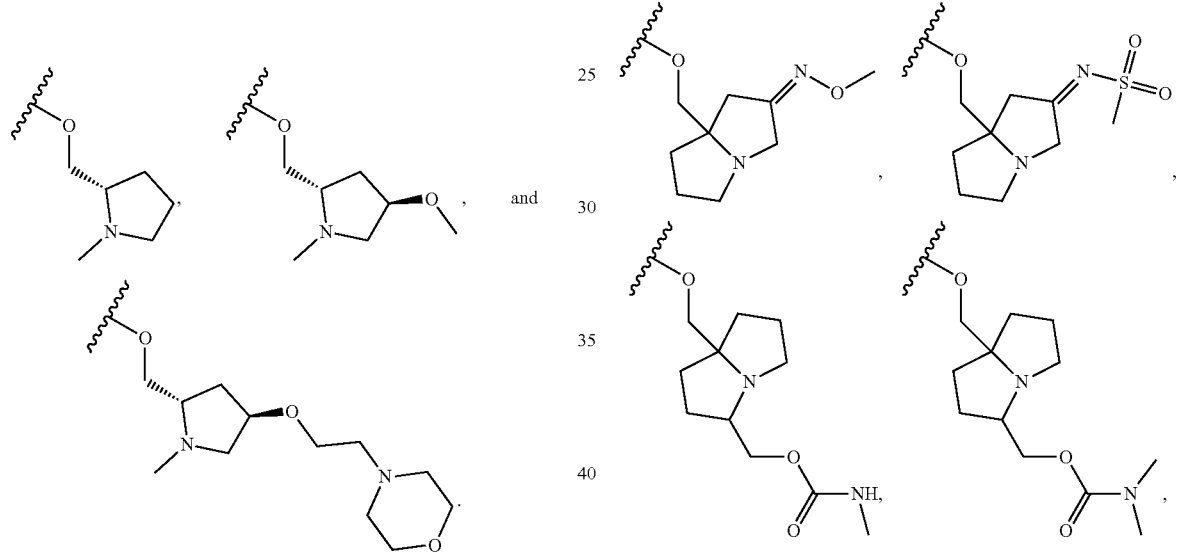
In some cases, Y—R² is selected from
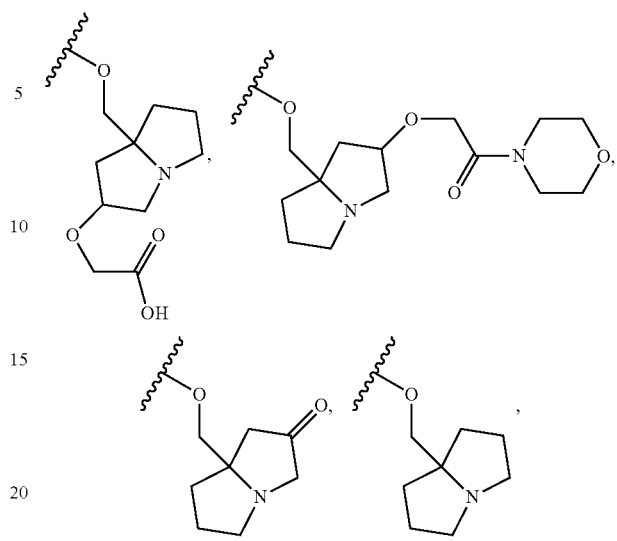
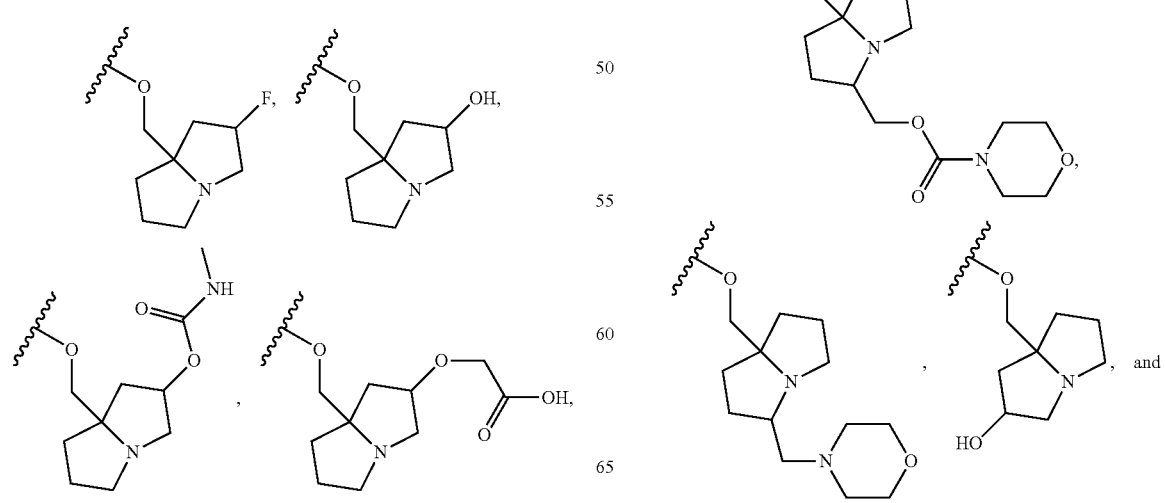

-continued

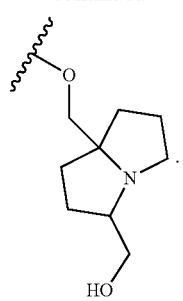

In some cases, Y—R² is selected from

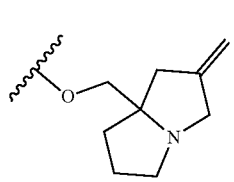 and 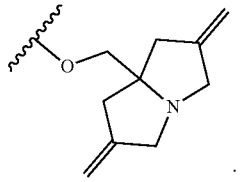

In some cases, Y—R² is selected from

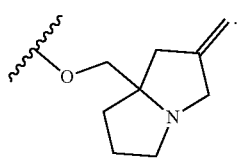 [SMILES: *OCC12CCCN1CC(=C)C2]

In some embodiments, for a compound or salt of Formula (I), R² is -L-heteroaryl, wherein the heteroaryl portion is optionally substituted with one or more R⁷. In some cases, the heteroaryl is selected from a 5- to 6-membered heteroaryl, wherein the heteroaryl portion is optionally substituted with one or more R⁷. In some cases, the heteroaryl is selected from a 5-membered heteroaryl, wherein the heteroaryl portion is optionally substituted with one or more R⁷. In some cases, the heteroaryl has at least one nitrogen atom. In some cases, the heteroaryl has two nitrogen atoms. In some cases, the heteroaryl has three nitrogen atoms. In some cases, the heteroaryl is selected from

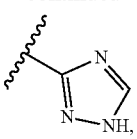

which is optionally substituted. In some cases, the heteroaryl is

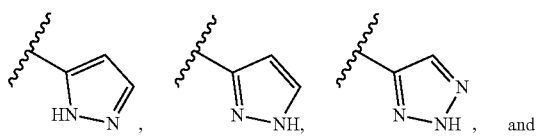

-continued

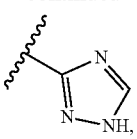

which is optionally substituted. In some cases, Y—R² is selected from

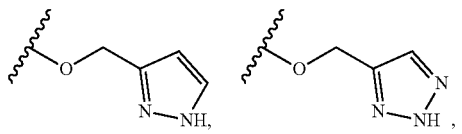

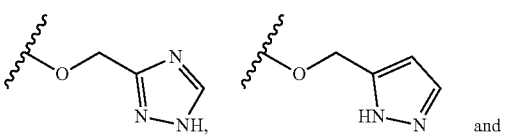 and

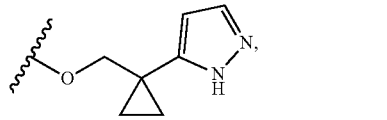

wherein the heteroaryl portion is optionally substituted with one or more R⁷. In some cases, each R⁷ is independently selected from $C_1$-$C_4$ alkyl, halogen, and $C_1$-$C_4$ haloalkyl. In some cases, Y—R² is selected from

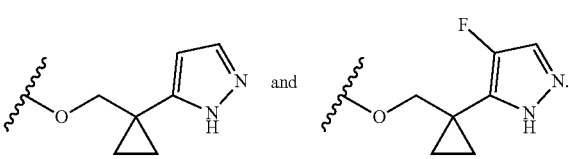 [SMILES: *OCC1(c2ccn[nH]2)CC1 ; *OCC1(c2[nH]ncc2F)CC1] and 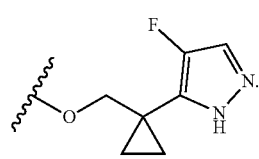

In some cases, Y—R² is selected from

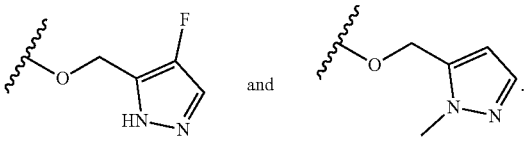

In some cases, Y—R² is selected from

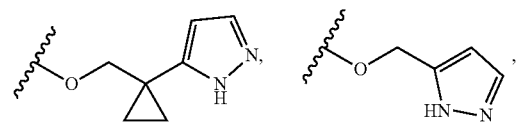

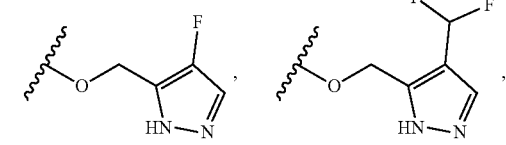

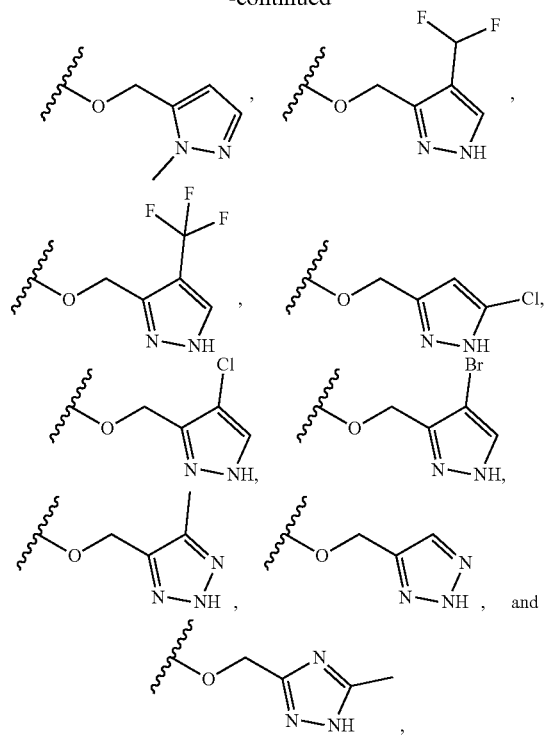

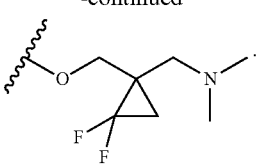

In some embodiments, for a compound or salt of Formula (I), $R^2$ is heterocycle, optionally substituted with one or more $R^6$. In some cases, the heterocycle of $R^2$ is

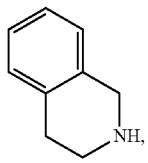

which is optionally substituted. In some cases, the heterocycle of $R^2$ is

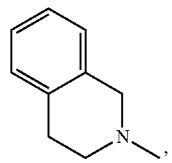

In some embodiments, for a compound or salt of Formula (I), $R^2$ is -L-aryl, optionally substituted with one or more $R^7$. In some cases, wherein Y—$R^2$ is selected from

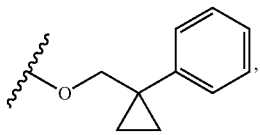 [SMILES: *OCC1(c2ccccc2)CC1]

wherein the heterocycle portion is optionally substituted with one or more $R^7$. In some cases, Y—$R^2$ is selected from

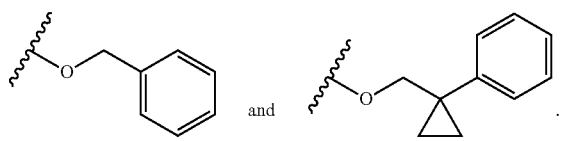 [SMILES: *OCc1ccccc1 ; *OCC1(c2ccccc2)CC1]

In some cases, Y—$R^2$ is

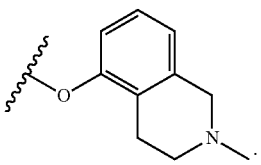 [SMILES: *Oc1cccc2c1CCN(C)C2]

In some embodiments, for a compound or salt of Formula (I), $R^2$ is selected from heterocycle, -L-heterocycle, wherein the heterocycle, and the heterocycle portion of -L-heterocycle, are each optionally substituted with one or more $R^6$; -L-aryl, and -L-heteroaryl, wherein the aryl of the -L-aryl, and the heteroaryl of -L-heteroaryl are each optionally substituted with one or more $R^7$; and -L-N($R^{23}$)$_2$. In some cases, the heterocycle of $R^2$ is selected from In some embodiments, for a compound or salt of Formula (I), $R^2$ is -L-N($R^{23}$)$_2$. In some cases, Y—$R^2$ is selected from

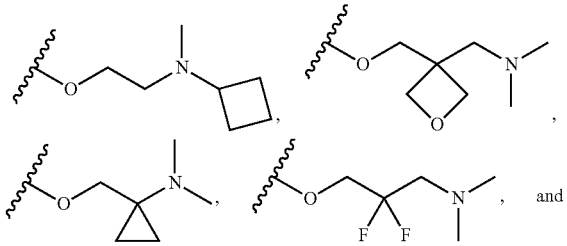

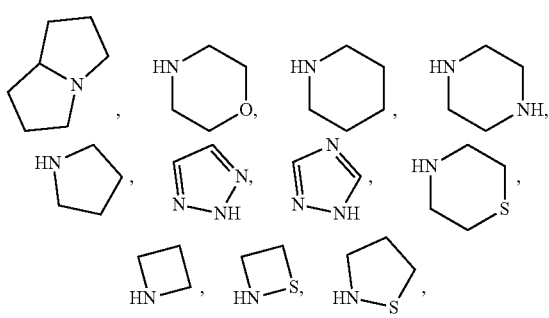

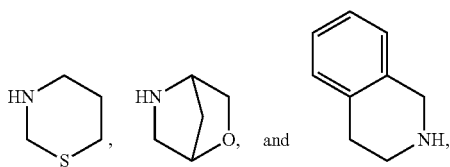

wherein the heterocycle of $R^2$ is optionally substituted with one or more $R^6$; wherein the aryl and heteroaryl of $R^2$ is selected from

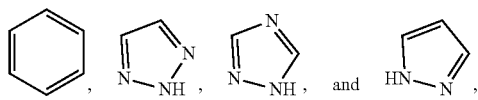

wherein the aryl and the heteroaryl are each optionally substituted with one or more $R^7$; and

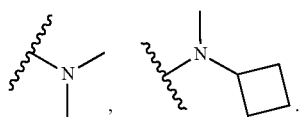

In some cases, the heterocycle of $R^2$ is selected from

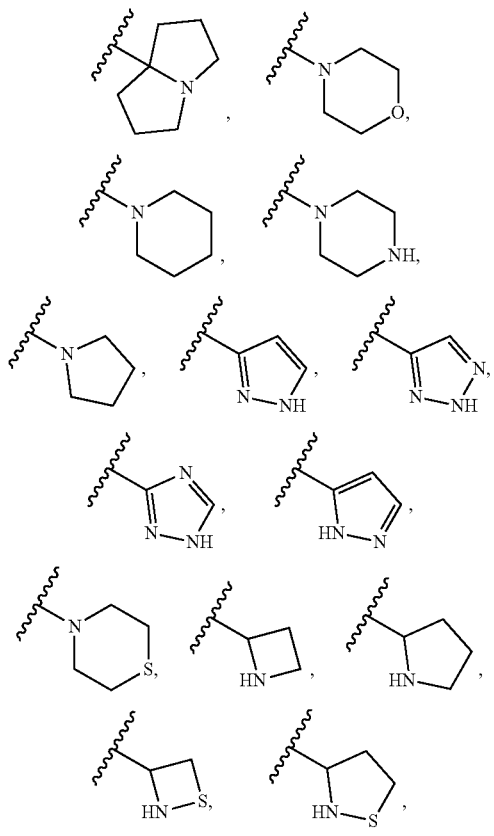

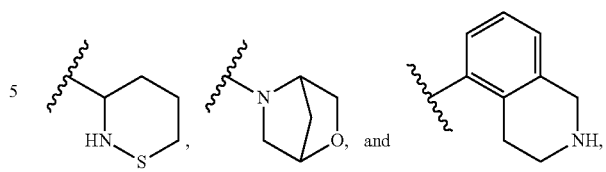

wherein the heterocycle is optionally substituted with one or more $R^6$; wherein the aryl and heteroaryl of $R^2$ is selected from

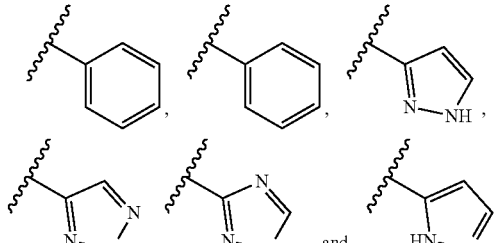

wherein the aryl and the heteroaryl are each optionally substituted with one or more $R^7$; and

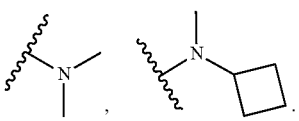

In some cases, each $R^6$ is independently selected from halogen, hydroxy, $C_1$-$C_3$ alkyl, $C_1$-$C_3$ haloalkyl, —N($R^5$)S(O)$_2$($R^5$), —OC(O)N($R^5$)$_2$, =CH$_2$, oxo, =NO—$C_1$-$C_3$ alkyl, —CH$_2$OC(O)heterocycle, —CH$_2$ heterocycle, —CH$_2$OC(O)N($R^5$)$_2$, and —O—$C_1$-$C_3$ alkyl, wherein the alkyl of —O—$C_1$-$C_3$ alkyl is optionally substituted with substituents selected from heterocycle, oxo, and hydroxy; and wherein each $R^7$ is selected from $C_1$-$C_3$ alkyl, halogen and $C_1$-$C_3$ haloalkyl. In some cases, the heterocycle of $R^2$, the aryl and heteroaryl of $R^2$, and —N($R^{20}$)$_2$ of $R^2$ is selected from

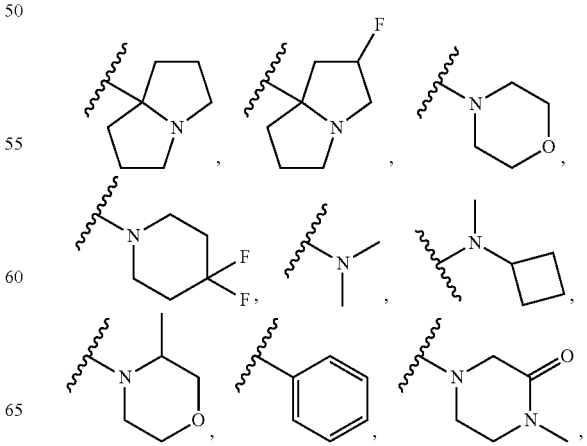

-continued

In some cases, Y—R² is selected from

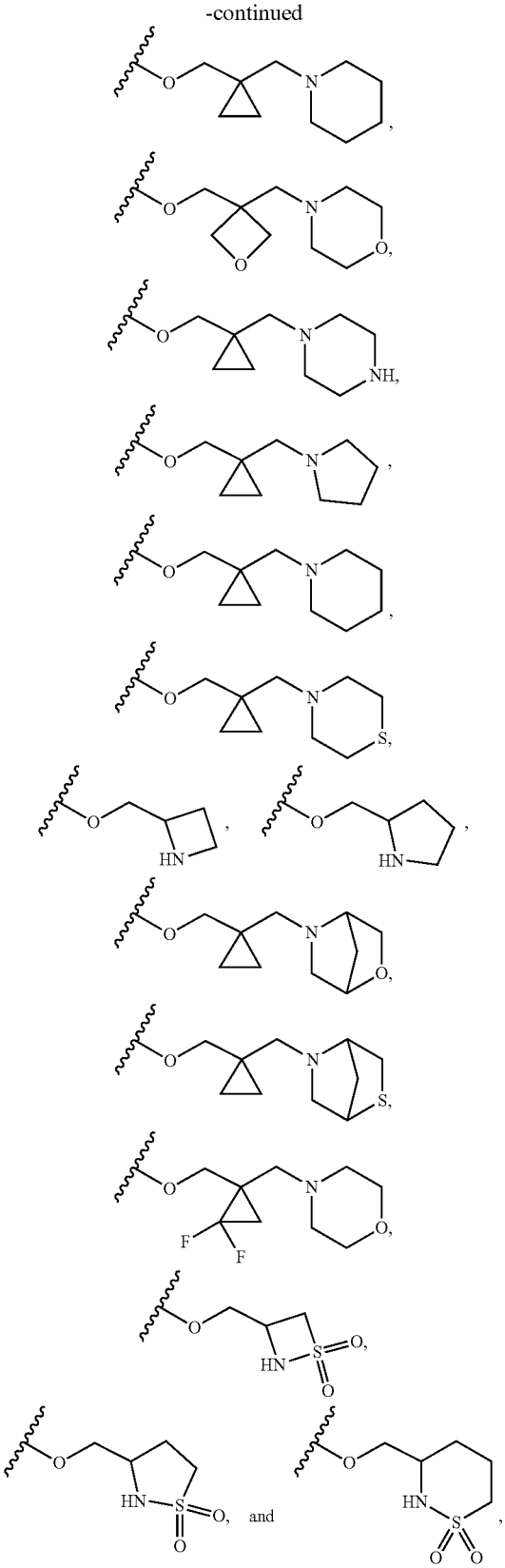
wherein the aryl of the -L-aryl, and the heteroaryl of -L-heteroaryl are each optionally substituted with one or more $R^7$; and
In some cases, Y—$R^2$ is selected from
wherein the heterocycle, and the heterocycle portion of -L-heterocycle, are each optionally substituted with one or more $R^6$;

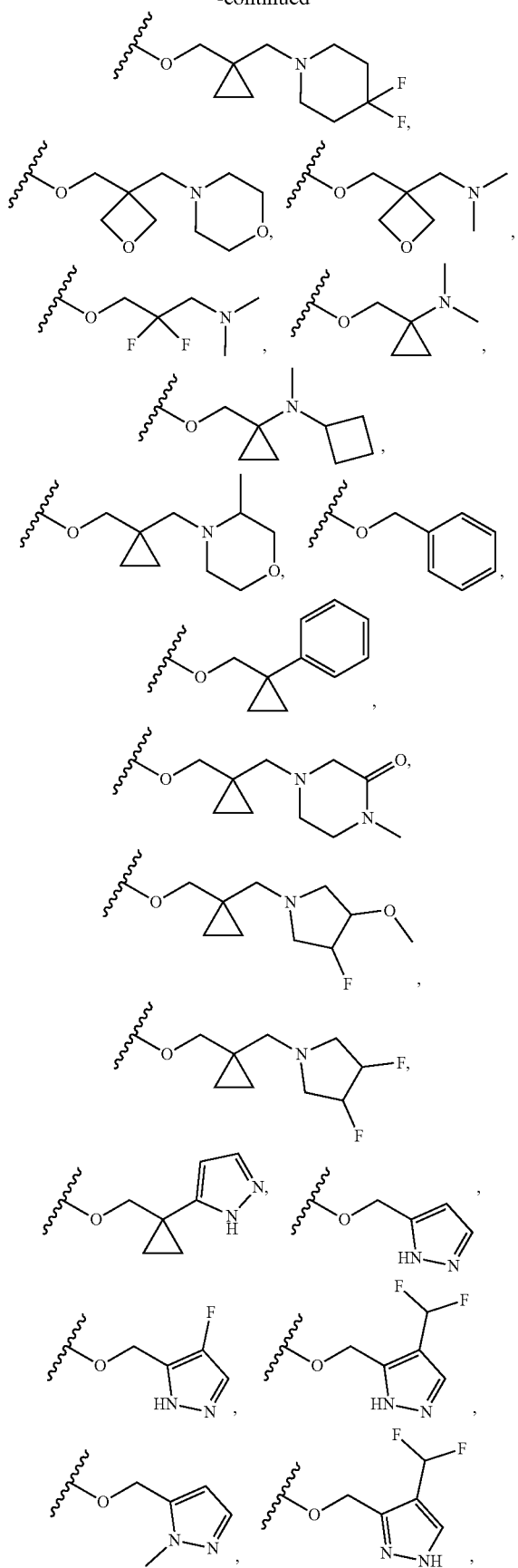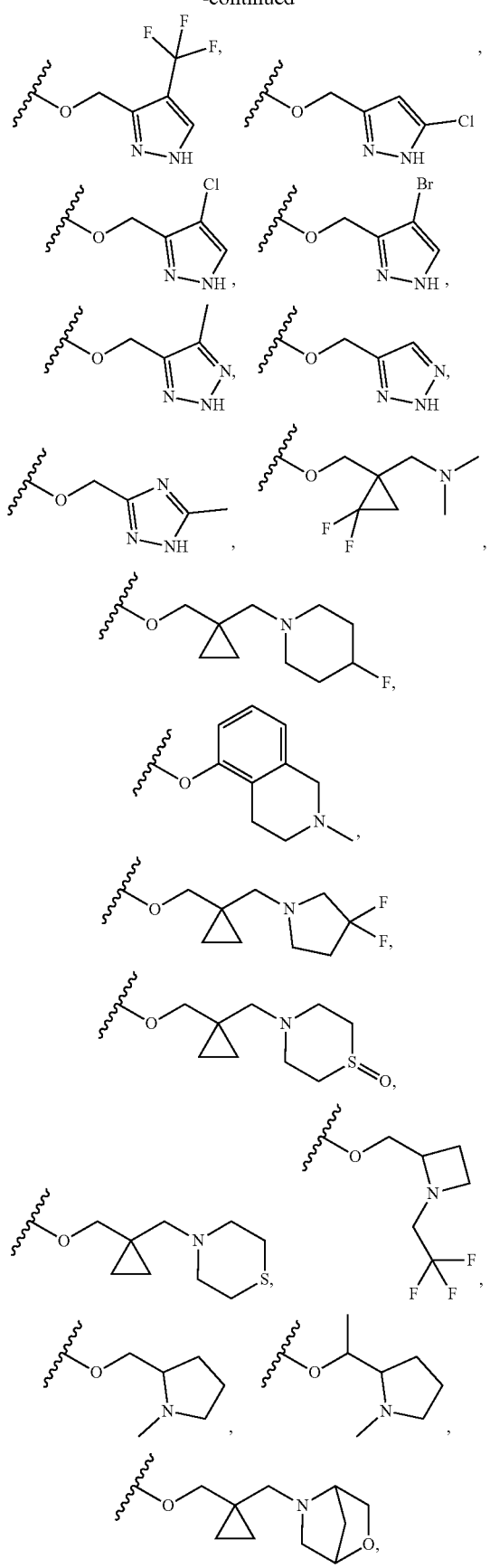

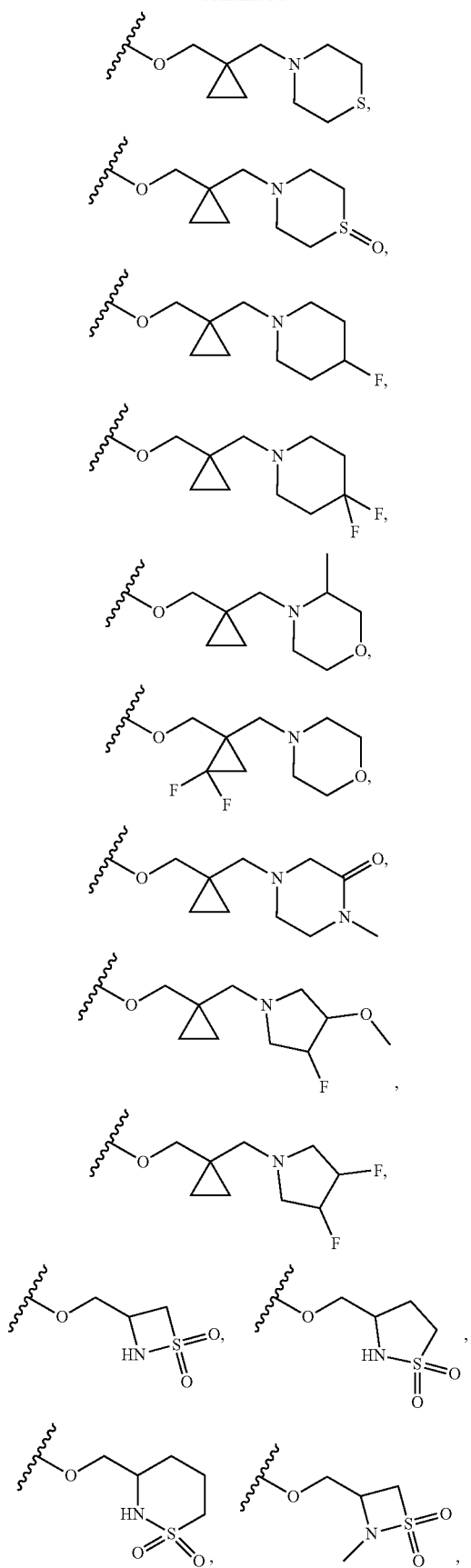
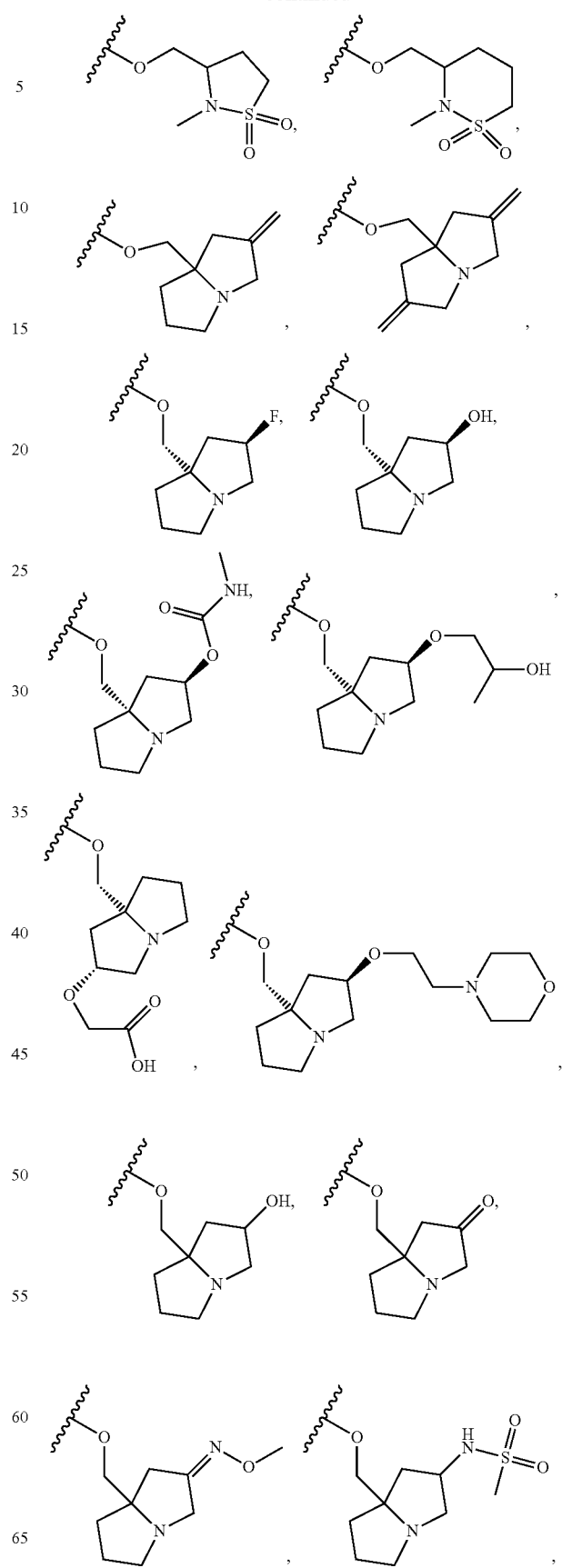

-continued
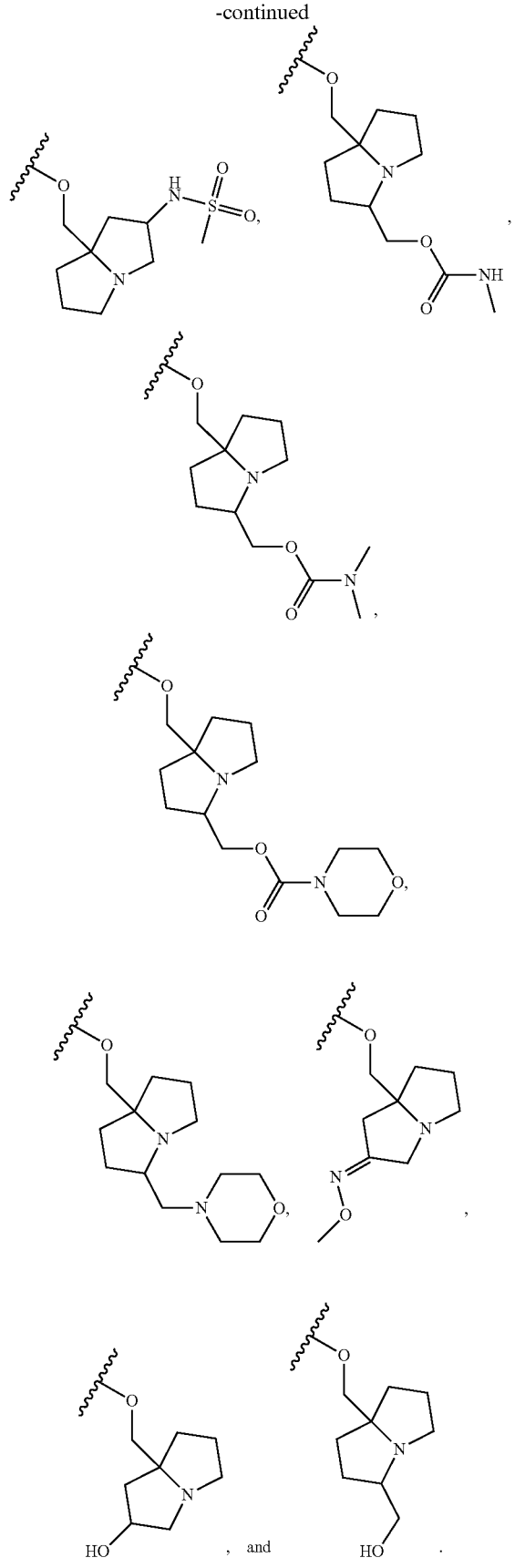
In some cases, Y—R² is selected from
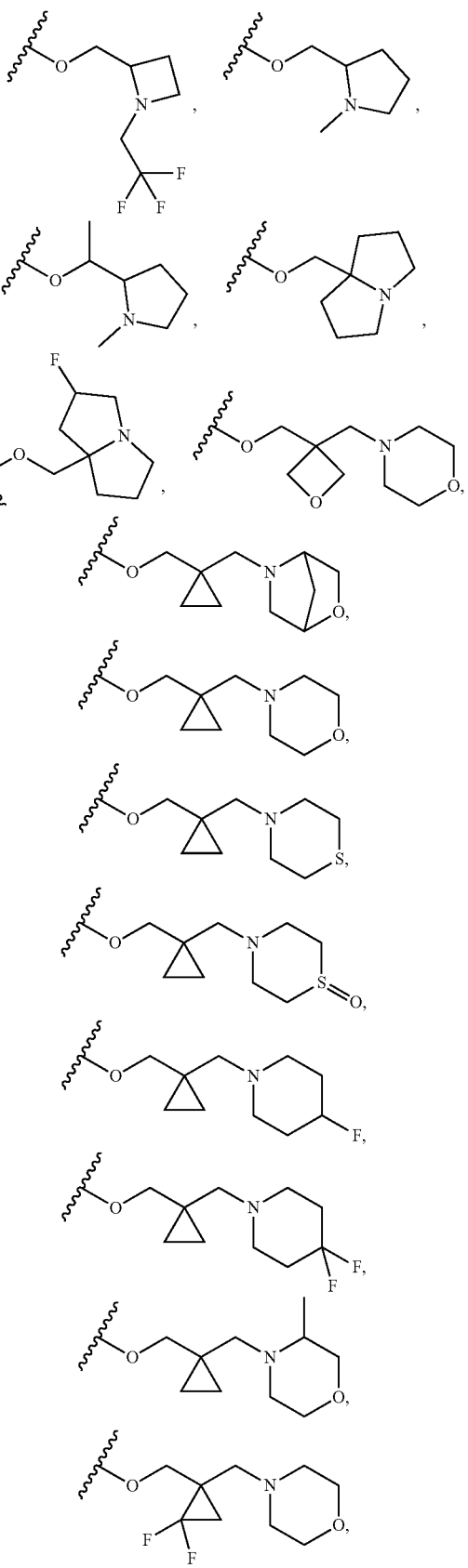

-continued

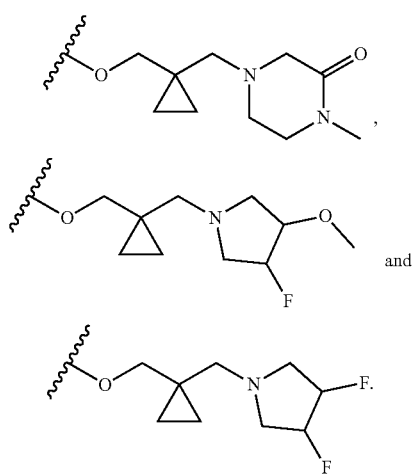

In some cases, Y—R² is selected from,

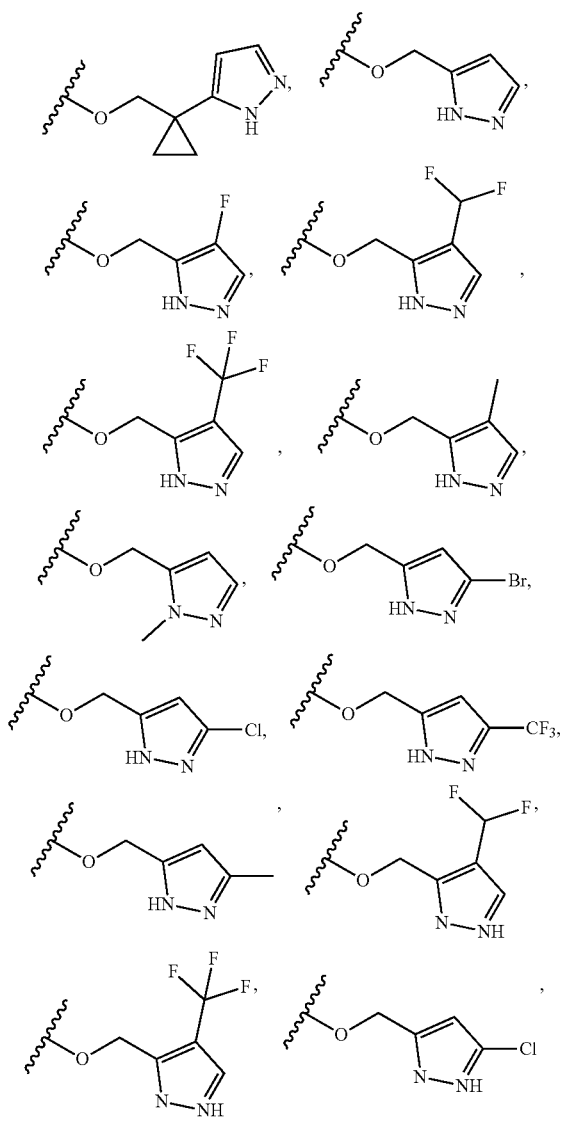

-continued

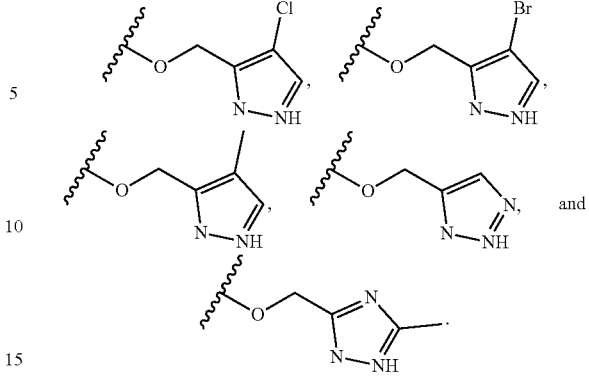

In some embodiments, for a compound or salt of Formula (I), L is independently selected from a $C_1$-$C_4$ alkylene optionally substituted with one or more substituents independently selected from hydroxy, $C_1$-$C_4$ hydroxyalkyl and $C_1$-$C_4$ alkyl. In some cases, L is independently selected from a $C_1$-$C_4$ alkylene optionally substituted with one or more substituents independently selected from $C_1$-$C_4$ alkyl. In some cases, L is selected from $C_1$-$C_4$ alkylene. In some cases, L is selected from $C_1$-$C_2$ alkylene. In some cases, L is

In some cases, L is

In some embodiments, for a compound or salt of Formula (I), each L is independently selected from an optionally substituted $C_1$-$C_4$ alkylene; and wherein optionally two substituents on the same carbon atom of L come together to form a $C_3$-$C_6$ carbocycle, wherein the $C_3$-$C_6$ carbocycle is optionally substituted with one or more substituents selected from halogen, —OH, —NO₂, =O, =S, —CN, $C_{1-6}$ aminoalkyl, $C_{1-6}$ alkoxy, $C_{1-6}$ hydroxyalkyl, $C_{1-6}$ haloalkyl. In some cases, the optional substituents of L are selected from $C_1$-$C_4$ hydroxyalkyl, $C_1$-$C_4$ alkyl, $C_3$-$C_6$ carbocycle; and wherein optionally two substituents on the same carbon atom of L come together to form a $C_3$-$C_6$ carbocycle or 3- to 8-membered heterocycle wherein the $C_3$-$C_6$ carbocycle and 3- to 8-membered heterocycle are optionally substituted with one or more substituents selected from halogen and $C_{1-6}$ haloalkyl.

In some embodiments, for a compound or salt of Formula (I), each L is independently selected from a substituted $C_1$-$C_4$ alkylene, wherein two substituents on the same carbon atom of L come together to form a $C_3$-$C_6$ carbocycle. In some cases, the $C_3$-$C_6$ carbocycle is optionally substituted with one or more substituents selected from halogen, —OH, —NO₂, =O, =S, —CN, $C_{1-6}$ aminoalkyl, $C_{1-6}$ alkoxy, $C_{1-6}$ hydroxyalkyl, $C_{1-6}$ haloalkyl.

In some embodiments, for a compound or salt of Formula (I), each L is independently selected from a substituted $C_1$-$C_4$ alkylene, and two substituents on the same carbon atom of L come together to form a $C_3$-$C_6$ carbocycle. In some cases, each L is independently selected from a substituted $C_3$ alkylene, and wherein two substituents on the same carbon atom of L come together to form a $C_3$ carbocycle. In some cases, each L is independently selected from

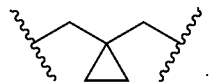 [SMILES: *CC1(C*)CC1]

In some embodiments, for a compound or salt of Formula (I), $R^2$ is selected from -L-heterocycle, wherein the heterocycle portion of -L-heterocycle is optionally substituted with one or more $R^6$. In some cases, the heterocycle is a saturated heterocycle. In some cases, the heterocycle has at least one nitrogen atom and at least one sulfur atom. In some cases, the heterocycle has at least one nitrogen atom. In some cases, the heterocycle has at least one sulfur atom.

In some embodiments, for a compound or salt of Formula (I), $R^2$ is selected from

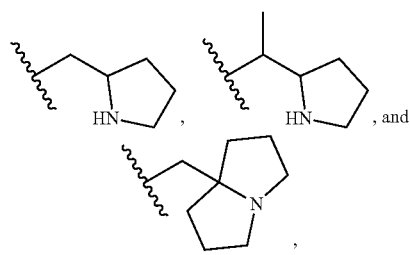

wherein the heterocycle portion is optionally substituted with one or more $R^6$.

In some embodiments, for a compound or salt of Formula (I), Y—$R^2$ is selected from

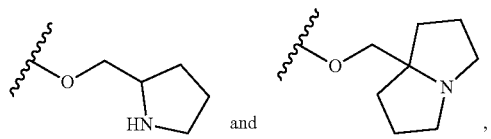 [SMILES: *OCC1CCCN1 ; *OCC12CCCN1CCC2]

wherein the heterocycle portion is optionally substituted with one or more $R^6$.

In some embodiments, for a compound or salt of Formula (I), Y—$R^2$ is selected from

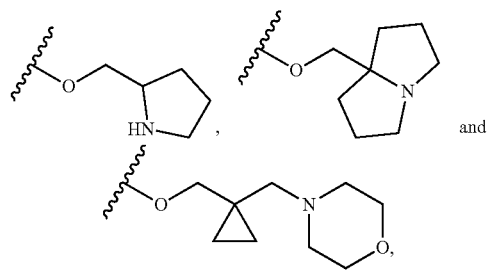

wherein the heterocycle portion is optionally substituted with one or more $R^6$.

In some embodiments, for a compound or salt of Formula (I), Y—$R^2$ is selected from

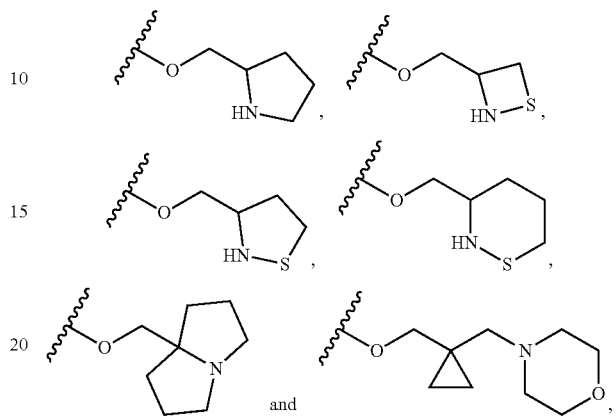

wherein the heterocycle portion is optionally substituted with one or more $R^6$.

In some embodiments, for a compound or salt of Formula (I), $R^2$ is selected from -L-saturated heterocycle, wherein the saturated heterocycle portion of the -L-saturated heterocycle is optionally substituted with one or more $R^6$, and contains one nitrogen atom and one sulfur atom. In some cases, Y—$R^2$ is selected from

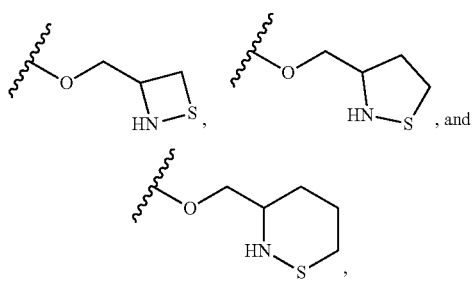

wherein the heterocycle portion is optionally substituted with one or more $R^6$. In some cases, Y—$R^2$ is selected from

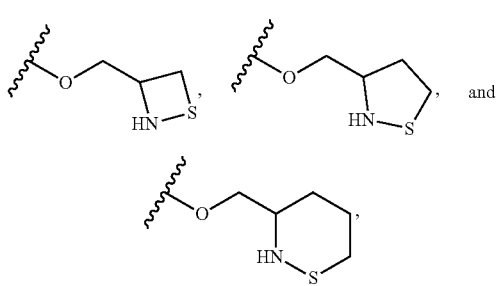

wherein the heterocycle portion is optionally substituted with one or more substituents selected from $C_1$-$C_3$ alkyl and oxo. In some cases, Y—$R^2$ is selected from

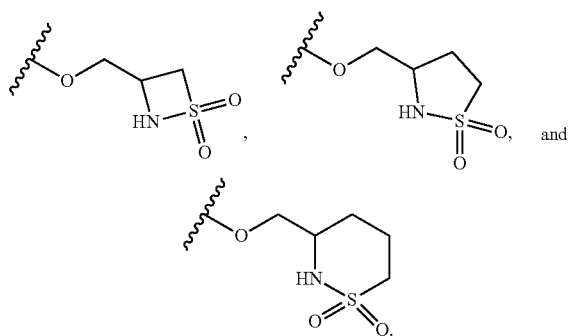

In some cases, Y—R² is selected from

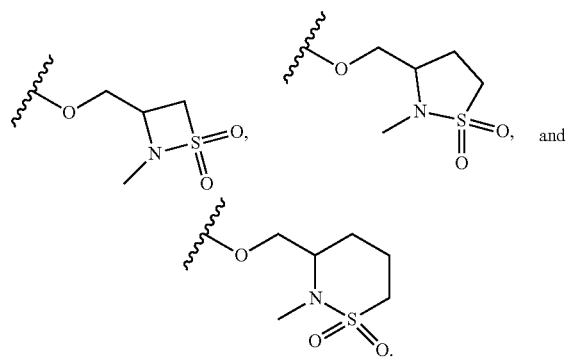

In some embodiments, for a compound or salt of Formula (I), Y is a bond. In some cases, R² is selected from an optionally substituted heteroaryl and optionally substituted aryl. In some cases, R² is selected from an optionally substituted heteroaryl. In some cases, the heteroaryl has at least one nitrogen atom. In some cases, the heteroaryl has at least two nitrogen atoms. In some cases, the heteroaryl only contain nitrogen atom(s). In some cases, the heteroaryl is a 6-membered heteroaryl. In some cases, the heteroaryl is a 5-membered heteroaryl. In some cases, the heteroaryl is selected from

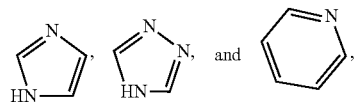

each of which is optionally substituted. In some cases, the heteroaryl is selected from

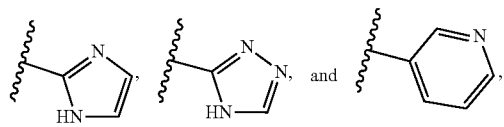

each of which is optionally substituted. In some cases, R² is selected from an optionally substituted aryl. In some cases, the aryl is a phenyl. In some cases, the heteroaryl is optionally substituted with one or more R⁶, wherein each R⁶ is selected from halogen, hydroxy, $C_1$-$C_3$ hydroxyalkyl, $C_1$-$C_3$ alkyl, $C_1$-$C_3$ haloalkyl, $C_1$-$C_3$ alkoxy, cyano, —$CH_2$ heterocycle, —$C_1$-$C_3$ alkyl-N(R⁵)₂, and —C(O)N(R⁵)₂. In some cases, R⁶ is selected from $C_1$-$C_3$ alkyl, —$CH_2$ heterocycle, and —C(O)N(R⁵)₂. In some cases, the aryl is optionally substituted with one or more R⁷. In some cases, Y—R² is selected from

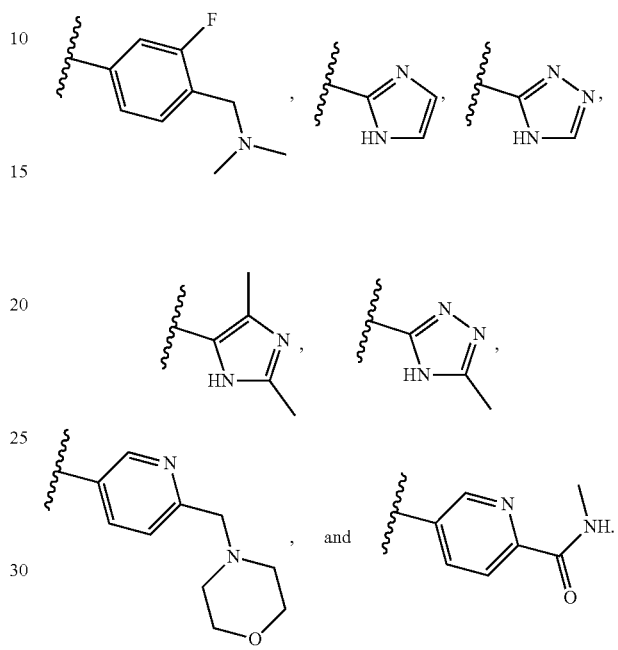

In some cases, Y—R² is selected from

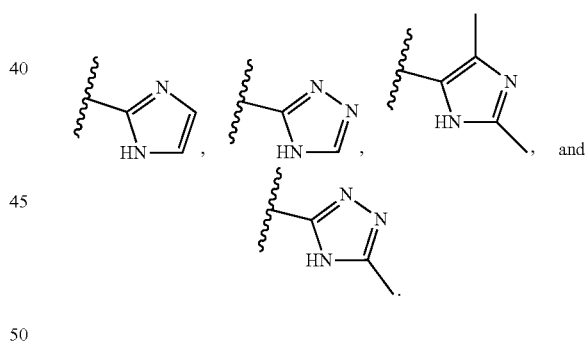

In some embodiments, for a compound or salt of Formula (I), Y is —O— and R² is selected from L-5-membered heteroaryl. In some cases, the heteroaryl has at least 1 nitrogen atom. In some cases, the heteroaryl has at least two nitrogen atoms. In some cases, the heteroaryl has 3 nitrogen atoms. In some cases, L is selected from an optionally substituted $C_1$-$C_4$ alkylene. In some cases, L is independently selected from a $C_1$-$C_4$ alkylene optionally substituted; and wherein optionally two substituents on the same carbon atom of L come together to form a $C_3$-$C_6$ carbocycle or 3- to 8-membered heterocycle wherein the $C_3$-$C_6$ carbocycle and 3- to 8-membered heterocycle are each optionally substituted with one or more substituents selected from halogen, —OH, —NO₂, =O, =S, —CN, $C_{1-6}$ aminoalkyl, $C_{1-6}$ alkoxy, $C_{1-6}$ hydroxyalkyl, $C_{1-6}$ haloalkyl. In some cases, L is selected from

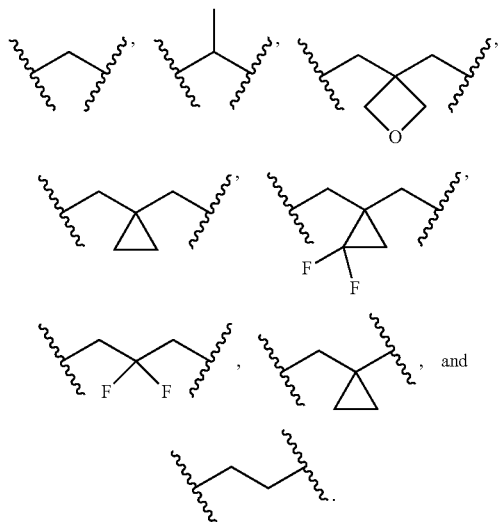

In some cases, L is selected from

In some cases, the heteroaryl is optionally substituted with one or more R⁷. In some cases, each R⁷ is selected from halogen, $C_1$-$C_4$ alkyl, and $C_1$-$C_4$ haloalkyl. In some cases, Y—R² is selected from

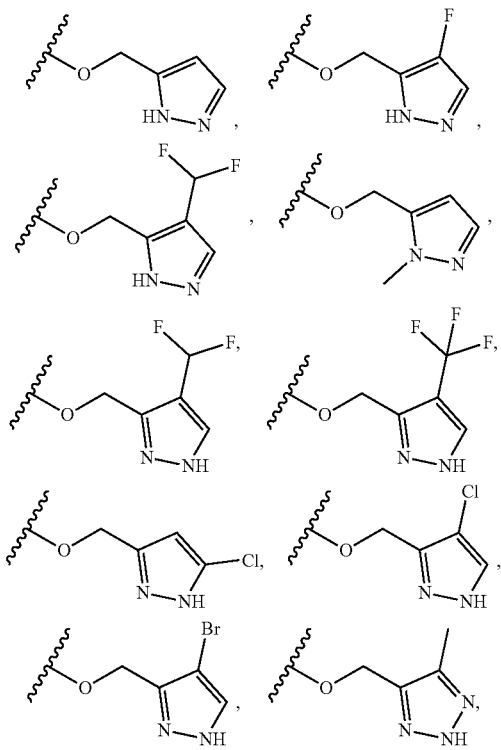

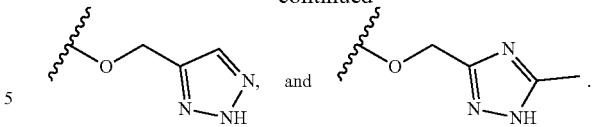

In some embodiments, for a compound or salt of Formula (I), each R⁶ is independently selected from halogen, —OH, $C_1$-$C_3$ hydroxyalkyl, $C_1$-$C_3$ alkyl, $C_1$-$C_3$ haloalkyl, $C_1$-$C_3$ alkoxy, —CN, $C_1$-$C_3$ aminoalkyl, -Q-phenyl, -Q-phenylSO₂F, —NHC(O)phenyl, —NHC(O)phenylSO₂F, $C_1$-$C_3$ alkyl substituted pyrazolyl, —N(R⁵)₂, ($C_1$-$C_3$ alkoxy) $C_1$-$C_3$ alkyl-, ($C_1$-$C_3$ alkyl)C(=O), oxo, ($C_1$-$C_3$ haloalkyl) C(=O)—, —SO₂F, ($C_1$-$C_3$ alkoxy)$C_1$-$C_3$ alkoxy, —CH₂OC (O)N(R⁵)₂, —CH₂NHC(O)OC₁-C₆ alkyl, —CH₂NHC(O)N (R⁵)₂, —CH₂NHC(O)C₁-C₆ alkyl, —CH₂(pyrazolyl), —CH₂NHSO₂C₁-C₆ alkyl, —CH₂O C(O)heterocycle, —OC(O)N(R⁵)₂, —OC(O)NH($C_1$-$C_3$ alkyl)O($C_1$-$C_3$ alkyl), —OC(O)NH($C_1$-$C_3$ alkyl)O($C_1$-$C_3$ alkyl)phenyl($C_1$-$C_3$ alkyl)N(CH₃)₂, —OC(O)NH($C_1$-$C_3$ alkyl)O($C_1$-$C_3$ alkyl) phenyl, —OC(O)heterocycle, and —CH₂ heterocycle, wherein the phenyl of —NHC(O)phenyl and —OC(O)NH ($C_1$-$C_3$ alkyl)($C_1$-$C_3$ alkyl)phenyl are each optionally substituted with —C(O)H and OH, and wherein the heterocycle of —CH₂ heterocyclyl is optionally substituted with oxo.

In some embodiments, for a compound or salt of Formula (I), each R⁶ is independently selected from halogen, —OH, $C_1$-$C_3$ hydroxyalkyl, $C_1$-$C_3$ alkyl, $C_1$-$C_3$ haloalkyl, $C_1$-$C_3$ alkoxy, —CN, and $C_1$-$C_3$ aminoalkyl. In some cases, each R⁶ is independently selected from halogen, $C_1$-$C_3$ alkyl, and $C_1$-$C_3$ haloalkyl.

In some embodiments, for a compound or salt of Formula (I), each R⁶ is independently selected from halogen, —OH, $C_1$-$C_3$ hydroxyalkyl, $C_1$-$C_3$ alkyl, $C_1$-$C_3$ aminoalkyl, $C_1$-$C_3$ haloalkyl, $C_1$-$C_3$ alkoxy, —N(R⁵)₂, and oxo. In some cases, each R⁶ is independently selected from —OH, $C_1$-$C_3$ hydroxyalkyl, $C_1$-$C_3$ alkyl, $C_1$-$C_3$ aminoalkyl, $C_1$-$C_3$ alkoxy, and —N(R⁵)₂. In some cases, each R⁶ is independently selected from $C_1$-$C_3$ alkyl, $C_1$-$C_3$ alkoxy, and —N(R⁵)₂. In some cases, each R⁶ is independently selected from halogen, hydroxy, $C_1$-$C_3$ alkyl, $C_1$-$C_3$ haloalkyl, —N(R⁵)S(O)₂(R⁵), —OC(O)N(R⁵)₂, =CH₂, oxo, =NO—$C_1$-$C_3$ alkyl, —CH₂O C(O)heterocycle, —CH₂ heterocycle, —CH₂OC (O)N(R⁵)₂, and —O—$C_1$-$C_3$ alkyl, wherein the alkyl of —O—$C_1$-$C_3$ alkyl is optionally substituted with substituents selected from heterocycle, oxo, and hydroxy; and wherein each R⁷ is selected from $C_1$-$C_3$ alkyl, halogen and $C_1$-$C_3$ haloalkyl.

In some embodiments, for a compound or salt of Formula (I), R⁶ is selected from halogen, —OH, $C_1$-$C_3$ hydroxyalkyl, $C_1$-$C_3$ alkyl, $C_1$-$C_3$ haloalkyl, $C_1$-$C_3$ alkoxy, —CN, and $C_1$-$C_3$ aminoalkyl. In some cases, R⁶ is selected from halogen and $C_1$-$C_3$ alkyl. In some cases, R⁶ is halogen. In some cases, R⁶ is $C_1$-$C_3$ alkyl. In some cases, R⁶ is selected from halogen and $C_1$-$C_3$ alkyl. In some cases, R⁶ is selected from methyl and fluorine.

In some embodiments, for a compound or salt of Formula (I), R² is selected from

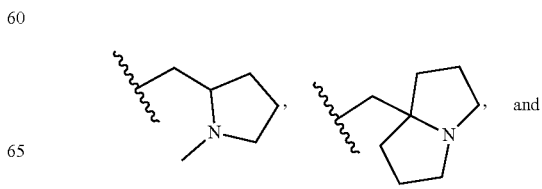

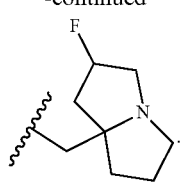

In some embodiments, for a compound or salt of Formula (I), Y—R² is selected from

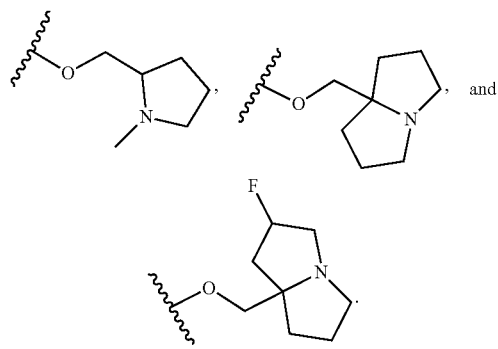

and

In some embodiments, for a compound or salt of Formula (I), Y—R² is selected from

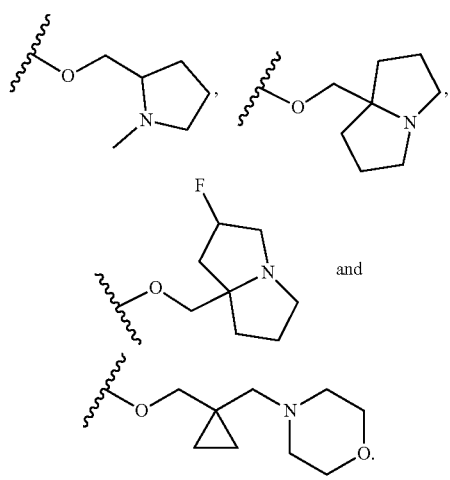

and

In some embodiments, for a compound or salt of Formula (I), Y—R² is

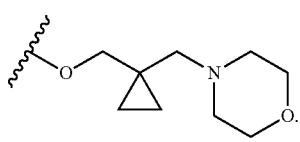 [SMILES: *OCC1(CN2CCOCC2)CC1]

In some embodiments, for a compound or salt of Formula (I), L is selected from unsubstituted $C_1$-$C_4$ alkylene.

In some embodiments, for a compound or salt of Formula (I), Y—R² is selected from

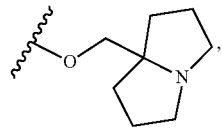 [SMILES: *OCC12CCCN1CCC2]

wherein the heterocycle portion is optionally substituted with one or more $R^6$.

In some embodiments, for a compound or salt of Formula (I), $R^6$ of R² is independently selected at each occurrence from halogen, hydroxy, $C_1$-$C_3$ hydroxyalkyl, $C_1$-$C_3$ alkyl, $C_1$-$C_3$ haloalkyl, $C_1$-$C_3$ alkoxy, cyano, and $C_1$-$C_3$ aminoalkyl.

In some embodiments, for a compound or salt of Formula (I), $R^6$ of R² is independently selected at each occurrence from $C_1$-$C_3$ alkyl and halogen.

In some embodiments, for a compound or salt of Formula (I), Y—R² is selected from

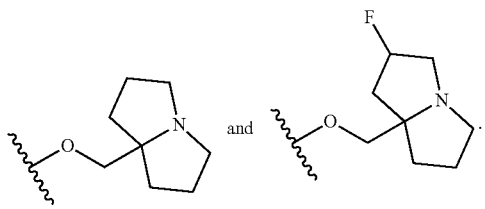 [SMILES: *OCC12CCCN1CCC2 ; *OCC12CCCN1CC(F)C2]

In some embodiments, for a compound or salt of Formula (I), R¹ is selected from an optionally substituted 5- to 12-membered heterocycle. In some cases, the heterocycle of R¹ is selected from a 5- to 12-membered heterocycle, 6- to 12-membered heterocycle, 7- to 12-membered heterocycle, and 8- to 12-membered heterocycle. In some cases, the heterocycle of R¹ is selected from a 5- to 11-membered heterocycle, 5- to 10-membered heterocycle, 5- to 9-membered heterocycle, and 5- to 8-membered heterocycle. In some cases, the heterocycle of R¹ is selected from a 6- to 11-membered heterocycle, 6- to 10-membered heterocycle, 6- to 9-membered heterocycle, and 6- to 8-membered heterocycle. In some cases, the heterocycle of R¹ is selected from a 7- to 11-membered heterocycle, 7- to 10-membered heterocycle, 7- to 9-membered heterocycle, and 7- to 8-membered heterocycle. In some cases, the heterocycle of R¹ is selected from a 5- to 6-membered heterocycle and 5- to 9-membered heterocycle. In some cases, the heterocycle of R¹ is selected from an 8- to 9-membered heterocycle. In some cases, R¹ is selected from an optionally substituted 5- to 7-membered heterocycle. In some cases, R¹ is selected from an optionally substituted 6- to 7-membered heterocycle. In some cases, R¹ is selected from an optionally substituted 7-membered heterocycle. In cases, the 5- to 12-membered heterocycle of R¹ is a bridged heterocycle. In cases, the 5- to 12-membered heterocycle of R¹ is not a bridged heterocycle. In some cases, the heterocycle of R¹ is saturated. In some cases, the heterocycle of R¹ is unsaturated. In some cases, the heterocycle of R¹ is an unbridged heterocycle. The heterocycle of R¹ is optionally substituted as described elsewhere herein.

In some embodiments, for a compound or salt of Formula (I), the heterocycle of R¹ contains at most 1 nitrogen atom. In some embodiments, the heterocycle of R¹ contains at most 1 heteroatom atom. In some cases, the heteroatom is selected from nitrogen, oxygen, and sulfur. In some embodiments, the heterocycle of $R^1$ contains at most 2 heteroatom atoms. In some cases, the heterocycle of $R^1$ contains 1 nitrogen atom. In some cases, the heterocycle of $R^1$ contains only 1 nitrogen atom. In some cases, the heterocycle of $R^1$ contains only 1 nitrogen atom and no other heteroatoms.

In some embodiments, for a compound or salt of Formula (I), $R^1$ is selected from 5- to 12-membered heterocycle, wherein the 5- to 12-membered heterocycle is optionally substituted with one or more substituents independently selected from halogen, —OH, —N($R^{20}$)$_2$, —NO$_2$, =O, —CN, $C_{1-6}$ aminoalkyl, $C_{1-6}$ alkoxy, $C_{1-6}$ hydroxyalkyl, and $C_{1-6}$ haloalkyl. In some cases, the 5- to 12-membered heterocycle of $R^1$ is an unsaturated heterocycle. In some cases, the 5- to 12-membered heterocycle of $R^1$ is selected from a saturated heterocycle and unsaturated heterocycle. In some cases, the 5- to 12-membered heterocycle of $R^1$ is a saturated heterocycle. In some cases, the 5- to 12-membered heterocycle of $R^1$ is an unsaturated heterocycle.

In some embodiments, for a compound or salt of Formula (I), $R^1$ is selected from 5- to 15-membered heterocycle, wherein the 5- to 15-membered heterocycle is optionally substituted. In some cases, $R^1$ is selected from an optionally substituted 6- to 15-membered heterocycle. In some cases, the heterocycle is a spiro heterocycle. In some cases, the heterocycle is a fused heterocycle. In some cases, the heterocycle is a bridged heterocycle. In some cases, the heterocycle is an unsaturated heterocycle.

In some embodiments, for a compound or salt of Formula (I), $R^1$ is a 6- to 12-membered fused heterocycle, which is optionally substituted.

In some embodiments, for a compound or salt of Formula (I), $R^1$ is a 6- to 12-membered spiroheterocycle, which is optionally substituted. In some cases, $R^1$ is selected from optionally substituted 7- to 8-membered spiroheterocycle.

In some embodiments, for a compound or salt of Formula (I), the heterocycle of $R^1$ is a 5- to 12-membered heterocycle, 6- to 12-membered heterocycle, 7- to 12-membered heterocycle, or 8- to 12-membered heterocycle. In some cases, the heterocycle of $R^1$ is a 5- to 11-membered heterocycle, 5- to 10-membered heterocycle, 5- to 9-membered heterocycle, or 5- to 8-membered heterocycle. In some cases, the heterocycle of $R^1$ is a 6- to 11-membered heterocycle, 6- to 10-membered heterocycle, 6- to 9-membered heterocycle, or 6- to 8-membered heterocycle. In some cases, the heterocycle of $R^1$ is a 7- to 11-membered heterocycle, 7- to 10-membered heterocycle, 7- to 9-membered heterocycle, or 7- to 8-membered heterocycle. In some cases, the heterocycle of $R^1$ is a 5- to 6-membered heterocycle or 5- to 9-membered heterocycle. In some cases, the heterocycle of $R^1$ is an 8- to 9-membered heterocycle. In some cases, the heterocycle of $R^1$ is saturated. The heterocycle is optionally substituted as described elsewhere herein.

In some embodiments, for a compound or salt of Formula (I), $R^1$ is a 5- to 12-membered monocyclic heterocycle. In some cases, the heterocycle of $R^1$ is a 5- to 12-membered monocyclic heterocycle, 6- to 12-membered monocyclic heterocycle, 7- to 12-membered monocyclic heterocycle, or 8- to 12-membered monocyclic heterocycle. In some cases, the heterocycle of $R^1$ is a 5- to 11-membered monocyclic heterocycle, 5- to 10-membered monocyclic heterocycle, 5- to 9-membered monocyclic heterocycle, or 5- to 8-membered monocyclic heterocycle. In some cases, the heterocycle of $R^1$ is a 6- to 11-membered monocyclic heterocycle, 6- to 10-membered monocyclic heterocycle, 6- to 9-membered monocyclic heterocycle, or 6- to 8-membered monocyclic heterocycle. In some cases, the heterocycle of $R^1$ is a monocyclic 7- to 11-membered heterocycle, 7- to 10-membered monocyclic heterocycle, 7- to 9-membered monocyclic heterocycle, or 7- to 8-membered monocyclic heterocycle. In some cases, the heterocycle of $R^1$ is a 5- to 6-membered monocyclic heterocycle or 5- to 9-membered monocyclic heterocycle. In some cases, the heterocycle of $R^1$ is an 8- to 9-membered monocyclic heterocycle. In some cases, the heterocycle of $R^1$ is saturated. The monocyclic heterocycle is optionally substituted as described elsewhere herein.

In some embodiments, for a compound or salt of Formula (I), $R^1$ is a bridged heterocycle. In some cases, the heterocycle of $R^1$ is a 5- to 12-membered bridged heterocycle, 6- to 12-membered bridged heterocycle, 7- to 12-membered bridged heterocycle, or 8- to 12-membered bridged heterocycle. In some cases, the heterocycle of $R^1$ is a 5- to 11-membered bridged heterocycle, 5- to 10-membered bridged heterocycle, 5- to 9-membered bridged heterocycle, or 5- to 8-membered bridged heterocycle. In some cases, the heterocycle of $R^1$ is a 6- to 11-membered bridged heterocycle, 6- to 10-membered bridged heterocycle, 6- to 9-membered bridged heterocycle, or 6- to 8-membered bridged heterocycle. In some cases, the heterocycle of $R^1$ is a bridged 7- to 11-membered heterocycle, 7- to 10-membered bridged heterocycle, 7- to 9-membered bridged heterocycle, or 7- to 8-membered bridged heterocycle. In some cases, the heterocycle of $R^1$ is a 5- to 6-membered bridged heterocycle or 5- to 9-membered bridged heterocycle. In some cases, the heterocycle of $R^1$ is an 8- to 9-membered bridged heterocycle. In some cases, the heterocycle of $R^1$ is saturated. In some cases, the bridged heterocycle is selected from

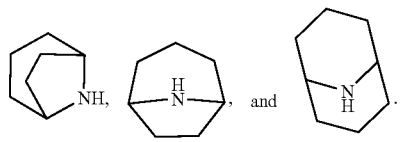

In some cases, the bridged heterocycle is selected from

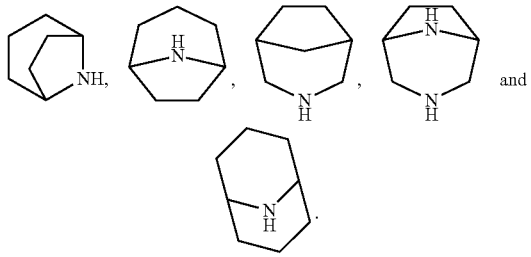

Each bridged heterocycle is optionally substituted as described elsewhere herein.

In some embodiments, for a compound or salt of Formula (I), $R^1$ is a spiro heterocycle. The spiro heterocycle of $R^1$ is a 7- to 12-membered spiro heterocycle, 7- to 12-membered spiro heterocycle, or 8- to 12-membered spiro heterocycle. In some cases, the spiro heterocycle of $R^1$ is a 7- to 11-membered spiro heterocycle, 7- to 10-membered spiro heterocycle, 7- to 9-membered spiro heterocycle, or 7- to 8-membered spiro heterocycle. In some cases, the spiro heterocycle of $R^1$ is a 7- to 11-membered spiro heterocycle, 7- to 10-membered spiro heterocycle, 7- to 9-membered spiro heterocycle, or 7- to 8-membered spiro heterocycle. In some cases, the spiro heterocycle of $R^1$ is a 7- to 11-membered spiro heterocycle. In some cases, the spiro heterocycle of $R^1$ is a 7-membered spiro heterocycle. In some cases, the spiro heterocycle of $R^1$ is an 8-membered spiro heterocycle. In some cases, the spiro heterocycle of $R^1$ is a 9-membered spiro heterocycle. In some cases, the spiro heterocycle of $R^1$ is a 10-membered spiro heterocycle. In some cases, the spiro heterocycle of $R^1$ contains at most 1 nitrogen atom. In some cases, the spiro heterocycle of $R^1$ contains only 1 nitrogen atom. In some cases, the spiroheterocycle of $R^1$ contains at most 2 heteroatom atoms. In some cases, the spiro heterocycle of $R^1$ contains at least 2 heteroatom atoms. In some cases, the spiro heterocycle of $R^1$ contains at least 3 heteroatom atoms. In some cases, the heteroatom is selected from nitrogen, oxygen, and sulfur. In some cases, the spiroheterocycle of $R^1$ is bound to the Formula via the nitrogen atom. In some embodiments, the spiro heterocycle of $R^1$ is selected from

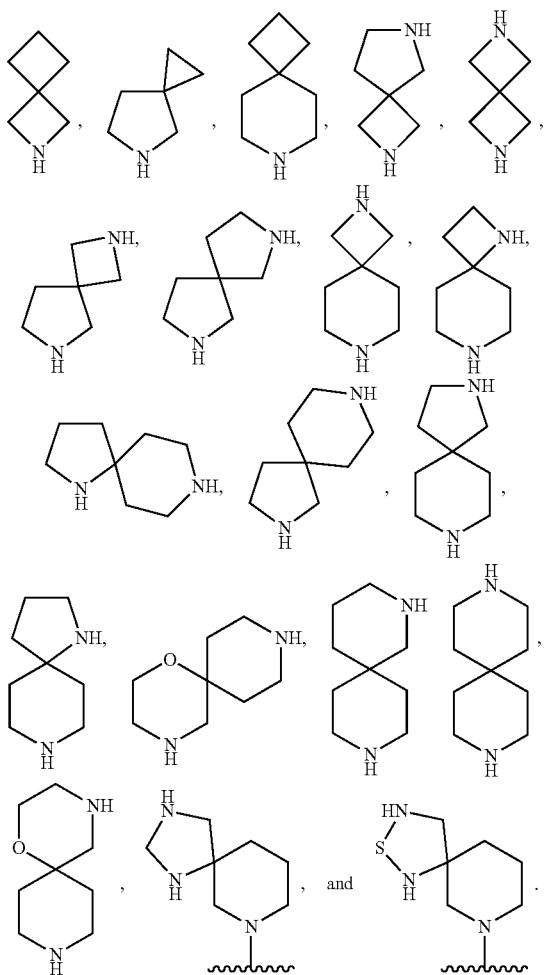

In some cases, the spiro heterocycle of $R^1$ is selected from

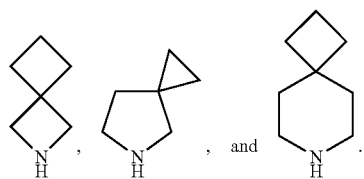

Each spiro heterocycle is optionally substituted as described elsewhere herein.

In some embodiments, for a compound or salt of Formula (I), $R^1$ is a fused heterocycle. In some cases, the fused heterocycle of $R^1$ is a 6- to 12-membered fused heterocycle, 6- to 12-membered fused heterocycle, 7- to 12-membered fused heterocycle, or 8- to 12-membered fused heterocycle. In some cases, the fused heterocycle of $R^1$ is a 6- to 11-membered fused heterocycle, 6- to 10-membered fused heterocycle, 6- to 9-membered fused heterocycle, or 6- to 8-membered fused heterocycle. In some cases, the fused heterocycle of $R^1$ is a 7- to 11-membered fused heterocycle, 7- to 10-membered fused heterocycle, 7- to 9-membered fused heterocycle, or 7- to 8-membered fused heterocycle. In some cases, the fused heterocycle of $R^1$ is an 8- to 11-membered fused heterocycle. In some cases, the fused heterocycle of $R^1$ is a 9-membered fused heterocycle. In some cases, the fused heterocycle of $R^1$ is a 10-membered fused heterocycle. In some cases, the fused heterocycle of $R^1$ is an 11-membered fused heterocycle. In some cases, the fused heterocycle of $R^1$ is a 6-membered fused heterocycle. In some cases, the fused heterocycle of $R^1$ is a 7-membered fused heterocycle. In some cases, the fused heterocycle of $R^1$ is a 10-membered fused heterocycle. In some cases, the fused heterocycle is selected from

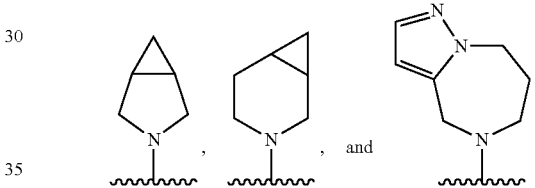

Each fused heterocycle is optionally substituted as described elsewhere herein.

In some embodiments, for a compound or salt of Formula (I), $R^1$ is selected from an optionally substituted 8- to 10-membered fused heterocycle. In some cases, the 8- to 10-membered fused heterocycle is a bicyclic heterocycle. In some cases, the 8- to 10-membered fused heterocycle is a saturated heterocycle. In some cases, the 8- to 10-membered fused heterocycle is an unsaturated heterocycle. In some cases, the 8- to 10-membered heterocycle is a non-aromatic heterocycle. In some cases, $R^1$ is selected from an optionally substituted 9-membered fused heterocycle. In some cases, $R^1$ is selected from an optionally substituted 10-membered fused heterocycle. In some cases, the 10-membered fused heterocycle is a bicyclic heterocycle. In some cases, the 10-membered fused heterocycle is a saturated heterocycle. In some cases, the 9-membered heterocycle is a non-aromatic heterocycle. In some cases, the 10-membered heterocycle is a non-aromatic heterocycle. In some cases, the fused heterocycle has one saturated ring and one aromatic ring. In some cases, the fused heterocycle has one saturated ring and one unsaturated ring. In some cases, the fused heterocycle has two saturated rings. In some cases, the 10-membered heterocycle contains at least 1 nitrogen atom. In some cases, the 10-membered heterocycle contains at least 2 nitrogen atoms. In some cases, the 10-membered heterocycle contains at least 3 nitrogen atoms. In some cases, the 9-membered heterocycle contains at least 1 nitrogen atom. In some cases, the 9-membered heterocycle contains at least 2 nitrogen atoms. In some cases, the 9-membered heterocycle contains at least 3 nitrogen atoms. In some cases, $R^1$ is selected from

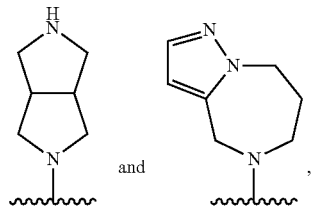 [SMILES: *N1CC2CNCC2C1 ; *N1CCCn2nccc2C1]

and each of which is optionally substituted with one or more substituents. In some cases, $R^1$ is

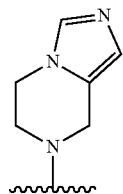

which is optionally substituted with one or more substituents. In some cases, $R^1$ is

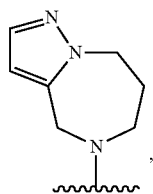

which is optionally substituted with one or more substituents. In some cases, the one or more optional substituents of $R^1$ are independently selected from halogen, —OH, —S(O)$_2$(R$^{20}$), —S(O)$_2$N(R$^{20}$)$_2$, —S(O)N(R$^{20}$)$_2$, —S(O)R$^{20}$(=NR$^{20}$), —C(=NR$^{20}$)N(R$^{20}$)$_2$, —C(O)N(R$^{20}$)$_2$, —C(O)NHOR$^{20}$, —N(R$^{20}$)$_2$, —C(O)R$^{20}$, —NO$_2$, =O, —CN, C$_{1-6}$ alkyl-N(R$^{20}$)$_2$, C$_{1-6}$ aminoalkyl, C$_{1-6}$ alkoxy, C$_{1-6}$ hydroxyalkyl, C$_{1-6}$ cyanoalkyl, C$_{1-6}$ haloalkyl, C$_{1-6}$ alkyl, C$_{2-6}$ alkynyl, and 5- to 12-membered heterocycle, wherein the 5- to 12-membered heterocycle are each optionally substituted independently with one or more $R^{1*}$. In some cases, the one or more optional substituents of $R^1$ are independently selected from halogen, —OH, —S(O)$_2$(R$^{20}$), —S(O)$_2$N(R$^{20}$)$_2$, —S(O)N(R$^{20}$)$_2$, —S(O)R$^{20}$(=NR$^{20}$), —C(O)N(R$^{20}$)$_2$, —C(O)NHOR$^{20}$, —N(R$^{20}$)$_2$, —C(O)R$^{20}$, —NO$_2$, =O, —CN, C$_{1-6}$ alkyl-N(R$^{20}$)$_2$, C$_{1-6}$ aminoalkyl, C$_{1-6}$ alkoxy, C$_{1-6}$ hydroxyalkyl, C$_{1-6}$ cyanoalkyl, C$_{1-6}$ haloalkyl, C$_{1-6}$ alkyl, and C$_{2-6}$ alkynyl. In some cases, the optional one or more substituents are independently selected from halogen, =O, —OH, —CN, —NHCN, —S(O)$_2$(R$^{20}$), —S(O)$_2$N(R$^{20}$)$_2$, —S(O)N(R$^{20}$)$_2$, —S(O)R$^{20}$(=NR$^{20}$), —C(O)R$^{20}$, —C(O)N(R$^{20}$)$_2$, —C(O)NR$^{20}$OR$^{20}$, C$_{1-6}$ alkyl-N(R$^{20}$)$_2$, C$_{1-6}$ aminoalkyl, C$_{1-6}$ hydroxyalkyl, C$_{1-6}$ cyanoalkyl, and C$_{1-6}$ alkyl. In some cases, the optional one or more substituents are independently selected from halogen, =O, C$_{1-6}$ alkyl-N(R$^{20}$)$_2$, —S(O)$_2$(R$^{20}$), —S(O)N(R$^{20}$)$_2$, —S(O)R$^{20}$(=NR$^{20}$), —C(O)R$^{20}$, —C(O)N(R$^{20}$)$_2$, and —C(O)NR$^{20}$OR$^{20}$. In some cases, the optional one or more substituents are independently selected from halogen, =O, —S(O)$_2$(R$^{20}$), —S(O)N(R$^{20}$)$_2$, —S(O)R$^{20}$(=NR$^{20}$), —C(O)R$^{20}$, —C(O)N(R$^{20}$)$_2$, and —C(O)NR$^{20}$OR$^{20}$. In some cases, the optional one or more substituents are independently selected from —C(O)R$^{20}$, —C(O)N(R$^{20}$)$_2$, and —C(O)NR$^{20}$OR$^{20}$. In some cases, the optional one or more substituents are independently selected from —S(O)$_2$(R$^{20}$), —S(O)$_2$N(R$^{20}$)$_2$, —S(O)N(R$^{20}$)$_2$, —S(O)R$^{20}$(=NR$^{20}$). In some cases, the optional one or more substituents are independently selected from —S(O)N(R$^{20}$)$_2$. In some cases, the optional one or more substituents are independently selected from S(O)$_2$(R$^{20}$). In some cases, the optional one or more substituents are independently selected from S(O)R$^{20}$(=NR$^{20}$). In some cases, the optional one or more substituents are independently selected from —C(O)R$^{20}$. In some cases, the optional one or more substituents are independently selected from —C(O)N(R$^{20}$)$_2$. In some cases, the optional one or more substituents are independently selected from —C(O)NR$^{20}$OR$^{20}$. In some cases, $R^1$ is selected from

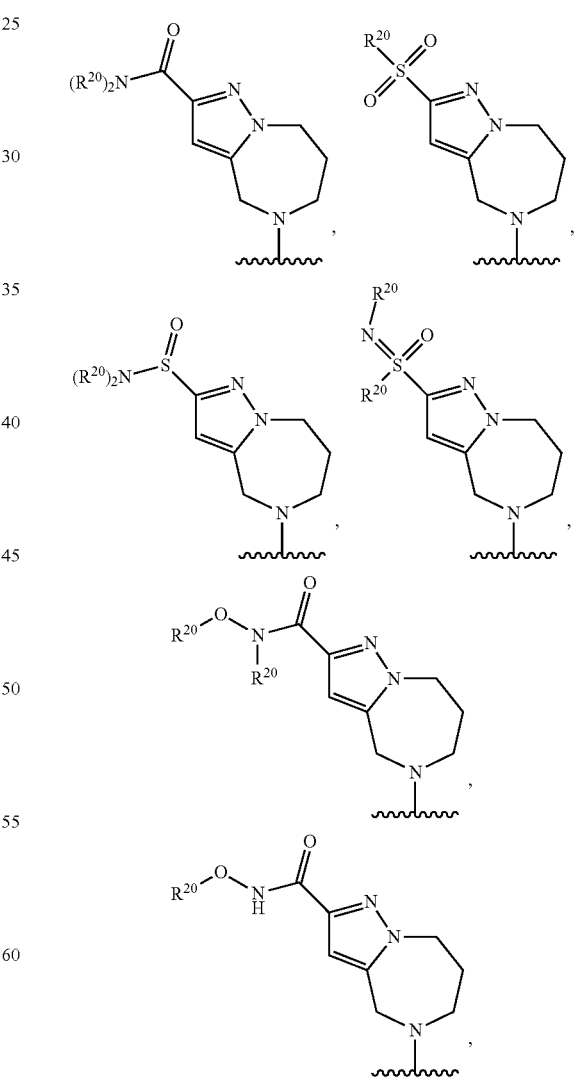

-continued

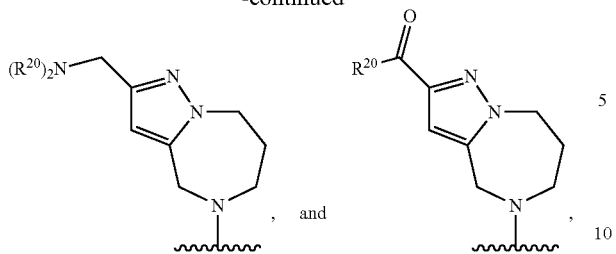

each of which is further optionally substituted. In some cases, the further one or more optional substituents are selected from halogen, —OH, =O, —CN, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, and $C_{2-6}$ alkynyl. In some cases, the further one or more optional substituents are selected from halogen, —CN, $C_2$ alkenyl, and $C_{1-6}$ alkyl. In some cases, the further one or more optional substituents are selected from halogen, and $C_{1-6}$ alkyl. In some cases, the further one or more optional substituents are selected from halogen. In some cases, each $R^{20}$ is independently selected from hydrogen; and $C_{1-6}$ alkyl, $C_{3-12}$ carbocycle, and 3- to 12-membered heterocycle. In some cases, each $R^{20}$ is independently selected from hydrogen; and $C_{1-6}$ alkyl, and 3- to 12-membered heterocycle. In some cases, each $R^{20}$ is independently selected from hydrogen; and $C_{1-6}$ alkyl, and 3- to 12-membered saturated heterocycle. In some cases, each $R^{20}$ is independently selected from 5- to 6-membered saturated heterocycle. In some cases, the heterocycle of $R^{20}$ has at least one nitrogen atom. In some cases, the heterocycle of $R^{20}$ has at least one sulfur atom. In some cases, the heterocycle of $R^{20}$ has at least one oxygen atom. In some cases, the heterocycle of $R^{20}$ contains only 1 heteroatom. In some cases, the heterocycle of $R^{20}$ has at least two heteroatoms. In some cases, the heterocycle of $R^{20}$ contains only 2 heteroatoms. In some cases, the optional one or more substituents of $R^1$ are independently selected from halogen, —CN, $C_2$ alkenyl,

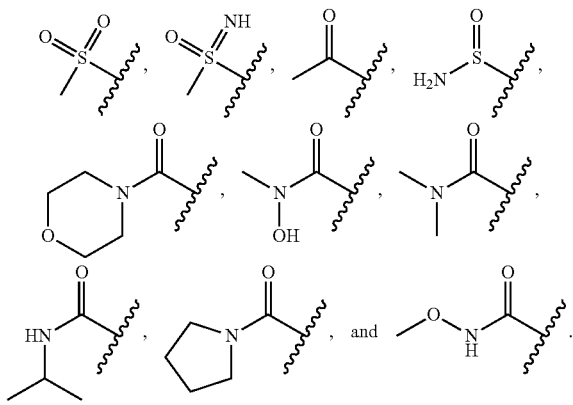

In some cases, the optional one or more substituents of $R^1$ are independently selected from halogen,

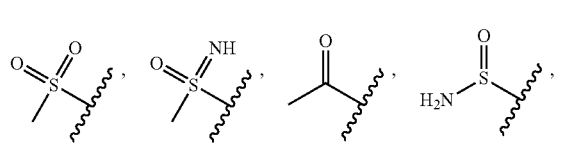

-continued

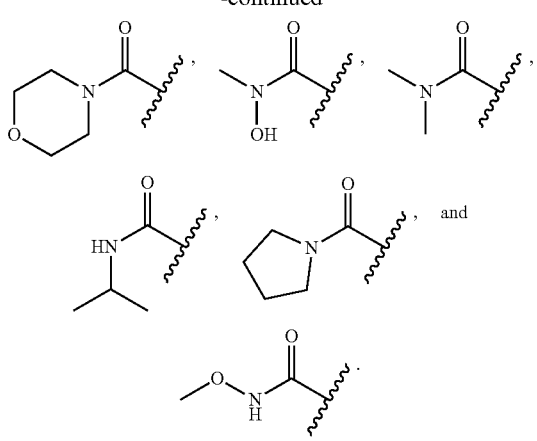

In some cases the optional one or more substituents of $R^1$ are independently selected from

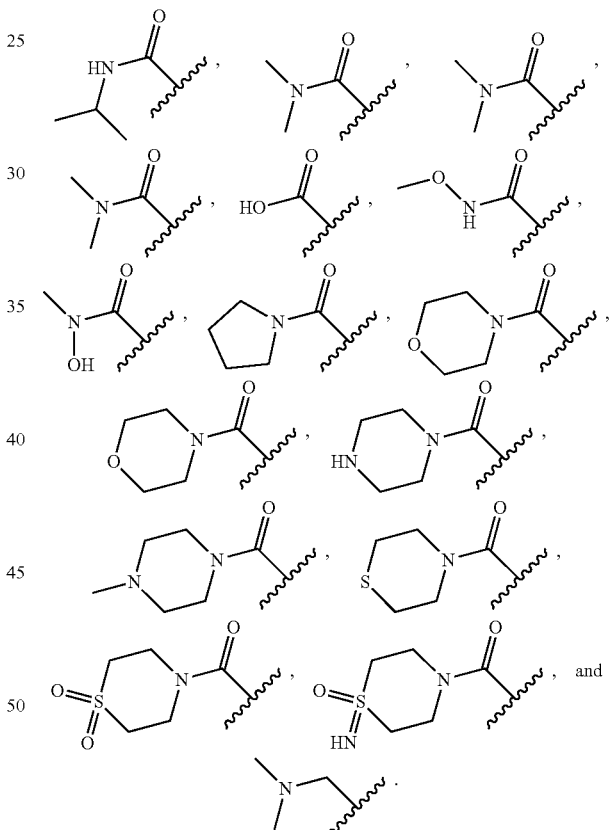

In some cases the optional one or more substituents of $R^1$ are independently selected from halogen,

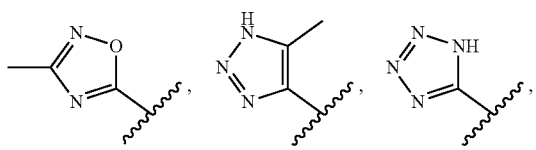

81
-continued
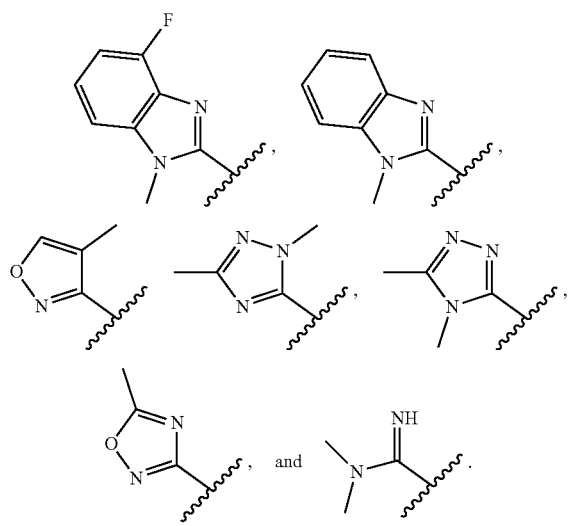
In some cases, R¹ is selected from
82
-continued
In some cases, R¹ is selected from

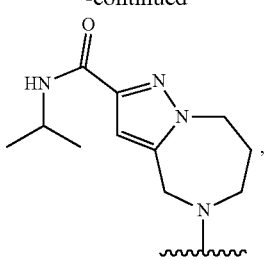
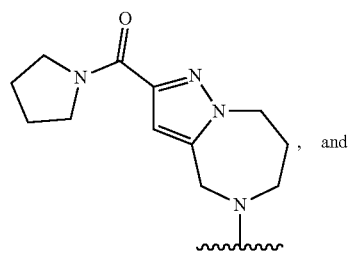
, and
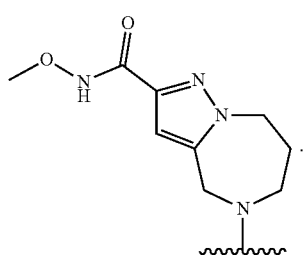
.
In some cases, R¹ is selected from
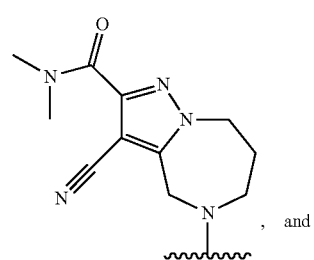
, and
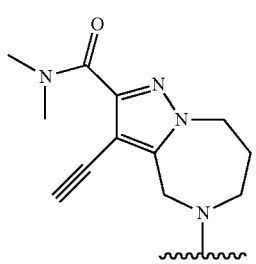
.
In some cases, R¹ is selected from
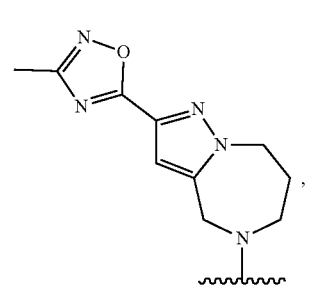
,
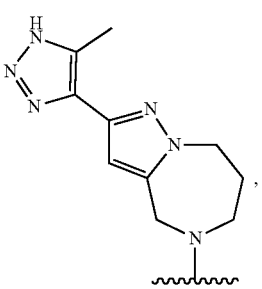
,
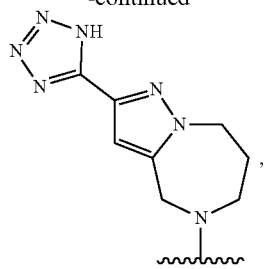
,
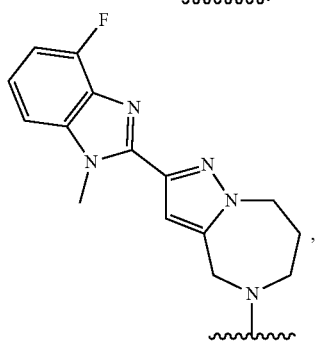
,
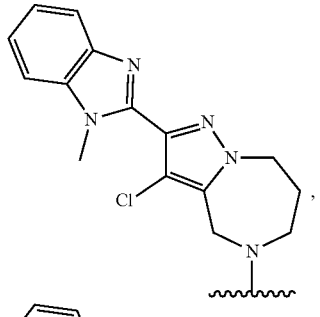
,
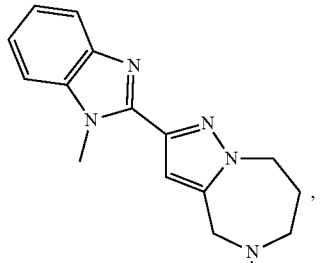
,
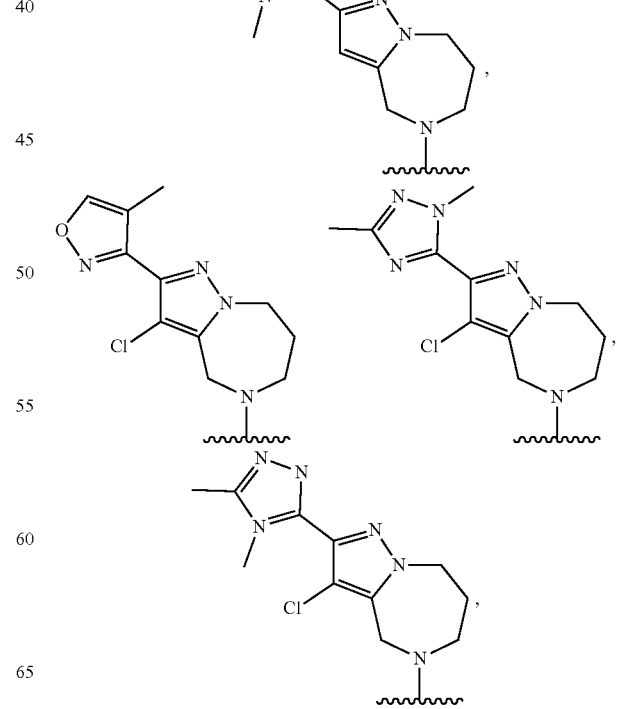

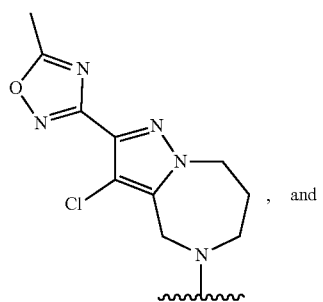, and

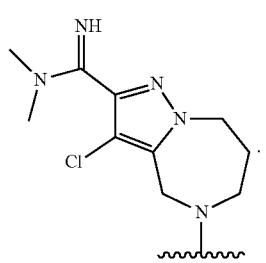

In some cases, the optional one or more substituents of $R^1$ are independently selected from halogen, and $C_{1-6}$ alkyl-N $(R^{20})_2$. In some cases, the optional one or more substituents of $R^1$ are independently selected from halogen,

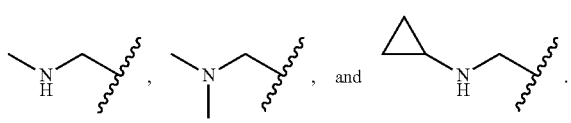

In some cases, $R^1$ is selected from

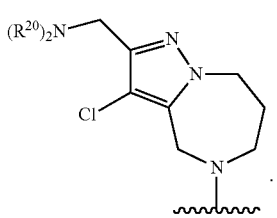

In some cases, each $R^{20}$ is independently selected from hydrogen, $C_{1-6}$ alkyl, and $C_{3-6}$ carbocycle. In some cases, $R^1$ is selected

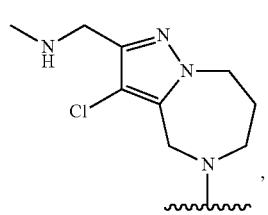, and

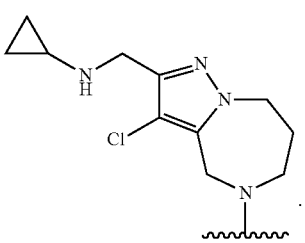

In some cases, $R^1$ is selected

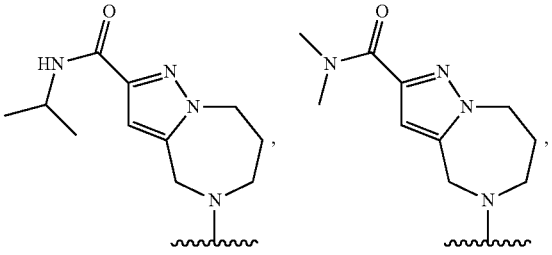

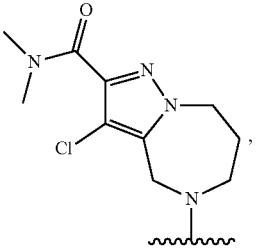

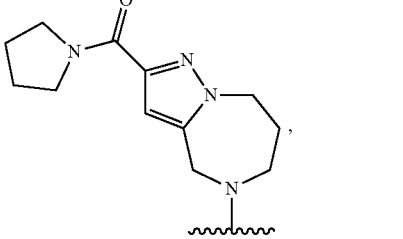

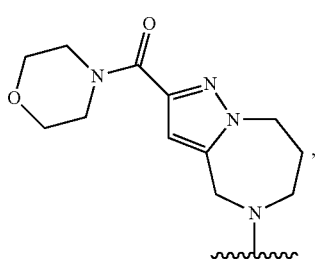

-continued


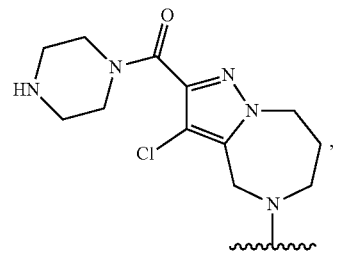

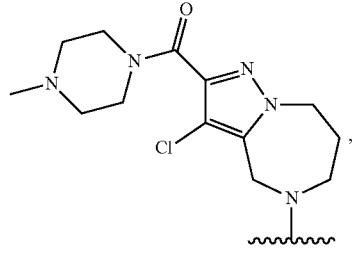

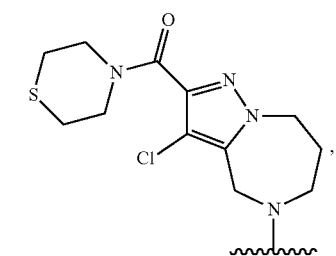

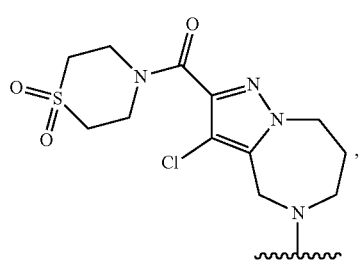

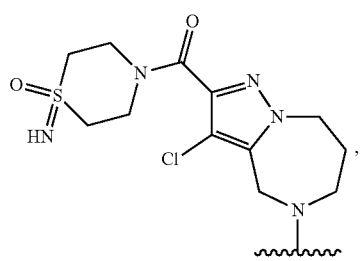

-continued

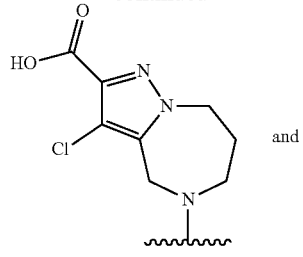
and

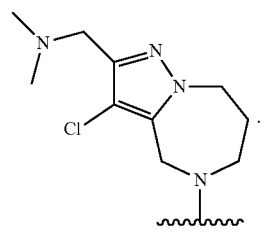

In some cases, $R^1$ is selected from

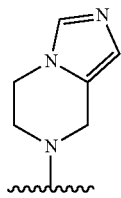

which is optionally substituted with one more substituents independently selected from halogen, —OH, —S(O)$_2$(R$^{20}$), —S(O)$_2$N(R$^{20}$)$_2$, —S(O)N(R$^{20}$)$_2$, —S(O)R$^{20}$(=NR$^{20}$), —C(O)N(R$^{20}$)$_2$, —C(=NR$^{20}$)N(R$^{20}$)$_2$, —C(O)OR$^{20}$, —C(O)NHOR$^{20}$, —N(R$^{20}$)$_2$, —C(O)R$^{20}$, —NO$_2$, =O, —CN, C$_{1-6}$ alkyl-N(R$^{20}$)$_2$, C$_{1-6}$ aminoalkyl, C$_{1-6}$ alkoxy, C$_{1-6}$ alkoxyalkyl, C$_{1-6}$ hydroxyalkyl, C$_{1-6}$ cyanoalkyl, C$_{1-6}$ haloalkyl, C$_{1-6}$ alkyl, C$_{2-6}$ alkynyl, 5- to 12-membered heterocycle, wherein the 5- to 12-membered heterocycle is optionally substituted with one or more substituents selected from halogen, —OR$^{20}$, and C$_{1-6}$ alkyl. In some cases, $R^1$ is selected from

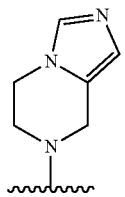

which is optionally substituted with one more substituents independently selected from halogen and C$_{1-6}$ alkyl. In some cases, $R^1$ is selected from

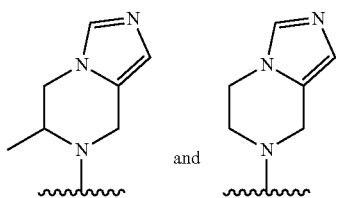

and

In some embodiments, for a compound or salt of Formula (I), $R^1$ is selected from a

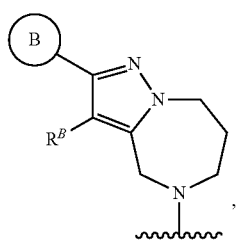

wherein (B) is selected from a 5- to 12-membered heterocycle, wherein the 5- to 12-membered heterocycle is optionally substituted independently with one or more $R^{1*}$; and $R^B$ is selected from hydrogen, halogen, $C_{1-6}$ alkyl, $C_{1-6}$ haloalkyl, $C_{2-6}$ alkynyl, and —CN. In some cases, $R^B$ is selected from hydrogen, and halogen. In some cases, $R^B$ is chloride. In some cases, $R^B$ is hydrogen. In some cases, (B) has at least 1, 2, 3, or 4 heteroatoms. In some cases, (B) has at least 1, 2, 3, or 4 nitrogen atoms. In some cases, (B) has at least 1 oxygen atom. In some cases, (B) is a monocyclic heterocycle. In some cases, (B) is a bicyclic heterocycle. In some cases, (B) is selected from an optionally substituted 5-membered heterocycle. In some cases, (B) is selected from an optionally substituted 9-membered heterocycle. In some cases, (B) is selected from

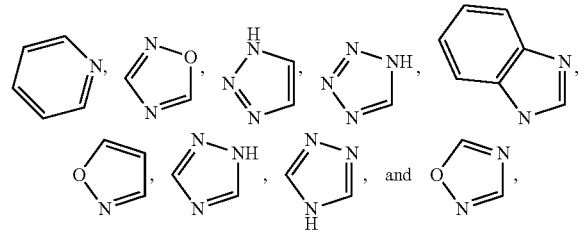

each of which is optionally substituted with one or more $R^{1*}$.

In some cases, (B) is selected from

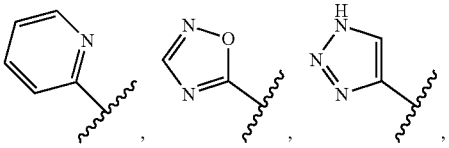

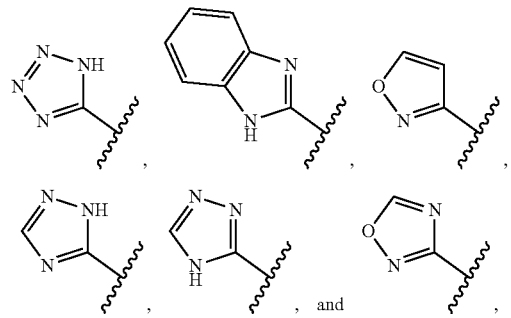

, and each of which is optionally substituted with one or more $R^{1*}$. In some cases, each $R^{1*}$ is independently selected from halogen, —$OR^{20}$, —$S(O)_2(R^{20})$, —$S(O)_2N(R^{20})_2$, —$S(O)N(R^{20})_2$, —$S(O)R^{20}(=NR^{20})$, —$NR^{20}S(O)_2R^{20}$, —$C(O)N(R^{20})_2$, —$C(O)NR^{20}OR^{20}$, —$N(R^{20})C(O)R^{20}$, —$N(R^{20})C(O)N(R^{20})_2$, —$N(R^{20})C(O)OR^{20}$, —$N(R^{20})_2$, —$C(O)R^{20}$, —$C(O)OR^{20}$, —$OC(O)R^{20}$, —$OC(O)N(R^{20})_2$, —$NO_2$, =O, =$N(R^{20})$, =$NO(R^{20})$, —CN, —NHCN, $C_{1-6}$ alkyl-N$(R^{20})_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, and $C_{1-6}$ alkyl. In some cases, each $R^{1*}$ is independently selected from halogen, $C_{1-6}$ alkyl-N$(R^{20})_2$, $C_{1-6}$ aminoalkyl, $C_{1-6}$ hydroxyalkyl, $C_{1-6}$ cyanoalkyl, $C_{1-6}$ haloalkyl, and $C_{1-6}$ alkyl. In some cases, each $R^{1*}$ is independently selected from halogen, and $C_{1-6}$ alkyl. In some cases, (B) is selected from

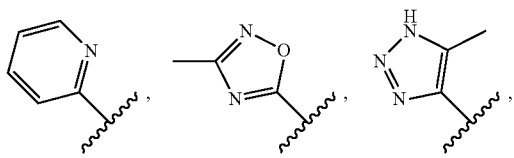

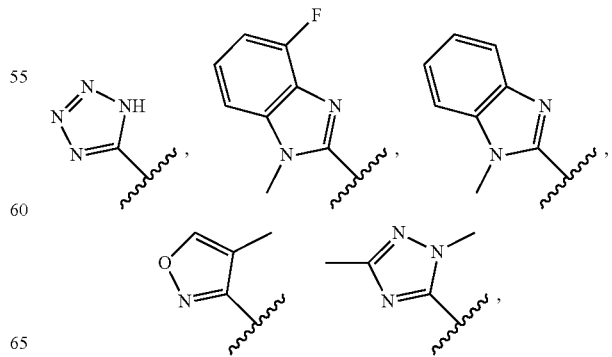

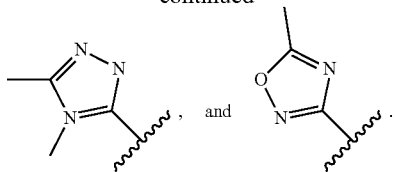, and .

In some embodiments, for a compound or salt of Formula (I), when $R^1$ is substituted with —C(O)$R^{20}$, $R^{20}$ is selected from a 5- to 12-membered heterocycle, which is optionally substituted. In some cases, $R^1$ is substituted with —C(O)$R^{20}$. In some cases, $R^{20}$ is selected from a 5- to 12-membered unsubstituted heterocycle. In some cases, $R^{20}$ is selected from a 5- to 6-membered heterocycle, which is optionally substituted. In some cases, the heterocycle has at least one nitrogen atom. In some cases, the heterocycle has at least one sulfur atom. In some cases, the heterocycle has at least one oxygen atom. In some cases, the heterocycle has two heteroatoms. In some cases, the heterocycle of $R^{20}$ is selected from

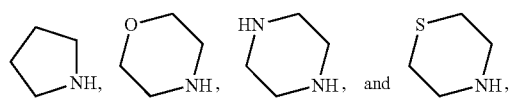

each of which is optionally substituted. In some cases, $R^{20}$ is selected from

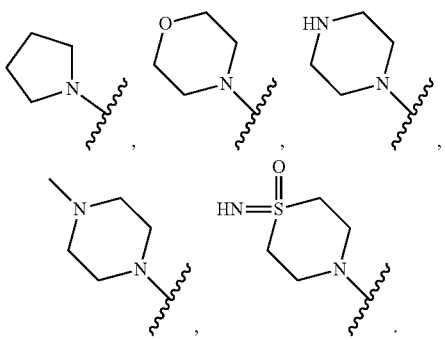

In some cases, the optional substituents are selected from $C_{1-10}$ alkyl, oxo, and =NH.

In some embodiments, for a compound or salt of Formula (I), each $R^{20}$ is independently selected from hydrogen; and $C_{1-6}$ alkyl, $C_{3-12}$ carbocycle, and 3- to 12-membered heterocycle, each of which is optionally substituted with one or more substituents independently selected from halogen, —OH, —CN, —NO$_2$, —NH$_2$, —N($C_{1-6}$ alkyl)$_2$, $C_{1-10}$ alkyl, —$C_{1-10}$ haloalkyl, —O—$C_{1-10}$ alkyl, oxo, and =NH. In some cases, each $R^{20}$ is independently selected from hydrogen; and unsubstituted $C_{1-6}$ alkyl, and 3- to 12-membered heterocycle which is optionally substituted with one or more substituents independently selected from halogen, —OH, —CN, —NO$_2$, —NH$_2$, —N($C_{1-6}$ alkyl)$_2$, $C_{1-10}$ alkyl, —$C_1$ haloalkyl, —O—$C_{1-10}$ alkyl, oxo, and =NH.

In some embodiments, for a compound or salt of Formula (I), each $R^{21}$ is independently selected from hydrogen; and $C_{1-6}$ alkyl, $C_{3-12}$ carbocycle, and 3- to 12-membered heterocycle, each of which is optionally substituted with one or more substituents independently selected from halogen, —OH, —CN, —NO$_2$, —NH$_2$, —N($C_{1-6}$ alkyl)$_2$, $C_{1-10}$ alkyl, —$C_{1-10}$ haloalkyl, —O—$C_{1-10}$ alkyl, oxo, and =NH. In some cases, each $R^{21}$ is independently selected from hydrogen; and unsubstituted $C_{1-6}$ alkyl, and 3- to 12-membered heterocycle which is optionally substituted with one or more substituents independently selected from halogen, —OH, —CN, —NO$_2$, —NH$_2$, —N($C_{1-6}$ alkyl)$_2$, $C_{1-10}$ alkyl, —$C_{1-10}$ haloalkyl, —O—$C_{1-10}$ alkyl, oxo, and =NH.

In some embodiments, for a compound or salt of Formula (I), each $R^{20}$ is independently selected from hydrogen; and $C_{1-6}$ alkyl, $C_{3-12}$ carbocycle, and 3- to 12-membered heterocycle, each of which is optionally substituted with one or more substituents independently selected from halogen, —OH, —CN, —NO$_2$, —NH$_2$, —N($C_{1-6}$ alkyl)$_2$, $C_{1-10}$ alkyl, —$C_{1-10}$ haloalkyl, —O—$C_{1-10}$ alkyl, oxo, and =NH. In some cases, each $R^{20}$ is independently selected from hydrogen; and unsubstituted $C_{1-6}$ alkyl, and 3- to 12-membered heterocycle which is optionally substituted with one or more substituents independently selected from halogen, —OH, —CN, —NO$_2$, —NH$_2$, —N($C_{1-6}$ alkyl)$_2$, $C_{1-10}$ alkyl, —$C_{1-10}$ haloalkyl, —O—$C_{1-10}$ alkyl, oxo, and =NH.

In some embodiments, for a compound or salt of Formula (I), each $R^{23}$ is independently selected from hydrogen; and $C_{1-6}$ alkyl, $C_{3-12}$ carbocycle, and 3- to 12-membered heterocycle, each of which is optionally substituted with one or more substituents independently selected from halogen, —OH, —CN, —NO$_2$, —NH$_2$, —N($C_{1-6}$ alkyl)$_2$, $C_{1-10}$ alkyl, —$C_{1-6}$ haloalkyl, —O—$C_{1-10}$ alkyl, oxo, and =NH. In some cases, each $R^{20}$ is independently selected from hydrogen; and unsubstituted $C_{1-6}$ alkyl, and 3- to 12-membered heterocycle which is optionally substituted with one or more substituents independently selected from halogen, —OH, —CN, —NO$_2$, —NH$_2$, —N($C_{1-6}$ alkyl)$_2$, $C_{1-6}$ alkyl, —$C_{1-10}$ haloalkyl, —O—$C_{1-10}$ alkyl, oxo, and =NH.

In some embodiments, for a compound or salt for Formula (I), $R^1$ is selected from 5- to 12-membered heterocycle, wherein the 5- to 12-membered heterocycle is optionally substituted with one or more substituents. In some cases, the one or more optional substituents are independently selected from halogen, —CN, —NO$_2$, =O, —N($R^{20}$)$_2$, —B(O$R^{20}$)$_2$, —O$R^{20}$, —S$R^{20}$, —S(O)$_2$($R^{20}$), —S(O)$_2$N($R^{20}$)$_2$, —N$R^{20}$S(O)$_2$$R^{20}$, —C(O)N($R^{20}$)$_2$, —N($R^{20}$)C(O)$R^{20}$, —N($R^{20}$)C(O)N($R^{20}$)$_2$, —N($R^{20}$)C(O)O$R^{20}$, —C(O)$R^{20}$, —C(O)O$R^{20}$, —OC(O)$R^{20}$, —OC(O)N($R^{20}$)$_2$, $C_{1-6}$ aminoalkyl, $C_{1-6}$ alkoxy, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkenyl, and $C_{2-6}$ alkynyl. In some cases, the one or more optional substituents are independently selected from halogen, —OH, —N($R^{20}$)$_2$, —NO$_2$, =O, —CN, $C_{1-6}$ aminoalkyl, $C_{1-6}$ alkoxy, $C_{1-6}$ hydroxyalkyl, and $C_{1-6}$ haloalkyl. In some cases, the one or more optional substituents are independently selected from halogen, —OH, —N($R^{20}$)$_2$, —NO$_2$, $C_{1-6}$ aminoalkyl, $C_{1-6}$ alkoxy, $C_{1-6}$ hydroxyalkyl, and $C_{1-6}$ haloalkyl. In some cases, $R^{20}$ is selected from hydrogen and $C_{1-3}$ alkyl.

In some embodiments, for a compound or salt for Formula (I), $R^1$ is selected from a saturated 5- to 12-membered heterocycle, which is optionally substituted with one or more substituents. In some cases, the 5- to 12-membered heterocycle of $R^1$ is bridged. In some cases, the 5- to 12-membered heterocycle of $R^1$ is not bridged. In some cases, the 5- to 12-membered heterocycle is selected from

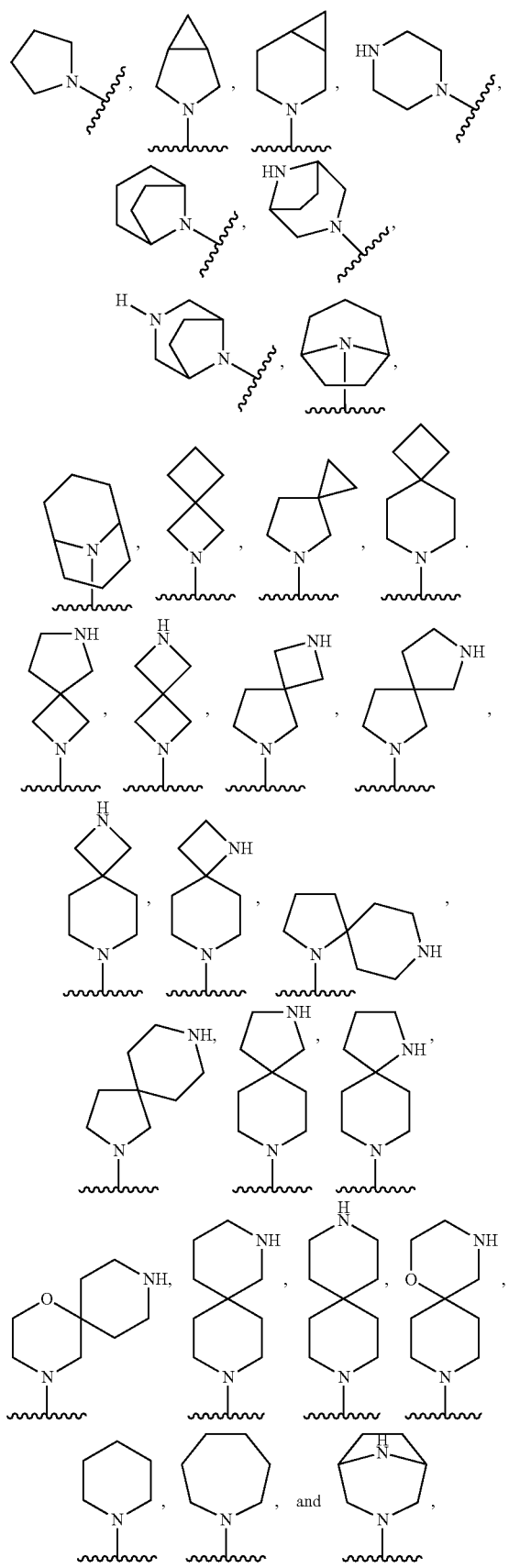
each of which is optionally substituted with one or more substituents.
In some embodiments, for a compound or salt of Formula (I), R[1] is selected from
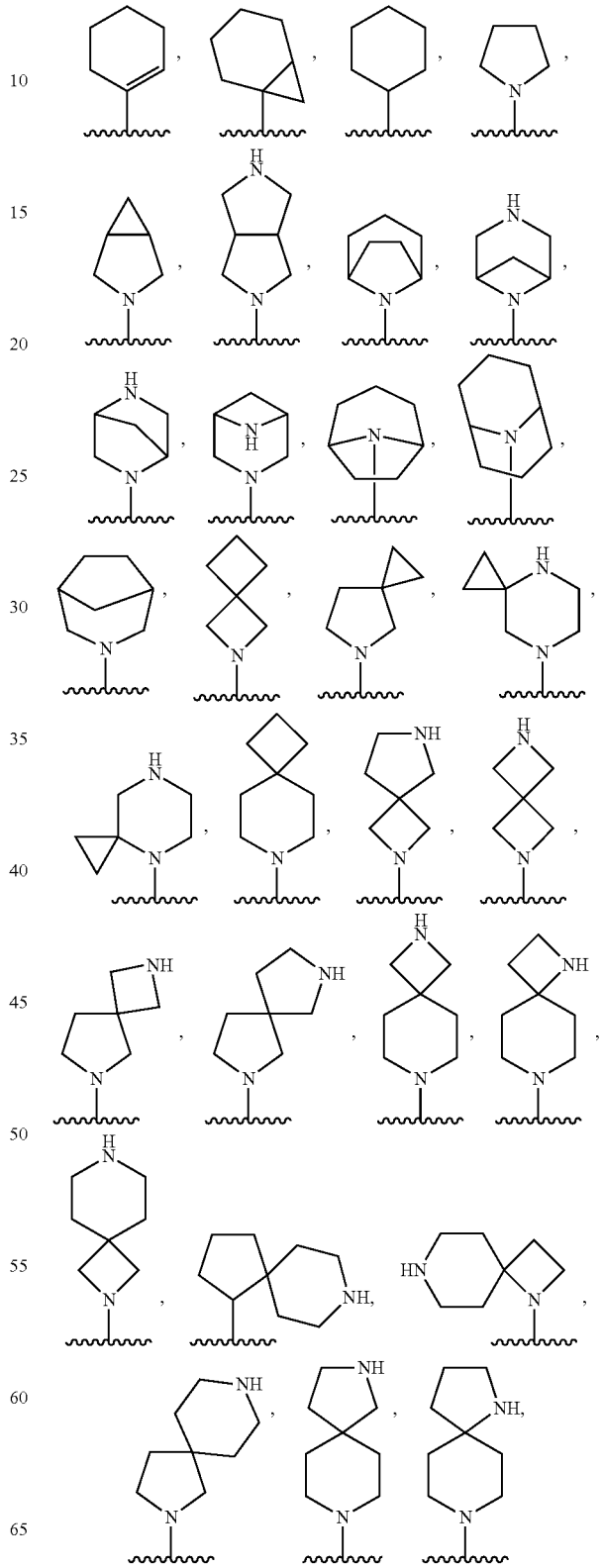

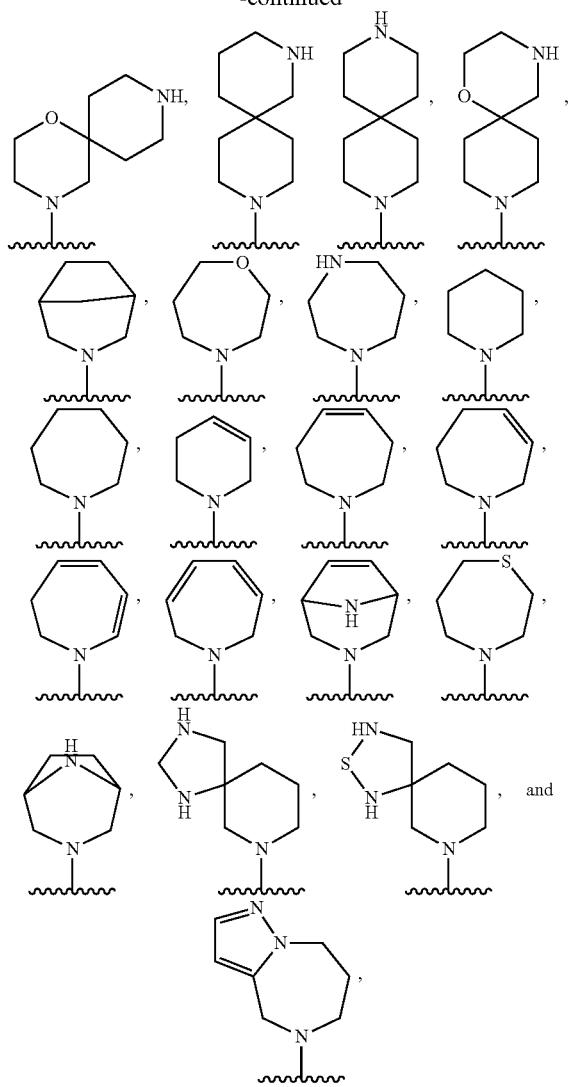
each of which is optionally substituted with one or more substituents. In some cases, the one or more of the optional substituents are independently selected from halogen, —OH, —N(R$^{20}$)$_2$, —B(OH)$_2$, —C(O)N(R$^{20}$)$_2$, —NHCN, —NO$_2$, C$_{1-6}$ alkoxy, =O, —CN, C$_{1-6}$ alkyl, C$_{2-6}$ alkenyl, C$_{1-6}$alkyl-N(R$^{20}$)$_2$, C$_{1-6}$ aminoalkyl, C$_{1-6}$ hydroxyalkyl, and C$_{1-6}$ haloalkyl. In some cases, R$^1$ is selected from
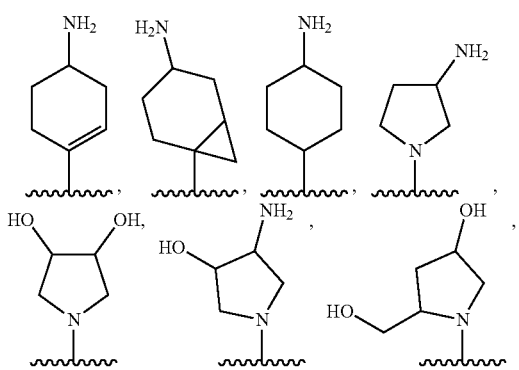
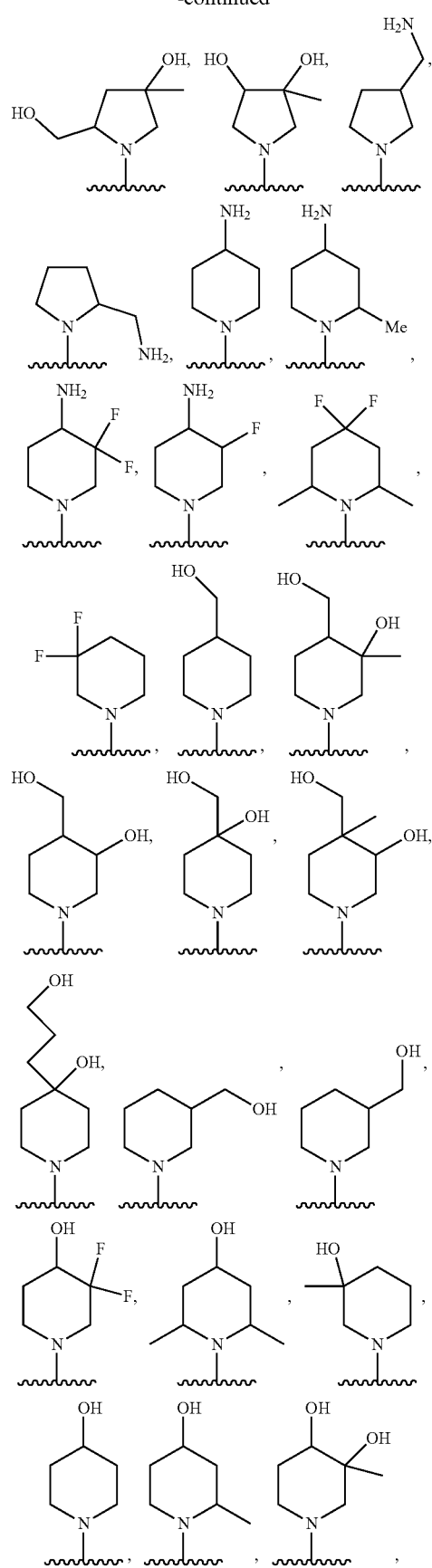

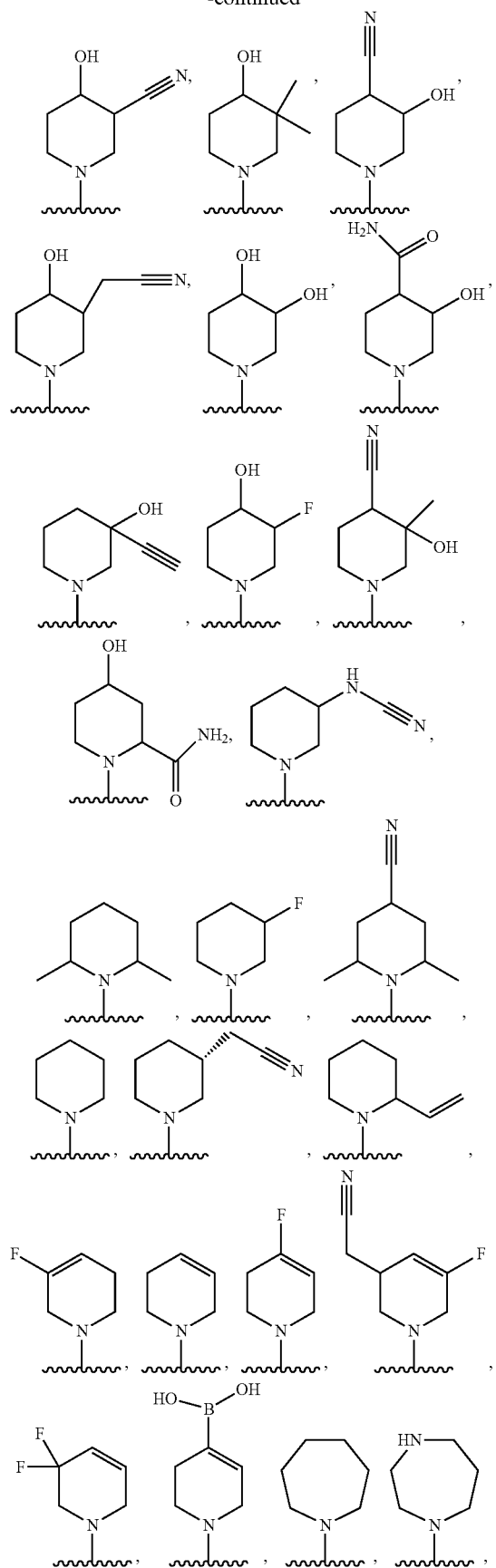
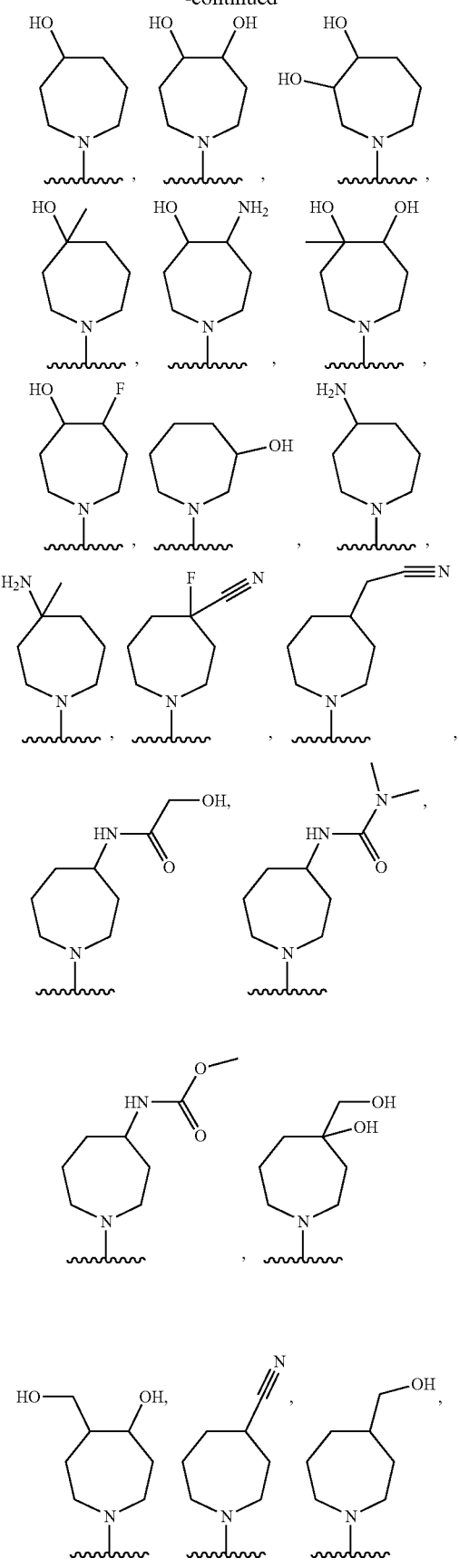

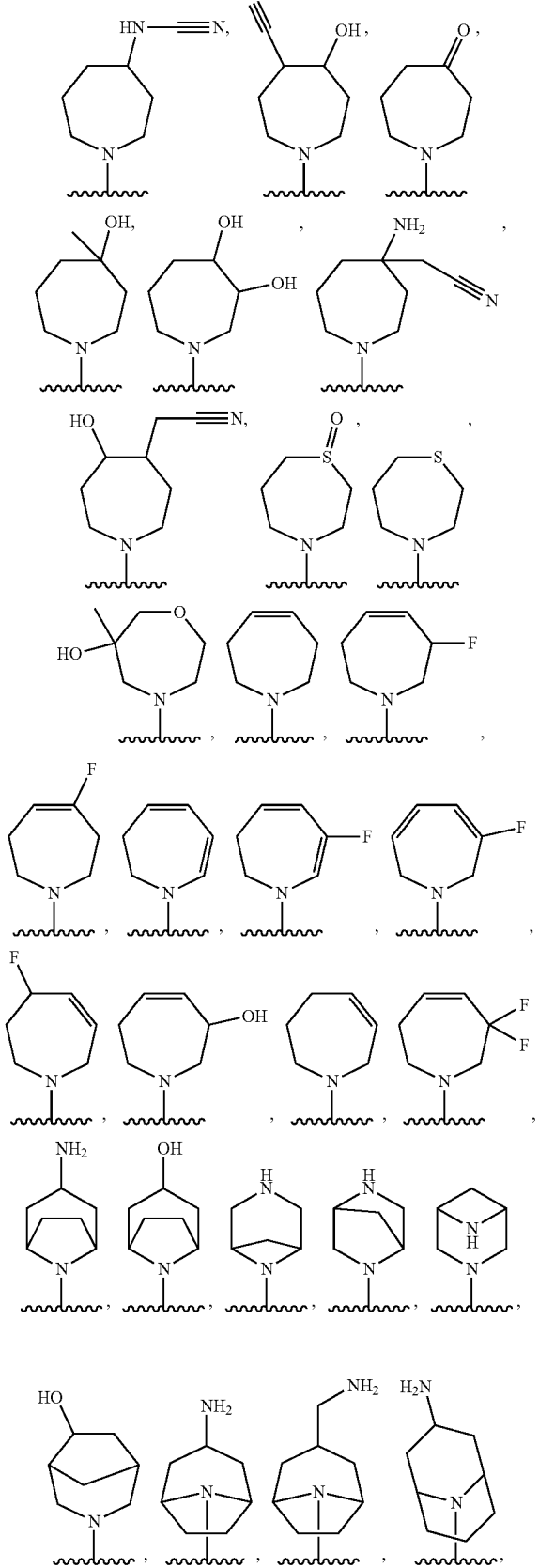
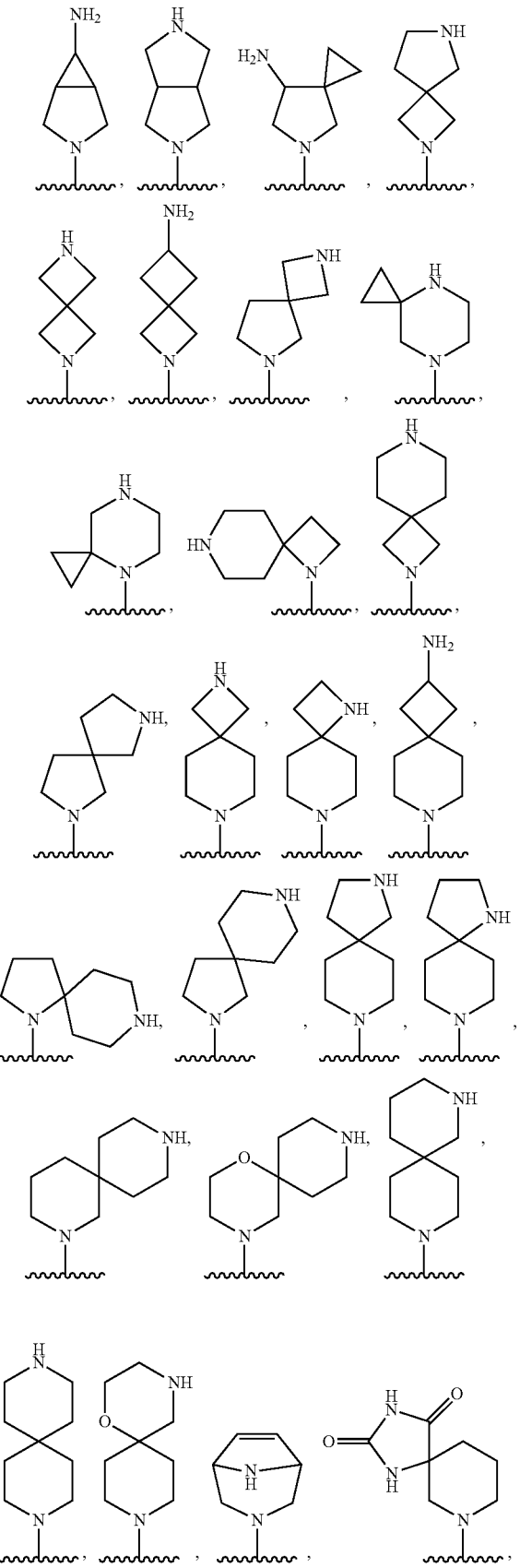

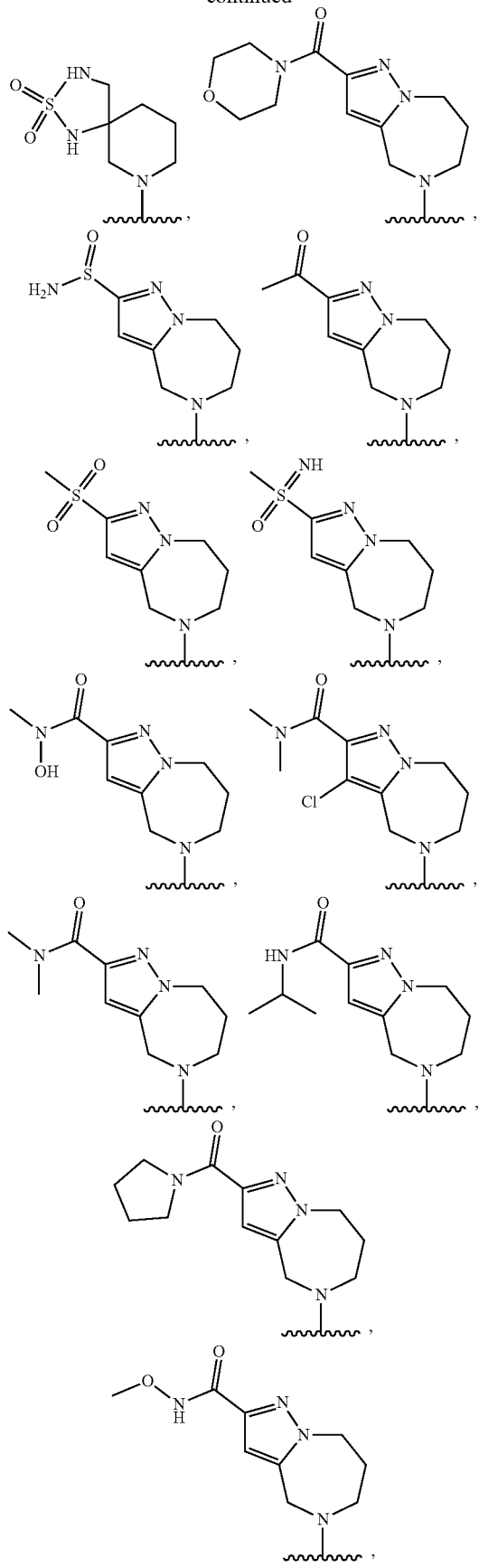

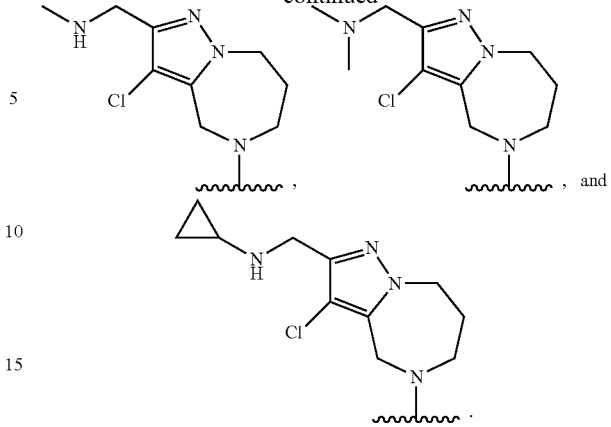

In some embodiments, for a compound or salt of Formula (I), $R^1$ is selected from an optionally substituted 5- to 12-membered unsaturated heterocycle, wherein the heterocycle has as most one nitrogen atom. In some cases, the 5- to 12-membered unsaturated heterocycle has at least one nitrogen atom. In some cases, the 5- to 12-membered unsaturated heterocycle has at most one nitrogen atom.

In some embodiments, for a compound or salt of Formula (I), the heterocycle of $R^1$ contains only 1 nitrogen atom and optionally one or more heteroatoms selected from oxygen, and sulfur. In some cases, the heterocycle is a fused heterocycle or a bridged heterocycle. In some cases, the heterocycle is a monocyclic heterocycle or a bridged heterocycle. In some cases, the heterocycle is a monocyclic heterocycle. In some cases, the heterocycle is a bridged heterocycle. In some cases, the heterocycle is selected from

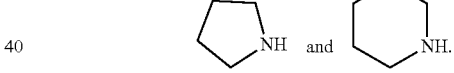

The heterocycle is optionally substituted as described elsewhere herein.

In some embodiments, for a compound or salt of Formula (I), the heterocycle of $R^1$ has at most 1 nitrogen atom. In some cases, the heterocycle of $R^1$ has only 1 nitrogen atom and optionally one or more other heteroatoms selected from oxygen and sulfur. In some cases, the heterocycle of $R^1$ has only 1 nitrogen atom and no other heteroatoms.

In some embodiments, for a compound or salt of Formula (I), $R^1$ is selected from an optionally substituted 5- to 12-membered saturated heterocycle, wherein the heterocycle has as most one nitrogen atom. In some cases, the 5- to 12-membered unsaturated heterocycle has at least one nitrogen atom. In some cases, the 5- to 12-membered unsaturated heterocycle has only one nitrogen atom and 0-2 other heteroatoms selected from nitrogen, oxygen, and sulfur. In some cases, the 5- to 12-membered unsaturated heterocycle has only one nitrogen atom and no further heteroatoms. In some cases, the 5- to 12-membered unsaturated heterocycle has three nitrogen atoms and no further heteroatoms.

In some embodiments, for a compound or salt of Formula (I), $R^1$ is selected from an optionally substituted 5- to 12-membered unsaturated heterocycle, wherein the heterocycle has as most one nitrogen atom. In some cases, the 5- to 12-membered unsaturated heterocycle has at least one nitrogen atom. In some cases, the 5- to 12-membered unsaturated heterocycle has only one nitrogen atom and no further heteroatoms.

In some embodiments, for a compound or salt of Formula (I), $R^1$ is selected from 6- to 7-membered heterocycle. In some cases, $R^1$ is selected from 7-membered heterocycle. In some cases, $R^1$ is selected from 6-membered heterocycle. In some cases, the 6- to 7-membered heterocycle contains only 1 nitrogen atom and optionally one or more additional heteroatoms selected from oxygen, and sulfur. In some cases, the optionally one or more additional heteroatoms are selected from sulfur. In some cases, the optionally one or more additional heteroatoms are selected from oxygen. In some cases, the 6- to 7-membered heterocycle contains only 1 nitrogen atom and no further additional heteroatoms. In some cases, the 6- to 7-membered heterocycle is a non-aromatic 6- to 7-membered heterocycle. In some cases, the 6- to 7-membered heterocycle of $R^1$ is bound to Formula (I) via the only 1 nitrogen atom. In some cases, $R^1$ is selected from

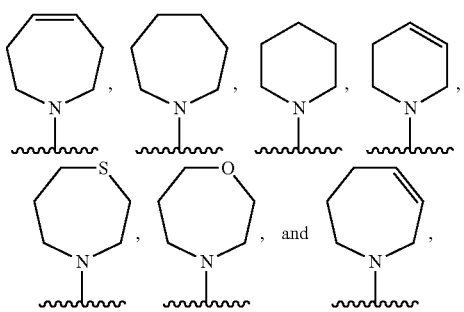

each of which is substituted. In some cases, $R^1$ is selected from

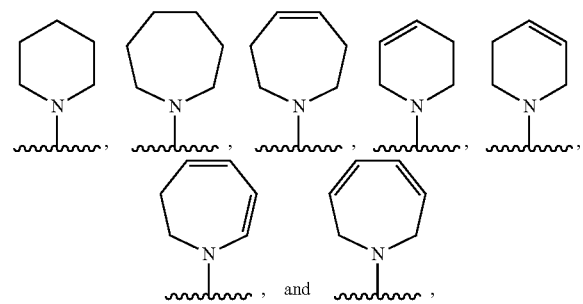

each of which is substituted. In some cases, the substituents of $R^1$ are each selected from one or more halogen, —$OR^{20}$, —$SR^{20}$, —$N(R^{20})_2$, —NHCN, —$NO_2$, =O, —CN, $C_{1-6}$ fluoroalkyl, and $C_{2-6}$ alkynyl; and further optionally substituted with one or more substituents independently selected from —C(O)N($R^{20}$)$_2$, $C_{1-6}$ aminoalkyl, $C_{1-6}$ hydroxyalkyl, $C_{1-6}$ cyanoalkyl, $C_{1-6}$ alkyl, and $C_{2-6}$ alkenyl. In some cases, the substituents of $R^1$ are each selected from one or more halogen, —$OR^{20}$, —$N(R^{20})_2$, —NHCN, =O, —CN, and $C_{2-6}$ alkynyl; and further optionally substituted with one or more substituents independently selected from —C(O)N($R^{20}$)$_2$, $C_{1-6}$ aminoalkyl, $C_{1-6}$ hydroxyalkyl, $C_{1-6}$ cyanoalkyl, and $C_{1-6}$ alkyl. In some cases, the substituents of $R^1$ are each selected from one or more halogen, —OH, —NHCN, =O, —CN, and $C_{2-6}$ alkynyl; and further optionally substituted with one or more substituents independently selected from $C_{1-6}$ alkyl. In some cases, $R^1$ is selected from

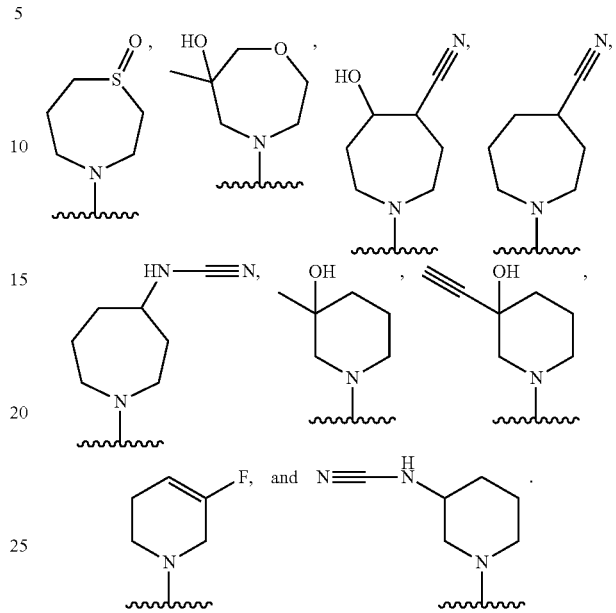

In some cases, $R^1$ is selected from

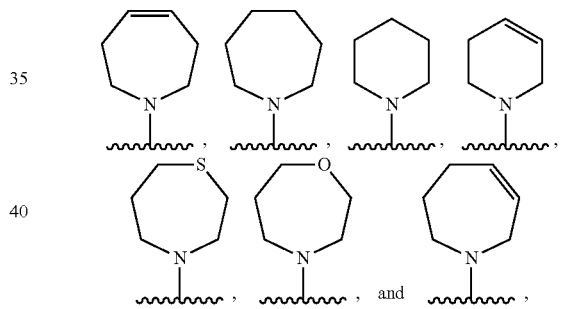

each of which is optionally substituted. In some cases, $R^1$ is selected from

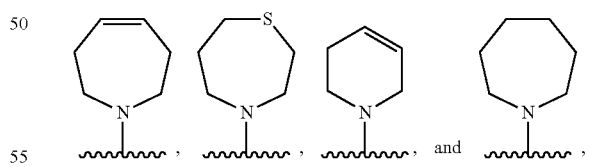

each of which is optionally substituted. In some cases, $R^1$ is selected from

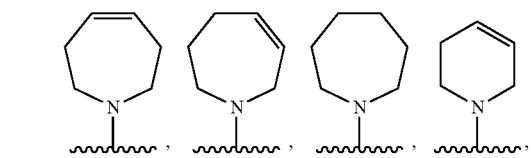

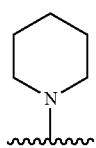

each of which is optionally substituted. In some cases, the one or more optional substituents of $R^1$ are each independently selected from fluorine, —OH, —C(O)NH$_2$, —NH—C(O)—(C$_{1-6}$ alkoxy), —NH—C(O)—(C$_{1-6}$ hydroxyalkyl), —NH$_2$, —NH(CN), =O, —CN, C$_{1-6}$ hydroxyalkyl, C$_{1-6}$ cyanoalkyl, C$_{1-6}$ alkyl, and C$_{2-6}$ alkynyl. In some cases, the one or more optional substituents of $R^1$ are each independently selected from halogen, —OH, —CN, C$_{1-6}$ cyanoalkyl, C$_{1-6}$ alkyl, and C$_{2-6}$ alkynyl. In some cases, the one or more optional substituents of $R^1$ are each independently selected from halogen, —OH, and —CN. In some cases, the one or more optional substituents of $R^1$ are each independently selected from fluorine, —OH, —CN, C$_{1-6}$ cyanoalkyl, C$_{1-6}$ alkyl, oxo, and C$_{2-6}$ alkynyl. In some cases, the one or more optional substituents of $R^1$ are each independently selected from fluorine, —OH, —CN, C$_{1-6}$ cyanoalkyl, C$_{1-6}$ alkyl, and C$_{2-6}$ alkynyl. In some cases, $R^1$ is selected from

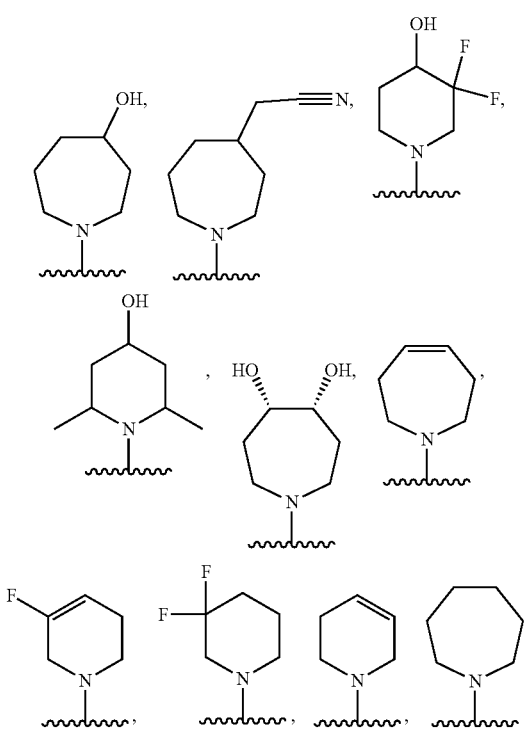

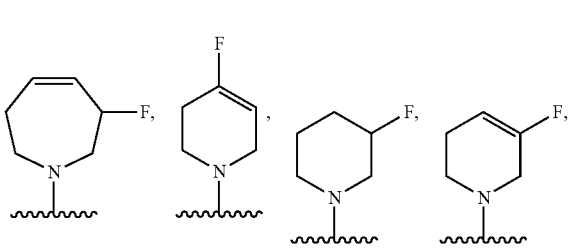

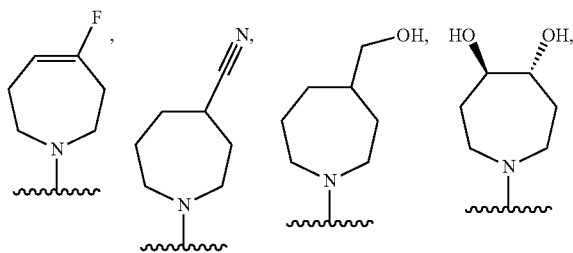

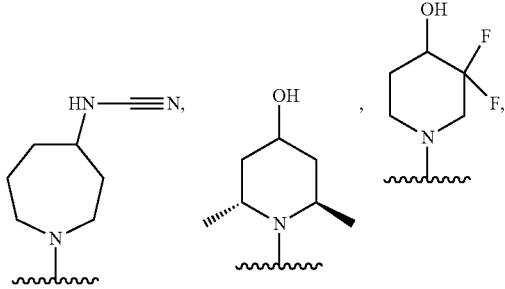

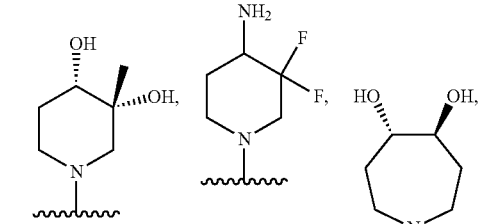

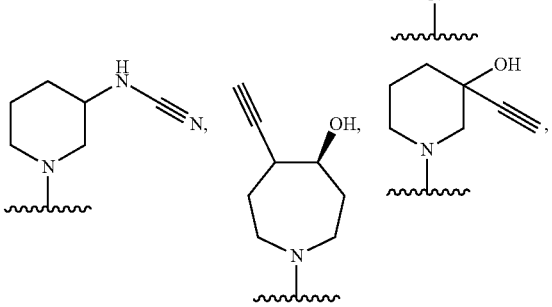

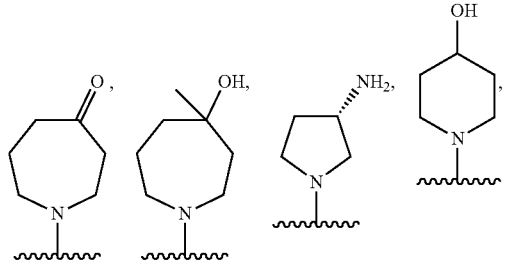

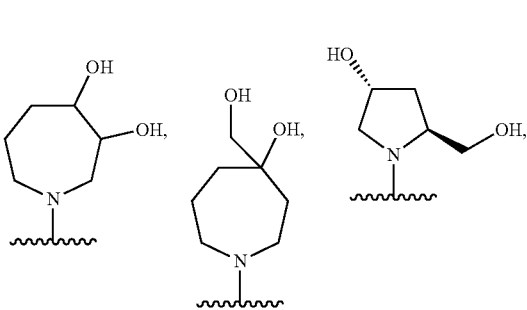

107
-continued
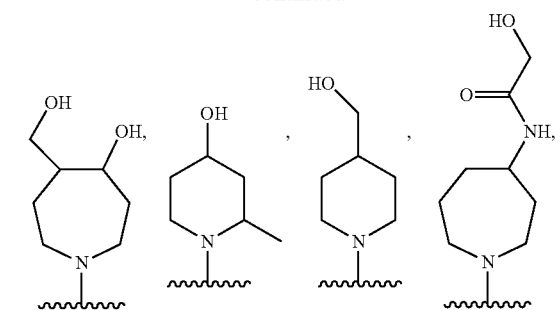
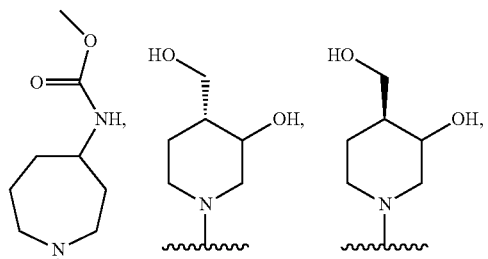
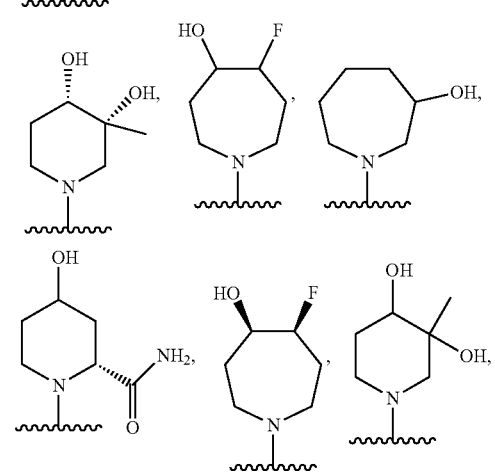
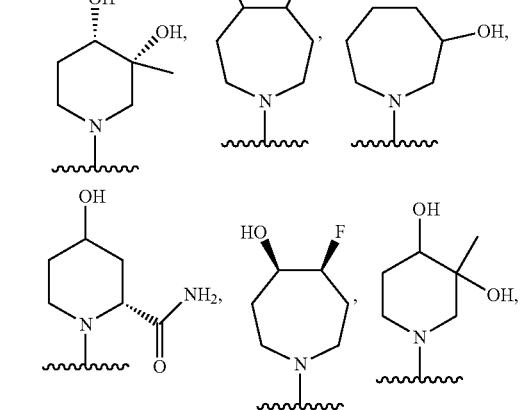
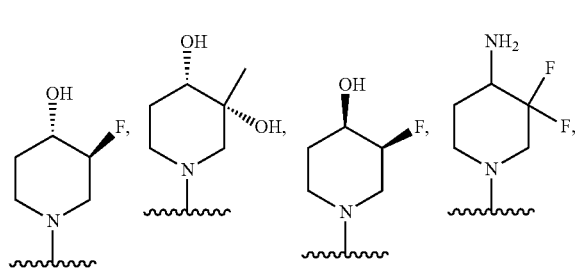
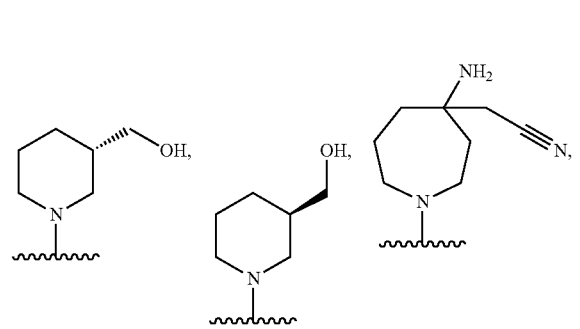
108
-continued
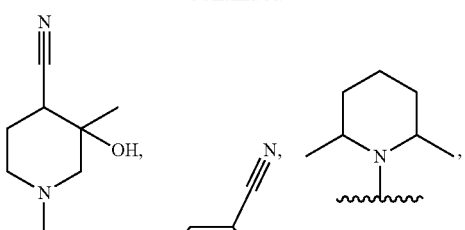
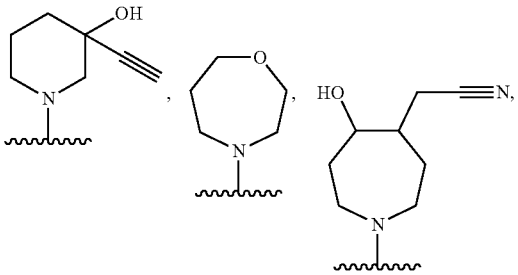
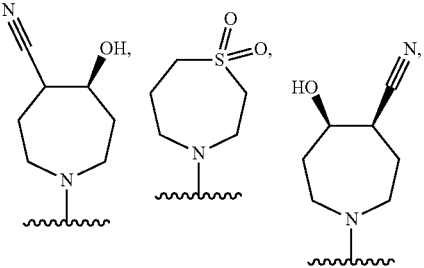
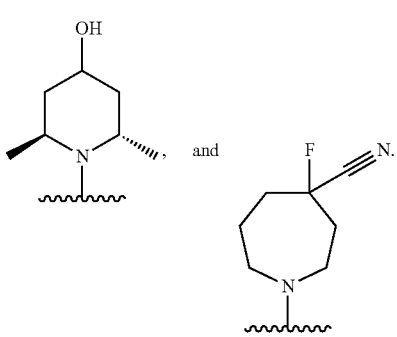
In some cases, $R^1$ is selected from
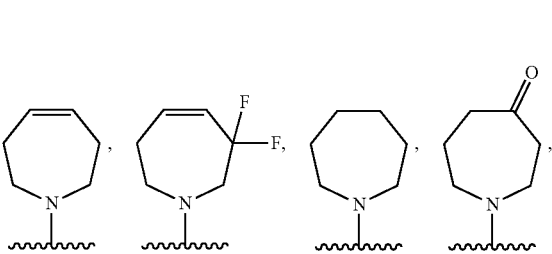

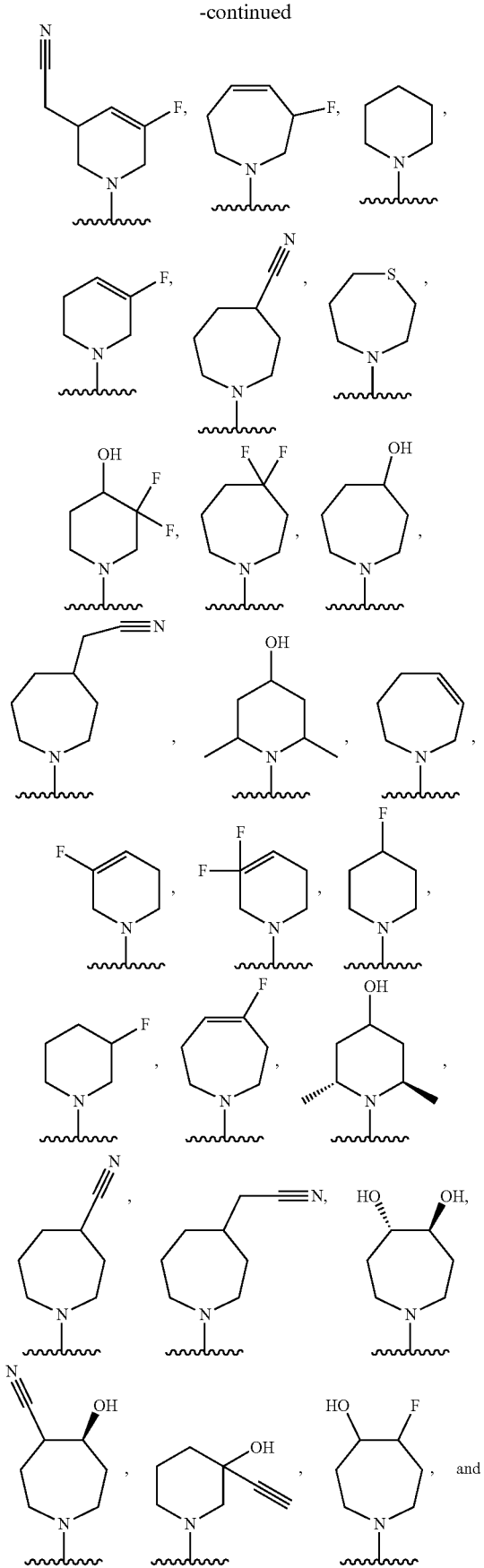
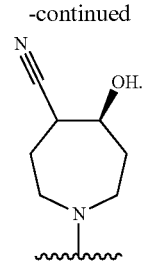
In some cases, R[1] is selected from
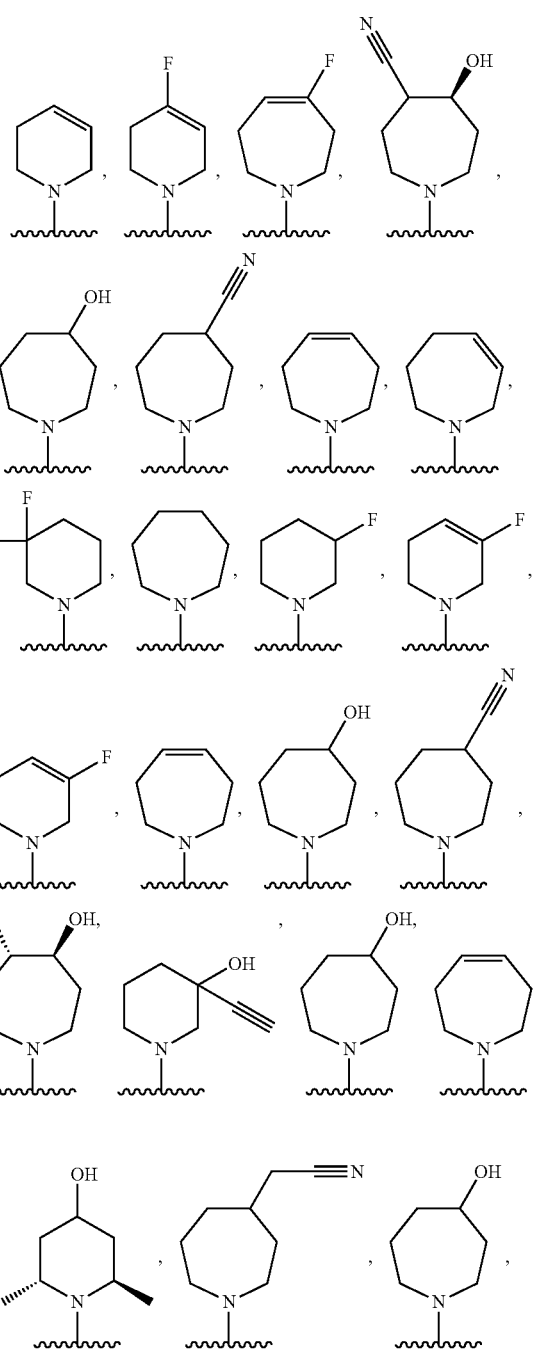

-continued
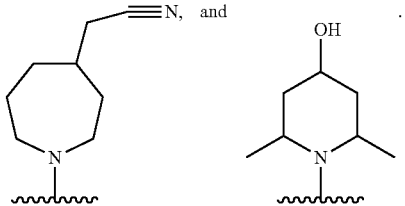
In some cases, $R^1$ is selected from
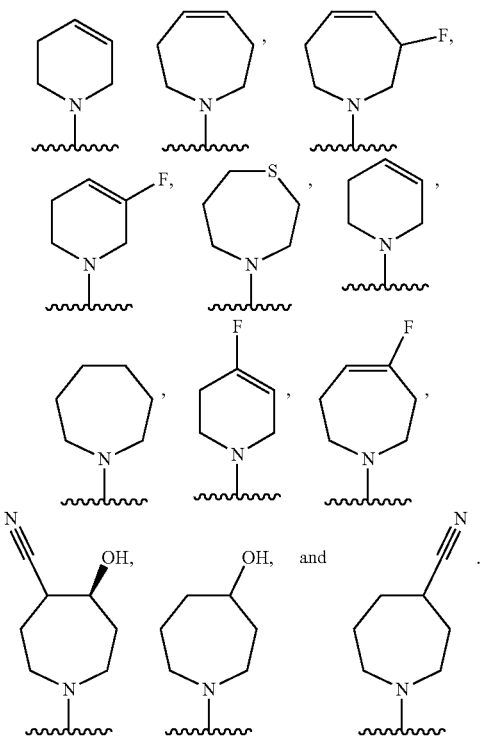
In some cases, $R^1$ is selected from
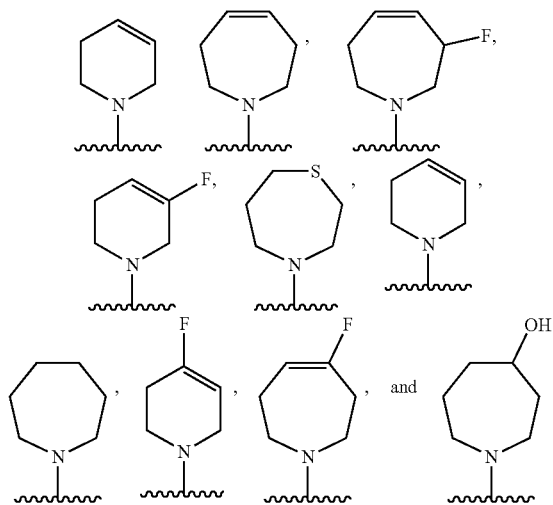
In some embodiments, for a compound or salt of Formula (I), $R^1$ is selected from
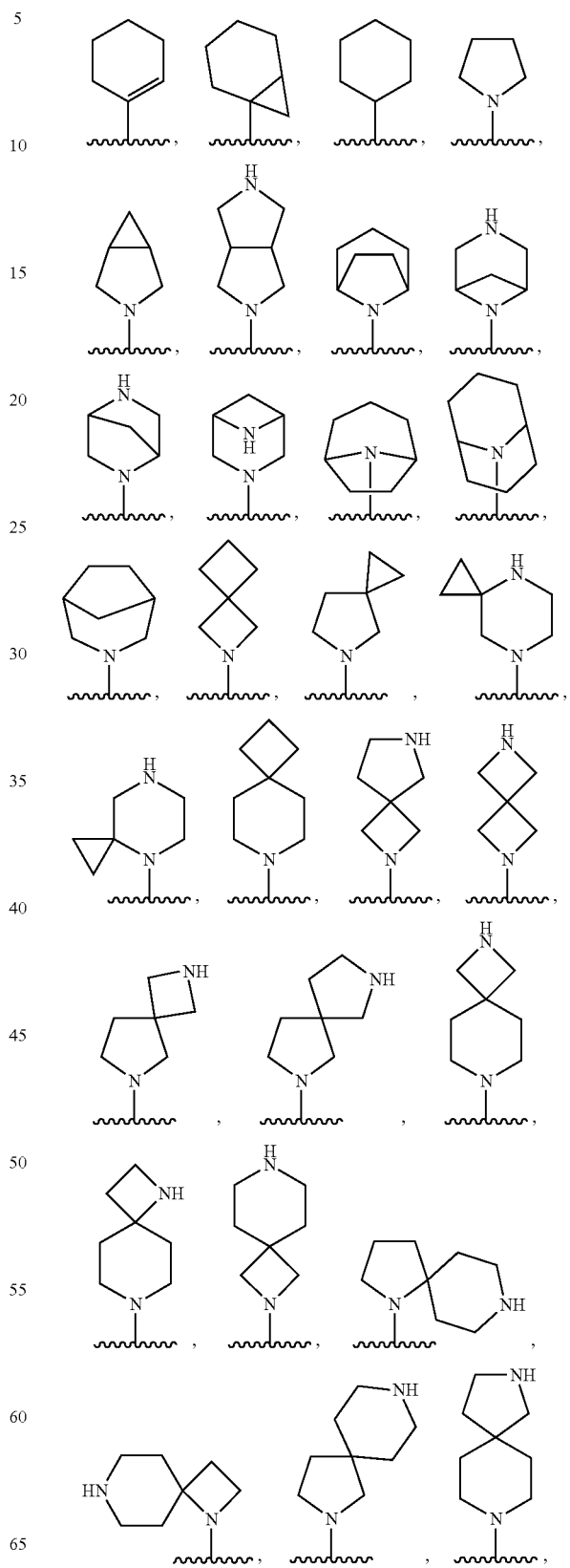

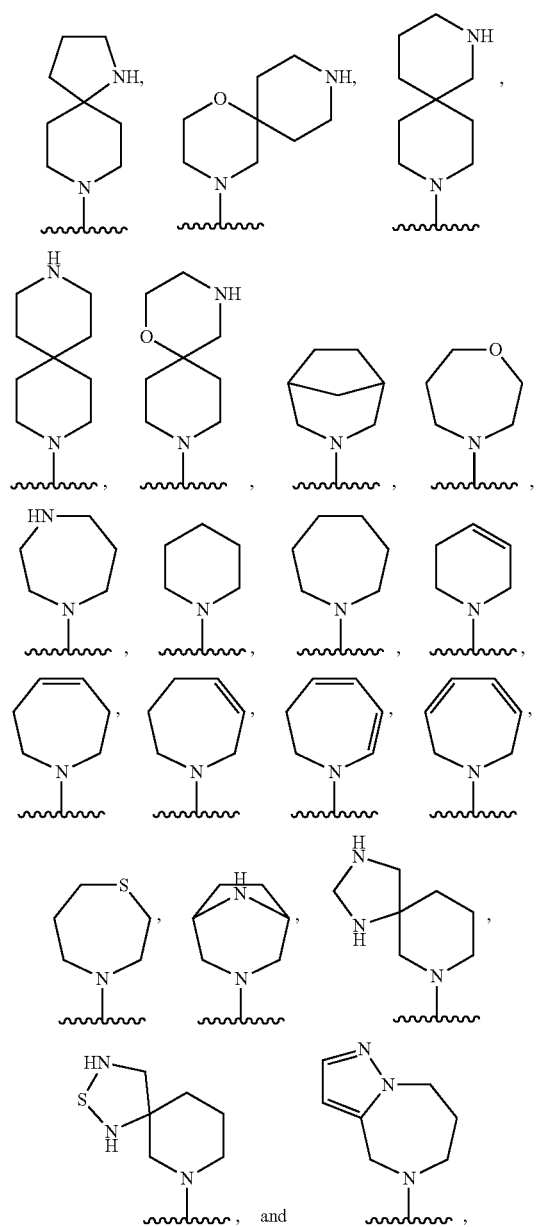
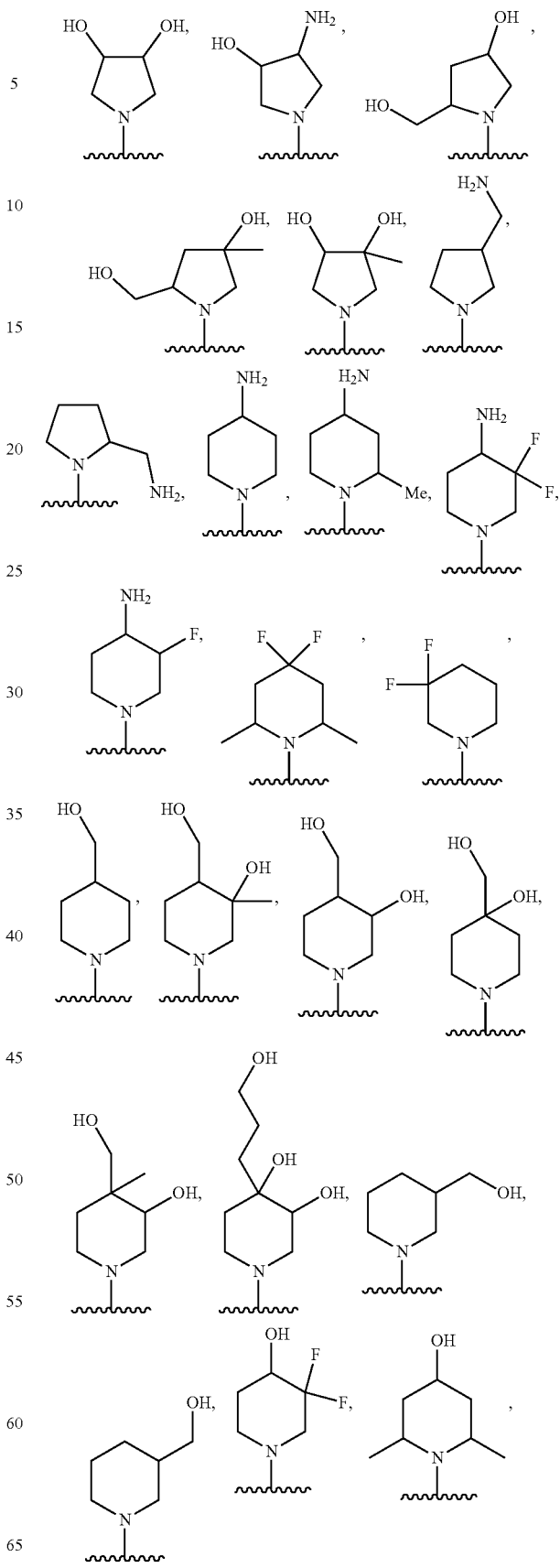
each of which is optionally substituted with one or more substituents. In some cases, the one or more of the optional substituents are independently selected from halogen, —OH, —N(R$^{20}$)$_2$, —B(OH)$_2$, —C(O)N(R$^{20}$)$_2$, —NHCN, —NO$_2$, C$_{1-6}$ alkoxy, =O, —CN, C$_{1-6}$ alkyl, C$_{2-6}$ alkenyl, C$_{1-6}$ aminoalkyl, C$_{1-6}$ hydroxyalkyl, and C$_{1-6}$ haloalkyl. In some cases, R$^1$ is selected from
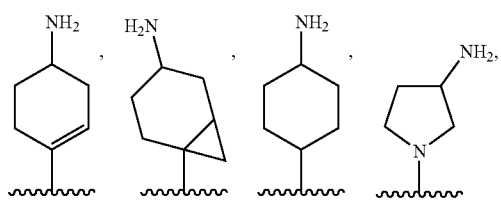

115
-continued
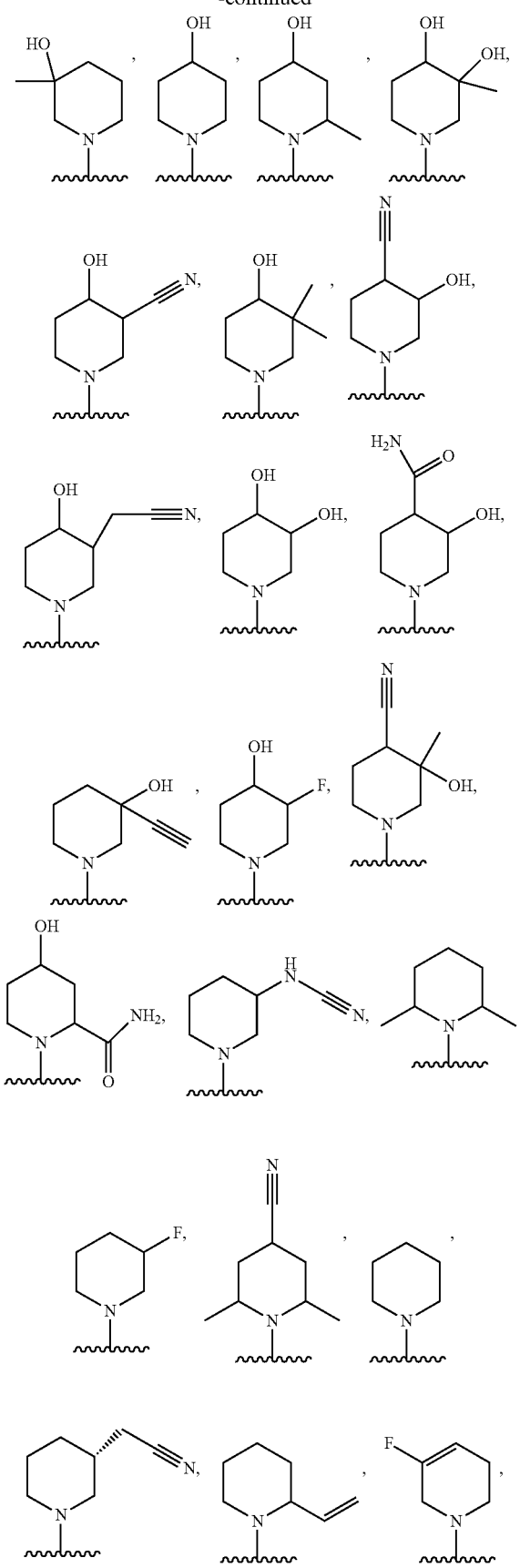
116
-continued
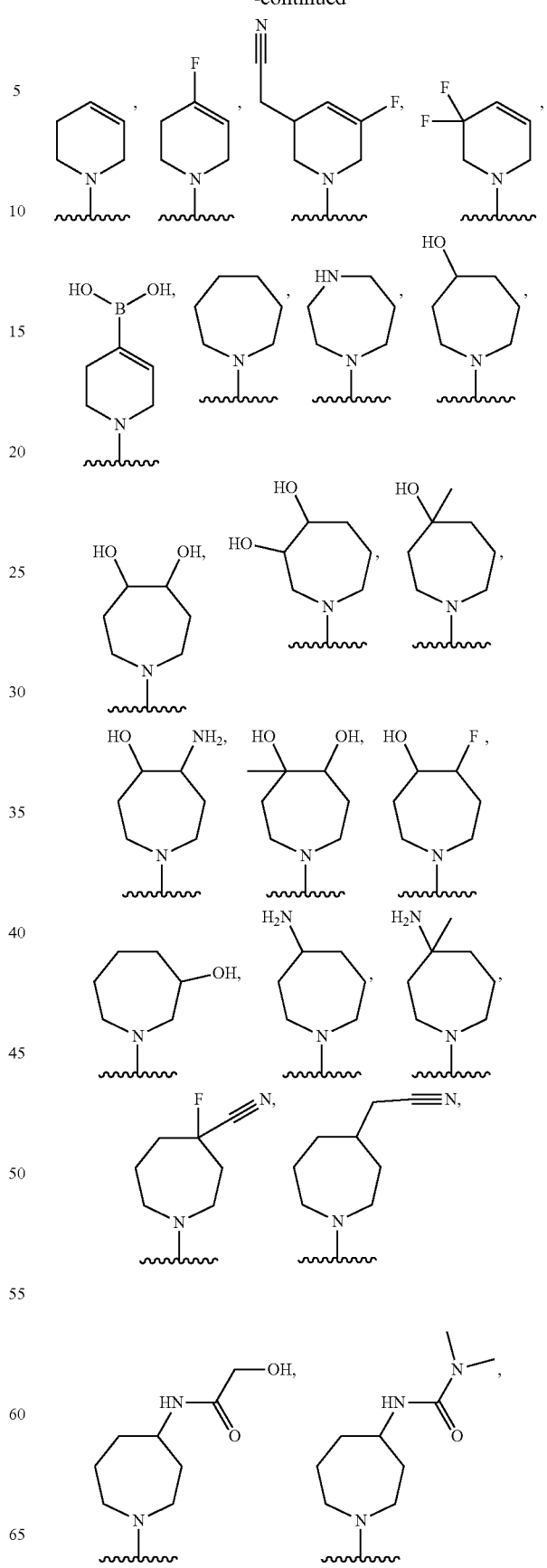

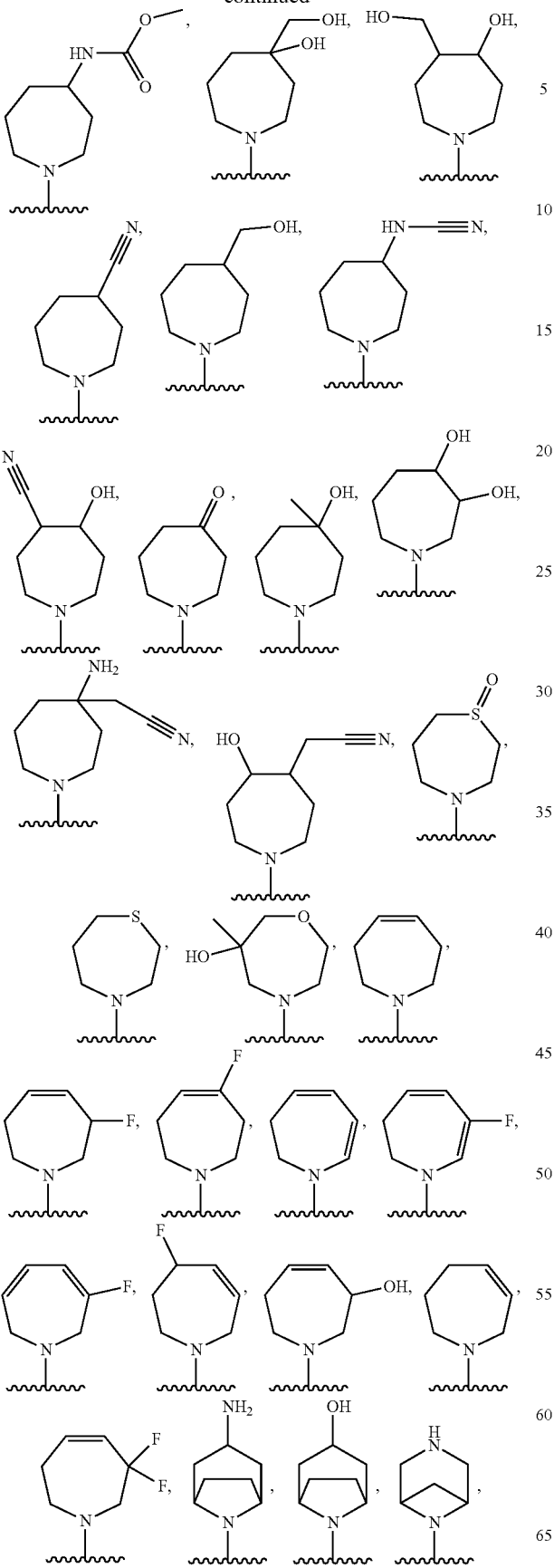
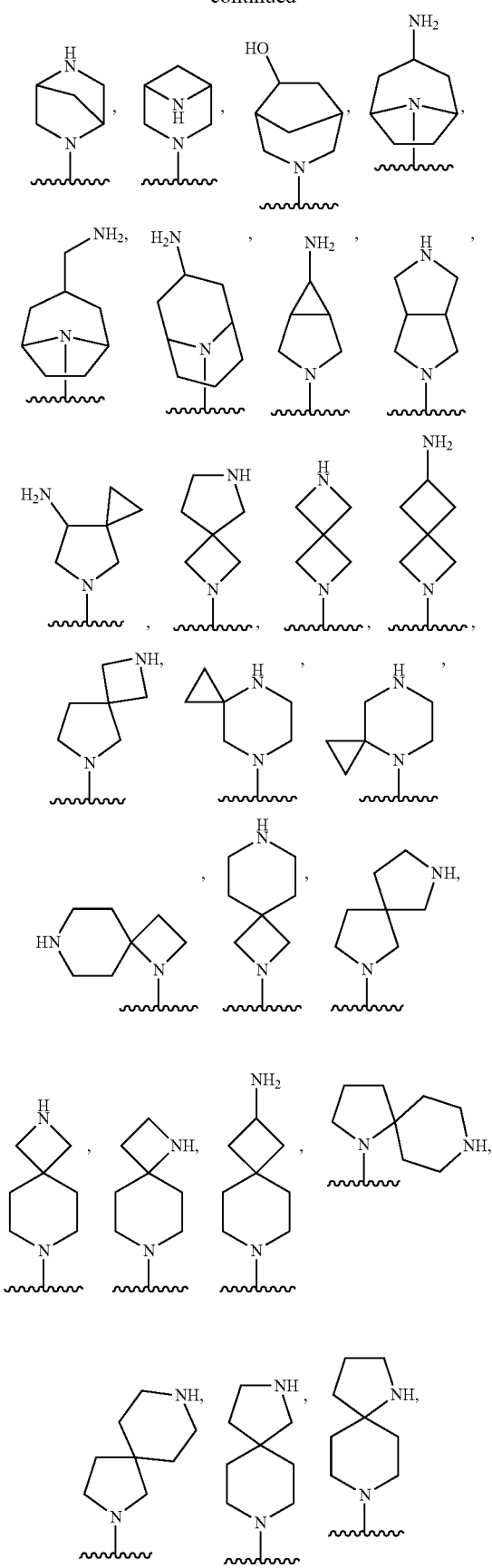

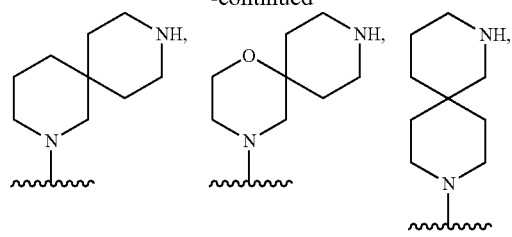
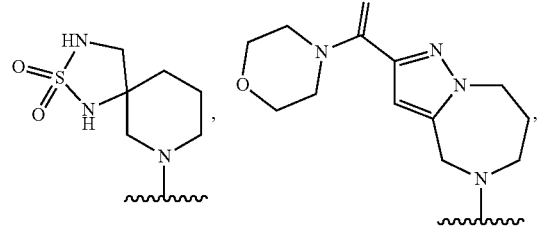
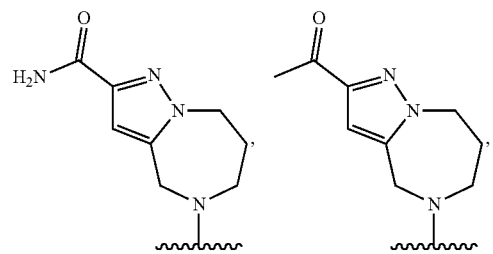
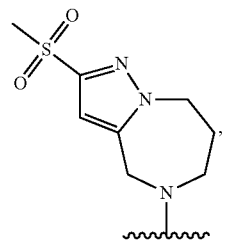
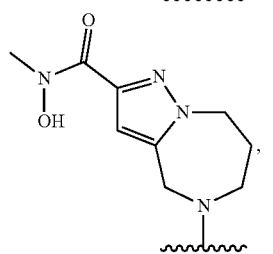
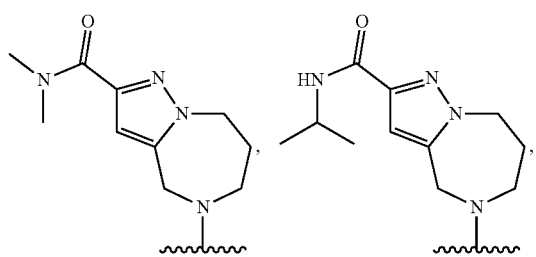
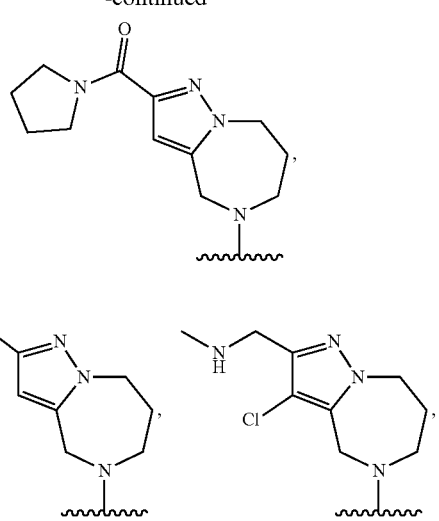
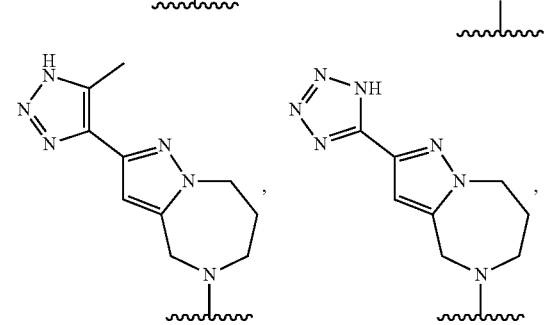
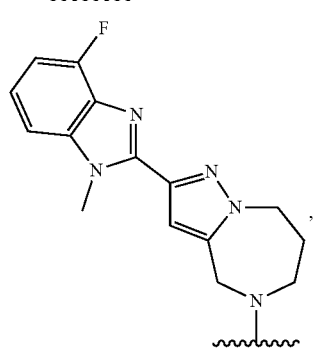
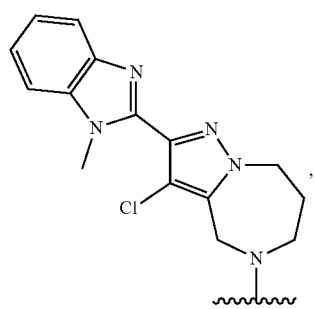

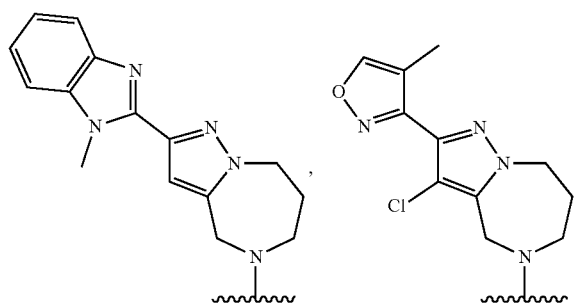

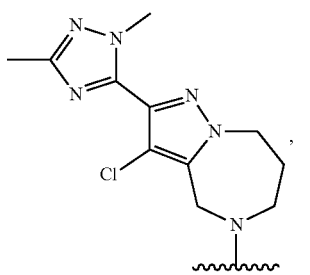

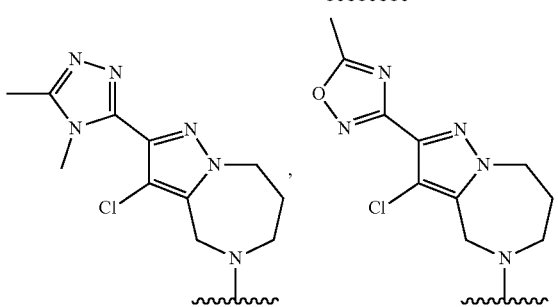

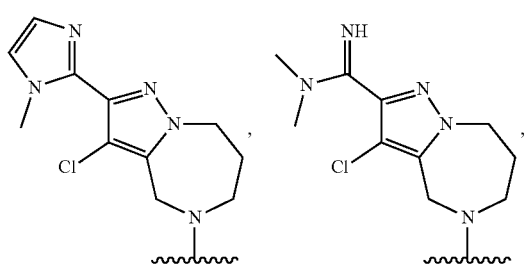

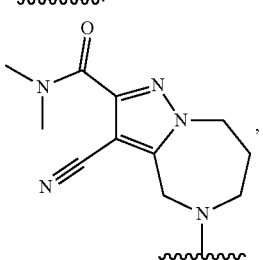

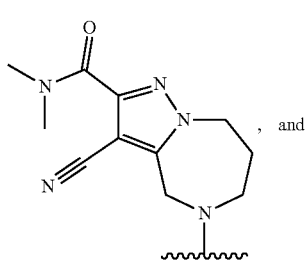

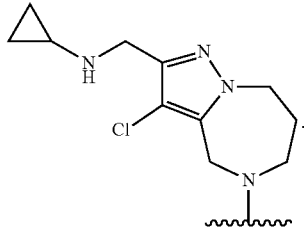 [SMILES: *N1CCCn2nc(CNC3CC3)c(Cl)c2C1]

In some embodiments, for a compound or salt of Formula (I), $R^1$ is selected from an optionally substituted unsaturated 6- to 8-membered heterocycle. In some cases, $R^1$ is selected from an optionally substituted unsaturated 6-membered heterocycle. In some cases, $R^1$ is selected from an optionally substituted unsaturated 7-membered heterocycle. In some cases, the heterocycle has 1 or 2 double bonds. In some cases, the heterocycle has only 1 double bond. In some cases, the heterocycle has only 2 double bonds. In some cases, $R^1$ is selected from

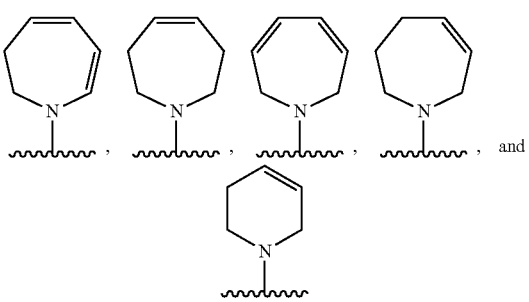

wherein each is optionally substituted with one or more substituents independently selected from halogen, —OH, —NH$_2$, —NO$_2$, C$_{1-6}$ aminoalkyl, C$_{1-6}$ alkoxy, C$_{1-6}$ hydroxyalkyl, C$_{1-6}$ haloalkyl, and C$_{1-6}$ alkyl. In some cases, $R^1$ is selected from

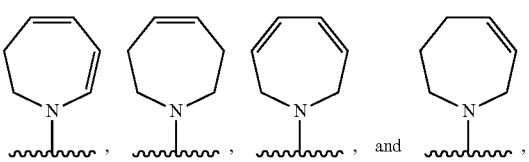

wherein each is optionally substituted with one or more substituents independently selected from halogen, —OH, —NH$_2$, —NO$_2$, C$_{1-6}$ aminoalkyl, C$_{1-6}$ alkoxy, C$_{1-6}$ hydroxyalkyl, C$_{1-6}$ haloalkyl, and C$_{1-6}$ alkyl. In some cases, $R^1$ is selected from

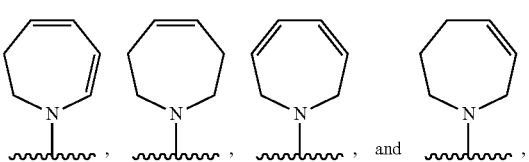

wherein each is optionally substituted with one or more substituents independently selected from halogen, —OH, —NH$_2$, —NO$_2$, C$_{1-6}$ aminoalkyl, C$_{1-6}$ alkoxy, C$_{1-6}$ hydroxyalkyl, C$_{1-6}$ haloalkyl, and C$_{1-6}$ alkyl. In some cases, R$^1$ is selected from

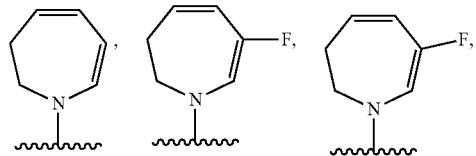

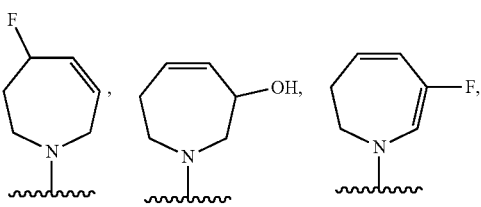

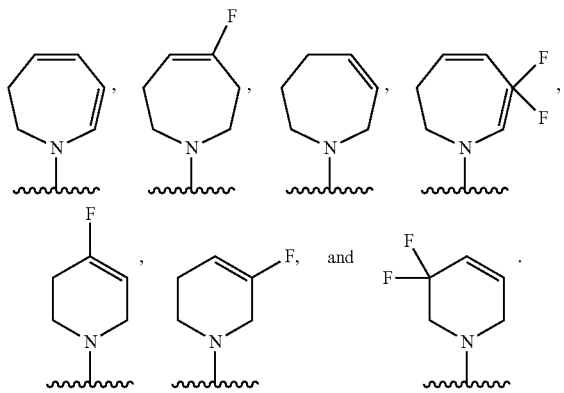

In some cases, R$^1$ is selected from

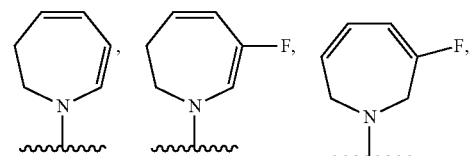

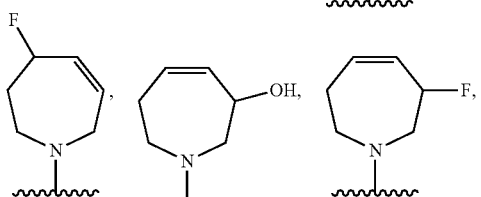

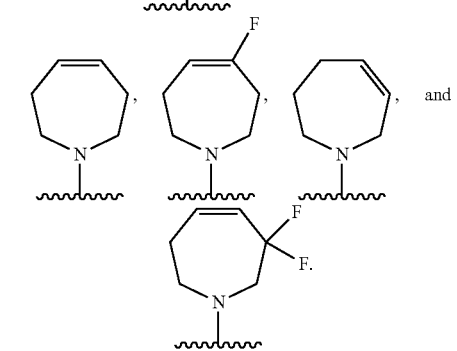

In some cases, R$^1$ is selected from

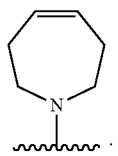

In some cases, R$^1$ is

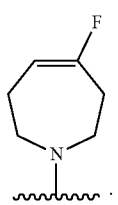 [SMILES: *N1CCC=C(F)CC1]

In some cases, R$^1$ is selected from

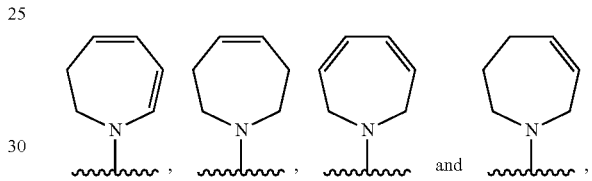

wherein each is substituted with one or more substituents independently selected from halogen.

In some embodiments, for a compound or salt of Formula (I), R$^1$ is selected from an unsaturated 6- to 7-membered heterocycle, wherein the unsaturated 6- to 7-membered heterocycle is substituted with one or more substituents selected from halogen. In some cases, the unsaturated 6- to 7-membered heterocycle is substituted with at least one halogen. In some cases, the unsaturated 6- to 7-membered heterocycle is substituted with at only one halogen. In some cases, the unsaturated 7-membered heterocycle is substituted with one fluorine. In some cases, R$^1$ is selected from an unsaturated 6-membered heterocycle, substituted with at least one halogen. In some cases, R$^1$ is selected from an unsaturated 7-membered heterocycle, substituted with at least one halogen. In some cases, R$^1$ is selected from

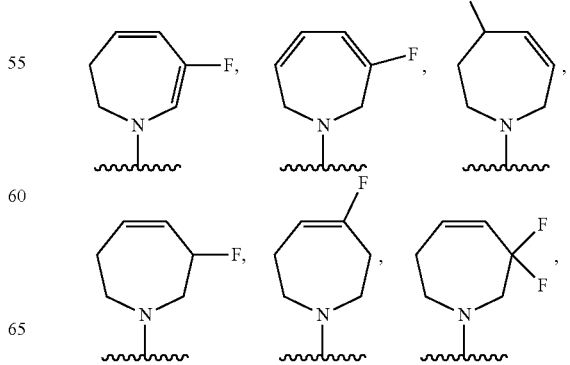

-continued

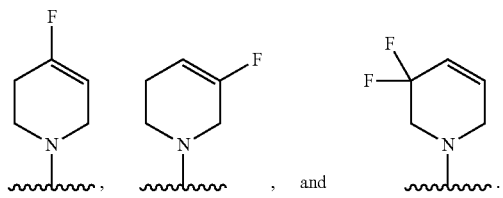

In some cases, R¹ is selected from

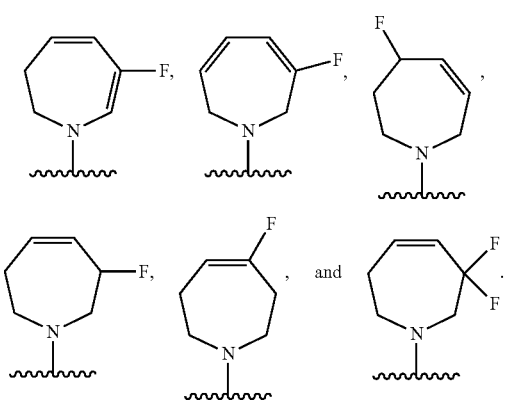

In some cases, R¹ is selected from

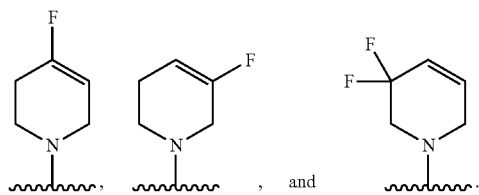

In some cases, R¹ is selected from

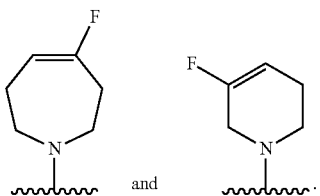 [SMILES: *N1CCC=C(F)CC1 ; *N1CCC=C(F)C1]

In some cases, R¹ is

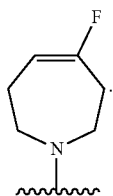

In some cases, R¹ is

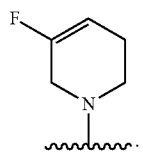

In some cases, R¹ is

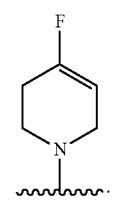

In some embodiments, for a compound or salt of Formula (I), R¹ is selected from an optionally substituted unsaturated 6- to 8-membered heterocycle. In some cases, R¹ is selected from an optionally substituted unsaturated 7-membered heterocycle. In some cases, R¹ is selected from

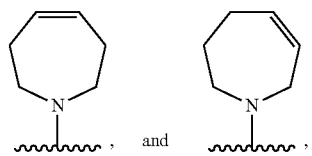 [SMILES: *N1CCC=CCC1 ; *N1CC=CCCC1]

wherein each is optionally substituted with one or more substituents independently selected from halogen, —OH, —NH₂, —NO₂, $C_{1-6}$ aminoalkyl, $C_{1-6}$ alkoxy, $C_{1-6}$ hydroxyalkyl, $C_{1-6}$ haloalkyl, and $C_{1-6}$ alkyl. In some cases, R¹ is selected from

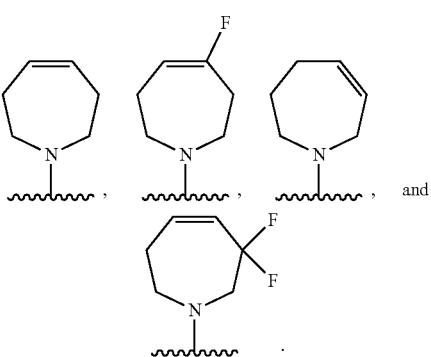

In some embodiments, for a compound or salt of Formula (I), R¹ is selected from an optionally substituted 6-membered heterocycle. In some cases, the 6-membered heterocycle contains only 1 nitrogen atom. In some cases, the 6-membered heterocycle of R¹ is bound to Formula (I) via the only 1 nitrogen atom. In some cases, R¹ is selected from

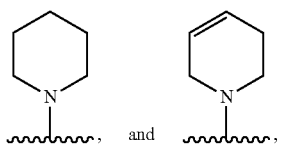 [SMILES: *N1CCCCC1 ; *N1CC=CCC1]

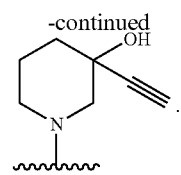

any of which is optionally substituted. In some cases, the one or more optional substituents of $R^1$ are each independently selected from halogen, —$OR^{20}$, —$N(R^{20})_2$, =O, —CN, $C_{1-6}$ hydroxyalkyl, $C_{1-6}$ cyanoalkyl, $C_{1-6}$ alkyl, and $C_{2-6}$ alkynyl. In some cases, the one or more optional substituents of $R^1$ are each independently selected from fluorine, —OH, —$NH_2$, —NH(CN), =O, —CN, $C_{1-6}$ hydroxyalkyl, $C_{1-6}$ cyanoalkyl, $C_{1-6}$ alkyl, and $C_{2-6}$ alkynyl. In some cases, the one or more optional substituents of $R^1$ are each independently selected from fluorine, —OH, —$NH_2$, —NH(CN), =O, —CN, $C_{1-6}$ hydroxyalkyl, $C_{1-6}$ alkyl, and $C_{2-6}$ alkynyl. In some cases, the 6-membered heterocycle is a partially unsaturated 6-membered heterocycle or a saturated 6-membered heterocycle. In some cases, the 6-membered heterocycle is partially unsaturated. In some cases, the 6-membered heterocycle is a saturated 6-membered heterocycle. In some cases, the 6-membered heterocycle is a monocyclic 6-membered heterocycle. In some cases, the 6-membered heterocycle is not a bridged heterocycle. In some cases, $R^1$ is selected from

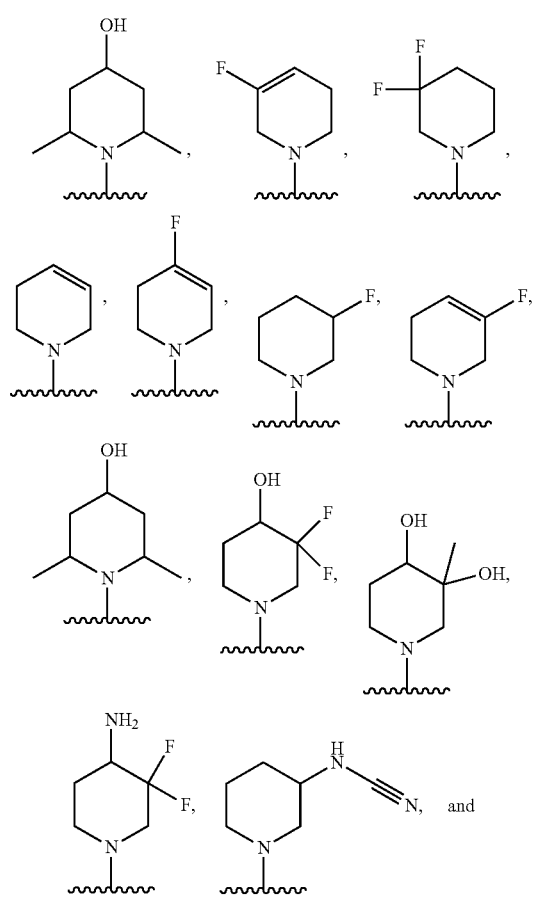

In some embodiments, for a compound of Formula (I), $R^1$ is selected from an optionally substituted 6-membered unsaturated heterocycle and 6-membered saturated heterocycle.

In some embodiments, for a compound or salt of Formula (I), $R^1$ is selected from

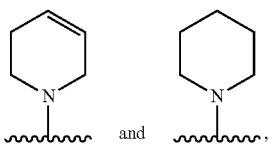 [SMILES: *N1CC=CCC1 ; *N1CCCCC1]

wherein each is optionally substituted with one or more substituents independently selected from halogen, —OH, —$NH_2$, —$NO_2$, $C_{1-6}$ aminoalkyl, $C_{1-6}$ alkoxy, $C_{1-6}$ hydroxyalkyl, $C_{1-6}$ haloalkyl, and $C_{1-6}$ alkyl.

In some embodiments, for a compound or salt of Formula (I), $R^1$ is selected from

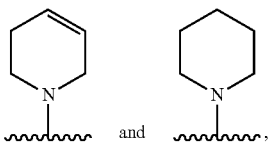 [SMILES: *N1CC=CCC1 ; *N1CCCCC1]

wherein each is optionally substituted with one or more substituents independently selected from halogen, and $C_{1-6}$ haloalkyl.

In some embodiments, for a compound or salt of Formula (I), $R^1$ is selected from

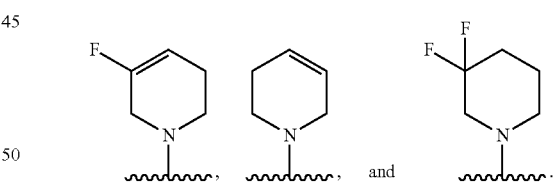

In some embodiments, for a compound or salt of Formula (I), $R^1$ is selected from

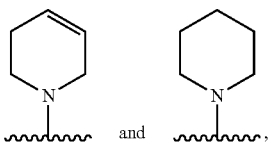 [SMILES: *N1CC=CCC1 ; *N1CCCCC1]

wherein each is optionally substituted two substituents independently selected from halogen, —OH, —$NH_2$, —$NO_2$, $C_{1-6}$ aminoalkyl, $C_{1-6}$ alkoxy, $C_{1-6}$ hydroxyalkyl, $C_{1-6}$ haloalkyl, and $C_{1-6}$ alkyl.

In some embodiments, for a compound or salt of Formula (I), R¹ is selected from

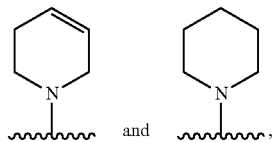 [SMILES: *N1CC=CCC1 ; *N1CCCCC1]

and, wherein each is optionally substituted with two substituents independently selected from halogen, and $C_{1-6}$ haloalkyl. In some cases, R¹ is

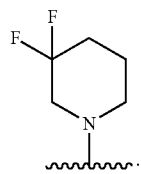 [SMILES: *N1CCCC(F)(F)C1]

In some embodiments, for a compound or salt of Formula (I), R¹ is selected from an optionally substituted 6- to 10-membered heterocycle. In some cases, the 6- to 10-membered heterocycle contains at least 1 nitrogen atom. In some cases, R¹ is selected from

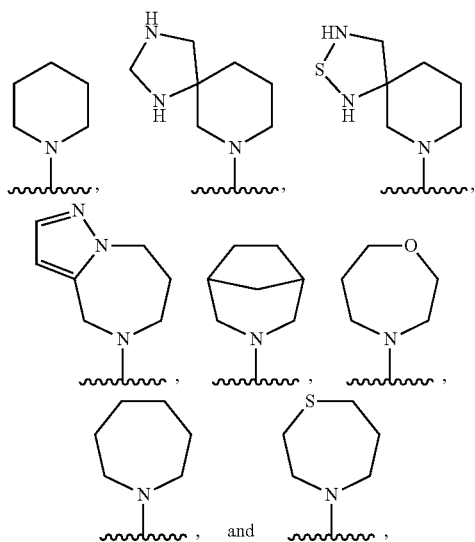

each of which is optionally substituted with one or more substituents independently selected from halogen, =O, —OH, —CN, —NHCN, —C(O)N(R²⁰)₂, $C_{1-6}$ aminoalkyl, $C_{1-6}$ hydroxyalkyl, $C_{1-6}$ cyanoalkyl, and $C_{1-6}$ alkyl. In some cases, each R²⁰ is independently selected from hydrogen; and $C_{1-6}$ alkyl, $C_{3-12}$ carbocycle, and 3- to 12-membered heterocycle, each of which is optionally substituted with one or more substituents independently selected from halogen, —OH, —CN, —NO₂, —NH₂, —N($C_{1-6}$ alkyl)₂, $C_{1-10}$ alkyl, —$C_{1-10}$ haloalkyl, —O—$C_{1-10}$ alkyl, oxo, $C_{3-12}$ carbocycle, and 3- to 12-membered heterocycle. In some cases, R¹ is selected from

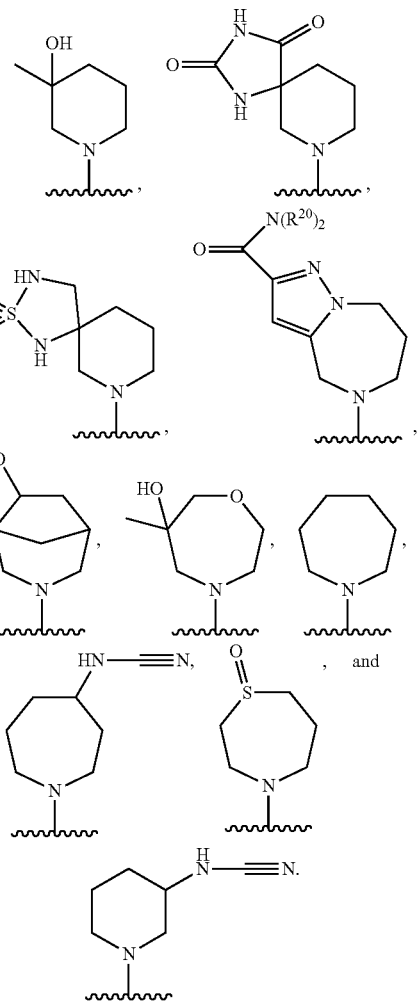

In some embodiments, for a compound or salt of Formula (I), R¹ is selected from 6- to 7-membered heterocycle. In some cases, R¹ is selected from 7-membered heterocycle. In some cases, R¹ is selected from 6-membered heterocycle. In some cases, the 6- to 7-membered heterocycle contains only 1 nitrogen atom and optionally one or more additional heteroatoms selected from oxygen, and sulfur. In some cases, the optionally one or more additional heteroatoms are selected from sulfur. In some cases, the optionally one or more additional heteroatoms are selected from oxygen. In some cases, the 6- to 7-membered heterocycle contains only 1 nitrogen atom and no further additional heteroatoms. In some cases, the 6- to 7-membered heterocycle is a non-aromatic 6- to 7-membered heterocycle. In some cases, the 6- to 7-membered heterocycle of R¹ is bound to Formula (I) via the only 1 nitrogen atom. In some cases, R¹ is selected from

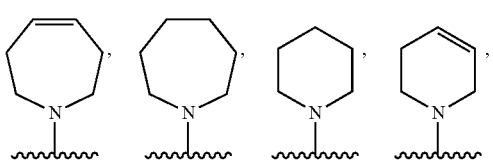

-continued

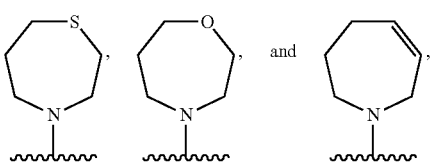

each of which is substituted. In some cases, $R^1$ is selected from

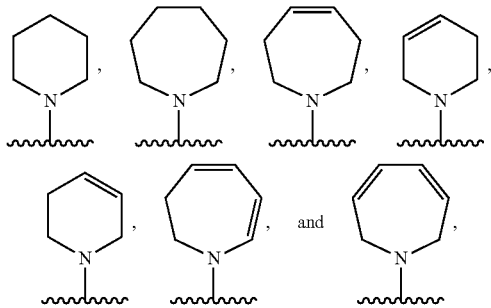

each of which is substituted. In some cases, the substituents of $R^1$ are each selected from one or more halogen, —$OR^{20}$, —$SR^{20}$, —$N(R^{20})_2$, —NHCN, —$NO_2$, =O, —CN, $C_{1-6}$ fluoroalkyl, and $C_{2-6}$ alkynyl; and further optionally substituted with one or more substituents independently selected from —$C(O)N(R^{20})_2$, $C_{1-6}$ aminoalkyl, $C_{1-6}$ hydroxyalkyl, $C_{1-6}$ cyanoalkyl, $C_{1-6}$ alkyl, and $C_{2-6}$ alkenyl. In some cases, the substituents of $R^1$ are each selected from one or more halogen, —$OR^{20}$, —$N(R^{20})_2$, —NHCN, =O, —CN, and $C_{2-6}$ alkynyl; and further optionally substituted with one or more substituents independently selected from —$C(O)N(R^{20})_2$, $C_{1-6}$ aminoalkyl, $C_{1-6}$ hydroxyalkyl, $C_{1-6}$ cyanoalkyl, and $C_{1-6}$ alkyl. In some cases, the substituents of $R^1$ are each selected from one or more halogen, —OH, —NHCN, =O, —CN, and $C_{2-6}$ alkynyl; and further optionally substituted with one or more substituents independently selected from $C_{1-6}$ alkyl. In some cases, $R^1$ is selected from

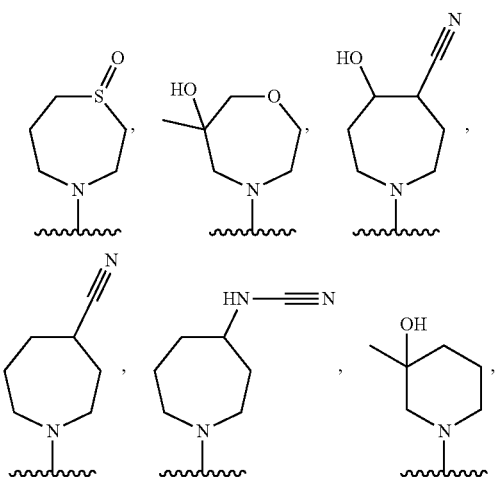

-continued

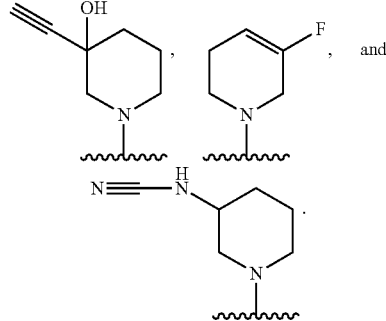

In some cases, $R^1$ is selected from

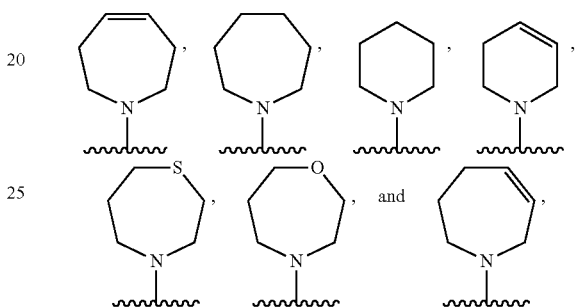

each of which is optionally substituted. In some cases, $R^1$ is selected from

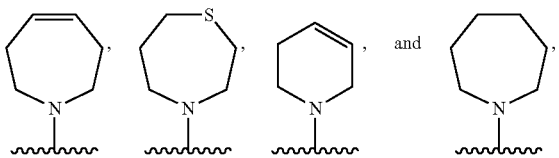

each of which is optionally substituted. In some cases, $R^1$ is selected from

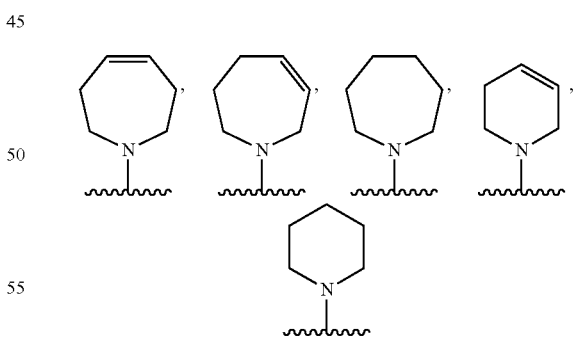

each of which is optionally substituted. In some cases, the one or more optional substituents of $R^1$ are each independently selected from fluorine, —OH, —$C(O)NH_2$, —NH—C(O)—($C_{1-6}$ alkoxy), —NH—C(O)—($C_{1-6}$ hydroxyalkyl), —$NH_2$, —NH(CN), =O, —CN, $C_{1-6}$ hydroxyalkyl, $C_{1-6}$ cyanoalkyl, $C_{1-6}$ alkyl, and $C_{2-6}$ alkynyl. In some cases, the one or more optional substituents of $R^1$ are each independently selected from halogen, —OH, —CN, $C_{1-6}$ cyanoalkyl, $C_{1-6}$ alkyl, and $C_{2-6}$ alkynyl. In some cases, the one or more optional substituents of $R^1$ are each independently selected from halogen, —OH, and —CN. In some cases, the one or more optional substituents of $R^1$ are each independently selected from fluorine, —OH, —CN, $C_{1-6}$ cyanoalkyl, $C_{1-6}$ alkyl, oxo, and $C_{2-6}$ alkynyl. In some cases, the one or more optional substituents of $R^1$ are each independently selected from fluorine, —OH, —CN, $C_{1-6}$ cyanoalkyl, $C_{1-6}$ alkyl, and $C_{2-6}$ alkynyl. In some cases, $R^1$ is selected from

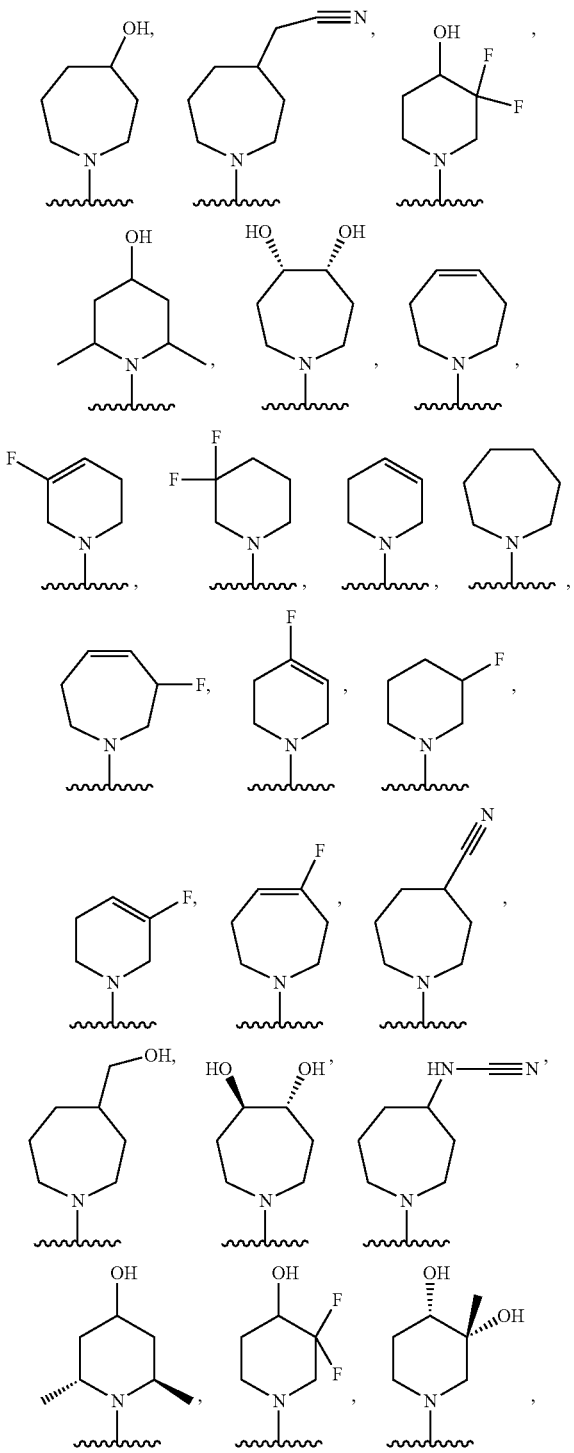

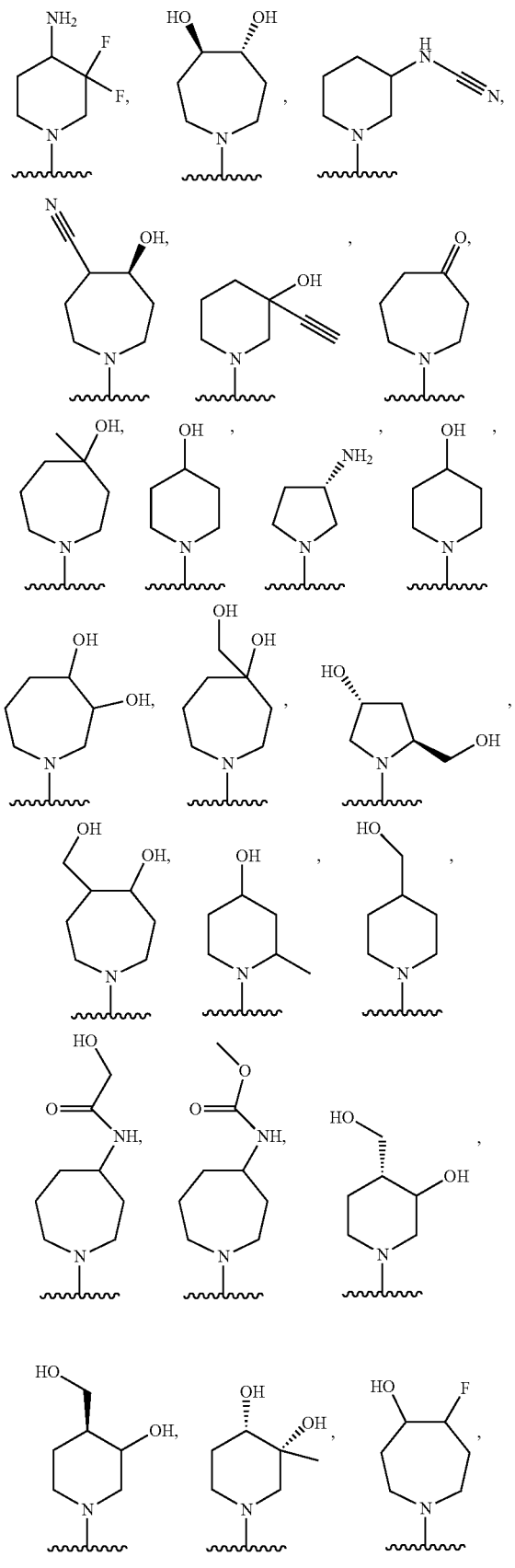

135
-continued
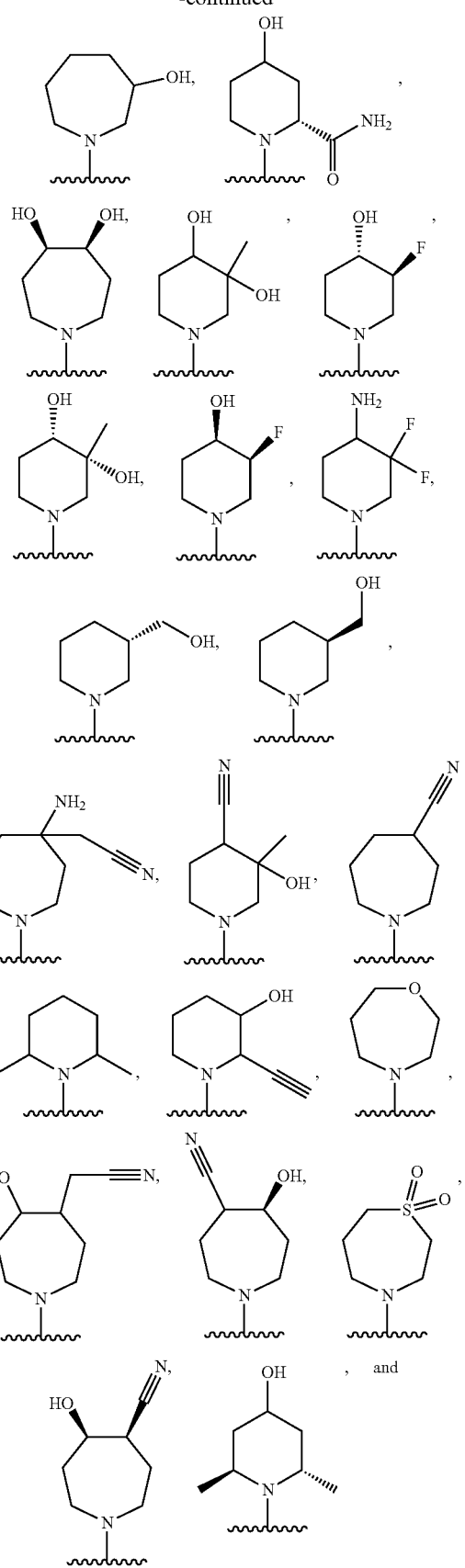
136
-continued
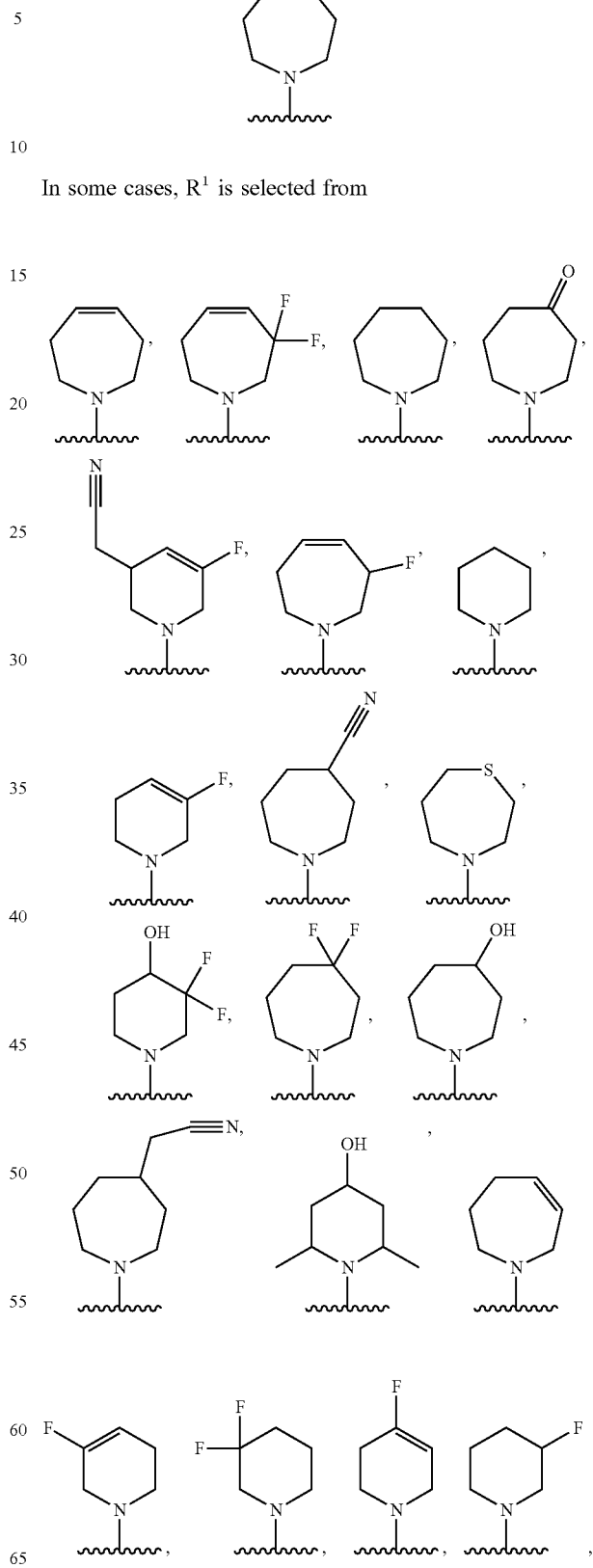
In some cases, R¹ is selected from -continued
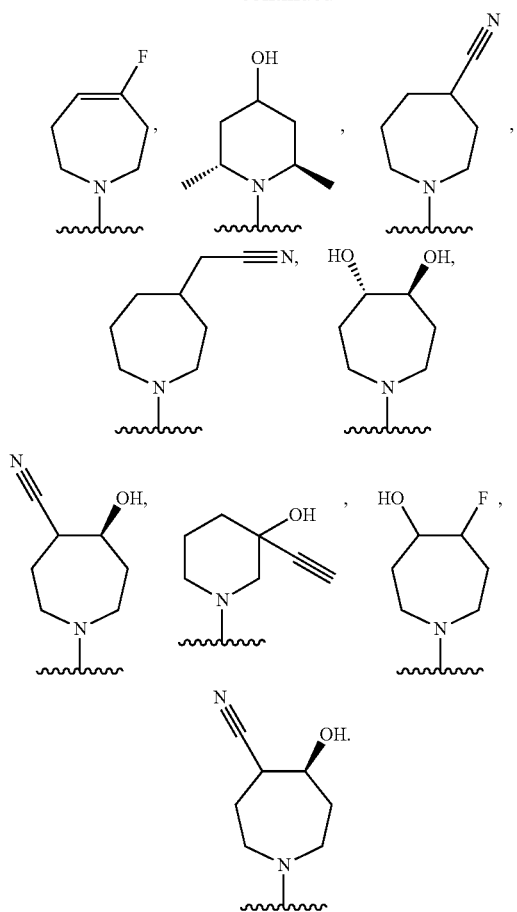
In some cases, R¹ is selected from
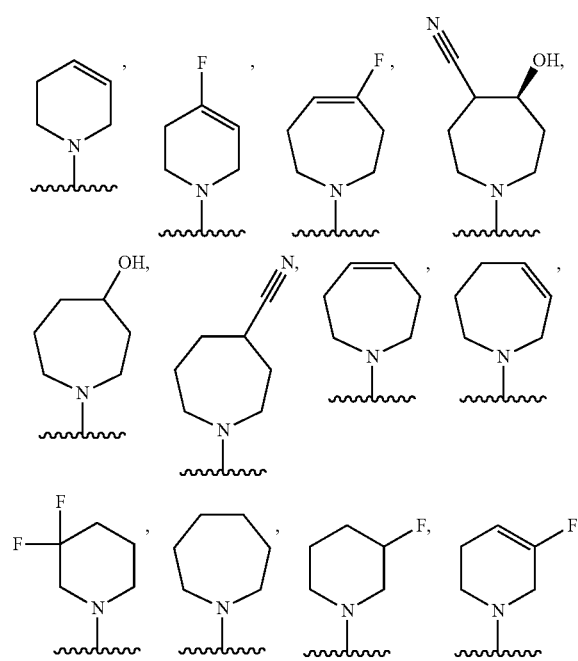
-continued
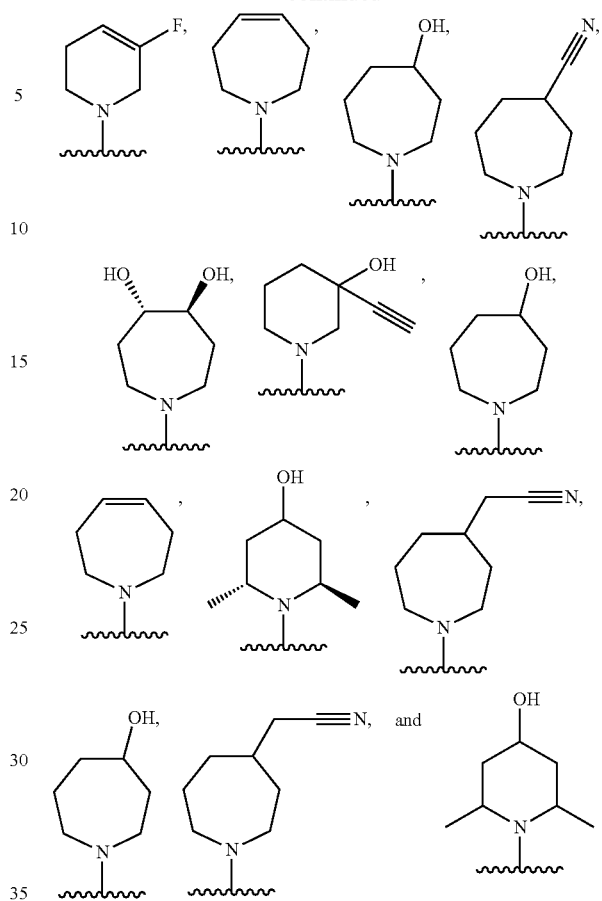
In some cases, R¹ is selected from
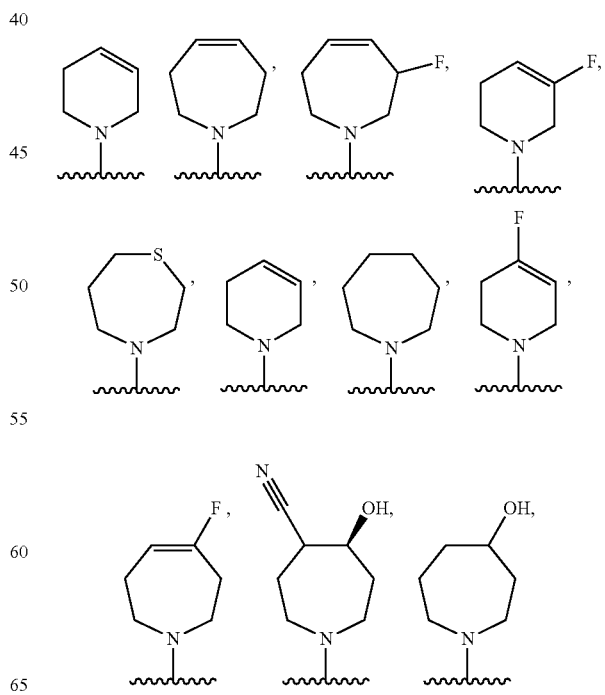

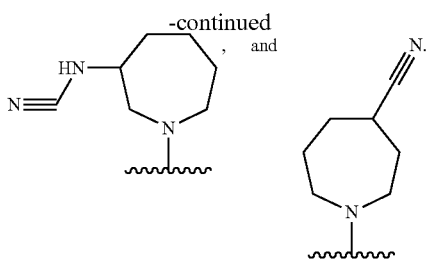

In some cases, $R^1$ is selected from

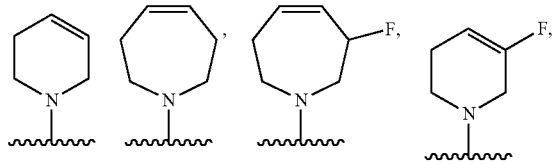

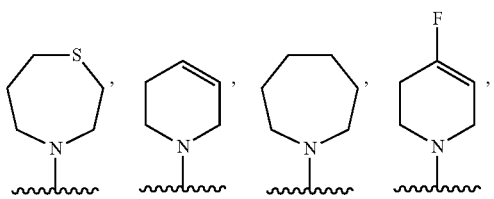

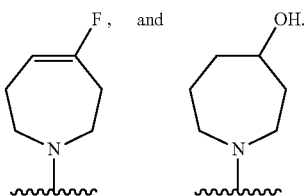

In some embodiments, for a compound or salt of Formula (I), $R^1$ is selected from 5- to 10-membered heterocycle, 7-, 8-, 10-, 11-membered spiro heterocycle, and 6-, 9-, 10-, 11-, and 12-membered fused heterocycle, and wherein each are optionally substituted with one or more substituents independently selected from halogen, —N($R^{20}$)$_2$, $C_{1-6}$ alkyl, —O$R^{20}$, —N($R^{20}$)C(O)N($R^{20}$)$_2$, —B(O$R^{20}$)$_2$, $C_{1-6}$ cyanoalkyl, —N($R^{20}$)C(O)N($R^{20}$)$_2$, =O, $C_{1-6}$ hydroxyalkyl, halogen, —N($R^{20}$)C(O)$R^{20}$, —N($R^{20}$) S(O)$_2$($R^{20}$), and $C_{1-6}$ aminoalkyl. In some cases, $R^1$ is selected from

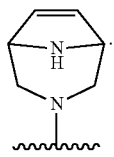

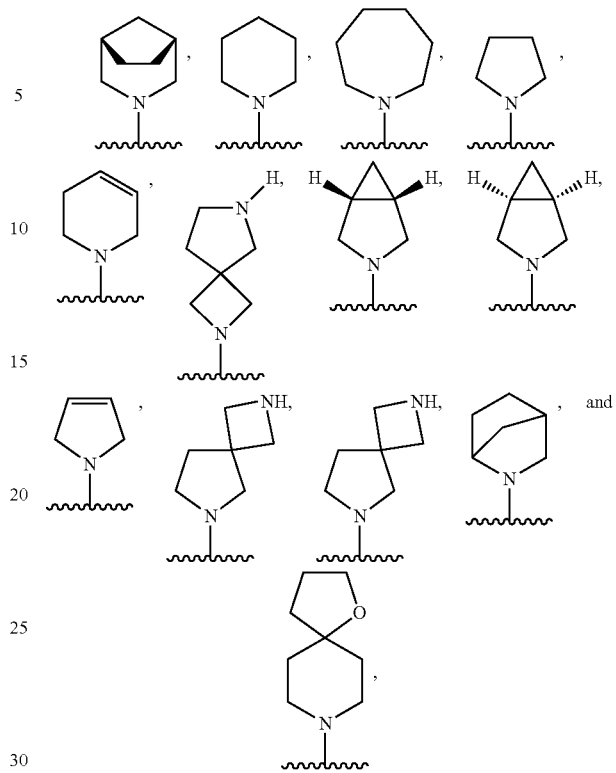

wherein each is optionally substituted with one or more substituents independently selected from halogen, —N($R^{20}$)$_2$, $C_{1-6}$ alkyl, —O$R^{20}$, —N($R^{20}$)C(O)N($R^{20}$)$_2$, —B(O$R^{20}$)$_2$, $C_{1-6}$ cyanoalkyl, —N($R^{20}$)C(O)N($R^{20}$)$_2$, =O, $C_{1-6}$ hydroxyalkyl, halogen, —N($R^{20}$)C(O)$R^{20}$, —N($R^{20}$) S(O)$_2$($R^{20}$), and $C_{1-6}$ aminoalkyl. In some cases, $R^1$ is selected from

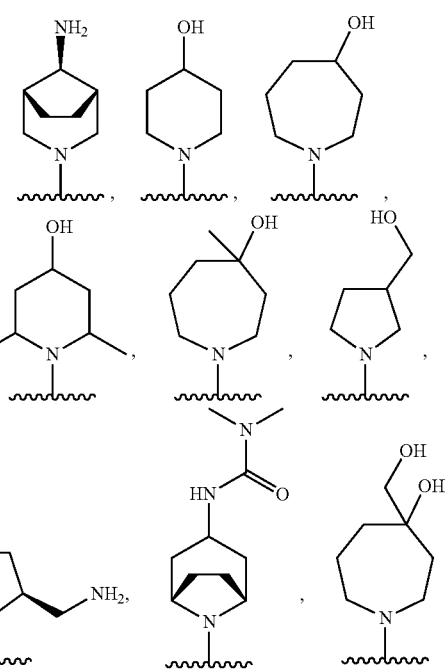

141
-continued
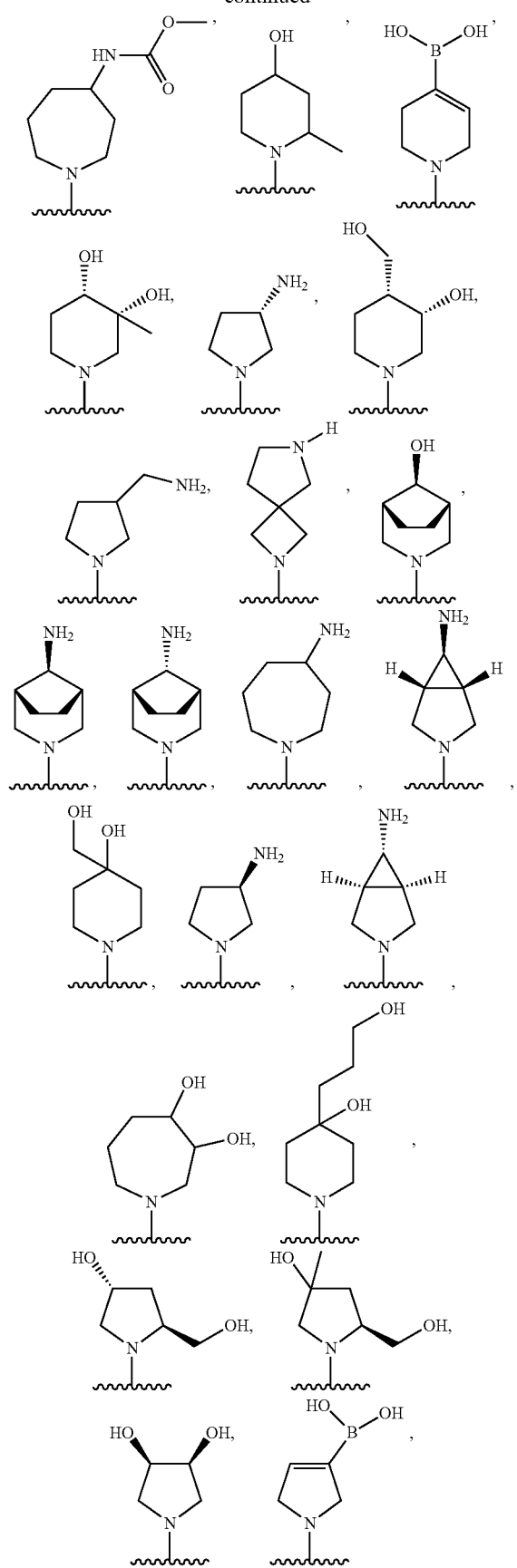
142
-continued
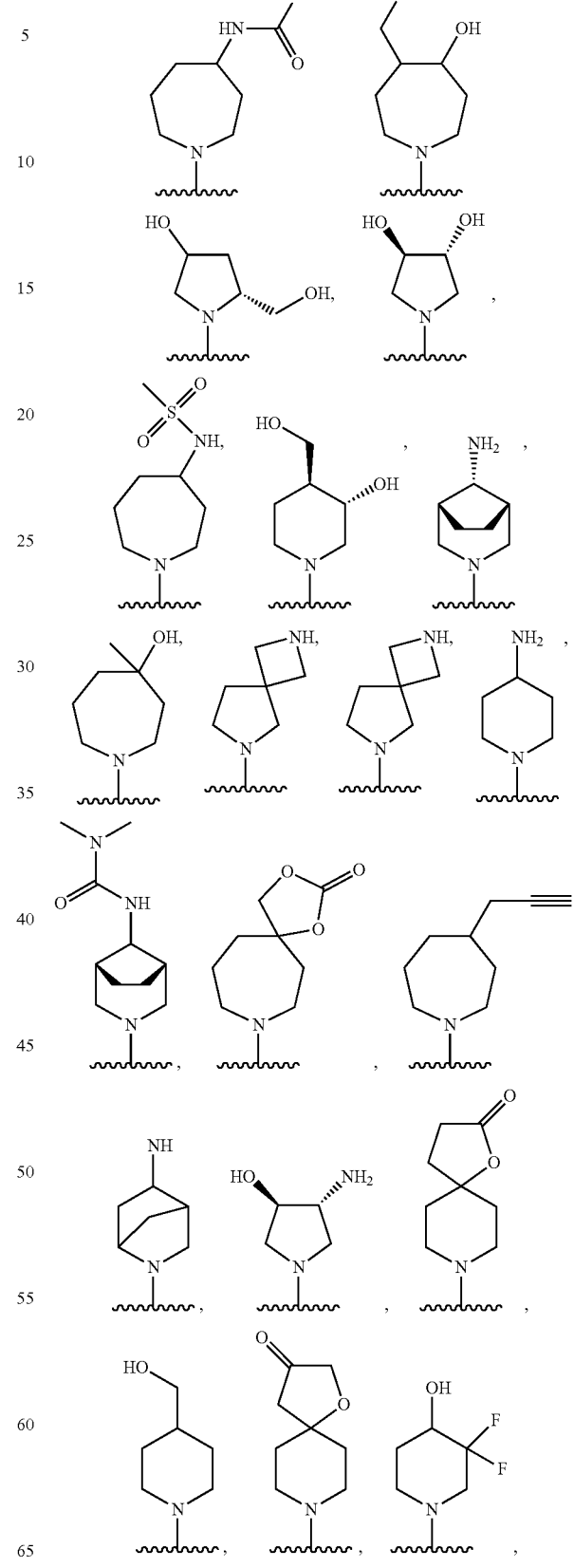

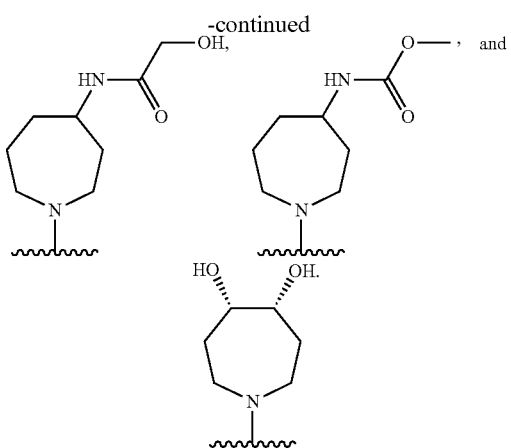

In some embodiments, for a compound or salt of Formula (I), $R^1$ is selected from an optionally substituted 10-membered heterocycle. In some cases, the 10-membered heterocycle is a bicyclic heterocycle. In some cases, the 10-membered heterocycle is a spiro heterocycle. In some cases, the 10-membered heterocycle is a fused heterocycle. In some cases, the 10-membered heterocycle is a saturated heterocycle. In some cases, the 10-membered heterocycle is a non-aromatic heterocycle. In some cases, the 10-membered heterocycle contains at least 1 nitrogen atom. In some cases, the 10-membered heterocycle contains at least 2 nitrogen atoms. In some cases, the 10-membered heterocycle contains at least 3 nitrogen atoms. In some cases, the 10-membered heterocycle contains at least 1 sulfur atom. In some cases, $R^1$ is selected from

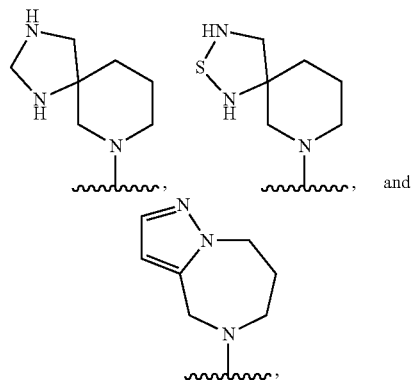

each of which is optionally substituted with one or more substituents independently selected from halogen, =O, —OH, —CN, —NHCN, —C(O)N($R^{20}$)$_2$, —C(O)NR$^{20}$OR$^{20}$, $C_{1-6}$ aminoalkyl, $C_{1-6}$ hydroxyalkyl, $C_{1-6}$ cyanoalkyl, and $C_{1-6}$ alkyl. In some cases, $R^1$ is selected from

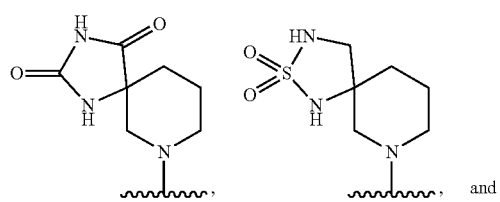

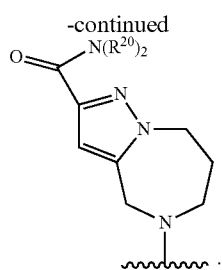

In some cases, $R^1$ is selected from

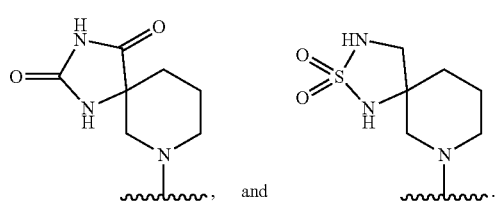 [SMILES: *N1CCCC2(C1)NC(=O)NC2=O ; *N1CCCC2(CNS(=O)(=O)N2)C1]

In some cases, $R^1$ is selected from

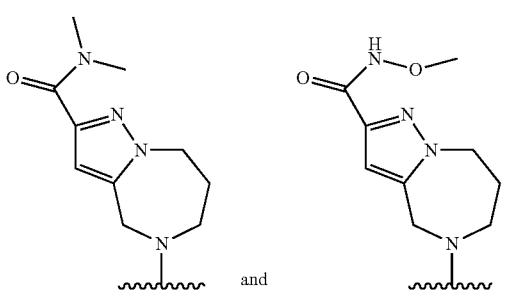

In some cases, $R^1$ is selected from

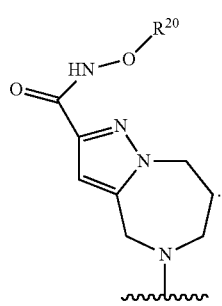

In some cases, $R^1$ is selected from

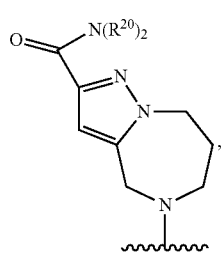

which is optionally substituted with one or more substituents independently selected from halogen, —OR²⁰, —SR²⁰, —N(R²⁰)₂, —NO₂, =O, —CN, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, $C_{2-6}$ alkenyl, and $C_{2-6}$ alkynyl.

In some embodiments, for a compound or salt of Formula (I), $R^1$ is selected from an optionally substituted unsaturated 9- to 11-membered heterocycle. In some cases, $R^1$ is selected from an optionally substituted unsaturated 10-membered heterocycle. In some cases, $R^1$ is selected from an optionally substituted unsaturated 10-membered fused heterocycle. In some cases, $R^1$ is

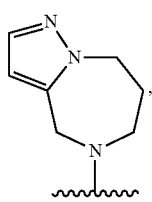

which is optionally substituted. In some cases, the one or more optional substituents are selected from halogen, —OH, —C(O)N(R²⁰)₂, —N(R²⁰)₂, —C(O)R²⁰, —NO₂, =O, —CN, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, and $C_{2-6}$ alkynyl. In some cases, $R^1$ is

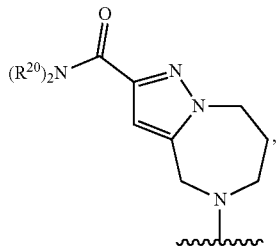

optionally substituted with one or more substituents selected from —N(R²⁰)₂, —C(O)R²⁰, —NO₂, =O, —CN, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, and $C_{2-6}$ alkynyl. In some cases, each $R^{20}$ is independently selected from hydrogen; and $C_{1-6}$ alkyl, and $C_{3-12}$ carbocycle, and each of which is optionally substituted with one or more substituents independently selected from halogen, —OH, —CN, —NO₂, —NH₂, $C_{1-10}$ alkyl, —$C_{1-10}$ haloalkyl, —O—$C_{1-10}$ alkyl, $C_{2-10}$ alkenyl, $C_{2-10}$ alkynyl, $C_3$-12 carbocycle, and 3- to 12-membered heterocycle.

In some embodiments, for a compound or salt of Formula (I), $R^1$ is selected from a 7- to 11-membered spiro heterocycle. In some cases, $R^1$ is selected from a 10-membered spiro heterocycle. In some cases, the spiro heterocycle has at least 3 nitrogen atoms. In some cases, the spiro heterocycle has at least 1 sulfur atom. In some cases, $R^1$ is selected from

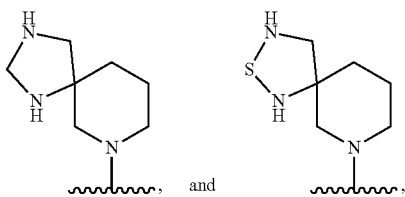 [SMILES: *N1CCCC2(CNCN2)C1 ; *N1CCCC2(CNSN2)C1]

each of which is optionally substituted. In some cases, the one or more optional substituents are independently selected from halogen, —OH, —N(R²⁰)₂, —NO₂, =O, —CN, —NHCN, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, $C_{2-6}$ alkenyl, and $C_{2-6}$ alkynyl. In some cases, $R^1$ is selected from

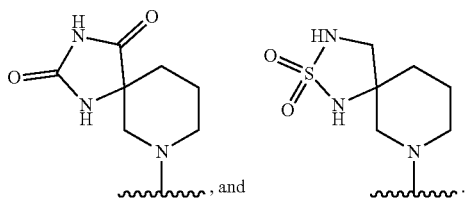 [SMILES: *N1CCCC2(C1)NC(=O)NC2=O ; *N1CCCC2(CNS(=O)(=O)N2)C1]

In some cases, $R^1$ is

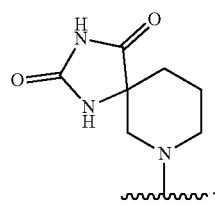 [SMILES: *N1CCCC2(C1)NC(=O)NC2=O]

In some cases, $R^1$ is

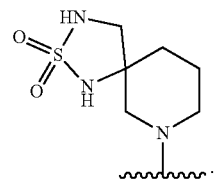 [SMILES: *N1CCCC2(CNS(=O)(=O)N2)C1]

In some embodiments, for a compound or salt of Formula (I), $R^1$ is selected from an optionally substituted 8- to 10-membered fused heterocycle. In some cases, the 8- to 10-membered fused heterocycle is a bicyclic heterocycle. In some cases, the 8- to 10-membered fused heterocycle is a saturated heterocycle. In some cases, the 8- to 10-membered fused heterocycle is an unsaturated heterocycle. In some cases, the 8- to 10-membered heterocycle is a non-aromatic heterocycle. In some cases, $R^1$ is selected from an optionally substituted 10-membered fused heterocycle. In some cases, the 10-membered fused heterocycle is a bicyclic heterocycle. In some cases, the 10-membered fused heterocycle is a saturated heterocycle. In some cases, the 10-membered heterocycle is a non-aromatic heterocycle. In some cases, the fused heterocycle has one saturated ring and one aromatic ring. In some cases, the fused heterocycle has one saturated ring and one unsaturated ring. In some cases, the fused heterocycle has two saturated rings. In some cases, the 10-membered heterocycle contains at least 1 nitrogen atom. In some cases, the 10-membered heterocycle contains at least 2 nitrogen atoms. In some cases, the 10-membered heterocycle contains at least 3 nitrogen atoms. In some cases, R[1] is selected from

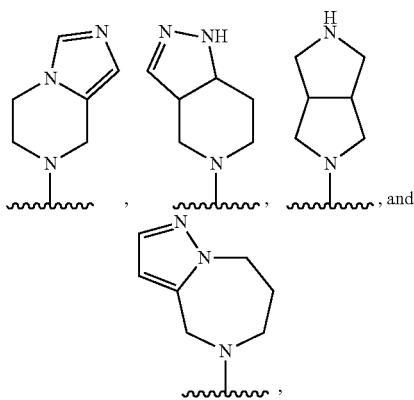

each of which is optionally substituted with one or more substituents. In some cases, R[1] is selected from

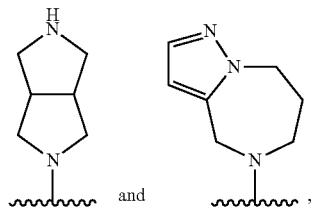 [SMILES: *N1CC2CNCC2C1 ; *N1CCCn2nccc2C1]

each of which is optionally substituted with one or more substituents. In some cases, R[1] is

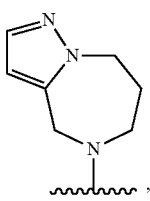

which is optionally substituted with one or more substituents. In some cases, the one or more optional substituents of R[1] are independently selected from halogen, —OH, —S(O)$_2$(R$^{20}$), —S(O)$_2$N(R$^{20}$)$_2$, —S(O)N(R$^{20}$)$_2$, —S(O)R$^{20}$(=NR$^{20}$), —C(O)N(R$^{20}$)$_2$, —C(O)NHOR$^{20}$, —N(R$^{20}$)$_2$, —C(O)R$^{20}$, —NO$_2$, =O, —CN, C$_{1-6}$ alkyl-N(R$^{20}$)$_2$, C$_{1-6}$ aminoalkyl, C$_{1-6}$ alkoxy, C$_{1-6}$ hydroxyalkyl, C$_{1-6}$ cyanoalkyl, C$_{1-6}$ haloalkyl, C$_{1-6}$ alkyl, and C$_{2-6}$ alkynyl. In some cases, the optional one or more substituents are independently selected from halogen, =O, —OH, —CN, —NHCN, —S(O)$_2$(R$^{20}$), —S(O)$_2$N(R$^{20}$)$_2$, —S(O)N(R$^{20}$)$_2$, —S(O)R$^{20}$(=NR$^{20}$), —C(O)R$^{20}$, —C(O)N(R$^{20}$)$_2$, —C(O)NR$^{20}$OR$^{20}$, C$_{1-6}$ alkyl-N(R$^{20}$)$_2$, C$_{1-6}$ aminoalkyl, C$_{1-6}$ hydroxyalkyl, C$_{1-6}$ cyanoalkyl, and C$_{1-6}$ alkyl. In some cases, the optional one or more substituents are independently selected from halogen, =O, C$_{1-6}$ alkyl-N(R$^{20}$)$_2$, —S(O)$_2$(R$^{20}$), —S(O)N(R$^{20}$)$_2$, —S(O)R$^{20}$(=NR$^{20}$), —C(O)R$^{20}$, —C(O)N(R$^{20}$)$_2$, and —C(O)NR$^{20}$OR$^{20}$. In some cases, the optional one or more substituents are independently selected from halogen, =O, —S(O)$_2$(R$^{20}$), —S(O)N(R$^{20}$)$_2$, —S(O)R$^{20}$(=NR$^{20}$), —C(O)R$^{20}$, —C(O)N(R$^{20}$)$_2$, and —C(O)NR$^{20}$OR$^{20}$. In some cases, the optional one or more substituents are independently selected from —C(O)R$^{20}$, —C(O)N(R$^{20}$)$_2$, and —C(O)NR$^{20}$OR$^{20}$. In some cases, the optional one or more substituents are independently selected from —S(O)$_2$(R$^{20}$), —S(O)$_2$N(R$^{20}$)$_2$, —S(O)N(R$^{20}$)$_2$, —S(O)R$^{20}$(=NR$^{20}$). In some cases, the optional one or more substituents are independently selected from —S(O)N(R$^{20}$)$_2$. In some cases, the optional one or more substituents are independently selected from S(O)$_2$(R$^{20}$). In some cases, the optional one or more substituents are independently selected from S(O)R$^{20}$(=NR$^{20}$). In some cases, the optional one or more substituents are independently selected from —C(O)R$^{20}$. In some cases, the optional one or more substituents are independently selected from —C(O)N(R$^{20}$)$_2$. In some cases, the optional one or more substituents are independently selected from —C(O)NR$^{20}$OR$^{20}$. In some cases, R[1] is selected from

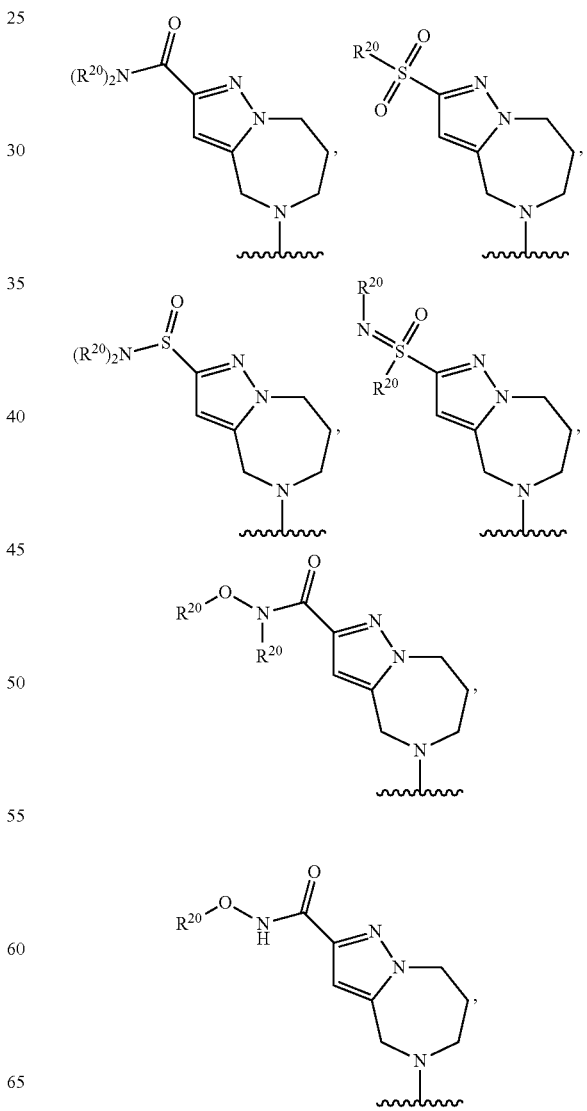

-continued

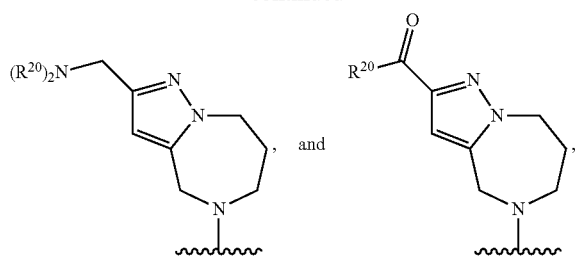
, and each of which is further optionally substituted. In some cases, the further one or more optional substituents are selected from halogen, —OH, =O, —CN, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, and $C_{2-6}$ alkynyl. In some cases, the further one or more optional substituents are selected from halogen and $C_{1-6}$ alkyl. In some cases, the further one or more optional substituents are selected from halogen. In some cases, each $R^{20}$ is independently selected from hydrogen; and $C_{1-6}$ alkyl, $C_{3-12}$ carbocycle, and 3- to 12-membered heterocycle. In some cases, each $R^{20}$ is independently selected from hydrogen; and $C_{1-6}$ alkyl, and 3- to 12-membered heterocycle. In some cases, each $R^{20}$ is independently selected from hydrogen; and $C_{1-6}$ alkyl, and 3- to 12-membered saturated heterocycle. In some cases, each $R^{20}$ is independently selected from 5- to 6-membered saturated heterocycle. In some cases, the heterocycle of $R^{20}$ has at least one nitrogen atom. In some cases, the heterocycle of $R^{20}$ has at least one sulfur atom. In some cases, the heterocycle of $R^{20}$ has at least one oxygen atom. In some cases, the heterocycle of $R^{20}$ contains only 1 heteroatom. In some cases, the heterocycle of $R^{20}$ has at least two heteroatoms. In some cases, the heterocycle of $R^{20}$ contains only 2 heteroatoms. In some cases, the optional one or more substituents of $R^1$ are independently selected from halogen,

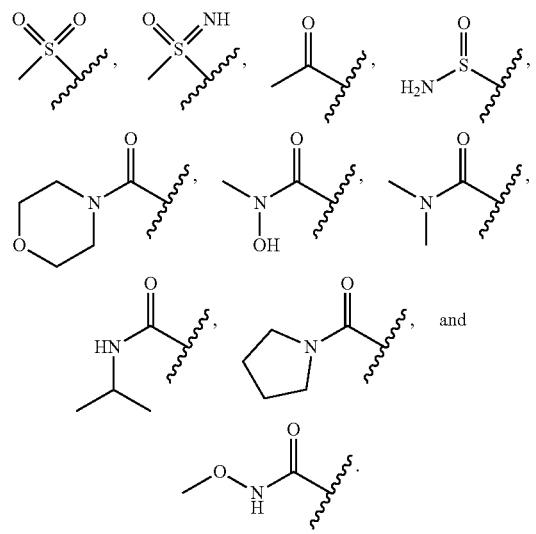

In some cases the optional one or more substituents of $R^1$ are independently selected from

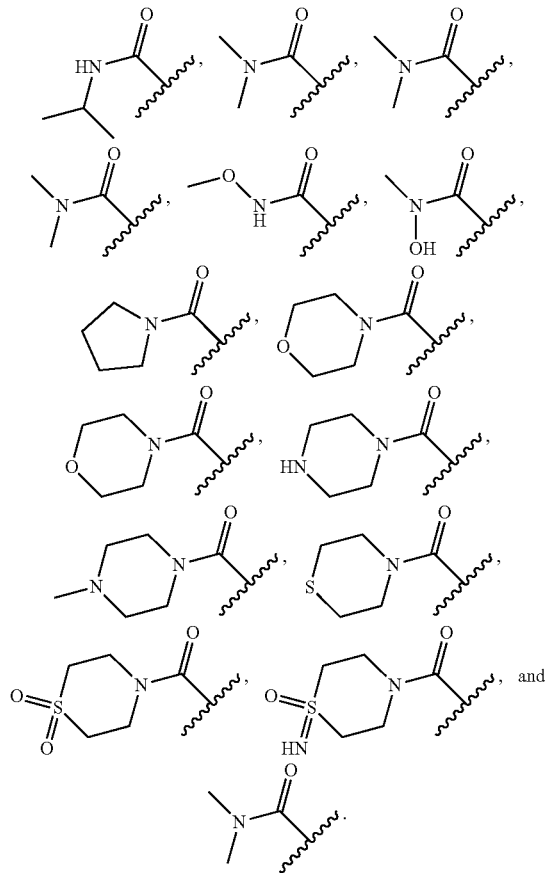

In some cases, $R^1$ is selected from

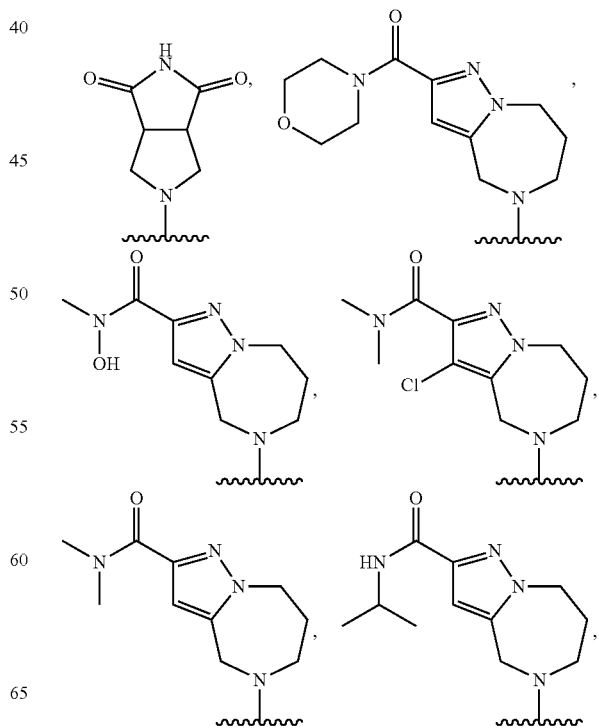

-continued
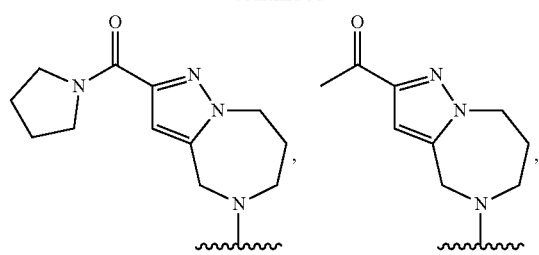
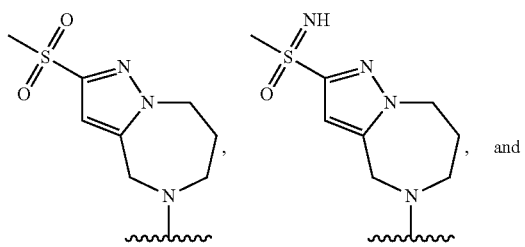
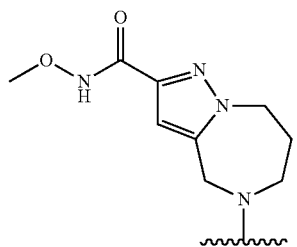
In some cases, $R^1$ is selected from
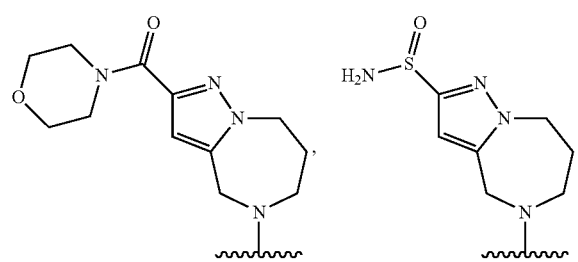
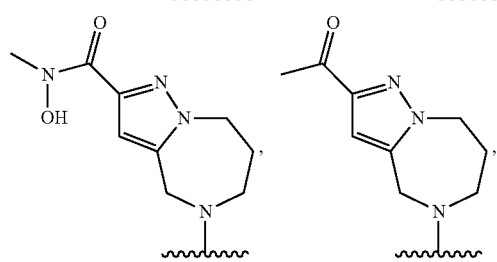
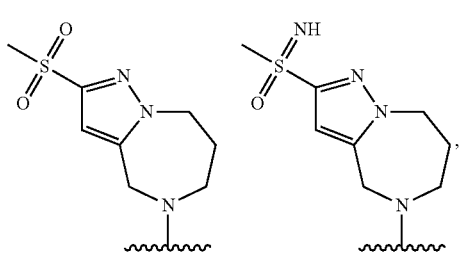
-continued
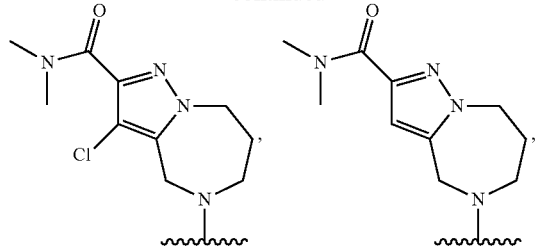
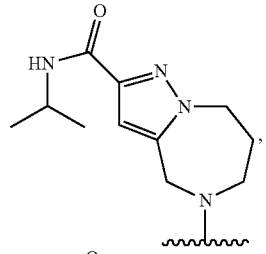
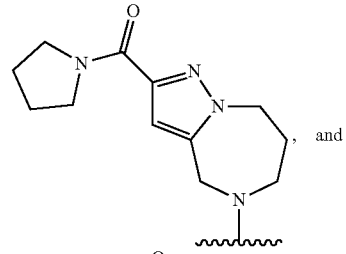
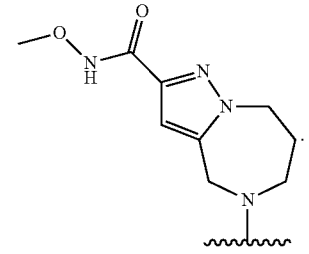
In some cases, the optional one or more substituents of $R^1$ are independently selected from halogen, and $C_{1-6}$ alkyl-N$(R^{20})_2$. In some cases, the optional one or more substituents of $R^1$ are independently selected from halogen,
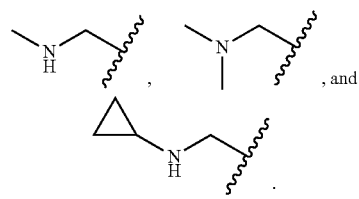
In some cases, $R^1$ is selected from
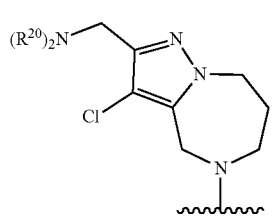

In some cases, each $R^{20}$ is independently selected from hydrogen, $C_{1-6}$ alkyl, and $C_{3-6}$ carbocycle. In some cases, $R^1$ is selected
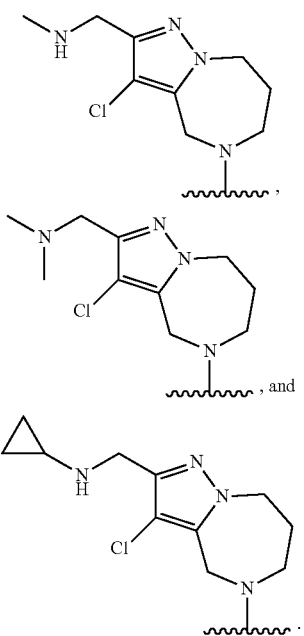
In some cases, $R^1$ is selected
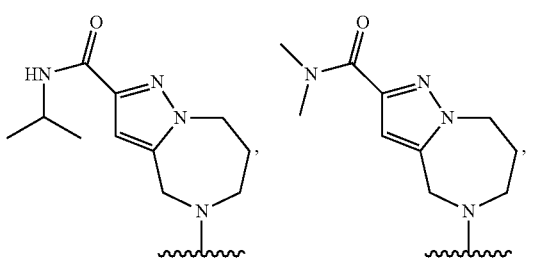
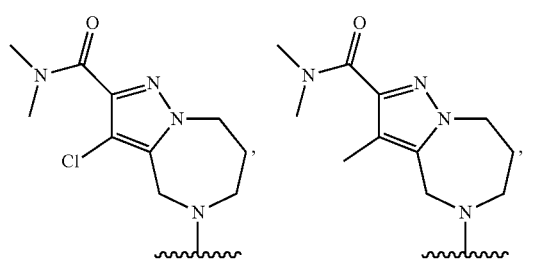
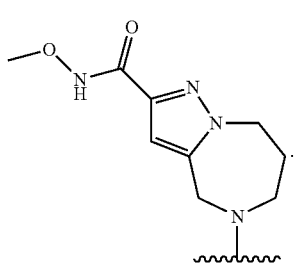
-continued
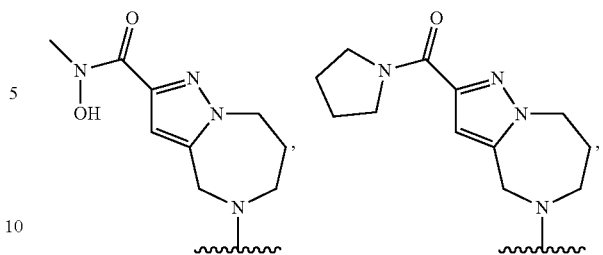

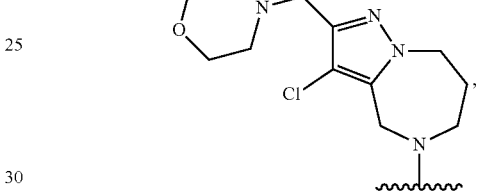
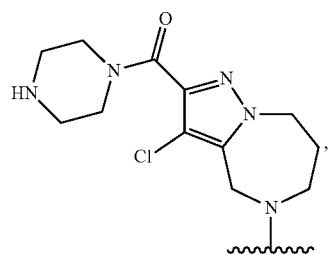
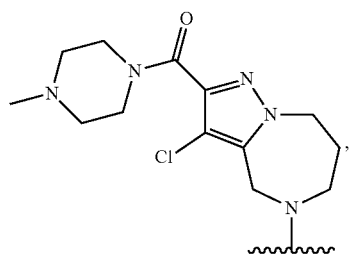
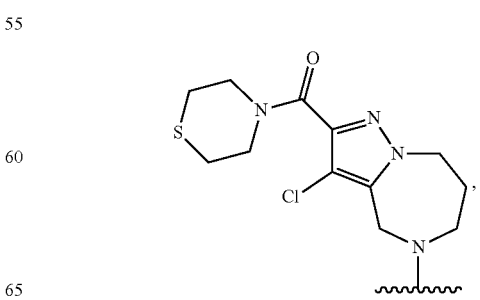

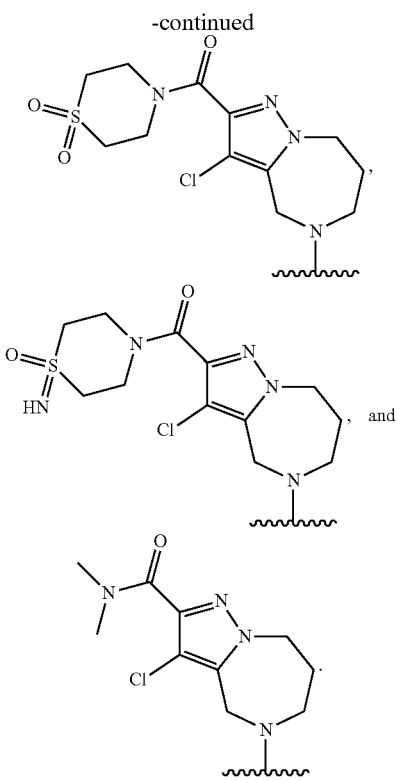

In some embodiments, for a compound or salt of Formula (I), when $R^1$ is substituted with —C(O)$R^{20}$, $R^{20}$ is selected from a 5- to 12-membered heterocycle.

In some embodiments, for a compound or salt of Formula (I), Formula (II), or Formula (III), $R^1$ is

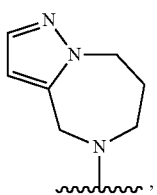

and the one or more optional substituents of $R^1$ are independently selected from halogen, —OH, —S(O)$_2$($R^{20}$), —S(O)$_2$N($R^{20}$)$_2$, —S(O)N($R^{20}$)$_2$, —S(O)$R^{20}$(=N$R^{20}$), —C(O)N($R^{20}$)$_2$, —C(=N$R^{20}$)N($R^{20}$)$_2$, —C(O)NHO$R^{20}$, —N($R^{20}$)$_2$, —C(O)$R^{20}$, —NO$_2$, =O, —CN, $C_{1-6}$ alkyl-N($R^{20}$)$_2$, $C_{1-6}$ aminoalkyl, $C_{1-6}$ alkoxy, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkynyl, and optionally substituted 5- to 12-membered heterocycle. In some cases, the one or more optional substituents of $R^1$ are independently selected from halogen, —OH, —S(O)$_2$($R^{20}$), —S(O)$_2$N($R^{20}$)$_2$, —S(O)N($R^{20}$)$_2$, —S(O)$R^{20}$(=N$R^{20}$), —C(O)N($R^{20}$)$_2$, —C(=N$R^{20}$)N($R^{20}$)$_2$, —C(O)NHO$R^{20}$, —N($R^{20}$)$_2$, —C(O)$R^{20}$, —NO$_2$, =O, —CN, $C_{1-6}$ alkyl-N($R^{20}$)$_2$, $C_{1-6}$ aminoalkyl, $C_{1-6}$ alkoxy, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkynyl, and optionally substituted 5- to 12-membered heterocycle. In some cases, the one or more optional substituents of $R^1$ are independently selected from halogen, —CN, $C_{2-6}$ alkynyl, —C(=N$R^{20}$)N($R^{20}$)$_2$, and optionally substituted 5- to 12-membered heterocycle. In some cases, the one or more optional substituents of $R^1$ are independently selected from halogen, —C(=N$R^{20}$)N($R^{20}$)$_2$, and optionally substituted 5- to 12-membered heterocycle. In some cases, the one or more optional substituents of $R^1$ are independently selected from —C(=N$R^{20}$)N($R^{20}$)$_2$, and optionally substituted 5- to 12-membered heterocycle. In some cases, the one or more optional substituents of $R^1$ are independently selected from optionally substituted 5- to 12-membered heterocycle. In some cases, the one or more optional substituents of $R^1$ are independently selected from a 5-membered heterocycle and 9-membered heterocycle, each of which is optionally substituted independently with one or more $R^{1*}$. In some cases, $R^1$ is substituted with at least one halogen atom and optionally substituted with one or more substituents are independently selected from —CN, $C_{2-6}$ alkynyl, —C(=N$R^{20}$)N($R^{20}$)$_2$, and 5- to 12-membered heterocycle, wherein the 5- to 12-membered heterocycle is optionally substituted independently with one or more $R^{1*}$. In some cases, the heterocycle has at least one nitrogen atom. In some cases, the heterocycle has at least oxygen atom. In some cases, the heterocycle has at least one nitrogen atom and at least one oxygen atom. In some cases, heterocycle has at least two heteroatoms. In some cases, the heterocycle has at least three heteroatoms. In some cases, the heterocycle has at least four heteroatoms. In some cases, the heterocycle of the one or more optional substituents of $R^1$ is selected from

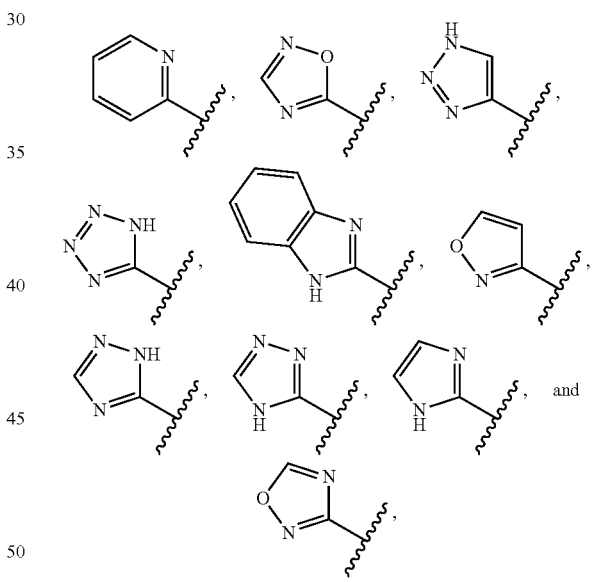

each of which is optionally substituted with one or more $R^{1*}$. In some cases, the heterocycle of the one or more optional substituents of $R^1$ is selected from

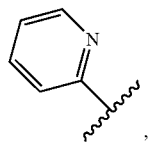 [SMILES: *c1ccccn1]

which is optionally substituted with one or more $R^{1*}$. In some cases, each $R^{1*}$ is independently selected from halogen, —O$R^{20}$, —S(O)$_2$($R^{20}$), —S(O)$_2$N($R^{20}$)$_2$, —S(O)N (R$^{20}$)$_2$, —S(O)R$^{20}$(=NR$^{20}$), —NR$^{20}$S(O)$_2$R$^{20}$, —C(O)N(R$^{20}$)$_2$, —C(O)NR$^{20}$OR$^{20}$, —N(R$^{20}$)C(O)R$^{20}$, —N(R$^{20}$)C(O)N(R$^{20}$)$_2$, —N(R$^{20}$)C(O)OR$^{20}$, —N(R$^{20}$)$_2$, —C(O)R$^{20}$, —C(O)OR$^{20}$, —OC(O)R$^{20}$, —OC(O)N(R$^{20}$)$_2$, —NO$_2$, =O, =N(R$^{20}$), =NO(R$^{20}$), —CN, —NHCN, C$_{1-6}$ alkyl-N(R$^{20}$)$_2$, C$_{1-6}$ aminoalkyl, C$_{1-6}$ alkoxy, C$_{1-6}$ hydroxyalkyl, C$_{1-6}$ cyanoalkyl, C$_{1-6}$ haloalkyl, and C$_{1-6}$ alkyl. In some cases, each R$^{1*}$ is independently selected from halogen, —OR$^{20}$, —S(O)$_2$(R$^{20}$), —S(O)$_2$N(R$^{20}$)$_2$, —S(O)N(R$^{20}$)$_2$, —S(O)R$^{20}$(=NR$^{20}$), —NR$^{20}$S(O)$_2$R$^{20}$, —C(O)N(R$^{20}$)$_2$, —C(O)NR$^{20}$OR$^{20}$, —N(R$^{20}$)C(O)R$^{20}$, —N(R$^{20}$)C(O)N(R$^{20}$)$_2$, —N(R$^{20}$)C(O)OR$^{20}$, —N(R$^{20}$)$_2$, —C(O)R$^{20}$, —C(O)OR$^{20}$, —OC(O)R$^{20}$, —OC(O)N(R$^{20}$)$_2$, —NO$_2$, =O, =N(R$^{20}$), =NO(R$^{20}$), —CN, —NHCN, C$_{1-6}$ alkyl-N(R$^{20}$)$_2$, C$_{1-6}$ aminoalkyl, C$_{1-6}$ alkoxy, C$_{1-6}$ hydroxyalkyl, C$_{1-6}$ cyanoalkyl, C$_{1-6}$ haloalkyl, and C$_{1-6}$ alkyl. In some cases, each R$^{1*}$ is independently selected from halogen, C$_{1-6}$ alkyl-N(R$^{20}$)$_2$, C$_{1-6}$ aminoalkyl, C$_{1-6}$ hydroxyalkyl, C$_{1-6}$ cyanoalkyl, C$_{1-6}$ haloalkyl, and C$_{1-6}$ alkyl. In some cases, each R$^{1*}$ is independently selected from halogen, C$_{1-6}$ haloalkyl, and C$_{1-6}$ alkyl. In some cases, each R$^{1*}$ is independently selected from halogen, and C$_{1-6}$ alkyl. In some cases, each R$^{1*}$ is independently selected from halogen. In some cases, each R$^{1*}$ is independently selected from C$_{1-6}$ alkyl. In some cases, each R$^{1*}$ is independently selected from —OR$^{20}$. In some cases, each R$^{1*}$ is independently selected from —OH. In some cases, each R$^{1*}$ is independently selected from —OMe. In some cases, the heterocycle of the one or more optional substituents of R$^1$ is selected from

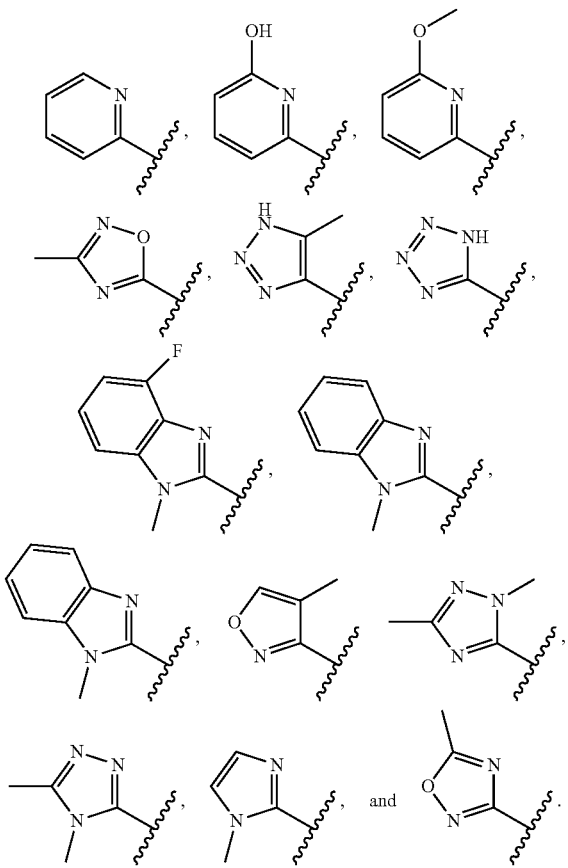

In some embodiments, for a compound or salt of Formula (I), Formula (II), or Formula (III), the one or more optional substituents of R$^1$ are independently selected from —C(=NR$^{20}$)N(R$^{20}$)$_2$, and optionally substituted 5- to 12-membered heterocycle. In some cases, the one or more optional substituents of R$^1$ are independently selected from optionally substituted 5- to 12-membered heterocycle. In some cases, the heterocycle is selected from

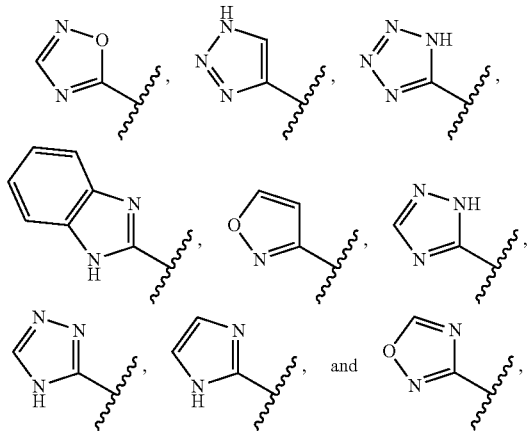

each of which is optionally substituted with one or more R$^{1*}$. In some cases, the one or more optional substituents of R$^1$ is selected from

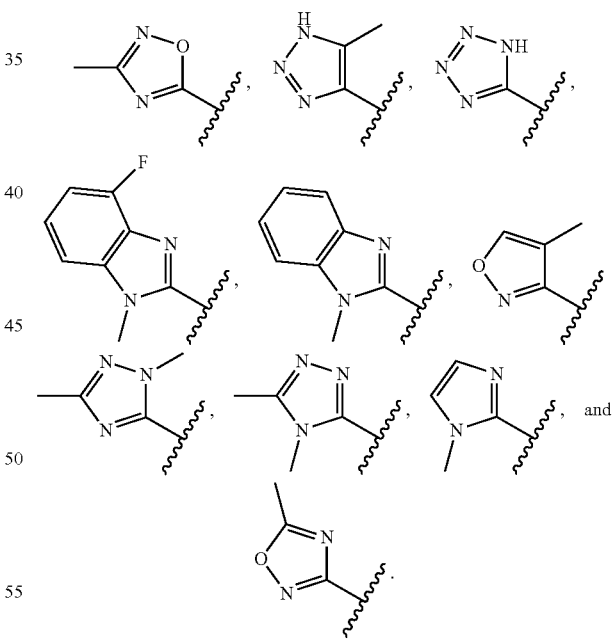

In some embodiments, for a compound or salt of Formula (I), Formula (II), or Formula (III), each R$^{1*}$ is independently selected from halogen, —OR$^{20}$, —S(O)$_2$(R$^{20}$), —S(O)$_2$N(R$^{20}$)$_2$, —S(O)N(R$^{20}$)$_2$, —S(O)R$^{20}$(=NR$^{20}$), —NR$^{20}$S(O)$_2$R$^{20}$, —C(O)N(R$^{20}$)$_2$, —C(O)NR$^{20}$OR$^{20}$, —N(R$^{20}$)C(O)R$^{20}$, —N(R$^{20}$)C(O)N(R$^{20}$)$_2$, —N(R$^{20}$)C(O)OR$^{20}$, —N(R$^{20}$)$_2$, —C(O)R$^{20}$, —C(O)OR$^{20}$, —OC(O)R$^{20}$, —OC(O)N(R$^{20}$)$_2$, —NO$_2$, =O, =N(R$^{20}$), =NO(R$^{20}$), —CN, —NHCN, C$_{1-6}$ alkyl-N(R$^{20}$)$_2$, C$_{1-6}$ aminoalkyl, C$_{1-6}$ alkoxy, $C_{1-6}$ hydroxyalkyl, $C_{1-6}$ cyanoalkyl, $C_{1-6}$ haloalkyl, and $C_{1-6}$ alkyl. In some cases, each $R^{1*}$ is independently selected from halogen, —$OR^{20}$, —$S(O)_2(R^{20})$, —$S(O)_2N(R^{20})_2$, —$S(O)N(R^{20})_2$, —$S(O)R^{20}(=NR^{20})$, —$NR^{20}S(O)_2R^{20}$, —$C(O)N(R^{20})_2$, —$C(O)NR^{20}OR^{20}$, —$N(R^{20})C(O)R^{20}$, —$N(R^{20})C(O)N(R^{20})_2$, —$N(R^{20})C(O)OR^{20}$, —$N(R^{20})_2$, —$C(O)R^{20}$, —$C(O)OR^{20}$, —$OC(O)R^{20}$, —$OC(O)N(R^{20})_2$, —$NO_2$, $=O$, $=N(R^{20})$, $=NO(R^{20})$, —CN, —NHCN, $C_{1-6}$ alkyl-$N(R^{20})_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, and $C_{1-6}$ alkyl. In some cases, each $R^{1*}$ is independently selected from halogen, $C_{1-6}$ alkyl-$N(R^{20})_2$, $C_{1-6}$ aminoalkyl, $C_{1-6}$ hydroxyalkyl, $C_{1-6}$ cyanoalkyl, $C_{1-6}$ haloalkyl, and $C_{1-6}$ alkyl. In some cases, each $R^{1*}$ is independently selected from halogen, $C_{1-6}$ haloalkyl, and $C_{1-6}$ alkyl. In some cases, each $R^{1*}$ is independently selected from halogen, and $C_{1-6}$ alkyl. In some cases, each $R^{1*}$ is independently selected from halogen. In some cases, each $R^{1*}$ is independently selected from $C_{1-6}$ alkyl.

In some embodiments, for a compound or salt of Formula (I), $R^1$ is selected from 5- to 15-membered heterocycle (preferably 8- to 10-membered heterocycle or preferably 10-membered heterocycle), each of which are optionally substituted with one or more substituents independently selected from halogen, oxo, —$C(O)N(R^{20})_2$, —$C(O)NR^{20}OR^{20}$, —$N(R^{20})_2$, —$C(O)R^{20}$, —$C(O)OR^{20}$, —$SO_2R^{20}$, —NHCN, $C_{1-6}$ cyanoalkyl, $C_{1-6}$ alkyl, $C_{1-6}$ alkyl-$N(R^{20})_2$, $C_{2-6}$ alkynyl, and 5- to 12-membered heterocycle (preferably 5- to 9-membered heterocycle), wherein the 5- to 12-membered heterocycle are each optionally substituted independently with one or more $R^{1*}$; each $R^{1*}$ is independently selected from halogen, $C_{1-6}$ haloalkyl, and $C_{1-6}$ alkyl. In some cases, the 8- to 10-membered heterocycle is bicyclic. In some cases, the 10-membered heterocycle is substituted. In some cases, $R^1$ is selected

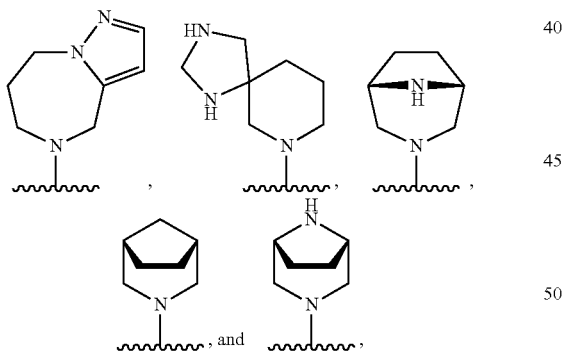

each of which is optionally substituted. In some cases, $R^1$ is selected

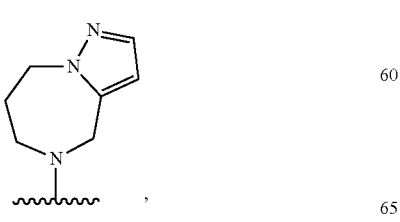

which is optionally substituted. In some cases, $R^1$ is selected

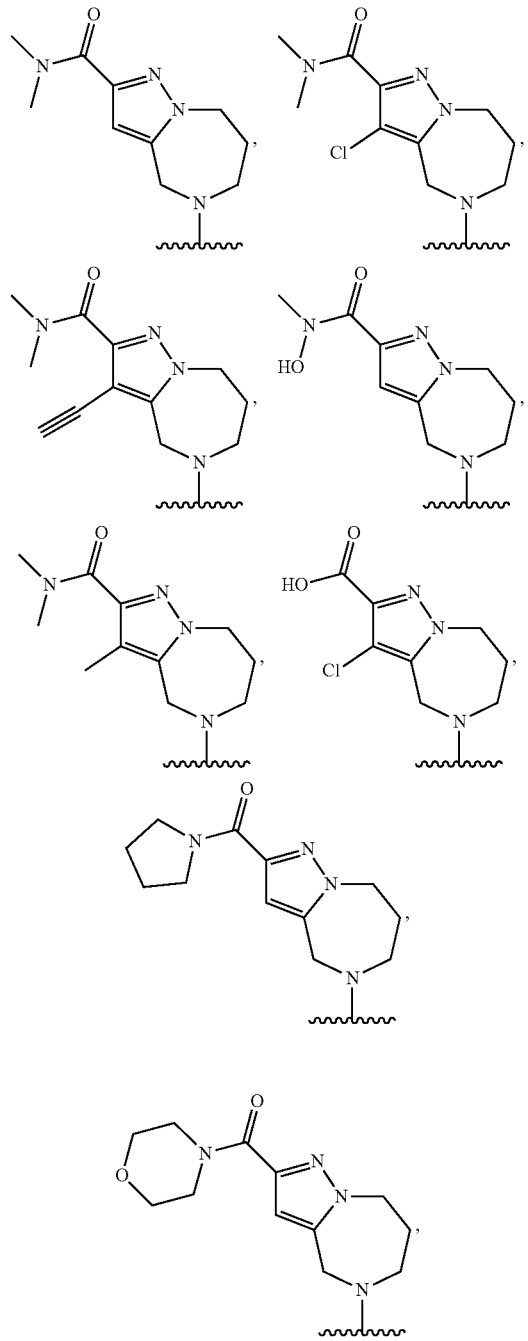

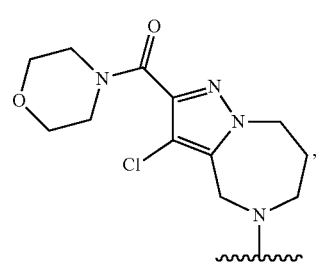

161
-continued
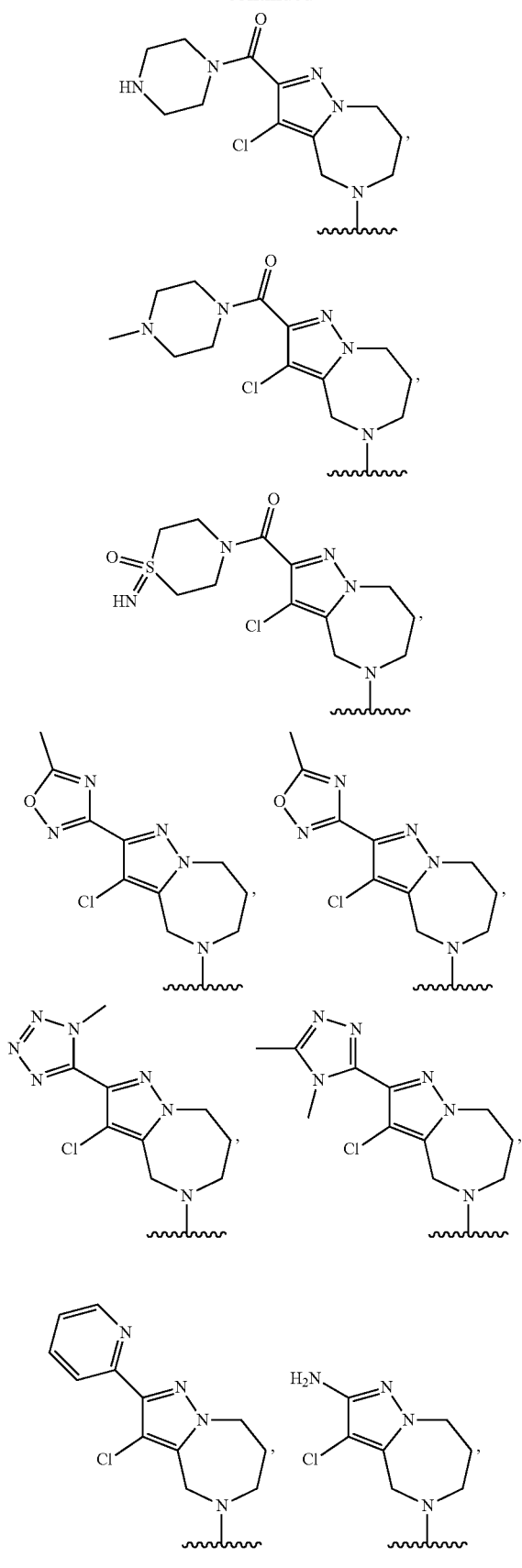
162
-continued
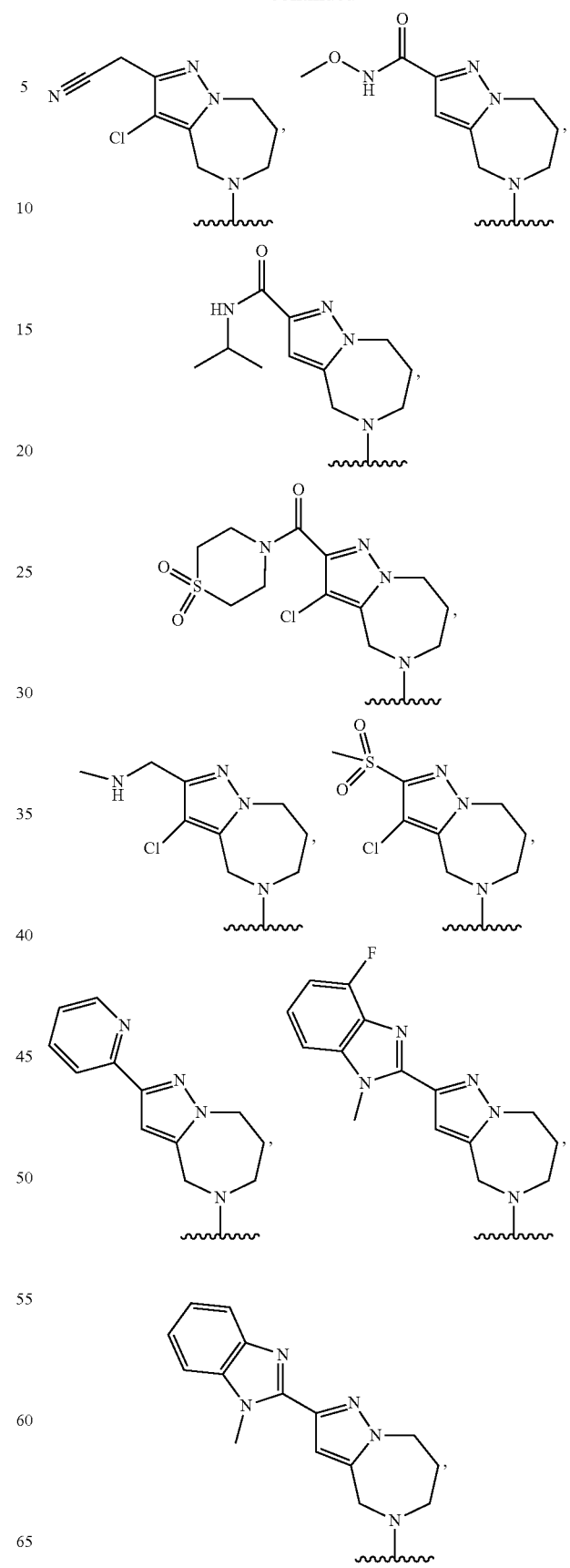

-continued

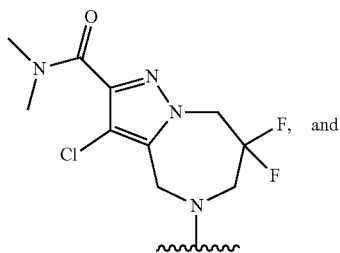, and

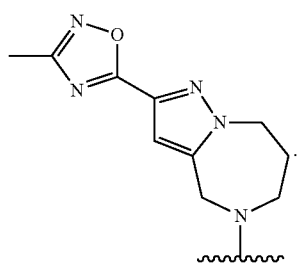 [SMILES: *N1CCCn2nc(-c3nc(C)no3)cc2C1]

In some cases, R¹ is selected

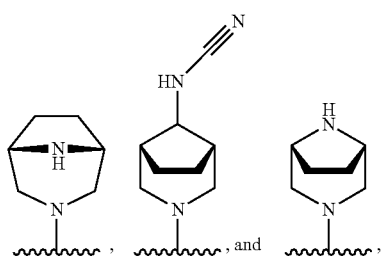

In some cases, R¹ is

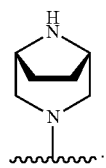

In some cases, R¹ is

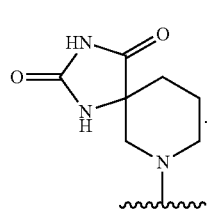 [SMILES: *N1CCCC2(C1)NC(=O)NC2=O]

In some cases, R¹ is selected

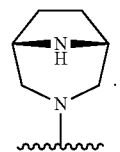

In some embodiments, for a compound or salt of Formula (I), R¹ is selected from 5- to 15-membered heterocycle (preferably 8- to 10-membered heterocycle or preferably 10-membered heterocycle or preferably 8-membered heterocycle), each of which are optionally substituted with one or more substituents independently selected from halogen, —C(O)N(R²⁰)₂, —C(O)NR²⁰OR²⁰, —N(R²⁰)₂, —C(O)R²⁰, —C(O)OR²⁰, —NHCN, $C_{1-6}$ cyanoalkyl, $C_{1-6}$ alkyl, $C_{2-6}$ alkynyl, and 5- to 12-membered heterocycle (preferably 5- to 6-membered heterocycle), wherein the 5- to 12-membered heterocycle are each optionally substituted independently with one or more R¹*; each R¹* is independently selected from halogen, $C_{1-6}$ haloalkyl, and $C_{1-6}$ alkyl. In some cases, the 8- to 10-membered heterocycle is bicyclic. In some cases, the 10-membered heterocycle is substituted. In some cases, R¹ is selected

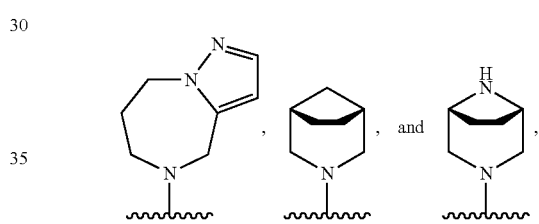

each of which is optionally substituted. In some cases, R¹ is selected

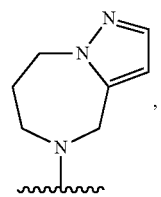

which is optionally substituted. In some cases, R¹ is selected

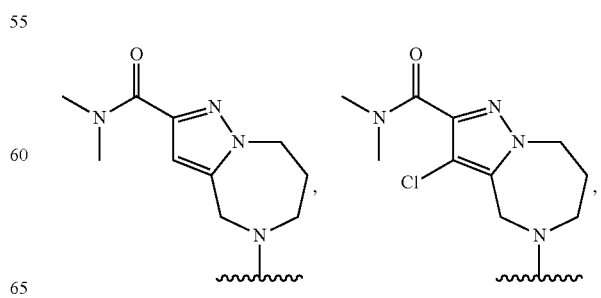

-continued
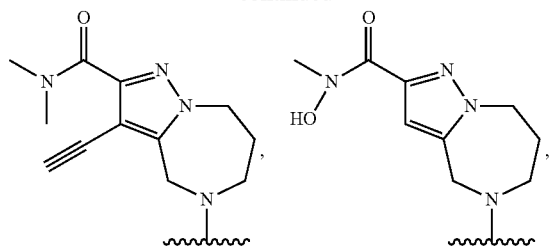
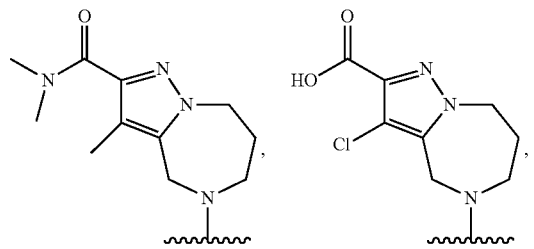
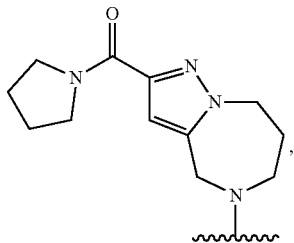
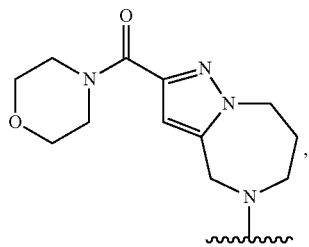
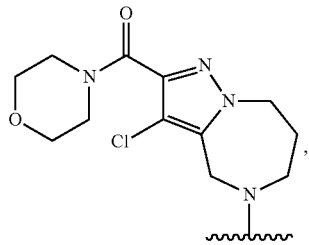
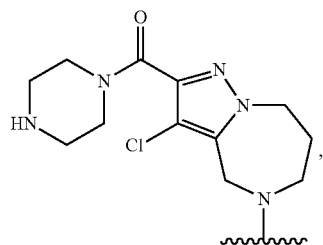
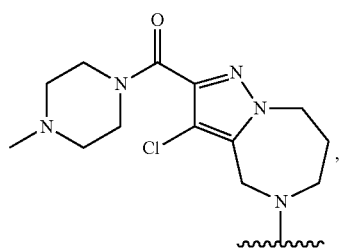
-continued
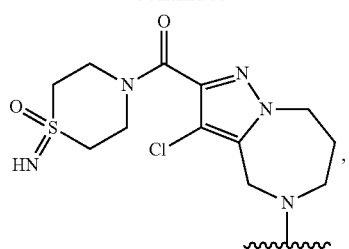
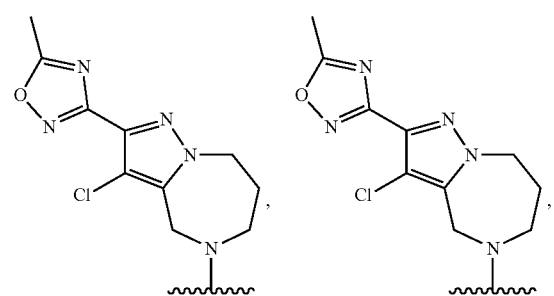
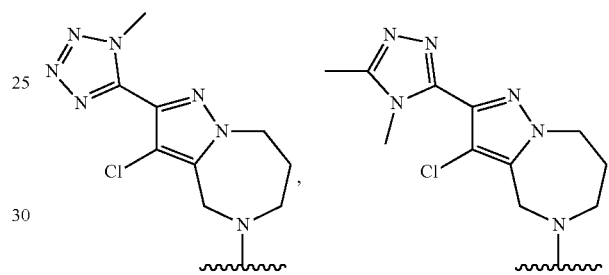
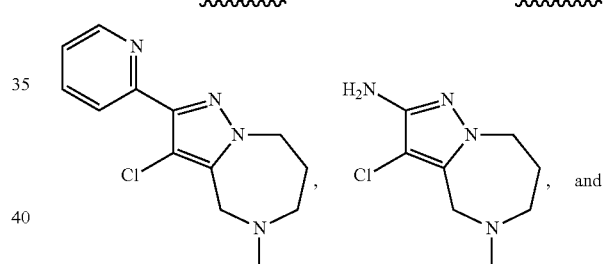
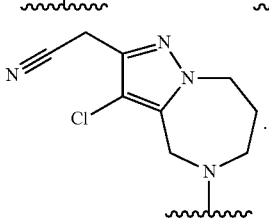
In some cases, $R^1$ is selected
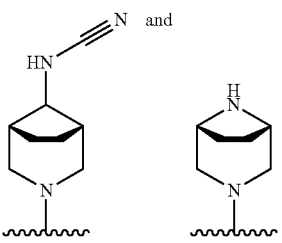
In some embodiments, for a compound or salt of Formula (I), $R^1$ is selected from

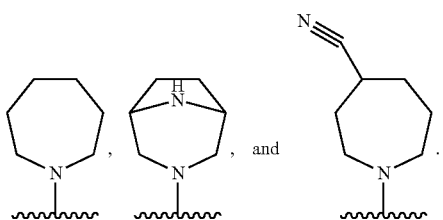

In some embodiments, for a compound or salt of Formula (I), $R^1$ is selected from an optionally substituted 7- to 10-membered spiro heterocycle and optionally substituted 7- to 10-membered fused heterocycle. In some cases, the heterocycle of $R^1$ has at least one nitrogen atom. In some cases, the at least one nitrogen at of the heterocycle of $R^1$ is bound to Formula (I). In some cases, $R^1$ is selected from an optionally substituted 10-membered spiro heterocycle and optionally substituted 10-membered fused heterocycle. In some cases, the optional one or more substituents of $R^1$ are independently selected from halogen, —OH, —S(O)$_2$(R$^{20}$), —S(O)$_2$N(R$^{20}$)$_2$, —S(O)N(R$^{20}$)$_2$, —S(O)R$^{20}$(=NR$^{20}$), —C(O)N(R$^{20}$)$_2$, —C(=NR$^{20}$)N(R$^{20}$)$_2$, —C(O)OR$^{20}$, —C(O)NHOR$^{20}$, —N(R$^{20}$)$_2$, —C(O)R$^{20}$, —NO$_2$, =O, —CN, $C_{1-6}$ alkyl-N(R$^{20}$)$_2$, $C_{1-6}$ aminoalkyl, $C_{1-6}$ alkoxy, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkynyl, 5- to 12-membered heterocycle, wherein the 5- to 12-membered heterocycle is optionally substituted with one or more substituents selected from halogen, and $C_{1-6}$ alkyl. In some cases, $R^1$ is selected from

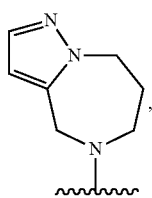

which is substituted with one or more substituents independently selected from halogen, —OH, —S(O)$_2$(R$^{20}$), —S(O)$_2$N(R$^{20}$)$_2$, —S(O)N(R$^{20}$)$_2$, —S(O)R$^{20}$(=NR$^{20}$), —C(O)N(R$^{20}$)$_2$, —C(=NR$^{20}$)N(R$^{20}$)$_2$, —C(O)OR$^{20}$, —C(O)NHOR$^{20}$, —N(R$^{20}$)$_2$, —C(O)R$^{20}$, —NO$_2$, =O, —CN, $C_{1-6}$ alkyl-N(R$^{20}$)$_2$, $C_{1-6}$ aminoalkyl, $C_{1-6}$ alkoxy, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkynyl, 5- to 12-membered heterocycle, wherein the 5- to 12-membered heterocycle is optionally substituted with one or more substituents selected from halogen, and $C_{1-6}$ alkyl. In some cases, $R^1$ is selected from

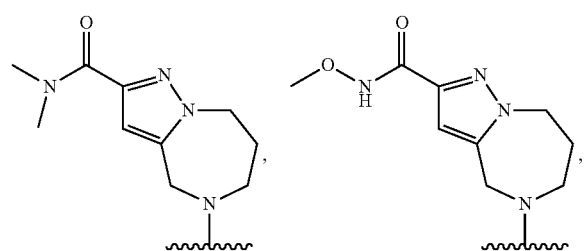

-continued

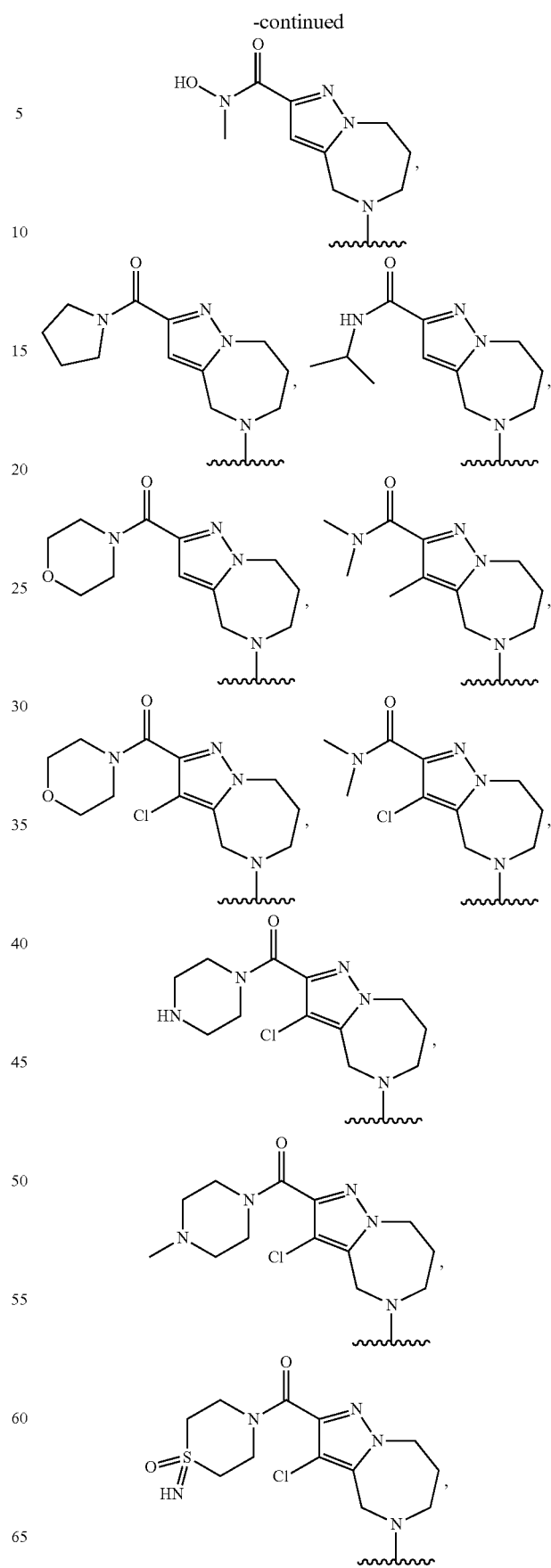

169
-continued
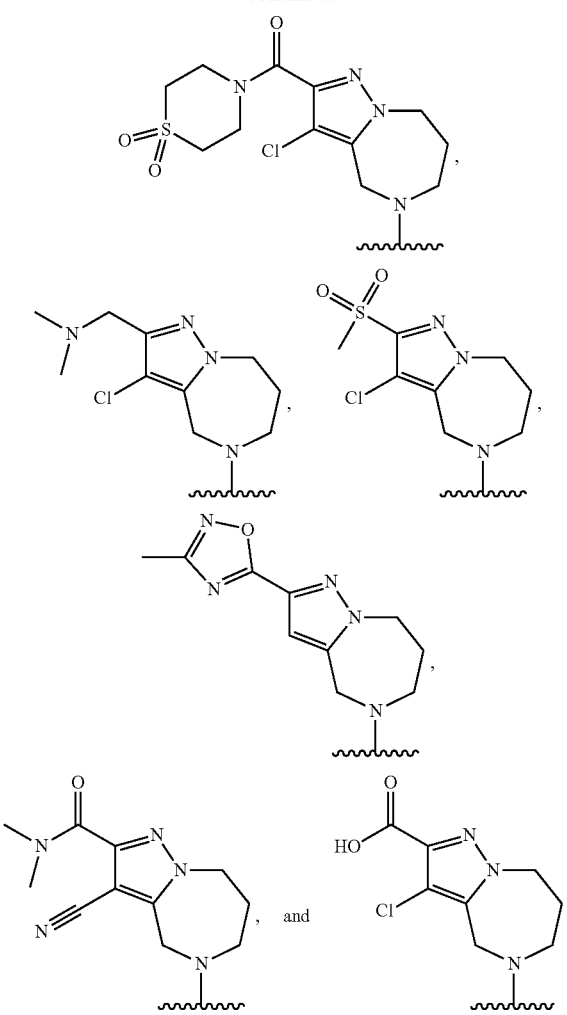
In some cases, R¹ is selected
170
-continued
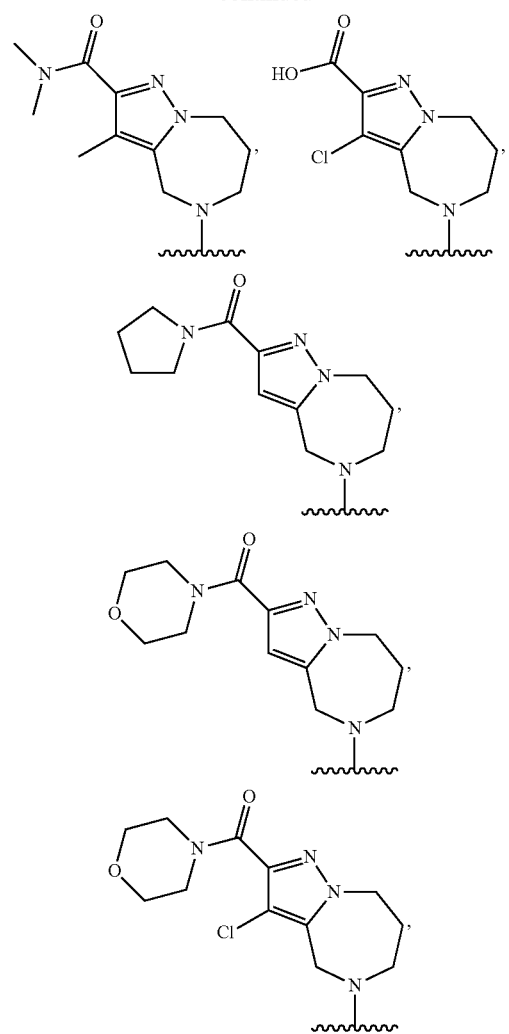
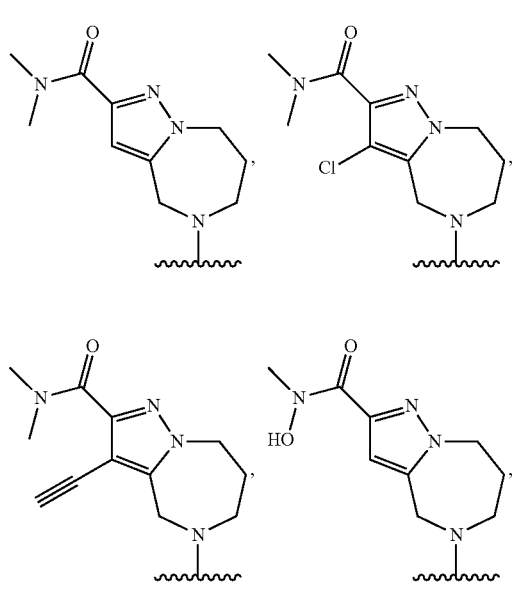
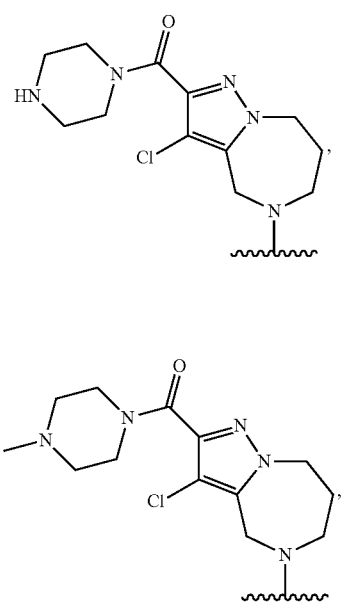

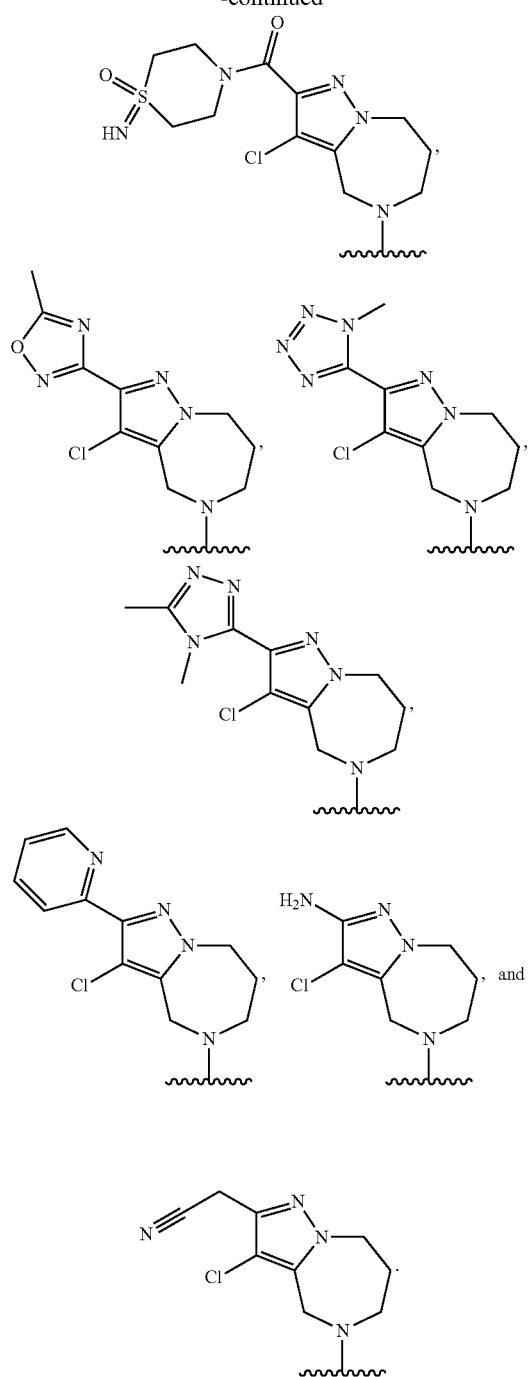

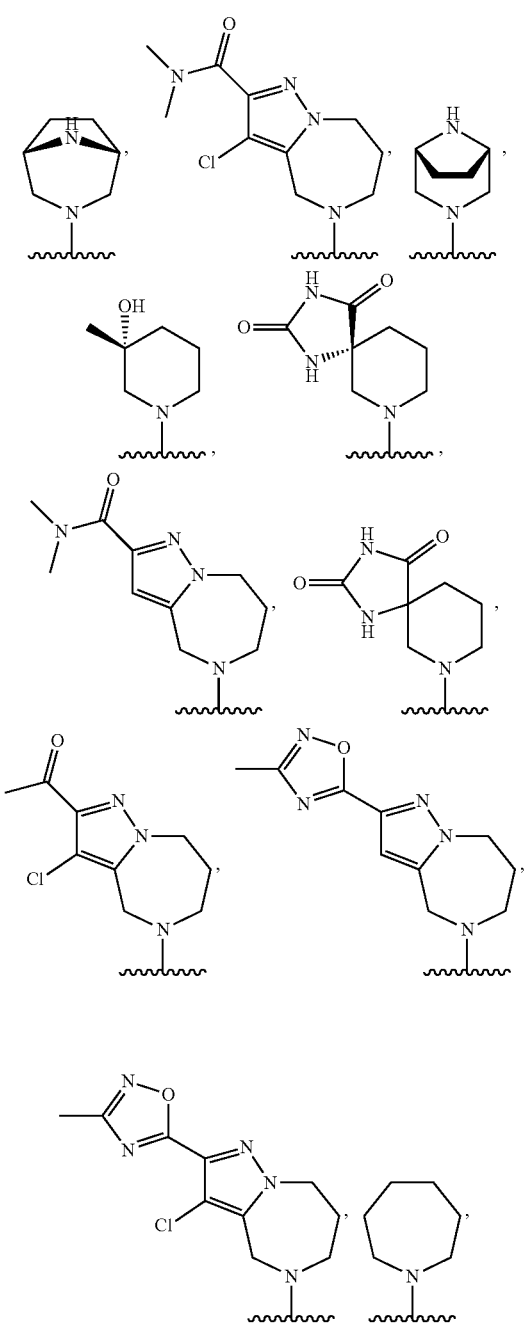

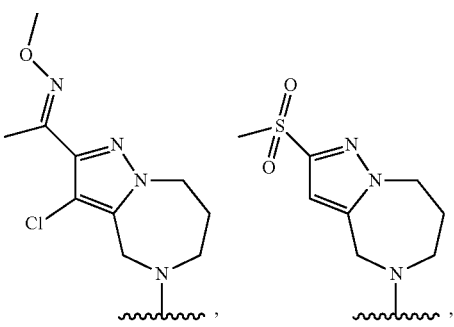

In some embodiments, for a compound or salt of Formula (I), $R^1$ is selected from an optionally substituted 6- to 11-membered heterocycle, wherein the 6- to 11-membered heterocycle has at least one nitrogen atom. In some cases, the one or more optional substituents of $R^1$ is selected from halogen, —$OR^{20}$, —$C(O)N(R^{20})_2$, —$C(O)R^{20}$, —$S(O)_2R^{20}$, =O, —$C_{1-6}$ alkyl(=$NOR^{20}$), =$NO(R^{20})$, —CN, —NHCN, $C_{1-6}$ alkyl, and 5- to 12-membered heterocycle, wherein the 5- to 12-membered heterocycle is optionally substituted independently with one or more $R^{1*}$; and wherein each $R^{1*}$ is independently selected from halogen, and $C_{1-6}$ alkyl. In some embodiments, $R^1$ is selected from

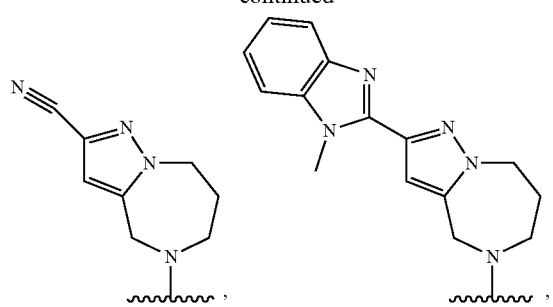
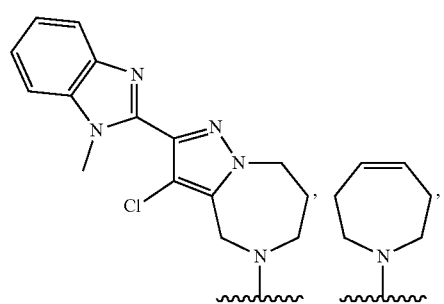
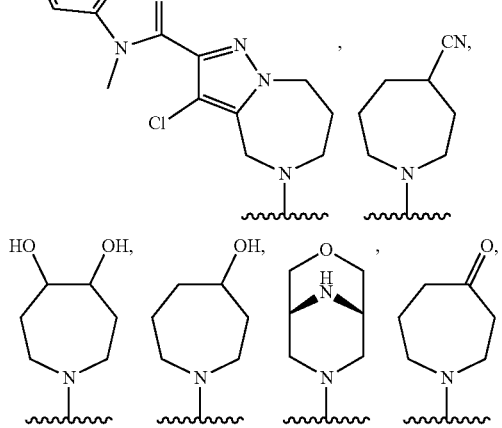
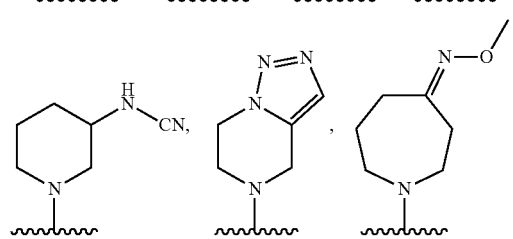
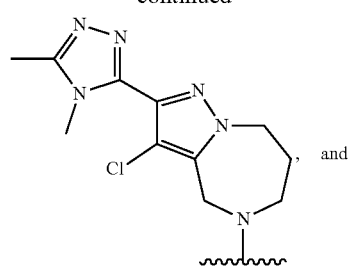
In some cases, $R^1$ is selected from hydrogen,
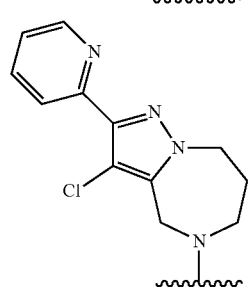

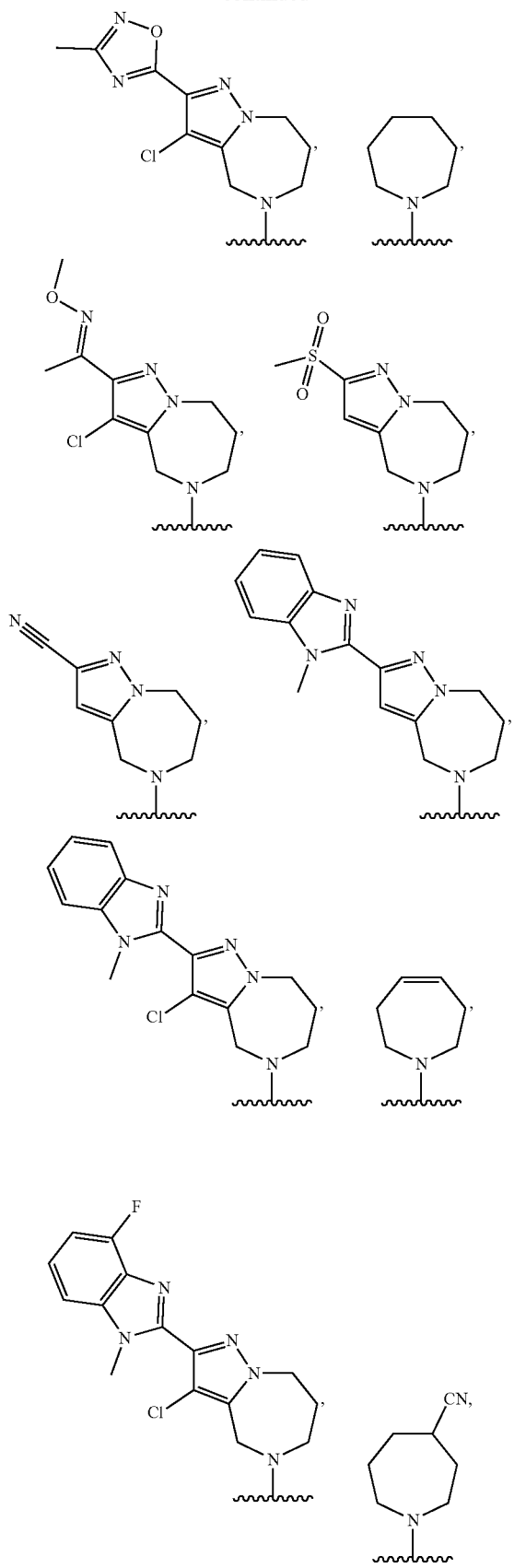
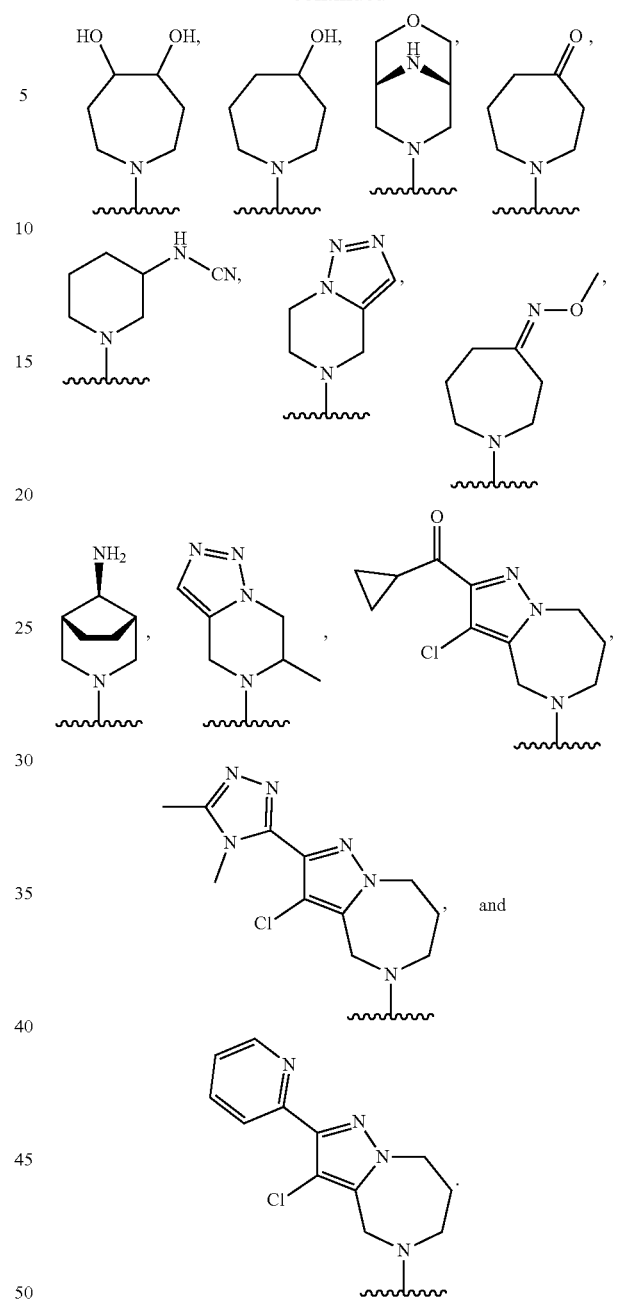
In some cases, R[1] is selected from hydrogen,
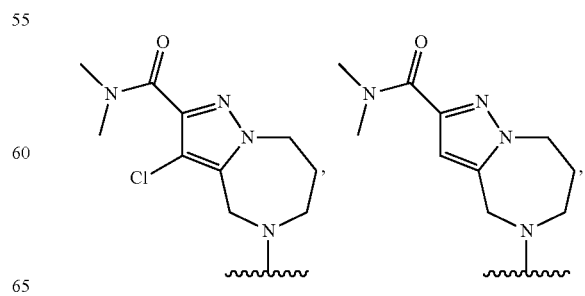

177
-continued
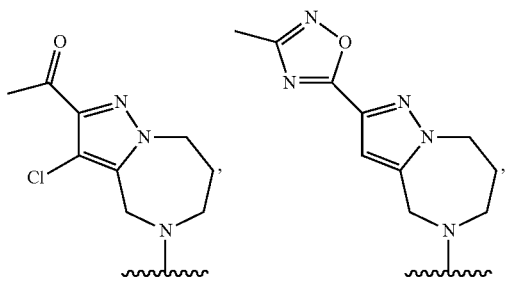
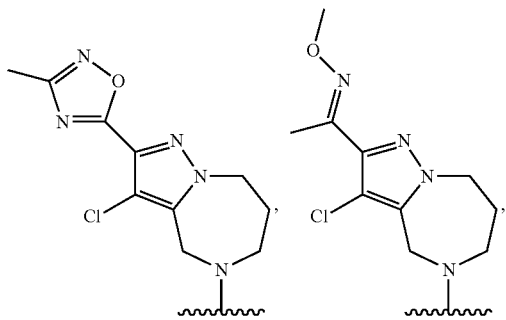
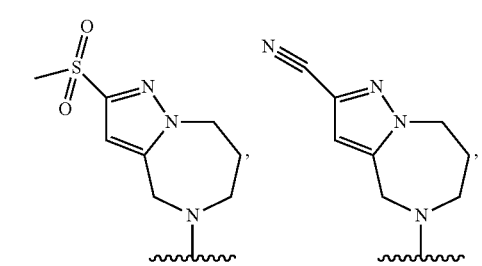
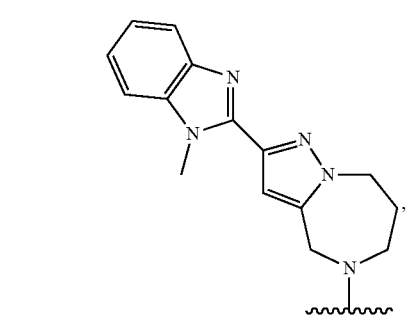
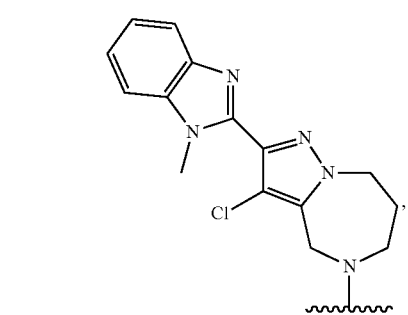
178
-continued
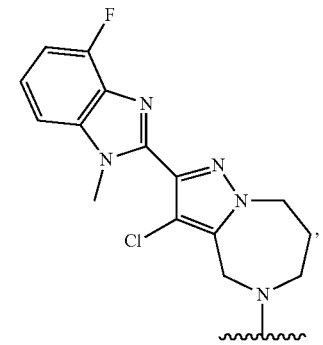
In some embodiments, for a compound or salt of Formula (I), $R^1$ is selected from hydrogen and optionally substituted 5- to 15-membered heterocycle. In some cases, $R^1$ is selected from
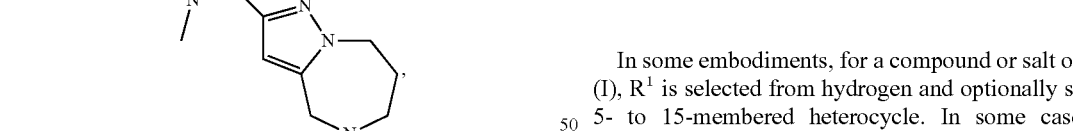
, and

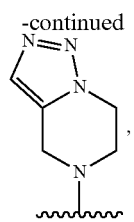

each of which is optionally substituted. In some cases, the optional one or more substituents of $R^1$ is selected from —OH, =NO($R^{20}$), —NHCN, and $C_{1-6}$ alkyl. In some cases, $R^1$ is selected from hydrogen,

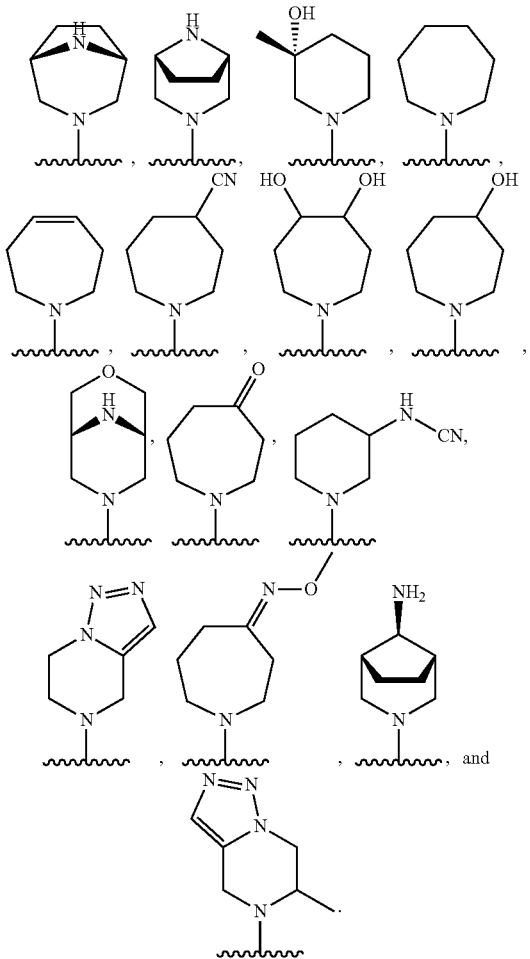

In some embodiments, for a compound or salt of Formula (I), $R^1$ is selected from hydrogen and optionally substituted 7- to 10-membered heterocycle. In some cases, $R^1$ is selected from hydrogen

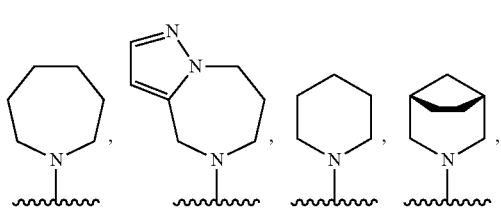

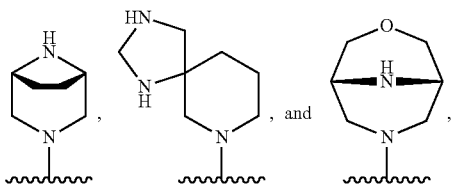

each of which is optionally substituted. In some cases, the optional one or more substituents of $R^1$ are independently selected from halogen, —NH$_2$, —S(O)$_2$($R^{20}$), —C(O)$R^{20}$, —C(O)N($R^{20}$)$_2$, =O, =NO($R^{20}$), —CN, —NHCN, $C_{1-6}$ alkyl, and 5- to 12-membered heterocycle, wherein the 5- to 12-membered heterocycle is optionally substituted independently with one or more $R^{1*}$; and wherein each $R^{1*}$ is independently selected from halogen, and $C_{1-6}$ alkyl. In some cases, $R^1$ is selected from hydrogen,

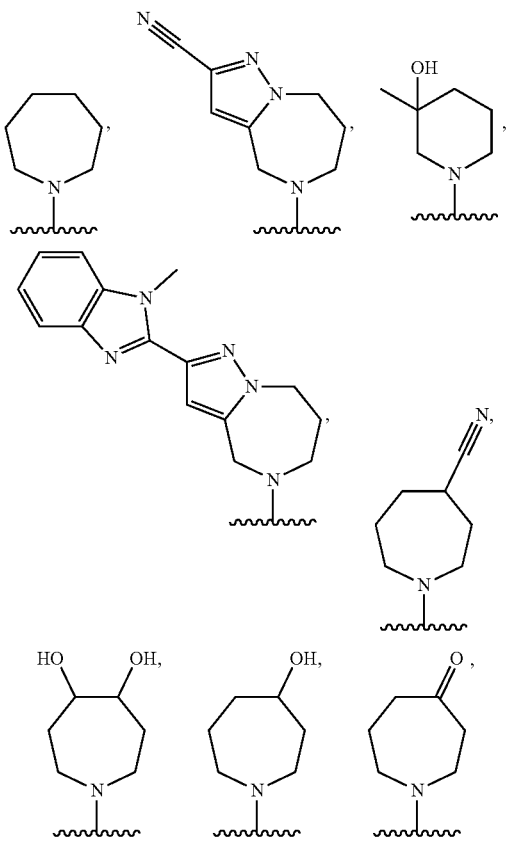

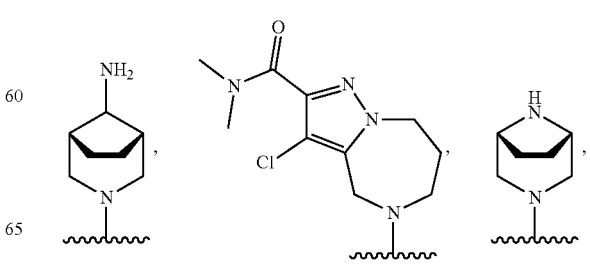

-continued

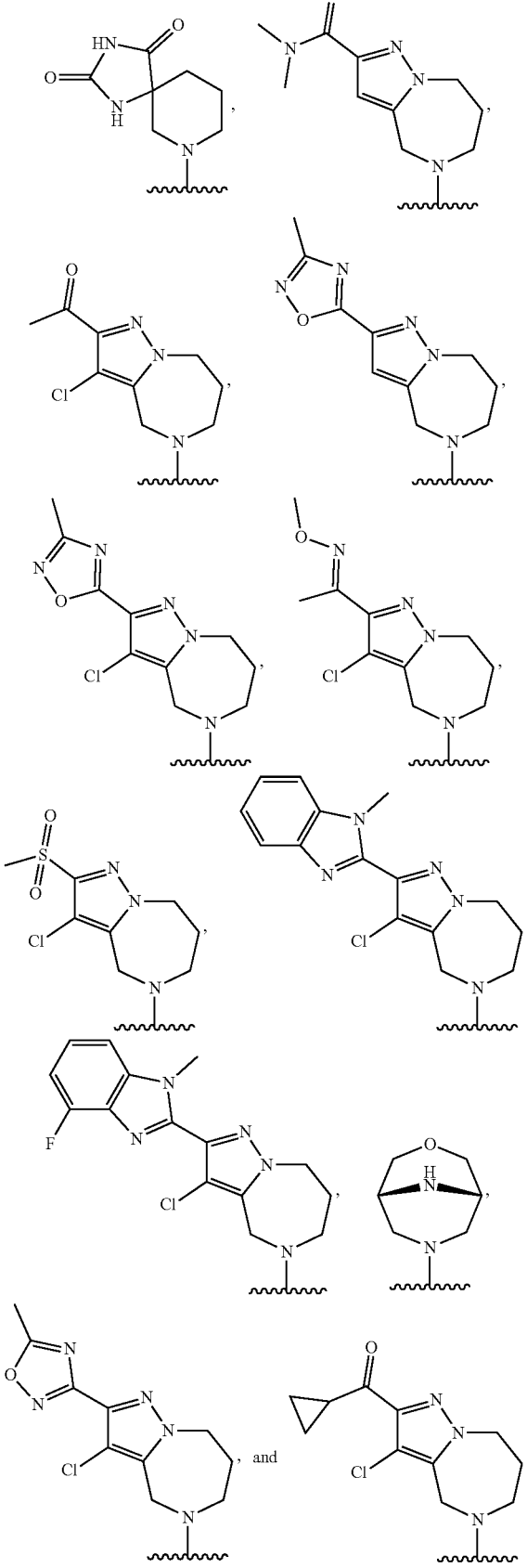

In some embodiments, for a compound or salt of Formula (I), $R^1$ is selected from an optionally substituted 8- to 10-membered heterocycle. In some cases, the heterocycle is bicyclic. In some cases, the heterocycle has at least one nitrogen atom. In some cases, the heterocycle has at least two nitrogen atoms. In some cases,

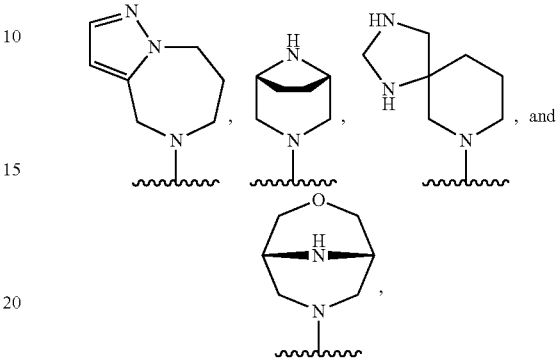

each of which is optionally substituted. In some cases, the optional one or more substituents of $R^1$ are independently selected from halogen,

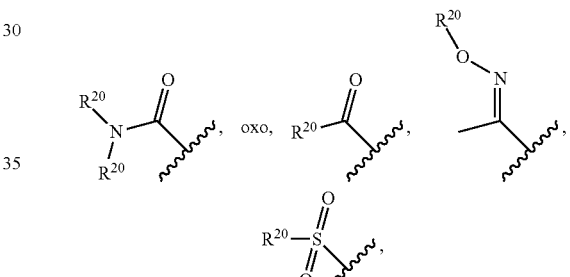

and 5- to 9-membered heteroaryl, wherein the 5- to 9-membered heteroaryl is substituted with at least one $R^{1*}$, wherein the $R^{1*}$ is selected from halogen, and $C_{1-6}$ alkyl. In some cases, the optional one or more substituents of $R^1$ are independently selected from chlorine,

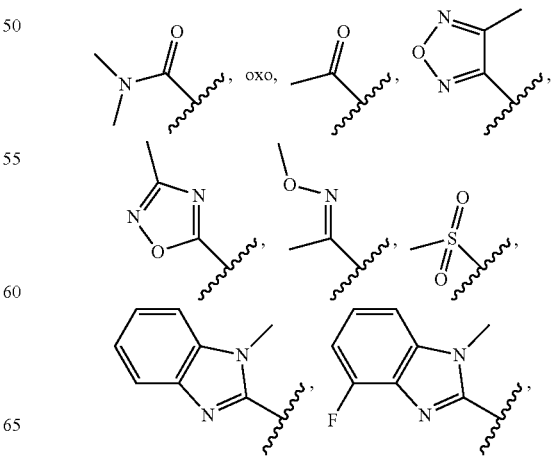

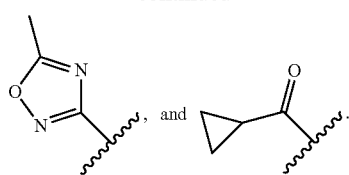

In some cases, $R^1$ is selected from

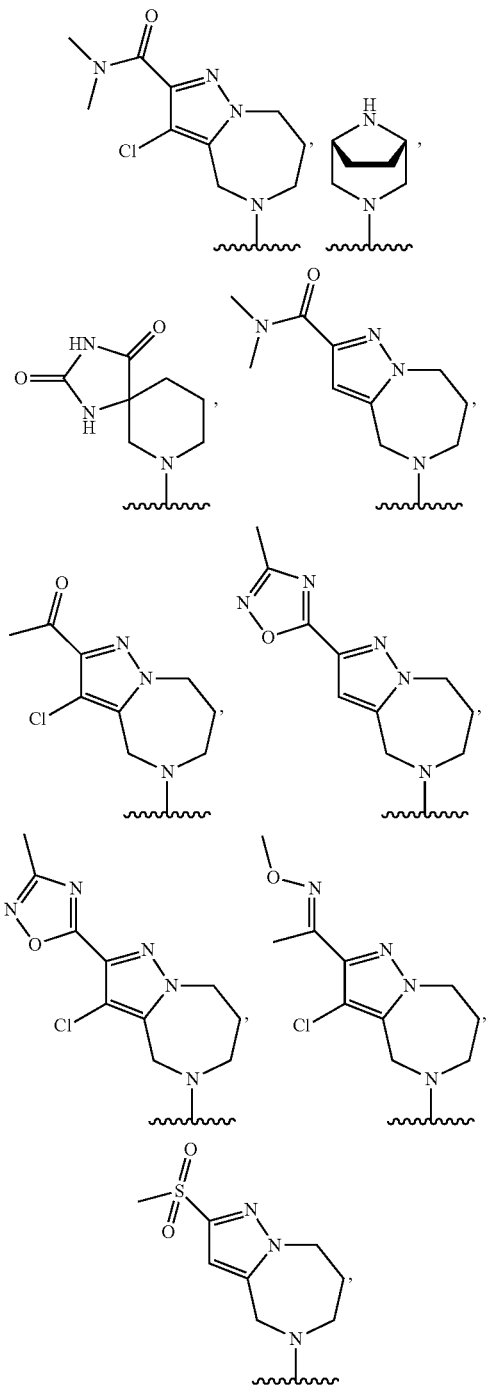

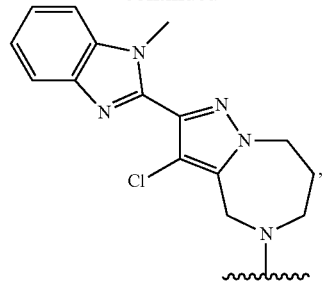

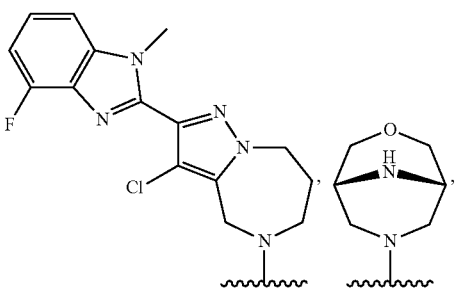

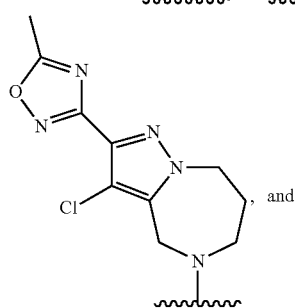

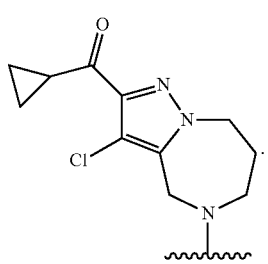

In some embodiments, for a compound or salt of Formula (I), $R^1$ is selected from an optionally substituted bridged 8- to 9-membered heterocycle. In some cases, the heterocycle of $R^1$ is selected from

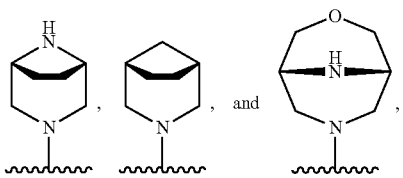

each of which is optionally substituted. In some cases, the one or more substituents of $R^1$ are selected from halogen, $C_{1-6}$ alkyl, $-N(R^{20})_2$, and $C_{1-6}$ aminoalkyl. In some cases, $R^1$ is selected

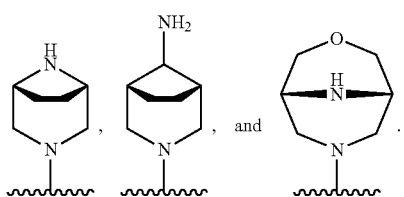

In some embodiments, for a compound or salt of Formula (I), $R^1$ is selected from an optionally substituted bridged 8-membered heterocycle, wherein the heterocycle contains heteroatoms selected from nitrogen. In some cases, the one or more substituents of $R^1$ are selected from $C_{1-6}$ alkyl, $-N(R^{20})_2$, and $C_{1-6}$ aminoalkyl. In some cases, the heterocycle of $R^1$ is selected from

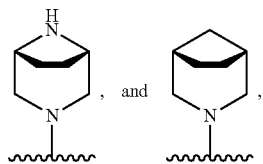

each of which is optionally substituted. In some cases, $R^1$ is selected

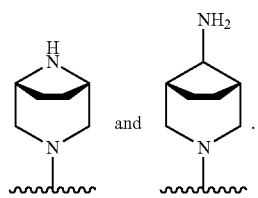

In some cases, $R^1$ is

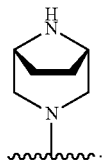

In some cases, $R^1$ is

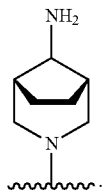

In some embodiments, for a compound or salt of Formula (I), $R^1$ is hydrogen.

In some embodiments, for a compound or salt of Formula (I), $R^1$ is an optionally substituted 12- to 15-membered heterocycle. In some cases, $R^1$ is an optionally substituted 12-membered heterocycle. In some cases, $R^1$ is an optionally substituted 13-membered heterocycle. In some cases, $R^1$ is an optionally substituted 14-membered heterocycle. In some cases, $R^1$ is an optionally substituted 15-membered heterocycle. In some cases, the heterocycle of $R^1$ is tricyclic. In some cases, the heterocycle of $R^1$ contains a fused heterocycle. In some cases, the heterocycle of $R^1$ contains a spiro-heterocycle. In some cases, the heterocycle of $R^1$ contains a fused and spiro-heterocycle. In some cases, the heterocycle of $R^1$ is an unsaturated heterocycle. In some cases, the heterocycle of $R^1$ is a non-aromatic heterocycle. In some cases, the heterocycle of $R^1$ has at least one double bond. In some cases, the heterocycle of $R^1$ has at least two double bonds. In some cases, the heterocycle of $R^1$ has at least 2 heteroatoms. In some cases, the heterocycle of $R^1$ has at least 3 heteroatoms. In some cases, the heterocycle of $R^1$ has at least 4 heteroatoms. In some cases, the heterocycle of $R^1$ has at least 5 heteroatoms. In some cases, the heterocycle of $R^1$ has at least 6 heteroatoms. In some cases, the heterocycle of $R^1$ has at least 7 heteroatoms. In some cases, the heteroatoms are selected from oxygen, nitrogen, and sulfur. In some cases, the heterocycle of $R^1$ has at least 3, 4, or 5 nitrogen atoms, and at least 1 sulfur atom. In some cases, the heterocycle of $R^1$ has at least 3, 4, or 5 nitrogen atoms, and at least 1 oxygen atom. In some cases, the heterocycle of $R^1$ has at least 3, 4, or 5 nitrogen atoms. In some cases, the heterocycle of $R^1$ has at least 3, 4, or 5 nitrogen atoms and no other heteroatoms. In some cases, the heteroatoms are selected from nitrogen and sulfur. In some cases the heteroatoms are selected from nitrogen and oxygen. In some cases, $R^1$ is selected from

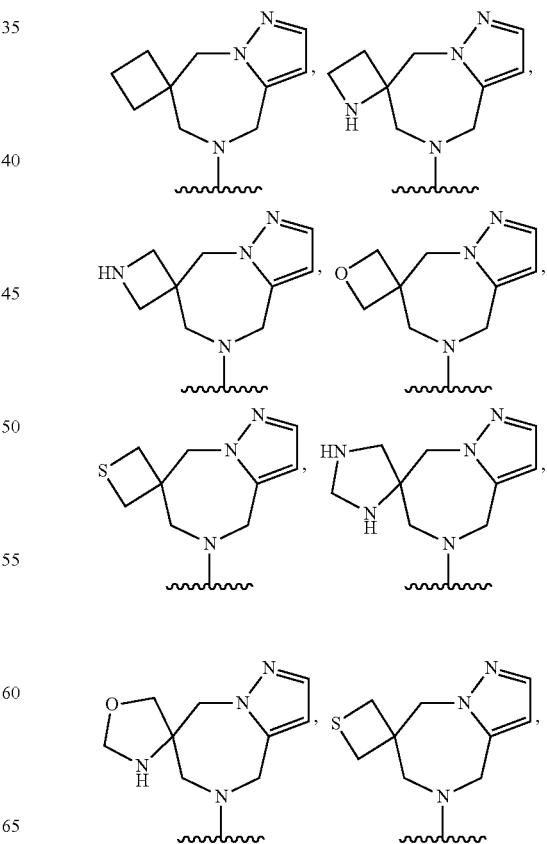

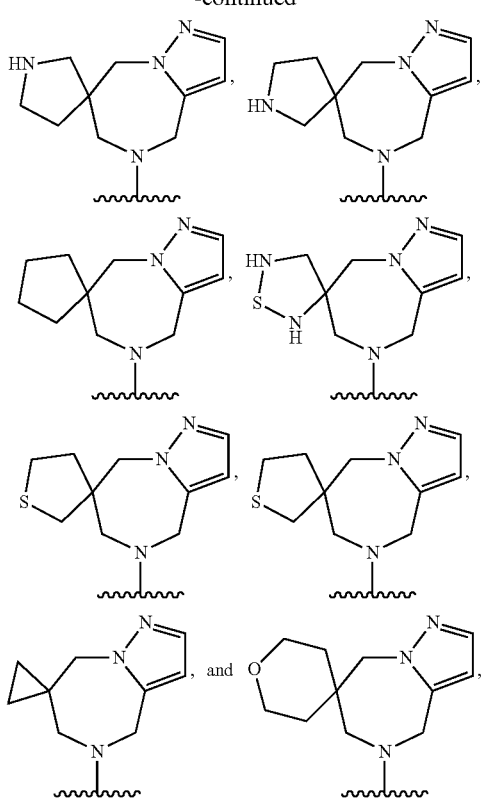

each of which is optionally substituted with one or more substituents. In some cases, R¹ is selected from

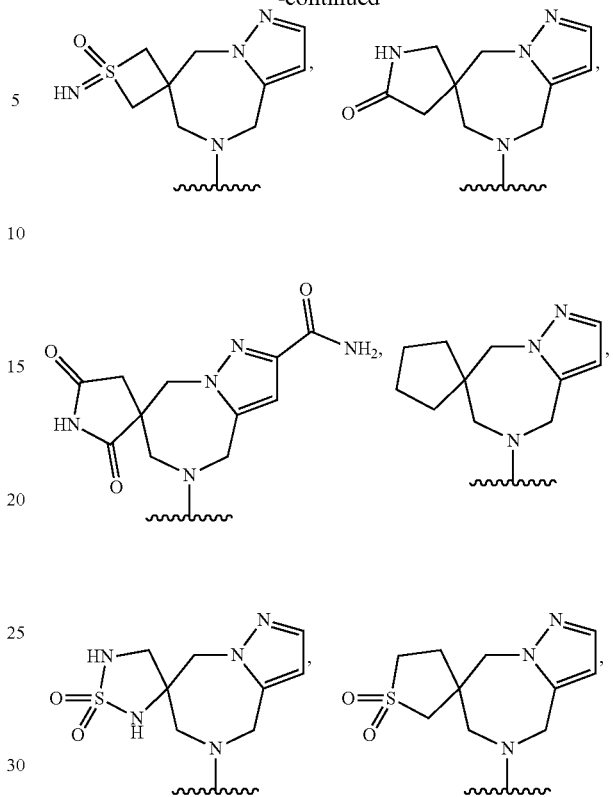

each of which is optionally substituted with one or more substituents. In some cases, the optional one or more substituents of $R^1$ are independently selected from halogen, —OH, —NHCN, —S(O)$_2$(R$^{20}$), —S(O)$_2$N(R$^{20}$)$_2$, —S(O)N(R$^{20}$)$_2$, —S(O)R$^{20}$(=NR$^{20}$), —C(O)N(R$^{20}$)$_2$, —C(O)NHOR$^{20}$, —N(R$^{20}$)$_2$, —C(O)R$^{20}$, —NO$_2$, =O, =NH, —CN, C$_{1-6}$ aminoalkyl, C$_{1-6}$ alkoxy, C$_{1-6}$ hydroxyalkyl, C$_{1-6}$ cyanoalkyl, C$_{1-6}$ haloalkyl, C$_{1-6}$ alkyl, and C$_{2-6}$ alkynyl. In some cases, the optional one or more substituents of R¹ are independently selected from halogen, —OH, —NHCN, —S(O)$_2$(R$^{20}$), —S(O)$_2$N(R$^{20}$)$_2$, —S(O)N(R$^{20}$)$_2$, —S(O)R$^{20}$(=NR$^{20}$), —C(O)N(R$^{20}$)$_2$, —C(O)NHOR$^{20}$, —N(R$^{20}$)$_2$, —C(O)R$^{20}$, —NO$_2$, =O, —CN, C$_{1-6}$ aminoalkyl, C$_{1-6}$ alkoxy, C$_{1-6}$ hydroxyalkyl, C$_{1-6}$ cyanoalkyl, C$_{1-6}$ haloalkyl, C$_{1-6}$ alkyl, and C$_{2-6}$ alkynyl. In some cases, the optional one or more substituents of R¹ are independently selected from halogen, —OH, C$_{1-6}$ alkyl, and —C(O)N(R$^{20}$)$_2$. In some cases, R¹ is selected from

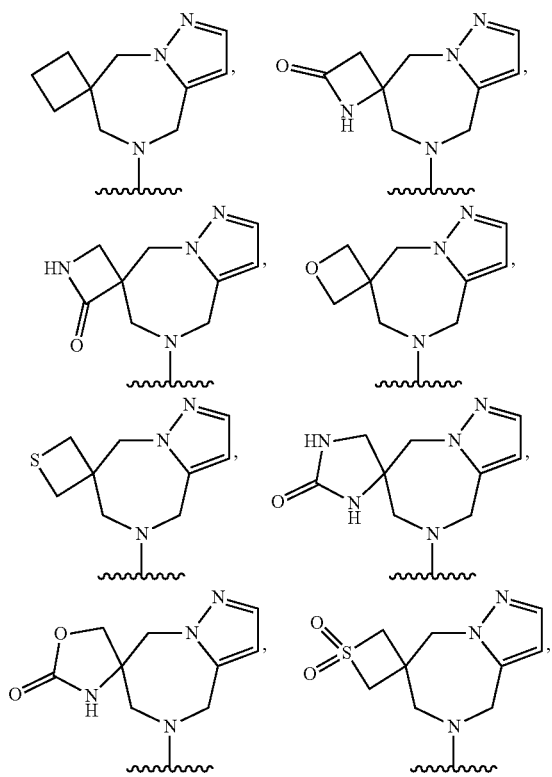

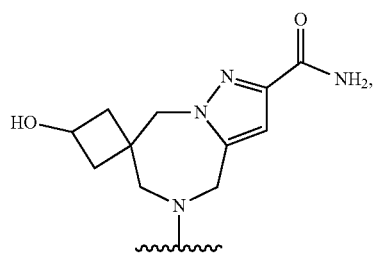
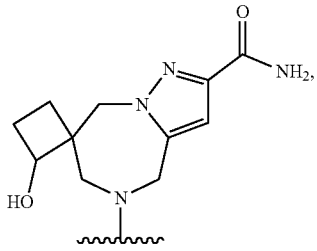
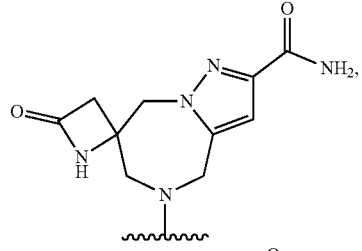
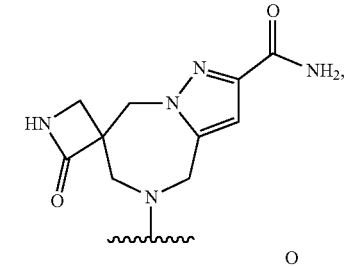
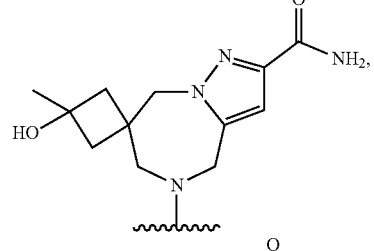
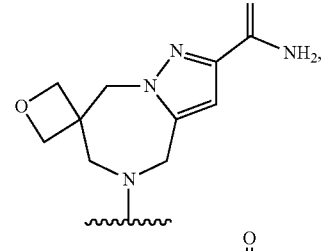
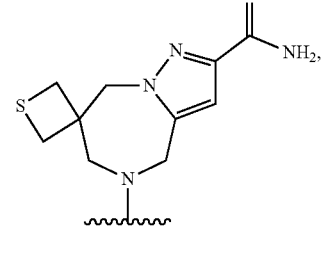
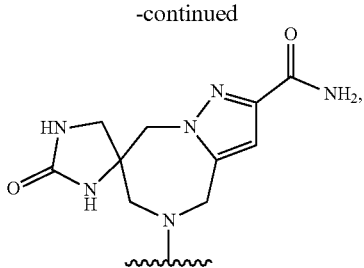
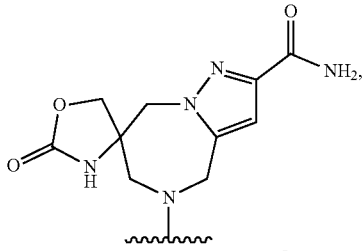
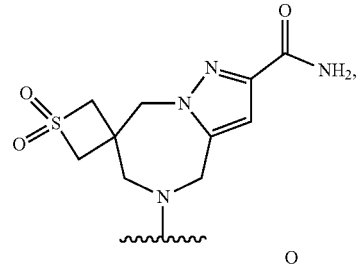
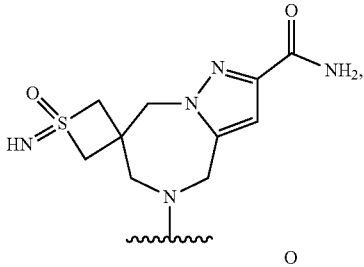
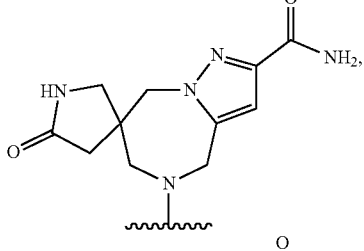
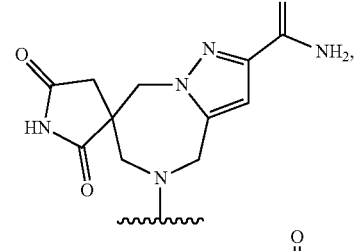
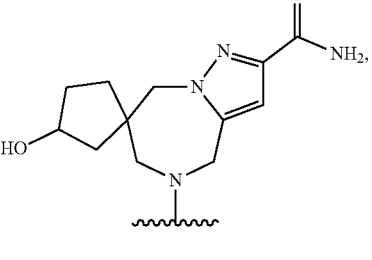

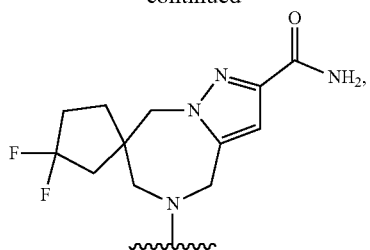

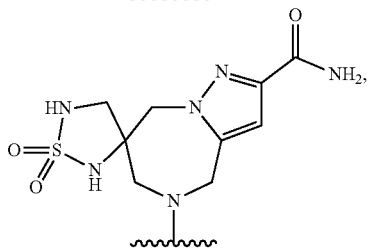

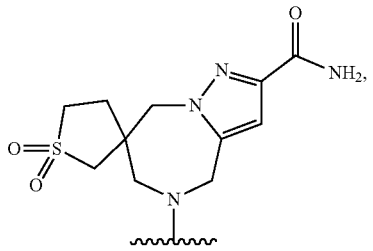

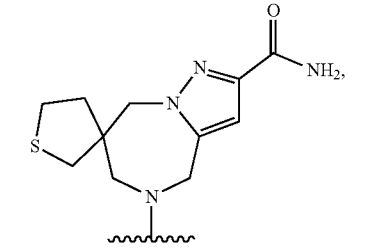

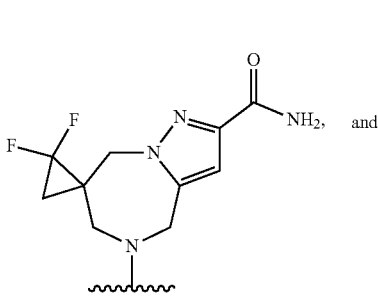 and

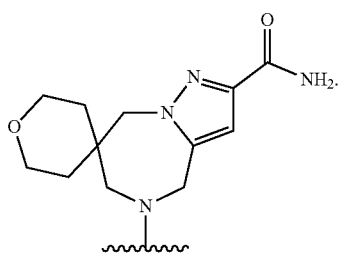

In some embodiments, for a compound or salt of Formula (I), R¹ is an optionally substituted 12- to 15-membered heterocycle. In some cases, R¹ is

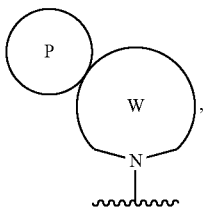

wherein Ring W is an optionally substituted heterocycle and Ring P is an optionally substituted carbocycle or optionally substituted heterocycle, wherein Ring P forms a spirocycle with Ring W. In some cases, Ring W is an optionally substituted fused heterocycle. In some cases, Ring P and Ring W combine to form a heterocycle having at least 12 atoms and most 15 atoms. In some cases, Ring P and Ring W have in total at least 12 atoms and most 15 atoms. In some cases, Ring W is an optionally substituted 10-membered fused heterocycle. In some cases, R¹ is

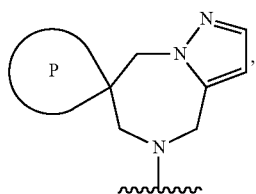

wherein Ring P is an optionally substituted carbocycle or optionally substituted heterocycle. In some cases, R¹ is

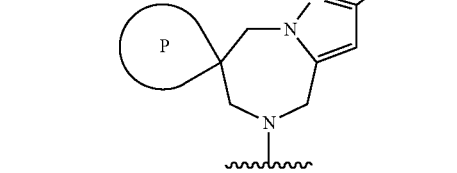

In some cases, Ring P is an optionally substituted carbocycle. In some cases, Ring P is an optionally substituted heterocycle. In some cases, Ring P forms an optionally substituted $C_3$-$C_6$ carbocycle or optionally substituted 4- to 6-membered heterocycle. In some cases, Ring P forms an optionally substituted $C_3$ carbocycle. In some cases, Ring P forms an optionally substituted $C_4$ carbocycle. In some cases, Ring P forms an optionally substituted $C_5$ carbocycle. In some cases, Ring P forms an optionally substituted 4-membered heterocycle. In some cases, Ring P forms an optionally substituted 5-membered heterocycle. In some cases, Ring P forms an optionally substituted 5-membered heterocycle. In some cases, Ring P has at least 1, 2, or 3 heteroatoms. In some cases, the heteroatoms are selected from oxygen, nitrogen, and sulfur. In some cases, Ring P has 1 sulfur atom. In some cases, Ring P has 1 nitrogen atom. In some cases, Ring P has 1 oxygen atom. In some cases, the one or more optional substituents of Ring P are independently selected from halogen, —OH, —NHCN, =O, =NR²⁰, —CN, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, and $C_{2-6}$ alkynyl. In some cases, the one or more optional substituents of Ring P are independently selected from halogen, —OH, =O, =NH, —CN, and $C_{1-6}$ alkyl. In some cases, the one or more optional substituents of Ring W are independently selected from halogen, —OH, —NHCN, —S(O)$_2$(R$^{20}$), —S(O)$_2$N(R$^{20}$)$_2$, —S(O)N(R$^{20}$)$_2$, —S(O)R$^{20}$(=NR$^{20}$), —C(O)N(R$^{20}$)$_2$, —C(O)NHOR$^{20}$, —N(R$^{20}$)$_2$, —C(O)R$^{20}$, —NO$_2$, —CN, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, and $C_{2-6}$ alkynyl. In some cases, the one or more optional substituents of Ring W are independently selected from halogen, —S(O)$_2$ (R$^{20}$), —S(O)$_2$N(R$^{20}$)$_2$, —S(O)N(R$^{20}$)$_2$, —S(O)R$^{20}$(=NR$^{20}$), —C(O)N(R$^{20}$)$_2$, —C(O)NR$^{20}$OR$^{20}$, —C(O)NHOR$^{20}$, —N(R$^{20}$)$_2$, —C(O)R$^{20}$, and $C_{1-6}$ alkyl. In some cases, the one or more optional substituents of Ring W are independently selected from —C(O)R$^{20}$. In some cases, Ring P is substituted. In some cases, Ring W is substituted.

In some embodiments, for a compound or salt for Formula (I), R$^1$ is selected from a 5- to 12-membered bridged heterocycle, which is optionally substituted with one or more substituents. In some cases, R$^1$ is selected from an 8-membered bridged heterocycle, which is optionally substituted with one or more substituents. In some cases, the bridged heterocycle has at least 1 heteroatom. In some cases, the bridged heterocycle has at least 2 heteroatoms. In some cases, the bridged heterocycle has at least 1 nitrogen atom. In some cases, the bridged heterocycle has at least 2 nitrogen atoms. In some cases, the bridged heterocycle has 2 nitrogen atoms. In some cases, R$^1$ is selected from

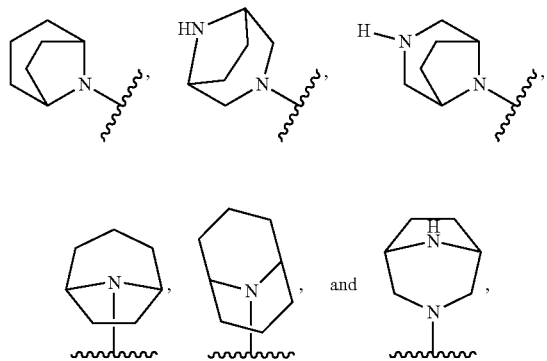

which are each optionally substituted with one or more substituents. In some cases, R$^1$ is selected from

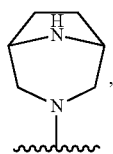

which is optionally substituted with one or more substituents.

In some embodiments, for a compound or salt for Formula (I), R$^1$ is selected from an unsaturated 5- to 12-membered heterocycle, which is optionally substituted with one or more substituents. In some cases, the unsaturated 5- to 12-membered heterocycle is selected from

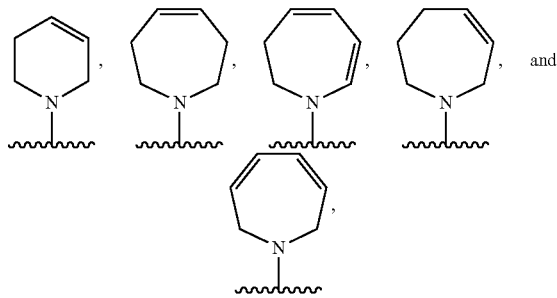

each of which is optionally substituted with one or more substituents.

In some embodiments, for a compound or salt of Formula (I), wherein the 5- to 12-membered heterocycle of R$^1$ is unsaturated and a bridged heterocycle. In some cases, R$^1$ is selected from an optionally substituted 7- to 8-membered unsaturated and bridged heterocycle. In some cases, R$^1$ is selected from

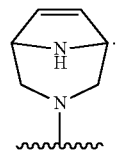

In some embodiments, for a compound or salt of Formula (I), R$^1$ is selected from an optionally substituted 10-membered heterocycle. In some cases, the 10-membered heterocycle is a bicyclic heterocycle. In some cases, the 10-membered heterocycle is a spiro heterocycle. In some cases, the 10-membered heterocycle is a fused heterocycle. In some cases, the 10-membered heterocycle is a saturated heterocycle. In some cases, the 10-membered heterocycle is a non-aromatic heterocycle. In some cases, the 10-membered heterocycle contains at least 1 nitrogen atom. In some cases, the 10-membered heterocycle contains at least 2 nitrogen atoms. In some cases, the 10-membered heterocycle contains at least 3 nitrogen atoms. In some cases, the 10-membered heterocycle contains at least 1 sulfur atom. In some cases, R$^1$ is selected from

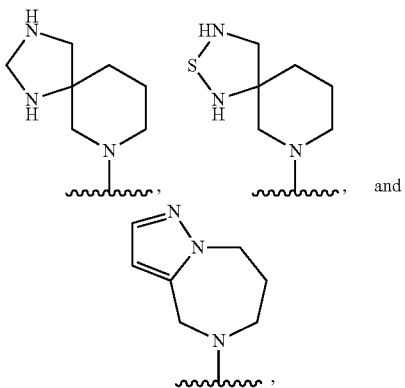

each of which is optionally substituted with one or more substituents independently selected from halogen, =O, —OH, —CN, —NHCN, —C(O)N(R$^{20}$)$_2$, —C(O)

$NR^{20}OR^{20}$, $C_{1-6}$ aminoalkyl, $C_{1-6}$ hydroxyalkyl, $C_{1-6}$ cyanoalkyl, and $C_{1-6}$ alkyl. In some cases, $R^1$ is selected from

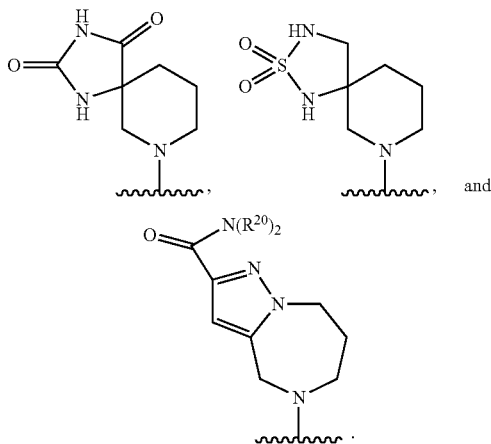

In some cases, $R^1$ is selected from

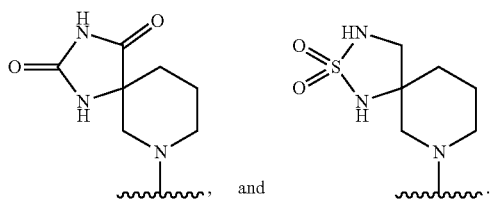 [SMILES: *N1CCCC2(C1)NC(=O)NC2=O ; *N1CCCC2(CNS(=O)(=O)N2)C1]

In some cases, $R^1$ is selected from

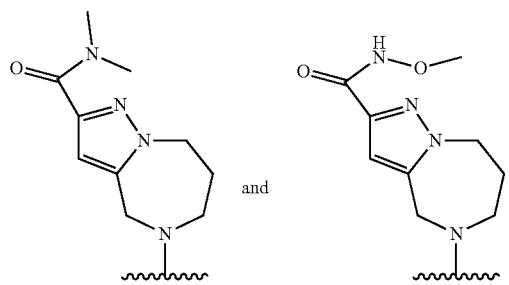

In some cases, $R^1$ is selected from

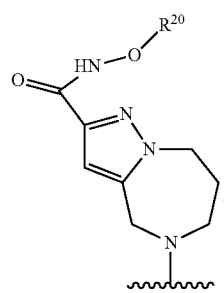

In some cases, $R^1$ is selected from

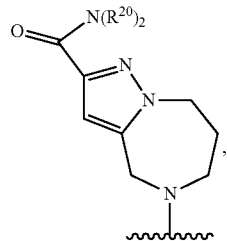

which is optionally substituted with one or more substituents independently selected from halogen, $-OR^{20}$, $-SR^{20}$, $-N(R^{20})_2$, $-NO_2$, $=O$, $-CN$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, $C_{2-6}$ alkenyl, and $C_{2-6}$ alkynyl.

In some embodiments, for a compound or salt of Formula (I), $R^1$ is selected from an optionally substituted 8- to 10-membered fused heterocycle. In some cases, the 8- to 10-membered fused heterocycle is a bicyclic heterocycle. In some cases, the 8- to 10-membered fused heterocycle is a saturated heterocycle. In some cases, the 8- to 10-membered heterocycle is a non-aromatic heterocycle. In some cases, $R^1$ is selected from an optionally substituted 10-membered fused heterocycle. In some cases, the 10-membered fused heterocycle is a bicyclic heterocycle. In some cases, the 10-membered fused heterocycle is a saturated heterocycle. In some cases, the 10-membered heterocycle is a non-aromatic heterocycle. In some cases, the fused heterocycle has one saturated ring and one aromatic ring. In some cases, the fused heterocycle has one saturated ring and one unsaturated ring. In some cases, the fused heterocycle has two saturated rings. In some cases, the 10-membered heterocycle contains at least 1 nitrogen atom. In some cases, the 10-membered heterocycle contains at least 2 nitrogen atoms. In some cases, the 10-membered heterocycle contains at least 3 nitrogen atoms. In some cases, $R^1$ is selected from

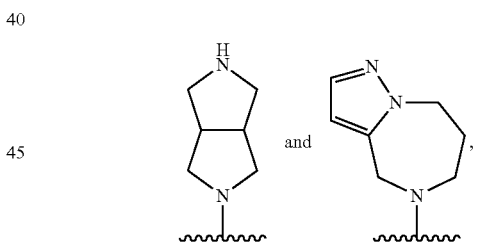

each of which is optionally substituted with one or more substituents. In some cases, $R^1$ is

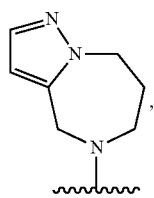

which is optionally substituted with one or more substituents. In some cases, the optional one or more substituents are independently selected from halogen, $=O$, $-OH$, $-CN$, $-NHCN$, $-C(O)R^{20}$, $-C(O)N(R^{20})_2$, $-C(O)NR^{20}OR^{20}$, $C_{1-6}$ aminoalkyl, $C_{1-6}$ hydroxyalkyl, $C_{1-6}$ cyanoalkyl, and $C_{1-6}$ alkyl. In some cases, the optional one or more substituents are independently selected from halogen, =O, —C(O)R$^{20}$, —C(O)N(R$^{20}$)$_2$, and —C(O)NR$^{20}$OR$^{20}$. In some cases, the optional one or more substituents are independently selected from —C(O)R$^{20}$, —C(O)N(R$^{20}$)$_2$, and —C(O)NR$^{20}$OR$^{20}$. In some cases, the optional one or more substituents are independently selected from —C(O)R$^{20}$. In some cases, the optional one or more substituents are independently selected from —C(O)N(R$^{20}$)$_2$. In some cases, the optional one or more substituents are independently selected from —C(O)NR$^{20}$OR$^{20}$. In some cases, each R$^{20}$ is independently selected from hydrogen; and $C_{1-6}$ alkyl, $C_{3-12}$ carbocycle, and 3- to 12-membered heterocycle. In some cases, each R$^{20}$ is independently selected from hydrogen; and $C_{1-6}$ alkyl, and 3- to 12-membered heterocycle. In some cases, each R$^{20}$ is independently selected from hydrogen; and $C_{1-6}$ alkyl, and 3- to 12-membered saturated heterocycle. In some cases, the optional one or more substituents of R$^1$ are independently selected from

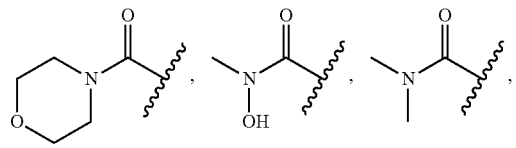

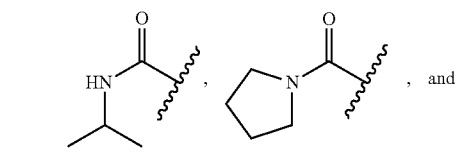

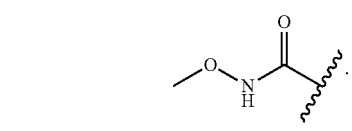

In some cases, R$^1$ is selected from

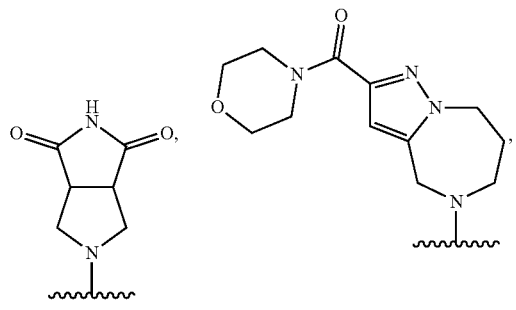

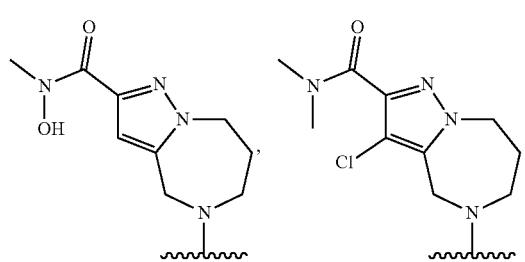

-continued

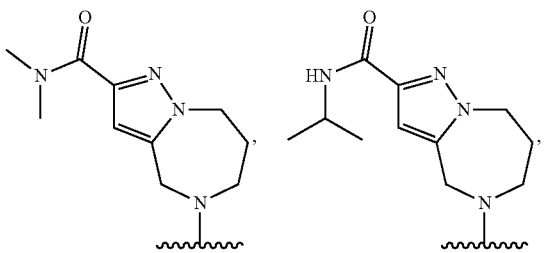

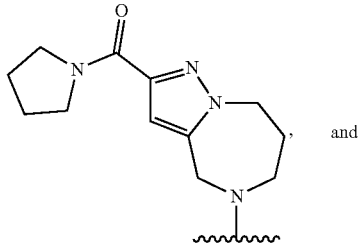

, and

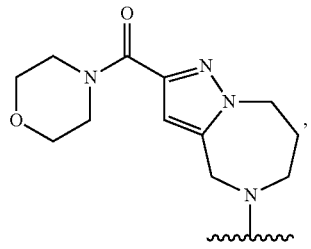

In some cases, R$^1$ is selected from

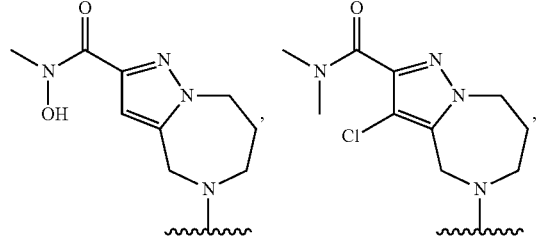

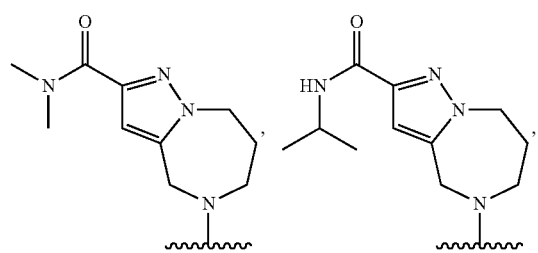

-continued

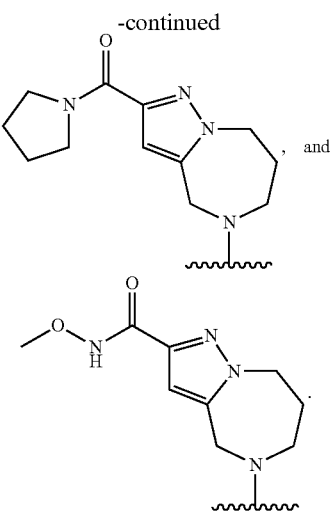, and

In some embodiments, for a compound or salt of Formula (I), $R^1$ is selected from an optionally substituted saturated 6- to 7-membered heterocycle. In some cases, $R^1$ is selected from an optionally substituted saturated 6-membered heterocycle. In some cases, $R^1$ is selected from

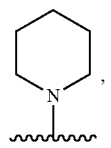, which is optionally substituted. In some cases, the optional one or more substituents are independently selected from halogen, —CN, —NHCN, $C_{1-6}$ cyanoalkyl, and $C_{1-6}$ alkyl. In some cases, the optional one or more substituents are independently selected from —CN, —NHCN, $C_{1-6}$ cyanoalkyl, and $C_{1-6}$ alkyl. In some cases, the optional one or more substituents are independently selected from —CN, —NHCN, $C_{1-6}$ cyanoalkyl, and $C_{1-6}$ alkyl. In some cases, the optional one or more substituents are independently selected from —NHCN, and $C_{1-6}$ alkyl. In some cases, $R^1$ is selected from

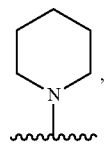, which is substituted with one or more substituents selected from —NHCN, and $C_{1-6}$ alkyl. In some cases, $R^1$ is selected from

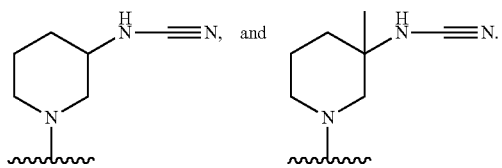 [SMILES: *N1CCCC(NC#N)C1 ; *N1CCCC(C)(NC#N)C1]

In some embodiments, for a compound or salt of Formula (I), $R^3$ is —CN, and $R^1$ is selected from

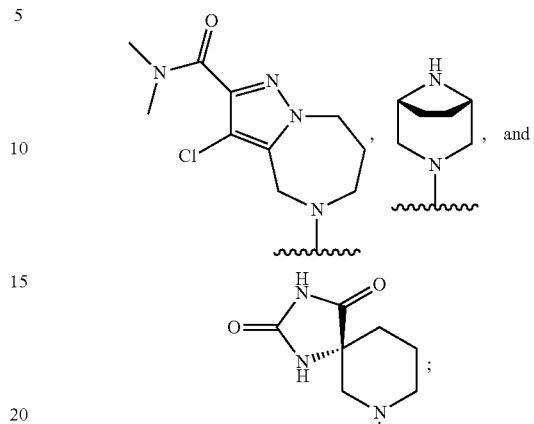

and B is an optionally substituted 8- to 9-membered fused heterocycle, wherein the 8- to 9-membered fused heterocycle has at least one sulfur atom. In some cases, $R^3$ is —CN, and $R^1$ is selected from

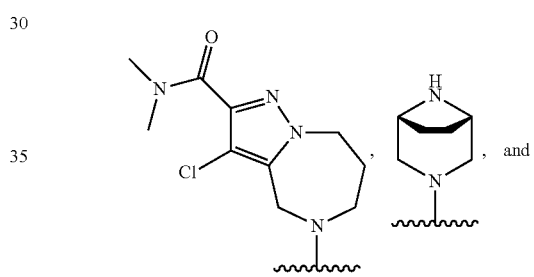

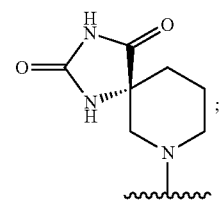

and B is selected from

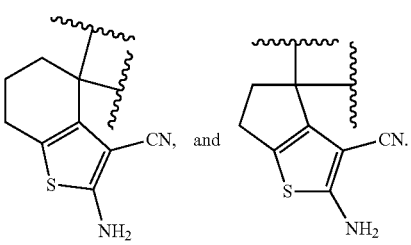 [SMILES: *C1(*)CCCc2sc(N)c(C#N)c21 ; *C1(*)CCc2sc(N)c(C#N)c21]

201
In some cases, R³ is —CN, and R¹ is selected from
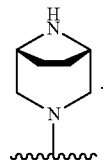
In some cases, R³ is —CN, and R¹ is selected from
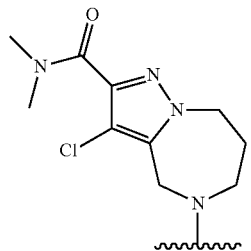
In some cases, R³ is —CN, and R¹ is selected from
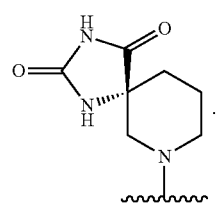 [SMILES: *N1CCC[C@]2(C1)NC(=O)NC2=O]
In some cases, R³ is —CN, B is
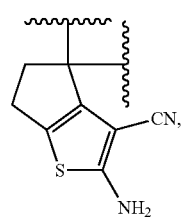 [SMILES: *C1(*)CCc2sc(N)c(C#N)c21]
and R¹ is selected from
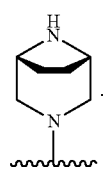
202
In some cases, R³ is —CN, B is
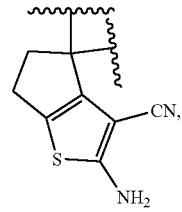
and R¹ is selected from
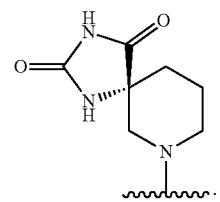 [SMILES: *N1CCC[C@]2(C1)NC(=O)NC2=O]
In some cases, R³ is —CN, B is
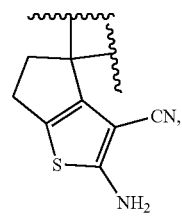 [SMILES: *C1(*)CCc2sc(N)c(C#N)c21]
and R¹ is selected from
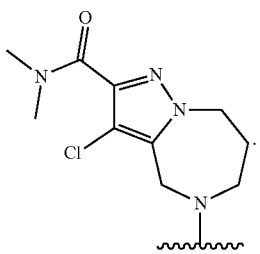 [SMILES: *N1CCCn2nc(C(=O)N(C)C)c(Cl)c2C1]
In some cases, R³ is —CN, and R¹ is selected from
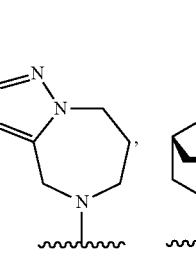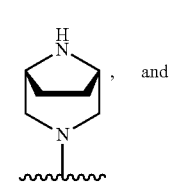, and

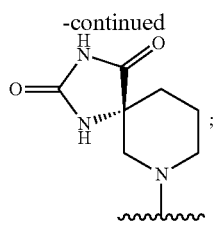

B is an optionally substituted 8- to 9-membered fused heterocycle, wherein the 8- to 9-membered fused heterocycle has at least one sulfur atom; and Y—R² is selected from —O-L-heterocycle, wherein the heterocycle portion of —O-L-heterocycle is optionally substituted with one or more R⁶.

In some embodiments, for a compound or salt of Formula (I), B is an optionally substituted 8- to 10-membered fused carbocycle. In some cases, B is a substituted 8- to 10-membered fused carbocycle. In some cases, B is an optionally substituted 9-membered fused carbocycle. In some cases, B is a substituted 9-membered fused carbocycle. In some cases, B is

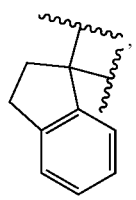

which is optionally substituted with one or more substituents. In some cases, B is

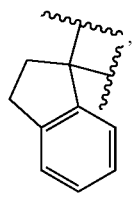

which is substituted with one or more substituents. In some cases, for B, the one or more substituents are independently selected from halogen, oxo, —NH₂, C₁-C₃ alkyl, —B(OH)₂, —OH, —C(O)NH₂, —NH₂, =O, —CN, C$_{1-6}$ alkoxy, C$_{1-6}$ hydroxyalkyl, and C$_{2-6}$ alkynyl. In some cases, B is substituted with at least one halogen. In some cases, B is substituted with at least one chlorine. In some cases, B is substituted with at least one fluorine. In some cases, B is selected from

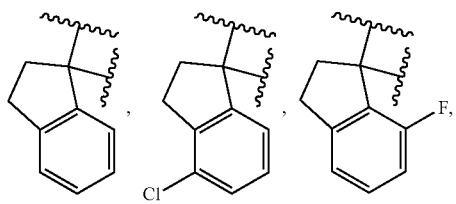

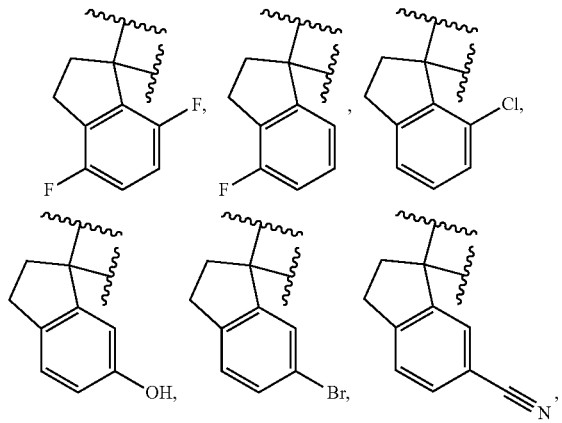

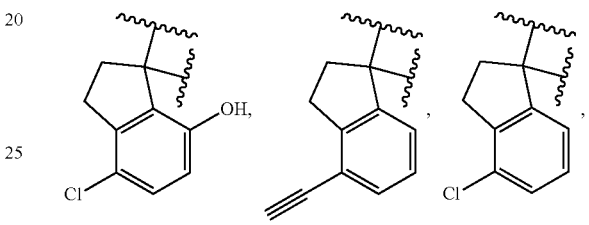

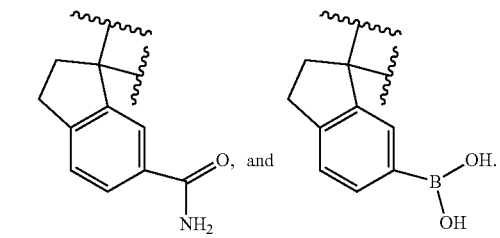

In some cases, B is

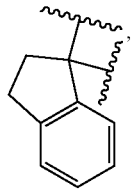

which is substituted with one or more substituents selected from halogen and C$_{1-6}$ haloalkyl. In some cases, B is

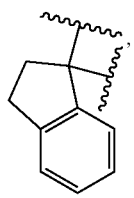

which is substituted with one or more substituents selected from halogen. In some cases, B is selected from

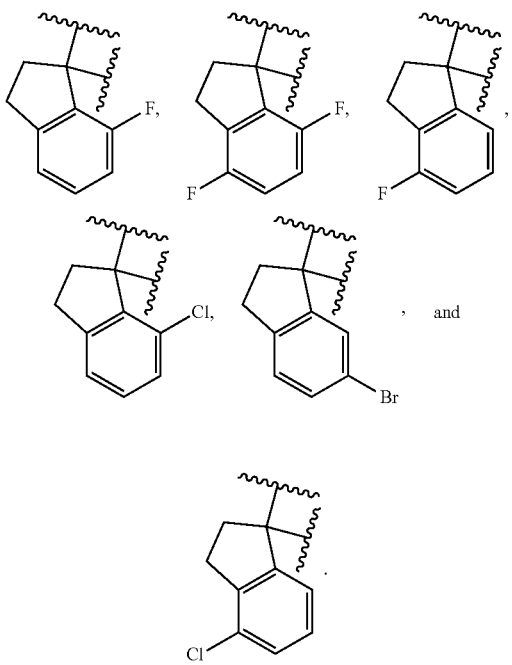

In some cases, B is

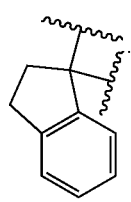 [SMILES: *C1(*)CCc2ccccc21]

which is substituted with one or more substituents selected from fluorine. In some cases, B is selected from

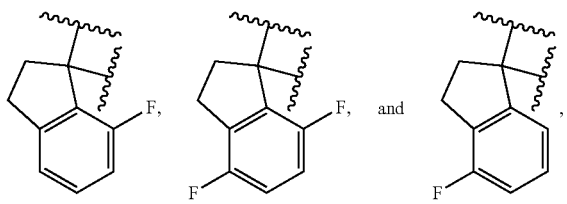

In some cases, B is

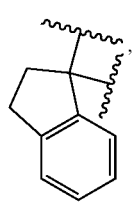

which is substituted with one or more substituents selected from chlorine. In some cases, B is selected from

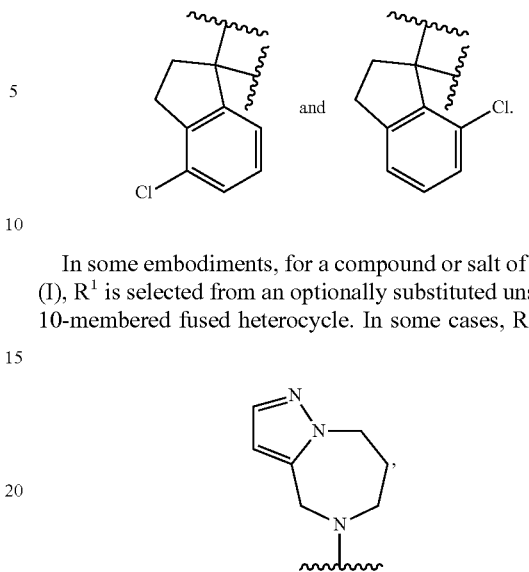

In some embodiments, for a compound or salt of Formula (I), $R^1$ is selected from an optionally substituted unsaturated 10-membered fused heterocycle. In some cases, $R^1$ is which is optionally substituted. In some cases, the optional one or more substituents of $R^1$ are independently selected from halogen, =O, —OH, —CN, —NHCN, —S(O)$_2$(R$^{20}$), —S(O)$_2$N(R$^{20}$)$_2$, —S(O)N(R$^{20}$)$_2$, —S(O)R$^{20}$(=NR$^{20}$), —C(O)R$^{20}$, —C(O)N(R$^{20}$)$_2$, —C(O)NR$^{20}$OR$^{20}$, $C_{1-6}$ alkyl-N(R$^{20}$)$_2$, $C_{1-6}$ aminoalkyl, $C_{1-6}$ hydroxyalkyl, $C_{1-6}$ cyanoalkyl, and $C_{1-6}$ alkyl. In some cases, B is an optionally substituted 8- to 10-membered fused heterocycle, wherein the heterocycle contains one sulfur atom. In some cases, B is selected from

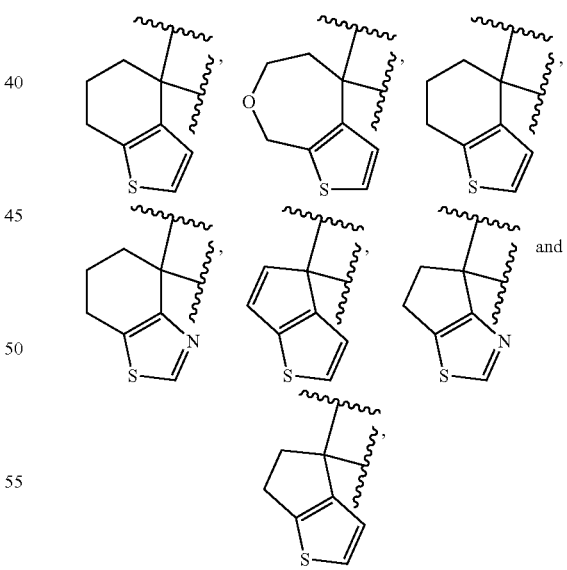

each of which is optionally substituted. In some cases, In some cases, for B, the one or more optional substituents of the heterocycle and carbocycle are independently selected at each occurrence from halogen, oxo, —NH$_2$, $C_1$-$C_3$ alkyl, —OH, —O—$C_1$-$C_3$ haloalkyl, —C(O)NH$_2$, —NH$_2$, =O, —CN, $C_{1-6}$ alkoxy, $C_{1-6}$ hydroxyalkyl, and $C_{2-6}$ alkynyl. In some cases, Y—$R^2$ is selected from

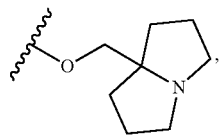 [SMILES: *OCC12CCCN1CCC2]

wherein the heterocycle portion is optionally substituted. In some cases, n is 0. In some cases, $R^3$ is selected from hydrogen, halogen, —CN, —N($R^{20}$)$_2$, —OH, —S(O)$_2$($R^{20}$), —C(O)$R^{20}$, $C_{1-6}$ alkyl-N($R^{20}$)$_2$, $C_{1-6}$ aminoalkyl, $C_{1-6}$ alkoxy, $C_{1-6}$ alkoxyalkyl, $C_{1-6}$ hydroxyalkyl, $C_{1-6}$ cyanoalkyl, $C_{1-6}$ haloalkyl, and $C_{1-6}$ alkyl. In some cases, $R^3$ is selected from hydrogen, halogen, and —CN.

In some embodiments, for a compound or salt of Formula (I), $R^1$ is selected from an optionally substituted 11-membered fused heterocycle. In some cases, $R^1$ is selected from an optionally substituted unsaturated 11-membered fused heterocycle. In some cases, the heterocycle contains at least one sulfur atom. In some cases, the heterocycle contains at least one nitrogen atom. In some cases, the heterocycle contains 3 heteroatoms. In some cases the heterocycle is

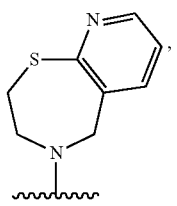 [SMILES: *N1CCSc2ncccc2C1]

which is optionally substituted. In some cases, $R^1$ is

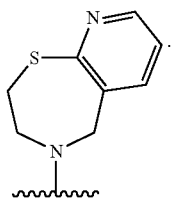 [SMILES: *N1CCSc2ncccc2C1]

In some embodiments, for a compound or salt of Formula (I), the one or more optional substituents of $R^1$ are each independently selected from halogen, —CN, —NO$_2$, =O, —N($R^{20}$)$_2$, —B(O$R^{20}$)$_2$, —O$R^{20}$, —S$R^{20}$, —S(O)$_2$($R^{20}$), —S(O)$_2$N($R^{20}$)$_2$, —N$R^{20}$S(O)$_2R^{20}$, $C_{1-6}$ aminoalkyl, $C_{1-6}$ alkoxy, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkenyl, and $C_{2-6}$ alkynyl. In some cases, the one or more optional substituents are independently selected from halogen, —OH, —N($R^{20}$)$_2$, —NO$_2$, =O, —CN, $C_{1-6}$ aminoalkyl, $C_{1-6}$ alkoxy, $C_{1-6}$ hydroxyalkyl, and $C_{1-6}$ haloalkyl. In some cases, the optional substituents for $R^1$ are each independently selected from halogen, —OH, —N($R^{20}$)$_2$, —NO$_2$, $C_{1-6}$ aminoalkyl, $C_{1-6}$ alkoxy, $C_{1-6}$ hydroxyalkyl, and $C_{1-6}$ haloalkyl. In some cases, the optional substituents for $R^1$ are each independently selected from halogen, —CN, —OH, —NH$_2$, $C_{1-6}$ aminoalkyl, $C_{1-6}$ hydroxyalkyl, $C_{1-6}$ cyanoalkyl, and $C_{1-6}$ haloalkyl. In some cases, the optional substituents for $R^1$ are each independently selected from —OH, and —NH$_2$. In some cases, $R^{20}$ is selected from hydrogen and $C_{1-3}$ alkyl.

In some embodiments, for a compound or salt for Formula (I), n is selected from 0 to 4. In some cases, n is selected from 0 to 3. In some cases, n is selected from 0 to 2. In some cases, n is selected from 0 and 1. In some cases, n is 0. In some cases, n is 1. In some cases, n is 2.

In some embodiments, for a compound or salt for Formula (I), each $R^4$ is independently selected from halogen, —NO$_2$, =O, =S, —CN, $C_{1-6}$ aminoalkyl, $C_{1-6}$ alkoxy, $C_{1-6}$ hydroxyalkyl, $C_{2-6}$ alkynyl, $C_{1-6}$ cyanoalkyl, and $C_{1-6}$ haloalkyl. In some cases, $R^4$ is independently selected from halogen, =O, —CN, $C_{1-6}$ cyanoalkyl, $C_{2-6}$ alkynyl, $C_{1-6}$ aminoalkyl, $C_{1-6}$ alkoxy, $C_{1-6}$ hydroxyalkyl, and $C_{1-6}$ haloalkyl. In some cases, $R^4$ is independently selected from halogen, =O, —CN, $C_{1-6}$ cyanoalkyl, $C_{2-6}$ alkynyl, and $C_{1-6}$ haloalkyl. In some cases, $R^4$ is independently selected from —CN, $C_{1-6}$ cyanoalkyl, and $C_{2-6}$ alkynyl. In some cases, each $R^4$ is independently selected from halogen, —NO$_2$, =O, =S, —CN, $C_{1-6}$ aminoalkyl, $C_{1-6}$ alkoxy, $C_{1-6}$ cyanoalkyl, $C_{1-6}$ hydroxyalkyl, and $C_{1-6}$ haloalkyl.

In some embodiments, for a compound or salt for Formula (I), Q is a bond. In some cases, Q is a S. In some cases, Q is a O.

In some embodiments, for a compound or salt for Formula (I), each $R^7$ is independently selected from halogen, hydroxy, HC(=O)—, $C_1$-$C_4$ alkyl, $C_1$-$C_4$ alkoxy, $C_1$-$C_4$ haloalkyl, $C_1$-$C_4$ hydroxyalkyl, and —N($R^5$)$_2$. In some cases, each $R^7$ is independently selected from halogen, hydroxy, $C_1$-$C_4$ alkyl, $C_1$-$C_4$ alkoxy, $C_1$-$C_4$ haloalkyl, and $C_1$-$C_4$ hydroxyalkyl.

In some embodiments, for a compound or salt for Formula (I), each $R^{20}$ is independently selected from hydrogen; and $C_{1-6}$ alkyl, $C_{3-12}$ carbocycle, and 3- to 12-membered heterocycle, each of which is optionally substituted with one or more substituents independently selected from halogen, —OH, —CN, —NO$_2$, —NH$_2$, —N($C_{1-6}$ alkyl)$_2$, $C_{1-10}$ alkyl, —$C_{1-10}$ haloalkyl, —O—$C_{1-10}$ alkyl, oxo, $C_{3-12}$ carbocycle, and 3- to 12-membered heterocycle. In some cases, each $R^{20}$ is independently selected from hydrogen and $C_{1-6}$ alkyl. In some cases, each $R^{20}$ is independently selected from $C_{1-6}$ alkyl.

In some embodiments, for a compound or salt for Formula (I), each $R^{21}$ is independently selected from hydrogen; and $C_{1-6}$ alkyl, $C_{3-12}$ carbocycle, and 3- to 12-membered heterocycle, each of which is optionally substituted with one or more substituents independently selected from halogen, —OH, —CN, —NO$_2$, —NH$_2$, —N($C_{1-6}$ alkyl)$_2$, $C_{1-10}$ alkyl, —$C_{1-10}$ haloalkyl, —O—$C_{1-10}$ alkyl, oxo, $C_{3-12}$ carbocycle, and 3- to 12-membered heterocycle. In some cases, each $R^{21}$ is independently selected from hydrogen and $C_{1-6}$ alkyl. In some cases, each $R^{21}$ is independently selected from $C_{1-6}$ alkyl.

In some embodiments, for a compound or salt for Formula (I), each $R^{20}$ is independently selected from hydrogen; and $C_{1-6}$ alkyl, $C_{3-12}$ carbocycle, and 3- to 12-membered heterocycle, each of which is optionally substituted with one or more substituents independently selected from halogen, —OH, —CN, —NO$_2$, —NH$_2$, —N($C_{1-6}$ alkyl)$_2$, $C_{1-10}$ alkyl, —$C_{1-10}$ haloalkyl, —O—$C_{1-10}$ alkyl, oxo, $C_{3-12}$ carbocycle, and 3- to 12-membered heterocycle. In some cases, each $R^{20}$ is independently selected from hydrogen and $C_{1-6}$ alkyl. In some cases, each $R^{20}$ is independently selected from $C_{1-6}$ alkyl.

In some embodiments, for a compound or salt for Formula (I), each $R^{23}$ is independently selected from hydrogen; and $C_{1-6}$ alkyl, $C_{3-12}$ carbocycle, and 3- to 12-membered heterocycle, each of which is optionally substituted with one or more substituents independently selected from halogen, —OH, —CN, —NO$_2$, —NH$_2$, —N($C_{1-6}$ alkyl)$_2$, $C_{1-10}$ alkyl, —$C_{1-10}$ haloalkyl, —O—$C_{1-10}$ alkyl, oxo, $C_{3-12}$ carbocycle, and 3- to 12-membered heterocycle. In some cases, each $R^{23}$ is independently selected from hydrogen and $C_{1-6}$ alkyl. In some cases, each $R^{23}$ is independently selected from $C_{1-6}$ alkyl.

In an aspect, the present disclosure provides a compound of Formula (I-A)

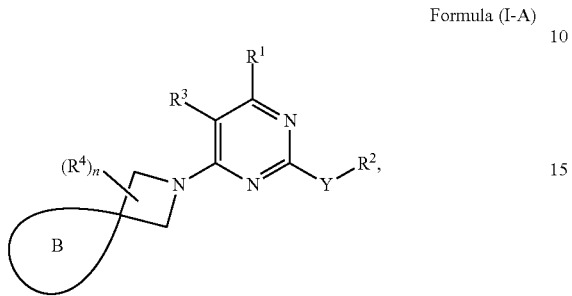

Formula (I-A)

or a pharmaceutically acceptable salt thereof wherein:

$R^1$ is selected from 8- to 10-membered heterocycle, wherein the 8- to 10-membered heterocycle is optionally substituted with one or more substituents independently selected from halogen, —$OR^{20}$, —$S(O)_2(R^{20})$, —$C(O)N(R^{20})_2$, —$C_{1-6}$ alkyl(=$NOR^{20}$), —$C(O)R^{20}$=O, —CN, —NHCN, $C_{1-6}$ alkyl-$N(R^{20})_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl-$SO_2R^{20}$, $C_{1-6}$ alkoxyalkyl, $C_{1-6}$ alkyl, $C_{2-6}$ alkynyl, and 5- to 12-membered heterocycle, wherein the 5- to 12-membered heterocycle are each optionally substituted independently with one or more $R^{1*}$;

each $R^{1*}$ is independently selected from halogen, —$B(OR^{20})_2$, —$OR^{20}$, —$SR^{20}$, —$S(O)_2(R^{20})$, —$S(O)_2N(R^{20})_2$, —$S(O)N(R^{20})_2$, —$S(O)R^{20}$(=$NR^{20}$), —$NR^{20}S(O)_2R^{20}$, —$C(O)N(R^{20})_2$, —$C(O)NR^{20}OR^{20}$, —$N(R^{20})C(O)R^{20}$, —$N(R^{20})C(O)N(R^{20})_2$, —$N(R^{20})C(O)OR^{20}$, —$N(R^{20})_2$, —$C(O)R^{20}$, —$C(O)OR^{20}$, —$OC(O)R^{20}$, —$OC(O)N(R^{20})_2$, —$NO_2$, =O, =$N(R^{20})$, =$NO(R^{20})$, —CN, —NHCN, $C_{1-6}$ alkyl-$N(R^{20})_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, and $C_3$-$C_{12}$ carbocycle;

B is selected from a 7- to 15-membered heterocycle and $C_7$-$C_{15}$ carbocycle, wherein the 7- to 15-membered heterocycle and $C_7$-$C_{15}$ carbocycle are each optionally substituted with one or more substituents independently selected from halogen, —CN, —$NO_2$, =O, —$N(R^{21})_2$, —$B(OR^{21})_2$, —$OR^{21}$, —$SR^{21}$, —$S(O)_2(R^{21})$, —$S(O)_2N(R^{21})_2$, —$NR^{21}S(O)_2R^{21}$, —$C(O)N(R^{21})_2$, —$C(O)NR^{21}OR^{21}$, —$N(R^{21})C(O)R^{21}$, —$N(R^{21})C(O)N(R^{21})_2$, —$N(R^{21})C(O)OR^{21}$, —$C(O)R^{21}$, $C(O)OR^{21}$, —$OC(O)R^{21}$, —$OC(O)N(R^{21})_2$, $C_{1-6}$ alkyl-$N(R^{20})_2$, $C_{1-6}$ aminoalkyl, $C_{1-6}$ alkoxy, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, $C_3$-$C_{12}$ carbocycle and 5- to 12-membered heterocycle;

Y is selected from a bond, —O—, —S—, and —$N(R^5)$—;

$R^2$ is selected from heterocycle, aryl, $C_1$-$C_6$ alkyl, -L-heterocycle, -L-$N(R^{23})_2$, -L-$OR^{23}$, -L-aryl, -L-heteroaryl, -L-cycloaryl, -L-NHC(=NH)$NH_2$, -L-C(O)N($R^{23})_2$, -L-$C_1$-$C_6$ haloalkyl, -L-$OR^{23}$, -L-$NR^{23}C(O)$-aryl, -L-COOH, -L-$NR^{23}S(O)_2(R^{23})$, -L-S(O)$_2N(R^{23})_2$, -L-$N(R^{23})C(O)(OR^{23})$, -L-$OC(O)N(R^{23})_2$, and -L-C(=O)$OC_1$-$C_6$ alkyl, wherein the heterocycle, the heterocycle portion of -L-heterocycle, and the cycloalkyl portion of the -L-cycloalkyl are each optionally substituted with one or more $R^6$, and wherein the aryl, aryl portion of -L-$NR^{23}C(O)$-aryl, the aryl portion of -L-$NR^{23}C(O)$-aryl, the aryl of the -L-aryl, and the heteroaryl of -L-heteroaryl are each optionally substituted with one or more $R^7$;

$R^3$ is selected from hydrogen, halogen, —CN, —$NO_2$, —$N(R^{20})_2$, —$OR^{20}$, —$SR^{20}$, —$S(O)_2(R^{20})$, —$S(O)_2N(R^{20})_2$, —$S(O)N(R^{20})_2$, —$S(O)_2R^{20}$, —$S(O)R^{20}$(=$NR^{20}$), —$NR^{20}S(O)_2R^{20}$, —$C(O)N(R^{20})_2$, —$N(R^{20})C(O)R^{20}$, —$N(R^{20})C(O)N(R^{20})_2$, —$N(R^{20})C(O)OR^{20}$, —$C(O)R^{20}$, —$C(O)OR^{20}$, —$OC(O)R^{20}$, —$OC(O)N(R^{20})_2$, $C_{1-6}$ alkyl-$N(R^{20})_2$, $C_{1-6}$ aminoalkyl, $C_{1-6}$ alkoxy, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, $C_3$-$C_{12}$ carbocycle and 5- to 12-membered heterocycle;

each $R^4$ is independently selected from halogen, —$NO_2$, =O, =S, —CN, $C_{1-6}$ alkyl, $C_{2-6}$ alkynyl, $C_{1-6}$ alkyl-$N(R^{20})_2$, $C_{1-6}$ aminoalkyl, $C_{1-6}$ alkoxy, $C_{1-6}$ cyanoalkyl, $C_{1-6}$ hydroxyalkyl, and $C_{1-6}$ haloalkyl;

n is selected from 0, 1, 2, 3, and 4;

each $R^5$ is independently selected from hydrogen and $C_1$-$C_6$ alkyl;

each $R^6$ is independently selected from halogen, hydroxy, $C_1$-$C_3$ hydroxyalkyl, $C_1$-$C_3$ alkyl, oxo, $C_1$-$C_3$ haloalkyl, $C_1$-$C_3$ alkoxy, cyano, =$CH_2$, =NO—$C_1$-$C_3$ alkyl, $C_1$-$C_3$ aminoalkyl, —$N(R^5)S(O)_2(R^5)$, -Q-phenyl, -Q-phenylSO$_2$F, —NHC(O)phenyl, —NHC(O)phenylSO$_2$F, $C_1$-$C_3$ alkyl substituted pyrazolyl, —$C_1$-$C_3$ alkyl-$N(R^5)_2$, —$C(O)N(R^5)_2$, tert-butyldimethylsilyloxy$CH_2$—, —$N(R^5)_2$, ($C_1$-$C_3$ alkoxy)$C_1$-$C_3$ alkyl-, ($C_1$-$C_3$ alkyl)C(=O), oxo, ($C_1$-$C_3$ haloalkyl)C(=O)—, —$SO_2F$, ($C_1$-$C_3$ alkoxy)$C_1$-$C_3$ alkoxy, —$CH_2OC(O)N(R^5)_2$, —$CH_2NHC(O)OC_1$-$C_6$ alkyl, —$CH_2NHC(O)N(R^5)_2$, —$CH_2NHC(O)C_1$-$C_6$ alkyl, —$CH_2$(pyrazolyl), —$CH_2NHSO_2C_1$-$C_6$ alkyl, —$CH_2O$ C(O)heterocycle, —$OC(O)N(R^5)_2$, —$OC(O)NH(C_1$-$C_3$ alkyl)$O(C_1$-$C_3$ alkyl), —$OC(O)NH(C_1$-$C_3$ alkyl)$O(C_1$-$C_3$ alkyl)phenyl($C_1$-$C_3$ alkyl)$N(CH_3)_2$, —$OC(O)NH(C_1$-$C_3$ alkyl)$O(C_1$-$C_3$ alkyl)phenyl, —$OC(O)$heterocycle, —O—$C_1$-$C_3$ alkyl, —$S(O)_2(R^{20})$, —$S(O)_2N(R^{20})_2$, —$S(O)N(R^{20})_2$, —$S(O)R^{20}$(=$NR^{20}$), —$NR^{20}S(O)_2R^{20}$, and —$CH_2$ heterocycle, wherein the phenyl of —NHC(O)phenyl and —OC(O)NH($C_1$-$C_3$ alkyl)($C_1$-$C_3$ alkyl)phenyl are optionally substituted with one or more substituents selected from —C(O)H and OH, and wherein the alkyl of —O—$C_1$-$C_3$ alkyl is optionally substituted with substituents selected from heterocycle, oxo and hydroxy; and wherein the heterocycle of —$CH_2$ heterocyclyl is optionally substituted with oxo;

each Q is selected from a bond, S, and O;

each $R^7$ is independently selected from halogen, hydroxy, HC(=O)—, $C_1$-$C_4$ alkyl, $C_1$-$C_4$ alkoxy, $C_1$-$C_4$ haloalkyl, $C_1$-$C_4$ hydroxyalkyl, —$C_1$-$C_3$ alkyl-$N(R^5)_2$, —$C(O)N(R^5)_2$, and —$N(R^5)_2$;

each L is independently selected from a $C_1$-$C_4$ alkylene optionally substituted with one or more substituents independently selected from halogen, hydroxy, $C_{1-6}$ alkoxy, $C_1$-$C_4$ hydroxyalkyl, $C_1$-$C_4$ alkyl, $C_3$-$C_6$ carbocycle, and 3- to 8-membered heterocycle, wherein the $C_3$-$C_6$ carbocycle and 3- to 8-membered heterocycle are each optionally substituted with one or more substituents independently selected from halogen, —OH, —$NO_2$, =O, =S, —CN, $C_{1-6}$ alkyl-$N(R^{20})_2$, $C_{1-6}$ aminoalkyl, $C_{1-6}$ alkoxy, $C_{1-6}$ hydroxyalkyl, $C_{1-6}$ haloalkyl; and wherein optionally two substituents on the same carbon atom of L come together to form a $C_3$-$C_6$ carbocycle or 3- to 8-membered heterocycle, wherein the $C_3$-$C_6$ carbocycle and 3- to 8-membered heterocycle are each optionally substituted with one or more substituents independently selected from halogen, —OH, —$NO_2$, =O, =S, —CN, $C_{1-6}$ alkyl-N$(R^{20})_2$, $C_{1-6}$ aminoalkyl, $C_{1-6}$ alkoxy, $C_{1-6}$ hydroxyalkyl, and $C_{1-6}$ haloalkyl;

each $R^{20}$ is independently selected from hydrogen; and $C_{1-6}$ alkyl, $C_{2-6}$ alkenyl, $C_{2-6}$ alkynyl, $C_{3-12}$ carbocycle, and 3- to 12-membered heterocycle, each of which is optionally substituted with one or more substituents independently selected from halogen, —OH, —CN, —$NO_2$, —$NH_2$, —N($C_{1-6}$ alkyl)$_2$, $C_{1-10}$ alkyl, —$C_{1-10}$ haloalkyl, —O—$C_{1-10}$ alkyl, oxo, $C_{3-12}$ carbocycle, and 3- to 12-membered heterocycle;

each $R^{21}$ is independently selected from hydrogen; and $C_{1-6}$ alkyl, $C_{2-6}$ alkenyl, $C_{2-6}$ alkynyl, $C_{3-12}$ carbocycle, and 3- to 12-membered heterocycle, each of which is optionally substituted with one or more substituents independently selected from halogen, —OH, —CN, —$NO_2$, —$NH_2$, —N($C_{1-6}$ alkyl)$_2$, $C_{1-10}$ alkyl, —$C_{1-10}$ haloalkyl, —O—$C_{1-10}$ alkyl, oxo, $C_{3-12}$ carbocycle, and 3- to 12-membered heterocycle;

each $R^{23}$ is independently selected from hydrogen; and $C_{1-6}$ alkyl, $C_{2-6}$ alkenyl, $C_{2-6}$ alkynyl, $C_{3-12}$ carbocycle, and 3- to 12-membered heterocycle, each of which is optionally substituted with one or more substituents independently selected from halogen, —OH, —CN, —$NO_2$, —$NH_2$, —N($C_{1-6}$ alkyl)$_2$, $C_{1-10}$ alkyl, —$C_{1-10}$ haloalkyl, —O—$C_{1-10}$ alkyl, oxo, $C_{3-12}$ carbocycle, and 3- to 12-membered heterocycle.

In some embodiments, Formula (I) or Formula (I-A) is represented by Formula (I-B), Formula (I-B)

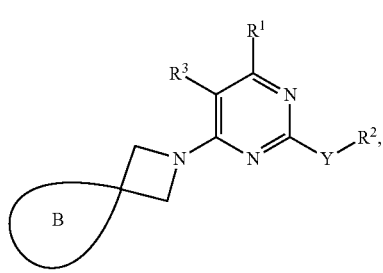

or a pharmaceutically acceptable salt thereof wherein:
wherein $R^1$ is selected from

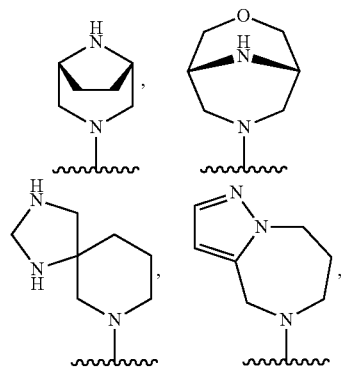

is optionally substituted with one or more substituents independently selected from halogen, —S(O)$_2$($R^{20}$), —C(O)N($R^{20})_2$, —$C_{1-6}$ alkyl(=NO$R^{20}$), —C(O)$R^{20}$, =O, and 5- to 9-membered heterocycle, wherein the 5- to -membered heterocycle are each optionally substituted independently with one or more $R^{1*}$; and
each $R^{1*}$ is independently selected from halogen, $C_{1-6}$ haloalkyl, and $C_{1-6}$ alkyl.

In some embodiments, a compound or salt of Formula (I), Formula (I-A), or Formula (I-B), Y is —O—.

In some embodiments, a compound or salt of Formula (I), Formula (I-A), or Formula (I-B), $R^2$ is selected from optionally substituted -L-heterocycle, and -L-N($R^{23})_2$. In some cases, $R^2$ is selected from optionally substituted -L-5- to each of which is optionally substituted with one or more substituents independently selected from halogen, —S(O)$_2$($R^{20}$), —C(O)N($R^{20})_2$, —$C_{1-6}$ alkyl (=NO$R^{20}$), —C(O)$R^{20}$, =O, and 5- to 12-membered heterocycle, wherein the 5- to 12-membered heterocycle are each optionally substituted independently with one or more $R^{1*}$;

each $R^{1*}$ is independently selected from halogen, —O$R^{20}$, —N($R^{20})_2$, —$NO_2$, =O, =N($R^{20}$), =NO($R^{20}$), —CN, —NHCN, $C_{1-6}$ alkyl-N($R^{20})_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, and $C_{1-6}$ alkyl;

Y is —O—;

$R^2$ is selected from -L-heterocycle, -L-N($R^{23})_2$, wherein the heterocycle portion of -L-heterocycle is optionally substituted with one or more $R^6$.

B is selected from a 7- to 15-membered heterocycle, wherein the 7- to 15-membered heterocycle is optionally substituted with one or more substituents independently selected from halogen, —CN, =O, —N($R^{21})_2$, —O$R^{21}$, $C_{1-6}$ alkyl-N($R^{20})_2$, $C_{1-6}$ aminoalkyl, $C_{1-6}$ alkoxy, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, and $C_{2-6}$ alkynyl;

$R^3$ is selected from hydrogen, halogen, —CN, —N($R^{20})_2$, —O$R^{20}$, —C(O)$R^{20}$, $C_{1-6}$ alkyl-N($R^{20})_2$, $C_{1-6}$ aminoalkyl, $C_{1-6}$ alkoxy, $C_{1-6}$ alkoxyalkyl, $C_{1-6}$ hydroxyalkyl, $C_{1-6}$ cyanoalkyl, $C_{1-6}$ haloalkyl, and $C_{1-6}$ alkyl; and each $R^{20}$ is independently selected from hydrogen; and $C_{1-6}$ alkyl, and $C_{3-12}$ carbocycle, each of which is optionally substituted with one or more substituents independently selected from halogen, —OH, —CN, —$NH_2$, —N($C_{1-6}$ alkyl)$_2$, $C_{1-10}$ alkyl, —$C_{1-10}$ haloalkyl, —O—$C_{1-10}$ alkyl, and oxo.

In some embodiments, a compound or salt of Formula (I), Formula (I-A), or Formula (I-B), $R^1$ is selected from

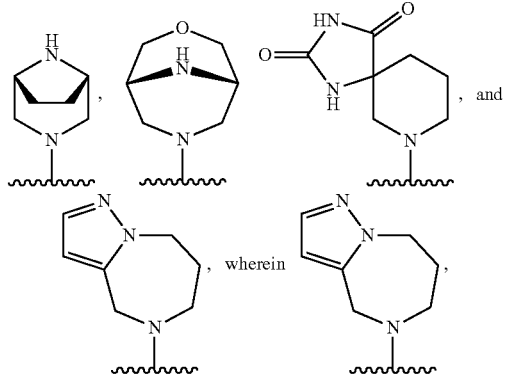

, and

, wherein 8-membered heterocycle, and -L-N(R²³)₂. In some cases, R² is selected from optionally substituted -L-heterocycle. In some cases, R² is selected from -L-N(R²³)₂. In some cases, the heterocycle contains at least one nitrogen atom. In some cases, the heterocycle contains at least one sulfur atom. In some cases, the heterocycle contains at least one oxygen atom. In some cases, the heterocycle is a heteroaryl. In some cases, the heterocycle is a saturated heterocycle. In some cases, each R⁶ is independently selected from halogen, hydroxy, $C_1$-$C_3$ hydroxyalkyl, $C_1$-$C_3$ alkyl, oxo, $C_1$-$C_3$ haloalkyl, $C_1$-$C_3$ alkoxy, cyano, =CH₂, =NO—$C_1$-$C_3$ alkyl, $C_1$-$C_3$ aminoalkyl, $C_1$-$C_3$ alkyl substituted pyrazolyl, —$C_1$-$C_3$ alkyl-N(R⁵)₂, —C(O)N(R⁵)₂, —N(R⁵)₂, ($C_1$-$C_3$ alkoxy)$C_1$-$C_3$ alkyl-, ($C_1$-$C_3$ alkyl)C(=O), oxo, —O—$C_1$-$C_3$ alkyl. In some cases, each R⁶ is independently selected from halogen, hydroxy, $C_1$-$C_3$ hydroxyalkyl, $C_1$-$C_3$ alkyl, oxo, =CH₂, and —O—$C_1$-$C_3$ alkyl. In some cases, when R² is a heteroaryl, R⁶ is selected from halogen and $C_1$-$C_3$ haloalkyl, $C_1$-$C_3$ alkyl. In some cases, when R² is a heteroaryl, R⁶ is selected from a halogen. In some cases, R²³ is selected from hydrogen and $C_1$-$C_3$ alkyl. In some cases, each R²³ is selected from $C_1$-$C_3$ alkyl. In some cases, each R²³ is selected from methyl. In some cases, each L is independently selected from a $C_1$-$C_4$ alkylene optionally substituted with one or more substituents independently selected from halogen, and $C_1$-$C_4$ alkyl; and wherein optionally two substituents on the same carbon atom of L come together to form a $C_3$-$C_6$ carbocycle or 4- to 6-membered heterocycle, wherein the $C_3$-$C_6$ carbocycle and 3- to 6-membered heterocycle are each optionally substituted with one or more substituents independently selected from halogen. In some cases, each L is selected from

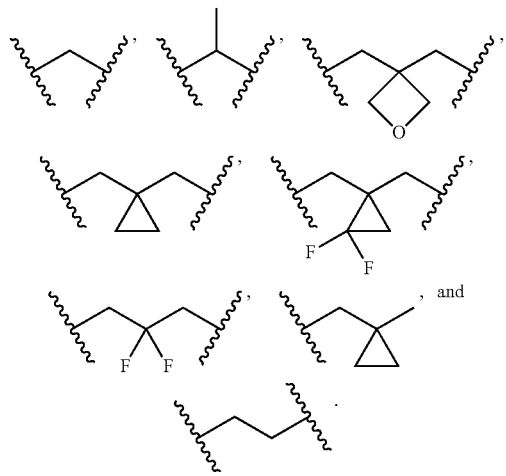

In some cases, L is selected from

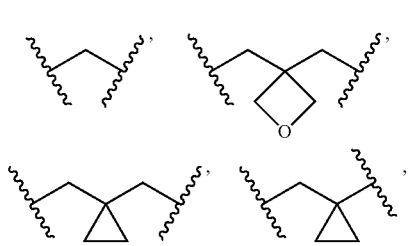

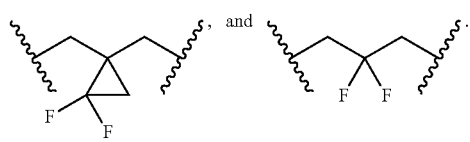

In some cases, R² is selected from

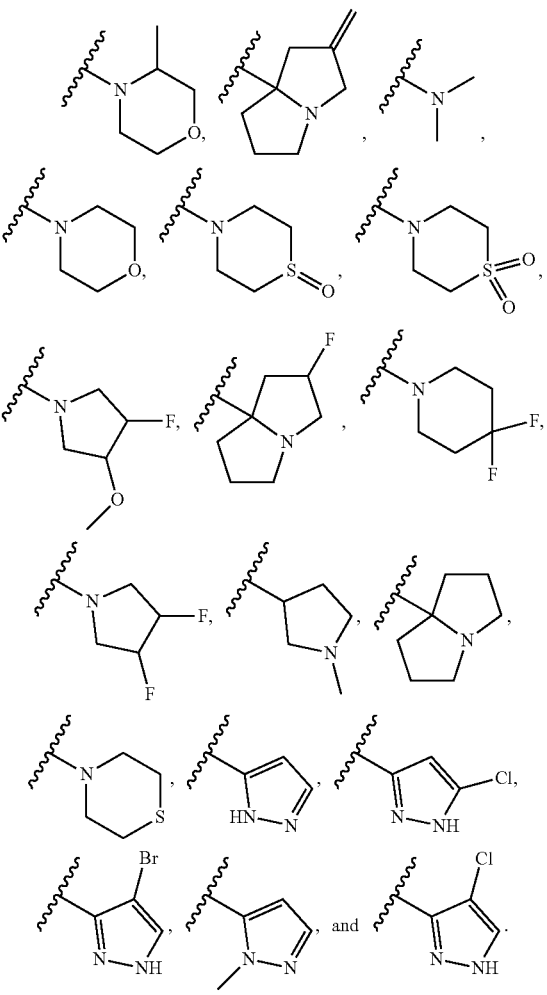

In some embodiments, a compound or salt of Formula (I), Formula (I-A), or Formula (I-B), Y—R² is selected from

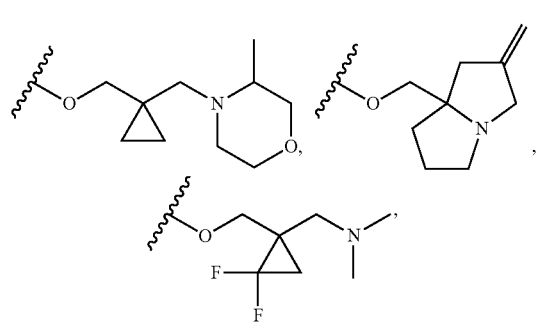

215
-continued
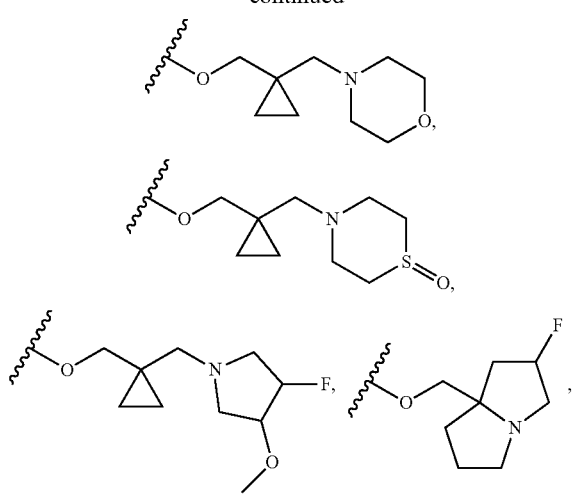
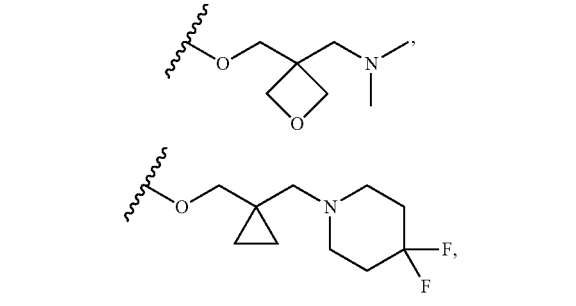
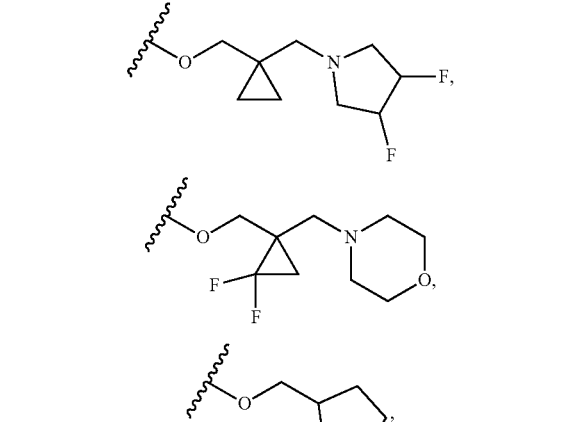
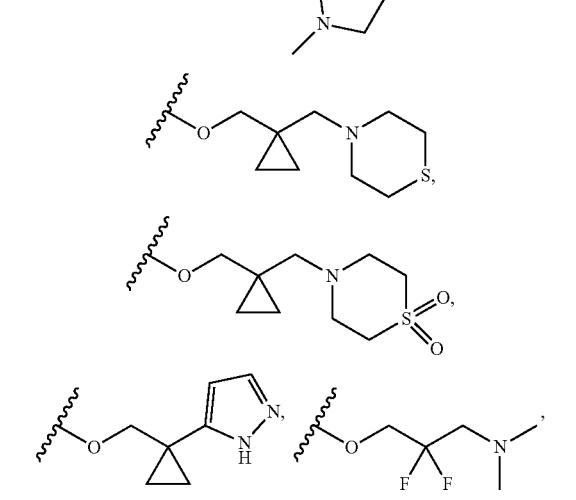
216
-continued
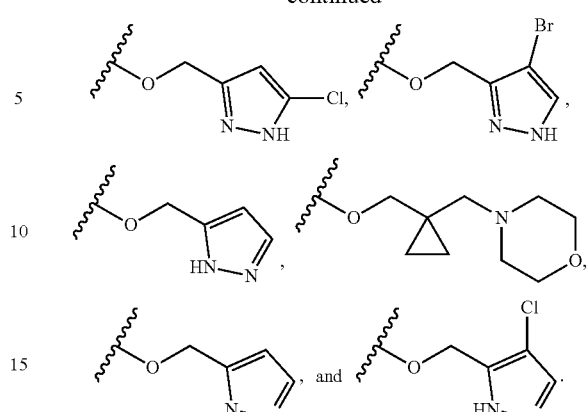
In some cases, Y—R² is selected
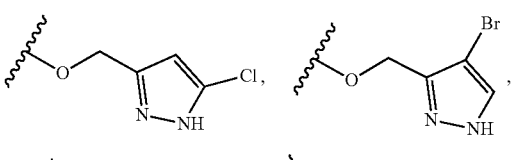
In some cases, Y—R² is selected
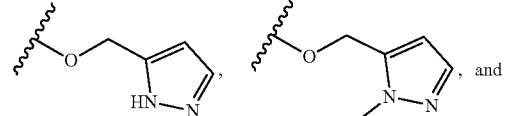
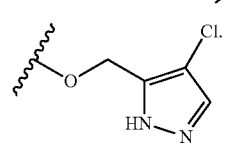
In some cases, Y—R² is selected
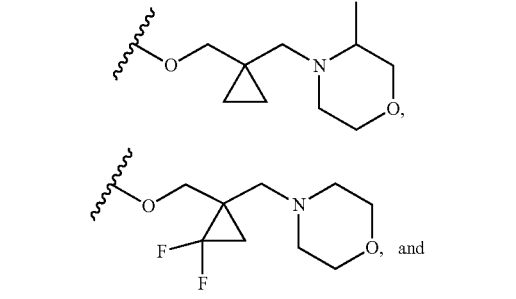

-continued

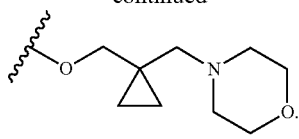

In some cases, Y—R² is selected

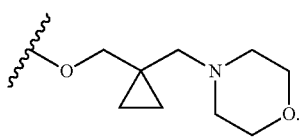 [SMILES: *OCC1(CN2CCOCC2)CC1]

In some cases, Y—R² is selected from

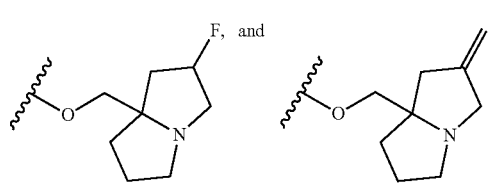

In some cases, Y—R² is

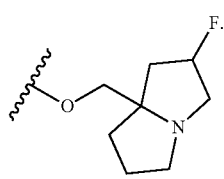 [SMILES: *OCC12CCCN1CC(F)C2]

In some cases, Y—R² is

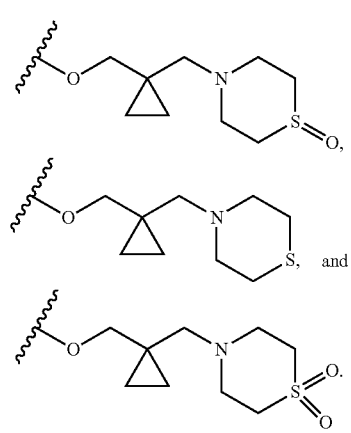

In some embodiments, a compound or salt of Formula (I), Formula (I-A), or Formula (I-B), B is selected from an 8- to 10-membered heterocycle, wherein the 8- to 10-membered heterocycle is optionally substituted with one or more substituents independently selected from halogen, —CN, —NH₂, and $C_{1-6}$ alkyl. In some cases, the heterocycle of B is selected from

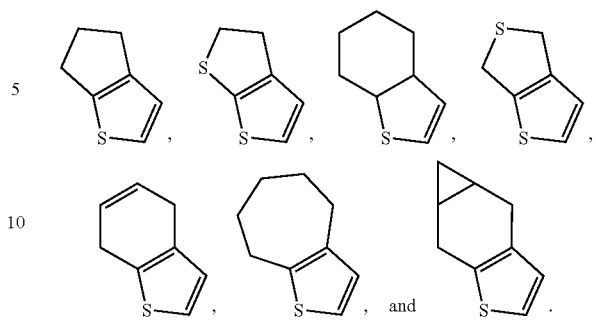

In some cases, B is selected from

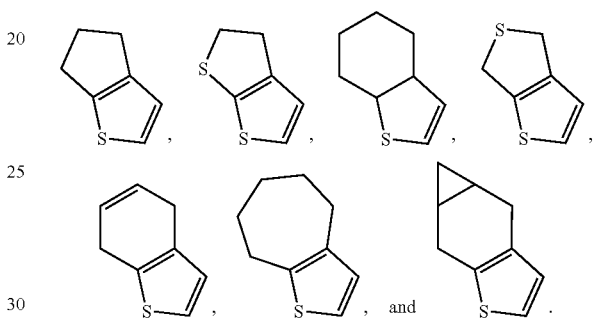

each of which is optionally substituted with one or more substituents independently selected from halogen, —CN, —NH₂, and $C_{1-6}$ alkyl. In some cases, B is selected from

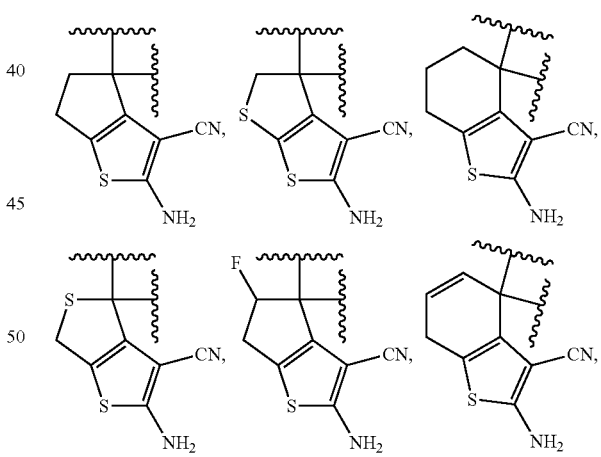

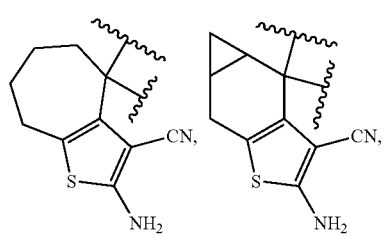

-continued

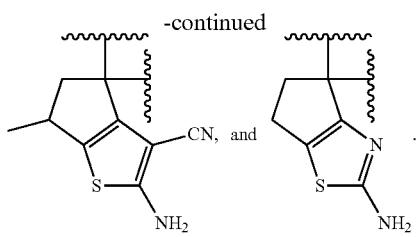

In some embodiments, a compound or salt of Formula (I), Formula (I-A), or Formula (I-B), $R^3$ is —CN. In some cases, $R^3$ is hydrogen. In some cases, $R^3$ is halogen. In some cases, $R^3$ is fluorine.

In some embodiments, a compound or salt of Formula (I), Formula (I-A), or Formula (I-B), $R^1$ is

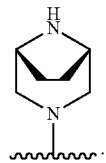

In some cases, $R^1$ is

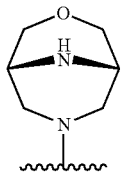

In some cases, $R^1$ is

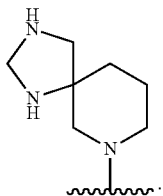 [SMILES: *N1CCCC2(CNCN2)C1]

In some cases, $R^1$ is

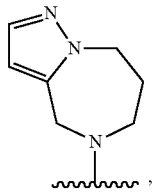

which is optionally substituted with one or more substituents. In some cases, the one or more optional substituents are independently selected from halogen, —S(O)$_2$(R$^{20}$), —C(O)N(R$^{20}$)$_2$, —C$_{1-6}$ alkyl(=NOR$^{20}$), —C(O)R$^{20}$, =O, and 5- to 9-membered heterocycle, wherein the 5- to -membered heterocycle are each optionally substituted independently with one or more $R^{1*}$. In some cases, the one or more optional substituents are independently selected from halogen, —S(O)$_2$(R$^{20}$), —C(O)N(R$^{20}$)$_2$, —C$_{1-6}$ alkyl(=NOR$^{20}$), —C(O)R$^{20}$, =O, and 5- to 9-membered heterocycle, wherein the 5- to -membered heterocycle are each optionally substituted independently with one or more $R^{1*}$. In some cases, the one or more optional substituents are independently selected from halogen, —C(O)N(R$^{20}$)$_2$, —C$_{1-6}$ alkyl(=NOR$^{20}$), —C(O)R$^{20}$, and 5- to 9-membered heterocycle, wherein the 5- to -membered heterocycle are each optionally substituted independently with one or more $R^{1*}$. In some cases, $R^1$ is

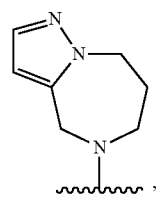

which is substituted with at least one substituent. In some cases, $R^1$ is

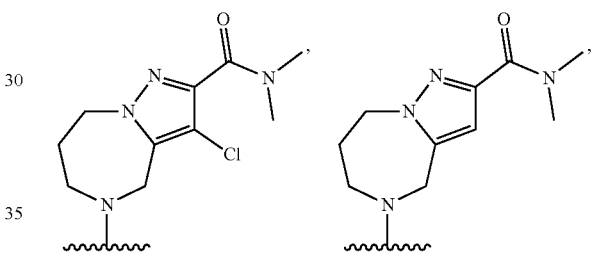

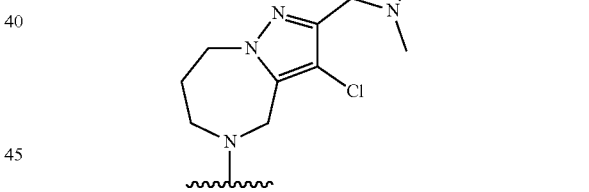

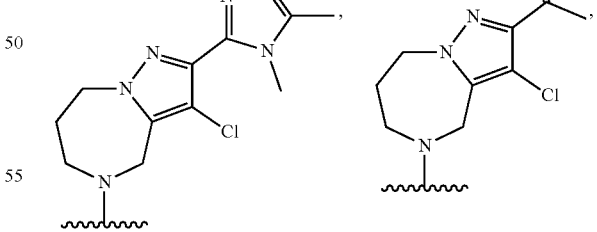

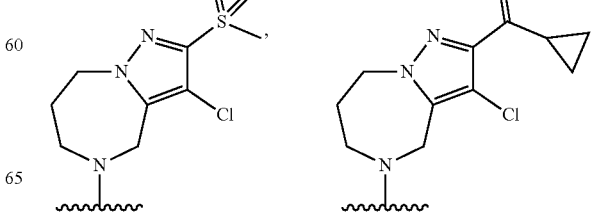

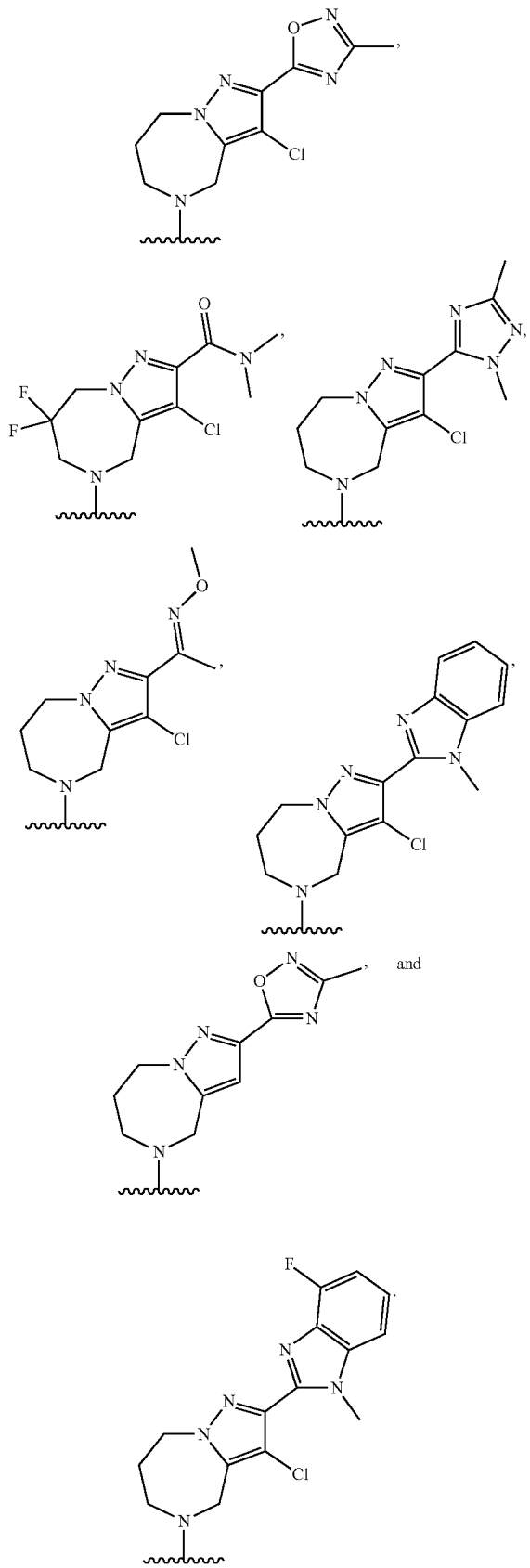

In some cases, $R^1$ is

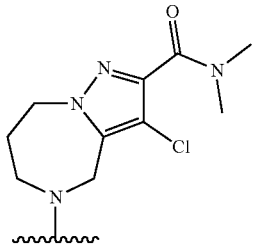

In some cases, each $R^{1*}$ is independently selected from halogen, $C_{1-6}$ haloalkyl, and $C_{1-6}$ alkyl.

In some embodiments, for a compound or salt of Formula (I), Formula (I-A), or Formula (I-B), does not contain an electrophile moiety.

In some embodiments, for a compound or salt of Formula (I), Formula (I-A), or Formula (I-B), the one or more optional substituents of $R^1$ are not electrophiles.

In some embodiments, for a compound or salt of Formula (I), $R^1$ is selected from a compound in the Examples. In some cases, B is selected from a compound in the Examples. In some cases, Y is selected from a compound in the Examples. In some cases, $R^2$ is selected from a compound in the Examples. In some cases, $R^3$ is selected from a compound in the Examples.

In some embodiments, for a compound or salt of Formula (I), each $R^{20}$ is selected from hydrogen and $C_{1-3}$ alkyl. In some cases, each $R^{20}$ is selected from hydrogen and $C_1$ alkyl.

In an aspect, the present disclosure provides a compound of Formula (II):

Formula (II)

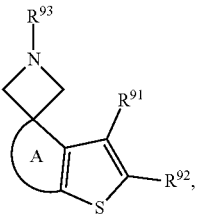

or a pharmaceutically acceptable salt thereof wherein:
A is selected from a $C_5$-$C_8$ carbocycle, wherein the $C_5$-$C_8$ carbocycle is optionally substituted with one or more substituents independently selected from $R^{94}$;
$R^{91}$ is selected from halogen, —CN, —NO$_2$, =O, —N(R$^{21}$)$_2$, —B(OR$^{21}$)$_2$, —OR$^{21}$, —SR$^{21}$, —S(O)$_2$(R$^{21}$), —S(O)$_2$N(R$^{21}$)$_2$, —NR$^{21}$S(O)$_2$R$^{21}$, —C(O)N(R$^{21}$)$_2$, —C(O)NR$^{21}$OR$^{21}$, —N(R$^{21}$)C(O)R$^{21}$, —N(R$^{21}$)C(O)N(R$^{21}$)$_2$, —N(R$^{21}$)C(O)OR$^{21}$, —C(O)R$^{21}$, —C(O)OR$^{21}$, —OC(O)R$^{21}$, —OC(O)N(R$^{21}$)$_2$, $C_{1-6}$ alkyl-N(R$^{20}$)$_2$, $C_{1-6}$ aminoalkyl, $C_{1-6}$ alkoxy, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, $C_3$-$C_{12}$ carbocycle and 5- to 12-membered heterocycle;
$R^{92}$ is selected from hydrogen, halogen, —CN, —NO$_2$, =O, —N(R$^{21}$)$_2$, —B(OR$^{21}$)$_2$, —OR$^{21}$, —SR$^{21}$, —S(O)$_2$(R$^{21}$), —S(O)$_2$N(R$^{21}$)$_2$, —NR$^{21}$S(O)$_2$R$^{21}$, —C(O)N(R$^{21}$)$_2$, —C(O)NR$^{21}$OR$^{21}$, —N(R$^{21}$)C(O)R$^{21}$, —N(R$^{21}$)C(O)N(R$^{21}$)$_2$, —N(R$^{21}$)C(O)OR$^{21}$, —C(O)R$^{21}$, —C(O)OR$^{21}$, —OC(O)R$^{21}$, —OC(O)N(R$^{21}$)$_2$, $C_{1-6}$ alkyl-N(R$^{20}$)$_2$, $C_{1-6}$ aminoalkyl, $C_{1-6}$ alkoxy, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, $C_3$-$C_{12}$ carbocycle and 5- to 12-membered heterocycle;

$R^{93}$ is selected from hydrogen, —C(O)OR$^{21}$, —C(O)R$^{21}$, and —SO$_2$R$^{21}$;

each $R^{94}$ is independently selected from halogen, —CN, —NO$_2$, =O, —N(R$^{21}$)$_2$, —B(OR$^{21}$)$_2$, —OR$^{21}$, —SR$^{21}$, —S(O)$_2$(R$^{21}$), —S(O)$_2$N(R$^{21}$)$_2$, —NR$^{21}$S(O)$_2$R$^{21}$, —C(O)N(R$^{21}$)$_2$, —C(O)NR$^{21}$OR$^{21}$, —N(R$^{21}$)C(O)R$^{21}$, —N(R$^{21}$)C(O)N(R$^{21}$)$_2$, —N(R$^{21}$)C(O)OR$^{21}$, —C(O)R$^{21}$, —C(O)OR$^{21}$, —OC(O)R$^{21}$, —OC(O)N(R$^{21}$)$_2$, $C_{1-6}$ alkyl-N(R$^{20}$)$_2$, $C_{1-6}$ aminoalkyl, $C_{1-6}$ alkoxy, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, $C_3$-$C_{12}$ carbocycle and 5- to 12-membered heterocycle; and each $R^{21}$ is independently selected from hydrogen; and $C_{1-6}$ alkyl, $C_{2-6}$ alkenyl, $C_{2-6}$ alkynyl, $C_{3-12}$ carbocycle, and 3- to 12-membered heterocycle, each of which is optionally substituted with one or more substituents independently selected from halogen, —OH, —CN, —NO$_2$, —NH$_2$, —N(C$_{1-6}$ alkyl)$_2$, $C_{1-10}$ alkyl, —C$_{1-10}$ haloalkyl, —O—C$_{1-10}$ alkyl, oxo, C$_{3-12}$ carbocycle, and 3- to 12-membered heterocycle.

In some embodiments, for a compound or salt of Formula (II), A is selected from an optionally substituted $C_5$-$C_7$ carbocycle. In some cases, A is selected from an optionally substituted unsaturated $C_5$-$C_7$ carbocycle. In some cases, A is selected from an optionally substituted $C_5$ carbocycle. In some cases, A is selected from an optionally substituted $C_6$ carbocycle. In some cases, A is selected from an optionally substituted $C_7$ carbocycle. In some cases, the $C_7$ carbocycle of A is monocyclic. In some cases, the $C_7$ carbocycle of A is bicyclic. In some cases, A is selected from

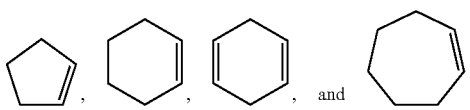

In some cases, A is selected from

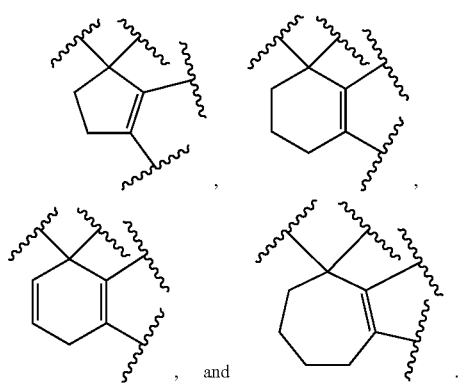

In some cases, each $R^{94}$ is independently selected from halogen, —CN, —NO$_2$, =O, —N(R$^{21}$)$_2$, —B(OR$^{21}$)$_2$, —OR$^{21}$, $C_{1-6}$ alkyl-N(R$^{20}$)$_2$, $C_{1-6}$ aminoalkyl, $C_1$. 6 alkoxy, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, $C_3$-$C_{12}$ carbocycle and 5- to 12-membered heterocycle. In some cases, each $R^{94}$ is independently selected from halogen, $C_{1-6}$ alkyl-N(R$^{20}$)$_2$, $C_{1-6}$ aminoalkyl, $C_{1-6}$ alkoxyalkyl, $C_{1-6}$ hydroxyalkyl, $C_{1-6}$ cyanoalkyl, $C_{1-6}$ haloalkyl, and $C_{1-6}$ alkyl. In some cases, each $R^{94}$ is independently selected from $C_{1-6}$ alkyl. In some cases, each $R^{94}$ is independently selected from methyl.

In some embodiments, Formula (II) is represented by Formula (II-A)

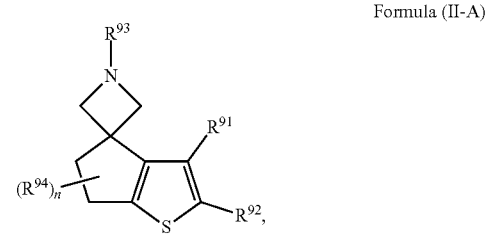

Formula (II-A)

or pharmaceutically acceptable salt;
wherein n is selected from 0, 1, and 2.

In some embodiments, Formula (II) is represented by Formula (II-B)

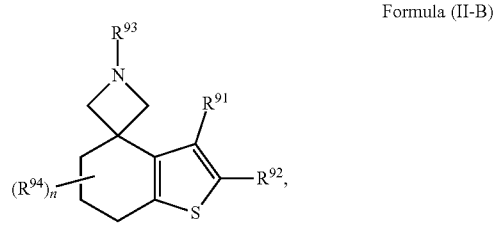

Formula (II-B)

or pharmaceutically acceptable salt;
wherein n is selected from 0, 1, and 2.

In some embodiments, Formula (II) is represented by Formula (II-C)

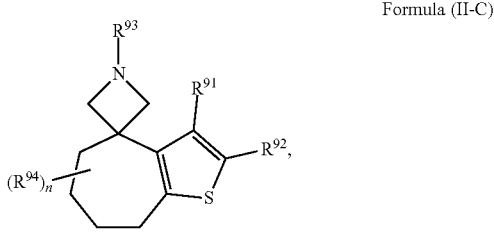

Formula (II-C)

or pharmaceutically acceptable salt;
wherein n is selected from 0, 1, and 2.

In some embodiments, for a compound or salt of Formula (II), A is an optionally substituted fused $C_6$-$C_7$ carbocycle. In some cases, A is selected from an optionally substituted fused $C_6$-$C_7$ unsaturated carbocycle. In some cases, A is selected from

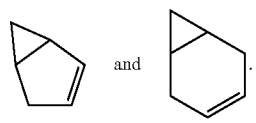

In some cases, A is selected from

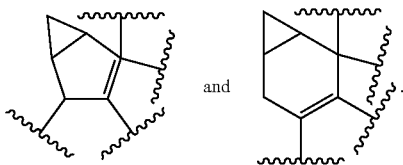

and

In some embodiments, Formula (II) is represented by Formula (II-D).

Formula (II-D)

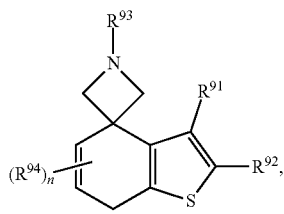

or pharmaceutically acceptable salt;
wherein n is selected from 0, 1, and 2.

In some embodiments, for a compound or salt of Formula (II), Formula (II-A), Formula (II-B), Formula (II-C), or Formula (II-D), $R^{91}$ is selected from halogen, —CN, —NO$_2$, —N(R$^{21}$)$_2$, —OR$^{21}$, —C(O)R$^{21}$, C$_{1-6}$ alkyl-N(R$^{20}$)$_2$, C$_{1-6}$ aminoalkyl, C$_{1-6}$ alkoxyalkyl, C$_{1-6}$ hydroxyalkyl, C$_{1-6}$ cyanoalkyl, C$_{1-6}$ haloalkyl, C$_{1-6}$ alkyl, C$_{2-6}$ alkenyl, C$_{2-6}$ alkynyl, C$_3$-C$_{12}$ carbocycle and 5- to 12-membered heterocycle. In some cases, $R^{91}$ is selected from —CN.

In some embodiments, for a compound or salt of Formula (II), Formula (II-A), Formula (II-B), Formula (II-C), or Formula (II-D), $R^{92}$ is selected from hydrogen, halogen, —CN, —NO$_2$, —N(R$^{21}$)$_2$, —OR$^{21}$, —SR$^{21}$, —C(O)R$^{21}$, —C(O)OR$^{21}$, —OC(O)R$^{21}$, C$_{1-6}$ alkyl-N(R$^{20}$)$_2$, C$_{1-6}$ aminoalkyl, C$_{1-6}$ alkoxy, C$_{1-6}$alkoxyalkyl, C$_{1-6}$ hydroxyalkyl, C$_{1-6}$ cyanoalkyl, C$_{1-6}$haloalkyl, C$_{1-6}$ alkyl, C$_{2-6}$ alkenyl, C$_{2-6}$ alkynyl, C$_3$-C$_{12}$ carbocycle and 5- to 12-membered heterocycle. In some cases, $R^{92}$ is selected from hydrogen, halogen, —CN, and —N(R$^{21}$)$_2$. In some cases, $R^{92}$ is selected —N(R$^{21}$)$_2$. In some cases, $R^{92}$ is selected from —NH$_2$. In some cases, $R^{92}$ is —N(R$^{21}$)C(O)R$^{21}$. In some cases, $R^{92}$ is —N(H)C(O)C$_{1-6}$ alkyl. In some cases, $R^{92}$ is —N(H)C(O) tert-butyl.

In some embodiments, for a compound or salt of Formula (II), Formula (II-A), Formula (II-B), Formula (II-C), or Formula (II-D), $R^{93}$ is selected from hydrogen. In some cases, $R^{93}$ is selected from —C(O)OR$^{21}$. In some cases, $R^{93}$ is selected from hydrogen and —C(O)OR$^{21}$. In some cases, $R^{93}$ is selected from —C(O)O-tert-butyl. In some cases, $R^{93}$ is selected from —C(O)OC$_{1-6}$ alkyl.

In some embodiments, for a compound or salt of Formula (II-A), Formula (II-B), Formula (II-C), or Formula (II-D), each $R^{94}$ is independently selected from halogen, —CN, —NO$_2$, =O, —N(R$^{21}$)$_2$, —B(OR$^{21}$)$_2$, —OR$^{21}$, C$_{1-6}$ alkyl-N(R$^{20}$)$_2$, C$_{1-6}$ aminoalkyl, C$_{1-6}$ alkoxy, C$_{1-6}$ alkoxyalkyl, C$_{1-6}$ hydroxyalkyl, C$_{1-6}$ cyanoalkyl, C$_{1-6}$ haloalkyl, C$_{1-6}$ alkyl, C$_{2-6}$ alkenyl, C$_{2-6}$ alkynyl, C$_3$-C$_{12}$ carbocycle and 5- to 12-membered heterocycle. In some cases, each $R^{94}$ is independently selected from halogen, C$_{1-6}$ alkyl-N(R$^{20}$)$_2$, C$_{1-6}$ aminoalkyl, C$_{1-6}$ alkoxyalkyl, C$_{1-6}$ hydroxyalkyl, C$_{1-6}$ cyanoalkyl, C$_{1-6}$ haloalkyl, and C$_{1-6}$ alkyl. In some cases, each $R^{94}$ is independently selected from C$_{1-6}$ alkyl. In some cases, each $R^{94}$ is independently selected from methyl.

In an aspect, the present disclosure provides a process of preparing a compound or salt of Formula (II).

In an aspect, the present disclosure provides a compound of Formula (III):

Formula (III)

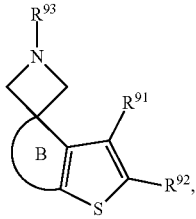

or a pharmaceutically acceptable salt thereof wherein:
B is selected from a 5- to 8-membered heterocycle, wherein the 5- to 8-membered heterocycle is optionally substituted with one or more substituents independently selected from halogen, —CN, —NO$_2$, =O, —N(R$^{21}$)$_2$, —B(OR$^{21}$)$_2$, —OR$^{21}$, —SR$^{21}$, —S(O)$_2$(R$^{21}$), —S(O)$_2$N(R$^{21}$)$_2$, —NR$^{21}$S(O)$_2$R$^{21}$, —C(O)N(R$^{21}$)$_2$, —C(O)NR$^{21}$OR$^{21}$, —N(R$^{21}$)C(O)R$^{21}$, —N(R$^{21}$)C(O)N(R$^{21}$)$_2$, —N(R$^{21}$)C(O)OR$^{21}$, —C(O)R$^{21}$, —C(O)OR$^{21}$, —OC(O)R$^{21}$, —OC(O)N(R$^{21}$)$_2$, C$_{1-6}$ alkyl-N(R$^{20}$)$_2$, C$_{1-6}$ aminoalkyl, C$_{1-6}$ alkoxy, C$_{1-6}$ alkoxyalkyl, C$_{1-6}$ hydroxyalkyl, C$_{1-6}$ cyanoalkyl, C$_{1-6}$ haloalkyl, C$_{1-6}$ alkyl, C$_{2-6}$ alkenyl, C$_{2-6}$ alkynyl, C$_3$-C$_{12}$ carbocycle and 5- to 12-membered heterocycle;

$R^{91}$ is selected from fluorine, iodine, —CN, —NO$_2$, =O, —N(R$^{21}$)$_2$, —B(OR$^{21}$)$_2$, —OR$^{21}$, —SR$^{21}$, —S(O)$_2$(R$^{21}$), —S(O)$_2$N(R$^{21}$)$_2$, —NR$^{21}$S(O)$_2$R$^{21}$, —C(O)N(R$^{21}$)$_2$, —C(O)NR$^{21}$OR$^{21}$, —N(R$^{21}$)C(O)R$^{21}$, —N(R$^{21}$)C(O)N(R$^{21}$)$_2$, —N(R$^{21}$)C(O)OR$^{21}$, —C(O)R$^{21}$, —C(O)OR$^{21}$, —OC(O)R$^{21}$, —OC(O)N(R$^{21}$)$_2$, C$_{1-6}$ alkyl-N(R$^{20}$)$_2$, C$_{1-6}$ aminoalkyl, C$_{1-6}$ alkoxy, C$_{1-6}$ alkoxyalkyl, C$_{1-6}$ hydroxyalkyl, C$_{1-6}$ cyanoalkyl, C$_{1-6}$ haloalkyl, C$_{1-6}$ alkyl, C$_{2-6}$ alkenyl, C$_{2-6}$ alkynyl, C$_3$-C$_{12}$ carbocycle and 5- to 12-membered heterocycle;

$R^{92}$ is selected from hydrogen, halogen, —CN, —NO$_2$, =O, —N(R$^{21}$)$_2$, —B(OR$^{21}$)$_2$, —OR$^{21}$, —SR$^{21}$, —S(O)$_2$(R$^{21}$), —S(O)$_2$N(R$^{21}$)$_2$, —NR$^{21}$S(O)$_2$R$^{21}$, —C(O)N(R$^{21}$)$_2$, —C(O)NR$^{21}$OR$^{21}$, —N(R$^{21}$)C(O)R$^{21}$, —N(R$^{21}$)C(O)N(R$^{21}$)$_2$, —N(R$^{21}$)C(O)OR$^{21}$, —C(O)R$^{21}$, —C(O)OR$^{21}$, —OC(O)R$^{21}$, —OC(O)N(R$^{21}$)$_2$, C$_{1-6}$ alkyl-N(R$^{20}$)$_2$, C$_{1-6}$ aminoalkyl, C$_{1-6}$ alkoxy, C$_{1-6}$ alkoxyalkyl, C$_{1-6}$ hydroxyalkyl, C$_{1-6}$ cyanoalkyl, C$_{1-6}$ haloalkyl, C$_{1-6}$ alkyl, C$_{2-6}$ alkenyl, C$_{2-6}$ alkynyl, C$_3$-C$_{12}$ carbocycle and 5- to 12-membered heterocycle;

$R^{93}$ is selected from hydrogen, —C(O)OR$^{21}$, —C(O)R$^{21}$, and —SO$_2$R$^{21}$; and each $R^{21}$ is independently selected from hydrogen; and C$_{1-6}$ alkyl, C$_{2-6}$ alkenyl, C$_{2-6}$ alkynyl, C$_{3-12}$ carbocycle, and 3- to 12-membered heterocycle, each of which is optionally substituted with one or more substituents independently selected from halogen, —OH, —CN, —NO$_2$, —NH$_2$, —N(C$_{1-6}$ alkyl)$_2$, C$_{1-10}$ alkyl, —C$_{1-10}$ haloalkyl, —O—C$_{1-10}$ alkyl, oxo, C$_{3-12}$ carbocycle, and 3- to 12-membered heterocycle.

In some embodiments, for a compound or salt of Formula (III), B is selected from an optionally substituted 5- to 7-membered heterocycle. In some cases, B is selected from an optionally substituted unsaturated 5- to 7-membered heterocycle. In some cases, B is selected from an optionally substituted 5-membered heterocycle. In some cases, the heterocycle of B has at least one sulfur atom. In some cases, the heterocycle of B has one sulfur atom.

In some embodiments, Formula (III) is represented by Formula (III-A).

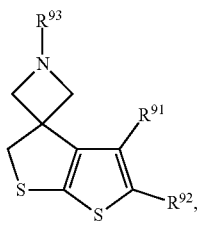

Formula (III-A)

or a pharmaceutically acceptable salt.

In some embodiments, for a compound or salt of Formula (III) and Formula (III-A), $R^{91}$ is selected from halogen, —CN, —NO$_2$, —N(R$^{21}$)$_2$, —OR$^{21}$, —C(O)R$^{21}$, $C_{1-6}$ alkyl-N(R$^{20}$)$_2$, $C_{1-6}$ aminoalkyl, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, $C_3$-$C_{12}$ carbocycle and 5- to 12-membered heterocycle. In some cases, $R^{91}$ is selected from —CN.

In some embodiments, for a compound or salt of Formula (III) and Formula (III-A), $R^{92}$ is selected from hydrogen, halogen, —CN, —NO$_2$, —N(R$^{21}$)$_2$, —OR$^{21}$, —SR$^{21}$, —C(O)R$^{21}$, —C(O)OR$^{21}$, —OC(O)R$^{21}$, $C_{1-6}$ alkyl-N(R$^{20}$)$_2$, $C_{1-6}$ aminoalkyl, $C_{1-6}$ alkoxy, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, $C_3$-$C_{12}$ carbocycle and 5- to 12-membered heterocycle. In some cases, $R^{92}$ is selected from hydrogen, halogen, —CN, and —N(R$^{21}$)$_2$. In some cases, $R^{92}$ is selected from —N(R$^{21}$)$_2$. In some cases, $R^{92}$ is —NH$_2$. In some cases, $R^{92}$ is —N(R$^{21}$)C(O)R$^{21}$. In some cases, $R^{92}$ is —N(H)C(O)C$_{1-6}$ alkyl. In some cases, $R^{92}$ is —N(H)C(O)tert-butyl.

In some embodiments, for a compound or salt of Formula (III) and Formula (III-A), $R^{93}$ is selected from hydrogen. In some cases, $R^{93}$ is selected from —C(O)OR$^{21}$. In some cases, is selected from hydrogen and —C(O)OR$^{21}$. In some cases, $R^{93}$ is selected from —C(O)O-tert-butyl. In some cases, $R^{93}$ is selected from —C(O)OC$_{1-6}$ alkyl.

In an aspect, the present disclosure provides a process of preparing a compound or salt of any one of Formula (III).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Chemical entities having carbon-carbon double bonds or carbon-nitrogen double bonds may exist in Z- or E-form (or cis- or trans-form). Furthermore, some chemical entities may exist in various tautomeric forms. Unless otherwise specified, compounds or salts of Formula (I), are intended to include all Z-, E- and tautomeric forms as well.

"Isomers" are different compounds that have the same molecular formula. "Stereoisomers" are isomers that differ only in the way the atoms are arranged in space. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" or "diastereomers" are stereoisomers that have at least two asymmetric atoms but are not mirror images of each other. The absolute stereochemistry is specified according to the Cahn-Ingold-Prelog R—S system. When a compound is a pure enantiomer, the stereochemistry at each chiral carbon can be specified by either R or S. Resolved compounds whose absolute configuration is unknown can be designated (+) or (−) depending on the direction (dextro- or levorotatory) in which they rotate plane polarized light at the wavelength of the sodium D line. Certain compounds described herein contain one or more asymmetric centers and can thus give rise to enantiomers, diastereomers, and other stereoisomeric forms, the asymmetric centers of which can be defined, in terms of absolute stereochemistry, as (R)- or (S)—. The present chemical entities, pharmaceutical compositions and methods are meant to include all such possible stereoisomers, including racemic mixtures, optically pure forms, mixtures of diastereomers and intermediate mixtures. Optically active (R)- and (S)-isomers can be prepared using chiral synthons or chiral reagents, or resolved using conventional techniques. The optical activity of a compound can be analyzed via any suitable method, including but not limited to chiral chromatography and polarimetry, and the degree of predominance of one stereoisomer over the other isomer can be determined.

The compounds or salts for Formula (I), herein may in some cases exist as diastereomers, enantiomers, or other stereoisomeric forms. The compounds presented herein include all diastereomeric, enantiomeric, and epimeric forms as well as the racemates, mixtures of diastereomers, and other mixtures thereof, to the extent they can be made by one of ordinary skill in the art by routine experimentation. Separation of stereoisomers may be performed by chromatography or by forming diastereomers and separating by recrystallization, or chromatography, or any combination thereof. (Jean Jacques, Andre Collet, Samuel H. Wilen, "Enantiomers, Racemates and Resolutions", John Wiley And Sons, Inc., 1981, herein incorporated by reference for this disclosure). Stereoisomers may also be obtained by stereoselective synthesis. Furthermore, a mixture of two enantiomers enriched in one of the two can be purified to provide further optically enriched form of the major enantiomer by recrystallization and/or trituration.

A "tautomer" refers to a molecule wherein a proton shift from one atom of a molecule to another atom of the same molecule is possible. In certain embodiments, the compounds or salts for Formula (I), exist as tautomers. In circumstances where tautomerization is possible, a chemical equilibrium of the tautomers may exist. The exact ratio of the tautomers depends on several factors, including physical state, temperature, solvent, and pH. Some non-limiting examples of tautomeric equilibrium include:

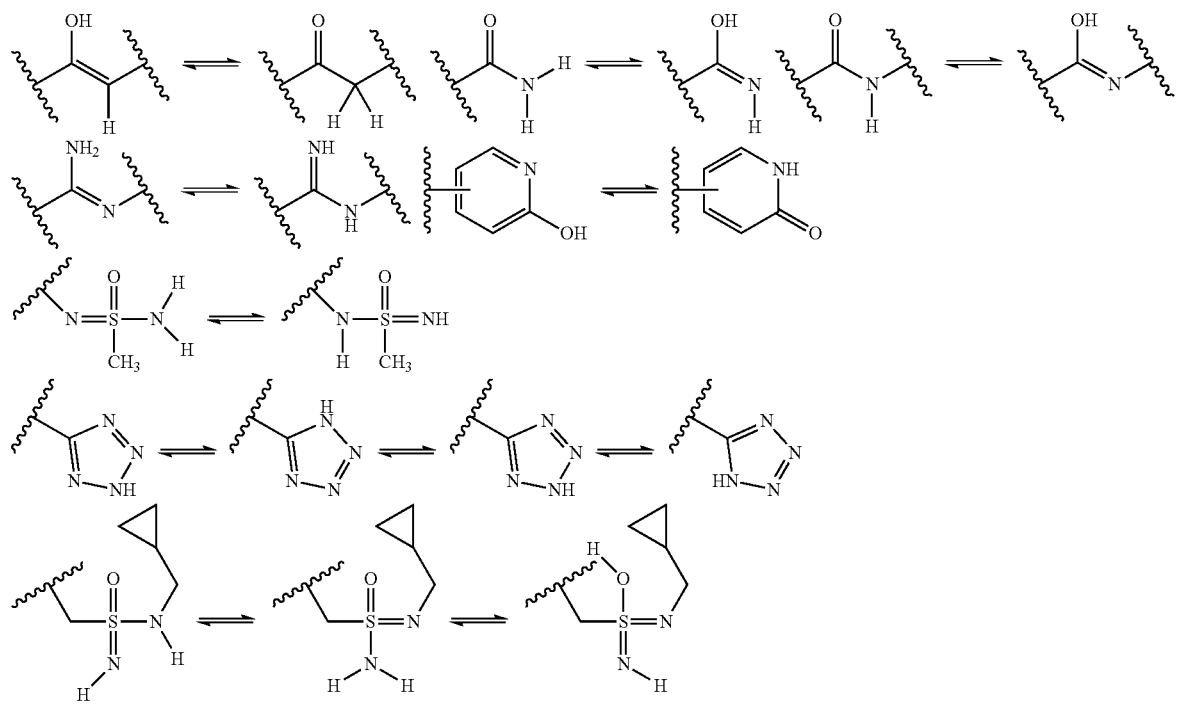

The compounds disclosed herein, in some embodiments, are used in different enriched isotopic forms, e.g., enriched in the content of $^2H$, $^3H$, $^{11}C$, $^{13}C$ and/or $^{14}C$. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, compounds described herein are intended to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^2H$), tritium (H), iodine-125 ($^{125}I$) or carbon-14 ($^{14}C$). Isotopic substitution with $^2H$, $^{11}C$, $^{13}C$, $^{14}C$, $^{15}C$, $^{12}N$, $^{13}N$, $^{15}N$, $^{16}N$, $^{16}O$, $^{17}O$, $^{14}F$, $^{15}F$, $^{16}F$, $^{17}F$, $^{18}F$, $^{33}S$, $^{34}S$, $^{35}S$, $^{36}S$, $^{35}Cl$, $^{37}Cl$, $^{79}Br$, $^{81}Br$, and $^{125}I$ are all contemplated. All isotopic variations of the compounds of the present invention, whether radioactive or not, are encompassed within the scope of the present invention.

In certain embodiments, the compounds disclosed herein have some or all of the $^1H$ atoms replaced with $^2H$ atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Compounds of the present invention also include crystalline and amorphous forms of those compounds, pharmaceutically acceptable salts, and active metabolites of these compounds having the same type of activity, including, for example, polymorphs, pseudopolymorphs, solvates, hydrates, unsolvated polymorphs (including anhydrates), conformational polymorphs, and amorphous forms of the compounds, as well as mixtures thereof.

The compounds described herein may in some cases exist as diastereomers, enantiomers, or other stereoisomeric forms. Where absolute stereochemistry is not specified, the compounds presented herein include all diastereomeric, enantiomeric, and epimeric forms as well as the appropriate mixtures thereof. Separation of stereoisomers may be performed by chromatography or by forming diastereomers and separating by recrystallization, or chromatography, or any combination thereof. (Jean Jacques, Andre Collet, Samuel H. Wilen, "Enantiomers, Racemates and Resolutions", John Wiley And Sons, Inc., 1981, herein incorporated by reference for this disclosure). Stereoisomers may also be obtained by stereoselective synthesis.

The methods and compositions described herein include the use of amorphous forms as well as crystalline forms (also known as polymorphs). The compounds described herein may be in the form of pharmaceutically acceptable salts. As well, in some embodiments, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

In certain embodiments, compounds or salts of the compounds may be prodrugs, e.g., wherein a hydroxyl in the parent compound is presented as an ester or a carbonate, or carboxylic acid present in the parent compound is presented as an ester. The term "prodrug" is intended to encompass compounds which, under physiologic conditions, are converted into pharmaceutical agents of the present disclosure. One method for making a prodrug is to include one or more selected moieties which are hydrolyzed under physiologic conditions to reveal the desired molecule. In other embodiments, the prodrug is converted by an enzymatic activity of the host animal such as specific target cells in the host animal. For example, esters or carbonates (e.g., esters or carbonates of alcohols or carboxylic acids and esters of phosphonic acids) are preferred prodrugs of the present disclosure.

Prodrug forms of the herein described compounds, wherein the prodrug is metabolized in vivo to produce a compound as set forth herein are included within the scope of the claims. In some cases, some of the herein-described compounds may be a prodrug for another derivative or active compound.

Prodrugs are often useful because, in some situations, they may be easier to administer than the parent drug. They may, for instance, be bioavailable by oral administration whereas the parent is not. Prodrugs may help enhance the cell permeability of a compound relative to the parent drug. The prodrug may also have improved solubility in pharmaceutical compositions over the parent drug. Prodrugs may be designed as reversible drug derivatives, for use as modifiers to enhance drug transport to site-specific tissues or to increase drug residence inside of a cell.

In some embodiments, the design of a prodrug increases the lipophilicity of the pharmaceutical agent. In some embodiments, the design of a prodrug increases the effective water solubility. See, e.g., Fedorak et al., *Am. J Physiol.*, 269:G210-218 (1995); McLoed et al., *Gastroenterol,* 106: 405-413 (1994); Hochhaus et al., *Biomed. Chrom.,* 6:283-286 (1992); J. Larsen and H. Bundgaard, *Int. J Pharmaceutics,* 37, 87 (1987); J. Larsen et al., *Int. J Pharmaceutics,* 47, 103 (1988); Sinkula et al., *J Pharm. Sci.,* 64:181-210 (1975); T. Higuchi and V. Stella, *Pro-drugs as Novel Delivery Systems*, Vol. 14 of the A.C.S. Symposium Series; and Edward B. Roche, *Bioreversible Carriers in Drug Design*, American Pharmaceutical Association and Pergamon Press, 1987, all incorporated herein for such disclosure). According to another embodiment, the present disclosure provides methods of producing the above-defined compounds. The compounds may be synthesized using conventional techniques. Advantageously, these compounds are conveniently synthesized from readily available starting materials.

Synthetic chemistry transformations and methodologies useful in synthesizing the compounds described herein are known in the art and include, for example, those described in R. Larock, *Comprehensive Organic Transformations* (1989); T. W. Greene and P. G. M. Wuts, *Protective Groups in Organic Synthesis,* 2d. Ed. (1991); L. Fieser and M. Fieser, *Fieser and Fieser's Reagents for Organic Synthesis* (1994); and L. Paquette, ed., *Encyclopedia of Reagents for Organic Synthesis* (1995).

Pharmaceutical Formulations

Provided herein, in certain embodiments, are compositions comprising a therapeutically effective amount of any compound or salt of Formula (I), Formula (I-A), or Formula (I-B), (also referred to herein as "a pharmaceutical agent").

Pharmaceutical compositions may be formulated using one or more physiologically acceptable carriers including excipients and auxiliaries which facilitate processing of the pharmaceutical agent into preparations which are used pharmaceutically. Proper formulation is dependent upon the route of administration chosen. A summary of pharmaceutical compositions is found, for example, in Remington: The Science and Practice of Pharmacy, Nineteenth Ed (Easton, Pa., Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins, 1999).

The compositions and methods of the present disclosure may be utilized to treat an individual in need thereof. In certain embodiments, the individual is a mammal such as a human, or a non-human mammal. When administered to an animal, such as a human, the composition or the pharmaceutical agent, is preferably administered as a pharmaceutical composition comprising, for example, a pharmaceutical agent and a pharmaceutically acceptable carrier or excipient. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration, e.g., routes, such as injection or implantation, that circumvent transport or diffusion through an epithelial barrier, the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule, granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable excipient can contain physiologically acceptable agents that act, for example, to stabilize, increase solubility or to increase the absorption of a compound such as a pharmaceutical agent. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable excipient, including a physiologically acceptable agent, depends, for example, on the route of administration of the composition. The preparation or pharmaceutical composition can be a self emulsifying drug delivery system or a self microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

A pharmaceutical composition (preparation) can be administered to a subject by any of a number of routes of administration including, for example, orally, for example, drenches as in aqueous or non-aqueous solutions or suspensions, tablets, capsules, including sprinkle capsules and gelatin capsules, boluses, powders, granules, pastes for application to the tongue; absorption through the oral mucosa, e.g., sublingually; anally, rectally or vaginally, for example, as a pessary, cream or foam; parenterally, including intramuscularly, intravenously, subcutaneously or intrathecally as, for example, a sterile solution or suspension; nasally; intraperitoneally; subcutaneously; transdermally, for example, as a patch applied to the skin; and topically, for example, as a cream, ointment or spray applied to the skin, or as an eye drop. The compound may also be formulated for inhalation. In certain embodiments, a compound may be simply dissolved or suspended in sterile water.

A pharmaceutical composition may be a sterile aqueous or non-aqueous solution, suspension or emulsion, e.g., a microemulsion. The excipients described herein are examples and are in no way limiting. An effective amount or therapeutically effective amount refers to an amount of the one or more pharmaceutical agents administered to a subject, either as a single dose or as part of a series of doses, which is effective to produce a desired therapeutic effect.

Subjects may generally be monitored for therapeutic effectiveness using assays and methods suitable for the condition being treated, which assays will be familiar to those having ordinary skill in the art and are described herein. Pharmacokinetics of a pharmaceutical agent, or one or more metabolites thereof, that is administered to a subject may be monitored by determining the level of the pharmaceutical agent or metabolite in a biological fluid, for example, in the blood, blood fraction, e.g., serum, and/or in the urine, and/or other biological sample or biological tissue from the subject. Any method practiced in the art and described herein to detect the agent may be used to measure the level of the pharmaceutical agent or metabolite during a treatment course.

The dose of a pharmaceutical agent described herein for treating a disease or disorder may depend upon the subject's condition, that is, stage of the disease, severity of symptoms caused by the disease, general health status, as well as age, gender, and weight, and other factors apparent to a person skilled in the medical art. Pharmaceutical compositions may be administered in a manner appropriate to the disease to be treated as determined by persons skilled in the medical arts. In addition to the factors described herein and above related to use of pharmaceutical agent for treating a disease or disorder, suitable duration and frequency of administration of the pharmaceutical agent may also be determined or adjusted by such factors as the condition of the patient, the type and severity of the patient's disease, the particular form of the active ingredient, and the method of administration. Optimal doses of an agent may generally be determined using experimental models and/or clinical trials. The optimal dose may depend upon the body mass, weight, or blood volume of the subject. The use of the minimum dose that is sufficient to provide effective therapy is usually preferred. Design and execution of pre-clinical and clinical studies for a pharmaceutical agent, including when administered for prophylactic benefit, described herein are well within the skill of a person skilled in the relevant art. When two or more pharmaceutical agents are administered to treat a disease or disorder, the optimal dose of each pharmaceutical agent may be different, such as less than when either agent is administered alone as a single agent therapy. In certain particular embodiments, two pharmaceutical agents in combination may act synergistically or additively, and either agent may be used in a lesser amount than if administered alone. An amount of a pharmaceutical agent that may be administered per day may be, for example, between about 0.01 mg/kg and 100 mg/kg, e.g., between about 0.1 to 1 mg/kg, between about 1 to 10 mg/kg, between about 10-50 mg/kg, between about 50-100 mg/kg body weight. In other embodiments, the amount of a pharmaceutical agent that may be administered per day is between about 0.01 mg/kg and 1000 mg/kg, between about 100-500 mg/kg, or between about 500-1000 mg/kg body weight. The optimal dose, per day or per course of treatment, may be different for the disease or disorder to be treated and may also vary with the administrative route and therapeutic regimen.

Pharmaceutical compositions comprising a pharmaceutical agent can be formulated in a manner appropriate for the delivery method by using techniques routinely practiced in the art. The composition may be in the form of a solid, e.g., tablet, capsule, semi-solid, e.g., gel, liquid, or gas, e.g., aerosol. In other embodiments, the pharmaceutical composition is administered as a bolus infusion.

Pharmaceutical acceptable excipients are well known in the pharmaceutical art and described, for example, in Rowe et al., Handbook of Pharmaceutical Excipients: A Comprehensive Guide to Uses, Properties, and Safety, $5^{th}$ Ed., 2006, and in *Remington: The Science and Practice of Pharmacy* (Gennaro, $21^{st}$ Ed. Mack Pub. Co., Easton, PA (2005)). Exemplary pharmaceutically acceptable excipients include sterile saline and phosphate buffered saline at physiological pH. Preservatives, stabilizers, dyes, buffers, and the like may be provided in the pharmaceutical composition. In addition, antioxidants and suspending agents may also be used. In general, the type of excipient is selected based on the mode of administration, as well as the chemical composition of the active ingredient(s). Alternatively, compositions described herein may be formulated as a lyophilizate. A composition described herein may be lyophilized or otherwise formulated as a lyophilized product using one or more appropriate excipient solutions for solubilizing and/or diluting the pharmaceutical agent(s) of the composition upon administration. In other embodiments, the pharmaceutical agent may be encapsulated within liposomes using technology known and practiced in the art. In certain particular embodiments, a pharmaceutical agent is not formulated within liposomes for application to a stent that is used for treating highly, though not totally, occluded arteries. Pharmaceutical compositions may be formulated for any appropriate manner of administration described herein and in the art.

A pharmaceutical composition, e.g., for oral administration or for injection, infusion, subcutaneous delivery, intramuscular delivery, intraperitoneal delivery or other method, may be in the form of a liquid. A liquid pharmaceutical composition may include, for example, one or more of the following: a sterile diluent such as water, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral composition can be enclosed in ampoules, disposable syringes or multiple dose vials made of glass or plastic. The use of physiological saline is preferred, and an injectable pharmaceutical composition is preferably sterile. In another embodiment, for treatment of an ophthalmological condition or disease, a liquid pharmaceutical composition may be applied to the eye in the form of eye drops. A liquid pharmaceutical composition may be delivered orally.

For oral formulations, at least one of the pharmaceutical agents described herein can be used alone or in combination with appropriate additives to make tablets, powders, granules or capsules, and if desired, with diluents, buffering agents, moistening agents, preservatives, coloring agents, and flavoring agents. The pharmaceutical agents may be formulated with a buffering agent to provide for protection of the compound from low pH of the gastric environment and/or an enteric coating. A pharmaceutical agent included in a pharmaceutical composition may be formulated for oral delivery with a flavoring agent, e.g., in a liquid, solid or semi-solid formulation and/or with an enteric coating.

A pharmaceutical composition comprising any one of the pharmaceutical agents described herein may be formulated for sustained or slow release, also called timed release or controlled release. Such compositions may generally be prepared using well known technology and administered by, for example, oral, rectal, intradermal, or subcutaneous implantation, or by implantation at the desired target site. Sustained-release formulations may contain the compound dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of pharmaceutical agent contained within a sustained release formulation depends upon the site of implantation, the rate and expected duration of release, and the nature of the condition, disease or disorder to be treated or prevented.

In certain embodiments, the pharmaceutical compositions comprising a pharmaceutical agent are formulated for transdermal, intradermal, or topical administration. The compositions can be administered using a syringe, bandage, transdermal patch, insert, or syringe-like applicator, as a powder/talc or other solid, liquid, spray, aerosol, ointment, foam, cream, gel, paste. This preferably is in the form of a controlled release formulation or sustained release formulation administered topically or injected directly into the skin adjacent to or within the area to be treated, e.g., intradermally or subcutaneously. The active compositions can also be delivered via iontophoresis. Preservatives can be used to prevent the growth of fungi and other microorganisms. Suitable preservatives include, but are not limited to, benzoic acid, butylparaben, ethyl paraben, methyl paraben, propylparaben, sodium benzoate, sodium propionate, benzalkonium chloride, benzethonium chloride, benzyl alcohol, cetypyridinium chloride, chlorobutanol, phenol, phenylethyl alcohol, thimerosal, and combinations thereof.

Pharmaceutical compositions comprising a pharmaceutical agent can be formulated as emulsions for topical application. An emulsion contains one liquid distributed in the body of a second liquid. The emulsion may be an oil-in-water emulsion or a water-in-oil emulsion. Either or both of the oil phase and the aqueous phase may contain one or more surfactants, emulsifiers, emulsion stabilizers, buffers, and other excipients. The oil phase may contain other oily pharmaceutically approved excipients. Suitable surfactants include, but are not limited to, anionic surfactants, non-ionic surfactants, cationic surfactants, and amphoteric surfactants. Compositions for topical application may also include at least one suitable suspending agent, antioxidant, chelating agent, emollient, or humectant.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. Liquid sprays may be delivered from pressurized packs, for example, via a specially shaped closure. Oil-in-water emulsions can also be used in the compositions, patches, bandages and articles. These systems are semisolid emulsions, micro-emulsions, or foam emulsion systems.

In some embodiments, the pharmaceutical agent described herein can be formulated as in inhalant. Inhaled methods can deliver medication directly to the airway. The pharmaceutical agent can be formulated as aerosols, microspheres, liposomes, or nanoparticles. The pharmaceutical agent can be formulated with solvents, gases, nitrates, or any combinations thereof. Compositions described herein are optionally formulated for delivery as a liquid aerosol or inhalable dry powder. Liquid aerosol formulations are optionally nebulized predominantly into particle sizes that can be delivered to the terminal and respiratory bronchioles. Liquid aerosol and inhalable dry powder formulations are preferably delivered throughout the endobronchial tree to the terminal bronchioles and eventually to the parenchymal tissue.

Aerosolized formulations described herein are optionally delivered using an aerosol forming device, such as a jet, vibrating porous plate or ultrasonic nebulizer, preferably selected to allow the formation of aerosol particles having with a mass medium average diameter predominantly between 1 to 5. Further, the formulation preferably has balanced osmolarity ionic strength and chloride concentration, and the smallest aerosolizable volume able to deliver effective dose of the pharmaceutical agent. Additionally, the aerosolized formulation preferably does not impair negatively the functionality of the airways and does not cause undesirable side effects.

Aerosolization devices suitable for administration of aerosol formulations described herein include, for example, jet, vibrating porous plate, ultrasonic nebulizers and energized dry powder inhalers, that are able to nebulize the formulation into aerosol particle size predominantly in the size range from 1-5. Predominantly in this application means that at least 70% but preferably more than 90% of all generated aerosol particles are within 1-5 range. A jet nebulizer works by air pressure to break a liquid solution into aerosol droplets. Vibrating porous plate nebulizers work by using a sonic vacuum produced by a rapidly vibrating porous plate to extrude a solvent droplet through a porous plate. An ultrasonic nebulizer works by a piezoelectric crystal that shears a liquid into small aerosol droplets. A variety of suitable devices are available, including, for example, AeroNeb™ and AeroDose™ vibrating porous plate nebulizers (AeroGen, Inc., Sunnyvale, California), Sidestream® nebulizers (Medic-Aid Ltd., West Sussex, England), Pari LC® and Pari LC Star® jet nebulizers (Pari Respiratory Equipment, Inc., Richmond, Virginia), and Aerosonic™ (DeVilbiss Medizinische Produkte (Deutschland) GmbH, Heiden, Germany) and UltraAire® (Omron Healthcare, Inc., Vernon Hills, Illinois) ultrasonic nebulizers.

In some embodiments, the pharmaceutical agent(s) can be formulated with oleaginous bases or ointments to form a semisolid composition with a desired shape. In addition to the pharmaceutical agent, these semisolid compositions can contain dissolved and/or suspended bactericidal agents, preservatives and/or a buffer system. A petrolatum component that may be included may be any paraffin ranging in viscosity from mineral oil that incorporates isobutylene, colloidal silica, or stearate salts to paraffin waxes. Absorption bases can be used with an oleaginous system. Additives may include cholesterol, lanolin (lanolin derivatives, beeswax, fatty alcohols, wool wax alcohols, low HLB (hydrophobel-lipophobe balance) emulsifiers, and assorted ionic and nonionic surfactants, singularly or in combination.

Controlled or sustained release transdermal or topical formulations can be achieved by the addition of time-release additives, such as polymeric structures, matrices, that are available in the art. For example, the compositions may be administered through use of hot-melt extrusion articles, such as bioadhesive hot-melt extruded film. The formulation can comprise a cross-linked polycarboxylic acid polymer formulation. A cross-linking agent may be present in an amount that provides adequate adhesion to allow the system to remain attached to target epithelial or endothelial cell surfaces for a sufficient time to allow the desired release of the compound.

An insert, transdermal patch, bandage or article can comprise a mixture or coating of polymers that provide release of the pharmaceutical agents at a constant rate over a prolonged period of time. In some embodiments, the article, transdermal patch or insert comprises water-soluble pore forming agents, such as polyethylene glycol (PEG) that can be mixed with water insoluble polymers to increase the durability of the insert and to prolong the release of the active ingredients.

Transdermal devices (inserts, patches, bandages) may also comprise a water insoluble polymer. Rate controlling polymers may be useful for administration to sites where pH change can be used to effect release. These rate controlling polymers can be applied using a continuous coating film during the process of spraying and drying with the active compound. In one embodiment, the coating formulation is used to coat pellets comprising the active ingredients that are compressed to form a solid, biodegradable insert.

A polymer formulation can also be utilized to provide controlled or sustained release. Bioadhesive polymers described in the art may be used. By way of example, a sustained-release gel and the compound may be incorporated in a polymeric matrix, such as a hydrophobic polymer matrix. Examples of a polymeric matrix include a microparticle. The microparticles can be microspheres, and the core may be of a different material than the polymeric shell. Alternatively, the polymer may be cast as a thin slab or film, a powder produced by grinding or other standard techniques, or a gel such as a hydrogel. The polymer can also be in the form of a coating or part of a bandage, stent, catheter, vascular graft, or other device to facilitate delivery of the pharmaceutical agent. The matrices can be formed by solvent evaporation, spray drying, solvent extraction and other methods known to those skilled in the art.

Kits with unit doses of one or more of the agents described herein, usually in oral or injectable doses, are provided. Such kits may include a container containing the unit dose, an informational package insert describing the use and attendant benefits of the drugs in treating disease, and optionally an appliance or device for delivery of the composition.

Methods of Treatment

In an aspect, the present disclosure provides compounds that inhibit KRas G12 mutants. In some cases, the method may inhibit KRas G12 mutants activity in a cell. In some cases, inhibiting KRas G12 mutants activity in a cell may include contacting the cell in which inhibition of KRas G12 mutants activity is desired with an effective amount of a compound of Formula (I) or pharmaceutically acceptable salt thereof, or a pharmaceutical compositions containing a compound or salt of Formula (I), Formula (I-A), or Formula (I-B), and a pharmaceutically acceptable excipient. In some cases, the contacting is in vitro. In some cases, the contacting is in vivo. As used herein, the term "contacting" refers to the bringing together of indicated moieties in an in vitro system or an in vivo system. For example, "contacting" a KRas G12D and/or other G12 mutants with a compound provided herein includes the administration of a compound provided herein to an individual or patient, such as a human, having KRas G12D and/or other G12 mutants, as well as, for example, introducing a compound provided herein into a sample containing a cellular or purified preparation containing the KRas G12D and/or other G12 mutants. In some cases, a cell in which inhibition of KRas G12D and/or other G12 mutants activity is desired is contacted with an effective amount of a compound or salt of Formula (I) or a pharmaceutical composition thereof to negatively modulate the activity of KRas G12D and/or other G12 mutants. In some cases, by negatively modulating the activity of KRas G12D and/or other G12 mutants, the methods described herein are designed to inhibit undesired cellular proliferation resulting from enhanced KRas G12D and/or other G12 mutants activity within the cell. The cells may be contacted in a single dose or multiple doses in accordance with a particular treatment regimen to effect the desired negative modulation of KRas G12D and/or other G12 mutants. The ability of compounds to bind KRas G12D and/or other G12 mutants may be monitored in vitro using well known methods.

In some embodiments, the inhibitory activity of exemplary compounds in cells may be monitored, for example, by measuring the inhibition of KRas G12D and/or other G12 mutants activity of the amount of phosphorylated ERK.

In another aspect, methods of treating cancer in a patient in need thereof, comprising administering to said patient a therapeutically effective amount of a compound of Formula (I), Formula (I-A), or Formula (I-B), or a pharmaceutically acceptable salt of any one thereof, or a pharmaceutical composition comprising the compound or pharmaceutically acceptable salt thereof and a pharmaceutically acceptable excipient are provided. The compositions and methods provided herein may be used for the treatment of a KRas G12D and/or other G12 mutants-associated cancer in a patient in need thereof, comprising administering to the patient a therapeutically effective amount of a compound of Formula (I), Formula (I-A), or Formula (I-B), or a pharmaceutically acceptable salt of any one thereof, or a pharmaceutical composition comprising the compound or pharmaceutically acceptable salt of any one thereof are provided. In some cases, the KRas G12D and/or other G12 mutants associated cancer is lung cancer. The compositions and methods provided herein may be used for the treatment of a wide variety of cancers including tumors such as lung, prostate, breast, brain, skin, cervical carcinomas, testicular carcinomas, etc. More particularly, cancers that may be treated by the compositions and methods of the invention include, but are not limited to tumor types such as astrocytic, breast, cervical, colorectal, endometrial, esophageal, gastric, head and neck, hepatocellular, laryngeal, lung, oral, ovarian, prostate and thyroid carcinomas and sarcomas. More specifically, these compounds can be used to treat: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Biliary tract: gall bladder carcinoma, ampullary carcinoma, cholangiocarcinoma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosathecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma. In some cases, the cancer is non-small cell lung cancer, small cell lung cancer, colorectal cancer, rectal cancer or pancreatic cancer. In some cases, the cancer is non-small cell lung cancer. In some cases, the concentration and route of administration to the patient will vary depending on the cancer to be treated. The compounds, pharmaceutically acceptable salts thereof and pharmaceutical compositions comprising such compounds and salts also may be co-administered with other anti-neoplastic compounds, e.g., chemotherapy, or used in combination with other treatments, such as radiation or surgical intervention, either as an adjuvant prior to surgery or post-operatively.

Also provided herein is a compound of Formula (I), Formula (I-A), or Formula (I-B), or a pharmaceutically acceptable salt of any one thereof, or a pharmaceutical composition of any one thereof, for use in therapy.

Also provided herein is a compound of Formula (I), Formula (I-A), or Formula (I-B), or a pharmaceutically acceptable salt of any one thereof, or a pharmaceutical composition of any one thereof, for use in the treatment of cancer.

Also provided herein is a compound of Formula (I), Formula (I-A), or Formula (I-B), or a pharmaceutically acceptable salt of any one thereof, or a pharmaceutical composition of any one thereof, for use in the inhibition of KRas G12D and/or other G12 mutants.

Also provided herein is a compound of Formula (I) or a pharmaceutically acceptable salt thereof, or a pharmaceutical composition thereof, for use in the treatment of a KRas G12D and/or other G12 mutants associated disease or disorder.

Also provided herein is the use of a compound of Formula (I), Formula (I-A), or Formula (I-B), or a pharmaceutically acceptable salt thereof, or a pharmaceutical composition thereof, in the manufacture of a medicament for the treatment of cancer.

Also provided herein is a use of a compound of Formula (I), Formula (I-A), or Formula (I-B), or a pharmaceutically acceptable salt of any one thereof, or a pharmaceutical composition thereof, in the manufacture of a medicament for the inhibition of activity of KRas G12D and/or other G12 mutants.

Also provided herein is the use of a compound of Formula (I), Formula (I-A), or Formula (I-B), or a pharmaceutically acceptable salt of any one thereof, or a pharmaceutical composition of any one thereof, in the manufacture of a medicament for the treatment of a KRas G12D and/or other G12 mutants-associated disease or disorder.

In another aspect, the present disclosure provides a method for treating cancer in a patient in need thereof, the method comprising (a) determining that cancer is associated with a KRas G12D mutation and/or other G12 mutants (e.g., a KRas G12D and/or other G12 mutants-associated cancer) (e.g., as determined using a regulatory agency-approved, e.g., FDA-approved, assay or kit); and (b) administering to the patient a therapeutically effective amount of a compound of Formula (I) or a pharmaceutically acceptable salt thereof, or a pharmaceutical composition thereof.

The compounds described herein can be used in the preparation of medicaments for the prevention or treatment of diseases or conditions. In addition, a method for treating any of the diseases or conditions described herein in a subject in need of such treatment, involves administration of pharmaceutical compositions containing at least one compound described herein, or a pharmaceutically acceptable salt, pharmaceutically acceptable prodrug, or pharmaceutically acceptable solvate thereof, in therapeutically effective amounts to said subject.

The compositions containing the compound(s) described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician.

In prophylactic applications, compositions containing the compounds described herein are administered to a patient susceptible to or otherwise at risk of a particular disease, diso(Donohue, et al., 2019) (Tran, et al., 2021)rder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, disease or condition and its severity, the identity (e.g., weight) of the subject or host in need of treatment, but can nevertheless be determined in a manner recognized in the field according to the particular circumstances surrounding the case, including, e.g., the specific agent being administered, the route of administration, the condition being treated, and the subject or host being treated. In general, however, doses employed for adult human treatment will typically be in the range of about 0.02-about 5000 mg per day, in some embodiments, about 1-about 1500 mg per day. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

In certain embodiments, the invention provides a method of treating or preventing a disease, state or condition in a patient in need thereof comprising administering to the patient an effective amount of a compound of any one of embodiments of the invention or a pharmaceutically acceptable salt thereof. The disease, state or condition may be selected from a group as described elsewhere herein.

Bifunctional Compounds

In some embodiments, compounds herein can adopt to selectively eliminate an over activated KRas signaling which is induced by KRas mutations by directly binding with the mutated KRas protein, either by stabilizing its GDP bound form (the inactive form) or by blocking the interaction between GTP bound form and its downstream target protein. In some embodiments, another way is to hijack the protein degradation mechanism in a cell and leverage E3 ligases' (like VHL, CRBN or IAPs) substrate specificity through a bi-functional molecule called Proteolysis targeting chimera (PROTAC) (Winter G E, Buckley D L, Paulk J, Roberts J M, Souza A, Dhe-Paganon S, Bradner J E. DRUG DEVELOPMENT. Phthalimide conjugation as a strategy for in vivo target protein degradation. Science. 2015 Jun. 19; 348 (6241): 1376-81), which can bind with both mutated KRas protein and E3 ligase, create interactions between those two proteins and induce KRas degradation.

Disclosed herein is a bifunctional compound composed of a target protein (i.e., KRAS G12D)-binding moiety and an E3 ubiquitin ligase-binding moiety, which may induce proteasome-mediated degradation of selected proteins. In some embodiments, the bifunctional compound comprises a target protein (i.e., KRAS G12D)-binding moiety and an E3 ubiquitin ligase-binding moiety known in the art. In some embodiments, disclosed herein is the use of the compound disclosed herein in the preparation of degrading a target protein compound by using chemical modification of the compound disclosed herein. In some cases, the target protein-binding moiety is derived from a compound of Formula (I), Formula (I-A), or Formula (I-B).

Preparation of Compounds

The compounds of the present disclosure can generally be prepared in a number of ways well known to those skilled in the art of organic synthesis. By way of example, compounds of the present disclosure can be synthesized using the methods described herein, together with synthetic methods known in the art of synthetic organic chemistry, or variations thereof as appreciated by those skilled in the art.

The compounds of the present disclosure may be prepared as described in the schemes and examples described elsewhere herein.

EXAMPLES

The following examples further illustrate the invention but, of course, should not be construed as in any way limiting its scope.

The following synthetic schemes are provided for purposes of illustration, not limitation. The following examples illustrate the various methods of making compounds described herein. It is understood that one skilled in the art may be able to make these compounds by similar methods or by combining other methods known to one skilled in the art. It is also understood that one skilled in the art would be able to make, in a similar manner as described below by using the appropriate starting materials and modifying the synthetic route as needed. In general, starting materials and reagents can be obtained from commercial vendors or synthesized according to sources known to those skilled in the art or prepared as described herein.

The present disclosure provides processes for preparing compounds the compounds described herein (described in greater detail below). Certain compounds of Tables herein can be prepared employing appropriate reagents in the schemes described herein.

Synthesis of Intermediates

Intermediate 1. Synthesis of 3-chloro-N,N-dimethyl-5,6,7,8-tetrahydro-4H-pyrazolo[1,5-a][1,4]diazepine-2-carboxamide

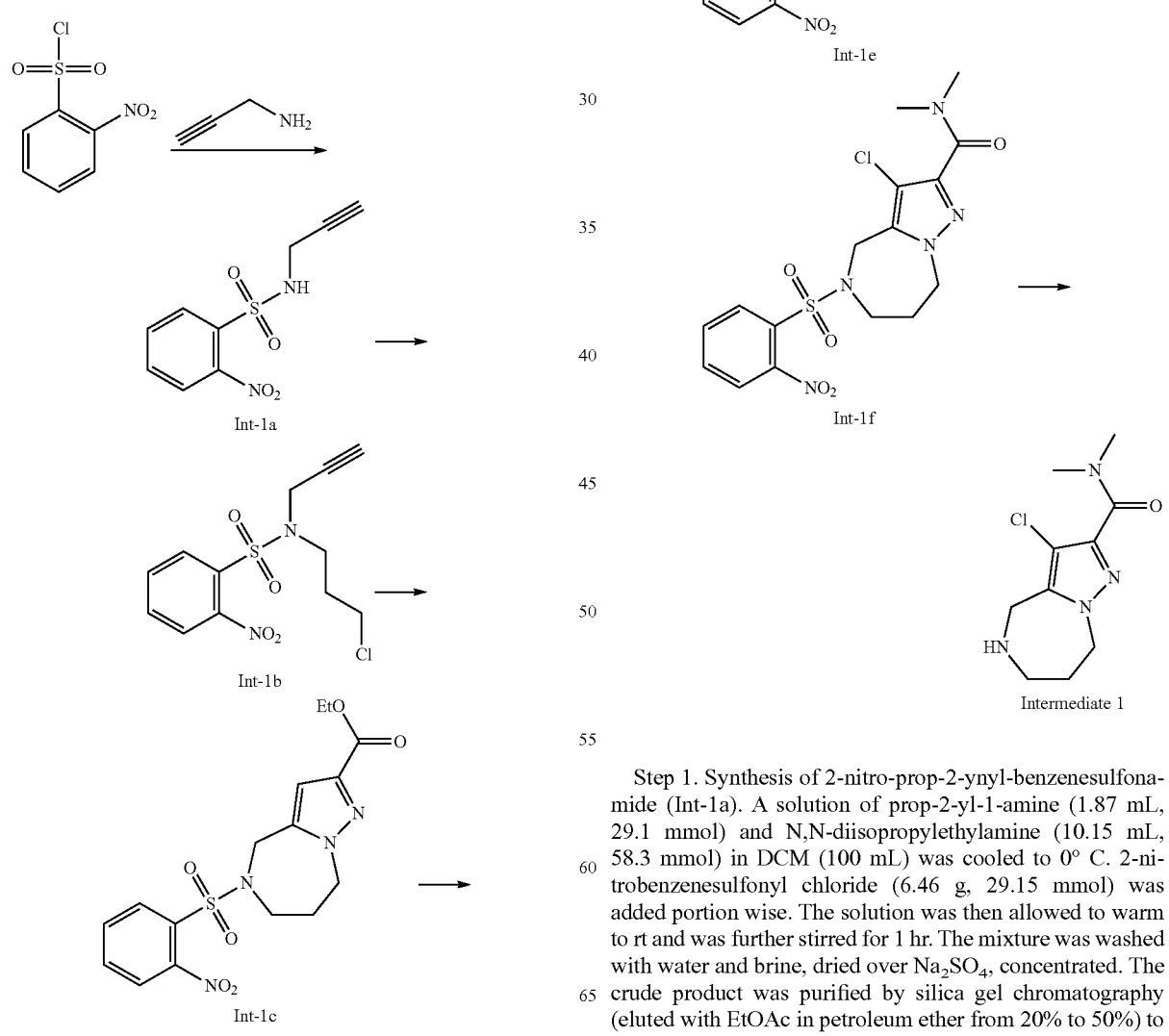

Step 1. Synthesis of 2-nitro-prop-2-ynyl-benzenesulfonamide (Int-1a). A solution of prop-2-yl-1-amine (1.87 mL, 29.1 mmol) and N,N-diisopropylethylamine (10.15 mL, 58.3 mmol) in DCM (100 mL) was cooled to 0° C. 2-nitrobenzenesulfonyl chloride (6.46 g, 29.15 mmol) was added portion wise. The solution was then allowed to warm to rt and was further stirred for 1 hr. The mixture was washed with water and brine, dried over Na$_2$SO$_4$, concentrated. The crude product was purified by silica gel chromatography (eluted with EtOAc in petroleum ether from 20% to 50%) to afford 2-nitro-prop-2-ynyl-benzenesulfonamide (Int-1a, 5.98 g, 24.9 mmol, 85.4% yield) as a yellow solid. LCMS calcld for $C_9H_9N_2O_4S$ (M+H)$^+$ m/z=241.0, found: 241.0.

Step 2. Synthesis of (3-chloropropyl)-2-nitro-prop-2-ynyl-benzenesulfonamide (Int-1b). A solution of 2-nitro-prop-2-ynyl-benzenesulfonamide (Int-1a, 1.0 g, 4.16 mmol) and cesium carbonate (6.764 g, 20.81 mmol) in acetone (30 mL) was added neat 1-bromo-3-chloro-propane (6.05 mL, 61.19 mmol) dropwise. Upon complete addition, the reaction mixture was stirred at rt for 2 hrs. The mixture was concentrated, then washed with water and brine, dried over $Na_2SO_4$, concentrated. The crude product was purified by silica gel chromatography (eluted with EtOAc in petroleum ether from 20% to 50%). (3-chloropropyl)-2-nitro-prop-2-ynyl-benzenesulfonamide (Int-1b, 2.43 g, 7.67 mmol, 92.1% yield) was obtained as a yellow oil. LCMS calcld for $C_{12}H_{14}ClN_2O_4S$ (M+H)$^+$ m/z=317.0, found: 317.0.

Step 3. Synthesis of ethyl 5-(2-nitrophenyl)sulfonyl-4,6,7,8-tetrahydropyrazolo[1,5-a][1,4]diazepine-2-carboxylate (Int-1c). To solution of (3-chloropropyl)-2-nitro-prop-2-ynyl-benzenesulfonamide (Int-1b, 10.0 g, 31.6 mmol) and ethyl 2-diazoacetate (5.4 g, 47.3 mmol) in chlorobenzene (80 mL) was added N,N-diisopropylethylamine (5.5 mL, 31.57 mmol). Then heated at 140° C. for 1.5 hours. Followed by the addition of cesium carbonate (12.3 g, 37.9 mmol), then heated at 140° C. for 30 minutes. The solvent was concentrated, and the mixture was extracted with EtOAc, washed with brine, dried over $Na_2SO_4$, concentrated. The crude product was purified by silica gel chromatography (eluted with EtOAc in petroleum ether from 20% to 90%), then triturated in EtOAc to afford ethyl 5-(2-nitrophenyl)sulfonyl-4,6,7,8-tetrahydropyrazolo[1,5-a][1,4]diazepine-2-carboxylate (Int-1c, 5.80 g, 14.7 mmol, 46.6% yield) as a yellow solid. LCMS calcld for $C_{16}H_{19}N_4O_6S$ (M+H)$^+$ m/z=395.1, found: 395.0.

Step 4. Synthesis of ethyl 5-(2-nitrophenyl)sulfonyl-4,6,7,8-tetrahydropyrazolo[1,5-a][1,4]diazepine-2-carboxylate (Int-1d). To a solution of ethyl 5-(2-nitrophenyl)sulfonyl-4,6,7,8-tetrahydropyrazolo[1,5-a][1,4]diazepine-2-carboxylate (Int-1c, 12.6 g, 31.95 mmol) in THF (100 mL) and methanol (25 mL) was added 1M LiOH (128 mL, 128 mmol) at 25° C. The mixture was stirred at 55° C. for 2 h. The mixture was acidified with HCl (1 mol/L in $H_2O$) to pH=6 and the crude product was triturated in water and filtered. 5-(2-nitrophenyl)sulfonyl-4,6,7,8-tetrahydropyrazolo[1,5-a][1,4]diazepine-2-carboxylic acid (Int-1d, 11.5 g, 31.1 mmol, 97.3% yield) was obtained as yellow solid. LCMS calcld for $C_{14}H_{14}N_4O_6S$ (M+H)$^+$ m/z=367.1, found: 367.0.

Step 5. Synthesis of N,N-dimethyl-5-(2-nitrophenyl)sulfonyl-4,6,7,8-tetrahydropyrazolo[1,5-a][1,4]diazepine-2-carboxamide (Int-1e). To a solution of 5-(2-nitrophenyl)sulfonyl-4,6,7,8-tetrahydropyrazolo[1,5-a][1,4]diazepine-2-carboxylic acid (Int-1d, 9.6 mg, 26.2 mmol), DIEA (18.3 mL, 104.8 mmol) and HATU (14.95 g, 39.3 mmol) in DMF (90 mL) was added 2M methylmethanamine in THF (20 mL, 39.3 mmol) at 30° C. The mixture was stirred at 30° C. for 2 h. The mixture was diluted with DCM (300×2 mL), washed with water (400 mL) and brine (400×2 mL), dried over $Na_2SO_4$ and concentrated to afford a crude product N,N-dimethyl-5-(2-nitrophenyl)sulfonyl-4,6,7,8-tetrahydropyrazolo[1,5-a][1,4]diazepine-2-carboxamide (Int-1e, 10.1 g, 24.4 mmol, 93.1% yield) as yellow oil. LCMS calcld for $C_{16}H_{20}N_4O_3S$ (M+H)$^+$ m/z=394.1, found: 394.2.

Step 6. Synthesis of 3-chloro-N,N-dimethyl-5-(2-nitrophenyl)sulfonyl-4,6,7,8-tetrahydropyrazolo[1,5-a][1,4]diazepine-2-carboxamide (Int-1f). To a solution of N,N-dimethyl-5-(2-nitrophenyl)sulfonyl-4,6,7,8-tetrahydropyrazolo[1,5-a][1,4]diazepine-2-carboxamide (Int-1e, 10 g, 25.67 mmol) in DMF (100 mL) was added Chlorosuccinimide (3.428 g, 25.67 mmol) at 0° C. under argon. The mixture was stirred at 45° C. for 1 h. The mixture was concentrated to afford a crude product. The crude product was triturated in water and filtered to afford 3-chloro-N,N-dimethyl-5-(2-nitrophenyl)sulfonyl-4,6,7,8-tetrahydropyrazolo[1,5-a][1,4]diazepine-2-carboxamide (Int-1f, 10.2 g, 23.4 mmol, 91.0% yield) was obtained as crude yellow solid. LCMS calcld for $C_{16}H_{17}ClN_4O_6S$ (M+H)$^+$ m/z=428.1, found: 428.0.

Step 7. Synthesis of 3-chloro-N,N-dimethyl-5,6,7,8-tetrahydro-4H-pyrazolo[1,5-a][1,4]diazepine-2-carboxamide (Intermediate 1). To a solution of 3-chloro-N,N-dimethyl-5-(2-nitrophenyl)sulfonyl-4,6,7,8-tetrahydropyrazolo[1,5-a][1,4]diazepine-2-carboxamide (Int-1f, 10.2 g, 23.84 mmol), 4-methoxybenzenethiol (8.8 mL, 71.52 mmol) and $Cs_2CO_3$ (31067.73 mg, 95.36 mmol) in acetonitrile (100 mL). The mixture was stirred at 25° C. for 2 h. The mixture was concentrated, and the crude product was purified by silica gel chromatography (eluted with MeOH in DCM from 3% to 10%) to afford 3-chloro-N,N-dimethyl-5,6,7,8-tetrahydro-4H-pyrazolo[1,5-a][1,4]diazepine-2-carboxamide (Intermediate 1, 3.2 g, 13.2 mmol, 55.3% yield) as yellow solid. LCMS calcld for $C_{10}H_{15}ClN_4O$ (M+H)$^+$ m/z=243.1, found: 243.0.

Alternative Synthesis of Intermediate 1. Synthesis of 3-chloro-N,N-dimethyl-5,6,7,8-tetrahydro-4H-pyrazolo[1,5-a][1,4]diazepine-2-carboxamide

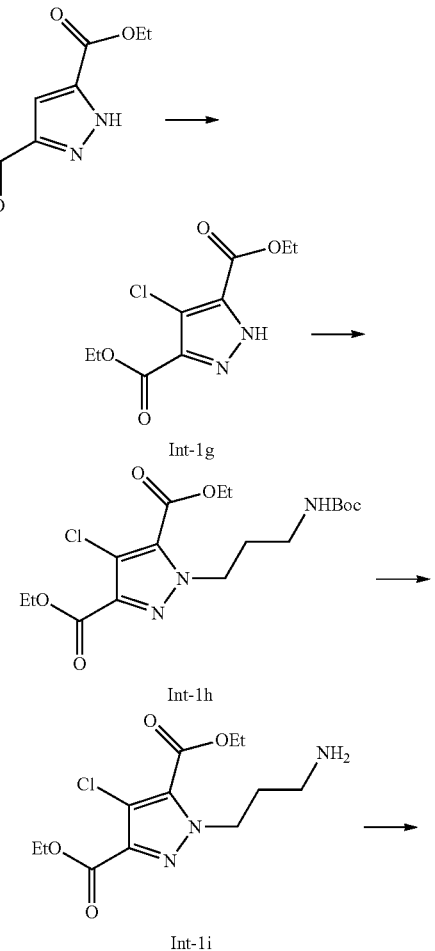

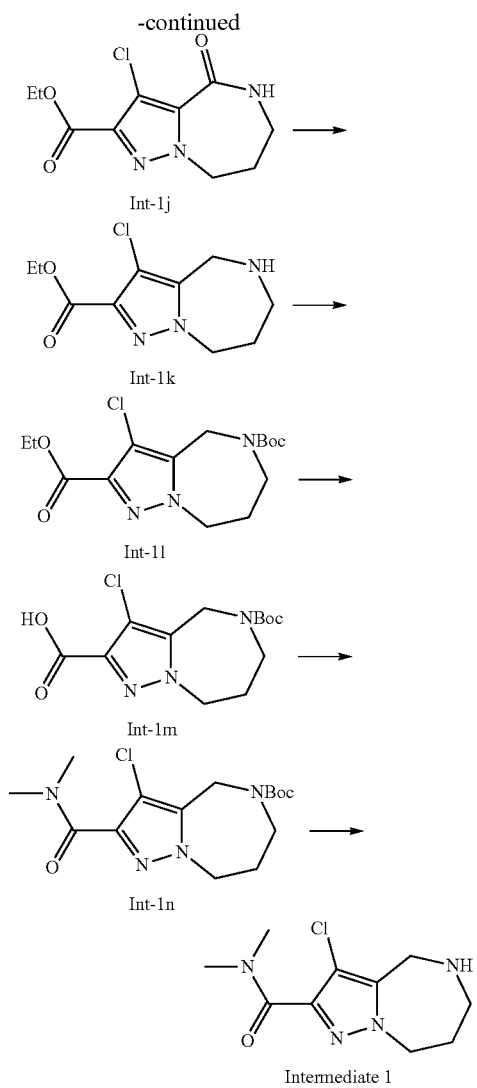

Step 1. Synthesis of diethyl 4-chloro-1H-pyrazole-3,5-dicarboxylate (Int-1g). To a solution of diethyl 1H-pyrazole-3,5-dicarboxylate (20 g, 94.25 mmol) in Acetic acid (360 mL) was added dropwise NaClO (264 mL, 1980 mmol). After stirring for 3 h at 25° C., the remaining mixture was diluted with water, and the mixture was extracted with ethyl acetate. The combined organic layers were concentrated to afford yellowish solid, the solid was dissolved of Petroleum Ether (160 mL) and EtOAc (20 mL), then filtered and collected solids to afford diethyl 4-chloro-1H-pyrazole-3,5-dicarboxylate (Int-1g, 15.20 g, 61.6 mmol, 65.38% yield) as a white solid and mother liquid 7 g. LCMS calculated for $C_9H_{12}ClN_2O_4(M+H)^+$ m/z=247.6; found: 247. $^1$H NMR (400 MHz, $CD_3OD$) δ 4.44-4.36 (m, 4H), 1.39 (t, J=7.1 Hz, 6H).

Step 2. Synthesis of diethyl 1-[3-(tert-butoxycarbonylamino)propyl]-4-chloro-pyrazole-3,5-dicarboxylate (Int-1h). To a solution of diethyl 1-[3-(tert-butoxycarbonylamino)propyl]-4-chloro-pyrazole-3,5-dicarboxylate (Int-1g, 24.7 g, 24.46 mmol, 39.70% yield) in DMF (150 mL) was added tert-butyl N-(3-bromopropyl)carbamate (16141.77 mg, 67.79 mmol), Potassium Iodide (204.6 mg, 1.2 3 mmol), $Cs_2CO_3$ (40157.83 mg, 123.25 mmol), then the mixture was stirred at rt for 16 h. The reaction was quenched with water, extracted it with EtOAc three times, combined the organic phase, washed it with water for 3 times, dry and filter it, collected the filtrate, and concentrated afford diethyl 1-[3-(tert-butoxycarbonylamino)propyl]-4-chloro-pyrazole-3,5-dicarboxylate (Int-1h, 24.70 g, 24.5 mmol, 39.70% yield as reddish brown oil. LCMS calculated for $C_{17}H_{27}ClN_3O_6$ $(M+H)^+$ m/z=404.8; found: 304.1 (M+H-Boc).

Step 3. Synthesis of diethyl 1-(3-aminopropyl)-4-chloro-pyrazole-3,5-dicarboxylate; hydrochloride (Int-1i). To a solution of diethyl 1-(3-aminopropyl)-4-chloro-pyrazole-3,5-dicarboxylate; hydrochloride (Int-1h, 25.5 g, 23.99 mmol, 98.05% yield) in 1,4-Dioxane (50 mL) was added HCl/Dioxane (150 mL, 600 mmol), then the mixture was stirred at 25° C. for 1 h. The reaction was concentrated to afford diethyl 1-(3-aminopropyl)-4-chloro-pyrazole-3,5-dicarboxylate; hydrochloride (Int-1i, 25.50 g, 24.0 mmol, 98.05% yield) as yellow oil for next step. LCMS calculated for $C_{12}H_{19}ClN_3O_4(M+H)^+$ m/z=304.1; found: 304.3.

Step 4. Synthesis of ethyl 3-chloro-4-oxo-5,6,7,8-tetrahydropyrazolo[1,5-a][1,4]diazepine-2-carboxylate (Int-1j). To a solution of diethyl 1-(3-aminopropyl)-4-chloro-pyrazole-3,5-dicarboxylate; hydrochloride (Int-1i, 25.5 g, 23.99 mmol) in Methanol (500 mL) was added $Et_3N$ (16.74 mL, 119.93 mmol), the mixture was stirred overnight at 80° C. The reaction was concentrated to a volume of 20 mL, the resulting white solid was filtered, then diluted with MeOH, stirred for 10 min, filtered. Then the solid was washed with water for three times, and extracted by DCM for three times to give ethyl 3-chloro-4-oxo-5,6,7,8-tetrahydropyrazolo[1,5-a][1,4]diazepine-2-carboxylate (Int-1j, 4.80 g, 18.6 mmol, 77.66% yield). LCMS calculated for $C_{10}H_{13}ClN_3O_3(M+H)^+$ m/z=258.67; found: 258.1.

Step 5. Synthesis of ethyl 3-chloro-5,6,7,8-tetrahydro-4H-pyrazolo[1,5-a][1,4]diazepine-2-carboxylate (Int-1k). To a solution of ethyl 3-chloro-4-oxo-5,6,7,8-tetrahydropyrazolo[1,5-a][1,4]diazepine-2-carboxylate (Int-1j, 4.8 g, 18.63 mmol) in THF (60 mL) was added Borane-Methyl Sulfide Complex (27.94 mL, 55.89 mmol) under $N_2$. The reaction was stirred at rt for 2 h and then was stirred at 45° C. for 32 h. MeOH to added to quench the reaction at 0° C., then the mixture was concentrated to afford ethyl 3-chloro-5,6,7,8-tetrahydro-4H-pyrazolo[1,5-a][1,4]diazepine-2-carboxylate (Int-1k, 4.50 g, 18.5 mmol). LCMS calculated for $C_{10}H_{15}ClN_3O_2(M+H)^+$ m/z=244.7; found: 244.3.

Step 6. Synthesis of O5-tert-butyl O2-ethyl 3-chloro-4,6,7,8-tetrahydropyrazolo[1,5-a][1,4]diazepine-2,5-dicarboxylate (Int-1l). To a solution of ethyl 3-chloro-5,6,7,8-tetrahydro-4H-pyrazolo[1,5-a][1,4]diazepine-2-carboxylate (Int-1k, 4.5 g, 18.47 mmol) in DCM (60 mL) was added $Et_3N$ (7.73 mL, 55.4 mmol) and DMAP (225.6 mg, 1.85 mmol), then the mixture was stirred at rt for 10 min, $Boc_2O$ (8.87 g, 40.63 mmol) was added, the mixture was stirred at 25° C. for 4 h. The mixture was concentrated and purified by flash column chromatography (silica gel, eluting with 0% to 6% EtOAc/DCM) to afford O5-tert-butyl O2-ethyl 3-chloro-4,6,7,8-tetrahydropyrazolo[1,5-a][1,4]diazepine-2,5-dicarboxylate (Int-1l, 4.10 g, 9.54 mmol, 51.66% yield). LCMS calculated for $C_{15}H_{23}ClN_3O_4$ $(M+H)^+$ m/z=344.8; found: 344.1.

Step 7. Synthesis of 5-tert-butoxycarbonyl-3-chloro-4,6,7,8-tetrahydropyrazolo[1,5-a][1,4]diazepine-2-carboxylic acid (Int-1m). To a solution of O5-tert-butyl O2-ethyl 3-chloro-4,6,7,8-tetrahydropyrazolo[1,5-a][1,4]diazepine-2,5-dicarboxylate (Int-1l, 4.1 g, 9.54 mmol) in THF (36 mL) and Methanol (9 mL) a was added hydroxylithium (913.95 mg, 38.16 mmol) in Water (38.16 mL) at 25° C. The mixture was stirred at 55° C. for 2 h. The mixture was concentrated and acidified with HCl (1 mol/L in $H_2O$) to pH=1 and the crude product was triturated in water and filtered. 5-tert-butoxycarbonyl-3-chloro-4,6,7,8-tetrahydropyrazolo[1,5-a][1,4]diazepine-2-carboxylic acid (Int-1m, 2.4 g, 7.60 mmol, 79.67% yield) was obtained as white solid. LCMS calculated for $C_{13}H_{19}ClN_3O_4$ (M+H)$^+$ m/z=316.7, found: 316.1.

Step 8. Synthesis of tert-butyl 3-chloro-2-(dimethylcarbamoyl)-4,6,7,8-tetrahydropyrazolo[1,5-a][1,4]diazepine-5-carboxylate (Int-1n). The mixture of 5-tert-butoxycarbonyl-3-chloro-4,6,7,8-tetrahydropyrazolo[1,5-a][1,4]diazepine-2-carboxylic acid (Int-1m, 100 mg, 0.32 mmol) in DCM (1 mL) was added Oxalyl Chloride (0.32 mL, 0.63 mmol) at 0° C., the mixture was stirred at 0° C. for 0.5 h and rt for 0.5 h. Then the mixture was concentrated, diluted it with DCM (1 mL), and drop it into Dimethylamine (0.63 mL, 1.27 mmol) (2M in THF), then the mixture was stirred at rt for 1 h. The mixture was quenched with $NH_4Cl$ aqueous, extracted with EtOAc. washed with water and brine, dried over $Na_2SO_4$ and concentrated to afford a crude product tert-butyl 3-chloro-2-(dimethylcarbamoyl)-4,6,7,8-tetrahydropyrazolo[1,5-a][1,4]diazepine-5-carboxylate (Int-1n, 108 mg, 0.315 mmol) as yellow oil. LCMS calcld for $C_{15}H_{24}ClN_4O_3$(M+H)$^+$ m/z=343.8, found: 343.2. $^1$H NMR (400 MHz, DMSO) δ 4.45-4.58 (m, 2H), 4.33-4.43 (m, 2H), 3.69-3.78 (m, 2H), 3.09 (s, 6H), 1.92-2.01 (m, 2H), 1.44 (s, 9H).

Step 9. Synthesis if 3-chloro-N,N-dimethyl-5,6,7,8-tetrahydro-4H-pyrazolo[1,5-a][1,4]diazepine-2-carboxamide (Intermediate 1). To a solution of tert-butyl 3-chloro-2-(dimethylcarbamoyl)-4,6,7,8-tetrahydropyrazolo[1,5-a][1,4]diazepine-5-carboxylate (108 mg, 0.32 mmol), tert-butyl 3-chloro-2-(dimethylcarbamoyl)-4,6,7,8-tetrahydropyrazolo[1,5-a][1,4]diazepine-5-carboxylate (199 mg, 0.58 mmol) and tert-butyl 3-chloro-2-(dimethylcarbamoyl)-4,6,7,8-tetrahydropyrazolo[1,5-a][1,4]diazepine-5-carboxylate (9.96 g, 27.6 mmol) in 1,4-Dioxane (50 mL) was added HCl/Dioxane (150 mL, 600 mmol). The mixture was stirred at 20° C. for 2 h. The mixture was concentrated and the crude product was purified by Prep-HPLC on a $C_{18}$ column (5 uM, 50×150 mm) with mobile phase: $H_2O$ (0.1% $NH_4HCO_3$)/MeCN at flow rate: 35 mL/min to afford 3-chloro-N,N-dimethyl-5,6,7,8-tetrahydro-4H-pyrazolo[1,5-a][1,4]diazepine-2-carboxamide (6.18 g, 25.46 mmol, 89.36% yield) as white solid. LCMS calcld for $C_{10}H_{15}ClN_4O$ (M+H)$^+$ m/z=243.1, found: 243.1. $^1$H NMR (400 MHz, DMSO) δ 4.24-4.38 (m, 2H), 3.26-3.37 (m, 2H), 3.00-3.05 (m, 2H), 2.98 (d, J=15.2 Hz, 6H), 1.66-1.77 (m, 2H).

Intermediate 2

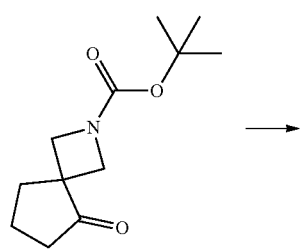

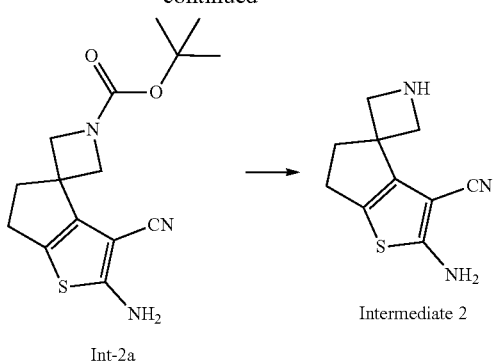

Step 1. Synthesis of tert-butyl 2-amino-3-cyano-spiro[5,6-dihydrocyclopenta[b]thiophene-4,3'-azetidine]-1'-carboxylate (Int-2a). A solution of propanedinitrile (219.93 mg, 3.33 mmol) tert-butyl 5-oxo-2-azaspiro[3.4]octane-2-carboxylate (500 mg, 2.22 mmol) in DMF (5 mL) was added L-proline (255 mg, 2.22 mmol) and sulfur (113.5 mg, 3.33 mmol) at 25° C. under $N_2$. Then the mixture was stirred at 60° C. for 4 h. The mixture was filtered to afford a crude solution. The reaction mixture was purified by prep-HPLC (eluted with $CH_3CN$ in $H_2O$ from 5.0% to 95%) to afford tert-butyl 2-amino-3-cyano-spiro[5,6-dihydrocyclopenta[b]thiophene-4,3'-azetidine]-1'-carboxylate (Int-2a, 380 mg, 1.244 mmol, 56.1% yield) as yellow solid. LCMS calcld for $C_{15}H_{19}N_3O_2S$ (M+H)$^+$ m/z=306.1, found: 306.1. $^1$H NMR (400 MHz, $CD_3OD$) δ 4.19 (s, 2H), 3.95 (d, J=8.1 Hz, 2H), 2.76-2.69 (m, 2H), 2.69-2.61 (m, 2H), 1.45 (s, 9H).

Step 2. Synthesis of 2-aminospiro[5,6-dihydrocyclopenta[b]thiophene-4,3'-azetidine]-3-carbonitrile (Intermediate 2). A solution of tert-butyl 2-amino-3-cyano-spiro[5,6-dihydrocyclopenta[b]thiophene-4,3'-azetidine]-1'-carboxylate (Int-2a, 380 mg, 1.24 mmol) in DCM (5 mL) was added TFA (1.91 mL, 24.89 mmol) at 25° C. under $N_2$. Then the mixture was stirred at 20° C. for 1 h. The mixture was concentrated and the crude product 2-aminospiro[5,6-dihydrocyclopenta[b]thiophene-4,3'-azetidine]-3-carbonitrile (Intermediate 2, 380 mg, 0.678 mmol, 54.5% yield) was used directly for the next step. LCMS calcld for $C_{10}H_{11}N_3S$ (M+H)$^+$ m/z=206.2, found: 206.1.

Intermediate 3

Intermediate 3

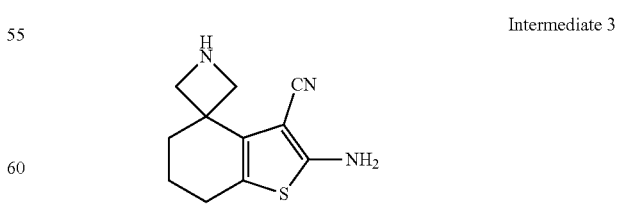

Intermediate 3 was prepared similarly to that of Intermediate 2 from 5-oxo-2-azaspiro[3.5]nonane (ref. *Angew. Chem. Int. Ed.* 2021, 60, 7360-7365). LCMS calcld for $C_{11}H_{13}N_3S$ (M+H)$^+$ m/z=220.1, found: 220.1.

Intermediate 4. 2-aminospiro[5,6,7,8-tetrahydrocyclohepta[b]thiophene-4,3'-azetidine]-3-carbonitrile

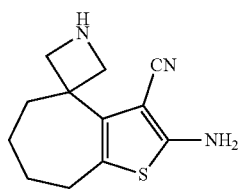

Intermediate 4

Intermediate 4 was prepared similarly to that of Intermediate 2. LCMS calcld for $C_{12}H_{15}N_3S$ (M+H)$^+$ m/z=234.1, found: 234.1.

Intermediate 5. Synthesis of 1-(3-chloro-5,6,7,8-tetrahydro-4H-pyrazolo[1,5-a][1,4]diazepin-2-yl)ethanone

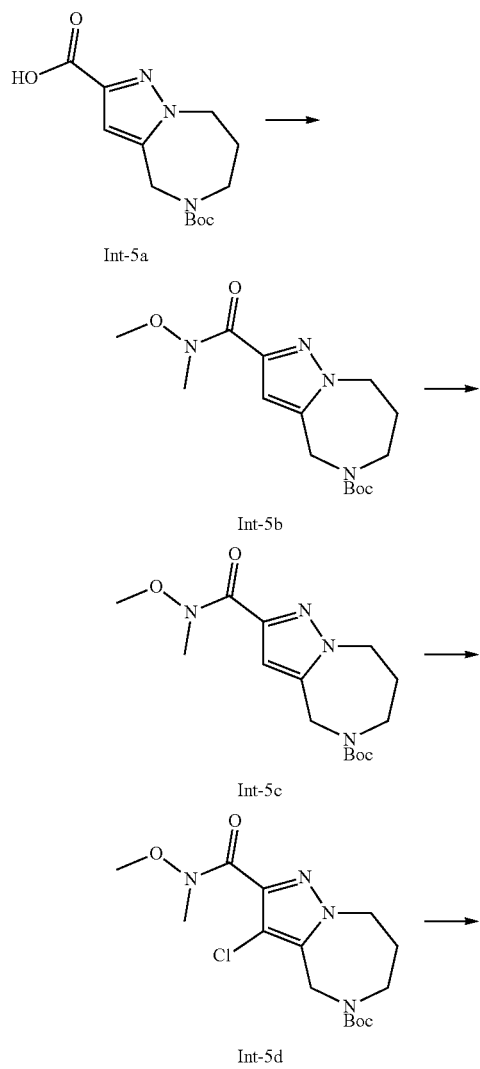

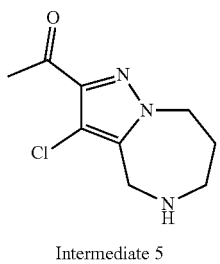

Intermediate 5

Step 1. Preparation of tert-butyl 2-[methoxy(methyl)carbamoyl]-4,6,7,8-tetrahydropyrazolo[1,5-a][1,4]diazepine-5-carboxylate (Int-5b). To a solution of 5-tert-butoxycarbonyl-4,6,7,8-tetrahydropyrazolo[1,5-a][1,4]diazepine-2-carboxylic acid (Int 5a prepared similarly to Int-1m, 500 mg, 1.78 mmol), DIEA (1.24 mL, 7.11 mmol) and HATU (1013.76 mg, 2.67 mmol) in DMF (10 mL) was added N,O-Dimethylhydroxylamine Hydrochloride (260.05 mg, 2.67 mmol) at 25° C. The mixture was stirred at 25° C. for 1 h. The mixture was diluted with EtOAC (50×2 mL), washed with water (50 mL) and brine (50 ml), dried over $Na_2SO_4$, concentrated. The crude product was purified by silica gel chromatography (eluted with EtOAc in petroleum ether from 10% to 90%). tert-butyl 2-[methoxy(methyl)carbamoyl]-4,6,7,8-tetrahydropyrazolo[1,5-a][1,4]diazepine-5-carboxylate (Int-5b, 300 mg, 0.925 mmol, 52.03% yield) was obtained as white solid. LCMS calcld for $C_{15}H_{24}N_4O_4$(M+H)$^+$ m/z=325.2, found: 325.1. $^1$H NMR (400 MHz, CDCl$_3$) δ 6.63 (s, 1H), 4.47 (dd, J=14.7, 9.4 Hz, 4H), 3.74 (s, 5H), 3.42 (s, 3H), 1.94 (s, 2H), 1.41 (s, 9H).

Step 2. Preparation of tert-butyl 3-chloro-2-[methoxy(methyl)carbamoyl]-4,6,7,8-tetrahydropyrazolo[1,5-a][1,4]diazepine-5-carboxylate (Int-5c). To a solution of tert-butyl 2-[methoxy(methyl)carbamoyl]-4,6,7,8-tetrahydropyrazolo[1,5-a][1,4]diazepine-5-carboxylate (Int-5b, 400 mg, 1.23 mmol) in Acetic acid (1 mL) was added NCS (246.99 mg, 1.85 mmol) at 60° C. The mixture was stirred at 60° C. for 3 h. The mixture was concentrated to afford a crude product and used without further purification. tert-butyl 3-chloro-2-[methoxy(methyl)carbamoyl]-4,6,7,8-tetrahydropyrazolo[1,5-a][1,4]diazepine-5-carboxylate (Int-5c, 300 mg, 67.80% yield). LCMS calcld for $C_{15}H_{24}ClN_4O_4$ (M+H)$^+$ m/z=359.82, found: 359.2.

Step 3. Preparation of tert-butyl 2-acetyl-3-chloro-4,6,7,8-tetrahydropyrazolo[1,5-a][1,4]diazepine-5-carboxylate (Int-5d). To a solution of tert-butyl 3-chloro-2-[methoxy(methyl)carbamoyl]-4,6,7,8-tetrahydropyrazolo[1,5-a][1,4]diazepine-5-carboxylate (Int-5c, 240 mg, 0.67 mmol) in THF (1 mL) was added chloro(methyl)magnesium (0.67 mL, 2.01 mmol) at −20° C. The resulting mixture was allowed to rt and stirred for 16 h. The reaction mixture was added sat. NH$_4$Cl aq. (30 mL) and extracted with EtOAc (2×30 mL) and the combined organic layers were dried over Na$_2$SO$_4$ and concentrated in vacuum to give the residue. The crude product was purified by flash chromatography (eluted with EtOAc in petroleum ether from 10% to 90%). tert-butyl 2-acetyl-3-chloro-4,6,7,8-tetrahydropyrazolo[1,5-a][1,4]diazepine-5-carboxylate (Int-5d, 140 mg, 0.446 mmol, 66.71% yield) was obtained as white solid. LCMS calcld for $C_{14}H_{20}ClN_3O_3$(M+H)$^+$ m/z=314.1, found: 314.2.

Step 4. Preparation of 1-(3-chloro-5,6,7,8-tetrahydro-4H-pyrazolo[1,5-a][1,4]diazepin-2-yl)ethanone (Intermediate 5). tert-butyl 2-acetyl-3-chloro-4,6,7,8-tetrahydropyrazolo[1,5-a][1,4]diazepine-5-carboxylate (Int-5d, 140 mg, 0.45 mmol) in HCl in Dioxane (56 mL, 224 mmol). The mixture was stirred at 25° C. The mixture was concentrated to afford a crude product and used without further purification. 1-(3-chloro-5,6,7,8-tetrahydro-4H-pyrazolo[1,5-a][1,4]diazepin-2-yl)ethanone (Intermediate 5, 150 mg) was obtained as white solid. LCMS calcld for $C_9H_{13}ClN_3O$ $(M+H)^+$ m/z=214.66, found: 214.2.

Intermediate 6. Synthesis of 2-amino-6-methyl-spiro[5,6-dihydrocyclopenta[b]thiophene-4,3'-azetidine]-3-carbonitrile

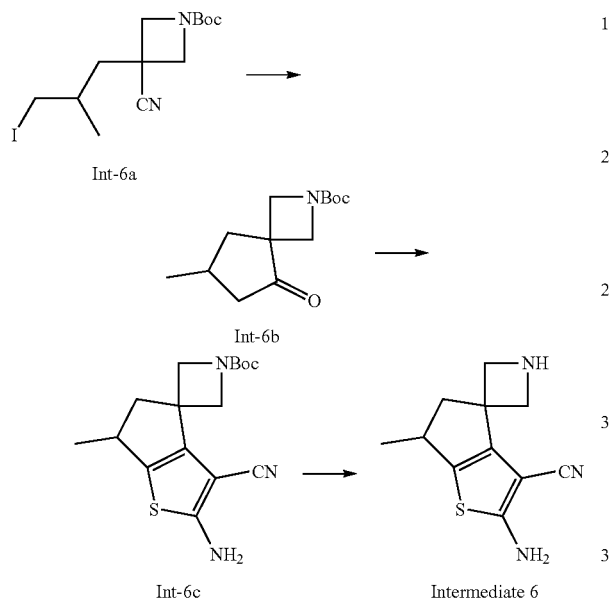

Step 1. Preparation of tert-butyl 7-methyl-5-oxo-2-azaspiro[3.4]octane-2-carboxylate (Int-6b) To a solution of THF (4 mL) was added 1.6M butyllithium in hexane (4.12 mL, 6.59 mmol) at −68° C. The mixture was stirred at −68° C. for 10 min. Then, a solution of tert-butyl 3-cyano-3-(3-iodo-2-methyl-propyl)azetidine-1-carboxylate (Int-6a, CN 11257408, 800 mg, 2.2 mmol) in THF (4 mL) was added at −68° C. The mixture was stirred at −68° C. for 3 h. The mixture was quenched with Acetic acid (5 mL) at −40° C., extracted with tert-Butyl methyl ether (60×2 mL) and water (60 mL). The solution was washed with $NaHCO_3$ (60 mL), $Na_2S_2O_3$ (20% 60 mL) and brine (60 mL), dried over $Na_2SO_4$, concentrated. The crude product was purified by silica gel chromatography (eluted with EtOAc in petroleum ether from 0% to 5%). tert-butyl 7-methyl-5-oxo-2-azaspiro[3.4]octane-2-carboxylate (Int-6b, 110 mg, 0.45 mmol, 20.93% yield) was obtained as yellow oil.

Step 2. Preparation of tert-butyl 2-amino-3-cyano-6-methyl-spiro[5,6-dihydrocyclopenta[b]thiophene-4,3'-azetidine]-1'-carboxylate (Int-6c). A solution of propanedinitrile (45.55 mg, 0.69 mmol) tert-butyl 7-methyl-5-oxo-2-azaspiro[3.4]octane-2-carboxylate (Int-6b, 110 mg, 0.46 mmol) in DMF (1 mL) was added L-Proline (52.92 mg, 0.46 mmol) and Sulfur (23.5 mg, 0.69 mmol) at 25° C. under $N_2$. Then the mixture was stirred at 60° C. for 6 h. The mixture was filtered to afford a crude solution. The reaction mixture was purified by flash chromatography (eluted with $CH_3CN$ in $H_2O$ from 40% to 60%). tert-butyl 2-amino-3-cyano-6-methyl-spiro[5,6-dihydrocyclopenta[b]thiophene-4,3'-azetidine]-1'-carboxylate (Int-6c, 30 mg, 0.094 mmol, 20.43% yield) was obtained as yellow solid. LCMS calcld for $C_{16}H_{21}N_3O_2S$ $(M+Na)^+$ m/z=342.1, found: 342.1.

Step 3. Preparation of 2-amino-6-methyl-spiro[5,6-dihydrocyclopenta[b]thiophene-4,3'-azetidine]-3-carbonitrile (Intermediate 6). To a solution of tert-butyl 2-amino-3-cyano-6-methyl-spiro[5,6-dihydrocyclopenta[b]thiophene-4,3'-azetidine]-1'-carboxylate (Int-6c, 30 mg, 0.09 mmol) in DCM (1 mL) was added TFA (0.14 mL, 1.8 mmol) at rt. The reaction mixture was then stirred at 25° C. for 30 min. The mixture was concentrated to afford a crude product. The crude product 2-amino-6-methyl-spiro[5,6-dihydrocyclopenta[b]thiophene-4,3'-azetidine]-3-carbonitrile (Intermediate 6, 30 mg) was used without purification. LCMS calcld for $C_{11}H_{13}N_3S$ $(M+H)^+$ m/z=220.1, found: 220.1.

Intermediate 7. Synthesis of 3-methyl-5-(5,6,7,8-tetrahydro-4H-pyrazolo[1,5-a][1,4]diazepin-2-yl)-1,2,4-oxadiazole

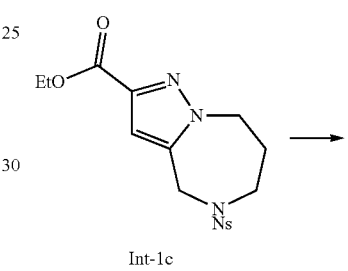

Int-1c

Intermediate 7

Preparation of 3-methyl-5-(5,6,7,8-tetrahydro-4H-pyrazolo[1,5-a][1,4]diazepin-2-yl)-1,2,4-oxadiazole. To a solution of N-hydroxyacetamidine (375.66 mg, 5.07 mmol) and 3 Å molecular sieves in THF (5 mL) were added NaH (76.06 mg, 3.17 mmol), The mixture was stirred at RT for 15 min. ethyl 5-(2-nitrophenyl)sulfonyl-4,6,7,8-tetrahydropyrazolo[1,5-a][1,4]diazepine-2-carboxylate (Int-1c, 500 mg, 1.27 mmol) was added to the mixture. The mixture was stirred at 25° C. for 3 h. The mixture was filtered over celite and concentrated. The crude product was purified by flash chromatography (eluted with $CH_3CN$ in $H_2O$ from 5.0% to 95%). The product 3-methyl-5-(5,6,7,8-tetrahydro-4H-pyrazolo[1,5-a][1,4]diazepin-2-yl)-1,2,4-oxadiazole (230 mg, 1.05 mmol, 82.75% yield) was obtained as a yellow solid. LCMS calcld for $C_{10}H_{13}N_5O$ (M+H) m/z=220.1, found: 220.1.

Intermediate 8. Synthesis of 2-methylsulfanyl-5,6,7,8-tetrahydro-4H-pyrazolo[1,5-a][1,4]diazepine

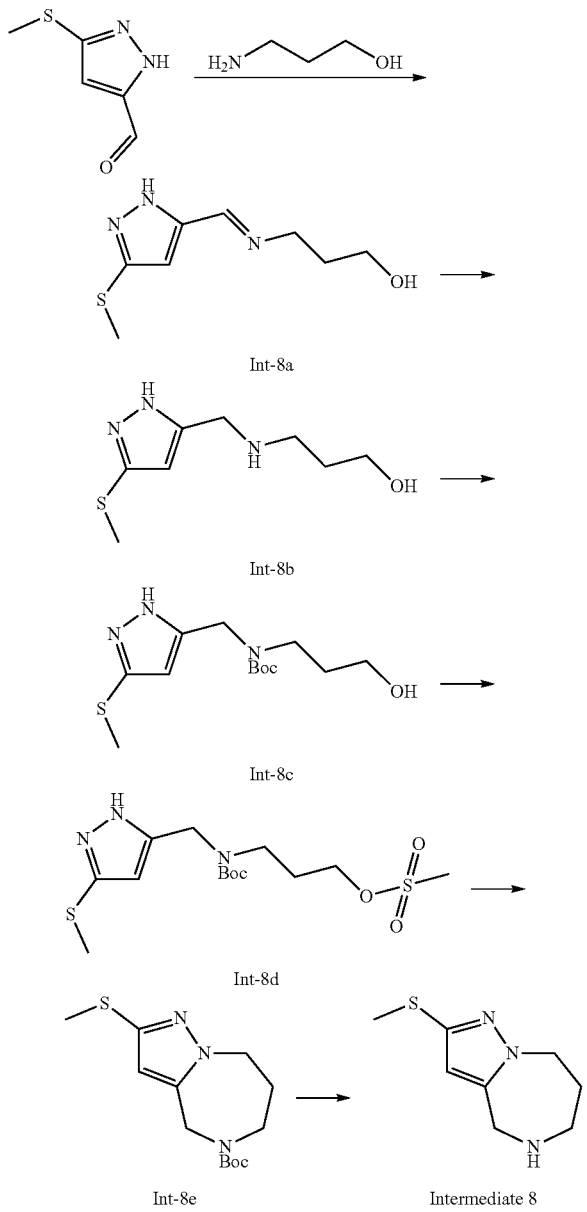

Step 1. Preparation of 3-[(E)-(3-methylsulfanyl-1H-pyrazol-5-yl)methyleneamino]propan-1-ol (Int-8a). The solution of 3-methylsulfanyl-1H-pyrazole-5-carbaldehyde (*Bioorganic and Medicinal Chemistry*, 2012, vol. 20, #3, p. 1319-1336, 1.1 g, 7.74 mmol) and 3-aminopropan-1-ol (639.21 mg, 8.51 mmol) in Ethanol (10 mL) was stirred at 80° C. for 16 h. The mixture was concentrated to afford a crude product which was used directly in the next step. 3-[(E)-(3-methylsulfanyl-1H-pyrazol-5-yl)methyleneamino]propan-1-ol (Int-8a, 1.7 g, 3.23 mmol, 41.79% yield) was obtained as crude yellow oil. LCMS calcld for $C_8H_{13}N_3S$ (M−H)⁻ m/z=199.1, found: 199.1.

Step 2. Preparation of 3-[(3-methylsulfanyl-1H-pyrazol-5-yl)methylamino]propan-1-ol (Int-8b) To a solution of 3-[(E)-(3-methylsulfanyl-1H-pyrazol-5-yl)methyleneamino]propan-1-ol (Int-8a crude, 1.7 g, 8.53 mmol) in Methanol (30 mL) was added Sodium triacetoxyborohydride (3.62 g, 17.06 mmol) at 0° C. The mixture was stirred at 25° C. for 6 h. The mixture was concentrated directly to 10 mL. The crude product was purified by C18 flash chromatography (eluted with $CH_3CN$ in water from 0% to 7%) to afford 3-[(3-methylsulfanyl-1H-pyrazol-5-yl)methylamino]propan-1-ol (Int-8b, 1.5 g, 7.452 mmol, 87.35% yield). LCMS calcld for $C_8H_{15}N_3OS$ (M+H)⁺ m/z=202.2, found: 202.2.

Step 3. Preparation of tert-butyl N-(3-hydroxypropyl)-N-[(3-methylsulfanyl-1H-pyrazol-5-yl)methyl]carbamate (Int-8c). To a solution of 3-[(3-methylsulfanyl-1H-pyrazol-5-yl)methylamino]propan-1-ol (Int-8b, 100 mg, 0.5 mmol) and $Et_3N$ (0.14 mL, 0.99 mmol) in DCM (3 mL) was added $Boc_2O$ (0.14 mL, 0.6 mmol) at 0° C. The mixture was stirred at 25° C. for 2 h. The mixture was diluted with DCM (10 mL) and filtered. The solution was washed with water (10 mL) and brine (10 mL), dried over $Na_2SO_4$, concentrated. The crude product was purified by Prep-TLC (eluted with EtOAc 100%). tert-butyl N-(3-hydroxypropyl)-N-[(3-methylsulfanyl-1H-pyrazol-5-yl)methyl]carbamate (Int-8c, 50 mg, 0.149 mmol, 30.05% yield) was obtained as colorless viscous semi-solid. LCMS calcld for $C_{13}H_{24}N_3O_3S$ (M+H)⁺ m/z=302.1, found: 302.1.

Step 4. Preparation of 3-[tert-butoxycarbonyl-[(3-methylsulfanyl-1H-pyrazol-5-yl)methyl]amino]propyl methanesulfonate (Int-8d). To a solution of tert-butyl N-(3-hydroxypropyl)-N-[(3-methylsulfanyl-1H-pyrazol-5-yl)methyl]carbamate (Int-8c, 50 mg, 0.17 mmol) and in DCM (2 mL) was added MsCl (28.5 mg, 0.25 mmol) at 0° C. The mixture was stirred at 25° C. for 2 h. The mixture was quenched with $H_2O$ (20 mL), extracted with DCM (10×2 mL), dried over $Na_2SO_4$, concentrated. The crude product was purified by Prep-TLC (eluted with EtOAc in petroleum ether 50%). 3-[tert-butoxycarbonyl-[(3-methylsulfanyl-1H-pyrazol-5-yl)methyl]amino]propyl methanesulfonate (Int-8d, 27 mg, 0.069 mmol, 41.60% yield) was obtained as colorless viscous semi-solid. LCMS calcld for $C_{14}H_{25}N_3O_5S_2$(M+Na)⁺ m/z=402.1, found: 402.0.

Step 5. Preparation of tert-butyl 2-methylsulfanyl-4,6,7,8-tetrahydropyrazolo[1,5-a][1,4]diazepine-5-carboxylate (Int-8e). To a solution of 3-[tert-butoxycarbonyl-[(3-methylsulfanyl-1H-pyrazol-5-yl)methyl]amino]propyl methanesulfonate (Int-8d 200 mg, 0.53 mmol) in THF (20 mL) was added sodium hydride (63.24 mg, 1.58 mmol) at 0° C. under $N_2$. The mixture was stirred at 25° C. for 3 h. The mixture was quenched with the mixture of $NH_4Cl$ (20 mL) and iced water (20 mL), extracted with EtOAC (20*3 mL), dried over $Na_2SO_4$, concentrated.

The crude product was purified by flash chromatography (eluted with EtOAc in petroleum ether from 0% to 35%). tert-butyl 2-methylsulfanyl-4,6,7,8-tetrahydropyrazolo[1,5-a][1,4]diazepine-5-carboxylate (Int-8e, 50 mg, 0.1764 mmol, 33.479% yield) was obtained as crude yellow oil.

Step 6. Preparation of 2-methylsulfanyl-5,6,7,8-tetrahydro-4H-pyrazolo[1,5-a][1,4]diazepine (Intermediate 8). To a solution of tert-butyl 2-methylsulfanyl-4,6,7,8-tetrahydropyrazolo[1,5-a][1,4]diazepine-5-carboxylate (Int-8e, 120 mg, 0.42 mmol) in DCM (4 mL) was added TFA (0.4 mL, 5.23 mmol) at 0° C. The mixture was stirred at 25° C. for 1 h. The mixture was concentrated to afford a crude product and was used without purified. 2-methylsulfanyl-5,6,7,8-tetrahydro-4H-pyrazolo[1,5-a][1,4]diazepine (Intermediate 8, 70 mg) was obtained as crude yellow oil.

Intermediate 9. Synthesis of

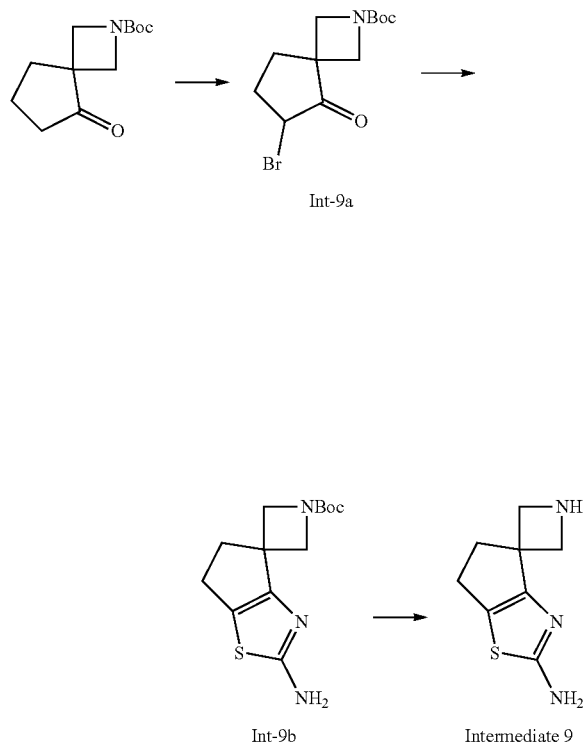

Intermediate 10. Synthesis of tert-butyl 2-cyano-4,6,7,8-tetrahydropyrazolo[1,5-a][1,4]diazepine-5-carboxylate

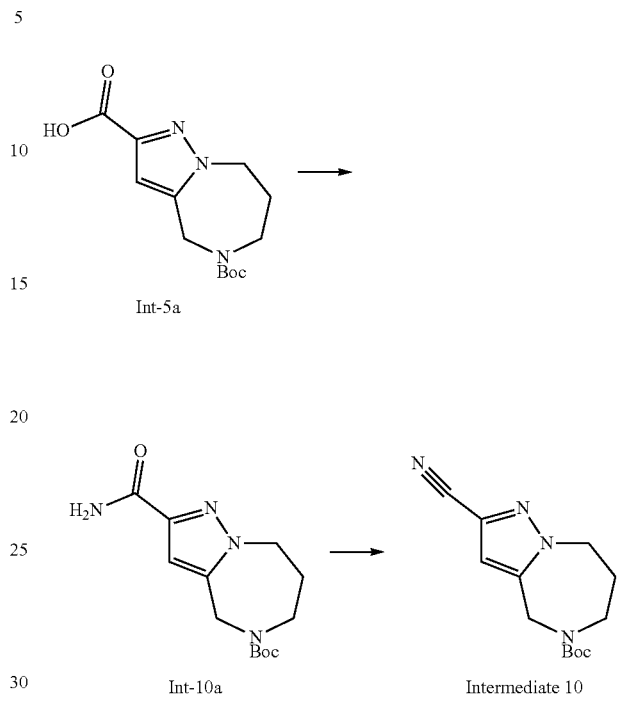

Step 1. Preparation of tert-butyl 6-bromo-5-oxo-2-azaspiro[3.4]octane-2-carboxylate (Int-9a). To the solution of tert-butyl 5-oxo-2-azaspiro[3.4]octane-2-carboxylate (200 mg, 0.89 mmol) in Ether (5 mL) was added 5,5-dibromohexahydropyrimidine-2,4,6-trione (507.6 mg, 1.78 mmol), and the mixture was stirred at 35° C. for 48 h. The mixture was extracted with Ether and water, dried with brine and Na$_2$SO$_4$, concentrated and purified by silica gel chromatography (PE:EtOAc=15:1) to get tert-butyl 6-bromo-5-oxo-2-azaspiro[3.4]octane-2-carboxylate (Int-9a, 140 mg, 0.460 mmol, 51.84% yield).

Step 2. Preparation of tert-butyl 2-aminospiro[5,6-dihydrocyclopenta[d]thiazole-4,3'-azetidine]-1'-carboxylate (Int-9b). To the solution of tert-butyl 6-bromo-5-oxo-2-azaspiro[3.4]octane-2-carboxylate (Int-9a 140 mg, 0.46 mmol) in Ethanol (2 mL) was added Thiourea (35.03 mg, 0.46 mmol), and the mixture was stirred at 80° C. for 2 h. The solvent was removed and purified by prep-TLC (DCM:MeOH=15:1) to get tert-butyl 2-aminospiro[5,6-dihydrocyclopenta[d]thiazole-4,3'-azetidine]-1'-carboxylate (Int-9b, 20 mg, 0.0711 mmol, 15.44% yield). LCMS calcld for C$_{13}$H$_{19}$N$_3$O$_2$S (M+H)$^+$ m/z=282.37, found: 282.2.

Step 3. Preparation of spiro[5,6-dihydrocyclopenta[d]thiazole-4,3'-azetidine]-2-amine (Intermediate 9). The solution of tert-butyl 2-aminospiro[5,6-dihydrocyclopenta[d]thiazole-4,3'-azetidine]-1'-carboxylate (Int-9b, 15 mg, 0.05 mmol) and Trifluoroacetic acid (0.04 mL, 0.53 mmol) in DCM (2 mL) was stirred at 25° C. for 1 h. The solvent was removed to get spiro[5,6-dihydrocyclopenta[d]thiazole-4,3'-azetidine]-2-amine (Intermediate 9, 15 mg). LCMS calcld for C$_{13}$H$_{19}$N$_3$O$_2$S (M+H)$^+$ m/z=182.26, found: 182.2.

Step 1. Synthesis of tert-butyl 2-carbamoyl-4,6,7,8-tetrahydropyrazolo[1,5-a][1,4]diazepine-5-carboxylate (Int-10a). To a solution of 5-tert-butoxycarbonyl-4,6,7,8-tetrahydropyrazolo[1,5-a][1,4]diazepine-2-carboxylic acid (Int-5a, 450 mg, 1.6 mmol), DIEA (0.84 mL, 4.8 mmol) and HATU (0.91 g, 2.4 mmol) in DMF (45 mL) was added NH$_4$Cl (0.12 g, 1.92 mmol) at 30° C. The mixture was stirred at 30° C. for 2 h. The mixture was diluted with EtOAc (60 mL), washed with water (40 mL) and brine (40 mL), dried over Na$_2$SO$_4$, concentrated. The mixture was concentrated to afford a crude product. The crude product was purified by flash chromatography (eluted with CH$_3$CN in H$_2$O (0.1% TFA) from 5.0% to 95%); tert-butyl 2-carbamoyl-4,6,7,8-tetrahydropyrazolo[1,5-a][1,4]diazepine-5-carboxylate (Int-10a, 350 mg, 1.25 mmol, 78.05% yield) was obtained as yellow solid. LCMS calcld for C$_{13}$H$_{20}$N$_4$O$_3$ (M+H)$^+$ m/z=281.0, found: 281.0.

Step 2. Synthesis of tert-butyl 2-cyano-4,6,7,8-tetrahydropyrazolo[1,5-a][1,4]diazepine-5-carboxylate (Intermediate 10). To a solution of tert-butyl 2-carbamoyl-4,6,7,8-tetrahydropyrazolo[1,5-a][1,4]diazepine-5-carboxylate (Int-10a, 300 mg, 1.07 mmol) and Pyridine (0.26 mL, 3.21 mmol) in THF (1 mL) was added TFAA (674.36 mg, 3.21 mmol) slowly at 25° C. The mixture was stirred at 25° C. for 48 h. The mixture was quenched with H$_2$O (8 mL) at 25° C., extracted with EtOAC (10 mL), dried over Na$_2$SO$_4$, concentrated. The crude product was purified by flash chromatography (eluted with CH$_3$CN in H$_2$O (0.1% TFA) from 5.0% to 95%). tert-butyl 2-cyano-4,6,7,8-tetrahydropyrazolo[1,5-a][1,4]diazepine-5-carboxylate (Intermediate 10, 145 mg, 0.553 mmol, 51.65% yield) was obtained as yellow solid. LCMS calcld for C$_{13}$H$_{18}$N$_4$O$_2$ (M+H)$^+$ m/z=263.3, found: 263.3.

Intermediate 11. Synthesis of 2-(1-methylbenzimidazol-2-yl)-5,6,7,8-tetrahydro-4H-pyrazolo[1,5-a][1,4]diazepine

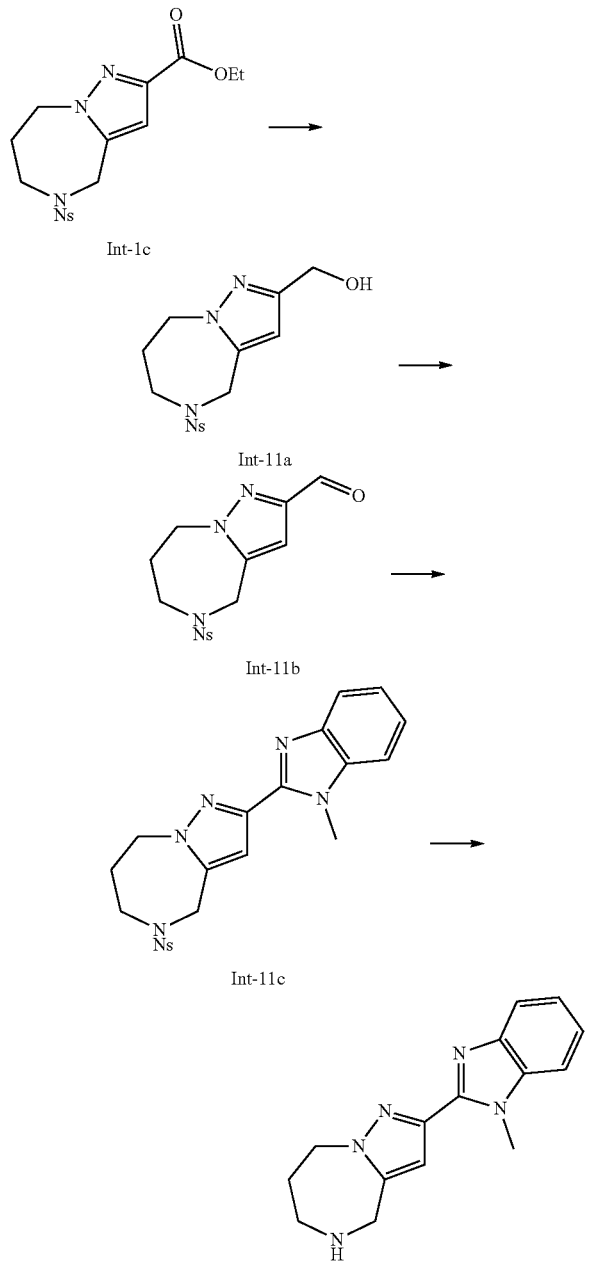

Step 1. Synthesis of [5-(2-nitrophenyl)sulfonyl-4,6,7,8-tetrahydropyrazolo[1,5-a][1,4]diazepin-2-yl]methanol (Int-11a). To a solution of ethyl 5-(2-nitrophenyl)sulfonyl-4,6,7,8-tetrahydropyrazolo[1,5-a][1,4]diazepine-2-carboxylate (Int-1c 1500 mg, 3.8 mmol) in THF (15 mL) was added 1M DABAL-H in hexane (11.41 mL, 11.41 mmol) at −68° C. under argon. The mixture was stirred at 25° C. for 2 h. The reaction was added water and Isopropyl alcohol (1:1.12 mL) and extracted with EtOAc (50 mL×3), and concentrated. The crude product [5-(2-nitrophenyl)sulfonyl-4,6,7,8-tetrahydropyrazolo[1,5-a][1,4]diazepin-2-yl]methanol (Int-11a, 850 mg, 2.39 mmol, 62.79% yield) was used without purification. LCMS calcld for $C_{14}H_{16}N_4O_5S$ $(M+H)^+$ m/z=353.1, found: 353.1.

Step 2. Synthesis of 5-(2-nitrophenyl)sulfonyl-4,6,7,8-tetrahydropyrazolo[1,5-a][1,4]diazepine-2-carbaldehyde (Int-11b). To a solution of [5-(2-nitrophenyl)sulfonyl-4,6,7,8-tetrahydropyrazolo[1,5-a][1,4]diazepin-2-yl]methanol (Int-11a, 850 mg, 2.41 mmol) in DMSO (8 mL) was added IBX (514.6 mg, 3.62 mmol) at 25° C. under argon. The mixture was stirred at 25° C. for 16 h. The mixture was filtered to afford a crude solution. The crude product was purified by flash chromatography (eluted with $CH_3CN$ in $H_2O$ from 50% to 55%). 5-(2-nitrophenyl)sulfonyl-4,6,7,8-tetrahydropyrazolo[1,5-a][1,4]diazepine-2-carbaldehyde (Int-11b, 570 mg, 1.59 mmol, 66.10% yield) was obtained as white solid. LCMS calcld for $C_{14}H_{13}ClN_4O_5S$ $(M+H)^+$ m/z=351.1, found: 351.1.

Step 3. Synthesis of 2-(1-methylbenzimidazol-2-yl)-5-(2-nitrophenyl)sulfonyl-4,6,7,8-tetrahydropyrazolo[1,5-a][1,4]diazepine (Int-11c). The solution of 5-(2-nitrophenyl)sulfonyl-4,6,7,8-tetrahydropyrazolo[1,5-a][1,4]diazepine-2-carbaldehyde (Int-11b, 250 mg, 1 mmol) and $N_2$-methylbenzene-1,2-diamine (244.34 mg, 2 mmol) in DMF (2 mL) was stirred at 100° C. for 18 h. The mixture was extracted with EtOAc and water, dried with brine and $Na_2SO_4$, concentrated and purified by silica gel chromatography (DCM:MeOH=50:1) to get the 2-(1-methylbenzimidazol-2-yl)-5-(2-nitrophenyl)sulfonyl-4,6,7,8-tetrahydropyrazolo[1,5-a][1,4]diazepine (Int-11c, 320 mg, 0.707 mmol, 70.72% yield). LCMS calcld for $C_{21}H_{20}N_6O_4S$ $(M+H)^+$ m/z=453.49, found: 453.3.

Step 4. Synthesis of 2-(1-methylbenzimidazol-2-yl)-5,6,7,8-tetrahydro-4H-pyrazolo[1,5-a][1,4]diazepine (Intermediate 11). A solution of $Cs_2CO_3$ (230.42 mg, 0.71 mmol), 2-(1-methylbenzimidazol-2-yl)-5-(2-nitrophenyl)sulfonyl-4,6,7,8-tetrahydropyrazolo[1,5-a][1,4]diazepine (Int-11c, 160 mg, 0.35 mmol) and 4-Methoxythiophenol (74.36 mg, 0.53 mmol) in $CH_3CN$ (5 mL) was stirred at 25° C. for 3 h. The mixture was filtered and the solvent was removed and purified by silica gel chromatography (DCM:MeOH=11:1) to get the 2-(1-methylbenzimidazol-2-yl)-5,6,7,8-tetrahydro-4H-pyrazolo[1,5-a][1,4]diazepine (Intermediate 11, 70 mg, 0.262 mmol, 74.05% yield). LCMS calcld for $C_{15}H_{17}N_5$ $(M+H)^+$ m/z=268.33, found: 268.3.

Intermediate 12. Synthesis of 2',2'-difluorospiro[azetidine-3,1'-tetralin]

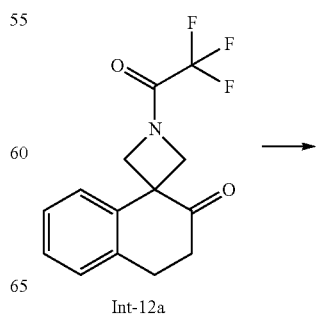

Int-12a

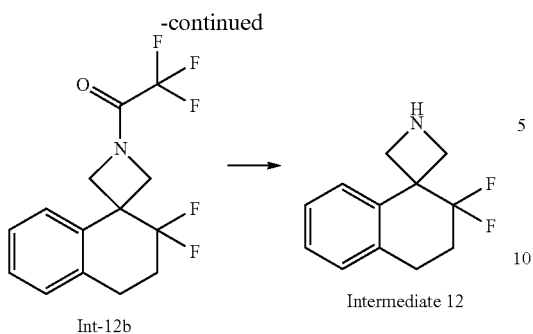

Int-12b → Intermediate 12

Step 1. Synthesis of 1-(2',2'-difluorospiro[azetidine-3,1'-tetralin]-1-yl)-2,2,2-trifluoro-ethanone (Int-12b). 1-(2,2,2-trifluoroacetyl)spiro[azetidine-3,1'-tetralin]-2'-one (Int-12a ref. *Angew. Chem. Int. Ed.* 2021, 60, 7360-7365, 120 mg, 0.42 mmol) was weighed in a vial and DCM (1.69 mL) was added. Diethylaminosulfur Trifluoride (0.11 mL, 0.85 mmol) was added, and mixture stirred at room temperature for 3 hrs. Reaction was purified by silica gel column eluting with 10% Ethyl Acetate/Hexanes to yield 1-(2',2'-difluorospiro[azetidine-3,1'-tetralin]-1-yl)-2,2,2-trifluoro-ethanone (Int-12b, 20 mg, 0.066 mmol, 15.47% yield). LCMS calculated for $C_{14}H_{12}F_5NO$ $(M+H)^+$ m/z=306.08; found: 306.1. $^1$H NMR (500 MHz, $CD_3Cl$) δ ppm 2.18-2.30 (m, 2H) 3.06 (t, J=6.72 Hz, 2H) 4.17 (d, J=10.88 Hz, 1H) 4.42 (d, J=10.09 Hz, 1H) 4.58 (d, J=10.88 Hz, 1H) 4.79-4.88 (m, 1H) 7.17 (d, J=7.64 Hz, 1H) 7.28-7.32 (m, 1H) 7.36-7.42 (m, 1H) 7.56-7.60 (m, 1H).

Step 2. Synthesis of 2',2'-difluorospiro[azetidine-3,1'-tetralin]. (Intermediate 12). 1-(2',2'-difluorospiro[azetidine-3,1'-tetralin]-1-yl)-2,2,2-trifluoro-ethanone (Int-12b, 20 mg, 0.07 mmol) was weighed in a vial and Methanol (0.65 mL) was added. Potassium Carbonate (13.58 mg, 0.1 mmol) was added, and reaction was heated to reflux for 1 hour. Reaction was then evaporated and redissolved in 10% MeOH/DCM. MeOH/DCM was then filtered and evaporated to yield crude product 2',2'-difluorospiro[azetidine-3,1'-tetralin] (Intermediate 12, 12 mg, 0.057 mmol, 87.53% yield) which was used without any further purification.

Intermediate 13. Synthesis of spiro[7-thia-9,11-diazatricyclo[6.4.0.02,6]dodeca-1(8), 2(6), 10-triene-3,3'-azetidine]-12-one

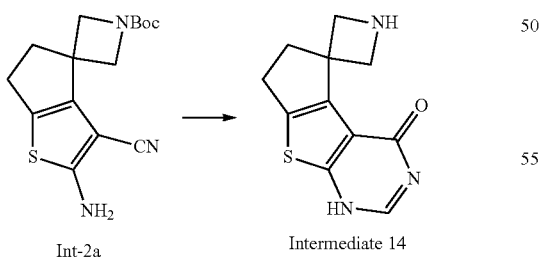

Int-2a → Intermediate 14

To a solution of tert-butyl 2-amino-3-cyano-spiro[5,6-dihydrocyclopenta[b]thiophene-4,3'-azetidine]-1'-carboxylate (Int-2a, 10 mg, 0.03 mmol) in Formic Acid (1 mL, 26.2 mmol) was added 1 drop $H_2SO_4$ and stirred at 105° C. for 3 h under argon. Then the reaction mixture was concentrated in vacuum to give the residue. The residue was recrystallized in ethanol to afford spiro[7-thia-9,11-diazatricyclo[6.4.0.02, 6]dodeca-1(8), 2(6), 10-triene-3,3'-azetidine]-12-one (Intermediate 13, 7 mg, 0.03 mmol, 91.64% yield) as white solid. LCMS calcld for $C_{11}H_{11}N_3OS$ $(M+H)^+$ m/z=234.1, found: 234.1.

Intermediate 14. Synthesis of 3-(3-chloro-5,6,7,8-tetrahydro-4H-pyrazolo[1,5-a][1,4]diazepin-2-yl)-5-methyl-1,2,4-oxadiazole

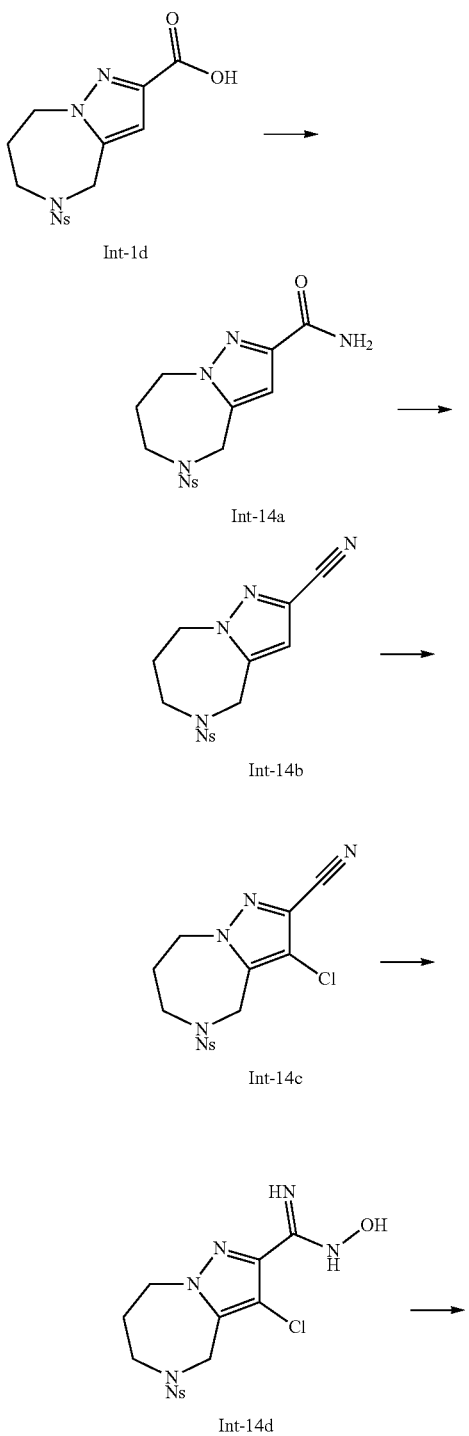

Int-1d

Int-14a

Int-14b

Int-14c

Int-14d

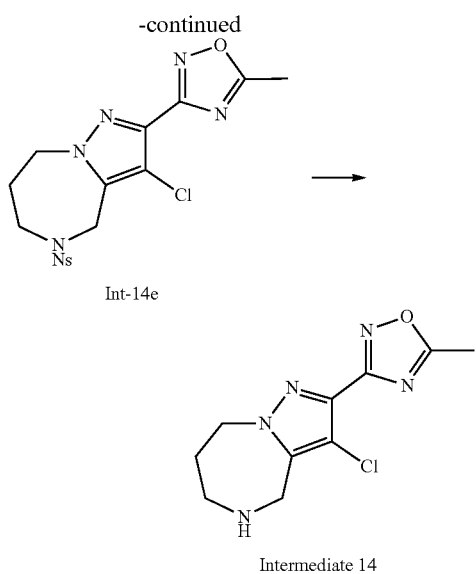

Int-14e

Intermediate 14

Step 1. Synthesis of 5-(2-nitrophenyl)sulfonyl-4,6,7,8-tetrahydropyrazolo[1,5-a][1,4]diazepine-2-carboxamide (Int-14a). To a solution of 5-(2-nitrophenyl)sulfonyl-4,6,7,8-tetrahydropyrazolo[1,5-a][1,4]diazepine-2-carboxylic acid (Int-1d, 870 mg, 2.37 mmol), DIEA (1.65 mL, 9.5 mmol) and HATU (1354.48 mg, 3.56 mmol) in DMF (2 mL) was added $NH_4Cl$ (171.13 mg, 2.85 mmol) at 30° C. The mixture was stirred at 30° C. for 2 h. The mixture was diluted with DCM (30×2 mL), washed with water (40 mL) and brine (40 mL), dried over $Na_2SO_4$, concentrated. The mixture was concentrated to afford a crude product. The crude product was purified by flash chromatography (eluted with $CH_3CN$ in $H_2O$ from 5.0% to 95%) to afford 5-(2-nitrophenyl)sulfonyl-4,6,7,8-tetrahydropyrazolo[1,5-a][1,4]diazepine-2-carboxamide (Int-14a, 760 mg, 2.08 mmol, 87.59% yield) as yellow solid. LCMS calcld for $C_{14}H_{15}N_5O_5S$ $(M+H)^+$ m/z=366.0, found: 366.0.

Step 2. Synthesis of 5-(2-nitrophenyl)sulfonyl-4,6,7,8-tetrahydropyrazolo[1,5-a][1,4]diazepine-2-carbonitrile (Int-14b). To a solution of 5-(2-nitrophenyl)sulfonyl-4,6,7,8-tetrahydropyrazolo[1,5-a][1,4]diazepine-2-carboxamide (Int-14a, 1.5 g, 4.11 mmol) and Pyridine (1 mL, 12.32 mmol) in THF (10 mL) was added TFAA (2586.98 mg, 12.32 mmol) slowly at 25° C. The mixture was stirred at 25° C. for 48 h. The mixture was quenched with $H_2O$ (20 mL) at 25° C., extracted with EtOAC (20×3 mL), dried over $Na_2SO_4$, concentrated. The crude product was purified by silica gel chromatography (eluted with EtOAc in petroleum ether from 10% to 90%) to afford 5-(2-nitrophenyl)sulfonyl-4,6,7,8-tetrahydropyrazolo[1,5-a][1,4]diazepine-2-carbonitrile (Int-14b, 0.8 g, 2.303 mmol, 56.10% yield) as yellow solid. LCMS calcld for $C_{14}H_{14}N_5O_4S$ $(M+H)^+$ m/z=348.35, found: 348.0. Step 3. Synthesis of 3-chloro-5-(2-nitrophenyl)sulfonyl-4,6,7,8-tetrahydropyrazolo[1,5-a][1,4]diazepine-2-carbonitrile (Int-14c). To a solution of 5-(2-nitrophenyl)sulfonyl-4,6,7,8-tetrahydropyrazolo[1,5-a][1,4]diazepine-2-carbonitrile (500 mg, 1.44 mmol) in MeCN (5 mL) were added NCS (192.21 mg, 1.44 mmol), The mixture was stirred at 60° C. for 4 h. The mixture was quenched with $H_2O$ (10 mL) at 25° C., extracted with EtOAC (30 mL), dried over $Na_2SO_4$, concentrated. The crude product was purified by flash chromatography (eluted with EtOAc in petroleum ether from 10% to 90%). The product 3-chloro-5-(2-nitrophenyl)sulfonyl-4,6,7,8-tetrahydropyrazolo[1,5-a][1,4]diazepine-2-carbonitrile (Int-14c, 400 mg, 1.05 mmol, 72.78% yield) was obtained as white solid. LCMS calcld for $C_{14}H_{12}ClN_5O_4S$ $(M+H)^+$ m/z=382.1, found: 382.1.

Step 4. Synthesis of 3-chloro-N-hydroxy-5-(2-nitrophenyl)sulfonyl-4,6,7,8-tetrahydropyrazolo[1,5-a][1,4]diazepine-2-carboxamidine (Int-14d). To a solution of 3-chloro-5-(2-nitrophenyl)sulfonyl-4,6,7,8-tetrahydropyrazolo[1,5-a][1,4]diazepine-2-carbonitrile (Int-14c, 400 mg, 1.05 mmol) and $K_2CO_3$ (433.75 mg, 3.14 mmol) in Ethanol (2 mL) was added HCl $NH_2OH$ (144.58 mg, 2.1 mmol). The mixture was stirred at 80° C. for 12 h. The solution was concentrated. The crude product was washed with water 10 mL, filtrate to obtain a white solid. The product 3-chloro-N-hydroxy-5-(2-nitrophenyl)sulfonyl-4,6,7,8-tetrahydropyrazolo[1,5-a][1,4]diazepine-2-carboxamidine (Int-14d, 183 mg, 0.441 mmol, 42.11% yield) was obtained as white solid. LCMS calcld for $C_{14}H_{15}ClN_6O_5S$ $(M+H)^+$ m/z=415.0, found: 415.0.

Step 5. Synthesis of 3-[3-chloro-5-(2-nitrophenyl)sulfonyl-4,6,7,8-tetrahydropyrazolo[1,5-a][1,4]diazepin-2-yl]-5-methyl-1,2,4-oxadiazole (Int-14e). To a solution of 3-chloro-N-hydroxy-5-(2-nitrophenyl)sulfonyl-4,6,7,8-tetrahydropyrazolo[1,5-a][1,4]diazepine-2-carboxamidine (Int-14d, 183 mg, 0.441 mmol) in Acetic acid (2 mL) were added Acetic anhydride (67.56 mg, 0.66 mmol), The mixture was stirred at 100° C. for 16 h. The mixture was filtered to afford a crude product. The crude product was purified by flash chromatography (eluted with $CH_3CN$ in $H_2O$ from 5.0% to 43%). 3-[3-chloro-5-(2-nitrophenyl)sulfonyl-4,6,7,8-tetrahydropyrazolo[1,5-a][1,4]diazepin-2-yl]-5-methyl-1,2,4-oxadiazole (Int-14e, 163 mg, 0.371 mmol, 84.19% yield) was obtained as white solid. LCMS calcld for $C_{16}H_{15}ClN_6O_5S$ $(M+H)^+$ m/z=439.1, found: 439.1.

Step 6. Synthesis of 3-(3-chloro-5,6,7,8-tetrahydro-4H-pyrazolo[1,5-a][1,4]diazepin-2-yl)-5-methyl-1,2,4-oxadiazole. To a solution of 3-[3-chloro-5-(2-nitrophenyl)sulfonyl-4,6,7,8-tetrahydropyrazolo[1,5-a][1,4]diazepin-2-yl]-5-methyl-1,2,4-oxadiazole (Int-14e, 150 mg, 0.34 mmol), 4-methoxybenzenethiol (0.13 mL, 1.03 mmol) and cesium carbonate (444.34 mg, 1.37 mmol) in $CH_3CN$ (4 mL). The mixture was stirred at 20° C. for 1 h. The mixture was filtrated and purified by prep-HPLC on a C18 column with mobile phase: $H_2O$ (0.1% $NH_4HCO_3$)/$CH_3CN$ to afford 3-(3-chloro-5,6,7,8-tetrahydro-4H-pyrazolo[1,5-a][1,4]diazepin-2-yl)-5-methyl-1,2,4-oxadiazole (Intermediate 14, 80 mg, 0.315 mmol, 92.26% yield) as white solid. LCMS calcld for $C^{10}H^{13}ClN^5O$ $(M+H)^+$ m/z=254.07, found: 254.0.

Intermediate 15. Synthesis of 3-chloro-2-(4,5-dimethyl-1,2,4-triazol-3-yl)-5,6,7,8-tetrahydro-4H-pyrazolo[1,5-a][1,4]diazepine

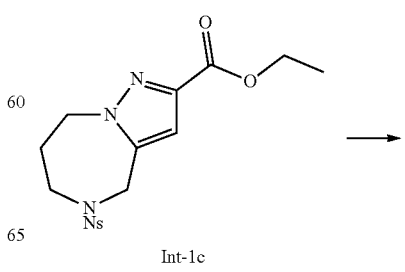

Int-1c

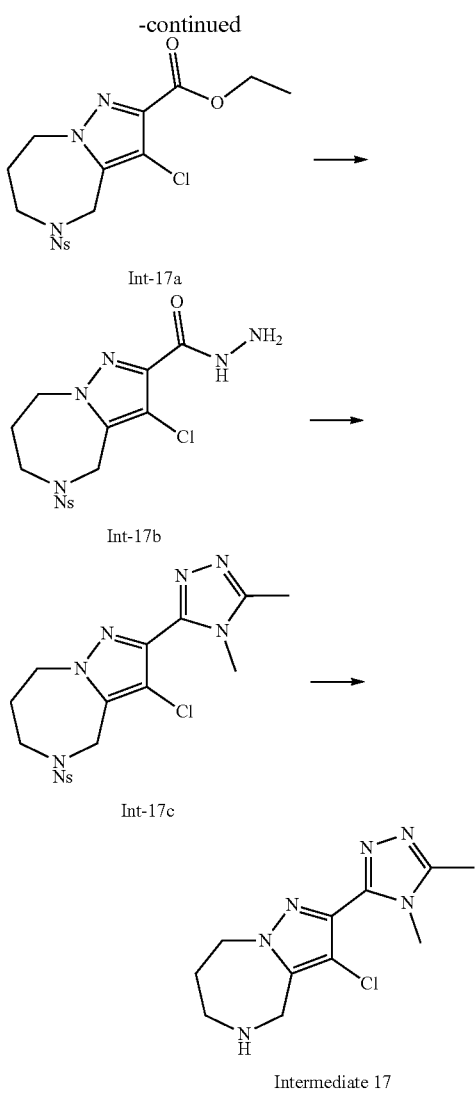

Intermediate 17

Step 1. Synthesis of ethyl 3-chloro-5-(2-nitrophenyl)sulfonyl-4,6,7,8-tetrahydropyrazolo[1,5-a][1,4]diazepine-2-carboxylate (Int-17a). A solution of ethyl 5-(2-nitrophenyl)sulfonyl-4,6,7,8-tetrahydropyrazolo[1,5-a][1,4]diazepine-2-carboxylate (Int-1c 1000 mg, 2.54 mmol) in DMF (10 mL) was added NCS (372.42 mg, 2.79 mmol) at 25° C. Then the mixture was stirred at 80° C. for 1 h. The solution was extracted with EtOAc (10 ml), the organic phase was concentrated. The residue was purified by silica gel chromatography (eluting with EtOAc in PE from 5% to 85%). The product ethyl 3-chloro-5-(2-nitrophenyl)sulfonyl-4,6,7,8-tetrahydropyrazolo[1,5-a][1,4]diazepine-2-carboxylate (Int-17a, 914 mg, 2.131 mmol, 84.06% yield) was obtained as an oil. LCMS calcld for $C_{16}H_{17}ClN_4O_6S$ $(M+H)^+$ m/z=429.06, found: 429.2.

Step 2. Synthesis of 3-chloro-5-(2-nitrophenyl)sulfonyl-4,6,7,8-tetrahydropyrazolo[1,5-a][1,4]diazepine-2-carboxamide (Int-17b). A solution of ethyl 3-chloro-5-(2-nitrophenyl)sulfonyl-4,6,7,8-tetrahydropyrazolo[1,5-a][1,4]diazepine-2-carboxylate (Int-17a, 500 mg, 1.17 mmol) in Ethanol (5 mL) was added $NH_2NH_2 \cdot H_2O$ (594.85 mg, 11.66 mmol) at 25° C. Then the mixture was stirred at 85° C. for 2 h. The solution was extracted with EtOAc (5 ml), the organic phase was concentrated. The residue was purified by silica gel chromatography (eluting with EtOAc in PE from 5% to 95%). The product 3-chloro-5-(2-nitrophenyl)sulfonyl-4,6,7,8-tetrahydropyrazolo[1,5-a][1,4]diazepine-2-carbohydrazide (Int-17b, 300 mg, 0.723 mmol, 62.03% yield) was obtained as a white solid. LCMS calcld for $C_{14}H_{15}ClN_6O_5S$ $(M+H)^+$ m/z=415.06, found: 415.0.

Step 3. Synthesis of 3-chloro-2-(4,5-dimethyl-1,2,4-triazol-3-yl)-5-(2-nitrophenyl)sulfonyl-4,6,7,8-tetrahydropyrazolo[1,5-a][1,4]diazepine (Int-17c). To a solution of 3-chloro-5-(2-nitrophenyl)sulfonyl-4,6,7,8-tetrahydropyrazolo[1,5-a][1,4]diazepine-2-carbohydrazide (Int-17b, 150 mg, 0.36 mmol) in 1,4-Dioxane (3 mL) was added 1,1,1-trimethoxyethane (65.17 mg, 0.54 mmol), Methylamine in EtOH (0.17 mL, 1.08 mmol) and a drop of AcOH (21.7 mg, 0.36 mmol) at rt. The mixture was stirred at 120° C. for 16 h in a sealed vial. The solution was extracted with EtOAc (2 ml), The water phase was concentrated. The residue was purified by silica gel chromatography (eluting with MeOH in DCM from 1% to 3%). The product 3-chloro-2-(4,5-dimethyl-1,2,4-triazol-3-yl)-5-(2-nitrophenyl)sulfonyl-4,6,7,8-tetrahydropyrazolo[1,5-a][1,4]diazepine (Int-17c, 95 mg, 0.210 mmol, 58.14% yield) was obtained as a white solid. LCMS calcld for $C_{17}H_{18}ClN_7O_4S$ $(M+H)^+$ m/z=452.09, found: 452.2.

Step 4. Synthesis of 3-chloro-2-(4,5-dimethyl-1,2,4-triazol-3-yl)-5,6,7,8-tetrahydro-4H-pyrazolo[1,5-a][1,4]diazepine (Intermediate 17). To a solution of 3-chloro-2-(4,5-dimethyl-1,2,4-triazol-3-yl)-5-(2-nitrophenyl)sulfonyl-4,6,7,8-tetrahydropyrazolo[1,5-a][1,4]diazepine (Int-17c, 75 mg, 0.17 mmol) in $CH_3CN$ (0.5 mL) was added 4-Methoxythiophenol (44.21 mg, 0.32 mmol) and $CS_2CO_3$ (137.07 mg, 0.42 mmol) at rt. The mixture was stirred at 25° C. for 2 h. The solution was concentrated. The residue was purified by silica gel on chromatography (eluting with MeOH in DCM from 3% to 11%). The 3-chloro-2-(4,5-dimethyl-1,2,4-triazol-3-yl)-5,6,7,8-tetrahydro-4H-pyrazolo[1,5-a][1,4]diazepine (Intermediate 17, 40 mg, 0.15 mmol, 71.33% yield) was obtained as a white solid. LCMS calcld for $C_{11}H_{15}ClN_6$ $(M+H)^+$ m/z=267.11, found: 267.1.

Intermediate 16. Synthesis of (3-chloro-5,6,7,8-tetrahydro-4H-pyrazolo[1,5-a][1,4]diazepin-2-yl)-cyclopropyl-methanone

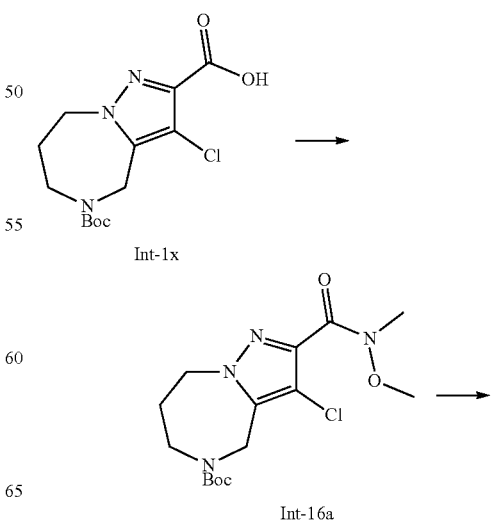

267

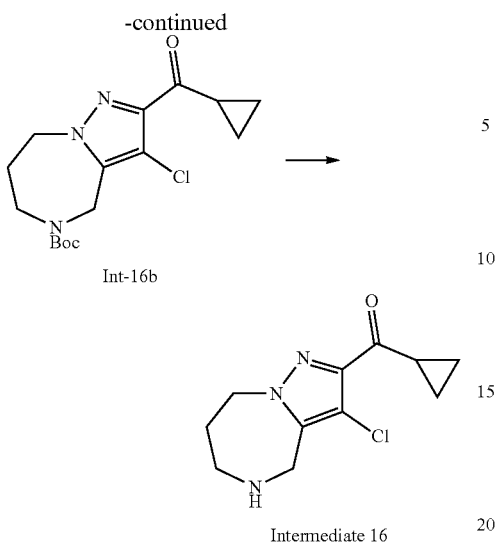

Int-16b

Intermediate 16

Step 1. Synthesis of tert-butyl 3-chloro-2-[methoxy (methyl)carbamoyl]-4,6,7,8-tetrahydropyrazolo[1,5-a][1,4] diazepine-5-carboxylate. The mixture of 5-tert-butoxycarbonyl-3-chloro-4,6,7,8-tetrahydropyrazolo[1,5-a][1,4]diazepine-2-carboxylic acid (350 mg, 1.11 mmol) and HATU (0.41 mL, 1.66 mmol) in DMF (2 mL) was added N,O-Dimethylhydroxylamine Hydrochloride (162.18 mg, 1.66 mmol) at 25° C. The mixture was stirred at 25° C. for 2 h. The mixture was filtered to afford a crude solution. The crude product was purified by flash chromatography (eluted with $CH_3CN$ in $H_2O$ from 51% to 72%). tert-butyl 3-chloro-2-[methoxy(methyl)carbamoyl]-4,6,7,8-tetrahydropyrazolo [1,5-a][1,4]diazepine-5-carboxylate (230 mg, 0.641 mmol, 57.83% yield). LCMS calcld for $C_{15}H_{23}ClN_4O_4$ $(M+H)^+$ m/z=359.1, found: 359.2.

Step 2. Synthesis of tert-butyl 3-chloro-2-(cyclopropanecarbonyl)-4,6,7,8-tetrahydropyrazolo[1,5-a][1,4]diazepine-5-carboxylate. To a solution of tert-butyl 3-chloro-2-[methoxy(methyl)carbamoyl]-4,6,7,8-tetrahydropyrazolo[1, 5-a][1,4]diazepine-5-carboxylate (230 mg, 0.64 mmol) in THF (1.5 mL) was added 1M bromo (cyclopropyl)magnesium in THF (372.49 mg, 2.56 mmol) at 0° C. under argon. The mixture was stirred at 0° C. for 2 h. The mixture was concentrated to afford a crude product. The crude product was used directly for the next step. tert-butyl 3-chloro-2-(cyclopropanecarbonyl)-4,6,7,8-tetrahydropyrazolo[1,5-a] [1,4]diazepine-5-carboxylate (150 mg, 0.441 mmol, 68.86% yield) was obtained as brown oil. LCMS calcld for $C_{16}H_{22}ClN_3O_3$ $(M+H)^+$ m/z=340.1, found: 340.1.

Step 3. Synthesis of (3-chloro-5,6,7,8-tetrahydro-4H-pyrazolo[1,5-a][1,4]diazepin-2-yl)-cyclopropyl-methanone. To a solution of tert-butyl 3-chloro-2-(cyclopropanecarbonyl)-4,6,7,8-tetrahydropyrazolo[1,5-a][1,4]diazepine-5-carboxylate (150 mg, 0.44 mmol) in DCM (1 mL) was added Trifluoroacetic Acid (0.3 mL, 3.89 mmol) at 25° C. under argon. The mixture was stirred at 25° C. for 2 h. The mixture was concentrated to afford a crude product. The crude product was purified by flash chromatography (eluted with $CH_3CN$ in $H_2O$ from 5.0% to 45%). (3-chloro-5,6,7,8-tetrahydro-4H-pyrazolo[1,5-a][1,4]diazepin-2-yl)-cyclopropyl-methanone (100 mg, 0.4172 mmol, 94.513% yield) was obtained as brown oil. LCMS calcld for $C_{11}H_{14}ClN_3O$ $(M+H)^+$ m/z=240.3, found: 240.3.

268

Intermediate 17. Synthesis of tert-butyl N-(4-cyanospiro[2H-thieno[2,3-b]thiophene-3,3'-azetidine]-5-yl)carbamate

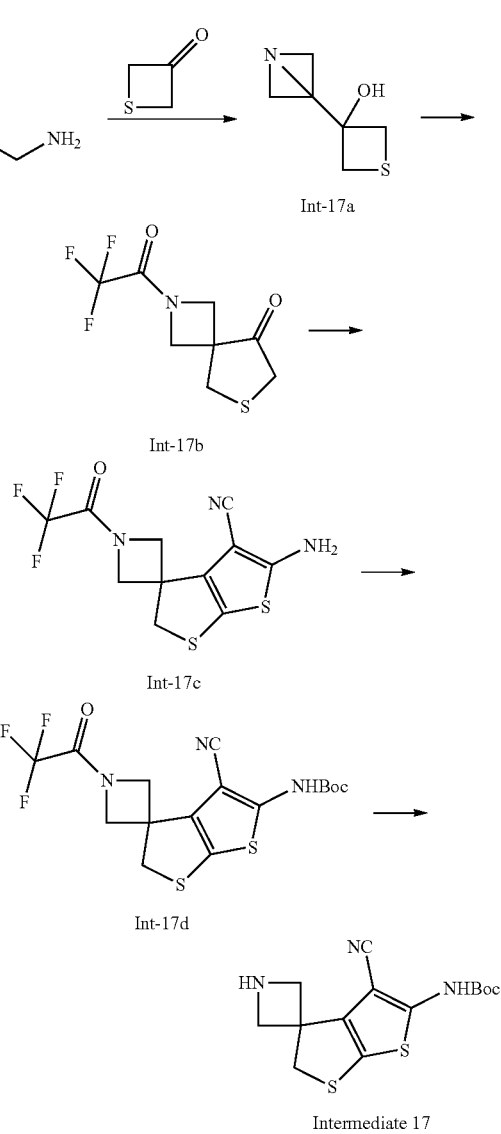

Intermediate 17

Step 1. Synthesis of 3-(1-azabicyclo[1.1.0]butan-3-yl) thietan-3-ol (Int-17a). 2,3-dibromopropan-1-amine; hydrobromide (5000 mg, 16.79 mmol) in THF (100 mL) at −78° C., Phenyllithium (50.37 mL, 50.37 mmol) was added, The mixture was stirred at −78° C. for 2 h, After this time, the reaction mixture was removed from the cooling bath and warmed to room temperature over 10 minutes with stirring. After cooling back down to −78° C., TMEDA (4877.27 mg, 41.97 mmol) was then added followed by s-BuLi (32.29 mL, 41.97 mmol) dropwise, and the resulting solution stirred for 1 hour at −78° C. After this time, thietan-3-one (1479.63 mg, 16.79 mmol) was added dropwise in THF. The reaction was stirred for a further 1 hour at −78° C. The mixture was diluted with EtOAC (100 mL×2), washed with water (100 mL), dried over $Na_2SO_4$, concentrated. The crude product was used directly for the next step. 3-(1-azabicyclo[1.1.0] butan-3-yl)thietan-3-ol (Int-17a, 4000 mg, 27.93 mmol, 166.36% yield) was obtained as crude yellow oil.

Step 2. Synthesis of 2-(2,2,2-trifluoroacetyl)-6-thia-2-azaspiro[3.4]octan-8-one (Int-17b). 3-(1-azabicyclo[1.1.1.0]butan-3-yl)thietan-3-ol (Int-17a, 3000 mg, 20.95 mmol) in DCM at −78° C., TFAA (2.91 mL, 20.95 mmol) was added. The mixture was stirred at −78° C. for 2 h. The mixture was quenched with NaHCO₃ (100 mL), extracted with DCM (100 mL×2), dried over Na₂SO₄, concentrated. The crude product was purified by flash chromatography (eluted with EtOAc in petroleum ether from 10% to 20%) to afford 2-(2,2,2-trifluoroacetyl)-6-thia-2-azaspiro[3.4]octan-8-one (Int-17b, 525 mg, 2.195 mmol, 10.48% yield) was obtained as crude yellow oil. LCMS calcld for $C_8H_8F_3NO_2S$ (M+H)⁺ m/z=239.21, found: 240.2.

Step 3. Synthesis of 5-amino-1'-(2,2,2-trifluoroacetyl)spiro[2H-thieno[2,3-b]thiophene-3,3'-azetidine]-4-carbonitrile (Int-17c). To a solution of 2-(2,2,2-trifluoroacetyl)-6-thia-2-azaspiro[3.4]octan-8-one (Int-17b, 500 mg, 2.09 mmol) L-Proline (240.65 mg, 2.09 mmol) propanedinitrile (207.12 mg, 3.14 mmol) in DMF (5 mL), Sulfur (100.52 mg, 3.14 mmol) was added. The mixture was stirred at 60° C. for 12 h. The mixture was extracted with EtOAC (25 mL), dried over Na₂SO₄, concentrated. The crude product was purified by Flash chromatography eluted with CH₃CN in H₂O from 5.0% to 95%. 5-amino-1'-(2,2,2-trifluoroacetyl)spiro[2H-thieno[2,3-b]thiophene-3,3'-azetidine]-4-carbonitrile (Int-17c, 330 mg, 1.03 mmol, 49.44% yield) was reddish-brown solid. LCMS calcld for $C_{11}H_8F_3N_3OS_2$ (M+H)⁺ m/z=320.1, found: 320.1.

Step 4. Synthesis of tert-butyl N-tert-butoxycarbonyl-N-[4-cyano-1'-(2,2,2-trifluoroacetyl)spiro[2H-thieno[2,3-b]thiophene-3,3'-azetidine]-5-yl]carbamate (Int-17d). To a solution of 5-amino-1'-(2,2,2-trifluoroacetyl)spiro[2H-thieno[2,3-b]thiophene-3,3'-azetidine]-4-carbonitrile (Int-17c, 250 mg, 0.78 mmol) in MeCN (3 mL) was added Boc₂O (341.73 mg, 1.57 mmol) and DMAP (9.56 mg, 0.08 mmol) at 25° C. The reaction stirred at 25° C. for 1 h. The mixture was concentrated. The crude product was purified by silica gel chromatography (eluted with EtOAc in petroleum ether from 10% to 50%). tert-butyl N-tert-butoxycarbonyl-N-[4-cyano-1'-(2,2,2-trifluoroacetyl)spiro[2H-thieno[2,3-b]thiophene-3,3'-azetidine]-5-yl]carbamate (300 mg, 0.577 mmol, 73.75% yield) was obtained as brown solid. LCMS calculated for $C_{16}H_{16}F_3N_3O_3S_2$ (M+Na)⁺ m/z=442.2, found: 442.2.

Step 5. Synthesis of tert-butyl N-(4-cyanospiro[2H-thieno[2,3-b]thiophene-3,3'-azetidine]-5-yl)carbamate (Intermediate 17). To a solution of tert-butyl N-[4-cyano-1'-(2,2,2-trifluoroacetyl)spiro[2H-thieno[2,3-b]thiophene-3,3'-azetidine]-5-yl]carbamate (Int-17d, 300 mg, 0.58 mmol) in Methanol (3 mL) was added K₂CO₃ (239.41 mg, 1.73 mmol) at 25° C. The reaction stirred at 70° C. for 1 h. The mixture was filtered. The crude product was purified by silica gel chromatography (eluted with MeOH in DCM from 5% to 30%). tert-butyl N-(4-cyanospiro[2H-thieno[2,3-b]thiophene-3,3'-azetidine]-5-yl)carbamate (Intermediate 17, 110 mg, 0.340 mmol, 58.90% yield) was obtained as yellow solid. LCMS calculated for $C_{14}H_{17}N_3O_2S_2$(M+H)⁺ m/z=324.2, found: 324.2.

Intermediate 18. Synthesis of spiro[azetidine-3,1'-tetralin]-2'-one

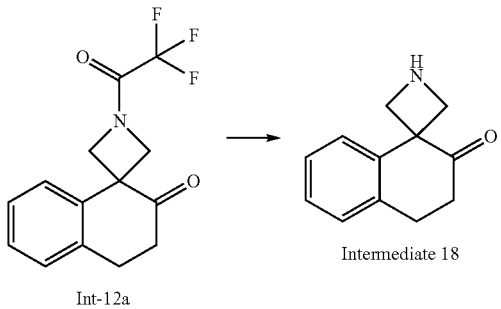 [SMILES: O=C(N1CC2(C1)C(=O)CCc1ccccc12)C(F)(F)F ; O=C1CCc2ccccc2C12CNC2]

1-(2,2,2-trifluoroacetyl)spiro[azetidine-3,1'-tetralin]-2'-one (20 mg, 0.07 mmol) was weighed in a vial and Methanol was added. Potassium Carbonate (19.52 mg, 0.14 mmol) was added, and reaction stirred at 80° C. for 1 hour. Reaction was evaporated and redissolved in 10% MeOH/DCM and then filtered. MeOH/DCM was evaporated to yield product spiro[azetidine-3,1'-tetralin]-2'-one (13 mg, 0.069 mmol, 98.33% yield). ¹H NMR (500 MHz, CD₃Cl) 6 ppm 2.62-2.69 (m, 2H) 3.00 (t, J=6.66 Hz, 2H) 3.73 (d, J=8.07 Hz, 2H) 4.28 (d, J=8.07 Hz, 2H) 7.20 (s, 1H) 7.23-7.29 (m, 14H) 7.38 (s, 1H) 7.82 (d, J=7.82 Hz, 1H).

Intermediate 19. Synthesis of 2-aminospiro[6H-thieno[2,3-c]thiophene-4,3'-azetidine]-3-carbonitrile

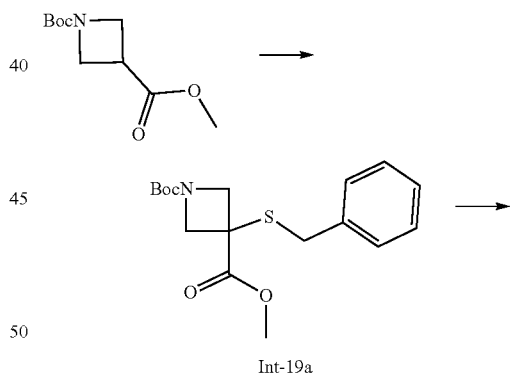

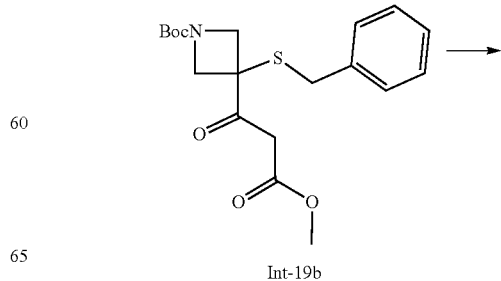

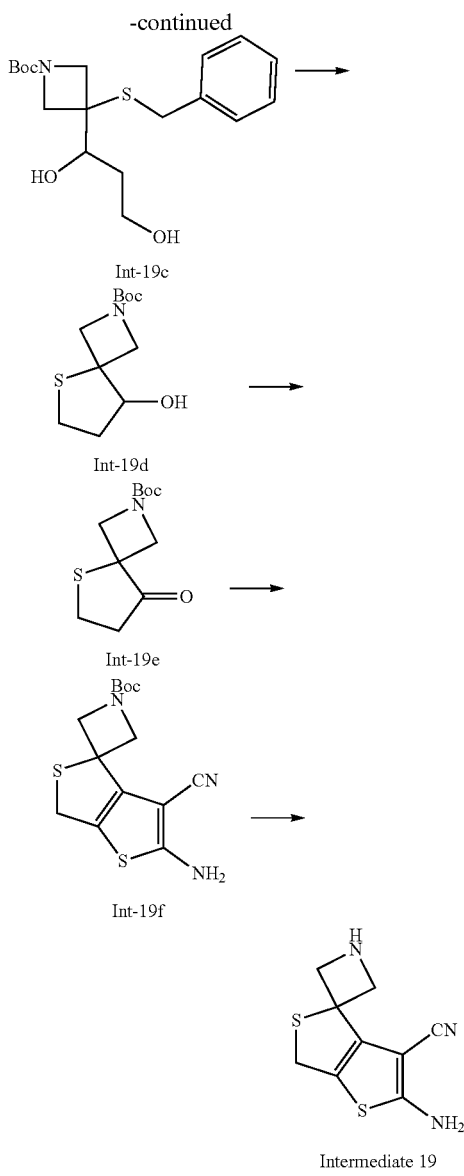

nylazetidine-1,3-dicarboxylate (Int-19a, 610 mg, 1.81 mmol) was added at −78° C. The resulting mixture was stirred for 1 h at −78° C. and then allowed to warm up to room temperature for 45 min. The reaction mixture was quenched by NH₄Cl (5 mL), diluted with EtOAc (20×2 mL), washed with brine (10 ml), dried over Na₂SO₄, concentrated.

The crude product was purified by silica gel chromatography (eluted with EtOAc in petroleum ether from 0% to 20%) to afford tert-butyl 3-benzylsulfanyl-3-(3-methoxy-3-oxo-propanoyl)azetidine-1-carboxylate (Int-19b 270 mg, 0.712 mmol, 39.36% yield) as a colorless oil.

Step 3. Preparation of tert-butyl 3-benzylsulfanyl-3-(1,3-dihydroxypropyl)azetidine-1-carboxylate (Int-19c). To a solution of tert-butyl 3-benzylsulfanyl-3-(3-methoxy-3-oxo-propanoyl)azetidine-1-carboxylate (Int-19b, 1200 mg, 3.16 mmol) in DCM (10 mL) was added 1M DIBAL-H in PhMe (12.6 mL, 12.65 mmol) at −78° C. The mixture was stirred at 25° C. for 16 h under argon. The mixture was quenched with MeOH (20 mL) at 0° C. and filtered, extracted with EtOAC (30×3 mL), dried over Na₂SO₄, concentrated. The crude product was purified by silica gel chromatography (eluted with MeOH in DCM from 0% to 10%). The product tert-butyl 3-benzylsulfanyl-3-(1,3-dihydroxypropyl)azetidine-1-carboxylate (Int-19c, 350 mg, 0.99 mmol, 31.31% yield) was obtained as a colorless oil. LCMS calcld for $C_{18}H_{27}NO_4SNa$ $(M+Na)^+$ m/z=376.2; found: 376.2.

Step 4. Preparation of tert-butyl 8-hydroxy-5-thia-2-azaspiro[3.4]octane-2-carboxylate (Int-19d)

To a solution of tert-butyl 3-benzylsulfanyl-3-(1,3-dihydroxypropyl)azetidine-1-carboxylate (Int-19c, 300 mg, 0.85 mmol) in pyridine (8 mL) was added TosCl (404.51 mg, 2.12 mmol) at 25° C. The mixture was stirred at 25° C. for 16 h. The mixture was concentrated to afford a crude product. The crude product was purified by silica gel chromatography (eluted with EtOAc in petroleum ether from 10% to 40%) to afford tert-butyl 8-hydroxy-5-thia-2-azaspiro[3.4]octane-2-carboxylate (Int-19d, 130 mg, 0.530 mmol, 62.43% yield) as a colorless oil. LCMS calcld for $C_{11}H_{20}NO_3S$ $(M+H)^+$ m/z=246.1, found: 190.1 (−tBu).

Step 5. Preparation of tert-butyl 8-oxo-5-thia-2-azaspiro [3.4]octane-2-carboxylate (Int-19e). To a solution of tert-butyl 8-hydroxy-5-thia-2-azaspiro[3.4]octane-2-carboxylate (Int-19d, 350 mg, 1.43 mmol) in DCM (8 mL) and DMSO (2 mL) was added TEA (0.99 mL, 7.13 mmol) and pyridine sulfur trioxide (681.17 mg, 4.28 mmol) at 0° C. The mixture was stirred at 25° C. for 16 h. The mixture was quenched with H₂O at 25° C., extracted with DCM, dried over Na₂SO₄ and concentrated. The crude product was purified by silica gel chromatography (eluted with EtOAc in petroleum ether from 10% to 25%). Tert-butyl 8-oxo-5-thia-2-azaspiro[3.4] octane-2-carboxylate (Int-19e, 260 mg, 1.07 mmol, 74.90% yield) was obtained as a white solid. LCMS calcld for $C_{11}H_{18}NO_3S$ (M+H)+m/z=244.1, found: 188.1 (−tBu).

Step 6. Preparation of tert-butyl 2-amino-3-cyano-spiro[6H-thieno[3,4-b]thiophene-4,3'-azetidine]-1'-carboxylate (Int-19f)

A solution of tert-butyl 8-oxo-5-thia-2-azaspiro[3.4]octane-2-carboxylate (Int-19e, 300 mg, 1.23 mmol), sulfur (63.03 mg, 1.85 mmol), NH₄OAc (143.88 mg, 1.85 mmol) in ethanol (3 mL) was added propanedinitrile (122.17 mg, 1.85 mmol) slowly at 15° C. Then the mixture was stirred at 60° C. for 16 h. The crude product was purified by flash Step 1. Preparation of O1-tert-butyl O3-methyl 3-benzylsulfanylazetidine-1,3-dicarboxylate (Int-19a). To a solution of 01-tert-butyl 03-methyl azetidine-1,3-dicarboxylate (1000 mg, 4.65 mmol) in THF (10 mL) was added 1M LDA in THF (4.65 mL, 9.29 mmol) at −78° C., the mixture was then stirred at −78° C. for 1 h, then dibenzyldisulfide (2289.34 mg, 9.29 mmol) was added at −78° C. The mixture was then stirred at −78° C. for 1 h. The reaction mixture was quenched by NH₄Cl (5 mL), diluted with EtOAc (30×2 mL), washed with brine (20 ml), dried over Na₂SO₄, concentrated. The crude product was purified by silica gel chromatography (eluted with EtOAc in petroleum ether from 0% to 10%). 01-tert-butyl 03-methyl 3-benzylsulfanylazetidine-1,3-dicarboxylate (Int-19a, 610 mg) was obtained as a crude yellow oil.

Step 2. Preparation of tert-butyl 3-benzylsulfanyl-3-(3-methoxy-3-oxo-propanoyl)azetidine-1-carboxylate (Int-19b). To a solution of methyl acetate (0.58 mL, 7.23 mmol) in THF (10 mL) was added 1M LiHMDS in THF (7.23 mL, 7.23 mmol) at −78° C. The mixture was then stirred at −78° C. for 1 h before 01-tert-butyl 03-methyl 3-benzylsulfachromatography (eluted with CH₃CN in H₂0 from 5.0% to 95%). tert-butyl 2-amino-3-cyano-spiro[6H-thieno[3,4-b]thiophene-4,3'-azetidine]-1'-carboxylate (Int-19f, 150 mg, 0.464 mmol, 37.62% yield) was obtained as a white solid. LCMS calcld for $C_{14}H_{17}N_3O_2S_2Na$ $(M+Na)^+$ m/z=346.1, found: 346.1.

Step 7. Preparation of 2-aminospiro[6H-thieno[2,3-c]thiophene-4,3'-azetidine]-3-carbonitrile; 2,2,2-trifluoroacetic acid (Intermediate 19)

A solution of trifluoroacetic acid (0.31 mL, 4.11 mmol) and tert-butyl 2-amino-3-cyano-spiro[6H-thieno[2,3-c]thiophene-4,3'-azetidine]-1'-carboxylate (Int-19f, 50 mg, 0.15 mmol) in DCM (3 mL) was stirred at 25° C. for 1 h. The solvent was removed to get 2-aminospiro[6H-thieno[2,3-c]thiophene-4,3'-azetidine]-3-carbonitrile (Intermediate 19, 52 mg, 99.71% -yield) as a crude brown oil. LCMS calculated for $C_9H_{10}N_3S_2(M+H)^+$ m/z=224.1, found: 224.1.

Intermediate 20. Synthesis of 2-amino-5-fluoro-spiro[5,6-dihydrocyclopenta[b]thiophene-4,3'-azetidine]-3-carbonitrile

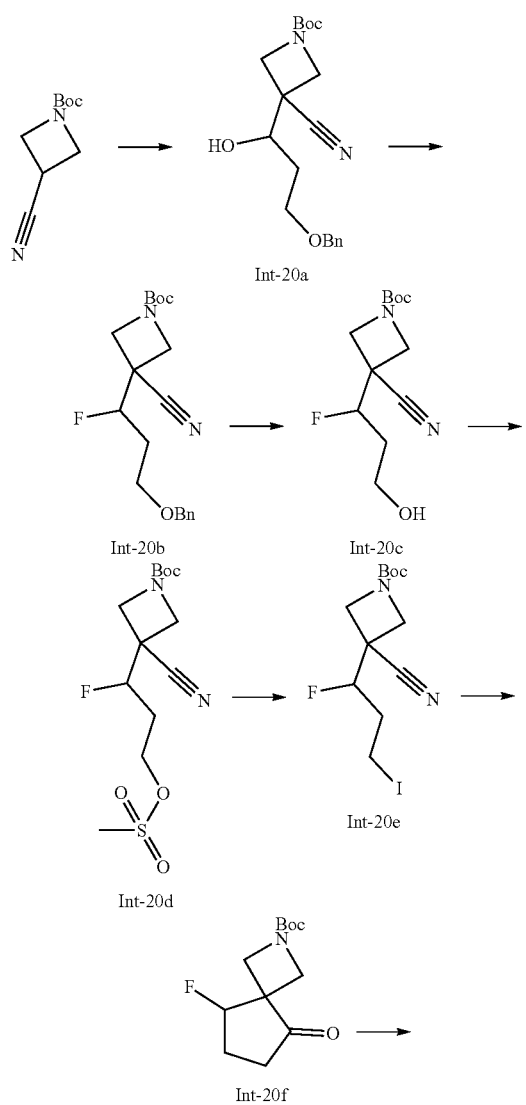

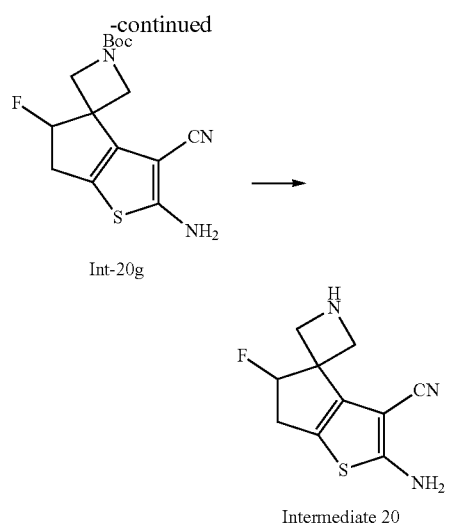

Step 1. Preparation of tert-butyl 3-(3-benzyloxy-1-hydroxy-propyl)-3-cyano-azetidine-1-carboxylate (Int-20a). To a solution of tert-butyl 3-cyanoazetidine-1-carboxylate (500 mg, 2.74 mmol) in THF (5 mL) was added LDA (1.92 mL, 3.84 mmol) portion wise at −70° C. under N₂. Then the mixture was stirred at −70° C. for 1 h, and 3-benzyloxy-propanal (630.78 mg, 3.84 mmol) was added at −70° C. The resulting mixture was stirred at −70° C. for 30 min and warmed to rt for 1 h. The reaction mixture was quenched with saturated NH₄Cl solution, and then extracted with EtOAc. The organic layer was washed with water and brine, dried over Na₂SO₄, concentrated and purified by flash column chromatography (silica gel, eluting with 0% to 40% EtOAc/PE) to afford tert-butyl 3-(3-benzyloxy-1-hydroxy-propyl)-3-cyano-azetidine-1-carboxylate (Int-20a, 450 mg, 1.30 mmol, 47.34% yield) as a colorless oil. LCMS calculated for $C_{19}H_{27}N_2O_4$ $(M+H)^+$ m/z=347.20; found: 247.3 (−Boc).

Step 2. Preparation of tert-butyl 3-(3-benzyloxy-1-fluoro-propyl)-3-cyano-azetidine-1-carboxylate (Int-20b). To a solution of tert-butyl 3-(3-benzyloxy-1-hydroxy-propyl)-3-cyano-azetidine-1-carboxylate (Int-20a, 100 mg, 0.29 mmol) in DCM (2 mL) was added diethylaminosulfur trifluoride (0.08 mL, 0.58 mmol) portion-wise at −70° C. under N₂. The mixture was stirred at −70° C. for 30 min, then warmed to rt for 4 h. The reaction mixture was quenched with ice water and extracted with EtOAc. The organic layer was washed with water and brine, dried over Na₂SO₄, concentrated, and purified by flash column chromatography (silica gel, eluting with 0% to 40% EtOAc/PE) to afford tert-butyl 3-(3-benzyloxy-1-fluoro-propyl)-3-cyano-azetidine-1-carboxylate (Int-20b, 72 mg, 0.207 mmol, 71.59% yield) as a colorless oil. LCMS calculated for $C_{19}H_{26}FN_2O_3(M+H)^+$ m/z=349.19; found: 249.3 (−Boc).

Step 3. Preparation of tert-butyl 3-cyano-3-(1-fluoro-3-hydroxy-propyl)azetidine-1-carboxylate (Int-20c). The mixture of tert-butyl 3-(3-benzyloxy-1-fluoro-propyl)-3-cyano-azetidine-1-carboxylate (Int-20b, 2000 mg, 5.74 mmol), 2,3-dichloro-5,6-dicyano-1,4-benzoquinone (5212.25 mg, 22.96 mmol) in DCM (20 mL) and water (3 mL) was stirred at 45° C. for 20 h. The resulting mixture was filtered. The filtrate was treated with saturated NaHCO₃, extracted with DCM. The organic layer was washed with brine, dried over Na₂SO₄, concentrated and purified by flash column chromatography (silica gel, eluting with 0% to 60% EtOAc/PE)

to afford tert-butyl 3-cyano-3-(1-fluoro-3-hydroxy-propyl) azetidine-1-carboxylate (Int-20c, 1090 mg, 4.22 mmol, 73.52% yield) as a brown oil. LCMS calculated for $C_{12}H_{20}FN_2O_3(M+H)^+$ m/z=259.2; found: 203.2 (-tBu).

Step 4. Preparation of tert-butyl 3-cyano-3-(1-fluoro-3-methylsulfonyloxy-propyl)azetidine-1-carboxylate (Int-20d). To a solution of tert-butyl 3-cyano-3-(1-fluoro-3-hydroxy-propyl)azetidine-1-carboxylate (Int-20c, 100 mg, 0.39 mmol) in DCM (2 mL) were added methanesulfonyl chloride (0.05 mL, 0.58 mmol) and TEA (0.11 mL, 0.77 mmol) at 0° C. Then the mixture was stirred at rt for 1 h. The resulting mixture was quenched with water, and then extracted with EtOAc. The organic layer was washed with brine, dried over $Na_2SO_4$, concentrated to afford tert-butyl 3-cyano-3-(1-fluoro-3-methylsulfonyloxy-propyl)azetidine-1-carboxylate (Int-20d, 130 mg, 0.387 mmol, 99.82% yield) as a green oil. LCMS calculated for $C_{13}H_{22}FN_2O_5S$ $(M+H)^+$ m/z=337.13; found: 281.0 (-tBu).

Step 5. Preparation of tert-butyl 3-cyano-3-(1-fluoro-3-iodo-propyl)azetidine-1-carboxylate (Int-20e). The mixture of tert-butyl 3-cyano-3-(1-fluoro-3-methylsulfonyloxy-propyl)azetidine-1-carboxylate (Int-20d, 130 mg, 0.39 mmol) and NaI (173.78 mg, 1.16 mmol) in acetone (2 mL) was stirred at rt overnight. The reaction mixture was stirred at 60° C. for 5 h. The mixture was cooled to room temperature and the solvent was removed under reduced pressure. The mixture was diluted with water, extracted with EtOAc, washed with brine, dried over $Na_2SO_4$, concentrated and purified by flash column chromatography (silica gel, eluting with 0% to 70% EtOAc/PE) to afford tert-butyl 3-cyano-3-(1-fluoro-3-iodo-propyl)azetidine-1-carboxylate (Int-20e, 103 mg, 0.28 mmol, 72.39% yield) as a colorless oil. LCMS calculated for $C_{12}H_{19}FIN_2O_2(M+H)^+$ m/z=369.05; found: 313.0 (-tBu).

Step 6. Preparation of tert-butyl 5-fluoro-8-oxo-2-azaspiro[3.4]octane-2-carboxylate (Int-20f) To a solution of tert-butyl 3-cyano-3-(1-fluoro-3-iodo-propyl)azetidine-1-carboxylate (Int-20e, 1450 mg, 3.94 mmol) in THF (15 mL) was added n-butyllithium (504.56 mg, 7.88 mmol) at −78° C. under $N_2$. Then the mixture was stirred at −78° C. for 30 min. After completion of the reaction, HOAc (0.68 mL, 11.81 mmol) was added dropwise at −78° C. The resulting mixture was diluted with EtOAc and water was added. The organic layer was washed with brine, dried over $Na_2SO_4$, concentrated and purified by flash column chromatography (silica gel, eluting with 0% to 70% EtOAc/PE) to afford tert-butyl 5-fluoro-8-oxo-2-azaspiro[3.4]octane-2-carboxylate (Int-20f, 655 mg, 2.69 mmol, 68.37% yield) as a yellow oil. LCMS calculated for $C_{12}H_{19}FNO_3$ $(M+H)^+$ m/z=244.14; found: 188.0 (-tBu).

Step 7. Preparation of tert-butyl 2-amino-3-cyano-5-fluoro-spiro[5,6-dihydrocyclopenta[b]thiophene-4,3'-azetidine]-1'-carboxylate (Int-20g)

To a solution of tert-butyl 5-fluoro-8-oxo-2-azaspiro[3.4] octane-2-carboxylate (Int-20f, 600 mg, 2.47 mmol), sulfur (118.68 mg, 3.7 mmol), $NH_4OAc$ (287.83 mg, 3.7 mmol) in ethanol (12 mL) was added propanedinitrile (244.4 mg, 3.7 mmol) at rt. Then the mixture was stirred at 30° C. for 3 h. Diluted with water and extracted with EtOAc. The combined extracts were dried, filtered and concentrated and the crude product was purified to afford tert-butyl 2-amino-3-cyano-5-fluoro-spiro[5,6-dihydrocyclopenta[b]thiophene-4,3'-azetidine]-1'-carboxylate (Int-20g, 407 mg, 1.26 mmol, 51.03% yield) as a light-yellow solid. LCMS calculated for $C_{15}H_{19}FN_3O_2S$ $(M+H)^+$ m/z=324.12; found: 224.0 (-tBu).

Step 8. Preparation of 2-amino-5-fluoro-spiro[5,6-dihydrocyclopenta[b]thiophene-4,3'-azetidine]-3-carbonitrile; hydrochloride (Intermediate 20). To a solution of tert-butyl 2-amino-3-cyano-5-fluoro-spiro[5,6-dihydrocyclopenta[b] thiophene-4,3'-azetidine]-1'-carboxylate (Int-20g, 360 mg, 1.11 mmol) in DCM (15 mL) was added HCl in dioxane (3 mL, 12 mmol). Then the mixture was stirred at rt overnight. The resulting mixture was diluted with DCM, concentrated to afford 2-amino-5-fluoro-spiro[5,6-dihydrocyclopenta[b] thiophene-4,3'-azetidine]-3-carbonitrile; hydrochloride (Intermediate 20, 322 mg, 1.103 mmol, 99.12% yield) as a brown solid. LCMS calculated for $C_{10}H_{11}FN_3S$ $(M+H)^+$ m/z=224.07; found: 224.2.

Intermediate 21. Synthesis of 2-aminospiro[4a,5,5a, 6-tetrahydrocyclopropa[f]benzothiophene-4,3'-azetidine]-3-carbonitrile

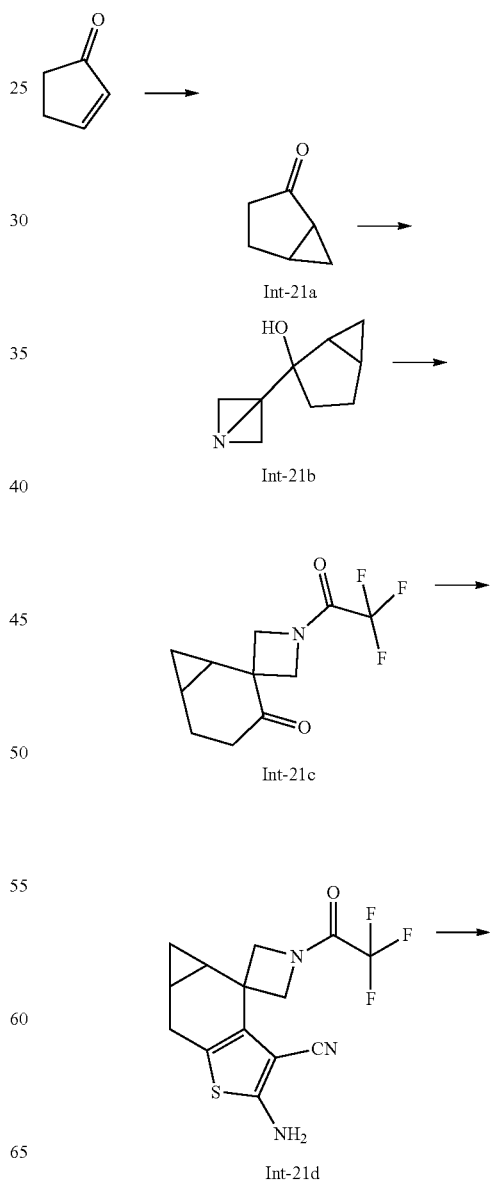

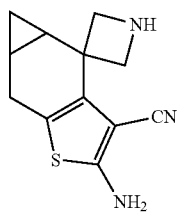

Intermediate 21

Step 1. Preparation of bicyclo[3.1.0]hexan-2-one (Int-21a). NaH (4872.11 mg, 121.8 mmol) in DMSO (50 mL) was added trimethylsulfoxonium iodide (26805.12 mg, 121.8 mmol) at 25° C. Then the mixture was stirred at 25° C. for 1 h. The cyclopent-2-en-1-one (10.2 mL, 121.8 mmol) was added to the mixture at 25° C. for 30 mins. After 30 mins, the mixture was stirred at 50° C. for 2 h. The solution was extracted with MTBE (100 ml), the organic phase was concentrated. The residue was purified by silica gel on chromatography (eluting with 100% DCM). The product bicyclo[3.1.0]hexan-2-one (Int-21a, 2000 mg, 20.81 mmol, 17.08% yield) was obtained as a colorless oil. LCMS calculated for $C_6H_9O$ $(M+H)^+$ m/z=97.07, found: 97.2.

Step 2. Preparation of 2-(1-azabicyclo[1.1.0]butan-3-yl)bicyclo[3.1.0]hexan-2-ol (Int-21b). To a solution of 2,3-dibromopropan-1-amine; hydrobromide (4000 mg, 13.43 mmol) in THF (80 mL) at −78° C., PhLi (3386.32 mg, 40.29 mmol) was added. The mixture was stirred at −78° C. for 2 h. The reaction mixture was then removed from the cooling bath and warmed to rt for over 10 mins with stirring. After cooling back down to −78° C., TMDEA (3901.82 mg, 33.58 mmol) was added, followed by the dropwise addition of s-BuLi (6703.94 mg, 33.58 mmol). The resulting solution was stirred for 1 hour at −78° C. Then, bicyclo[3.1.0]hexan-2-one (Int-21a, 1291.16 mg, 13.43 mmol) was added dropwise in THF. The reaction was stirred for another 1 hour at −78° C. The mixture was diluted with EtOAc (40 mL), washed with water (200 mL), dried over $Na_2SO_4$, concentrated to afford 2-(1-azabicyclo[1.1.0]butan-3-yl)bicyclo[3.1.0]hexan-2-ol (Int-21b, 3500 mg) as a crude yellow oil.

Step 3. Preparation of 1-(2,2,2-trifluoroacetyl)spiro[azetidine-3,2'-norcarane]-3'-one (Int-21c). A solution of 2-(1-azabicyclo[1.1.0]butan-3-yl)bicyclo[3.1.0]hexan-2-ol (Int-21b, 3500 mg, 23.15 mmol) in DCM (66 mL) was added TFAA (6.44 mL, 46.29 mmol) at −78° C. Then the mixture was stirred at −78° C. for 1 h. The solution was added EtOAc (20 ml), washed with aqueous $NaHCO_3$ until pH=7. Then the organic phase was concentrated. The residue was purified by silica gel chromatography (eluting with EtOAc in PE from 17% to 50%). The product 1-(2,2,2-trifluoroacetyl)spiro[azetidine-3,2'-norcarane]-3'-one (Int-21c, 1000 mg, 4.05 mmol, 17% yield) was obtained as a brown oil. LCMS calculated for $C_1H_{13}F_3NO_2$ $(M+H)^+$ m/z=248.09, found: 248.1.

Step 4. Preparation of 2-amino-1'-(2,2,2-trifluoroacetyl)spiro[4a,5,5a,6-tetrahydrocyclopropa[f]benzothiophene-4,3'-azetidine]-3-carbonitrile (Int-21d)

To a solution of 1-(2,2,2-trifluoroacetyl)spiro[azetidine-3,2'-norcarane]-3'-one (Int-21c, 180 mg, 0.73 mmol) in ethanol (2 mL) was added $NH_4OAc$ (84.97 mg, 1.09 mmol), propanedinitrile (72.15 mg, 1.09 mmol) and $S_8$ (34.95 mg, 1.09 mmol) at 25° C. The reaction stirred at 55° C. for 16 h.

The solution was concentrated and purified by prep-HPLC (eluting with $CH_3CN$ in $H_2O$ from 5% to 95%). The product of 2-amino-1'-(2,2,2-trifluoroacetyl)spiro[4a,5,5a,6-tetrahydrocyclopropa[f]benzothiophene-4,3'-azetidine]-3-carbonitrile (Int-21d, 100 mg, 0.306 mmol, 41.96% yield) was obtained as a yellow solid. LCMS calculated for $C_{14}H_{13}F_3N_3OS$ $(M+H)^+$ m/z=328.1, found: 328.0.

Step 5. Preparation of 2-aminospiro[4a,5,5a,6-tetrahydrocyclopropa[f]benzothiophene-4,3'-azetidine]-3-carbonitrile (Intermediate 21)

To a solution of 2-amino-1-(2,2,2-trifluoroacetyl)spiro[4a,5,5a,6-tetrahydrocyclopropa[f]benzothiophene-4,3'-azetidine]-3-carbonitrile (Int-21d, 80 mg, 0.24 mmol) in methanol (5 mL) was added $K_2CO_3$ (67.56 mg, 0.49 mmol) at 25° C. The reaction stirred at 80° C. for 1 h. The solution was concentrated, and the crude product was purified by silica gel chromatography (eluting with MeOH in DCM from 0% to 20%). The product of 2-aminospiro[4a,5,5a,6-tetrahydrocyclopropa[f]benzothiophene-4,3'-azetidine]-3-carbonitrile (Intermediate 21, 52 mg, 0.225 mmol, 91.98% yield) was obtained as a yellow solid. LCMS calculated for $C_{12}H_{14}N_3S$ $(M+H)^+$ m/z=232.1, found: 232.1.

Intermediate 22. Synthesis of 2,3,4,5-tetrahydropyrido[3,2-f][1,4]thiazepine

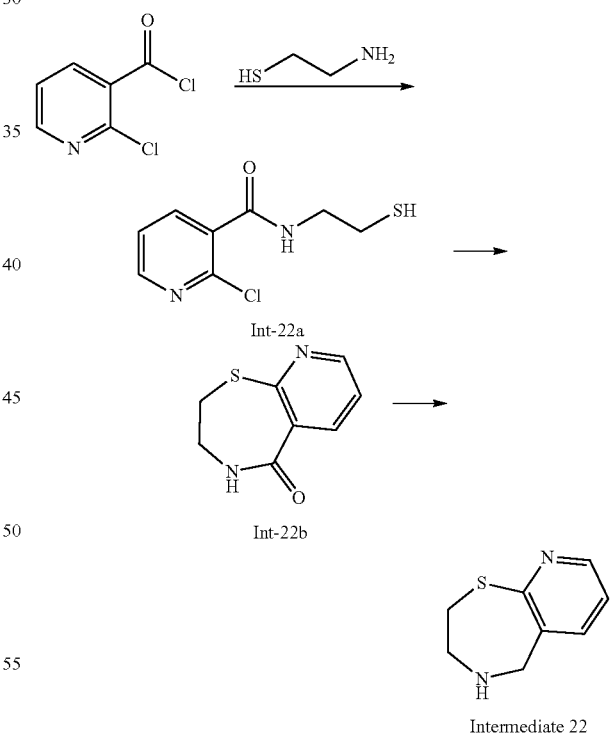

Intermediate 22

Step 1: Synthesis of 2-(2-aminoethylsulfanyl)pyridine-3-carboxamide (Int-22a) To the suspension of 2-aminoethanethiol; hydrochloride (4.25 g, 37.41 mmol) and 2-chloropyridine-3-carboxamide (3.91 g, 24.97 mmol) in Ethanol (50 mL) was added the solution of KOH (4.2 g, 70 mmol) in Ethanol (25 mL) at reflux dropwise over 0.5 h. The mixture was stirred for 1 h and cooled to rt. It was diluted with $Na_2CO_3$ solution (100 mL) and extracted with EtOAc (100 mL). It was dried over Na₂SO₄ and concentrated in vacuo to give the crude product 2-(2-aminoethylsulfanyl)pyridine-3-carboxamide (Int-22a, 6.00 g) as a white solid. LCMS calculated for $C_8H_{12}N_3OS$ (M+H)⁺ m/z=198.26; found: 198.4. ¹H NMR (400 MHz, DMSO) δ 8.48 (dd, J=4.8, 1.7 Hz, 1H), 8.00 (s, 1H), 7.81 (dd, J=7.6, 1.7 Hz, 1H), 7.54 (s, 1H), 7.16 (dd, J=7.6, 4.8 Hz, 1H), 3.18-3.06 (m, 2H), 2.74 (t, J=6.9 Hz, 2H), 1.56 (br, 2H).

Step 2. Synthesis of 3,4-dihydro-2H-pyrido[3,2-f][1,4]thiazepin-5-one (Int-22b). The suspension of 2-(2-aminoethylsulfanyl)pyridine-3-carboxamide (Int-22a, 2 g, 8.11 mmol) and Benzoic Acid (0.2 g, 1.64 mmol) in m-Xylene (100 mL) was heated to 120° C. for 16 h. It was cooled to rt and the solvent was removed in vacuo and the residue was diluted with DMSO (10 mL) and purified using reverse phase FC (eluant with MeCN in base water 5 to 20%), concentrated in vacuo to give the product 3,4-dihydro-2H-pyrido[3,2-f][1,4]thiazepin-5-one (Int-22b, 420 mg, 2.33 mmol, 28.73% yield) as a white solid. LCMS calculated for $C_8H_8N_2OS$ (M+H)⁺ m/z=181.04; found: 181.4. ¹H NMR (400 MHz, DMSO) δ 8.48 (dd, J=4.8, 1.7 Hz, 1H), 8.00 (s, 1H), 7.81 (dd, J=7.6, 1.7 Hz, 1H), 7.54 (s, 1H), 7.16 (dd, J=7.6, 4.8 Hz, 1H), 3.18-3.06 (m, 2H), 2.74 (t, J=6.9 Hz, 2H), 1.56 (br, 2H).

Step 3: Synthesis of 2,3,4,5-tetrahydropyrido[3,2-f][1,4]thiazepine (Intermediate 22). A solution of LiAlH₄ (84.23 mg, 2.22 mmol) in THF (30 mL) was cooled 0° C., then a solution of 3,4-dihydro-2H-pyrido[3,2-f][1,4]thiazepin-5-one (Int-22b, 200 mg, 1.11 mmol) in THF (30 mL) was added dropwise. The reaction mixture was stirred at rt overnight and quenched with 10H₂O·Na₂SO₄. The mixture was filtrated, and the filtrate was concentrated under reduced pressure. The crude residue was purified by silica gel column chromatography (DCM/MeOH, 20:1) to afford the title product 2,3,4,5-tetrahydropyrido[3,2-f][1,4]thiazepine, 82 mg, 44.45% yield as a colorless oil. LCMS calculated for $C_8H_{10}N_2S$ (M+H)⁺ m/z=167.06; found: 167.1.

Example 1: Exemplary Synthesis of 1-[6-[(1R,5S)-3,8-diazabicyclo[3.2.1]octan-3-yl]-2-[[(2R,8S)-2-fluoro-1,2,3,5,6,7-hexahydropyrrolizin-8-yl]methoxy]pyrimidin-4-yl]spiro[azetidine-3,9'-fluorene]-3'-ol (Compound 1)

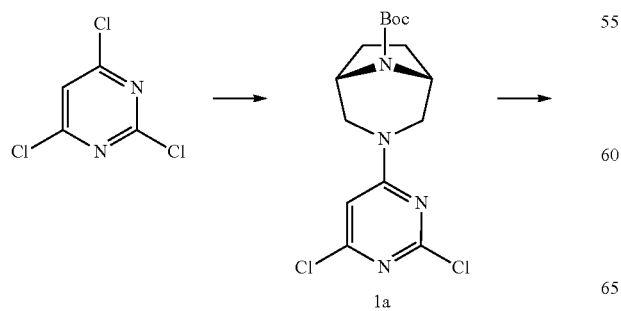

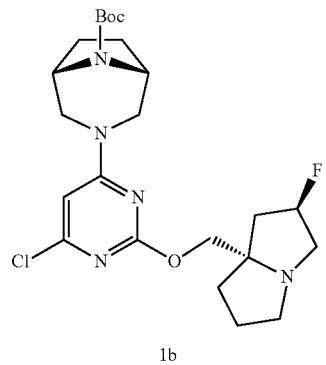

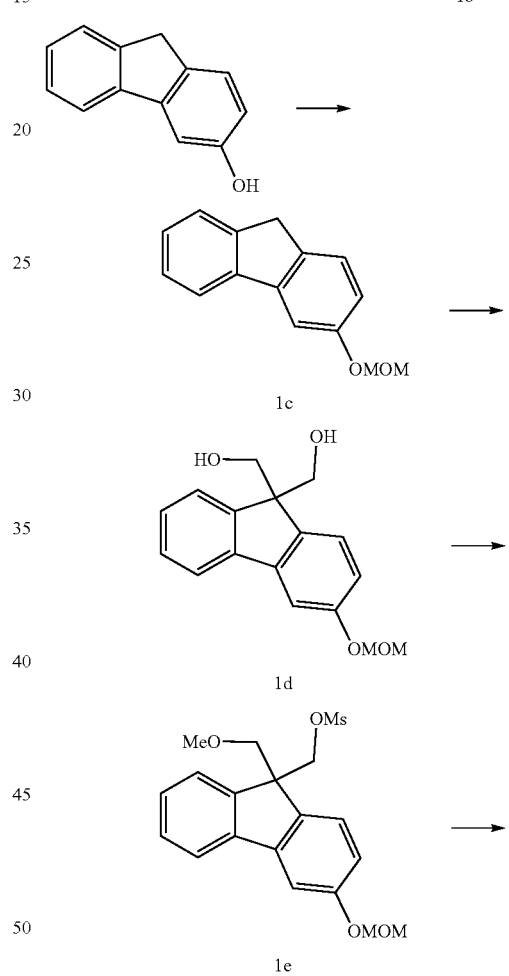

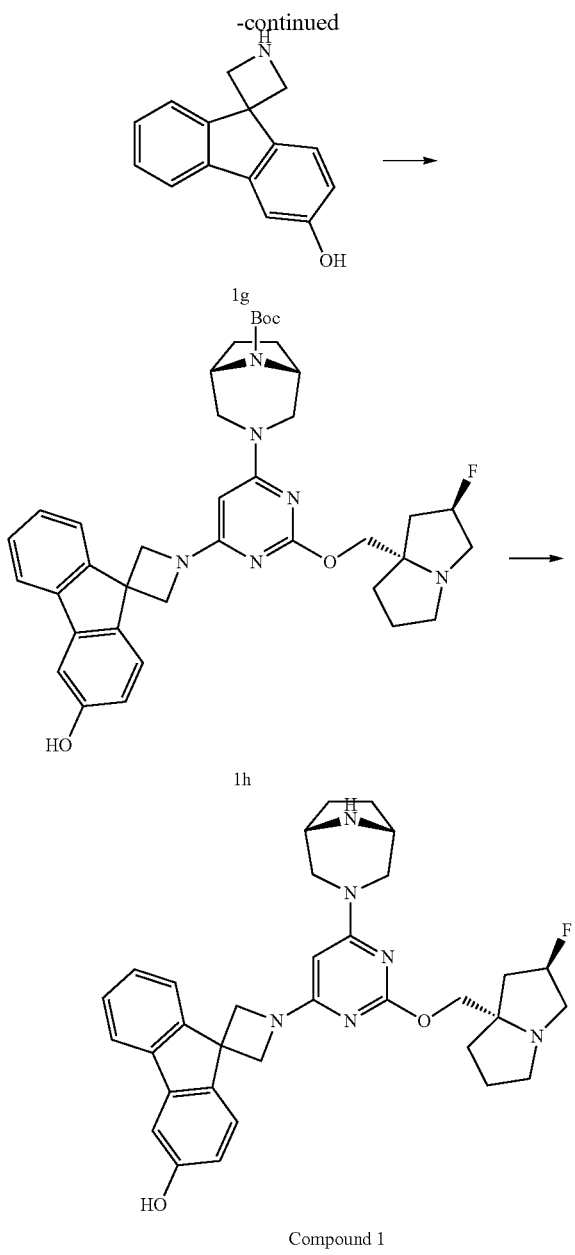

Compound 1

Step 1: Synthesis of tert-butyl (1R,5S)-3-(2,6-dichloropyrimidin-4-yl)-3,8-diazabicyclo[3.2.1]octane-8-carboxylate (1a). To a solution of tert-butyl (1R,5S)-3,8-diazabicyclo[3.2.1]octane-8-carboxylate (1.157 g, 5.45 mmol) in DCM (20 mL) at −60° C. were added 2,4,6-trichloropyrimidine (1 g, 5.45 mmol) and DIEA (2.7 mL, 16.36 mmol) under $N_2$. Then the mixture was stirred at −60° C. for 1 h. The resulting mixture was quenched with saturated aqueous $NH_4Cl$ (60 mL), and then extracted with DCM (60 mL×2). The organic layer was washed with brine (50 mL), dried over $Na_2SO_4$, concentrated and purified by flash column chromatography (silica gel, eluting with 0% to 50% petroleum ether/EtOAc) to afford crude tert-butyl (1R,5S)-3-(2,6-dichloropyrimidin-4-yl)-3,8-diazabicyclo[3.2.1]octane-8-carboxylate (1a, 1.566 g, 4.359 mmol, 79.9% yield) as a light white solid. LCMS calcld for $C_{15}H_{21}Cl_2N_4O_2$ (M+H)$^+$ m/z=359.1; found: 359.2.

Step 2: Synthesis of tert-butyl (1R,5S)-3-(6-chloro-2-(((2R,7aS)-2-fluorotetrahydro-1H-pyrrolizin-7a (5H)-yl) methoxy)pyrimidin-4-yl)-3,8-diazabicyclo[3.2.1]octane-8-carboxylate (1b). The mixture of tert-butyl (1R,5S)-3-(2,6-dichloropyrimidin-4-yl)-3,8-diazabicyclo[3.2.1]octane-8-carboxylate (1a, 700 mg, 1.95 mmol) and [(2R,8S)-2-fluoro-1,2,3,5,6,7-hexahydropyrrolizin-8-yl]methanol (931 mg, 5.85 mmol) in 1,4-dioxane (1 mL) was added DIEA (1.02 mL, 5.85 mmol) and it was stirred at 90° C. overnight. After the reaction was completed, the reaction mixture diluted with water, and extracted with DCM. The combined organic layers were washed with brine, dried over anhydrous $Na_2SO_4$, filtered, and concentrated to give the crude product. The crude product was purified by column chromatography on a silica gel column (DCM/MeOH=20/1 to 10/1) to afford tert-butyl (1R,5S)-3-[6-chloro-2-[[(2R,8S)-2-fluoro-1,2,3,5,6,7-hexahydropyrrolizin-8-yl]methoxy]pyrimidin-4-yl]-3,8-diazabicyclo[3.2.1]octane-8-carboxylate (1b, 501 mg, 1.04 mmol, 53.3% yield) and recovered starting material (198 mg). LCMS calcld for $C_{23}H_{34}ClFN_5O_3$(M+H)$^+$ m/z=482.23; found: 482.4.

Step 3: Synthesis of 3-(methoxymethoxy)-9H-fluorene (1c). To a solution of 9H-fluoren-3-ol (1.70 g, 9.33 mmol) and bromo(methoxy)methane (1.17 mL, 14.0 mmol) in acetonitrile (30 mL) was added DIEA (4.87 mL, 28.0 mmol). The mixture was stirred at rt for 1 h. The mixture was diluted with EtOAc (30 mL), washed with water (50 mL) and saturated brine (30 mL), dried over $Na_2SO_4$, concentrated, and purified by flash column chromatography (silica gel, eluting with EtOAc in petroleum ether 10% to 20%) to afford 3-(methoxymethoxy)-9H-fluorene (1c, 1.34 g, 5.92 mmol, 63.5% yield) as a white solid. LCMS calcld for $C_{15}H_{15}O_2$ (M+H)$^+$ m/z=227.1; found: 227.1.

Step 4: Synthesis of (9-(hydroxymethyl)-3-(methoxymethoxy)fluoren-9-yl)methanol (1d). To a solution of paraformaldehyde (497 mg, 5.52 mmol, 2.5 eq) in DMF (3 mL) was added MeONa (29.8 mg, 0.550 mmol, 0.25 eq) at 0° C. Then the mixture was stirred at 0° C. for 10 min, and 3-(methoxymethoxy)-9H-fluorene (1c, 500 mg, 2.21 mmol) in DMSO (1 mL) was added drop wise at 0° C. The mixture was allowed to warm to rt and stirred for 2 h. The mixture was quenched with 1N HCl, diluted with water (30 mL), extracted with EtOAc (30 mL). The organic phase was dried and purified by flash column chromatography (silica gel, eluting with 5% MeOH in DCM) to afford (9-(hydroxymethyl)-3-(methoxymethoxy)fluoren-9-yl)methanol (1d, 400 mg, 1.40 mmol, 63.2% yield) as a yellow oil. LCMS calcld for $C_{17}H_{19}O_4$(M+H)$^+$ m/z=287.1; found: 287.1.

Step 5: Synthesis of (3-(methoxymethoxy)-9-(methylsulfonyloxymethyl)fluoren-9-yl)methyl methanesulfonate (1e). To the solution of (9-(hydroxymethyl)-3-(methoxymethoxy)fluoren-9-yl)methanol (1d, 100 mg, 0.35 mmol, 1 eq) and $Et_3N$ (0.22 mL, 1.57 mmol) in DCM (3 mL) was added MsCl (160 mg, 1.40 mmol, 4 eq) at 0° C. and the mixture was stirred for 2 h. Then the mixture was partitioned between with EtOAc/$H_2O$. The combined organic layer was washed with brine, dried over $Na_2SO_4$ and concentrated. The residue was purified by FC (silica gel, eluting EtOAc in petroleum ether 0 to 50%) to afford (3-(methoxymethoxy)-9-(methylsulfonyloxymethyl)fluoren-9-yl)methyl methanesulfonate (1e, 150 mg, 0.339 mmol, 97.1% yield) as a colorless oil. LCMS calcld for $C_{19}H_{23}O_8S_2$ (M+H)$^+$ m/z=443.1; found: 459.8.

Step 6: Synthesis of 1-(3,4-dimethylbenzyl)-3'-(methoxymethoxy)spiro[azetidine-3,9'-fluorene] (1f). A mixture of (3-(methoxymethoxy)-9-(methylsulfonyloxymethyl)fluoren-9-yl)methyl methanesulfonate (1e, 150 mg, 0.34 mmol) and 2,4-Dimethoxybenzylamine (1 mL) was stirred at 110° C. for 16 h. Then the mixture was cooled to rt and NaHCO₃(5 mL) aqueous solution was added to quench the reaction. The mixture was extracted with EtOAc (10 mL). The combined organic layer was washed with brine, dried over Na₂SO₄ and concentrated. The residue was purified by FC (silica gel, eluting with EtOAc in petroleum ether 0 to 22%) to afford 1-(3,4-dimethylbenzyl)-3'-(methoxymethoxy)spiro[azetidine-3,9'-fluorene] (1f, 110 mg, 0.264 mmol, 77.7% yield) as a yellow oil. LCMS calcld for $C_{26}H_{28}NO_4$ $(M+H)^+$ m/z=418.2; found: 417.8.

Step 7: Synthesis of spiro[azetidine-3,9'-fluorene]-3'-ol (1g). To a solution of 1-(3,4-dimethylbenzyl)-3'-(methoxymethoxy)spiro[azetidine-3,9'-fluorene] (450 mg, 1.08 mmol) in DCE (5 mL) was added 1-chloroethyl carbonochloridate (462 mg, 3.23 mmol) and the reaction was stirred at 100° C. for 6 h. Then the mixture was concentrated in vacuo to dry. Methanol (5 mL) was added and the mixture was heated to 70° C. for 4 h. The mixture was filtered and purified by prep-HPLC on a $C_{18}$ column (5 um, 50×150 mm) with mobile phase: H₂O (0.1% NH₄HCO₃/MeOH) at flow rate: 35 mL/min to afford spiro[azetidine-3,9'-fluorene]-3'-ol (148 mg, 0.663 mmol, 61.5% yield) as a yellow solid. LCMS calcld for $C_{15}H_{14}NO$ $(M+H)^+$ m/z=224.1; found: 224.0.

Step 8: Synthesis of tert-butyl (1R,5S)-3-[6-(3'-hydroxyspiro[azetidine-3,9'-fluorene]-1-yl)-2-[[(2R,8S)-2-fluoro-1,2,3,5,6,7-hexahydropyrrolizin-8-yl]methoxy]pyrimidin-4-yl]-3,8-diazabicyclo[3.2.1]octane-8-carboxylate (1h). The mixture of tert-butyl (1R,5S)-3-[6-chloro-2-[[(2R,8S)-2-fluoro-1,2,3,5,6,7-hexahydropyrrolizin-8-yl]methoxy]pyrimidin-4-yl]-3,8-diazabicyclo[3.2.1]octane-8-carboxylate (30.0 mg, 0.06 mmol), spiro[azetidine-3,9'-fluorene]-3'-ol (69.5 mg, 0.31 mmol) and cesium carbonate (121 mg, 0.370 mmol) in NMP (1.5 mL) was irritated to 135° C. using microwave for 3 h under Ar. Then the mixture was purified by prep-HPLC on a $C_{18}$ column (5 um, 50×150 mm) with mobile phase: H₂O (0.1% NH₄HCO₃/MeOH) at flow rate: 35 mL/min to afford tert-butyl (1R,5S)-3-[6-(3'-hydroxyspiro[azetidine-3,9'-fluorene]-1-yl)-2-[[(2R,8S)-2-fluoro-1,2,3,5,6,7-hexahydropyrrolizi8-yl]methoxy]pyrimidi4-yl]-3,8-diazabicyclo[3.2.1]octane-8-carboxylate (1h, 16 mg, 0.0239 mmol, 38.4% yield) as a white solid. LCMS calcld for $C_{38}H_{46}FN_6O_4(M+H)^+$ m/z=669.4; found: 669.0.

Step 9: Synthesis of 1-[6-[(1R,5S)-3,8-diazabicyclo[3.2.1]octa3-yl]-2-[[(2R,8S)-2-fluoro-1,2,3,5,6,7-hexahydropyrrolizin-8-yl]methoxy]pyrimidin-4-yl]spiro[azetidine-3,9'-fluorene]-3'-ol (compound 1). To a solution of tert-butyl (1R,5S)-3-[6-(3'-hydroxyspiro[azetidine-3,9'-fluorene]-1-yl)-2-[[(2R,8S)-2-fluoro-1,2,3,5,6,7-hexahydropyrrolizin-8-yl]methoxy]pyrimidin-4-yl]-3,8-diazabicyclo[3.2.1]octane-8-carboxylate (1h, 24.0 mg, 0.04 mmol) in 1,4-dioxane (1 mL) was added HCl in 1,4-dioxane (1 mL, 4.0 mmol) at 0° C. and the reaction was stirred at rt for 2 h. Then the mixture was dried by N₂ and then purified by prep-HPLC on a $C_{18}$ column (5 um, 50×150 mm) with mobile phase: H₂O (0.1% NH₄HCO₃/MeOH) at flow rate: 35 mL/min to afford 1-[6-[(1R,5S)-3,8-diazabicyclo[3.2.1]octa3-yl]-2-[[(2R,8S)-2-fluoro-1,2,3,5,6,7-hexahydropyrrolizin-8-yl]methoxy]pyrimidin-4-yl]spiro[azetidine-3,9'-fluorene]-3'-ol (1, 12.3 mg, 0.0214 mmol, 59.7% yield) as a white solid. LCMS calcld for $C_{33}H_{38}FN_6O_2(M+H)^+$ m/z=569.3; found: 569.0. ¹H NMR (400 MHz, CD₃OD) δ 7.64-7.71 (m, 2H), 7.51 (d, J=8.0 Hz, 1H), 7.33-7.40 (m, 2H), 7.15 (d, J=2.4 Hz, 1H), 6.81 (dd, J=8.0, 2.4 Hz, 1H), 5.34 (s, 0.5H), 5.27 (s, 1H), 5.20 (s, 0.5H), 4.36 (s, 4H), 4.15 (d, J=10.4 Hz, 1H), 3.97-4.07 (m, 3H), 3.59 (s, 2H), 3.14-3.27 (m, 3H), 3.00-3.06 (m, 2H), 2.94-3.00 (m, 1H), 2.15-2.34 (m, 2H), 2.08-2.14 (m, 1H), 1.89-2.00 (m, 2H), 1.79-1.88 (m, 3H), 1.72-1.79 (m, 2H).

Example 2. Exemplary synthesis of 5-[6-(2-amino-3-cyano-spiro[5,6-dihydrocyclopenta[b]thiophene-4,3'-azetidine]-1'-yl)-5-cyano-2-[[(2R,8S)-2-fluoro-1,2,3,5,6,7-hexahydropyrrolizin-8-yl]methoxy]pyrimidin-4-yl]-3-chloro-N,N-dimethyl-4,6,7,8-tetrahydropyrazolo[1,5-a][1,4]diazepine-2-carboxamide (compound 2)

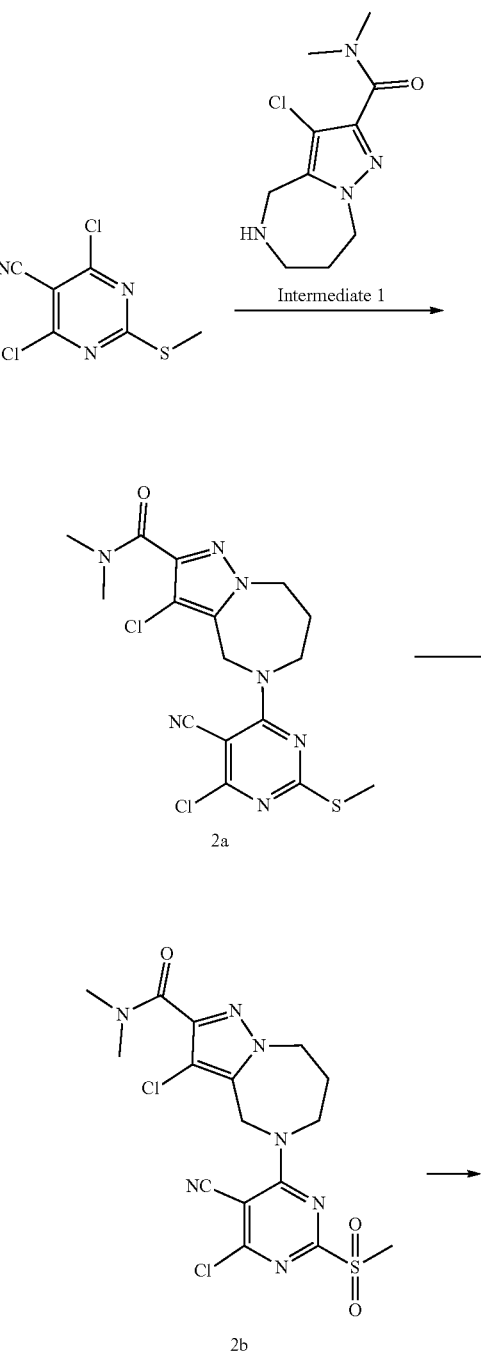

-continued

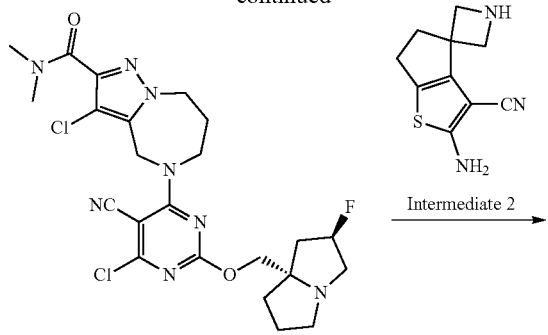

Intermediate 2

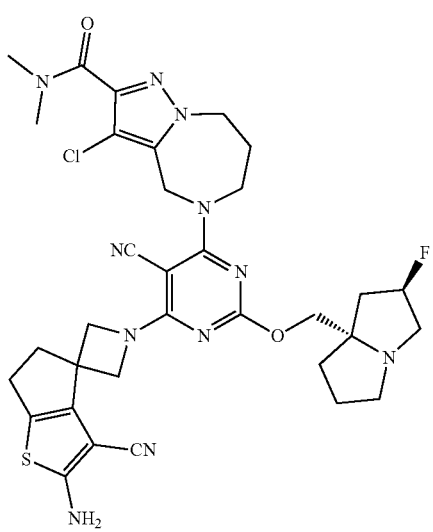

Compound 2

Step 1. Synthesis of 3-chloro-5-(6-chloro-5-cyano-2-methylsulfanyl-pyrimidin-4-yl)-N,N-dimethyl-4,6,7,8-tetrahydropyrazolo[1,5-a][1,4]diazepine-2-carboxamide (2a). The mixture of 3-chloro-N,N-dimethyl-5,6,7,8-tetrahydro-4H-pyrazolo[1,5-a][1,4]diazepine-2-carboxamide (Intermediate 1, 1.7 g, 7 mmol), 4,6-dichloro-2-methylsulfanyl-pyrimidine-5-carbonitrile (1.7 g, 7.7 mmol) and DIEA (2.71 mg, 21.0 mmol) in DCM (3 mL) was stirred at 25° C. for 0.5 h under argon. The mixture was concentrated, diluted with DCM (50 mL), washed with water (50×2 mL) and brine (50 ml), dried over Na$_2$SO$_4$, concentrated. The crude product 3-chloro-5-(6-chloro-5-cyano-2-methylsulfanyl-pyrimidin-4-yl)-N,N-dimethyl-4,6,7,8-tetrahydropyrazolo[1,5-a][1,4]diazepine-2-carboxamide (2a) was used without purification. LCMS calcld for C$_{16}$H$_{18}$Cl$_2$N$_7$OS (M+H)$^+$ m/z=426.1, found: 426.3.

Step 2. Synthesis of (2b). The mixture of 3-chloro-5-(6-chloro-5-cyano-2-methylsulfanyl-pyrimidin-4-yl)-N,N-dimethyl-4,6,7,8-tetrahydropyrazolo[1,5-a][1,4]diazepine-2-carboxamide (2a, 2.9 g, 6.8 mmol), oxone (6.272 g, 10.2 mmol), THF (20 mL) and water (10 mL) was stirred at 45° C. for 2 h under argon. The mixture was diluted with DCM (100 mL), washed with H$_2$O (2×100 mL) and brine (100 mL), dried over Na$_2$SO$_4$ and concentrated to afford crude product 3-chloro-5-(6-chloro-5-cyano-2-methylsulfonyl-pyrimidin-4-yl)-N,N-dimethyl-4,6,7,8-tetrahydropyrazolo[1,5-a][1,4]diazepine-2-carboxamide (2b, 2.35 g, 5.13 mmol, 75.4% yield). LCMS calcld for C$_{16}$H$_{18}$Cl$_2$N$_7$O$_3$S (M+H)$^+$ m/z=458.1, found: 458.1.

Step 3. Synthesis of 3-chloro-5-[6-chloro-5-cyano-2-[[(2R,8S)-2-fluoro-1,2,3,5,6,7-hexahydropyrrolizin-8-yl]methoxy]pyrimidin-4-yl]-N,N-dimethyl-4,6,7,8-tetrahydropyrazolo[1,5-a][1,4]diazepine-2-carboxamide (2c). The mixture of 3-chloro-5-(6-chloro-5-cyano-2-methylsulfonyl-pyrimidin-4-yl)-N,N-dimethyl-4,6,7,8-tetrahydropyrazolo[1,5-a][1,4]diazepine-2-carboxamide (2b, 1.9 g, 4.15 mmol) and [(2R,8S)-2-fluoro-1,2,3,5,6,7-hexahydropyrrolizin-8-yl]methanol (1.98 g, 12.44 mmol) in DCM (20 mL) was stirred at 25° C. for 1 h under argon. The mixture was concentrated to afford a crude product. The crude product was purified by silica gel chromatography (eluted with MeOH in DCM from 3% to 10%) to afford 3-chloro-5-[6-chloro-5-cyano-2-[[(2R,8S)-2-fluoro-1,2,3,5,6,7-hexahydropyrrolizin-8-yl]methoxy]pyrimidin-4-yl]-N,N-dimethyl-4,6,7,8-tetrahydropyrazolo[1,5-a][1,4]diazepine-2-carboxamide (2c, 1.2 g, 1.85 mmol, 44.7% yield) LCMS m/z calcld for C$_{23}$H$_{28}$Cl$_2$FN$_8$O$_2$(M+H)$^+$ m/z=537.2, found: 537.2.

Step 4. Synthesis of 5-[6-(2-amino-3-cyano-spiro[5,6-dihydrocyclopenta[b]thiophene-4,3'-azetidine]-1'-yl)-5-cyano-2-[[(2R,8S)-2-fluoro-1,2,3,5,6,7-hexahydropyrrolizin-8-yl]methoxy]pyrimidin-4-yl]-3-chloro-N,N-dimethyl-4,6,7,8-tetrahydropyrazolo[1,5-a][1,4]diazepine-2-carboxamide (compound 2). The mixture of 3-chloro-5-[6-chloro-5-cyano-2-[[(2R,8S)-2-fluoro-1,2,3,5,6,7-hexahydropyrrolizi8-yl]methoxy]pyrimidin-4-yl]-N,N-dimethyl-4,6,7,8-tetrahydropyrazolo[1,5-a][1,4]diazepine-2-carboxamide (2c, 200 mg, 0.37 mmol), 2-aminospiro[5,6-dihydrocyclopenta[b]thiophene-4,3'-azetidine]-3-carbonitrile (Intermediate 2, 244 mg, 0.6 mmol), DIEA (192 g, 1.49 mmol) in 1,4-dioxane (5 mL) was stirred at 90° C. for 1.5 h under argon. The mixture was diluted with EtOAc (50 mL), washed with H$_2$O (2×20 mL) and brine (50 mL), dried over Na$_2$SO$_4$ and concentrated. The crude product was purified by prep-HPLC (eluted with CH$_3$CN in H$_2$O from 5% to 95%) to afford 5-[6-(2-amino-3-cyano-spiro[5,6-dihydrocyclopenta[b]thiophene-4,3'-azetidine]-1'-yl)-5-cyano-2-[[(2R,8S)-2-fluoro-1,2,3,5,6,7-hexahydropyrrolizin-8-yl]methoxy]pyrimidin-4-yl]-3-chloro-N,N-dimethyl-4,6,7,8-tetrahydropyrazolo[1,5-a][1,4]diazepine-2-carboxamide (compound 2), 89 mg, 0.12 mmol, 32% yield) as yellow solid. LCMS calcld for C$_{33}$H$_{38}$ClFN$_{11}$O$_2$S (M+H)$^+$ m/z=706.2, found: 706.2. $^1$H NMR (400 MHz, CDCl$_3$) δ 8.05-7.94 (s, 2H), 5.17 (d, J=52.4 Hz, 1H), 4.93 (s, 1H), 4.79 (d, J=21.4 Hz, 2H), 4.61 (s, 2H), 4.54 (s, 1H), 4.35 (s, 2H), 4.17-3.87 (m, 4H), 3.13 (d, J=14.8 Hz, 2H), 3.03 (d, J=5.7 Hz, 6H), 2.87 (t, J=7.2 Hz, 1H), 2.77-2.59 (m, 4H), 2.22-1.91 (m, 5H), 1.79 (ddd, J=20.3, 19.1, 11.6 Hz, 4H).

Compound 3. 5-[6-(2-amino-3-cyano-spiro[6,7-di-hydro-5H-benzothiophene-4,3'-azetidine]-1'-yl)-5-cyano-2-[[(2R,8S)-2-fluoro-1,2,3,5,6,7-hexahydro-pyrrolizin-8-yl]methoxy]pyrimidin-4-yl]-3-chloro-N,N-dimethyl-4,6,7,8-tetrahydropyrazolo[1,5-a][1,4]diazepine-2-carboxamide

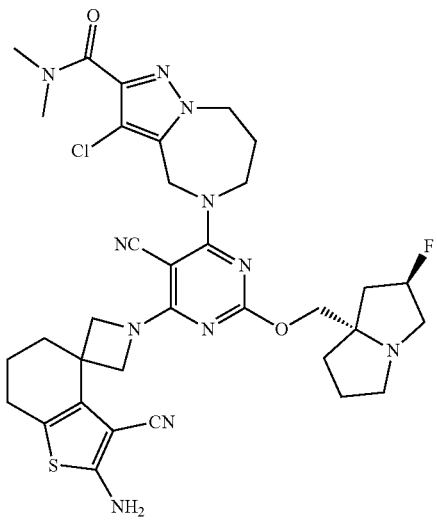 [SMILES: CN(C)C(=O)c1nn2c(c1Cl)CN(c1nc(OC[C@@]34CCCN3C[C@H](F)C4)nc(N3CC4(CCCc5sc(N)c(C#N)c54)C3)c1C#N)CCC2]

Compound 3 was prepared similarly to that of Ex. 2 as a TFA salt using Intermediate 3. LCMS calcd for $C_{34}H_{40}ClFN_{11}O_2S$ (M+H)$^+$ m/z=720.27; found: 720.2. $^1$H NMR (400 MHz, CD$_3$OD) δ 5.55 (d, J=52.0 Hz, 1H), 4.96 (s, 3H), 4.33 (m, 8H), 3.96-3.73 (m, 3H), 3.43 (m, 1H), 3.10 (m, 6H), 2.75-2.45 (m, 4H), 2.41-2.24 (m, 5H), 2.24-2.00 (m, 4H), 1.81 (s, 2H).

Example 3. Exemplary synthesis of 2-amino-1'-[5-cyano-2-[[1-(morpholinomethyl)cyclopropyl]methoxy]-6-[-(1R,5S)-3,8-diazabicyclo[3.2.1]octan-3-yl]pyrimidin-4-yl]spiro[5,6-dihydrocyclopenta[b]thiophene-4,3'-azetidine]-3-carbonitrile (Compound 4)

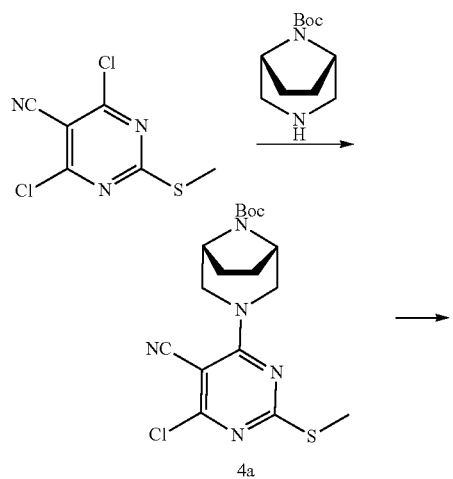

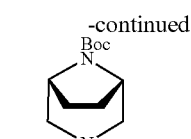

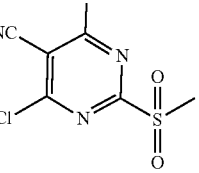

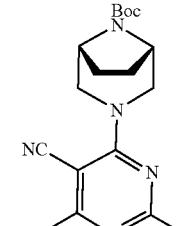

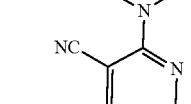

Compound 4

Step 1. Preparation of tert-butyl (1R,5S)-3-(6-chloro-5-cyano-2-methylsulfanyl-pyrimidin-4-yl)-3,8-diazabicyclo[3.2.1]octane-8-carboxylate (4a). To a solution of tert-butyl (1R,5S)-3,8-diazabicyclo[3.2.1]octane-8-carboxylate (1.93 g, 9.09 mmol) and 4,6-dichloro-2-methylsulfanyl-pyrimidine-5-carbonitrile (2.0 g, 9.09 mmol) in DCM (20 mL) was added DIEA (4.75 mL, 27.26 mmol) at 0° C. The mixture was stirred at 0° C. for 1 h. The mixture was diluted with EtOAc (50 mL), washed with $H_2O$ (2×30 mL) and brine (30 mL), dried over $Na_2SO_4$ and concentrated. The crude product was purified by silica gel chromatography (PE: EtOAc=20:1 to 5:1). The product tert-butyl (1R,5S)-3-(6-chloro-5-cyano-2-methylsulfanyl-pyrimidin-4-yl)-3,8-diazabicyclo[3.2.1]octane-8-carboxylate (4a, 3.35 g, 8.46 mmol, 93.11% yield) was obtained as white solid. LCMS calcld for $C_{17}H_{23}ClN_5O_2S$ (M+H)$^+$ m/z=396.1, found: 396.0.

Step 2. Preparation of tert-butyl (1R,5S)-3-(6-chloro-5-cyano-2-methylsulfonyl-pyrimidin-4-yl)-3,8-diazabicyclo[3.2.1]octane-8-carboxylate (4b). To a solution of tert-butyl (1R,5S)-3-(6-chloro-5-cyano-2-methylsulfanyl-pyrimidin-4-yl)-3,8-diazabicyclo[3.2.1]octane-8-carboxylate (4a, 3.35 g, 8.46 mmol) in THF (35 mL)/Water (35 mL) was added oxone (5.2 g, 16.92 mmol) at 25° C. The mixture was stirred at 25° C. for 3 h. The mixture was diluted with EtOAc (40 mL), washed with $H_2O$ (2×30 mL) and brine (30 mL), dried over $Na_2SO_4$ and concentrated. The crude product was used without purification. The product tert-butyl (1R,5S)-3-(6-chloro-5-cyano-2-methylsulfonyl-pyrimidin-4-yl)-3,8-diazabicyclo[3.2.1]octane-8-carboxylate (4b, 3.40 g, 7.95 mmol, 93.90% yield) was obtained as crude white solid. LCMS calcld for $C_{17}H_{23}ClN_5O_4S$ (M+H)$^+$ m/z=428.1, found: 428.2.

Step 3. Preparation of tert-butyl (1R,5S)-3-[5-cyano-2-methylsulfonyl-6-[[1(morpholinomethyl)cyclopropyl]methoxy]pyrimidin-4-yl]-3,8-diazabicyclo[3.2.1]octane-8-carboxylate (4c). To a solution of tert-butyl (1R,5S)-3-(6-chloro-5-cyano-2-methylsulfonyl-pyrimidin-4-yl)-3,8-diazabicyclo[3.2.1]octane-8-carboxylate (4b, 3.4 g, 7.95 mmol) in DCM (34 mL) was added [1-(morpholinomethyl)cyclopropyl]methanol (2.72 g, 15.89 mmol) at 25° C. The mixture was stirred at 25° C. for 3 h. The mixture was concentrated to afford a crude product. The crude product was purified by silica gel chromatography (PE:EtOAc=10:1 to 1:1). The product tert-butyl (1R,5S)-3-[6-chloro-5-cyano-2-[[1-(morpholinomethyl)cyclopropyl]methoxy]pyrimidin-4-yl]-3,8-diazabicyclo[3.2.1]octane-8-carboxylate (4c, 2.10 g, 4.05 mmol, 50.92% yield) was obtained as yellow oil. LCMS calcld for $C_{25}H_{36}ClN_6O_4$(M+H)$^+$ m/z=519.2, found: 519.2.

Step 4. Preparation of tert-butyl (1R,5S)-3-[6-(2-amino-3-cyano-spiro[5,6-dihydrocyclopenta[b]thiophene-4,3'-azetidine]-1'-yl)-5-cyano-2-[[1-(morpholinomethyl)cyclopropyl]methoxy]pyrimidin-4-yl]-3,8-diazabicyclo[3.2.1]octane-8-carboxylate (4d). To a solution of 2-aminospiro[5,6-dihydrocyclopenta[b]thiophene-4,3'-azetidine]-3-carbonitrile (Intermediate 2, 1.0 g, 4.88 mmol) and tert-butyl (1R,5S)-3-[6-chloro-5-cyano-2-[[1-(morpholinomethyl)cyclopropyl]methoxy]pyrimidin-4-yl]-3,8-diazabicyclo[3.2.1]octane-8-carboxylate (4c, 1.95 g, 3.76 mmol) in 1,4-Dioxane (20 mL) was added DIEA (3.27 mL, 18.78 mmol) at 25° C. The mixture was stirred at 90° C. for 2 h. The mixture was concentrated to afford a crude product. The crude product was purified by silica gel chromatography (PE: EtOAc=1:1 to 1:5). The product tert-butyl (1R,5S)-3-[6-(2-amino-3-cyano-spiro[5,6-dihydrocyclopenta[b]thiophene-4,3'-azetidine]-1'-yl)-5-cyano-2-[[1-(morpholinomethyl)cyclopropyl]methoxy]pyrimidin-4-yl]-3,8-diazabicyclo[3.2.1]octane-8-carboxylate (4d, 1.80 g, 2.62 mmol, 69.65% yield) was obtained as yellow oil. LCMS calcld for $C_{35}H_{46}N_9O_4S$ (M+H)$^+$ m/z=688.3, found: 688.2.

Step 5. Preparation of 2-amino-1'-[5-cyano-2-[[1-(morpholinomethyl)cyclopropyl]methoxy]-6-[(1R,5S)-3,8-diazabicyclo[3.2.1]octan-3-yl]pyrimidin-4-yl]spiro[5,6-dihydrocyclopenta[b]thiophene-4,3'-azetidine]-3-carbonitrile (4e). To a solution of tert-butyl (1R,5S)-3-[6-(2-amino-3-cyano-spiro[5,6-dihydrocyclopenta[b]thiophene-4,3'-azetidine]-1'-yl)-5-cyano-2-[[1-(morpholinomethyl)cyclopropyl]methoxy]pyrimidin-4-yl]-3,8-diazabicyclo[3.2.1]octane-8-carboxylate (4d, 1.8 g, 2.62 mmol) and TFA (6.0 mL, 78.35 mmol) in THF (18 mL) at 25° C. The mixture was stirred at 25° C. for 1 h. The mixture was concentrated to afford a crude product. The crude product was purified by Prep-HPLC (eluted with $CH_3CN$ in $H_2O$ (0.1% $NH_3$) from 5.0% to 95%). 2-amino-1'-[5-cyano-2-[[1-(morpholinomethyl)cyclopropyl]methoxy]-6-[(1R,5S)-3,8-diazabicyclo[3.2.1]octan-3-yl]pyrimidin-4-yl]spiro[5,6-dihydrocyclopenta[b]thiophene-4,3'-azetidine]-3-carbonitrile (Compound 4, 544.5 mg, 0.92 mmol, 35.16% yield) was obtained as white solid. LCMS calcld for $C_{30}H_{38}N_9O_2S$ (M+H)$^+$ m/z=588.3, found: 588.3. $^1$H NMR (400 MHz, $CD_3OD$) δ 4.68-4.13 (m, 8H), 3.68 (t, J=4.6 Hz, 4H), 3.56 (s, 2H), 3.32-3.20 (m, 2H), 2.86-2.65 (m, 4H), 2.49 (s, 4H), 2.39 (s, 2H), 1.82 (s, 4H), 0.66 (t, J=5.2 Hz, 2H), 0.46 (t, J=5.2 Hz, 2H)

Compound 5. 5-[6-(2-amino-3-cyano-spiro[5,6-dihydrocyclopenta[b]thiophene-4,3'-azetidine]-1'-yl)-5-cyano-2-[[1-(morpholinomethyl)cyclopropyl]methoxy]pyrimidin-4-yl]-3-chloro-N,N-dimethyl-4,6,7,8-tetrahydropyrazolo[1,5-a][1,4]diazepine-2-carboxamide

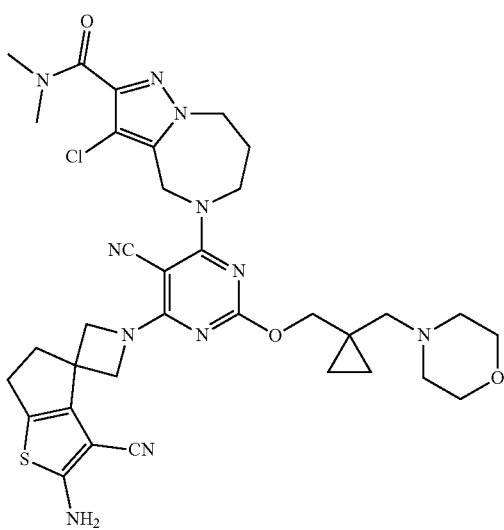 [SMILES: CN(C)C(=O)c1nn2c(c1Cl)CN(c1nc(OCC3(CN4CCOCC4)CC3)nc(N3CC4(CCc5sc(N)c(C#N)c54)C3)c1C#N)CCC2]

Compound 5 was prepared similarly to that of Ex. 2. LCMS calcld for $C_{34}H_{41}ClN_{11}O_3S$ (M+H)$^+$ m/z=718.3 found 718.2. $^1$H NMR (400 MHz, $CD_3OD$) δ 5.08-5.01 (m, 2H), 4.62-4.40 (m, 5H), 4.29-4.14 (m, 5H), 4.81-471 (m, 4H), 3.15-3.03 (m, 6H), 2.88-2.64 (m, 10H), 2.31-2.21 (m, 2H), 0.76-0.53 (m, 4H).

Example 4. Exemplary synthesis of 2-amino-1'-[5-fluoro-2-[[(2R,8S)-2-fluoro-1,2,3,5,6,7-hexahydro-pyrrolizin-8-yl]methoxy]-6-[(3R)-3-hydroxy-3-methyl-1-piperidyl]pyrimidin-4-yl]spiro[5,6-dihydrocyclopenta[b]thiophene-4,3'-azetidine]-3-carbonitrile (Compound 6)

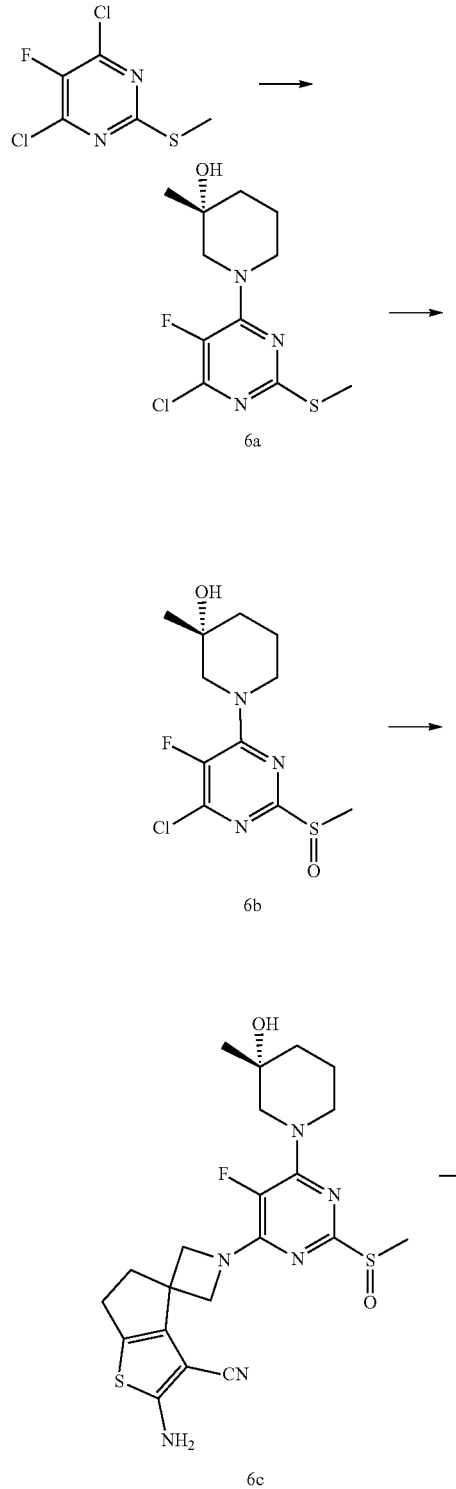

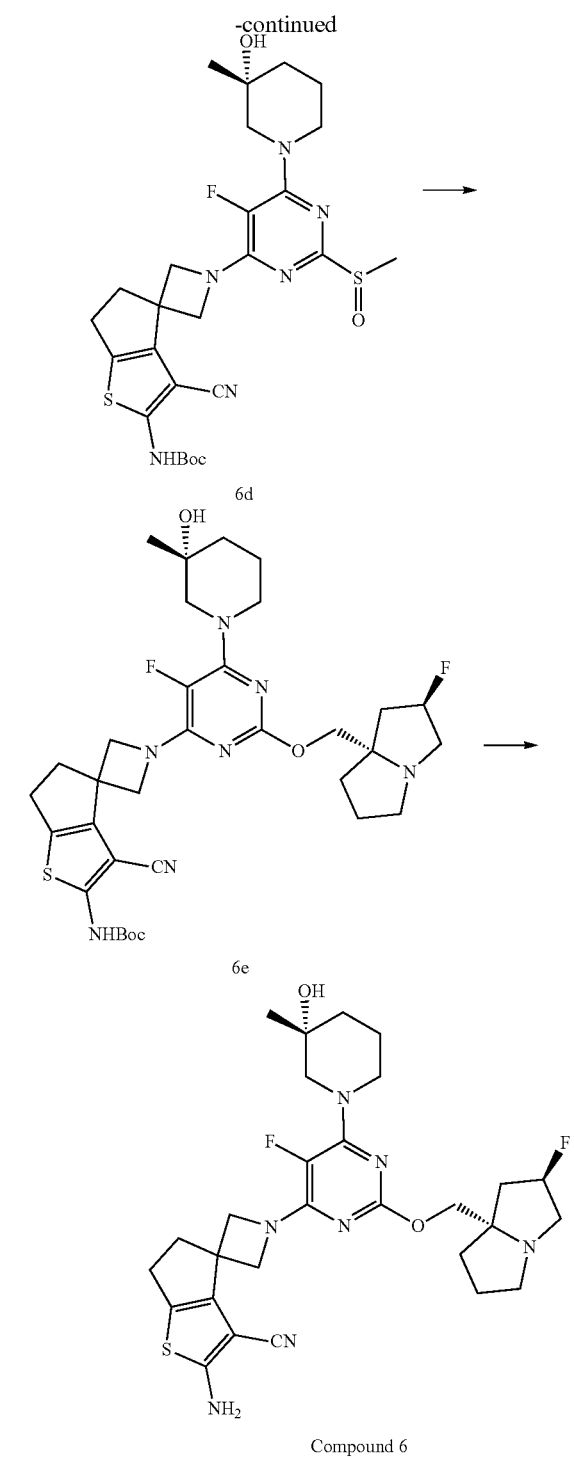

Step 1. Synthesis of (3R)-1-(6-chloro-5-fluoro-2-methylsulfanyl-pyrimidin-4-yl)-3-methyl-piperidin-3-ol (6a). A solution of 4,6-dichloro-5-fluoro-2-methylsulfanyl-pyrimidine (200 mg, 0.94 mmol) in DCM (8 mL) was added (3R)-3-methylpiperidin-3-ol (108.11 mg, 0.94 mmol) and DIEA (0.33 mL, 1.88 mmol) at 0° C. Then the mixture was stirred at 0° C. for 1 h. The solution was extracted with EtOAc (20 mL×3), dried over $Na_2SO_4$ and concentrated. The residue was purified by silica gel chromatography (DCM:MeOH=30:1). The product of (3R)-1-(6-chloro-5-fluoro-2-methylsulfanyl-pyrimidin-4-yl)-3-methyl-piperidin-3-ol (210 mg, 0.720 mmol, 76.67% yield) was obtained. LCMS calculated for $C_{11}H_{16}ClFN_3OS$ (M+H)$^+$ m/z=292.3, found: 292.3.

Step 2. Synthesis of (3R)-1-(6-chloro-5-fluoro-2-methylsulfinyl-pyrimidin-4-yl)-3-methyl-piperidin-3-ol (6b). A solution of (3R)-1-(6-chloro-5-fluoro-2-methylsulfanyl-pyrimidin-4-yl)-3-methyl-piperidin-3-ol (6a, 170 mg, 0.58 mmol) in THF (5 mL) and Water (2.5 mL) was added oxone (302.4 mg, 0.87 mmol) at 25° C. Then the mixture was stirred at 25° C. for 1 h. The solution was extracted with EtOAc (20 ml×3), dried over Na$_2$SO$_4$ and concentrated. The residue was purified by silica gel chromatography (eluting with MeOH in DCM from 3% to 6%). The product (3R)-1-(6-chloro-5-fluoro-2-methylsulfinyl-pyrimidin-4-yl)-3-methyl-piperidin-3-ol (180 mg, 0.585 mmol, quantitative yield) was obtained as a white solid. LCMS calculated for $C_{11}H_{16}ClFN_3O_2S$ (M+H)$^+$ m/z=308.0, found: 308.0.

Step 3. Synthesis of 2-amino-1'-[5-fluoro-2-methylsulfinyl-6-[(3R)-3-hydroxy-3-methyl-1-piperidyl]pyrimidin-4-yl]spiro[5,6-dihydrocyclopenta[b]thiophene-4,3'-azetidine]-3-carbonitrile (6c). The mixture of DIEA (0.12 mL, 0.71 mmol) 2-aminospiro[5,6-dihydrocyclopenta[b]thiophene-4,3'-azetidine]-3-carbonitrile (Intermediate 2, 146.74 mg, 0.71 mmol) and (3R)-1-(6-chloro-5-fluoro-2-methylsulfinyl-pyrimidin-4-yl)-3-methyl-piperidin-3-ol (6b, 110 mg, 0.36 mmol) in 1,4-Dioxane (1 mL) was stirred at 90° C. for 2 h under argon. The mixture was filtered to afford a crude solution. The crude product was purified by flash chromatography (eluted with CH$_3$CN in H$_2$O from 5.0% to 95%). The product 2-amino-1'-[5-fluoro-2-methylsulfinyl-6-[(3R)-3-hydroxy-3-methyl-1-piperidyl]pyrimidin-4-yl]spiro[5,6-dihydrocyclopenta[b]thiophene-4,3'-azetidine]-3-carbonitrile (80 mg, 0.168 mmol, 46.97% yield) was obtained as a white solid. LCMS calcld for $C_{21}H_{26}FN_6O_2S_2$ (M+H)$^+$ m/z=477.2, found: 477.2.

Step 4. Synthesis of tert-butyl N-tert-butoxycarbonyl-N-[3-cyano-1'-[5-fluoro-2-methylsulfinyl-6-[(3S)-3-hydroxy-3-methyl-1-piperidyl]pyrimidin-4-yl]spiro[5,6-dihydrocyclopenta[b]thiophene-4,3'-azetidine]-2-yl]carbamate (6d). The mixture of 2-amino-1'-[5-fluoro-2-methylsulfinyl-6-[(3S)-3-hydroxy-3-methyl-1-piperidyl]pyrimidin-4-yl]spiro[5,6-dihydrocyclopenta[b]thiophene-4,3'-azetidine]-3-carbonitrile (6c, 70 mg, 0.15 mmol) Boc$_2$ (70.52 mg, 0.32 mmol), DMAP (1.79 mg, 0.01 mmol) in CH$_3$CN (0.5 mL) was stirred at 25° C. for 0.2 h under argon. The mixture was concentrated to afford a crude product. The crude product was purified by flash chromatography H$_2$O:CH$_3$CN=90:10 to 50:50. tert-butyl N-[3-cyano-1'-[5-fluoro-2-methylsulfinyl-6-[(3S)-3-hydroxy-3-methyl-1-piperidyl]pyrimidin-4-yl]spiro[5,6-dihydrocyclopenta[b]thiophene-4,3'-azetidine]-2-yl]carbamate (80 mg, 0.139 mmol, 94.45% yield)) was obtained as yellow oil. LCMS calcld for $C_{26}H_{34}N_6O_4S_2$(M+H)$^+$ m/z=577.2, found: 577.2.

Step 5. Synthesis of tert-butyl N-[3-cyano-1'-[5-fluoro-2-[[(2R,8S)-2-fluoro-1,2,3,5,6,7-hexahydropyrrolizin-8-yl]methoxy]-6-[(3R)-3-hydroxy-3-methyl-1-piperidyl]pyrimidin-4-yl]spiro[5,6-dihydrocyclopenta[b]thiophene-4,3'-azetidine]-2-yl]carbamate (6e). The mixture of [(2R,8S)-2-fluoro-1,2,3,5,6,7-hexahydropyrrolizin-8-yl]methanol (44.17 mg, 0.28 mmol) and NaH (8.32 mg, 0.21 mmol) in DMF (0.5 mL) was stirred at 25° C. for 0.2 h under argon. Then, tert-butyl N-[3-cyano-1'-[5-fluoro-6-[(3R)-3-hydroxy-3-methyl-1-piperidyl]-2-methylsulfinyl-pyrimidin-4-yl]spiro[5,6-dihydrocyclopenta[b]thiophene-4,3'-azetidine]-2-yl]carbamate (6d, 40 mg, 0.07 mmol) was added at 25° C. The mixture was stirred at 25° C. for 0.2 h. The mixture was acidified with Acetic acid (1 mol/L in H$_2$O) to pH=5, extracted with EtOAc (3×10 mL), dried over Na$_2$SO$_4$ and concentrated. The crude product was used directly for the next step. tert-butyl N-[3-cyano-1'-[5-fluoro-2-[[(2R,8S)-2-fluoro-1,2,3,5,6,7-hexahydropyrrolizin-8-yl]methoxy]-6-[(3R)-3-hydroxy-3-methyl-1-piperidyl]pyrimidin-4-yl]spiro[5,6-dihydrocyclopenta[b]thiophene-4,3'-azetidine]-2-yl]carbamate (6e, 40 mg, 0.060 mmol) was obtained as yellow oil. LCMS calcld for $C_{33}H_{44}F_2N_7O_4$(M+H)$^+$ m/z=672.2, found: 672.4.

Step 6. Synthesis of 2-amino-1'-[5-fluoro-2-[[(2R,8S)-2-fluoro-1,2,3,5,6,7-hexahydropyrrolizin-8-yl]methoxy]-6-[(3R)-3-hydroxy-3-methyl-1-piperidyl]pyrimidin-4-yl]spiro[5,6-dihydrocyclopenta[b]thiophene-4,3'-azetidine]-3-carbonitrile (Compound 6). The mixture of tert-butyl N-[3-cyano-1'-[5-fluoro-2-[[(2R,8S)-2-fluoro-1,2,3,5,6,7-hexahydropyrrolizin-8-yl]methoxy]-6-[(3R)-3-hydroxy-3-methyl-1-piperidyl]pyrimidin-4-yl]spiro[5,6-dihydrocyclopenta[b]thiophene-4,3'-azetidine]-2-yl]carbamate (6e, 30 mg, 0.04 mmol) and TFA (0.1 mL, 1.31 mmol) in DCM (1 mL) was stirred at 25° C. for 0.2 h under argon. The mixture was stirred at 25° C. for 0.2 h. The mixture was concentrated to afford a crude product.

The crude product was purified by prep-HPLC (eluted with CH$_3$CN in H$_2$O (0.1% TFA) from 5.0% to 95%). 2-amino-1'-[5-fluoro-2-[[(2R,8S)-2-fluoro-1,2,3,5,6,7-hexahydropyrrolizin-8-yl]methoxy]-6-[(3R)-3-hydroxy-3-methyl-1-piperidyl]pyrimidin-4-yl]spiro[5,6-dihydrocyclopenta[b]thiophene-4,3'-azetidine]-3-carbonitrile (Compound 6, 8.16 mg, 0.0089 mmol, 19.83% yield). LCMS calcld for $C_{28}H_{36}F_2N_7OS$ (M+H)$^+$ m/z=572.3, found: 572.2. $^1$H NMR (400 MHz, CD$_3$OD) δ 5.64-5.44 (m, 1H), 4.51-4.41 (m, 2H), 4.41-4.36 (m, 1H), 4.28-4.16 (m, 2H), 4.06-3.71 (m, 4H), 3.69-3.60 (m, 1H), 3.52-3.35 (m, 4H), 3.35-3.33 (m, 2H), 2.82-2.66 (m, 4H), 2.63-2.44 (m, 1H), 2.40-2.03 (m, 4H), 1.92-1.78 (m, 1H), 1.73-1.62 (m, 2H), 1.62-1.46 (m, 1H), 1.20 (s, 3H).

Compound 7. 2-amino-1'-[6-[(5R)-2,4-dioxo-1,3,9-triazaspiro[4.5]decan-9-yl]-5-fluoro-2-[[(2R,8S)-2-fluoro-1,2,3,5,6,7-hexahydropyrrolizin-8-yl]methoxy]pyrimidin-4-yl]spiro[5,6-dihydrocyclopenta[b]thiophene-4,3'-azetidine]-3-carbonitrile

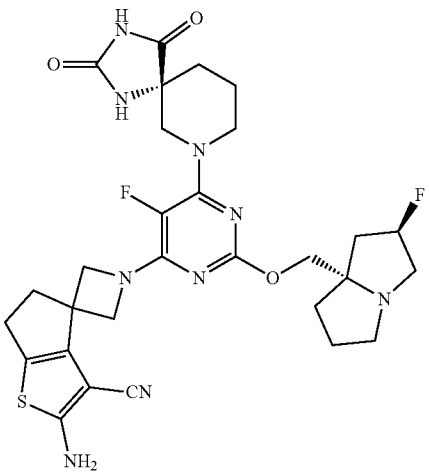 [SMILES: N#Cc1c(N)sc2c1C1(CC2)CN(c2nc(OC[C@@]34CCCN3C[C@H](F)C4)nc(N3CCC[C@]4(C3)NC(=O)NC4=O)c2F)C1]

Compound 7 was prepared similarly to that of Ex. 4 as a TFA salt. LCMS calcld for $C_{29}H_{34}F_2N_9O_3S$ (M+H)$^+$ m/z=626.2, found: 626.3. $^1$H NMR (400 MHz, CD$_3$OD) δ 5.56-5.38 (m, 1H), 4.48-4.15 (m, 6H), 3.87-3.62 (m, 2H), 3.40-3.33 (m, 2H), 3.26-3.17 (m, 1H), 2.82-2.67 (m, 3H), 2.60-2.36 (m, 2H), 2.33-1.98 (m, 9H), 1.90-1.75 (m, 3H), 1.70-1.56 (m, 1H).

Compound 8. 5-[6-(2-amino-3-cyano-spiro[5,6-di-hydrocyclopenta[b]thiophene-4,3'-azetidine]-1'-yl)-5-cyano-2-[[(2R,8S)-2-fluoro-1,2,3,5,6,7-hexahydro-pyrrolizin-8-yl]methoxy]pyrimidin-4-yl]-N,N-dimethyl-4,6,7,8-tetrahydropyrazolo[1,5-a][1,4]diazepine-2-carboxamide

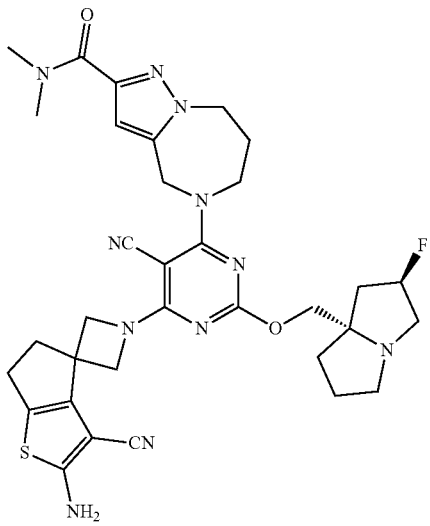 [SMILES: CN(C)C(=O)c1cc2n(n1)CCCN(c1nc(OC[C@@]34CCCN3C[C@H](F)C4)nc(N3CC4(CCc5sc(N)c(C#N)c54)C3)c1C#N)C2]

Compound 8 was prepared similarly to that of Ex. 2 as a formate salt. LCMS calcld for $C_{33}H_{39}FN_{11}O_2S$ (M+H)+ m/z=672.3, found: 672.5. $^1$H NMR (400 MHz, CD$_3$OD) δ 6.67 (s, 1H), 5.29 (d, J=53.1 Hz, 1H), 5.07 (s, 2H), 4.52-4.46 (m, 5H), 4.22-4.07 (m, 5H), 3.26-3.23 (m, 6H), 3.17-2.97 (m, 4H), 2.77-2.70 (m, 4H), 2.28-1.86 (m, 8H).

Compound 9. 5-[6-(2-amino-3-cyano-spiro[5,6-di-hydrocyclopenta[b]thiophene-4,3'-azetidine]-1'-yl)-5-fluoro-2-[[(2R,8S)-2-fluoro-1,2,3,5,6,7-hexahydro-pyrrolizin-8-yl]methoxy]pyrimidin-4-yl]-3-chloro-N,N-dimethyl-4,6,7,8-tetrahydropyrazolo[1,5-a][1,4]diazepine-2-carboxamide

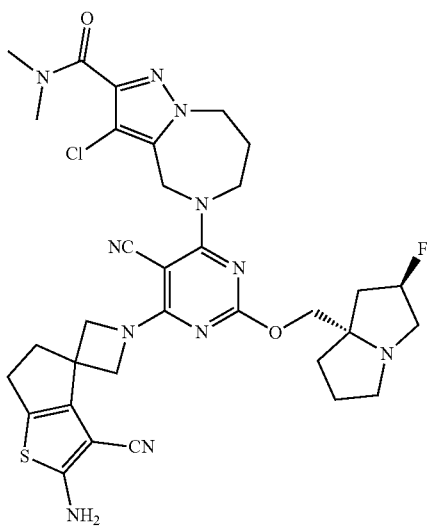 [SMILES: CN(C)C(=O)c1nn2c(c1Cl)CN(c1nc(OC[C@@]34CCCN3C[C@H](F)C4)nc(N3CC4(CCc5sc(N)c(C#N)c54)C3)c1C#N)CCC2]

Compound 9 was prepared similarly to that of Ex. 4 as a TFA salt. LCMS calcld for $C_{32}H_{38}ClF_2N_{10}O_2S$ (M+H)+ m/z=699.2, found: 699.3. $^1$H NMR (400 MHz, CD$_3$OD) δ 5.54 (d, J=52.0 Hz, 1H), 4.92-4.88 (m, 1H), 4.83-4.75 (m, 1H), 4.55-4.40 (m, 4H), 4.38 (s, J=6.1 Hz, 2H), 4.30-4.18 (m, 2H), 4.14-3.73 (m, 5H), 3.41 (dd, J=16.2, 11.2 Hz, 1H), 3.09 (d, J=6.8 Hz, 6H), 2.83-2.69 (m, 4H), 2.69-2.42 (m, 2H), 2.31 (td, J=9.9, 4.1 Hz, 3H), 2.19-1.99 (m, 3H).

Compound 10. 5-[6-(2-amino-3-cyano-spiro[5,6,7,8-tetrahydrocyclohepta[b]thiophene-4,3'-azetidine]-1'-yl)-5-cyano-2-[[(2R,8S)-2-fluoro-1,2,3,5,6,7-hexa-hydropyrrolizin-8-yl]methoxy]pyrimidin-4-yl]-3-chloro-N,N-dimethyl-4,6,7,8-tetrahydropyrazolo[1,5-a][1,4]diazepine-2-carboxamide

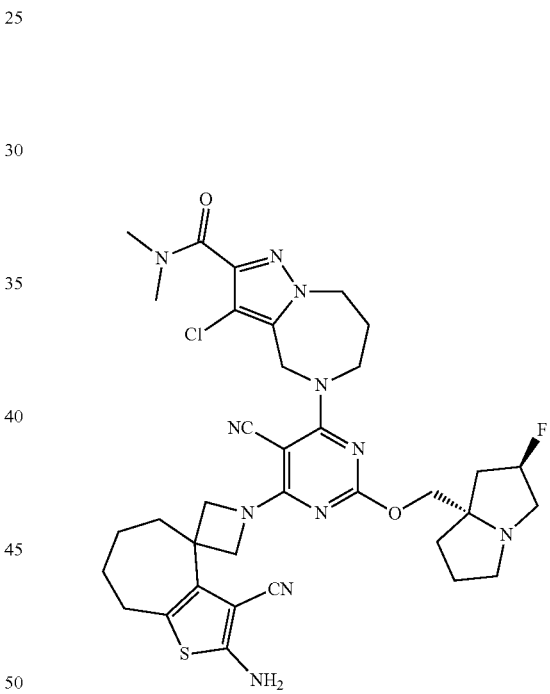

Compound 10 was prepared similarly to that of Ex. 2. LCMS calcld for $C_{35}H_{42}ClFN_{11}O_2S$ (M+H)+ m/z=734.28; found: 734.3. $^1$H NMR (CDCl$_3$, 500 MHz) δ 7.22-7.29 (m, 5H), 7.18 (d, J=7.2 Hz, 1H), 5.39-5.52 (m, 1H), 5.23-5.39 (m, 1H), 4.67-5.09 (m, 4H), 4.42 (br. s., 6H), 3.98-4.22 (m, 3H), 3.50-3.83 (m, 2H), 3.20-3.48 (m, 1H), 2.94-3.18 (m, 6H), 2.49-2.66 (m, 3H), 1.30-2.40 (m, 31H), 0.65-0.92 (m, 3H).

Compound 11. 2-amino-1'-[5-cyano-6-[(5R)-2,4-dioxo-1,3,9-triazaspiro[4.5]decan-9-yl]-2-[[(2R,8S)-2-fluoro-1,2,3,5,6,7-hexahydropyrrolizin-8-yl]methoxy]pyrimidin-4-yl]spiro[5,6-dihydrocyclopenta[b]thiophene-4,3'-azetidine]-3-carbonitrile

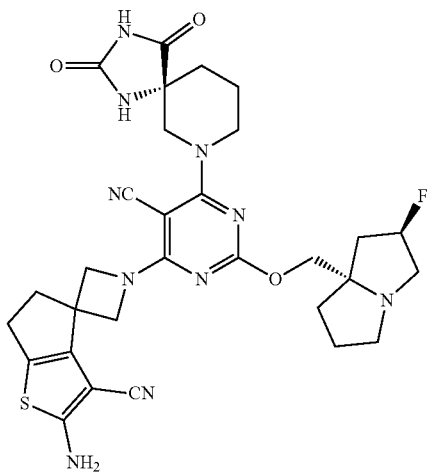 [SMILES: N#Cc1c(N2CC3(CCc4sc(N)c(C#N)c43)C2)nc(OC[C@@]23CCCN2C[C@H](F)C3)nc1N1CCC[C@]2(C1)NC(=O)NC2=O]

Compound 11 was prepared similarly to that of Ex. 2 as a TFA salt. LCMS calcld for $C_{30}H_{34}FN_{10}O_3S$ (M+H)⁺ m/z=633.2, found: 633.2. ¹H NMR (400 MHz, CD₃OD) δ 5.71-5.42 (m, 1H), 4.84-4.76 (m, 1H), 4.64-4.27 (m, 7H), 4.05-3.71 (m, 3H), 3.60-3.36 (m, 3H), 2.85-2.44 (m, 6H), 2.39-2.06 (m, 5H), 2.02-1.71 (m, 3H).

Compound 12. 2-amino-1'-[5-cyano-6-(2,4-dioxo-1,3,9-triazaspiro[4.5]decan-9-yl)-2-[[(2R,8S)-2-fluoro-1,2,3,5,6,7-hexahydropyrrolizin-8-yl]methoxy]pyrimidin-4-yl]spiro[5,6-dihydrocyclopenta[b]thiophene-4,3'-azetidine]-3-carbonitrile

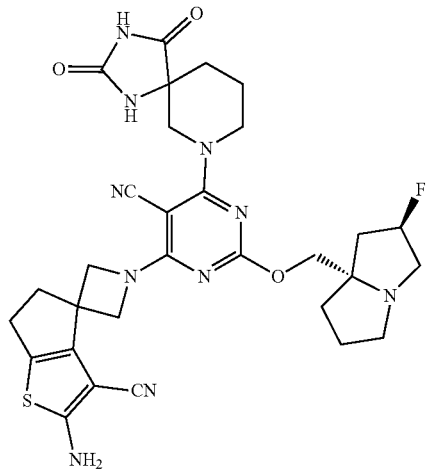 [SMILES: N#Cc1c(N2CCCC3(C2)NC(=O)NC3=O)nc(OC[C@@]23CCCN2C[C@H](F)C3)nc1N1CC2(CCc3sc(N)c(C#N)c32)C1]

Compound 12 was prepared similarly to that of Ex. 2 as a TFA salt. LCMS calcld for $C_{30}H_{34}FN_{10}O_3S$ (M+H)⁺ m/z=633.2, found: 633.4. ¹H NMR (400 MHz, CD₃OD) δ 5.65-5.39 (m, 1H), 4.65-4.25 (m, 8H), 4.03-3.75 (m, 3H), 3.60-3.37 (m, 3H), 2.89-2.47 (m, 6H), 2.39-2.22 (m, 3H), 2.21-2.08 (m, 2H), 2.02-1.73 (m, 3H).

Compound 13. 1'-[6-(2-acetyl-3-chloro-4,6,7,8-tetrahydropyrazolo[1,5-a][1,4]diazepin-5-yl)-5-cyano-2-[[(2R,8S)-2-fluoro-1,2,3,5,6,7-hexahydropyrrolizin-8-yl]methoxy]pyrimidin-4-yl]-2-amino-spiro[5,6-dihydrocyclopenta[b]thiophene-4,3'-azetidine]-3-carbonitrile

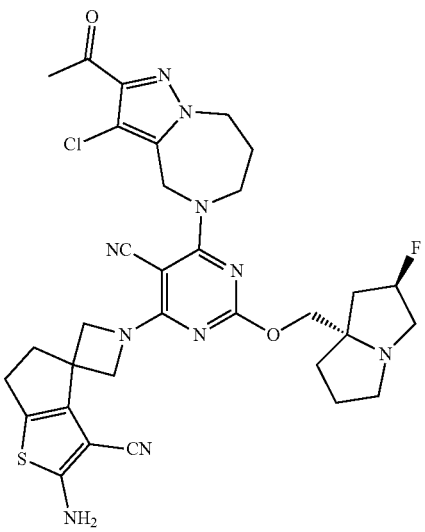 [SMILES: CC(=O)c1nn2c(c1Cl)CN(c1nc(OC[C@@]34CCCN3C[C@H](F)C4)nc(N3CC4(CCc5sc(N)c(C#N)c54)C3)c1C#N)CCC2]

Compound 13 was prepared similarly to that of Ex. 2 using Intermediate 5. LCMS calcld for $C_{32}H_{35}ClFN_{10}O_2S$ (M+H)⁺ m/z=677.2, found: 677.2. ¹H NMR (DMSO-d6, 400 MHz) δ 7.22 (s, 2H), 5.29 (d, J=52.8 Hz, 1H), 5.03 (s, 2H), 4.51 (s, 2H), 4.46-4.25 (m, 4H), 4.11 (s, 2H), 3.98 (d, J=10.4 Hz, 1H), 3.90 (d, J=10.4 Hz, 1H), 3.02 (br, 2H), 2.96-2.94 (m, 1H), 2.82-2.76 (m, 1H), 2.67-2.65 (m, 4H), 2.44 (s, 3H), 2.15 (br, 2H), 2.03 (s, 1H), 1.96 (s, 1H), 1.89-1.85 (m, 1H), 1.83-1.79 (m, 1H), 1.78-1.67 (m, 2H).

Compound 14. 5-[6-(2-amino-3-cyano-6-methyl-spiro[5,6-dihydrocyclopenta[b]thiophene-4,3'-azetidine]-1'-yl)-5-cyano-2-[[(2R,8S)-2-fluoro-1,2,3,5,6,7-hexahydropyrrolizin-8-yl]methoxy]pyrimidin-4-yl]-3-chloro-N,N-dimethyl-4,6,7,8-tetrahydropyrazolo[1,5-a][1,4]diazepine-2-carboxamide

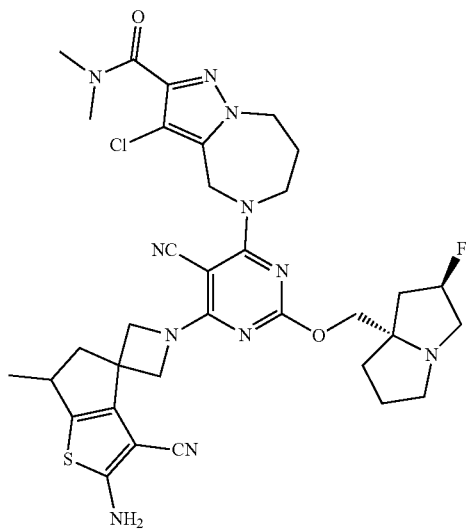 [SMILES: CC1CC2(CN(c3nc(OC[C@@]45CCCN4C[C@H](F)C5)nc(N4CCCn5nc(C(=O)N(C)C)c(Cl)c5C4)c3C#N)C2)c2c1sc(N)c2C#N]

Compound 13 was prepared similarly to that of Ex. 2 as a formate salt, using Intermediate 6. LCMS calcld for $C_{34}H_{40}ClFN_{11}O_2S$ (M+H)+ m/z=720.3, found: 720.2. $^1$H NMR (400 MHz, CD$_3$OD) δ 8.66-8.46 (s, 1H), 5.38-5.19 (m, 1H), 5.10-5.01 (m, 2H), 4.62-4.41 (m, 4H), 4.25-4.07 (m, 4H), 3.27-3.11 (m, 4H), 3.09 (d, J=4.1 Hz, 6H), 3.06-2.97 (m, 2H), 2.97-2.88 (m, 1H), 2.41-1.69 (m, 10H), 1.17 (d, J=6.8 Hz, 3H).

Compound 15. 2-amino-1'-[6-(3,8-diazabicyclo[3.2.1]octan-3-yl)-5-fluoro-2-[[(2R,8S)-2-fluoro-1,2,3,5,6,7-hexahydropyrrolizin-8-yl]methoxy]pyrimidin-4-yl]spiro[5,6-dihydrocyclopenta[b]thiophene-4,3'-azetidine]-3-carbonitrile

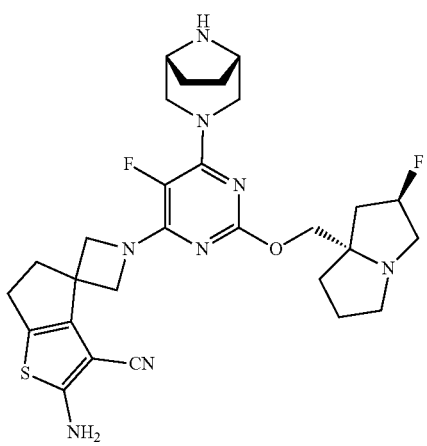

Compound 15 was prepared similarly to that of Ex. 4 as a TFA salt. LCMS calcld for $C_{28}H_{35}F_2N_8OS$ (M+H)+ m/z=569.3, found: 569.3. $^1$H NMR (400 MHz, CD$_3$OD) δ 5.51-5.29 (m, 1H), 4.51-4.41 (m, 2H), 4.30-4.12 (m, 6H), 4.08-3.99 (m, 2H), 3.66-3.46 (m, 3H), 3.38-3.32 (m, 2H), 3.27-3.15 (m, 1H), 2.83-2.63 (m, 4H), 2.53-1.91 (m, 10H).

Compound 16. 2-amino-1'-[5-cyano-6-[2-(3-methyl-1,2,4-oxadiazol-5-yl)-4,6,7,8-tetrahydropyrazolo[1,5-a][1,4]diazepin-5-yl]-2-[[(2R,8S)-2-fluoro-1,2,3,5,6,7-hexahydropyrrolizin-8-yl]methoxy]pyrimidin-4-yl]spiro[5,6-dihydrocyclopenta[b]thiophene-4,3'-azetidine]-3-carbonitrile

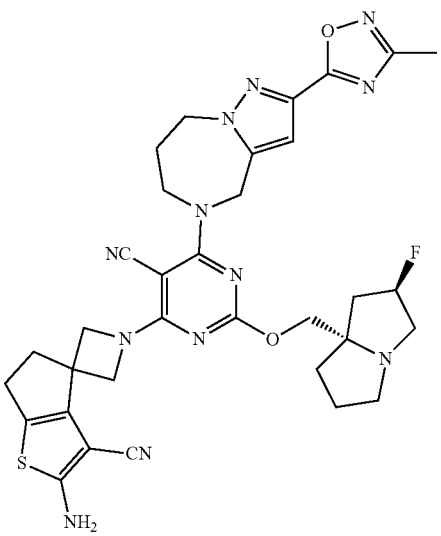 [SMILES: Cc1noc(-c2cc3n(n2)CCCN(c2nc(OC[C@@]45CCCN4C[C@H](F)C5)nc(N4CC5(CCc6sc(N)c(C#N)c65)C4)c2C#N)C3)n1]

Compound 16 was prepared similarly to that of Ex. 2 as a formate salt using Intermediate 7. LCMS calcld for $C_{33}H_{36}FN_{12}O_2S$ (M+H)+ m/z=683.3, found: 683.3. $^1$H NMR (400 MHz, CD$_3$OD) δ 7.03 (s, 1H), 5.39-5.07 (m, 3H), 4.65-4.02 (m, 10H), 3.29-3.09 (m, 3H), 3.08-2.97 (m, 1H), 2.78-2.68 (m, 4H), 2.40 (s, 3H), 2.28-1.80 (m, 8H).

Compound 17. 2-amino-1'-[6-[3-chloro-2-(3-methyl-1,2,4-oxadiazol-5-yl)-4,6,7,8-tetrahydropyrazolo[1,5-a][1,4]diazepin-5-yl]-5-cyano-2-[[(2R,8S)-2-fluoro-1,2,3,5,6,7-hexahydropyrrolizin-8-yl]methoxy]pyrimidin-4-yl]spiro[5,6-dihydrocyclopenta[b]thiophene-4,3'-azetidine]-3-carbonitrile

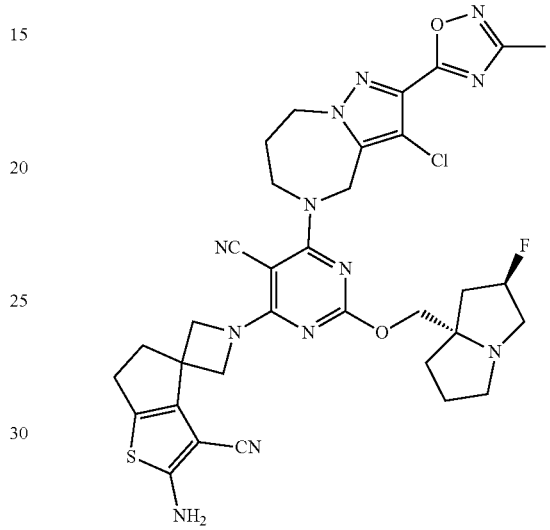

Compound 17 was prepared similarly to Compound 16 as a formate salt. LCMS calcld for $C_{33}H_{35}ClFN_{12}O_2S$ (M+H)+ m/z=717.2, found: 717.1. $^1$H NMR (400 MHz, CD$_3$OD) δ 5.46-5.26 (m, 1H), 5.16-4.97 (m, 2H), 4.59-4.14 (m, 10H), 3.55-3.36 (m, 3H), 3.20-3.08 (m, 1H), 2.82-2.66 (m, 4H), 2.44 (s, 3H), 2.40-2.00 (m, 7H), 1.95-1.85 (m, 1H).

Compound 18. 5-[6-(2-amino-3-cyano-spiro[5,6-dihydrocyclopenta[b]thiophene-4,3'-azetidine]-1'-yl)-5-cyano-2-(1,2,3,5,6,7-hexahydropyrrolizin-8-ylmethoxy)pyrimidin-4-yl]-3-chloro-N,N-dimethyl-4,6,7,8-tetrahydropyrazolo[1,5-a][1,4]diazepine-2-carboxamide

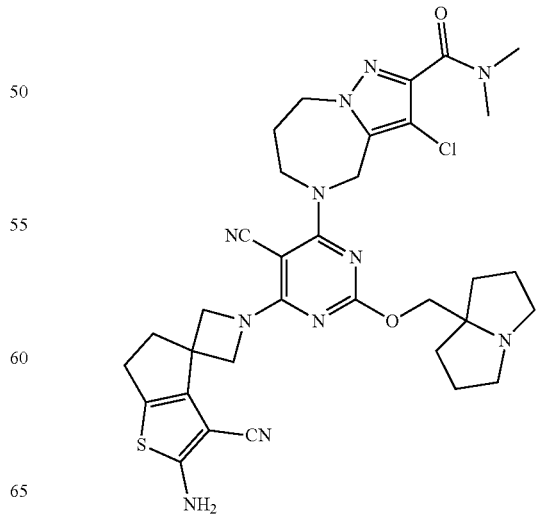

Compound 18 was prepared similarly to that of Ex. 2 as a formate salt. LCMS calcld for $C_{33}H_{39}ClN_{11}O_2S$ (M+H)$^+$ m/z=688.3; found: 688.2. $^1$H NMR (400 MHz, CD$_3$OD) δ 5.01 (s, 2H), 4.62-4.47 (m, 2H), 4.47-4.40 (m, 2H), 4.35 (s, 2H), 4.21 (dd, J=3.5, 2.9 Hz, 2H), 3.53-3.44 (m, 2H), 3.37-3.33 (m, 2H), 3.15-3.10 (m, 2H), 3.09 (dd, J=5.5, 2.1 Hz, 6H), 2.82-2.65 (m, 4H), 2.37-1.85 (in, 10H).

Compound 19. 2-amino-1'-[6-(azepan-1-yl)-5-cyano-2-[[(2R)-2-fluoro-1,2,3,5,6,7-hexahydropyrrolizin-8-yl]methoxy]pyrimidin-4-yl]spiro[5,6-dihydrocyclopenta[b]thiophene-4,3'-azetidine]-3-carbonitrile

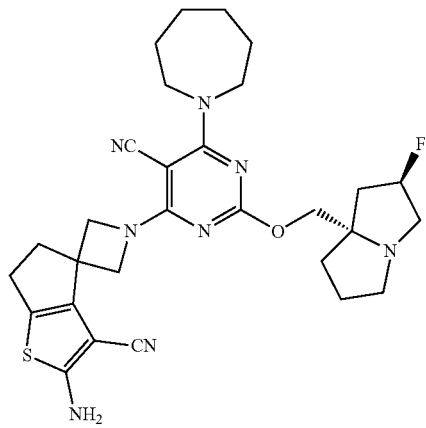 [SMILES: N#Cc1c(N2CCCCCC2)nc(OC[C@@]23CCCN2C[C@H](F)C3)nc1N1CC2(CCc3sc(N)c(C#N)c32)C1]

Compound 19 was prepared similarly to that of Ex. 2 as a formate salt. LCMS calcld for $C_{29}H_{36}FN_8OS$ (M+H)$^+$ m/z=563.3; found: 563.4. $^1$H NMR (400 MHz, CD$_3$OD) δ 5.27 (d, J=33.7, 23.2 Hz, 1H), 4.69-4.45 (m, 2H), 4.51-4.26 (m, 2H), 4.14 (dd, J=46.1, 10.8 Hz, 2H), 3.92-3.75 (m, 4H), 3.30-3.19 (m, 3H), 3.10-2.97 (m, 1H), 2.84-2.62 (m, 4H), 2.41-1.92 (m, 5H), 1.86 (d, J=5.3 Hz, 5H), 1.67-1.50 (m, 4H).

Example 5. Exemplary synthesis of 2-amino-1'-[6-[3-chloro-2-[(E)-N-methoxy-C-methyl-carbonimidoyl]-4,6,7,8-tetrahydropyrazolo[1,5-a][1,4]diazepin-5-yl]-5-cyano-2-[[(2R,8S)-2-fluoro-1,2,3,5,6,7-hexahydropyrrolizin-8-yl]methoxy]pyrimidin-4-yl]spiro[5,6-dihydrocyclopenta[b]thiophene-4,3'-azetidine]-3-carbonitrile (Compound 20)

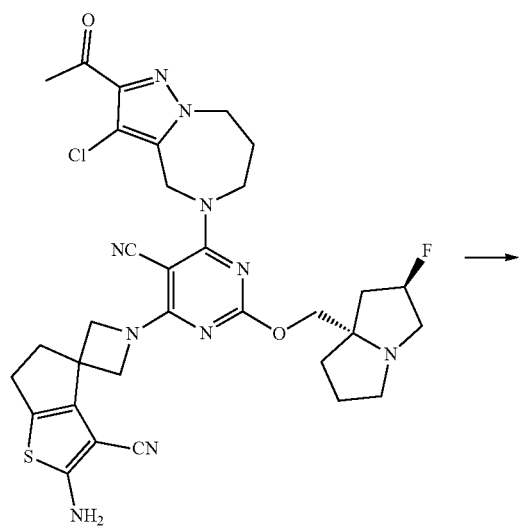

Compound 13

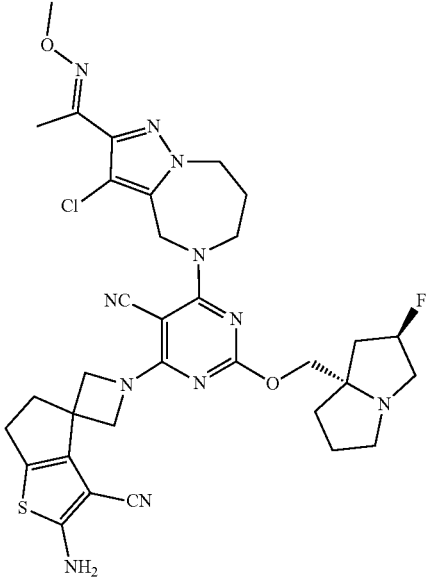

Compound 20

Preparation of 2-amino-1'-[6-[3-chloro-2-[(E)-N-methoxy-C-methyl-carbonimidoyl]-4,6,7,8-tetrahydropyrazolo[1,5-a][1,4]diazepin-5-yl]-5-cyano-2-[[(2R,8S)-2-fluoro-1,2,3,5,6,7-hexahydropyrrolizin-8-yl]methoxy]pyrimidin-4-yl]spiro[5,6-dihydrocyclopenta[b]thiophene-4,3'-azetidine]-3-carbonitrile (Compound 20). To a solution of Methoxyammonium chloride (1.23 mg, 0.01 mmol) and 1'-[6-(2-acetyl-3-chloro-4,6,7,8-tetrahydropyrazolo[1,5-a][1,4]diazepin-5-yl)-5-cyano-2-[[(2R,8S)-2-fluoro-1,2,3,5,6,7-hexahydropyrrolizin-8-yl]methoxy]pyrimidin-4-yl]-2-amino-spiro[5,6-dihydrocyclopenta[b]thiophene-4,3'-azetidine]-3-carbonitrile (Compound 13, 5 mg, 0.01 mmol) in Ethanol (1 mL) AcONa (1.21 mg, 0.01 mmol) was added. The mixture was stirred at rt for 3 h. The mixture was diluted with EtOAC (5 mL), washed with water (5 mL), dried over Na$_2$SO$_4$, concentrated. The crude product was purified by Prep-HPLC (eluted with CH$_3$CN in H$_2$O (0.1% NH$_4$HCO$_3$) from 5.0% to 95%). 2-amino-1'-[6-[3-chloro-2-[(E)-N-methoxy-C-methyl-carbonimidoyl]-4,6,7,8-tetrahydropyrazolo[1,5-a][1,4]diazepin-5-yl]-5-cyano-2-[[(2R,8S)-2-fluoro-1,2,3,5,6,7-hexahydropyrrolizin-8-yl]methoxy]pyrimidin-4-yl]spiro[5,6-dihydrocyclopenta[b]thiophene-4,3'-azetidine]-3-carbonitrile (Compound 20, 3.12 mg, 0.0038 mmol, 51.09% yield) was obtained as white solid. LCMS calcld for $C_{33}H_{38}ClFN_{11}O_2S$ (M+H)$^+$ m/z=706.3, found: 706.1. $^1$H NMR (DMSO-d6, 400 MHz) δ 7.22 (s, 2H), 5.24 (d, J=56.0 Hz, 1H), 5.00 (br, 2H), 4.43-4.41 (m, 2H), 4.37-4.17 (m, 2H), 4.09 (m, 2H), 4.00 (m, 1H), 3.91 (m, 1H), 3.88 (s, 3H), 3.04 (br, 2H), 2.95 (br, 1H), 2.82-2.76 (m, 1H), 2.68-2.63 (m, 5H), 2.15-2.12 (m, 1H), 2.11 (s, 3H), 2.05-2.03 (m, 1H), 2.01-1.96 (m, 3H), 1.90-1.87 (m, 1H), 1.82-1.78 (m, 1H), 1.74-1.70 (m, 2H).

Compound 21. 2-amino-1'-[5-cyano-2-[[(2R,8S)-2-fluoro-1,2,3,5,6,7-hexahydropyrrolizin-8-yl]methoxy]-6-(2-methylsulfonyl-4,6,7,8-tetrahydropyrazolo[1,5-a][1,4]diazepin-5-yl)pyrimidin-4-yl]spiro[5,6-dihydrocyclopenta[b]thiophene-4,3'-azetidine]-3-carbonitrile

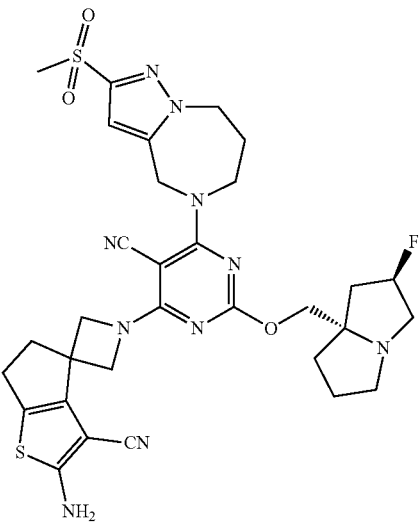 [SMILES: CS(=O)(=O)c1cc2n(n1)CCCN(c1nc(OC[C@@]34CCCN3C[C@H](F)C4)nc(N3CC4(CCc5sc(N)c(C#N)c54)C3)c1C#N)C2]

Compound 21 was prepared similarly to that of Ex. 2 using Intermediate 8. LCMS calcld for $C_{31}H_{36}FN_{10}O_3S_2$ $(M+H)^+$ m/z=679.2, found: 679.1. $^1H$ NMR (400 MHz, $CD_3OD$) δ 6.87 (s, 1H), 5.36-5.15 (m, 1H), 5.15-4.97 (m, 2H), 4.64-4.42 (m, 6H), 4.29-4.21 (m, 2H), 4.13-4.01 (m, 2H), 3.21 (m, 2H), 3.16 (s, 3H), 3.15 (s, 2H), 2.75 (dd, J=9.1, 5.2 Hz, 4H), 2.23-2.11 (m, 4H), 2.10-1.77 (m, 4H).

Compound 22. 2-amino-1'-[6-(3,8-diazabicyclo[3.2.1]octan-3-yl)-5-fluoro-2-[[1-(morpholinomethyl)cyclopropyl]methoxy]pyrimidin-4-yl]spiro[5,6-dihydrocyclopenta[b]thiophene-4,3'-azetidine]-3-carbonitrile

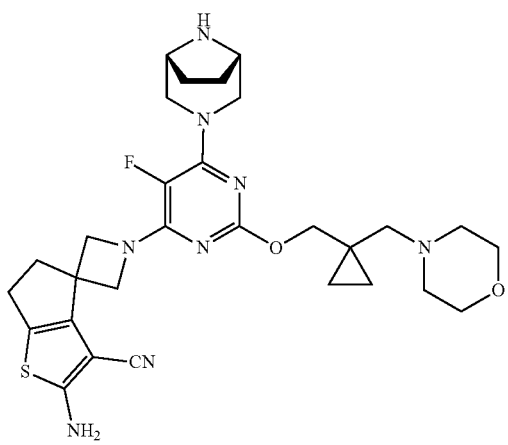

Compound 22 was prepared similarly to that of Ex. 4 as a TFA salt. LCMS calcld for $C_{29}H_{38}FN_8O_2S$ $(M+H)^+$ m/z=581.3, found: 581.4. $^1H$ NMR (400 MHz, $CD_3OD$) δ 4.49-4.41 (m, 2H), 4.29-4.22 (m, 4H), 4.19 (d, J=12.4 Hz, 2H), 4.14-4.07 (m, 2H), 3.91-3.78 (m, 4H), 3.39-3.33 (m, 2H), 3.18-2.89 (m, 6H), 2.82-2.70 (m, 4H), 2.15-2.05 (m, 4H), 0.80 (s, 2H), 0.69 (s, 2H).

Compound 23. 4-(2-aminospiro[5,6-dihydrocyclopenta[d]thiazole-4,3'-azetidine]-1'-yl)-2-[[1-(morpholinomethyl)cyclopropyl]methoxy]-6-[(1R,5S)-3,8-diazabicyclo[3.2.1]octan-3-yl]pyrimidine-5-carbonitrile

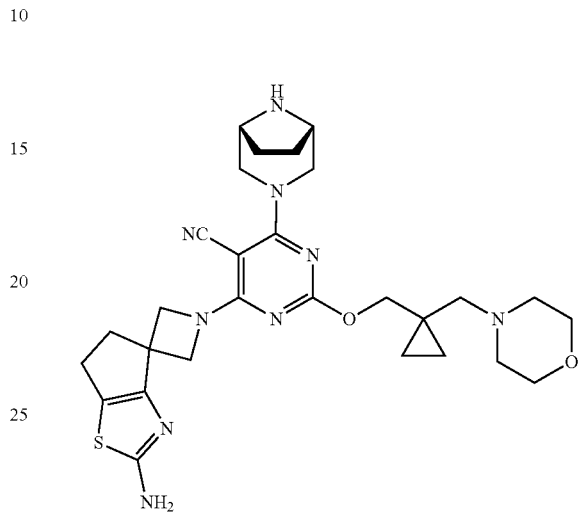

Compound 23 was prepared similarly to that of Ex. 3 using Intermediate 9. LCMS calcld for $C_{28}H_{38}N_9O_2S$ $(M+H)^+$ m/z=564.3, found: 564.2. $^1H$ NMR (400 MHz, $CD_3OD$) δ 4.45 (s, 6H), 4.24 (s, 2H), 3.98 (s, 2H), 3.67 (t, J=4.5 Hz, 4H), 3.42 (d, J=13.9 Hz, 2H), 2.89-2.69 (m, 4H), 2.51 (s, 4H), 2.41 (s, 2H), 2.01 (s, 4H), 0.64 (t, J=5.2 Hz, 2H), 0.47 (t, J=5.2 Hz, 1H).

Compound 24. 2-amino-1'-[5-cyano-6-(2-cyano-4,6,7,8-tetrahydropyrazolo[1,5-a][1,4]diazepin-5-yl)-2-[[(2R,8S)-2-fluoro-1,2,3,5,6,7-hexahydropyrrolizin-8-yl]methoxy]pyrimidin-4-yl]spiro[5,6-dihydrocyclopenta[b]thiophene-4,3'-azetidine]-3-carbonitrile

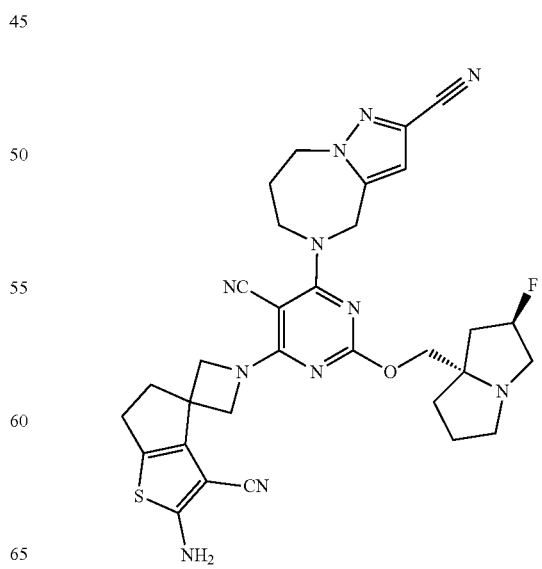

Compound 24 was prepared similarly to that of Ex. 2 using Intermediate 10. LCMS calcd for $C_{31}H_{33}FN_{11}OS$ $(M+H)^+$ m/z=626.3, found: 626.2. $^1H$ NMR (400 MHz, $CD_3OD$) δ 6.87 (s, 1H), 5.26 (d, J=53.8 Hz, 1H), 5.05 (s, 2H), 4.55 (m, 5H), 4.22 (s, 2H), 4.06 (m, 2H), 3.23 (s, 2H), 3.15 (m, 1H), 2.99 (s, 1H), 2.83-2.64 (m, 4H), 2.25-1.78 (m, 9H).

Compound 25. 2-amino-1'-[5-cyano-6-(3,8-diazabicyclo[3.2.1]octan-3-yl)-2-[[(2R,8S)-2-fluoro-1,2,3,5,6,7-hexahydropyrrolizin-8-yl]methoxy]pyrimidin-4-yl]spiro[5,6-dihydrocyclopenta[b]thiophene-4,3'-azetidine]-3-carbonitrile

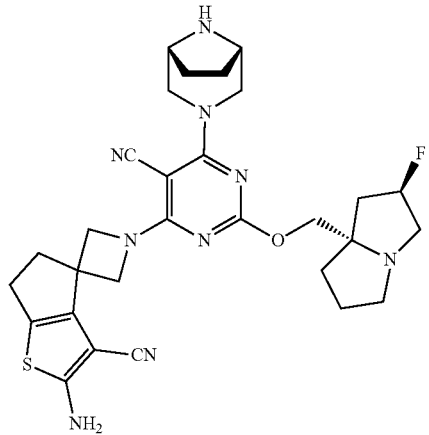

Compound 25 was prepared similarly to that of Ex. 3 as a formate salt. LCMS calcd for $C_{29}H_{35}FN_9OS$ $(M+H)^+$ m/z=576.3, found: 576.3. $^1H$ NMR (400 MHz, $CD_3OD$) δ 8.43 (s, 1H), 5.55-5.29 (m, 1H), 4.77-4.18 (m, 8H), 4.12-4.01 (m, 2H), 3.76-3.39 (m, 5H), 3.29-3.16 (m, 1H), 2.82-2.70 (m, 4H), 2.55-1.96 (m, 10H).

Compound 26. 2-amino-1'-[5-cyano-6-(3,8-diazabicyclo[3.2.1]octan-3-yl)-2-[3-(dimethylamino)-2,2-difluoro-propoxy]pyrimidin-4-yl]spiro[5,6-dihydrocyclopenta[b]thiophene-4,3'-azetidine]-3-carbonitrile

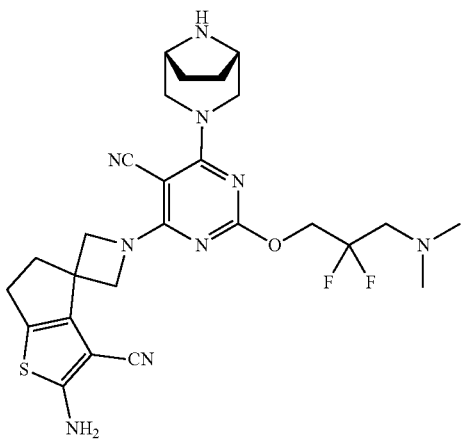

Compound 26 was prepared similarly to that of Ex. 3 as a formate salt. LCMS calcd for $C_{26}H_{32}F_2N_9OS$ $(M+H)^+$ m/z=556.2, found: 556.3. $^1H$ NMR (400 MHz, $CD_3OD$) δ 8.40 (s, 1H), 4.75-4.20 (m, 8H), 4.11 (s, 2H), 3.54-3.44 (m, 2H), 2.95-2.68 (m, 5H), 2.35 (s, 6H), 2.07 (s, 4H).

Compound 27. 2-amino-1'-[5-cyano-2-[[(2R,8S)-2-fluoro-1,2,3,5,6,7-hexahydropyrrolizin-8-yl]methoxy]-6-[(3R)-3-hydroxy-3-methyl-1-piperidyl]pyrimidin-4-yl]spiro[5,6-dihydrocyclopenta[b]thiophene-4,3'-azetidine]-3-carbonitrile

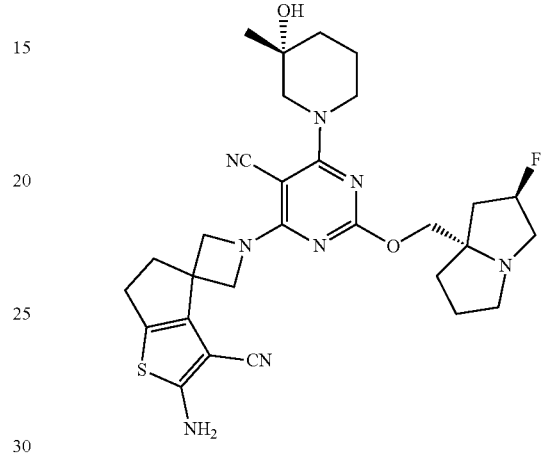

Compound 27 was prepared similarly to that of Ex. 2 as a TFA salt. LCMS m/z calcd for $C_{29}H_{36}FN_8O_2S$ $(M+H)^+$ m/z=579.3, found 579.2. $^1H$ NMR (400 MHz, $CD_3OD$) δ 5.63-5.38 (m, 1H), 4.93-4.87 (m, 1H), 4.67-4.32 (m, 5H), 4.12-3.79 (m, 5H), 3.60-3.37 (m, 3H), 2.86-2.70 (m, 4H), 2.69-2.46 (m, 2H), 2.41-2.23 (m, 3H), 2.21-2.06 (m, 1H), 2.00-1.85 (m, 1H), 1.81-1.55 (m, 3H), 1.21 (s, 3H).

Compound 28. 2-amino-1'-[5-cyano-6-(3,8-diazabicyclo[3.2.1]octan-3-yl)-2-[[1-[(4-fluoro-1-piperidyl)methyl]cyclopropyl]methoxy]pyrimidin-4-yl]spiro[5,6-dihydrocyclopenta[b]thiophene-4,3'-azetidine]-3-carbonitrile

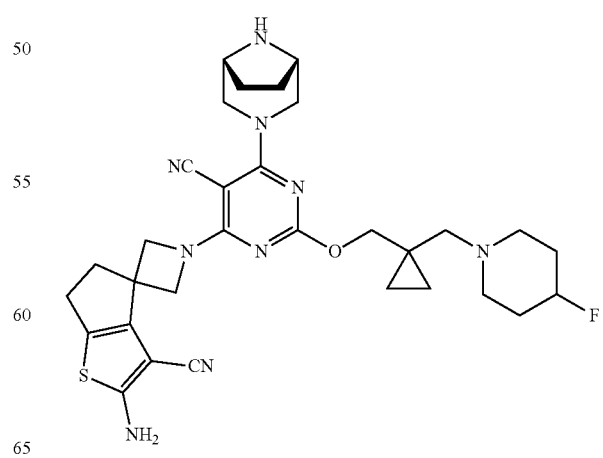

Compound 28 was prepared similarly to that of Ex. 3 as a TFA salt. LCMS calcld for $C_{31}H_{39}FN_9OS$ (M+H)$^+$ m/z=604.3, found: 604.2. $^1$H NMR (400 MHz, CD$_3$OD) δ 5.00 (d, J=41.6 Hz, 1H), 4.82-4.33 (m, 6H), 4.28 (s, 2H), 4.16 (s, 2H), 3.79-3.61 (m, 2H), 3.56-3.44 (m, 2H), 3.29-3.22 (m, 2H), 2.86-2.65 (m, 4H), 2.42-2.13 (m, 4H), 2.14-1.94 (m, 6H), 0.90 (d, J=3.5 Hz, 2H), 0.86-0.78 (m, 2H).

Compound 29. 2-amino-1'-[5-cyano-6-[2-(1-methyl-benzimidazol-2-yl)-4,6,7,8-tetrahydropyrazolo[1,5-a][1,4]diazepin-5-yl]-2-[[(2R,8S)-2-fluoro-1,2,3,5,6,7-hexahydropyrrolizin-8-yl]methoxy]pyrimidin-4-yl]spiro[5,6-dihydrocyclopenta[b]thiophene-4,3'-azetidine]-3-carbonitrile

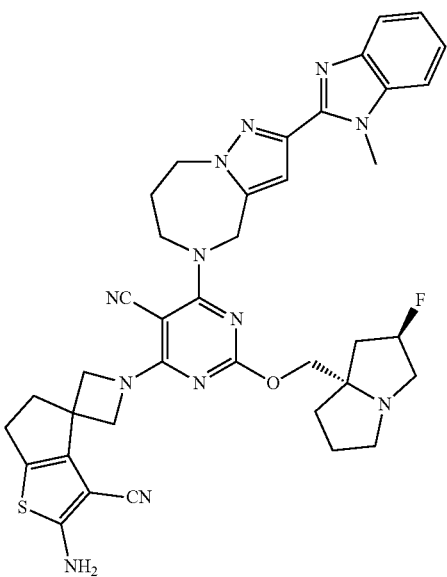 [SMILES: Cn1c(-c2cc3n(n2)CCCN(c2nc(OC[C@@]45CCCN4C[C@H](F)C5)nc(N4CC5(CCc6sc(N)c(C#N)c65)C4)c2C#N)C3)nc2ccccc21]

Compound 29 was prepared similarly to that of Ex. 2 as a formate salt using Intermediate 11. LCMS calcld for $C_{38}H_{40}FN_{12}OS$ (M+H)$^+$ m/z=731.3, found: 731.4. $^1$H NMR (400 MHz, CD$_3$OD) δ 7.66 (d, J=7.6 Hz, 1H), 7.55 (d, J=7.6 Hz, 1H), 7.42-7.26 (m, 2H), 7.05 (s, 1H), 5.43-5.25 (m, 1H), 5.24-5.13 (m, 2H), 4.76-4.38 (m, 5H), 4.34-3.99 (m, 8H), 3.32-3.19 (m, 3H), 3.10-2.98 (m, 1H), 2.82-2.68 (m, 4H), 2.40-1.83 (m, 8H).

Compound 30. 2-amino-1'-[5-cyano-2-[[(2R,8S)-2-fluoro-1,2,3,5,6,7-hexahydropyrrolizin-8-yl]methoxy]-6-(2,3,6,7-tetrahydroazepin-1-yl)pyrimidin-4-yl]spiro[5,6-dihydrocyclopenta[b]thiophene-4,3'-azetidine]-3-carbonitrile

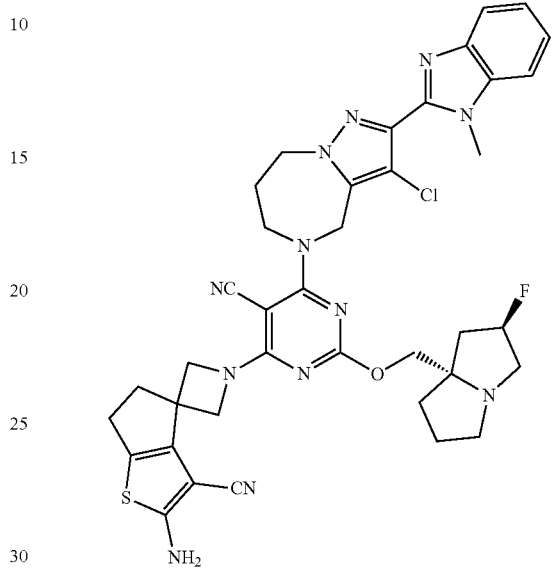

Compound 30 was prepared similarly to Compound 29 as a formate salt. LCMS calcld for $C_{38}H_{39}FN_{12}OS$ (M+H)$^+$ m/z=765.3, found: 765.5. $^1$H NMR (400 MHz, CD$_3$OD) δ 8.47 (s, 2H), 5.80-5.71 (m, 2H), 5.55-5.37 (m, 1H), 4.72-4.21 (m, 8H), 4.02-3.93 (m, 2H), 3.76-3.58 (m, 3H), 3.27-3.18 (m, 1H), 2.84-2.71 (m, 4H), 2.57-2.00 (m, 10H).

Compound 31. 2-amino-1'-[5-cyano-2-[[(2R,8S)-2-fluoro-1,2,3,5,6,7-hexahydropyrrolizin-8-yl]methoxy]-6-(2,3,6,7-tetrahydroazepin-1-yl)pyrimidin-4-yl]spiro[5,6-dihydrocyclopenta[b]thiophene-4,3'-azetidine]-3-carbonitrile

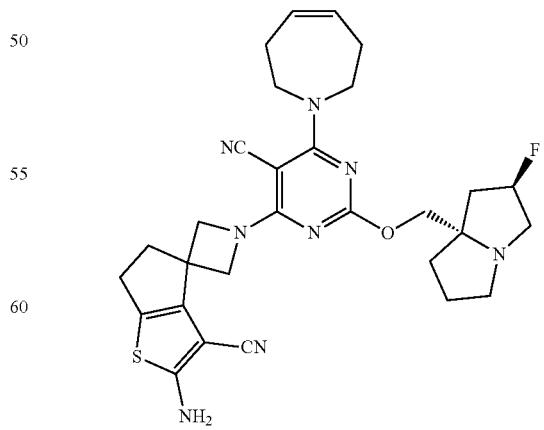

Compound 31 was prepared similarly to that of Ex. 2 as a formate salt. LCMS calcld for $C_{29}H_{34}FN_8OS$ (M+H)$^+$ m/z=561.3, found: 561.2. $^1$H NMR (400 MHz, CD$_3$OD) δ 8.47 (s, 2H), 5.80-5.71 (m, 2H), 5.55-5.37 (m, 1H), 4.72-4.21 (m, 8H), 4.02-3.93 (m, 2H), 3.76-3.58 (m, 3H), 3.27-3.18 (m, 1H), 2.84-2.71 (m, 4H), 2.57-2.00 (m, 10H).

Compound 32. 2-amino-1'-[6-[3-chloro-2-(4-fluoro-1-methyl-benzimidazol-2-yl)-4,6,7,8-tetrahydropyrazolo[1,5-a][1,4]diazepin-5-yl]-5-cyano-2-[[(2R,8S)-2-fluoro-1,2,3,5,6,7-hexahydropyrrolizin-8-yl]methoxy]pyrimidin-4-yl]spiro[5,6-dihydrocyclopenta[b]thiophene-4,3'-azetidine]-3-carbonitrile

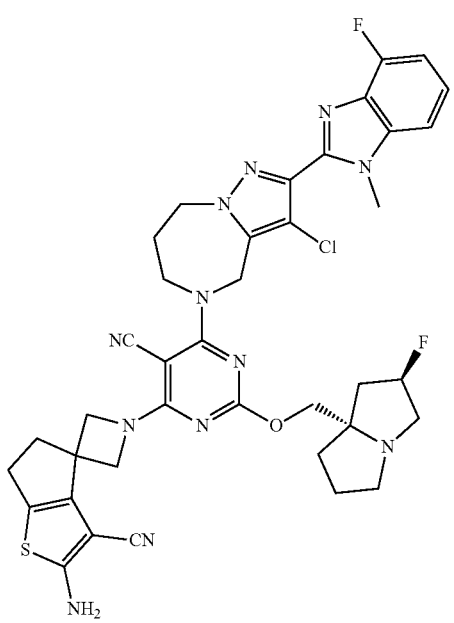 [SMILES: Cn1c(-c2nn3c(c2Cl)CN(c2nc(OC[C@@]45CCCN4C[C@H](F)C5)nc(N4CC5(CCc6sc(N)c(C#N)c65)C4)c2C#N)CCC3)nc2c(F)cccc21]

Compound 32 was prepared similarly Compound 29 as a formate salt. LCMS calcld for $C_{38}H_{38}ClF_2N_{12}OS$ (M+H)$^+$ m/z=783.3, found: 783.3. $^1$H NMR (400 MHz, CD$_3$OD) δ 7.46-7.29 (m, 2H), 7.11-7.01 (m, 1H), 5.67-5.47 (m, 1H), 5.18-4.90 (m, 3H), 4.61-4.22 (m, 9H), 4.00-3.76 (m, 6H), 3.50-3.36 (m, 1H), 2.83-2.47 (m, 6H), 2.43-2.10 (m, 6H).

Compound 33. 2-amino-1'-[5-cyano-6-(4-cyanoazepan-1-yl)-2-[[(2R,8S)-2-fluoro-1,2,3,5,6,7-hexahydropyrrolizin-8-yl]methoxy]pyrimidin-4-yl]spiro[5,6-dihydrocyclopenta[b]thiophene-4,3'-azetidine]-3-carbonitrile

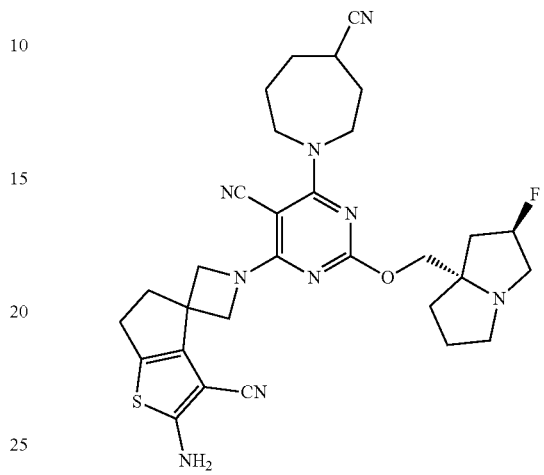

Compound 33 was prepared similarly to that of Ex. 2 as a TFA salt. LCMS calcld for $C_{30}H_{35}FN_9OS$ (M+H)$^+$ m/z=588.3, found: 588.3. $^1$H NMR (400 MHz, CD$_3$OD) δ: 5.55 (d, J=51.6 Hz, 1H), 4.55-4.36 (m, 6H), 4.02-3.81 (m, 7H), 3.48-3.40 (m, 1H), 3.08-3.04 (m, 1H), 2.80-2.70 (m, 4H), 2.68-2.49 (m, 2H), 2.37-1.91 (m, 10H).

Compound 34. 2-amino-1'-[5-cyano-6-(3,8-diazabicyclo[3.2.1]octan-3-yl)-2-[[1-[(4,4-difluoro-1-piperidyl)methyl]cyclopropyl]methoxy]pyrimidin-4-yl]spiro[5,6-dihydrocyclopenta[b]thiophene-4,3'-azetidine]-3-carbonitrile

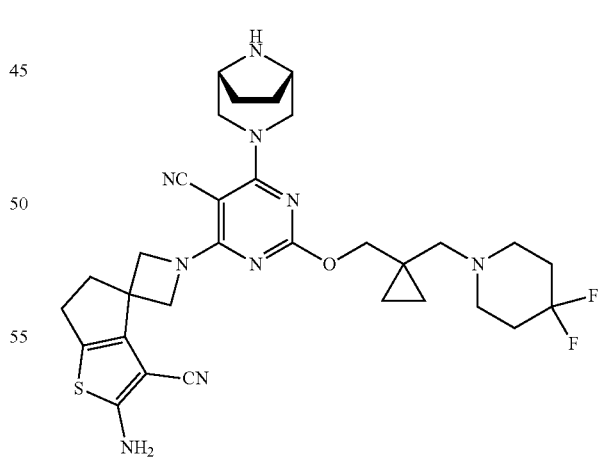

Compound 34 was prepared similarly to that of Ex. 3 as a TFA salt. LCMS calcld for $C_{31}H_{38}F_2N_9OS$ (M+H)$^+$ m/z=622.3, found: 622.2. $^1$H NMR (400 MHz, CD$_3$OD) δ 4.69-4.27 (m, 6H), 4.26-4.19 (m, 2H), 3.59-3.48 (m, 2H), 3.29-3.13 (m, 2H), 2.81-2.37 (m, 10H), 1.99-1.88 (m, 4H), 1.85-1.75 (m, 4H), 0.69-0.61 (m, 2H), 0.50-0.41 (m, 2H).

Compound 35. 3-chloro-5-[5-cyano-6-(2',2'-difluorospiro[azetidine-3,1'-tetralin]-1-yl)-2-[[(2R,8S)-2-fluoro-1,2,3,5,6,7-hexahydropyrrolizin-8-yl]methoxy]pyrimidin-4-yl]-N,N-dimethyl-4,6,7,8-tetrahydropyrazolo[1,5-a][1,4]diazepine-2-carboxamide

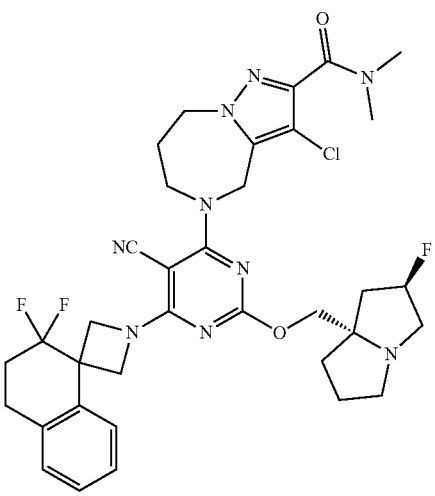 [SMILES: CN(C)C(=O)c1nn2c(c1Cl)CN(c1nc(OC[C@@]34CCCN3C[C@H](F)C4)nc(N3CC4(C3)c3ccccc3CCC4(F)F)c1C#N)CCC2]

Compound 35 was prepared similarly to that of Ex. 2 using Intermediate 12. LCMS calcld for C$_{35}$H$_{40}$ClF$_3$N$_9$O$_2$ (M+H)$^+$ m/z=710.3; found: 710.3. $^1$H NMR (500 MHz, CDCl$_3$) δ ppm 2.07-2.67 (m, 12H) 2.99-3.07 (m, 3H) 3.10 (d, J=10.03 Hz, 6H) 3.14-3.24 (m, 1H) 3.35-3.47 (m, 2H) 3.78-4.01 (m, 2H) 4.01-4.32 (m, 3H) 4.32-4.49 (m, 4H) 4.54 (d, J=11.55 Hz, 2H) 4.59-5.14 (m, 5H) 5.32-5.57 (m, 1H) 7.13 (d, J=7.64 Hz, 1H) 7.22-7.26 (m, 1H) 7.32-7.37 (m, 1H) 7.65 (d, J=7.89 Hz, 1H)

Compound 36. 3-chloro-5-[5-cyano-2-[[(2R,8S)-2-fluoro-1,2,3,5,6,7-hexahydropyrrolizin-8-yl]methoxy]-6-(2'-oxospiro[azetidine-3,1'-tetralin]-1-yl)pyrimidin-4-yl]-N,N-dimethyl-4,6,7,8-tetrahydropyrazolo[1,5-a][1,4]diazepine-2-carboxamide

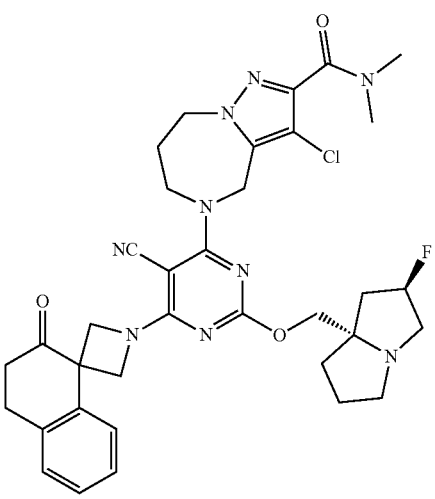 [SMILES: CN(C)C(=O)c1nn2c(c1Cl)CN(c1nc(OC[C@@]34CCCN3C[C@H](F)C4)nc(N3CC4(C3)C(=O)CCc3ccccc34)c1C#N)CCC2]

Compound 36 was prepared similarly to that of Ex. 2 using Intermediate 18. LCMS calcld for C$_{35}$H$_{40}$ClFN$_9$O$_2$ (M+H)$^+$ m/z=688.3; found: 688.3. $^1$H NMR (500 MHz, CDCl$_3$) δ 2.02-2.13 (m, 3H) 2.19-2.29 (m, 3H) 2.30-2.47 (m, 2H) 2.71 (t, J=6.79 Hz, 2H) 3.06 (t, J=6.79 Hz, 2H) 3.10 (s, 3H) 3.11 (s, 3H) 3.27-3.43 (m, 1H) 3.59-3.80 (m, 2H) 4.04-4.21 (m, 2H) 4.32 (d, J=11.19 Hz, 1H) 4.37-4.49 (m, 3H) 4.69-5.12 (m, 4H) 5.31-5.48 (m, 1H) 7.20-7.24 (m, 1H) 7.29 (td, J=7.47, 0.76 Hz, 1H) 7.38 (t, J=7.27 Hz, 1H) 7.63 (d, J=7.64 Hz, 1H)

Compound 37. 3-chloro-5-[5-cyano-2-[[(2R,8S)-2-fluoro-1,2,3,5,6,7-hexahydropyrrolizin-8-yl]methoxy]-6-(2'-oxospiro[azetidine-3,1'-indane]-1-yl)pyrimidin-4-yl]-N,N-dimethyl-4,6,7,8-tetrahydropyrazolo[1,5-a][1,4]diazepine-2-carboxamide

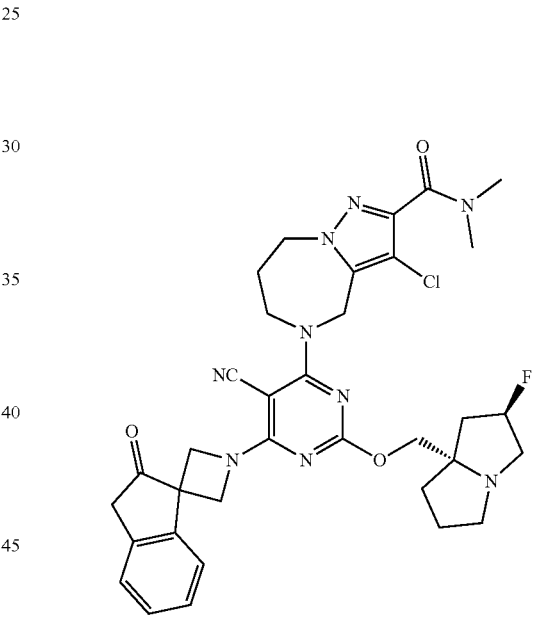

Compound 36 was prepared similarly to that of Ex. 2 using 5-oxo-2-azaspiro[3.4]octane (Angew. Chem. Int. Ed. 2021, 60, 7360-7365). LCMS calcld for C$_{34}$H$_{38}$ClFN$_9$O$_3$ (M+H)$^+$ m/z=674.3; found: 674.3. $^1$H NMR (CDCl$_3$) δ: 7.79 (d, J=7.6 Hz, 1H), 7.64 (t, J=7.5 Hz, 1H), 7.48 (d, J=7.6 Hz, 1H), 7.39-7.44 (t, J=7.5 Hz, 1H), 5.32-5.49 (d, J=55 Hz, 1H), 4.80-5.08 (dd, J=15 Hz, 1H), 3.99-4.72 (m, 10H), 3.73-3.94 (m, 2H), 3.54 (s, 2H), 3.46 (d, J=1.4 Hz, 1H), 3.38 (t, J=16.0 Hz, 1H), 3.12 (s, 2H), 3.09 (s, 3H), 2.32-2.56 (m, 2H), 2.20-2.31 (m, 3H), 2.13 (br. s., 3H).

313

Compound 38. 2-amino-1'-[5-cyano-6-(4,5-dihydroxyazepan-1-yl)-2-[[(2R,8S)-2-fluoro-1,2,3,5,6,7-hexahydropyrrolizin-8-yl]methoxy]pyrimidin-4-yl]spiro[5,6-dihydrocyclopenta[b]thiophene-4,3'-azetidine]-3-carbonitrile

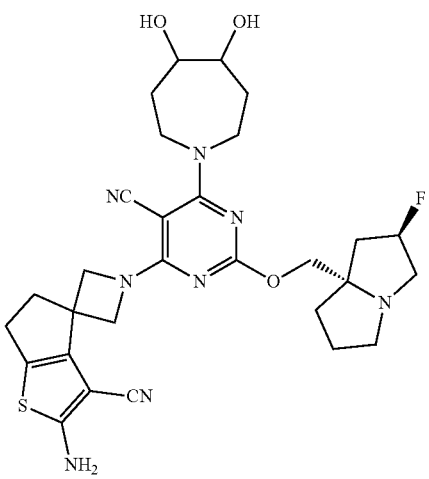 [SMILES: N#Cc1c(N2CCC(O)C(O)CC2)nc(OC[C@@]23CCCN2C[C@H](F)C3)nc1N1CC2(CCc3sc(N)c(C#N)c32)C1]

Compound 38 was prepared similarly to that of Ex. 2 as a TFA salt. LCMS calcld for $C_{29}H_{36}FN_8O_3S$ (M+H)$^+$ m/z=595.3, found: 595.3. $^1$H NMR (400 MHz, CD$_3$OD) δ 5.55 (d, J=51.6 Hz, 1H), 4.61-4.22 (m, 6H), 4.03-3.55 (m, 9H), 3.50-3.39 (m, 1H), 2.82-2.48 (m, 6H), 2.40-2.10 (m, 6H), 1.97-1.84 (m, 2H).

Compound 39. 2-[[1-(morpholinomethyl)cyclopropyl]methoxy]-4-(12-oxospiro[7-thia-9,11-diazatricyclo[6.4.0.0.2,6]dodeca-1(8), 2(6), 10-triene-3,3'-azetidine]-1'-yl)-6-[(1R,5S)-3,8-diazabicyclo[3.2.1]octan-3-yl]pyrimidine-5-carbonitrile

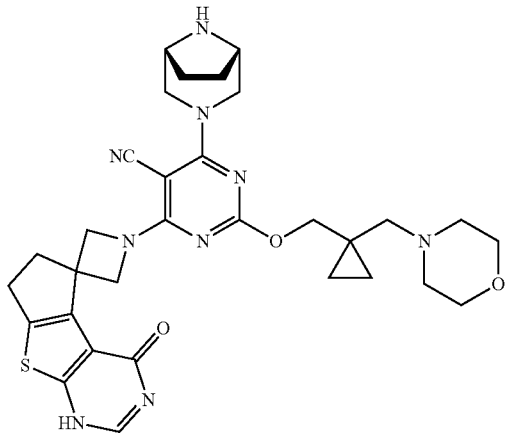

Compound 39 was prepared similarly to that of Ex. 3 using Intermediate 13 as a TFA salt. LCMS calcld for $C_{31}H_{38}N_9O_3S$ (M+H)$^+$ m/z=616.3, found: 616.2. $^1$H NMR (400 MHz, CD$_3$OD) δ 8.01 (s, 1H), 4.75-4.58 (m, 3H), 4.44-4.14 (m, 6H), 4.10-4.00 (m, 2H), 3.88-3.63 (m, 4H), 3.60-3.31 (m, 4H), 3.29-3.04 (m, 5H), 2.99-2.90 (m, 2H), 2.15-2.03 (m, 4H), 0.95-0.80 (m, 4H).

314

Compound 40. 2-amino-1'-[5-cyano-6-(4-hydroxyazepan-1-yl)-2-[[(2R,8S)-2-fluoro-1,2,3,5,6,7-hexahydropyrrolizin-8-yl]methoxy]pyrimidin-4-yl]spiro[5,6-dihydrocyclopenta[b]thiophene-4,3'-azetidine]-3-carbonitrile

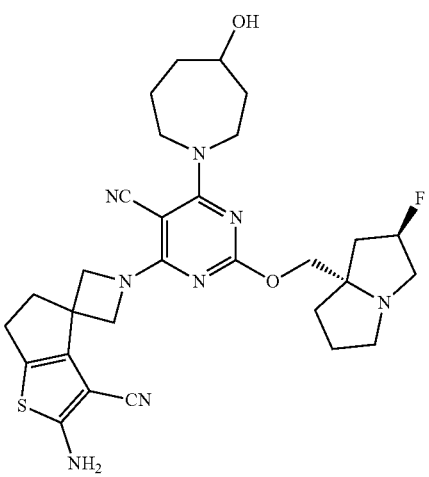 [SMILES: N#Cc1c(N2CCCC(O)CC2)nc(OC[C@@]23CCCN2C[C@H](F)C3)nc1N1CC2(CCc3sc(N)c(C#N)c32)C1]

Compound 40 was prepared similarly to that of Ex. 2 as a TFA salt. LCMS calcld for $C_{29}H_{36}FN_8O_2S$ (M+H)$^+$ m/z=579.3, found: 579.3. $^1$H NMR (400 MHz, CD$_3$OD) δ 5.66-5.40 (m, 1H), 4.64-4.29 (m, 6H), 4.02-3.72 (m, 8H), 3.52-3.38 (m, 1H), 2.82-2.47 (m, 6H), 2.41-2.24 (m, 3H), 2.18-2.01 (m, 3H), 1.93-1.60 (m, 4H).

Compound 41. 2-amino-1'-[5-cyano-2-[[1-(morpholinomethyl)cyclopropyl]methoxy]-6-[(1R,5S)-3,8-diazabicyclo[3.2.1]octan-3-yl]pyrimidin-4-yl]spiro[6,7-dihydro-5H-benzothiophene-4,3'-azetidine]-3-carbonitrile

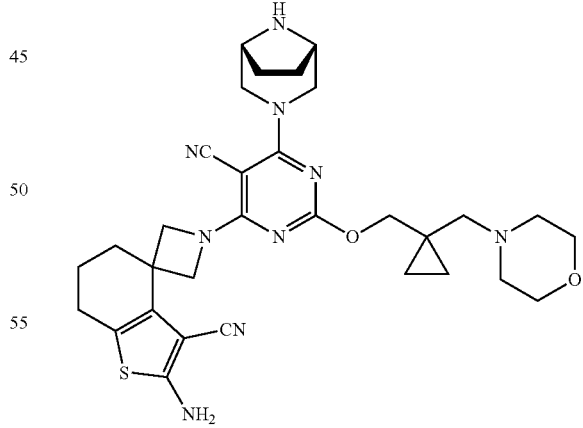

Compound 41 was prepared similarly to that of Ex. 3. LCMS calcld for $C_{31}H_{40}N_9O_2S$ (M+H)$^+$ m/z=602.3, found: 602.2. $^1$H NMR (400 MHz, CD$_3$OD) δ: 4.75-4.72 (m, 1H), 4.51-4.21 (m, 6H), 4.03-4.00 (m, 1H), 3.69-3.67 (m, 4H), 3.56-3.56 (m, 2H), 3.28-3.20 (m, 2H), 2.54-2.35 (m, 8H), 2.17-2.10 (m, 2H), 1.85-1.78 (m, 6H), 0.69-0.65 (m, 2H), 0.51-0.45 (m, 2H).

Compound 42. 2-amino-1'-[5-cyano-2-[[1-(morpholinomethyl)cyclopropyl]methoxy]-6-(3-oxa-7,9-diazabicyclo[3.3.1]nonan-7-yl)pyrimidin-4-yl]spiro[5,6-dihydrocyclopenta[b]thiophene-4,3'-azetidine]-3-carbonitrile

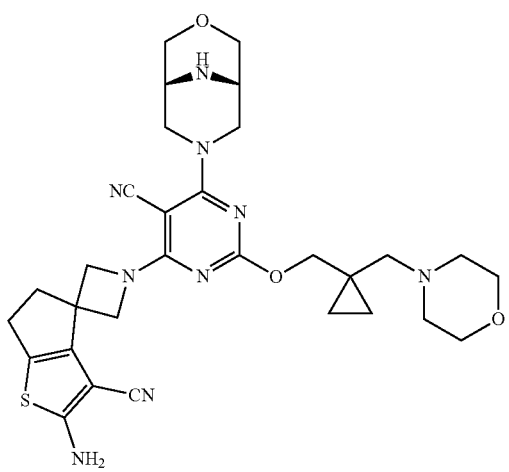 [SMILES: N#Cc1c(N2C[C@H]3COC[C@@H](C2)N3)nc(OCC2(CN3CCOCC3)CC2)nc1N1CC2(CCc3sc(N)c(C#N)c32)C1]

Compound 42 was prepared similarly to that of Ex. 3. LCMS calcld for C$_{30}$H$_{38}$N$_9$O$_3$S (M+H)$^+$ m/z=604.3, found: 604.4. $^1$H NMR (400 MHz, CD$_3$OD) δ 4.78 (d, J=13.2 Hz, 2H), 4.65-4.47 (m, 2H), 4.48-4.31 (m, 2H), 4.25 (s, 2H), 4.03-3.93 (m, 2H), 3.92-3.82 (m, 2H), 3.66 (t, J=4.4 Hz, 4H), 3.52 (d, J=13.4 Hz, 2H), 2.91 (s, 2H), 2.81-2.67 (m, 4H), 2.48 (s, 4H), 2.38 (s, 2H), 0.64 (t, J=5.2 Hz, 2H), 0.44 (t, J=5.2 Hz, 2H).

Compound 43. 2-amino-1'-[5-cyano-2-[[(2S,8R)-2-fluoro-1,2,3,5,6,7-hexahydropyrrolizin-8-yl]methoxy]-6-(3-oxa-7,9-diazabicyclo[3.3.1]nonan-7-yl)pyrimidin-4-yl]spiro[5,6-dihydrocyclopenta[b]thiophene-4,3'-azetidine]-3-carbonitrile

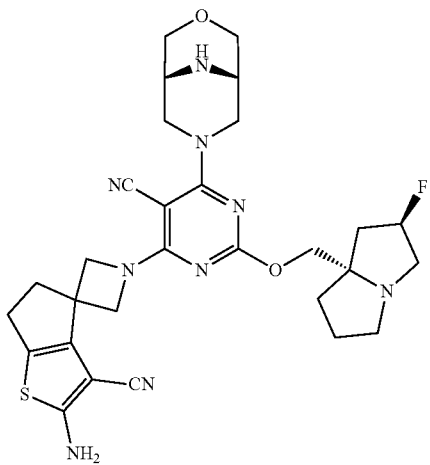

Compound 43 was prepared similarly to that of Ex. 3. LCMS calcld for C$_{29}$H$_{35}$FN$_9$O$_2$S (M+H)$^+$ m/z=592.3, found: 592.2. $^1$H NMR (DMSO-d6, 400 MHz) δ 7.23 (s, 2H), 5.25 (d, J=52.0 Hz, 1H), 4.60-4.57 (m, 2H), 4.34 (br, 4H), 3.97 (d, J=12.0 Hz, 1H), 3.84 (d, J=12.0 Hz, 1H), 3.80 (d, J=8.0 Hz, 2H), 3.70 (d, J=8.0 Hz, 2H), 3.41-3.89 (m, 2H), 3.05 (br, 2H), 3.01-2.93 (m, 1H), 2.84-2.79 (m, 3H), 2.67 (br, 4H), 2.07-2.05 (m, 1H), 1.99-1.98 (m, 1H), 1.95-1.93 (m, 1H), 1.83-1.80 (m, 1H), 1.75-1.71 (m, 2H).

Compound 44. 3-chloro-5-[5-cyano-2-[[(2R,8S)-2-fluoro-1,2,3,5,6,7-hexahydropyrrolizin-8-yl]methoxy]-6-(12-oxospiro[7-thia-9,11-diazatricyclo[6.4.0.02,6]dodeca-1(8), 2(6), 10-triene-3,3'-azetidine]-1'-yl)pyrimidin-4-yl]-N,N-dimethyl-4,6,7,8-tetrahydropyrazolo[1,5-a][1,4]diazepine-2-carboxamide

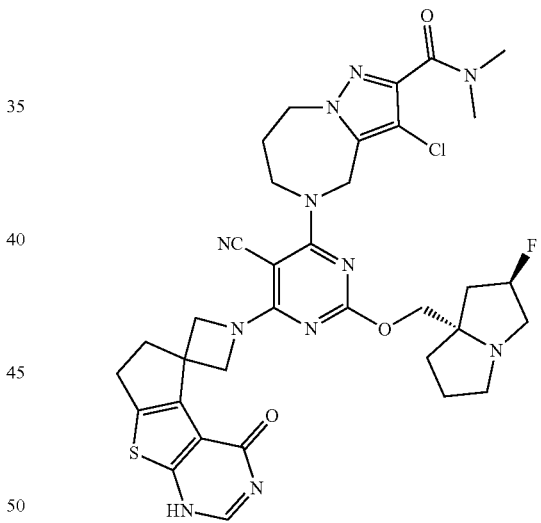

Compound 44 was prepared similarly to that of Ex. 2 as a formate salt using Intermediate 13. LCMS calcld for C$_{34}$H$_{38}$ClFN$_{11}$O$_3$S (M+H)$^+$ m/z=734.3, found: 734.2. $^1$H NMR (400 MHz, CD$_3$OD) δ 8.52 (s, 2H), 7.99 (s, 1H), 5.26 (d, J=56.2 Hz, 2H), 4.74-4.41 (m, 4H), 4.15 (m, 5H), 3.17 (m, 3H), 3.08 (m, 8H), 3.01-2.88 (m, 3H), 2.30-1.76 (m, 10H).

Compound 45. 2-amino-1-[5-cyano-2-[[1-(morpholinomethyl)cyclopropyl]methoxy]-6-[(1R,5S)-3,8-diazabicyclo[3.2.1]octan-3-yl]pyrimidin-4-yl]-6-methyl-spiro[5,6-dihydrocyclopenta[b]thiophene-4,3'-azetidine]-3-carbonitrile

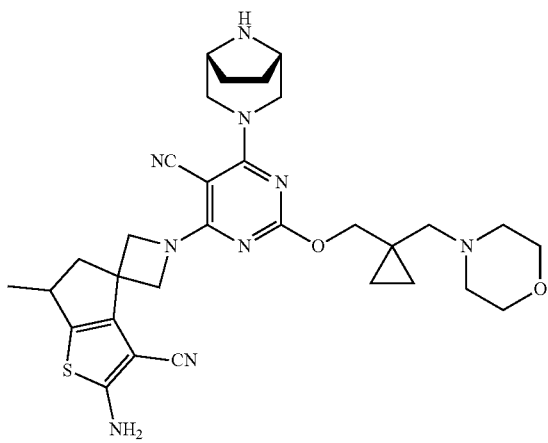

Compound 45 was prepared similarly to that of Ex. 2 as a TFA salt using Intermediate 6 (Compound 14). LCMS calcld for $C_{31}H_{40}N_9O_2S$ (M+H)$^+$ m/z=602.2, found: 602.3. $^1$H NMR (400 MHz, CD$_3$OD) δ 4.66-4.01 (m, 12H), 3.93-3.68 (m, 4H), 3.57-3.42 (m, 2H), 3.30-3.10 (m, 3H), 3.01-2.89 (m, 1H), 2.29-2.19 (m, 1H), 2.14-2.02 (m, 4H), 1.18 (d, J=6.8 Hz, 3H), 0.95-0.78 (m, 4H).

Compound 46. 2-amino-1'-[6-[3-chloro-2-(5-methyl-1,2,4-oxadiazol-3-yl)-4,6,7,8-tetrahydropyrazolo[1,5-a][1,4]diazepin-5-yl]-5-cyano-2-[[(2R,8S)-2-fluoro-1,2,3,5,6,7-hexahydropyrrolizin-8-yl]methoxy]pyrimidin-4-yl]spiro[5,6-dihydrocyclopenta[b]thiophene-4,3'-azetidine]-3-carbonitrile

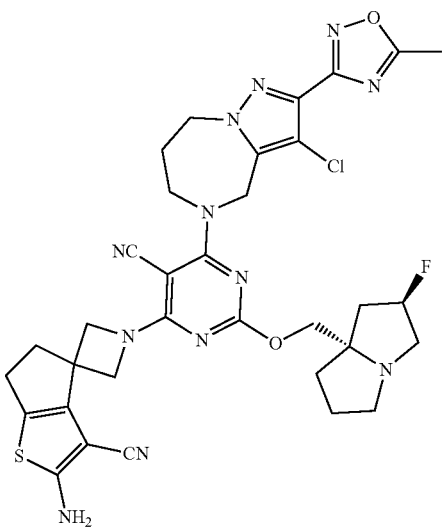 [SMILES: Cc1nc(-c2nn3c(c2Cl)CN(c2nc(OC[C@@]45CCCN4C[C@H](F)C5)nc(N4CC5(CCc6sc(N)c(C#N)c65)C4)c2C#N)CCC3)no1]

Compound 46 was prepared similarly to Ex. 2 as a formate salt using Intermediate 14. LCMS calcld for $C_{33}H_{35}ClFN_{12}O_2S$ (M+H)$^+$ m/z=717.2, found: 717.1. $^1$H NMR (400 MHz, CD$_3$OD) δ 5.34 (dd, J=35.3, 18.5 Hz, 1H), 5.12-5.02 (m, 2H), 4.74-4.44 (m, 6H), 4.29-4.09 (m, 5H), 3.47-3.33 (m, 2H), 3.15-3.00 (m, 1H), 2.79-2.68 (m, 4H), 2.66 (s, 3H), 2.43-1.78 (m, 9H).

Compound 47. 2-amino-1'-[5-cyano-6-[(1R,5S)-3,8-diazabicyclo[3.2.1]octan-3-yl]-2-[[1-(dimethylamino)cyclopropyl]methoxy]pyrimidin-4-yl]spiro[5,6-dihydrocyclopenta[b]thiophene-4,3'-azetidine]-3-carbonitrile

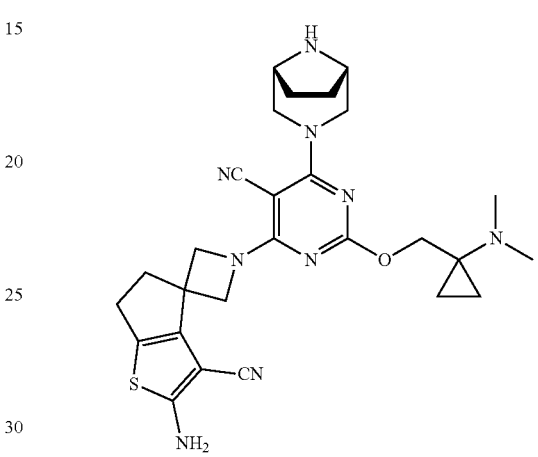

Compound 47 was prepared similarly to that of Ex. 3 as a TFA. LCMS calcld for $C_{27}H_{34}N_9OS$ (M+H)$^+$ m/z=532.3, found: 532.2. $^1$H NMR (400 MHz, CD$_3$OD) δ 4.66-4.53 (m, 4H), 4.44-4.37 (s, 2H), 4.35-4.16 (m, 2H), 3.62-3.48 (m, 2H), 3.29-3.10 (m, 2H), 2.83-2.67 (m, 4H), 2.46 (s, 6H), 1.89-1.71 (m, 4H), 0.80-0.66 (m, 4H).

Compound 48. 2-amino-1'-[5-cyano-2-[2-[cyclobutyl(methyl)amino]ethoxy]-6-[(1R,5S)-3,8-diazabicyclo[3.2.1]octan-3-yl]pyrimidin-4-yl]spiro[5,6-dihydrocyclopenta[b]thiophene-4,3'-azetidine]-3-carbonitrile

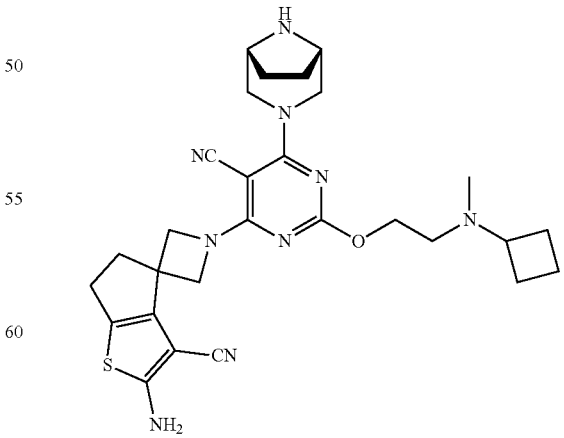

Compound 48 was prepared similarly to that of Ex. 3 as a TFA salt. LCMS calcld for $C_{28}H_{36}N_9OS$ (M+H)$^+$ m/z=546.3, found: 546.2. $^1$H NMR (400 MHz, CD$_3$OD) δ 4.75-4.33 (m, 7H), 4.23-4.15 (m, 2H), 3.89-3.78 (m, 1H), 3.66-3.43 (m, 3H), 3.43-3.34 (m, 2H), 2.85 (s, 3H), 2.83-2.70 (m, 4H), 2.45-2.17 (m, 4H), 2.11 (s, 4H), 1.96-1.79 (m, 2H).

Compound 49. 2-amino-1'-[5-cyano-2-[[(2R,8S)-2-fluoro-1,2,3,5,6,7-hexahydropyrrolizin-8-yl]methoxy]-6-(4-oxoazepan-1-yl)pyrimidin-4-yl]spiro[5,6-dihydrocyclopenta[b]thiophene-4,3'-azetidine]-3-carbonitrile

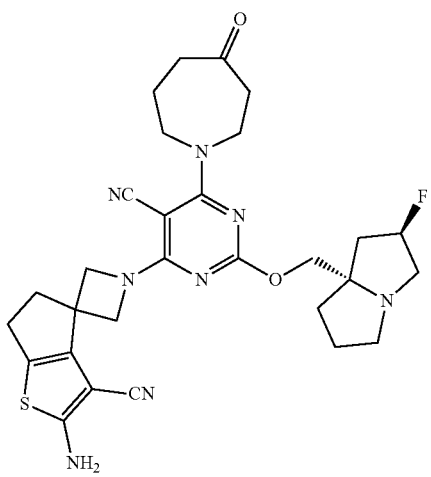

Compound 49 was prepared similarly to that of Ex. 2 as a TFA salt. LCMS calcld for C$_{29}$H$_{34}$FN$_8$O$_2$S (M+H)$^+$ m/z=577.2, found: 577.1. $^1$H NMR (400 MHz, CD$_3$OD) δ 5.57 (d, J=52 Hz, 1H), 4.57-4.39 (m, 6H), 4.21-4.18 (m, 2H), 4.12-4.01 (m, 2H), 4.00-3.83 (m, 4H), 3.50-3.41 (m, 2H), 2.81-2.51 (m, 10H), 2.40-2.31 (m, 3H), 2.29-1.89 (m, 3H).

Compound 50. 4-[(1R,5S)-3,8-diazabicyclo[3.2.1]octan-3-yl]-2-[[1-(morpholinomethyl)cyclopropyl]methoxy]-6-(2'-oxospiro[azetidine-3,1'-tetralin]-1-yl)pyrimidine-5-carbonitrile

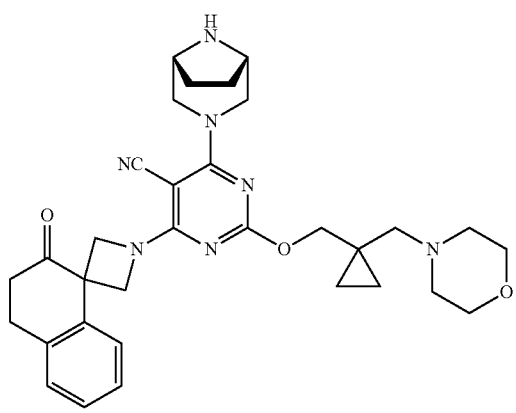

Compound 50 was prepared similarly to that of Ex. 3 using Intermediate 18. LCMS calcld for C$_{32}$H$_{40}$N$_7$O$_3$ (M+H)$^+$ m/z=570.3, found: 570.2. $^1$H NMR (400 MHz, DMSO-d6) δ 7.65 (d, J=8.0 Hz, 1H), 7.39-7.35 (m, 1H), 7.31-7.30 (m, 2H), 4.69 (br, 2H), 4.23-4.20 (m, 2H), 4.15 (s, 4H), 3.58 (br, 2H), 3.53 (br, 5H), 3.23 (d, J=12.0 Hz, 2H), 3.04 (m, 2H), 2.70 (m, 2H), 2.35 (br, 4H), 2.24 (s, 2H), 1.69-1.62 (m, 4H), 0.57 (s, 2H), 0.38 (s, 2H).

Compound 51. 2-amino-1'-[6-(4-cyanoazepan-1-yl)-5-fluoro-2-[[(2R,8S)-2-fluoro-1,2,3,5,6,7-hexahydropyrrolizin-8-yl]methoxy]pyrimidin-4-yl]spiro[5,6-dihydrocyclopenta[b]thiophene-4,3'-azetidine]-3-carbonitrile

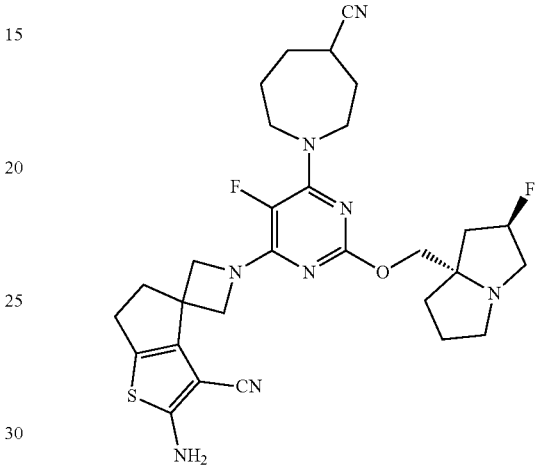

Compound 51 was prepared similarly to that of Ex. 4 as a TFA salt. LCMS calcld for C$_{29}$H$_{35}$F$_2$N$_8$OS (M+H)$^+$ m/z=581.3, found: 581.1. $^1$H NMR (400 MHz, CD$_3$OD) δ 5.54 (dt, J=51.6, 3.5 Hz, 1H), 4.52-4.30 (m, 4H), 4.24 (d, J=8.8 Hz, 2H), 4.04-3.86 (m, 2H), 3.85-3.68 (m, 5H), 3.49-3.39 (m, 1H), 3.04 (d, J=11.3 Hz, 1H), 2.82-2.71 (m, 4H), 2.70-2.45 (m, 2H), 2.39-2.24 (m, 3H), 2.22-1.90 (m, 7H).

Compound 52. 2-amino-1'-[5-cyano-6-[(1R,5S)-3,8-diazabicyclo[3.2.1]octan-3-yl]-2-[[3-[(dimethylamino)methyl]oxetan-3-yl]methoxy]pyrimidin-4-yl]spiro[5,6-dihydrocyclopenta[b]thiophene-4,3'-azetidine]-3-carbonitrile

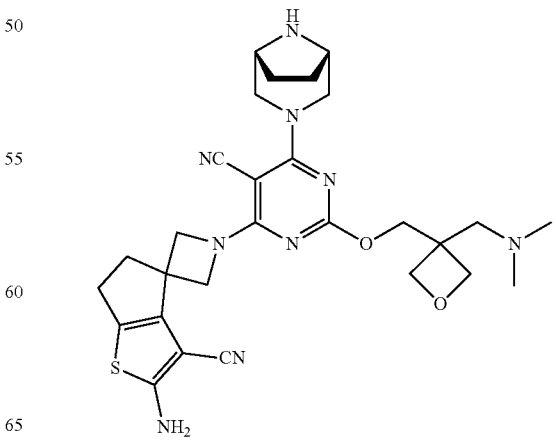

Compound 52 was prepared similarly to that of Ex. 3 as a TFA salt. LCMS calcld for $C_{28}H_{36}N_9O_2S$ (M+H)+ m/z=562.3, found: 562.2. 1H NMR (400 MHz, CD$_3$OD) δ 4.83-4.61 (m, 6H), 4.60-4.35 (m, 6H), 4.24-4.10 (m, 2H), 3.79-3.62 (m, 2H), 3.60-3.42 (m, 2H), 2.91 (s, 6H), 2.81-2.68 (m, 4H), 2.19-1.99 (m, 4H).

Compound 53. 4-[(1R,5S)-3,8-diazabicyclo[3.2.1]octan-3-yl]-6-(2'-hydroxyspiro[azetidine-3,1'-tetralin]-1-yl)-2-[[1-(morpholinomethyl)cyclopropyl]methoxy]pyrimidine-5-carbonitrile

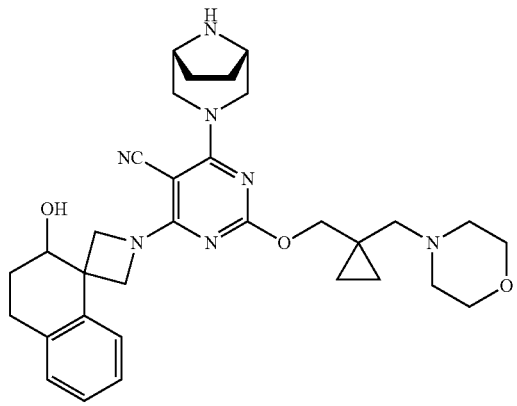

Compound 53 was prepared similarly to that of Ex. 3 as a TFA salt using Intermediate 18. LCMS calcld for $C_{32}H_{42}N_7O_7$ (M+H)+ m/z=572.3, found: 572.2. 1H NMR (DMSO-d$_6$, 400 MHz) δ 7.58 (d, J=8.0 Hz, 1H), 7.26 (t, J=8.0 Hz, 1H), 7.19 (t, J=8.0 Hz, 1H), 7.10 (m, 1H), 5.38 (m, 1H), 4.34 (br, 3H), 4.16 (s, 2H), 4.06 (br, 2H), 3.93-3.90 (m, 1H), 3.54 (m, 5H), 3.43-3.41 (m, 3H), 2.91-2.84 (m, 1H), 2.78-2.63 (m, 1H), 2.37-2.33 (m, 5H), 2.25 (br, 2H), 1.91-1.82 (m, 6H), 1.66 (br, 1H) 0.57 (s, 2H), 0.40 (s, 2H).

Compound 54. [1-[6-(2-amino-3-cyano-spiro[5,6-dihydrocyclopenta[b]thiophene-4,3'-azetidine]-1'-yl)-5-fluoro-2-[[(2R,8S)-2-fluoro-1,2,3,5,6,7-hexahydropyrrolizin-8-yl]methoxy]pyrimidin-4-yl]-3-piperidyl]cyanamide

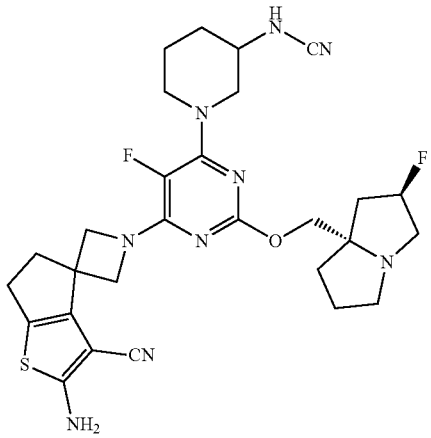

Compound 54 was prepared similarly to that of Ex. 4 as a TFA salt. LCMS calcd for $C_{28}H_{34}F_2N_9OS$ (M+H)+ m/z: 582.3, found: 582.4. 1H NMR (400 MHz, CD$_3$OD) δ 5.54 (d, J=52.1 Hz, 1H), 4.51-4.33 (m, 4H), 4.26-4.15 (m, 3H), 4.03-3.70 (m, 4H), 3.46-3.39 (m, 1H), 3.27-3.22 (m, 3H), 2.90-1.98 (m, 12H), 1.82 (s, 1H), 1.60 (s, 1H).

Compound 55. 2-amino-1'-[5-cyano-6-(6,7-dihydro-4H-triazolo[1,5-a]pyrazin-5-yl)-2-[[(2R,8S)-2-fluoro-1,2,3,5,6,7-hexahydropyrrolizin-8-yl]methoxy]pyrimidin-4-yl]spiro[5,6-dihydrocyclopenta[b]thiophene-4,3'-azetidine]-3-carbonitrile

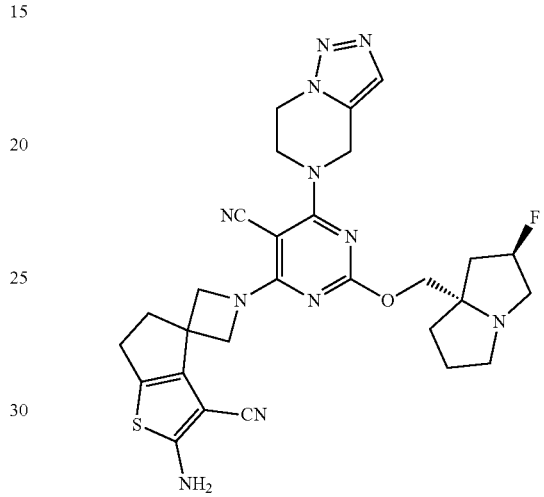

Compound 55 was prepared similarly to that of Ex. 2 as a TFA salt. LCMS calculated for $C_{28}H_{31}FN_{11}OS$ (M+H)+ m/z=588.2, found: 588.2. 1H NMR (400 MHz, CD$_3$OD) δ 7.65 (s, 1H), 5.65-5.46 (m, 1H), 5.12 (s, 2H), 4.75-4.20 (m, 9H), 4.00-3.82 (m, 3H), 3.50-3.40 (m, 1H), 2.82-2.50 (m, 6H), 2.41-2.26 (m, 3H), 2.20-2.10 (m, 1H).

Compound 56. 2-amino-1'-[5-cyano-6-[(1R,5S)-3,8-diazabicyclo[3.2.1]octan-3-yl]-2-[[1-[(4,4-difluoro-1-piperidyl)methyl]cyclopropyl]methoxy]pyrimidin-4-yl]spiro[6,7-dihydro-5H-benzothiophene-4,3'-azetidine]-3-carbonitrile

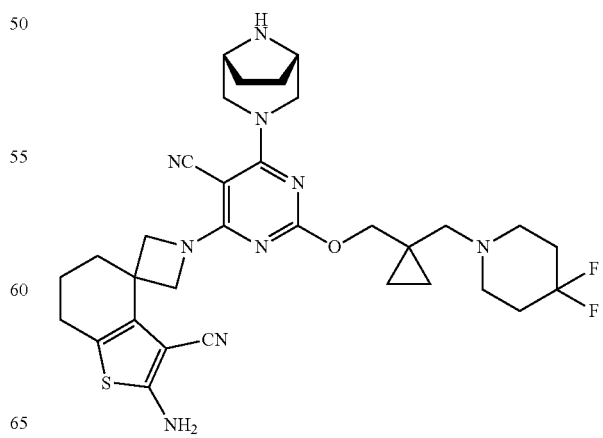

Compound 56 was prepared similarly to that of Ex. 3 as a TFA salt. LCMS calcld for $C_{32}H_{40}F_2N_9OS$ (M+H)$^+$ m/z=636.3, found: 636.2. $^1$H NMR (400 MHz, CD$_3$OD) δ 4.71-4.56 (m, 2H), 4.52 (s, 1H), 4.40 (s, 2H), 4.29 (d, J=16.0 Hz, 2H), 4.16 (s, 2H), 4.00 (s, 1H), 3.61-3.38 (m, 3H), 2.49 (m, 6H), 2.10 (m, 7H), 1.82 (s, 2H), 1.30 (s, 4H), 0.91 (s, 2H), 0.83 (s, 2H).

Compound 57. 2-amino-1'-[5-cyano-2-[(2-methyl-3,4-dihydro-1H-isoquinolin-5-yl)oxy]-6-[(1R,5S)-3,8-diazabicyclo[3.2.1]octan-3-yl]pyrimidin-4-yl]spiro[5,6-dihydrocyclopenta[b]thiophene-4,3'-azetidine]-3-carbonitrile

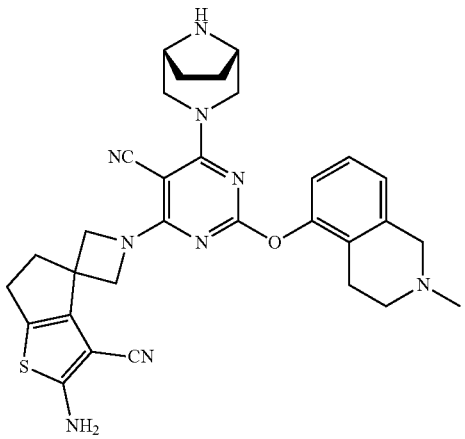

Compound 57 was prepared similarly to that of Ex. 3 as a TFA salt. LCMS calcld for $C_{31}H_{34}N_9O\ S$ (M+H)$^+$ m/z: 580.3, found: 580.4. $^1$H NMR (400 MHz, CD$_3$OD) δ 7.36 (t, J=7.9 Hz, 1H), 7.13 (dd, J=10.9, 7.9 Hz, 2H), 4.73-4.17 (m, 7H), 4.10 (s, 3H), 3.62-3.33 (m, 4H), 3.04 (s, 5H), 2.74-2.70 (m, 4H), 2.04 (s, 4H).

Compound 58. 2-amino-1'-[5-cyano-6-[(1R,5S)-3,8-diazabicyclo[3.2.1]octan-3-yl]-2-[[1-[(3,3-difluoropyrrolidin-1-yl)methyl]cyclopropyl]methoxy]pyrimidin-4-yl]spiro[5,6-dihydrocyclopenta[b]thiophene-4,3'-azetidine]-3-carbonitrile

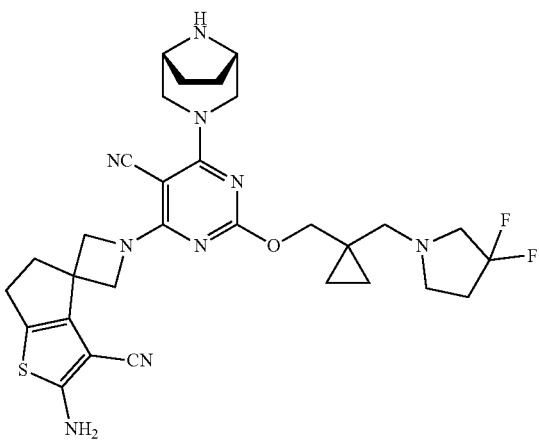

Compound 58 was prepared similarly to that of Ex. 3 as a formate salt. LCMS calcld for $C_{30}H_{36}F_2N_9OS$ (M+H)$^+$ m/z=608.3, found: 608.4. $^1$H NMR (400 MHz, CD$_3$OD) δ 4.58 (s, 6H), 4.24 (s, 2H), 3.63 (s, 2H), 2.88 (d, J=13.3 Hz, 2H), 2.79-2.67 (m, 6H), 2.47 (s, 2H), 2.22-2.15 (m, 3H), 2.03-1.98 (m, 2H), 1.84 (s, 3H), 0.63 (t, J=5.2 Hz, 2H), 0.45 (t, J=5.3 Hz, 2H).

Compound 59. 2-amino-1'-[5-cyano-2-[[(2R,8S)-2-fluoro-1,2,3,5,6,7-hexahydropyrrolizin-8-yl]methoxy]-6-[(4Z)-4-methoxyiminoazepan-1-yl]pyrimidin-4-yl]spiro[5,6-dihydrocyclopenta[b]thiophene-4,3'-azetidine]-3-carbonitrile

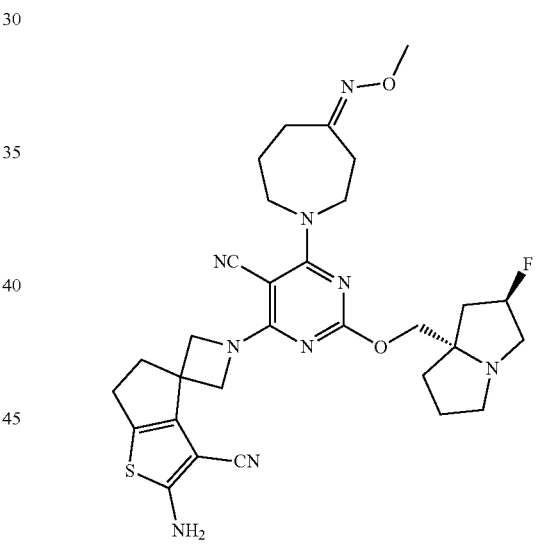

Compound 59 was prepared similarly to that of Ex. 2 as a TFA salt. LCMS calcld for $C_{30}H_{37}FN_9O_2S$ (M+H)$^+$ m/z=606.3, found: 606.2. $^1$H NMR (400 MHz, CD$_3$OD) δ: 5.54 (d, J=51.6 Hz, 1H), 4.57-4.39 (m, 6H), 4.07-3.84 (m, 7H), 3.77-3.76 (m, 3H), 3.48-3.41 (m, 1H), 2.80-2.57 (m, 8H), 2.38-2.29 (m, 3H), 2.27-2.10 (m, 1H), 1.91-1.78 (m, 1H).

Compound 60. 2-amino-1'-[6-[3-chloro-2-(4,5-dimethyl-1,2,4-triazol-3-yl)-4,6,7,8-tetrahydropyrazolo[1,5-a][1,4]diazepin-5-yl]-5-cyano-2-[[(2R,8S)-2-fluoro-1,2,3,5,6,7-hexahydropyrrolizin-8-yl]methoxy]pyrimidin-4-yl]spiro[5,6-dihydrocyclopenta[b]thiophene-4,3'-azetidine]-3-carbonitrile

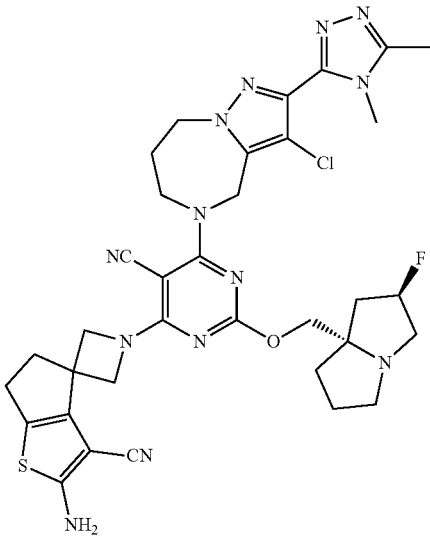 [SMILES: Cc1nnc(-c2nn3c(c2Cl)CN(c2nc(OC[C@@]45CCCN4C[C@H](F)C5)nc(N4CC5(CCc6sc(N)c(C#N)c65)C4)c2C#N)CCC3)n1C]

Compound 60 was prepared similarly to that of Ex. 2 as a TFA salt using Intermediate 15. LCMS calcd for $C_{34}H_{38}ClFN_{13}OS$ (M+H)$^+$ m/z=730.3, found: 730.4. $^1$H NMR (400 MHz, CD$_3$OD) δ: 5.58 (d, J=52 Hz, 1H), 5.14-5.01 (m, 2H), 4.59-4.43 (m, 8H), 4.34-4.25 (m, 2H), 3.98-3.85 (m, 3H), 3.808 (s, 3H), 3.50-3.41 (m, 1H), 2.79-2.72 (m, 4H), 2.69-2.50 (m, 5H), 2.41-2.11 (m, 6H).

Compound 61. 2-amino-1'-[6-[(1R,5S)-8-amino-3-azabicyclo[3.2.1]octan-3-yl]-5-cyano-2-[[1-(morpholinomethyl)cyclopropyl]methoxy]pyrimidin-4-yl]spiro[5,6-dihydrocyclopenta[b]thiophene-4,3'-azetidine]-3-carbonitrile

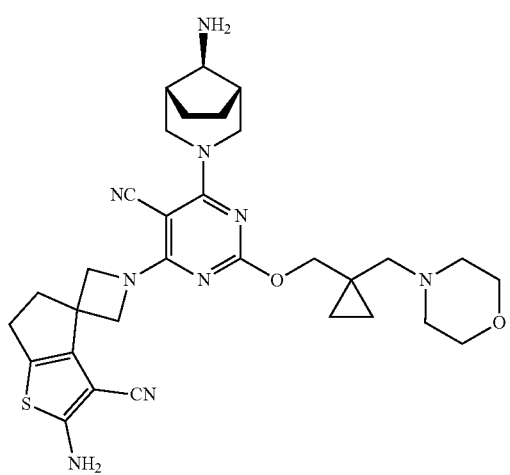

Compound 61 was prepared similarly to that of Ex. 2 as a TFA salt. LCMS calcd for $C_{31}H_{40}N_9O_2S$ (M+H)$^+$ m/z=602.2, found: 602.3. $^1$H NMR (400 MHz, CD$_3$OD) δ: 4.67-4.22 (m, 10H), 4.17-4.00 (m, 3H), 3.98-3.65 (m, 5H), 3.62-3.55 (m, 1H), 3.24-3.09 (m, 2H), 2.86-2.72 (m, 4H), 2.56-2.45 (m, 2H), 1.98-1.76 (m, 4H), 0.98-0.91 (m, 2H), 0.89-0.81 (m, 2H).

Compound 62. 2-amino-1'-[6-[3-chloro-2-(cyclopropanecarbonyl)-4,6,7,8-tetrahydropyrazolo[1,5-a][1,4]diazepin-5-yl]-5-cyano-2-[[(2R,8S)-2-fluoro-1,2,3,5,6,7-hexahydropyrrolizin-8-yl]methoxy]pyrimidin-4-yl]spiro[5,6-dihydrocyclopenta[b]thiophene-4,3'-azetidine]-3-carbonitrile

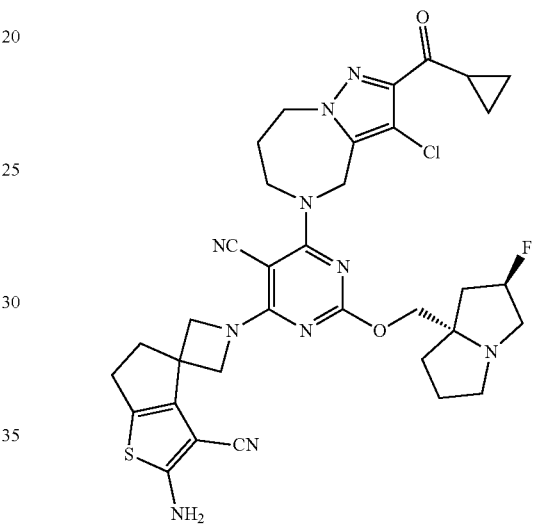

Compound 62 was prepared similarly to that of Ex. 2 as a formate salt using Intermediate 16. LCMS calcd for $C_{34}H_{37}ClFN_{10}O_2S$ (M+H)$^+$ m/z=703.2, found: 703.4. $^1$H NMR (400 MHz, CD$_3$OD) δ 8.51 (s, 1H), 5.37 (d, J=51.0 Hz, 1H), 5.07-4.97 (m, 2H), 4.68-4.38 (m, 6H), 4.29-4.17 (m, 4H), 3.45 (m, 3H), 3.18-3.09 (m, 1H), 3.01 (m, 1H), 2.74 (m, 4H), 2.34 (m, 4H), 2.18-1.96 (m, 3H), 1.92 (s, 1H), 1.09 (m, 2H), 1.02 (m, 2H).

Example 6. Exemplary synthesis of 2-amino-1'-[5-cyano-2-[[1-(morpholinomethyl)cyclopropyl]methoxy]pyrimidin-4-yl]spiro[6,7-dihydro-5H-benzothiophene-4,3'-azetidine]-3-carbonitrile (Compound 63)

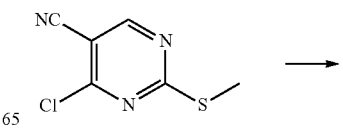

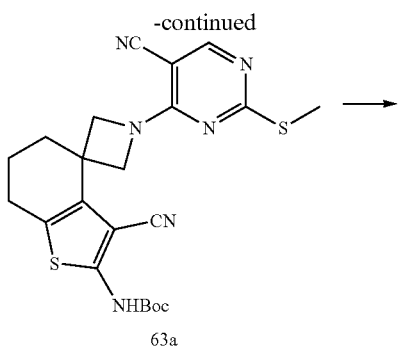

63a

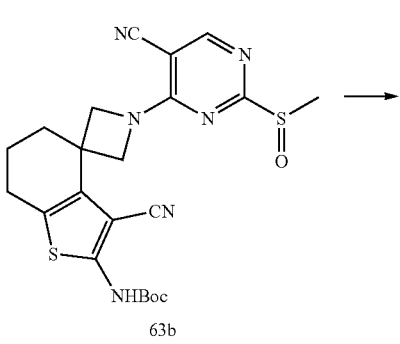

63b

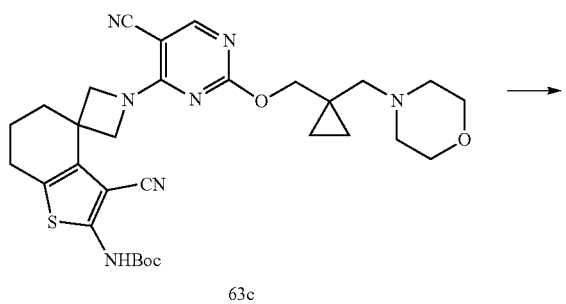

63c

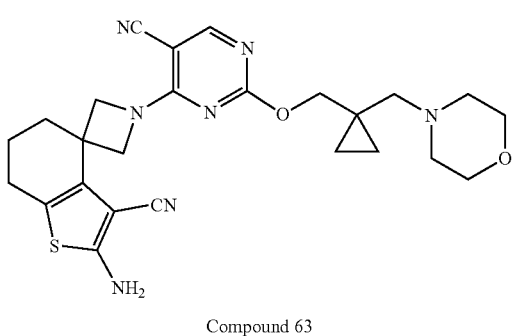

Compound 63

Step 1. Synthesis of tert-butyl N-[3-cyano-1'-(5-cyano-2-methylsulfanyl-pyrimidin-4-yl)spiro[6,7-dihydro-5H-benzothiophene-4,3'-azetidine]-2-yl]carbamate (63a). The solution of 4-chloro-2-methylsulfanyl-pyrimidine-5-carbonitrile (43.59 mg, 0.23 mmol), K$_2$CO$_3$ (108.01 mg, 0.78 mmol) and tert-butyl N-(3-cyanospiro[6,7-dihydro-5H-benzothiophene-4,3'-azetidine]-2-yl)carbamate (50 mg, 0.16 mmol) in IPA (5 mL) was stirred at 50° C. for 1 h. The solvent was removed and purified by silica gel chromatography (PE:EtOAc=3:1) to get tert-butyl N-[3-cyano-1'-(5-cyano-2-methylsulfanyl-pyrimidin-4-yl)spiro[6,7-dihydro-5H-benzothiophene-4,3'-azetidine]-2-yl]carbamate (63a, 45 mg, 0.0960 mmol, 61.35% yield) (crude, white solid). LCMS calculated for C$_{22}$H$_{25}$N$_6$O$_2$S$_2$(M+H)$^+$ m/z=469.1, found: 469.3.

Step 2. Synthesis of tert-butyl N-[3-cyano-1'-(5-cyano-2-methylsulfinyl-pyrimidin-4-yl)spiro[6,7-dihydro-5H-benzothiophene-4,3'-azetidine]-2-yl]carbamate (63b). The solution of oxone (118.07 mg, 0.19 mmol) and tert-butyl N-[3-cyano-1'-(5-cyano-2-methylsulfanyl-pyrimidin-4-yl)spiro[6,7-dihydro-5H-benzothiophene-4,3'-azetidine]-2-yl]carbamate (45 mg, 0.1 mmol) in Water (2 mL) and THF (2 mL) was stirred at 25° C. for 18 h. The mixture was extracted with EtOAc and water, dried with brine and Na$_2$SO$_4$, concentrated to get tert-butyl N-[3-cyano-1'-(5-cyano-2-methylsulfinyl-pyrimidin-4-yl)spiro[6,7-dihydro-5H-benzothiophene-4,3'-azetidine]-2-yl]carbamate (63b, 25 mg, 0.0516 mmol, 53.72% yield) (crude, white solid) LCMS calculated for C$_{22}$H$_{24}$N$_6$NaO$_3$S$_2$(M+Na)$^+$ m/z=507.1, found: 507.3.

Step 3. Synthesis of tert-butyl N-[3-cyano-1'-(5-cyano-2-hydroxy-pyrimidin-4-yl)spiro[6,7-dihydro-5H-benzothiophene-4,3'-azetidine]-2-yl]carbamate (63c). The NaH (12 mg, 0.3 mmol) was put into the solution of [1-(morpholinomethyl)cyclopropyl]methanol (51.37 mg, 0.3 mmol) in DMSO (1.5 mL) at 25° C. After stirring for 1 h, tert-butyl N-[3-cyano-1'-(5-cyano-2-methylsulfinyl-pyrimidin-4-yl)spiro[6,7-dihydro-5H-benzothiophene-4,3'-azetidine]-2-yl]carbamate (63b, 25 mg) and tert-butyl N-[3-cyano-1'-(5-cyano-2-methylsulfonyl-pyrimidin-4-yl)spiro[6,7-dihydro-5H-benzothiophene-4,3'-azetidine]-2-yl]carbamate (25 mg) in DMSO was added, and the mixture was stirred at rt for 1 h. The mixture was quenched with water, extracted with EtOAc, dried with brine and Na$_2$SO$_4$, concentrated and purified by prep-HPLC (DCM:MeOH=20:1) to get tert-butyl N-[3-cyano-1'-[5-cyano-2-[[1-(morpholinomethyl)cyclopropyl]methoxy]pyrimidin-4-yl]spiro[6,7-dihydro-5H-benzothiophene-4,3'-azetidine]-2-yl]carbamate (63c, 30 mg, 0.0507 mmol, 98.27% yield) (light yellow oil). LCMS calculated for C$_{30}$H$_{38}$N$_7$O$_4$S (M+H)$^+$ m/z=592.3, found: 592.4.

Step 4. Synthesis of 2-amino-1'-[5-cyano-2-[[1-(morpholinomethyl)cyclopropyl]methoxy]pyrimidin-4-yl]spiro[6,7-dihydro-5H-benzothiophene-4,3'-azetidine]-3-carbonitrile (Compound 63). The solution of Trifluoroacetic acid (0.06 mL, 0.51 mmol) and tert-butyl N-[3-cyano-1'-[5-cyano-2-[[1-(morpholinomethyl)cyclopropyl]methoxy]pyrimidin-4-yl]spiro[6,7-dihydro-5H-benzothiophene-4,3'-azetidine]-2-yl]carbamate (30 mg, 0.05 mmol) in DCM (3 mL) was stirred at rt for 5 h. The solvent was removed and purified by prep-HPLC (0.1% TFA) to get 2-amino-1'-[5-cyano-2-[[1-(morpholinomethyl)cyclopropyl]methoxy]pyrimidin-4-yl]spiro[6,7-dihydro-5H-benzothiophene-4,3'-azetidine]-3-carbonitrile (Compound 63, 10 mg, 0.0201 mmol, 39.72% yield). LCMS calculated for C$_{25}$H$_{30}$N$_7$O$_2$S (M+H)$^+$ m/z=492.2, found: 492.2. $^1$H NMR (400 MHz, CD$_3$OD) δ 8.39 (s, 1H), 4.87-4.85 (m, 1H), 4.50 (dd, J=22.9, 9.9 Hz, 2H), 4.32 (s, 2H), 4.07 (m, 3H), 3.83 (m, 2H), 3.71 (m, 2H), 3.32-3.26 (m, 2H), 3.19-3.05 (m, 2H), 2.51 (t, J=6.1 Hz, 2H), 2.15 (m, 2H), 1.98-1.75 (m, 2H), 1.02-0.76 (m, 4H).

Compound 64. 2-amino-1'-[5-cyano-2-[[3-(morpholinomethyl)oxetan-3-yl]methoxy]-6-[(1R,5S)-3,8-diazabicyclo[3.2.1]octan-3-yl]pyrimidin-4-yl]spiro[5,6-dihydrocyclopenta[b]thiophene-4,3'-azetidine]-3-carbonitrile Compound 66. 2-amino-1'-[5-cyano-2-[[1-(morpholinomethyl)cyclopropyl]methoxy]pyrimidin-4-yl]spiro[5,6-dihydrocyclopenta[b]thiophene-4,3'-azetidine]-3-carbonitrile

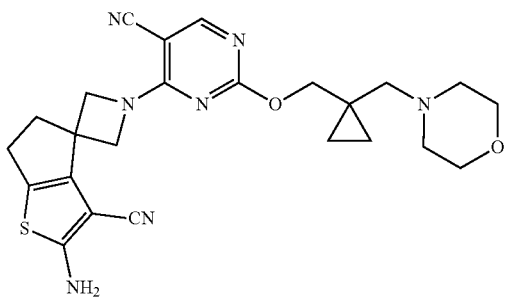

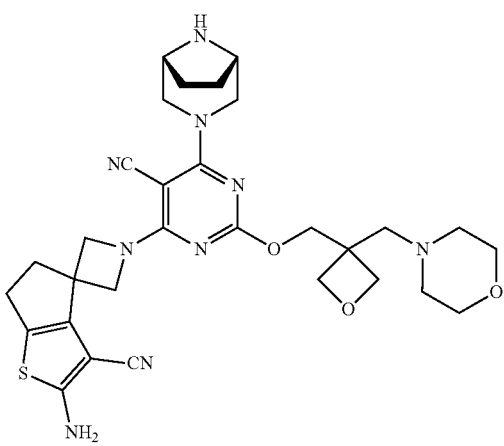

Compound 66 was prepared similarly to that of Ex. 6 as a TFA salt. LCMS calcld for $C_{24}H_{28}N_7O_2S$ (M+H)$^+$ m/z=478.2, found: 478.2. $^1$H NMR (400 MHz, CD$_3$OD) δ 8.40 (s, 1H), 4.75-4.67 (m, 2H), 4.33 (s, 6H), 4.07 (s, 2H), 3.82 (s, 2H), 3.73-3.66 (m, 2H), 3.13 (s, 2H), 2.78 (s, 4H), 0.95 (s, 2H), 0.84 (s, 2H).

Compound 67. 2-amino-1'-[5-cyano-6-(6-methyl-6,7-dihydro-4H-triazolo[1,5-a]pyrazin-5-yl)-2-[[(2R,8S)-2-fluoro-1,2,3,5,6,7-hexahydropyrrolizin-8-yl]methoxy]pyrimidin-4-yl]spiro[5,6-dihydrocyclopenta[b]thiophene-4,3'-azetidine]-3-carbonitrile Compound 64 was prepared similarly to that of Ex. 3 as a TFA salt. LCMS calcld for $C_{30}H_{38}N_9O_3S$ (M+H)$^+$ m/z=604.3, found: 604.1. $^1$H NMR (400 MHz, CD$_3$OD) δ 4.61 (s, 4H), 4.54 (dd, J=14.8, 6.2 Hz, 6H), 3.61 (s, 4H), 3.56 (s, 2H), 2.76 (m, 6H), 2.38 (s, 4H), 1.81 (s, 4H), 1.31 (d, J=17.6 Hz, 4H).

Compound 65. 2-amino-1'-[5-cyano-2-[[(2R,8S)-2-fluoro-1,2,3,5,6,7-hexahydropyrrolizin-8-yl]methoxy]pyrimidin-4-yl]spiro[5,6-dihydrocyclopenta[b]thiophene-4,3'-azetidine]-3-carbonitrile

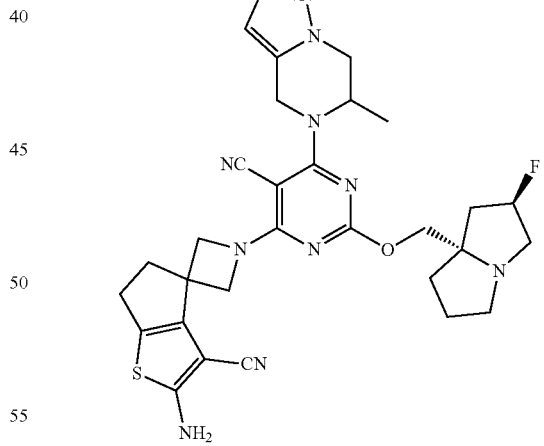

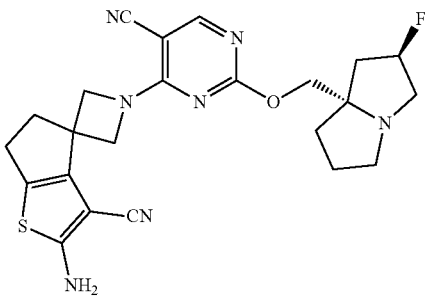 [SMILES: N#Cc1cnc(OC[C@@]23CCCN2C[C@H](F)C3)nc1N1CC2(CCc3sc(N)c(C#N)c32)C1]

Compound 65 was prepared similarly to that of Ex. 6 as a TFA salt. LCMS calcld for $C_{23}H_{25}FN_7OS$ (M+H)$^+$ m/z=466.2, found: 466.3. $^1$H NMR (400 MHz, CDCl$_3$) δ 8.28 (s, 1H), 5.39-5.26 (m, 1H), 4.84 (s, 2H), 4.59 (s, 2H), 4.27 (s, 2H), 3.53 (s, 2H), 3.33-3.25 (m, 1H), 3.05 (s, 1H), 2.82 (d, J=6.4 Hz, 2H), 2.74 (s, 2H), 2.38-2.15 (m, 5H), 2.08-1.98 (m, 3H).

Compound 67 was prepared similarly to that of Ex. 2 as a TFA salt. LCMS calculated for $C_{29}H_{33}FN_{11}OS$ (M+H)$^+$ m/z=602.3, found: 602.2. $^1$H NMR (400 MHz, CD$_3$OD) δ 7.64 (s, 1H), 5.66-5.46 (m, 1H), 5.33-5.22 (m, 1H), 4.86-4.75 (m, 1H), 4.64-4.40 (m, 6H), 4.04-3.81 (m, 4H), 3.51-3.38 (m, 1H), 2.84-2.50 (m, 7H), 2.41-2.24 (m, 3H), 2.20-2.09 (m, 1H), 1.69 (d, J=6.8 Hz, 3H).

Compound 68. 2-amino-1-[5-cyano-2-[[2,2-difluoro-1-(morpholinomethyl)cyclopropyl]methoxy]-6-[(1R,5S)-3,8-diazabicyclo[3.2.1]octan-3-yl]pyrimidin-4-yl]spiro[5,6-dihydrocyclopenta[b]thiophene-4,3'-azetidine]-3-carbonitrile

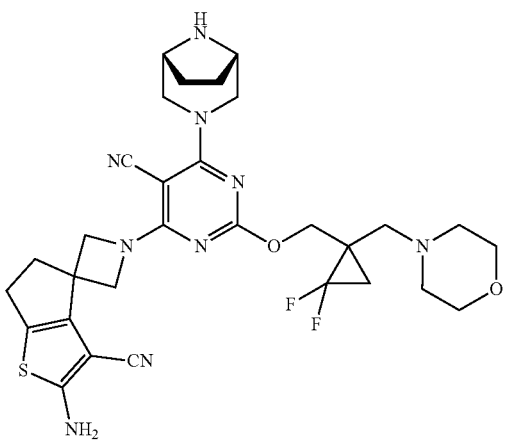

Compound 68 was prepared similarly to that of Ex. 3 as a TFA salt. LCMS calcd for $C_{30}H_{36}F_2N_9O_2S$ (M+H)$^+$ m/z=624.3. found: 624.4. 1H NMR (400 MHz, CD$_3$OD) δ 4.66-4.39 (m, 8H), 4.16 (s, 2H), 3.95 (s, 4H), 3.71-3.44 (m, 4H), 3.36-3.31 (m, 4H), 2.76 (d, J=5.9 Hz, 4H), 2.09 (s, 4H), 1.95-1.65 (m, 2H).

Compound 69. 5-[3-(5-amino-4-cyano-spiro[4,5-dihydro-2H-thieno[2,3-b]thiophene-3,3'-azetidine]-1'-yl)-2-cyano-5-[[(2R,8S)-2-fluoro-1,2,3,5,6,7-hexahydropyrrolizin-8-yl]methoxy]phenyl]-3-chloro-N,N-dimethyl-4,6,7,8-tetrahydropyrazolo[1,5-a][1,4]diazepine-2-carboxamide

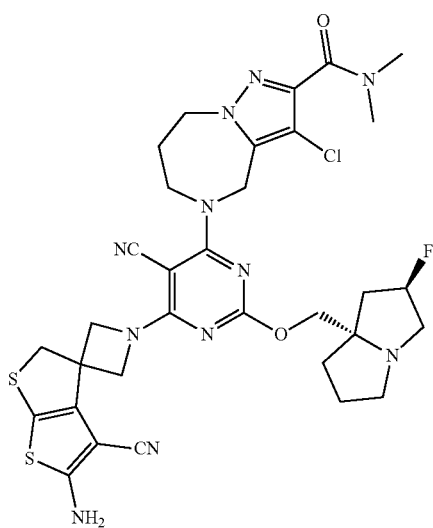 [SMILES: CN(C)C(=O)c1nn2c(c1Cl)CN(c1nc(OC[C@@]34CCCN3C[C@H](F)C4)nc(N3CC4(CSc5sc(N)c(C#N)c54)C3)c1C#N)CCC2]

Compound 69 was prepared similarly to that of Ex. 2 using Intermediate 17. LCMS calcd for $C_{32}H_{36}ClFN_{11}O_2S_2$ (M+H)$^+$ m/z=724.2, found: 724.5. $^1$H NMR (400 MHz, CD$_3$OD) δ 5.25 (d, J=54.6 Hz, 1H), 5.12-5.03 (m, 2H), 4.64-4.52 (m, 2H), 4.53-4.35 (m, 4H), 4.23-4.06 (m, 4H), 4.03 (s, 2H), 3.24-3.12 (m, 3H), 3.09 (s, 3H), 3.08 (s, 3H), 3.02-2.93 (m, 1H), 2.28-1.80 (m, 8H).

Compound 70. 2-amino-1'-[5-cyano-2-[[1-(morpholinomethyl)cyclopropyl]methoxy]-6-[(1R,5S)-3,8-diazabicyclo[3.2.1]octan-3-yl]pyrimidin-4-yl]spiro[5,6,7,8-tetrahydrocyclohepta[b]thiophene-4,3'-azetidine]-3-carbonitrile

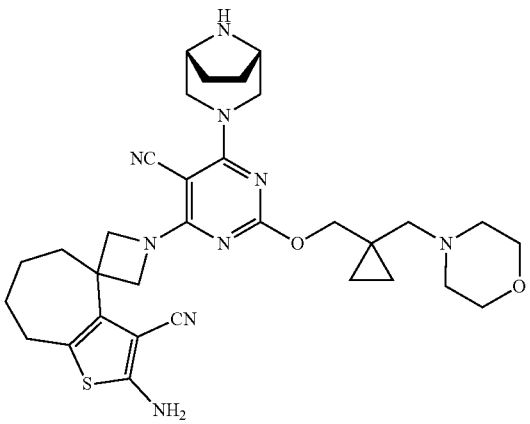

Compound 70 was prepared similarly to that of Ex. 3 as a TFA salt. LCMS calcd for $C_{32}H_{42}N_9O_2S$ (M+H)$^+$ m/z=616.3, found: 616.6. $^1$H NMR (400 MHz, CD$_3$OD) δ 4.80-4.24 (m, 7H), 4.19-4.00 (m, 5H), 3.93-3.67 (m, 4H), 3.60-3.43 (m, 2H), 3.39-3.31 (m, 2H), 3.21-3.06 (m, 2H), 2.85-2.58 (m, 2H), 2.38-2.23 (m, 2H), 2.15-1.99 (m, 4H), 1.93-1.72 (m, 4H), 0.98-0.79 (m, 4H).

Compound 71. 2-amino-1'-[5-cyano-6-[(1R,5S)-3,8-diazabicyclo[3.2.1]octan-3-yl]-2-[[1-[(1-oxo-1,4-thiazinan-4-yl)methyl]cyclopropyl]methoxy]pyrimidin-4-yl]spiro[5,6-dihydrocyclopenta[b]thiophene-4,3'-azetidine]-3-carbonitrile

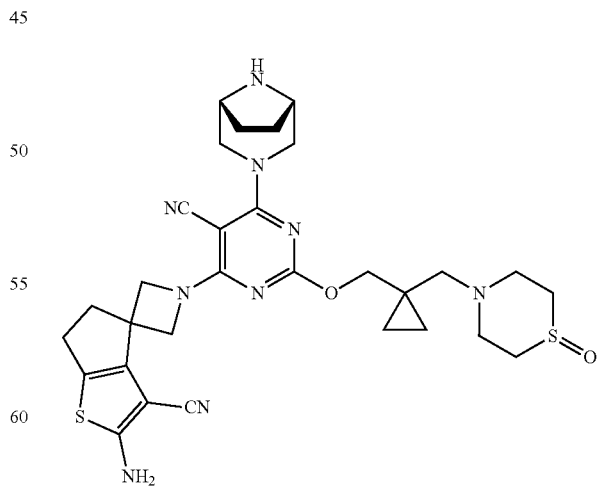

Compound 71 was prepared similarly to that of Ex. 3. LCMS calcld for $C_{30}H_{36}N_9O_2S$ (M−H)$^-$ m/z=618.3, found: 618.2.

Compound 72. 2-amino-1'-[5-cyano-6-[(1R,5S)-3,8-diazabicyclo[3.2.1]octan-3-yl]-2-[[1-(thiomorpholinomethyl)cyclopropyl]methoxy]pyrimidin-4-yl]spiro[5,6-dihydrocyclopenta[b]thiophene-4,3'-azetidine]-3-carbonitrile

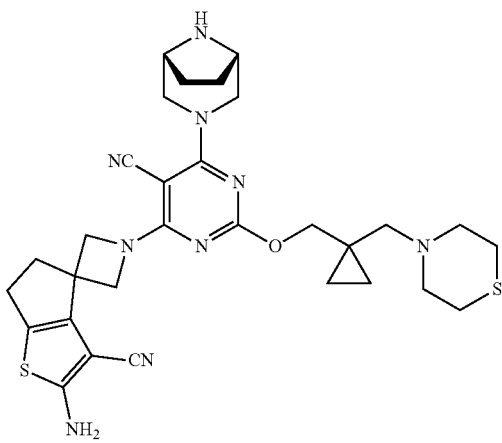

Compound 72 was prepared similarly to that of Ex. 3. LCMS calcld for $C_{30}H_{38}N_9OS_2$ (M+H)$^+$ m/z=604.3, found: 604.1.

Compound 73. 5-amino-1'-[5-cyano-2-[[1-(morpholinomethyl)cyclopropyl]methoxy]-6-[(1R,5S)-3,8-diazabicyclo[3.2.1]octan-3-yl]pyrimidin-4-yl]spiro[2H-thieno[2,3-b]thiophene-3,3'-azetidine]-4-carbonitrile

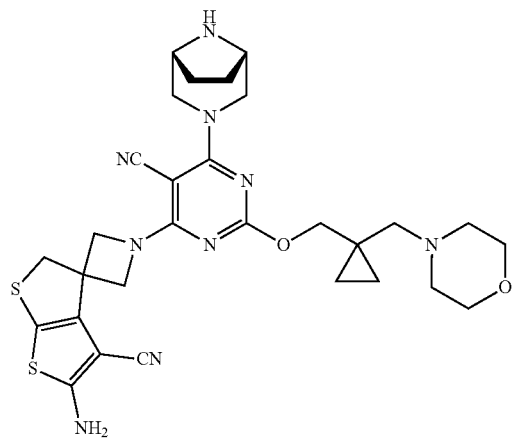

Compound 73 was prepared similarly to that of Ex. 3 as a TFA salt. LCMS calcld for $C_{29}H_{36}N_9O_2S_2$(M+H)$^+$ m/z=606.2, found: 606.1. $^1$H NMR (400 MHz, CD$_3$OD) δ 4.95-4.86 (m, 2H), 4.74-4.44 (m, 5H), 4.30-4.15 (m, 4H), 4.12-3.97 (m, 4H), 3.93-3.62 (m, 4H), 3.55-3.38 (m, 3H), 3.26-3.01 (m, 2H), 2.13-2.03 (m, 4H), 0.95-0.77 (m, 4H).

Compound 74. 2-amino-1'-[5-cyano-6-(3,8-diazabicyclo[3.2.1]octan-3-yl)-2-[[1-[(dimethylamino)methyl]-2,2-difluoro-cyclopropyl]methoxy]pyrimidin-4-yl]spiro[5,6-dihydrocyclopenta[b]thiophene-4,3'-azetidine]-3-carbonitrile

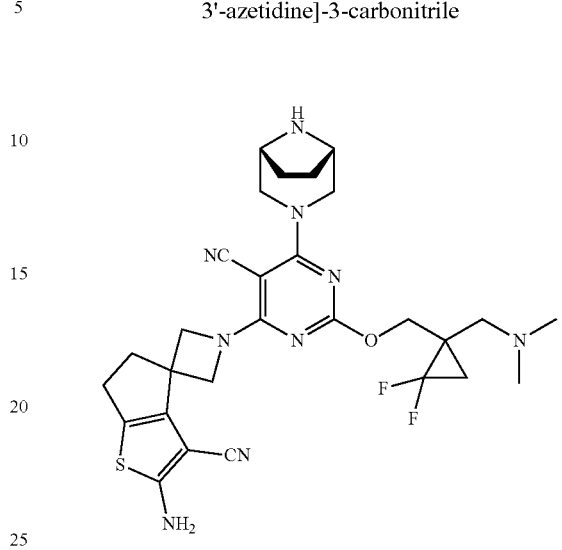

Compound 74 was prepared similarly to that of Ex. 3. LCMS calculated for $C_{28}H_{34}F_2N_9OS$ (m/z)=582.3; found: 582.3. $^1$H NMR (400 MHz, CD$_3$OD) δ 4.16-4.67 (m, 8H), 3.55 (s, 2H), 3.23-3.29 (m, 2H), 2.65-2.85 (m, 5H), 2.38 (d, J=12.8 Hz, 1H), 2.24 (s, 6H), 1.73-1.86 (m, 4H), 1.53-1.66 (m, 1H), 1.27-1.40 (m, 1H).

Compound 74A and 74B. 2-amino-1'-[5-cyano-6-(3,8-diazabicyclo[3.2.1]octan-3-yl)-2-[[(1*)-1-[(dimethylamino)methyl]-2,2-difluoro-cyclopropyl]methoxy]pyrimidin-4-yl]spiro[5,6-dihydrocyclopenta[b]thiophene-4,3'-azetidine]-3-carbonitrile

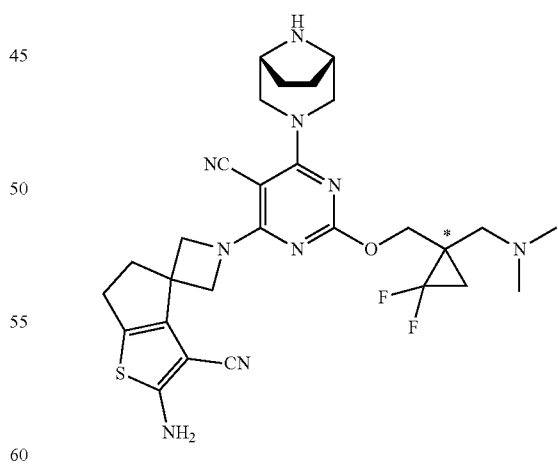

Compound 74 was purified on an DAICELCHIRAL-CEL® AD (250*25 mm 10 mm) column on a Waters SFC 150 system (Mobile Phase A: Supercritical C$_{02}$, Mobile Phase B EtOH [0.5% NH$_3$(7M in MeOH)]=75/25; Flow: 100 ml/min to give faster eluting P1 (74A) and slower eluting P2 (74B).

Compound 75. 2-amino-1'-[6-[3-chloro-2-(2-pyridyl)-4,6,7,8-tetrahydropyrazolo[1,5-a][1,4]diazepin-5-yl]-5-cyano-2-[[1-(morpholinomethyl)cyclopropyl]methoxy]pyrimidin-4-yl]spiro[5,6-dihydrocyclopenta[b]thiophene-4,3'-azetidine]-3-carbonitrile

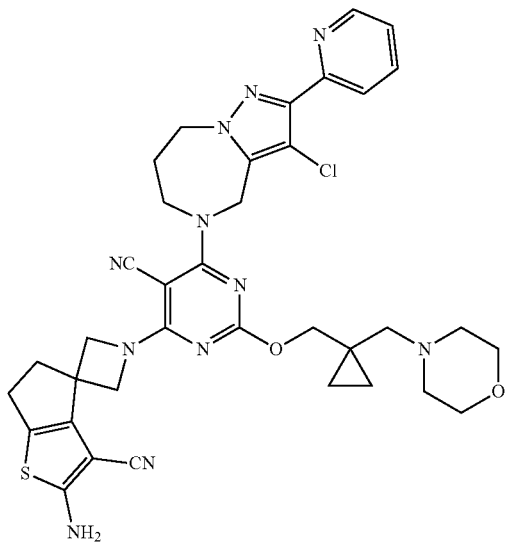 [SMILES: N#Cc1c(N2CCCn3nc(-c4ccccn4)c(Cl)c3C2)nc(OCC2(CN3CCOCC3)CC2)nc1N1CC2(CCc3sc(N)c(C#N)c32)C1]

Compound 75 was prepared similarly to that of Ex. 2 as a TFA salt. LCMS calcld for $C_{36}H_{39}ClN_{11}O_2S$ (M+H)$^+$ m/z=724.3, found: 724.5. $^1$H NMR (400 MHz, CD$_3$OD) δ 8.68 (m, 1H), 8.22 (m, 2H), 7.65 (m, 1H), 4.63-4.41 (m, 5H), 4.39-4.13 (m, 5H), 4.10-3.91 (m, 2H), 3.88-3.51 (m, 4H), 3.29-3.22 (m, 4H), 3.18-2.98 (m, 2H), 2.82-2.65 (m, 4H), 2.37-2.22 (m, 2H), 0.94-0.72 (m, 4H).

Compound 76. 2-amino-1'-[2-benzyloxy-5-cyano-6-[(1R,5S)-3,8-diazabicyclo[3.2.1]octan-3-yl]pyrimidin-4-yl]spiro[5,6-dihydrocyclopenta[b]thiophene-4,3'-azetidine]-3-carbonitrile

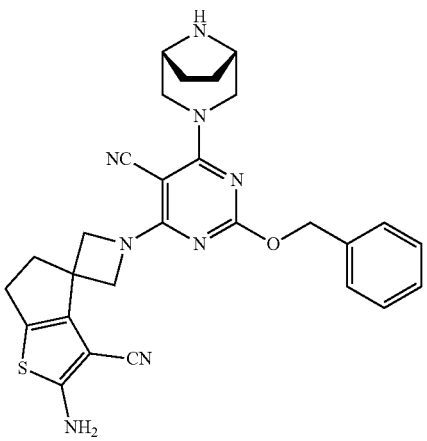

Compound 76 was prepared similarly to that of Ex. 3. LCMS calcld for $C_{28}H_{29}N_8OS$ (M+H)$^+$ m/z=525.2, found: 525.2. $^1$H NMR (400 MHz, CD$_3$OD) δ 7.45-7.37 (m, 2H), 7.37-7.32 (m, 2H), 7.32-7.26 (m, 1H), 5.33 (s, 2H), 4.73-4.11 (m, 6H), 3.63-3.44 (m, 2H), 3.25 (m, 2H), 2.81-2.63 (m, 4H), 1.89-1.55 (m, 4H).

Compound 77. 2-amino-1'-[5-cyano-6-[(1R,5S)-3,8-diazabicyclo[3.2.1]octan-3-yl]-2-[[1-[[(3S)-3-methylmorpholin-4-yl]methyl]cyclopropyl]methoxy]pyrimidin-4-yl]spiro[5,6-dihydrocyclopenta[b]thiophene-4,3'-azetidine]-3-carbonitrile

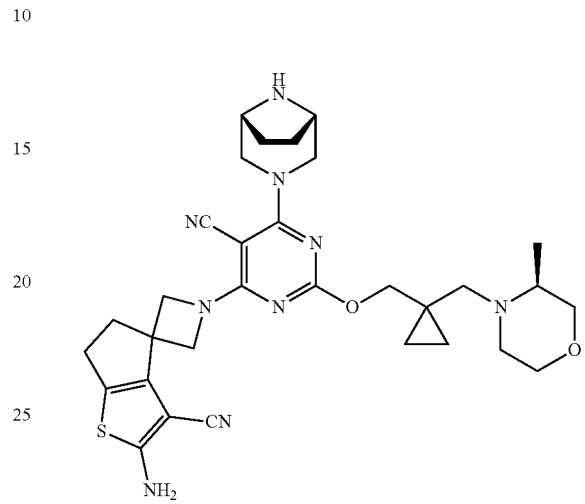

Compound 77 was prepared similarly to that of Ex. 3. LCMS calcld for $C_{31}H_{40}N_9O_2S$ (M+H)$^+$ m/z=602.3, found: 602.2. $^1$H NMR (400 MHz, CD$_3$OD) δ 4.51 (d, J=10.7 Hz, 4H), 4.32 (s, 3H), 3.92 (d, J=10.9 Hz, 1H), 3.72 (m, 3.1 Hz, 1H), 3.67-3.51 (m, 4H), 3.26 (s, 3H), 3.18 (m, 1H), 3.00 (m, 1H), 2.80-2.67 (m, 4H), 2.34 (m, 1H), 2.19 (m, 1H), 1.80 (s, 4H), 1.63 (d, J=12.6 Hz, 1H), 0.91 (d, J=6.3 Hz, 3H), 0.65 (m, 1H), 0.60-0.47 (m, 2H), 0.36 (m, 1H).

Compound 78. 2-amino-1'-[5-cyano-6-[(1R,5S)-3,8-diazabicyclo[3.2.1]octan-3-yl]-2-[[1-[[(3S,4R)-3,4-difluoropyrrolidin-1-yl]methyl]cyclopropyl]methoxy]pyrimidin-4-yl]spiro[5,6-dihydrocyclopenta[b]thiophene-4,3'-azetidine]-3-carbonitrile

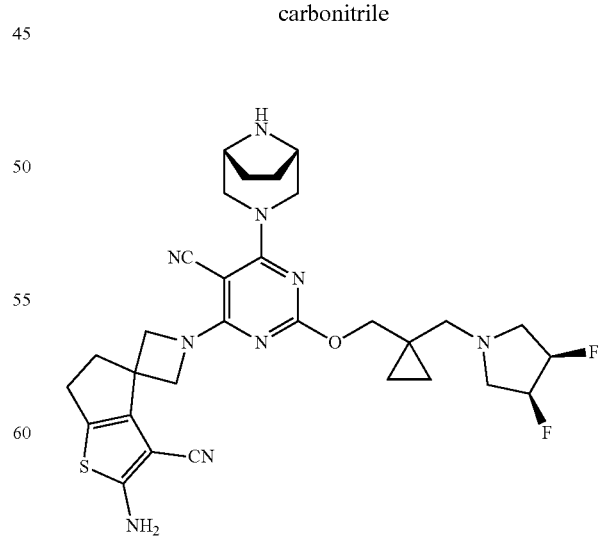

Compound 78 was prepared similarly to that of Ex. 3 as a TFA salt. LCMS calcld for $C_{30}H_{36}F_2N_9OS$ (M+H)$^+$ m/z=608.3, found: 608.3. ¹H NMR (400 MHz, CD₃OD) δ 5.56-5.33 (m, 2H), 4.75-4.20 (m, 5H), 4.27 (s, 2H), 4.19-3.93 (m, 4H), 3.89-3.63 (m, 2H), 3.57-3.32 (m, 5H), 2.83-2.68 (m, 4H), 2.08 (s, 4H), 0.94-0.79 (m, 4H).

Compound 79. 2-amino-1'-[5-cyano-6-[(1R,5S)-3,8-diazabicyclo[3.2.1]octan-3-yl]-2-(1H-pyrazol-5-ylmethoxy)pyrimidin-4-yl]spiro[5,6-dihydrocyclopenta[b]thiophene-4,3'-azetidine]-3-carbonitrile

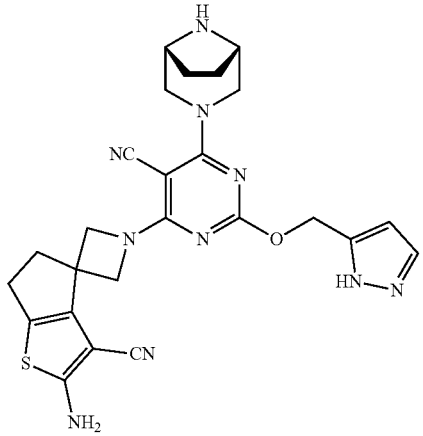

Compound 79 was prepared similarly to that of Ex. 3. LCMS calcd for C₂₅H₂₇N₁₀OS (M+H)⁺ m/z=515.2, found: 515.1. ¹H NMR (400 MHz, CD₃OD) δ 7.59 (s, 1H), 6.39 (d, J=2.0 Hz, 1H), 5.35 (s, 2H), 4.46 (m, 6H), 3.54 (s, 2H), 3.26 (m, 2H), 2.82-2.62 (m, 4H), 1.87-1.64 (m, 4H), 1.30 (s, 1H).

Compound 80. 2-amino-1'-[5-cyano-2-[[1-[(4-methyl-3-oxo-piperazin-1-yl)methyl]cyclopropyl]methoxy]-6-[(1R,5S)-3,8-diazabicyclo[3.2.1]octan-3-yl]pyrimidin-4-yl]spiro[5,6-dihydrocyclopenta[b]thiophene-4,3'-azetidine]-3-carbonitrile

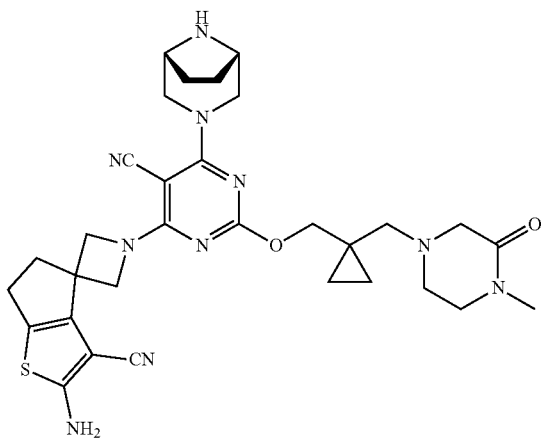

Compound 80 was prepared similarly to that of Ex. 3 as a TFA salt. LCMS calcd for C₃₁H₃₉N₁₀O₂S (M+H)⁺ m/z=615.3, found: 615.2. ¹H NMR (400 MHz, CD₃OD) δ 4.61 (s, 5H), 4.31 (s, 3H), 4.15 (s, 2H), 3.64 (s, 2H), 3.48 (t, J=15.8 Hz, 2H), 2.99 (s, 3H), 2.94-2.84 (m, 2H), 2.82-2.70 (m, 2H), 2.09 (s, 4H), 0.83-0.77 (m, 2H), 0.77-0.71 (m, 2H).

Compound 81. 2-amino-1'-[5-cyano-6-[(1R,5S)-3,8-diazabicyclo[3.2.1]octan-3-yl]-2-[[1-[[(3S,4S)-3-fluoro-4-methoxy-pyrrolidin-1-yl]methyl]cyclopropyl]methoxy]pyrimidin-4-yl]spiro[5,6-dihydrocyclopenta[b]thiophene-4,3'-azetidine]-3-carbonitrile

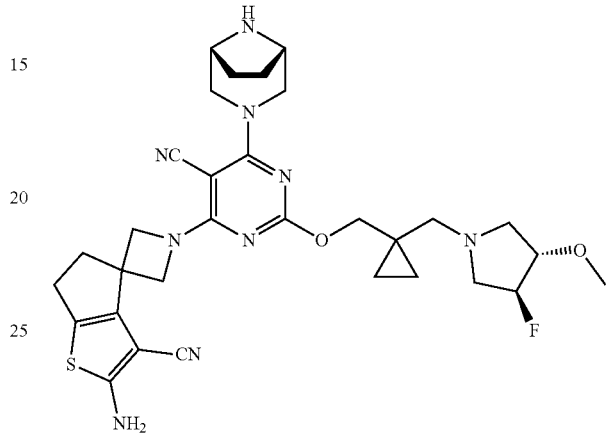

Compound 81 was prepared similarly to that of Ex. 3 as a TFA salt of a mixture of diastereomers. LCMS calcd for C₃₁H₃₉N₉O₂S (M+H)⁺ m/z=620.3, found: 602.3. ¹H NMR (400 MHz, CD₃OD) δ 5.35 (d, J=51.6 Hz, 1H), 4.72-4.40 (m, 5H), 4.38-4.12 (m, 4H), 3.57-3.42 (m, 6H), 3.60-3.42 (m, 7H), 3.33-3.20 (m, 4H), 2.81-2.70 (m, 4H), 0.96-0.76 (m, 4H).

Compound 82. 2-amino-1'-[5-cyano-6-[(1R,5S)-3,8-diazabicyclo[3.2.1]octan-3-yl]-2-[[1-[[(3R)-3-methylmorpholin-4-yl]methyl]cyclopropyl]methoxy]pyrimidin-4-yl]spiro[5,6-dihydrocyclopenta[b]thiophene-4,3'-azetidine]-3-carbonitrile

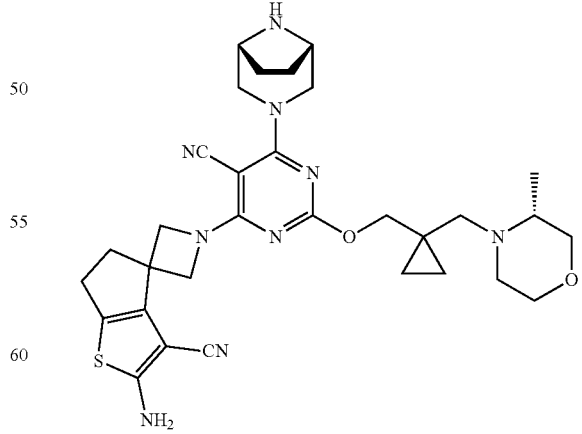

Compound 82 was prepared similarly to that of Ex. 3 as a TFA salt. LCMS calcd for C₃₁H₄₀N₉O₂S (M+H)⁺ m/z=602.3, found: 602.2. ¹H NMR (400 MHz, CD₃OD) δ

4.76-4.39 (m, 5H), 4.38-4.21 (m, 3H), 4.16 (s, 2H), 4.12-3.77 (m, 5H), 3.67-3.55 (m, 1H), 3.56-3.44 (m, 2H), 3.49-3.35 (m, 2H), 3.27-3.09 (m, 1H), 2.81-2.69 (m, 4H), 2.08 (s, 3H), 2.07-1.98 (m, 1H), 1.49-1.32 (m, 3H), 1.07-0.67 (m, 4H).

Compound 83. 2-amino-1'-[5-cyano-6-[(1R,5S)-3,8-diazabicyclo[3.2.1]octan-3-yl]-2-[[(2S)-1-methylpyrrolidin-2-yl]methoxy]pyrimidin-4-yl]spiro[5,6-dihydrocyclopenta[b]thiophene-4,3'-azetidine]-3-carbonitrile

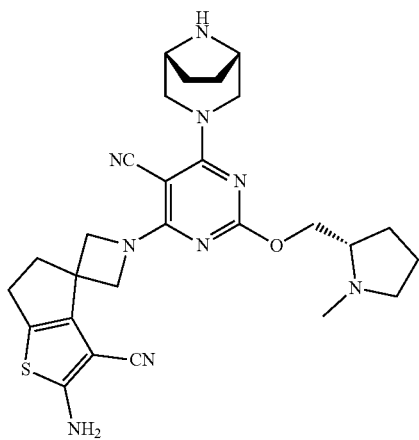

Compound 83 was prepared similarly to that of Ex. 3 as a formate salt. LCMS calcld for $C_{27}H_{34}N_9OS$ (M+H)$^+$ m/z=532.3, found: 532.2. $^1$H NMR (400 MHz, CD$_3$OD) δ 8.44 (s, 2H), 4.68-4.41 (m, 7H), 4.06 (s, 2H), 3.68-3.53 (m, 2H), 3.52-3.41 (m, 2H), 3.15-3.01 (m, 1H), 2.92 (s, 3H), 2.81-2.70 (m, 4H), 2.37-2.24 (m, 1H), 2.15-1.90 (m, 7H).

Compound 84. 2-amino-1'-[5-cyano-6-[(1R,5S)-3,8-diazabicyclo[3.2.1]octan-3-yl]-2-[(1-phenylcyclopropyl)methoxy]pyrimidin-4-yl]spiro[5,6-dihydrocyclopenta[b]thiophene-4,3'-azetidine]-3-carbonitrile

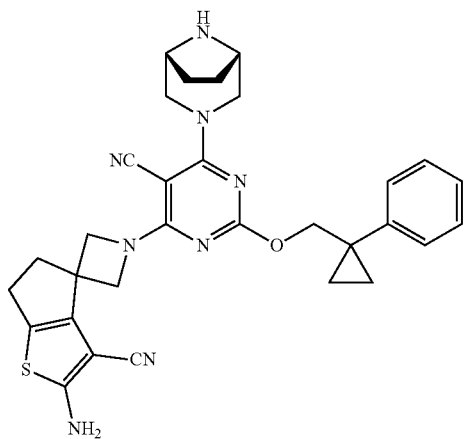

Compound 84 was prepared similarly to that of Ex. 3. LCMS calcld for $C_{31}H_{33}N_8OS$ (M+H)$^+$ m/z=565.2, found: 565.2. $^1$H NMR (400 MHz, CD$_3$OD) δ 7.35 (d, J=7.3 Hz, 2H), 7.25 (t, J=7.5 Hz, 2H), 7.15 (t, J=7.2 Hz, 1H), 4.66-4.47 (m, 2H), 4.47-4.37 (m, 3H), 4.36-4.09 (m, 3H), 3.56 (s, 2H), 3.23 (m, 2H), 2.79-2.65 (m, 4H), 1.89-1.73 (m, 4H), 1.05-0.87 (m, 4H).

Compound 85. 2-amino-1'-[6-[3-chloro-2-(2,5-dimethyl-1,2,4-triazol-3-yl)-4,6,7,8-tetrahydropyrazolo[1,5-a][1,4]diazepin-5-yl]-5-cyano-2-[[(2R,8S)-2-fluoro-1,2,3,5,6,7-hexahydropyrrolizin-8-yl]methoxy]pyrimidin-4-yl]spiro[5,6-dihydrocyclopenta[b]thiophene-4,3'-azetidine]-3-carbonitrile

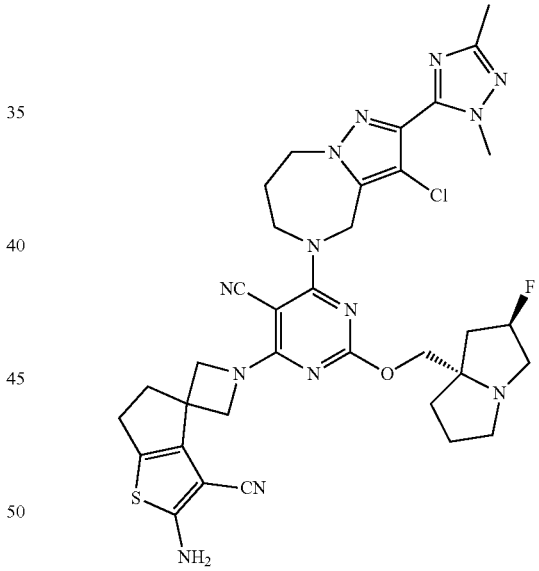

Compound 85 was prepared similarly to that of Ex. 2 as a TFA salt. LCMS calculated for $C_{34}H_{38}ClFN_{13}OS$ (M+H)$^+$ m/z=730.3, found: 730.2. $^1$H NMR (400 MHz, CD$_3$OD) δ 5.55 (d, J=51.6 Hz, 1H), 5.17-4.98 (m, 2H), 4.70-4.17 (m, 10H), 3.99 (s, 3H), 3.98-3.79 (m, 3H), 3.51-3.35 (m, 1H), 2.82-2.44 (m, 6H), 2.40-2.22 (m, 8H), 2.17-2.04 (m, 1H).

Compound 86. 2-amino-1'-[5-cyano-2-[[1-(morpholinomethyl)cyclopropyl]methoxy]-6-[(1R,5S)-3,8-diazabicyclo[3.2.1]octan-3-yl]pyrimidin-4-yl]spiro[7H-benzothiophene-4,3'-azetidine]-3-carbonitrile

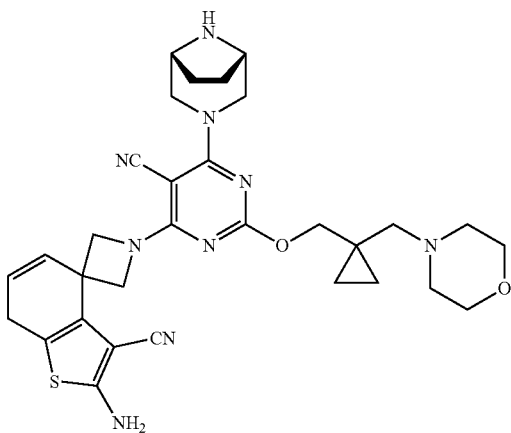

Compound 86 was prepared similarly to that of Ex. 3. LCMS calculated for $C_{31}H_{38}N_9O_2S$ (M+H)$^+$ m/z=600.3, found: 600.2. $^1$H NMR (400 MHz, CD$_3$OD) δ: 6.18-5.98 (m, 2H), 4.84-4.77 (m, 1H), 4.60-4.57 (m, 1H), 4.49-4.40 (m, 1H), 4.24-4.18 (m, 2H), 4.17-4.12 (m, 1H), 3.66-3.57 (m, 8H), 3.27-3.18 (m, 4H), 2.47-2.37 (m, 6H), 1.87-1.80 (m, 4H), 0.65-0.61 (m, 2H), 0.46-0.43 (m, 2H).

Compound 87. 5-[6-(2-amino-3-cyano-spiro[5,6-dihydrocyclopenta[b]thiophene-4,3'-azetidine]-1'-yl)-5-cyano-2-[[1-[(dimethylamino)methyl]-2,2-difluoro-cyclopropyl]methoxy]pyrimidin-4-yl]-3-chloro-N,N-dimethyl-4,6,7,8-tetrahydropyrazolo[1,5-a][1,4]diazepine-2-carboxamide

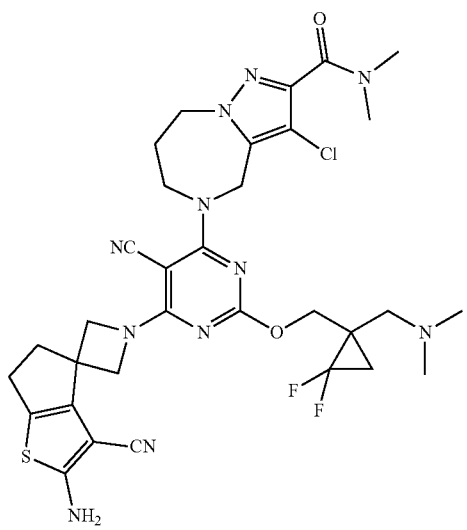 [SMILES: CN(C)CC1(COc2nc(N3CCCn4nc(C(=O)N(C)C)c(Cl)c4C3)c(C#N)c(N3CC4(CCc5sc(N)c(C#N)c54)C3)n2)CC1(F)F]

Compound 87 was prepared similarly to that of Ex. 2. LCMS calculated for $C_{32}H_{37}ClF_2N_{11}O_2S$ (M+H)$^+$ m/z=712.2; found: 712.3. $^1$H NMR (400 MHz, CD$_3$OD) δ 5.08 (s, 2H), 4.58 (s, 2H), 4.45-4.49 (m, 2H), 4.42 (s, 2H), 4.19 (s, 2H), 3.08 (d, J=2.8 Hz, 6H), 2.69-2.79 (m, 4H), 2.45 (s, 1H), 2.28 (s, 7H), 1.60 (s, 2H), 1.26-1.38 (m, 5H), 0.86-0.99 (m, 1H).

Compound 88. 2-amino-1'-[5-cyano-6-[(1R,5S)-3,8-diazabicyclo[3.2.1]octan-3-yl]-2-[(1S)-1-[(2S)-1-methylpyrrolidin-2-yl]ethoxy]pyrimidin-4-yl]spiro[5,6-dihydrocyclopenta[b]thiophene-4,3'-azetidine]-3-carbonitrile

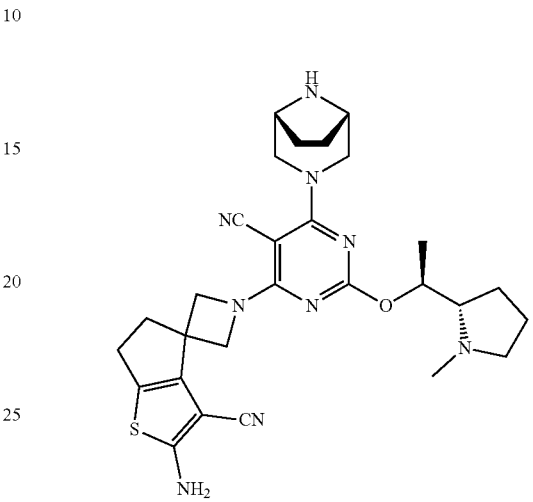

Compound 88 was prepared similarly to that of Ex. 3 as a formate salt. LCMS calcld for $C_{28}H_{36}N_9O\ S$ (M+H)$^+$ m/z=546.3, found: 546.2. $^1$H NMR (400 MHz, CD$_3$OD) δ 8.46 (s, 2H), 5.26-5.14 (m, 1H), 4.69-4.34 (m, 5H), 4.01 (s, 2H), 3.58-3.40 (m, 4H), 3.14-3.02 (m, 1H), 2.95 (s, 3H), 2.83-2.69 (m, 4H), 2.37-2.24 (m, 1H), 2.16-2.07 (m, 1H), 2.06-1.96 (m, 6H), 1.92-1.82 (m, 1H), 1.41 (d, J=6.1 Hz, 3H).

Compound 89. 2-amino-1'-[5-cyano-6-[(1R,5S)-3,8-diazabicyclo[3.2.1]octan-3-yl]-2-[[1-[[(1S,4S)-2-oxa-5-azabicyclo[2.2.1]heptan-5-yl]methyl]cyclopropyl]methoxy]pyrimidin-4-yl]spiro[5,6-dihydrocyclopenta[b]thiophene-4,3'-azetidine]-3-carbonitrile

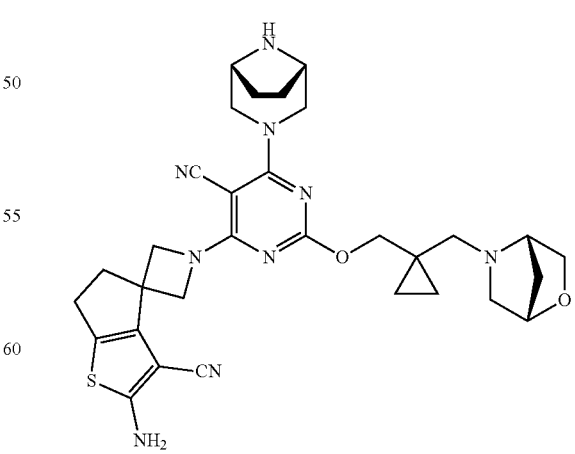

Compound 89 was prepared similarly to that of Ex. 3 as a TFA salt. LCMS calcld for $C_{31}H_{38}N_9O_2S$ (M+H)$^+$ m/z=600.3, found: 600.3. $^1$H NMR (400 MHz, CD$_3$OD) δ 5.05-4.88 (m, 2H), 4.74-4.44 (m, 6H), 4.40-4.07 (m, 5H), 4.01-3.75 (m, 2H), 3.67-3.41 (m, 3H), 3.22-2.94 (m, 2H), 2.85-2.62 (m, 4H), 2.32-1.98 (m, 6H), 1.10-0.74 (m, 4H).

Compound 90. 2-amino-1'-[5-cyano-6-[(1R,5S)-3,8-diazabicyclo[3.2.1]octan-3-yl]-2-[(4-fluoro-1H-pyrazol-5-yl)methoxy]pyrimidin-4-yl]spiro[5,6-dihydrocyclopenta[b]thiophene-4,3'-azetidine]-3-carbonitrile

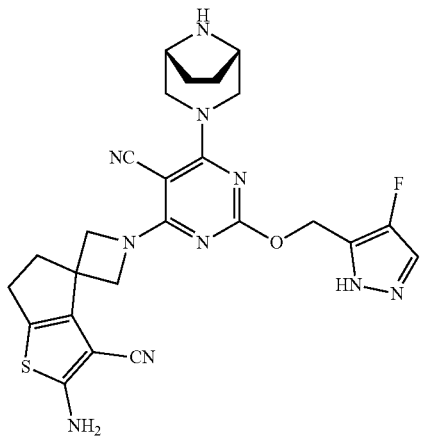

Compound 90 was prepared similarly to that of Ex. 3. LCMS calcld for C$_{25}$H$_{26}$FN$_{10}$OS (M+H)$^+$ m/z=533.2, found: 533.3. $^1$H NMR (400 MHz, CD$_3$OD) δ 8.46 (d, J=4.6 Hz, 1H), 4.67 (s, 2H), 4.66-4.60 (m, 2H), 4.59-4.26 (m, 4H), 3.63-3.53 (m, 2H), 3.39-3.32 (m, 2H), 2.89-2.65 (m, 4H), 1.87-1.74 (m, 4H).

Example 7. preparation of 5-[6-(2-amino-3-cyano-spiro[5,6-dihydrocyclopenta[b]thiophene-4,3'-azetidine]-1'-yl)-5-cyano-2-[[(2R,8S)-2-fluoro-1,2,3,5,6,7-hexahydropyrrolizin-8-yl]methoxy]pyrimidin-4-yl]-3-chloro-7,7-difluoro-N,N-dimethyl-6,8-dihydro-4H-pyrazolo[1,5-a][1,4]diazepine-2-carboxamide TFA salt Compound 91

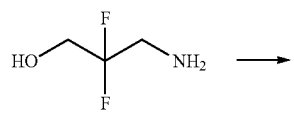

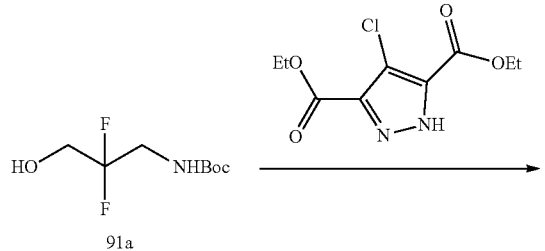

91a

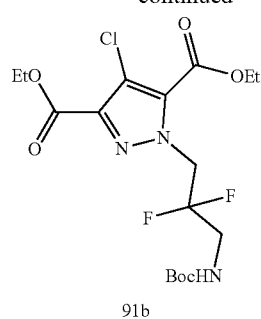

91b

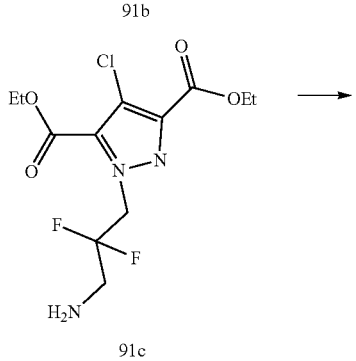

91c

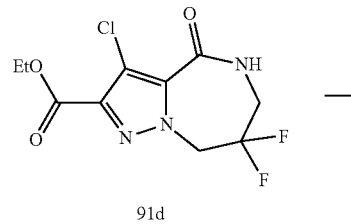

91d

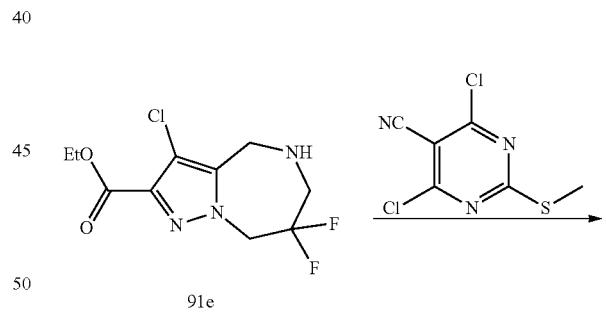

91e

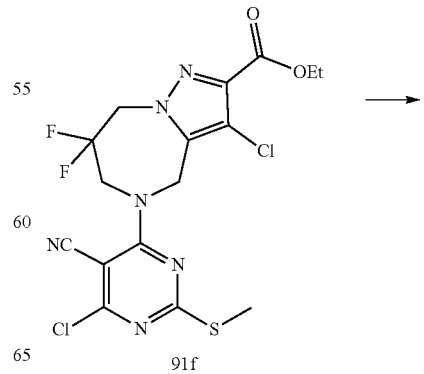

91f

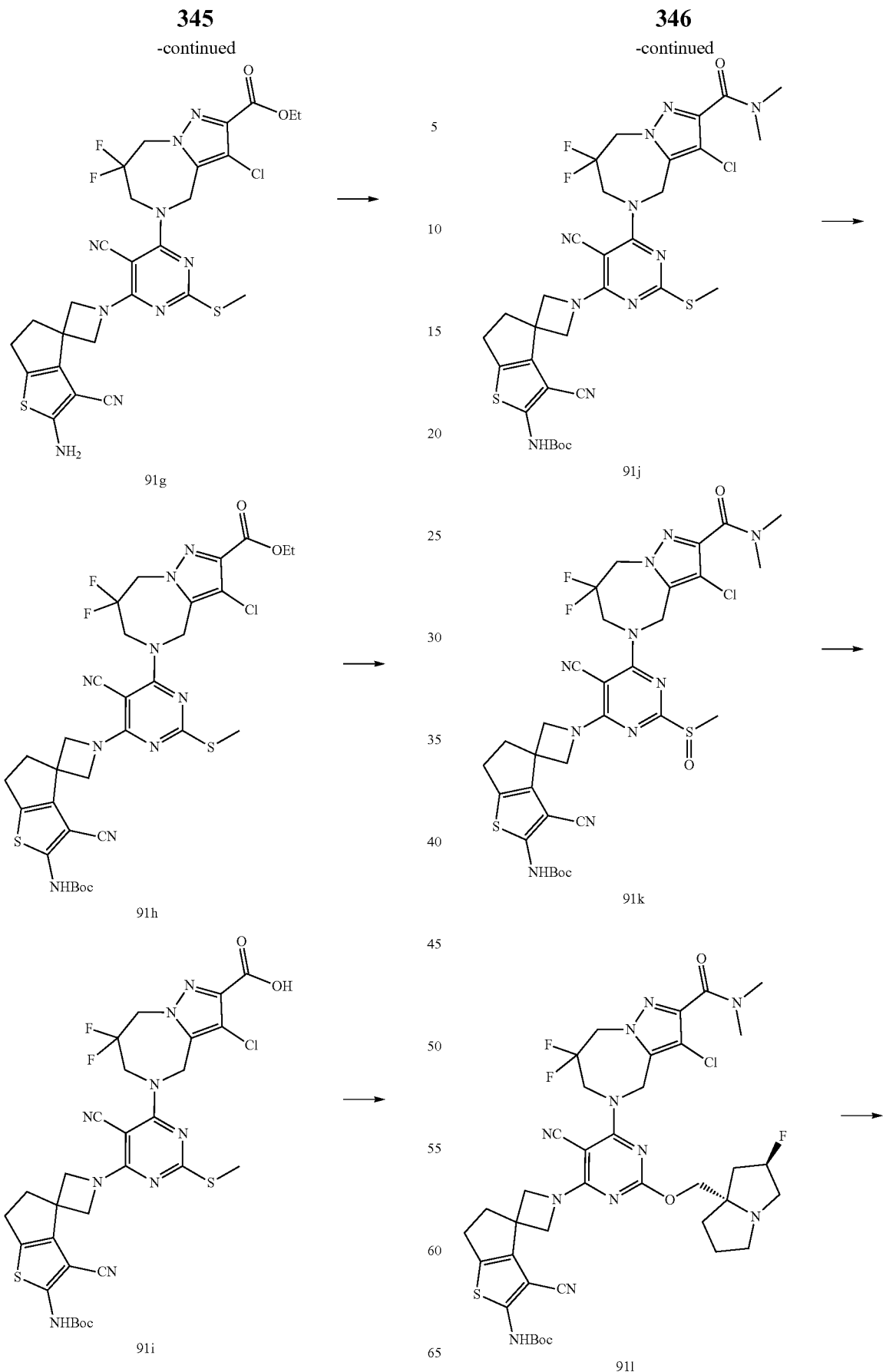

-continued

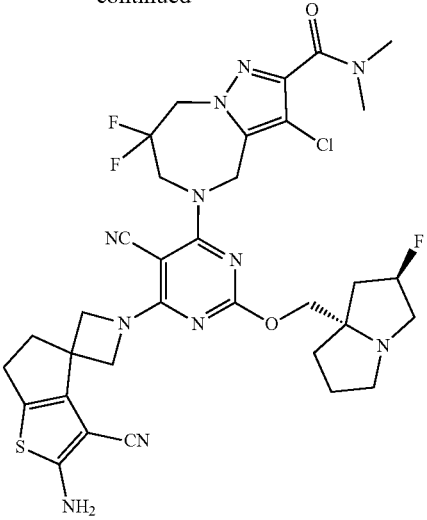

Compound 91

Step 1. Preparation of tert-butyl N-(2,2-difluoro-3-hydroxy-propyl)carbamate (91a)

To a solution of 3-amino-2,2-difluoro-propan-1-ol (2 g, 18 mmol) in THF (20 mL) and water (20 mL), was added Boc₂O (3.93 g, 18 mmol), and the reaction mixture was stirred at 25° C. for 16 h. The mixture was evaporated under reduced pressure to give crude product, and then the mixture was extracted by EtOAc (10 ml×3), washed by brine (10 ml×2), dried over Na₂SO₄, concentrated. The crude product was washed with hexane to afford tert-butyl N-(2,2-difluoro-3-hydroxy-propyl)carbamate (3.10 g, 14.7 mmol, 81.53%) yield as white solid.

Step 2. Preparation of diethyl 1-[3-(tert-butoxycarbonylamino)-2,2-difluoro-propyl]-4-chloro-pyrazole-3,5-dicarboxylate (91b)

To a solution of diethyl 4-chloro-TH-pyrazole-3,5-dicarboxylate (1 g, 4.05 mmol) and PPh3 (2.12 g, 8.11 mmol) in THF (5 mL), was added tert-butyl N-(2,2-difluoro-3-hydroxy-propyl)carbamate (91a, 1.71 g, 8.11 mmol) and BTBAD (1867.1 mg, 8.11 mmol), and the reaction mixture was stirred at 120° C. for 1 h in microwave. The mixture was concentrated to afford a crude product diethyl 1-[3-(tert-butoxycarbonylamino)-2,2-difluoro-propyl]-4-chloro-pyrazole-3,5-dicarboxylate (91b, 1.50 g) as a yellow oil. LCMS calcld for $C_{17}H_{25}ClF_2N_3O_6$ $(M+H)^+$ m/z=440.1, found: 384.0 (-tBu).

Step 3. Preparation of diethyl 1-(3-amino-2,2-difluoro-propyl)-4-chloro-pyrazole-3,5-dicarboxylate; hydrochloride (91c)

To a solution of diethyl 1-[3-(tert-butoxycarbonylamino)-2,2-difluoro-propyl]-4-chloro-pyrazole-3,5-dicarboxylate (91b, 3 g, 6.82 mmol) in 1,4-dioxane (45 mL), was added HCl/dioxane (4713.42 mg, 34.1 mmol), and the reaction mixture was stirred at 25° C. for 2 h. The mixture was concentrated to afford the crude product diethyl 1-(3-amino-2,2-difluoro-propyl)-4-chloro-pyrazole-3,5-dicarboxylate; hydrochloride (91c, 2.50 g) as a yellow solid. LCMS calcld for $C_{12}H_{17}ClF_2N_3O_4$ $(M+H)^+$ m/z=340.1, found: 340.1.

Step 4. Preparation of N,N-diethylethanamine; ethyl 3-chloro-7,7-difluoro-4-oxo-6,8-dihydro-5H-pyrazolo[1,5-a][1,4]diazepine-2-carboxylate; hydrochloride (91d)

To a solution of diethyl 1-(3-amino-2,2-difluoro-propyl)-4-chloro-pyrazole-3,5-dicarboxylate; hydrochloride (91c, 2.77 g, 7.36 mmol) in ethanol (42 mL), was added Et₃N (20.54 mL, 147.18 mmol), and the reaction mixture was stirred at 70° C. for 24 h. The mixture was concentrated and then purified by silica gel chromatography (eluted with CH₃CN in H₂O from 5.0% to 95%) to afford N,N-diethylethanamine; ethyl 3-chloro-7,7-difluoro-4-oxo-6,8-dihydro-5H-pyrazolo[1,5-a][1,4]diazepine-2-carboxylate; hydrochloride (91d, 1.80 g, 2.24 mmol, 30.40% yield) as a white solid. LCMS calcld for $C_{10}H_{11}ClF_2N_3O_3$ $(M+H)^+$ m/z=294.6, found: 294.6.

Step 5. Preparation of ethyl 3-chloro-7,7-difluoro-4,5,6,8-tetrahydropyrazolo[1,5-a][1,4]diazepine-2-carboxylate (91e)

To a solution of ethyl 3-chloro-7,7-difluoro-4-oxo-6,8-dihydro-5H-pyrazolo[1,5-a][1,4]diazepine-2-carboxylate (91d, 200 mg, 0.37 mmol) in THF (5 mL), was added BH₃ in SMe₂ (55.42 mg, 1.46 mmol), and the reaction mixture was stirred at 60° C. for 3 h. The mixture was diluted with CH₃OH (5 mL), and then the mixture was stirred at 60° C. for 3 h. The crude product was not purified. Ethyl 3-chloro-7,7-difluoro-4,5,6,8-tetrahydropyrazolo[1,5-a][1,4]diazepine-2-carboxylate (91e, 35 mg) was obtained as a colorless oil. LCMS calcld for $C_{10}H_{13}ClF_2N_3O_2(M+H)^+$ m/z=280.1, found: 280.1.

Step 6. Preparation of ethyl 3-chloro-5-(6-chloro-5-cyano-2-methylsulfanyl-pyrimidin-4-yl)-7,7-difluoro-6,8-dihydro-4H-pyrazolo[1,5-a][1,4]diazepine-2-carboxylate (91f)

To a solution of ethyl 3-chloro-7,7-difluoro-4,5,6,8-tetrahydropyrazolo[1,5-a][1,4]diazepine-2-carboxylate (200 mg, 0.72 mmol) in THF (10 mL), was added 4,6-dichloro-2-methylsulfanyl-pyrimidine-5-carbonitrile (91e, 157.39 mg, 0.72 mmol) and DIEA (138.63 mg, 1.07 mmol), and the reaction mixture was stirred at 40° C. for 3 h. The mixture was concentrated to afford a crude product. The crude product was purified by silica gel chromatography/flash chromatography (eluted with CH₃CN in H₂O from 5.0% to 95%); ethyl 3-chloro-5-(6-chloro-5-cyano-2-methylsulfanyl-pyrimidin-4-yl)-7,7-difluoro-6,8-dihydro-4H-pyrazolo[1,5-a][1,4]diazepine-2-carboxylate (91f, 270 mg, 0.583 mmol, 81.49% yield) was obtained as white solid. LCMS calcld for $C_{16}H_{15}Cl_2F_2N_6O_2S$ $(M+H)^+$ m/z=463.02, found: 463.02.

Step 7. Preparation of ethyl 5-[6-(2-amino-3-cyano-spiro[5,6-dihydrocyclopenta[b]thiophene-4,3'-azetidine]-1'-yl)-5-cyano-2-methylsulfanyl-pyrimidin-4-yl]-3-chloro-7,7-difluoro-6,8-dihydro-4H-pyrazolo[1,5-a][1,4]diazepine-2-carboxylate (91g)

To a solution of ethyl 3-chloro-5-(6-chloro-5-cyano-2-methylsulfanyl-pyrimidin-4-yl)-7,7-difluoro-6,8-dihydro-4H-pyrazolo[1,5-a][1,4]diazepine-2-carboxylate (91f, 100 mg, 0.22 mmol) in 1,4-dioxane (1 mL) was added DIEA (55.79 mg, 0.43 mmol) and 2-aminospiro[5,6-dihydrocyclopenta[b]thiophene-4,3'-azetidine]-3-carbonitrile (44.31 mg, 0.22 mmol) at 25° C. The mixture was stirred at 50° C. for 1 h. The mixture was concentrated, then purified by silica gel on chromatography (eluting with EtOAc in PE from 0% to 50%). The product ethyl 5-[6-(2-amino-3-cyano-spiro[5,6-dihydrocyclopenta[b]thiophene-4,3'-azetidine]-1'-yl)-5-cyano-2-methylsulfanyl-pyrimidin-4-yl]-3-chloro-7,7-difluoro-6,8-dihydro-4H-pyrazolo[1,5-a][1,4]diazepine-2-carboxylate (91 g, 135 mg, 0.214 mmol, 98.95% yield) was obtained as a white solid. LCMS calcld for $C_{26}H_{25}ClF_2N_9O_2S_2(M+H)^+$ m/z=632.1, found: 632.0.

Step 8. Preparation of ethyl 5-[6-[2-(tert-butoxycarbonylamino)-3-cyano-spiro[5,6-dihydrocyclopenta[b]thiophene-4,3'-azetidine]-1'-yl]-5-cyano-2-methylsulfanyl-pyrimidin-4-yl]-3-chloro-7,7-difluoro-6,8-dihydro-4H-pyrazolo[1,5-a][1,4]diazepine-2-carboxylate (91h)

To a solution of ethyl 5-[6-(2-amino-3-cyano-spiro[5,6-dihydrocyclopenta[b]thiophene-4,3'-azetidine]-1'-yl)-5-cyano-2-methylsulfanyl-pyrimidin-4-yl]-3-chloro-7,7-difluoro-6,8-dihydro-4H-pyrazolo[1,5-a][1,4]diazepine-2-carboxylate (91g, 135 mg, 0.21 mmol) in MeCN (1 mL) was added DMAP (2.61 mg, 0.02 mmol) and Boc$_2$O (16.21 mg, 0.43 mmol) at 25° C., The mixture was stirred at 25° C. for 1 h. The mixture was purified by silica gel on chromatography (eluting with EtOAc in PE from 0% to 50%). The mixture of product ethyl 5-[6-[2-(tert-butoxycarbonylamino)-3-cyano-spiro[5,6-dihydrocyclopenta[b]thiophene-4,3'-azetidine]-1'-yl]-5-cyano-2-methylsulfanyl-pyrimidin-4-yl]-3-chloro-7,7-difluoro-6,8-dihydro-4H-pyrazolo[1,5-a][1,4]diazepine-2-carboxylate (91h, 145 mg, 0.198 mmol, 92.72% yield). LCMS calcld for $C_{31}H_{33}ClF_2N_9O_4S_2(M+H)^+$ m/z=732.2, found: 732.0.

Step 9. Preparation of 5-[6-[2-(tert-butoxycarbonylamino)-3-cyano-spiro[5,6-dihydrocyclopenta[b]thiophene-4,3'-azetidine]-1'-yl]-5-cyano-2-methylsulfanyl-pyrimidin-4-yl]-3-chloro-7,7-difluoro-6,8-dihydro-4H-pyrazolo[1,5-a][1,4]diazepine-2-carboxylic acid (91i)

To a mixture of ethyl 5-[6-[2-(tert-butoxycarbonylamino)-3-cyano-spiro[5,6-dihydrocyclopenta[b]thiophene-4,3'-azetidine]-1'-yl]-5-cyano-2-methylsulfanyl-pyrimidin-4-yl]-3-chloro-7,7-difluoro-6,8-dihydro-4H-pyrazolo[1,5-a][1,4]diazepine-2-carboxylate (91h, 128.2 mg, 0.16 mmol) in THF (1 mL) and Water (1 mL) was added LiOH·H$_2$O (10.31 mg, 0.25 mmol) and the mixture was stirred at 25° C. for 1 h. The mixture was acidified with HCl (1 mol/L in H$_2$O) to PH=6, extracted with EtOAc (3×10 mL), dried over Na$_2$SO$_4$, concentrated. The mixture was not purified and used in the next step directly. The mixture of 5-[6-[2-(tert-butoxycarbonylamino)-3-cyano-spiro[5,6-dihydrocyclopenta[b]thiophene-4,3'-azetidine]-1'-yl]-5-cyano-2-methylsulfanyl-pyrimidin-4-yl]-3-chloro-7,7-difluoro-6,8-dihydro-4H-pyrazolo[1,5-a][1,4]diazepine-2-carboxylic acid (91i, 110 mg) was obtained as a white solid. LCMS calcld for $C_{29}H_{29}ClF_2N_9O_4S_2$ $(M+H)^+$ m/z=704.1, found: 704.2.

Step 10. Preparation of tert-butyl N-[1'-[6-[3-chloro-2-(dimethylcarbamoyl)-7,7-difluoro-6,8-dihydro-4H-pyrazolo[1,5-a][1,4]diazepin-5-yl]-5-cyano-2-methylsulfanyl-pyrimidin-4-yl]-3-cyano-spiro[5,6-dihydrocyclopenta[b]thiophene-4,3'-azetidine]-2-yl]carbamate (91j)

To a solution of 5-[6-[2-(tert-butoxycarbonylamino)-3-cyano-spiro[5,6-dihydrocyclopenta[b]thiophene-4,3'-azetidine]-1'-yl]-5-cyano-2-methylsulfanyl-pyrimidin-4-yl]-3-chloro-7,7-difluoro-6,8-dihydro-4H-pyrazolo[1,5-a][1,4]diazepine-2-carboxylic acid (91i, 100 mg, 0.13 mmol) in DCM (2 mL) was added Dimethylamine (0.01 mL, 0.15 mmol), DIEA (19.28 mg, 0.15 mmol) and HATU (56.73 mg, 0.15 mmol) at 25° C., The mixture was stirred at 25° C. for 1 h. The mixture was extracted DCM (3×10 mL), dried over Na$_2$SO$_4$, concentrated. The mixture was purified by silica gel (eluting with CH$_3$OH in DCM from 0% to 10%). The mixture of tert-butyl N-[1'-[6-[3-chloro-2-(dimethylcarbamoyl)-7,7-difluoro-6,8-dihydro-4H-pyrazolo[1,5-a][1,4]diazepin-5-yl]-5-cyano-2-methylsulfanyl-pyrimidin-4-yl]-3-cyano-spiro[5,6-dihydrocyclopenta[b]thiophene-4,3'-azetidine]-2-yl]carbamate (91j, 100 mg, 0.120 mmol, 97% yield) was obtained as a white solid. LCMS calcld for $C_{31}H_{34}ClF_2N_{10}O_3S_2$ $(M+H)^+$ m/z=731.2, found: 731.1.

Step 11. Preparation of tert-butyl N-[1'-[6-[3-chloro-2-(dimethylcarbamoyl)-7,7-difluoro-6,8-dihydro-4H-pyrazolo[1,5-a][1,4]diazepin-5-yl]-5-cyano-2-methylsulfinyl-pyrimidin-4-yl]-3-cyano-spiro[5,6-dihydrocyclopenta[b]thiophene-4,3'-azetidine]-2-yl]carbamate (91k)

To a solution of tert-butyl N-[1'-[6-[3-chloro-2-(dimethylcarbamoyl)-7,7-difluoro-6,8-dihydro-4H-pyrazolo[1,5-a][1,4]diazepin-5-yl]-5-cyano-2-methylsulfanyl-pyrimidin-4-yl]-3-cyano-spiro[5,6-dihydrocyclopenta[b]thiophene-4,3'-azetidine]-2-yl]carbamate (91j, 30 mg, 0.04 mmol) in THF (1 mL) and water (1 mL) was added oxone (18.92 mg, 0.06 mmol) at 25° C., The mixture was stirred at 25° C. for 4 h. The mixture was extracted with EtOAc (3 ml×3), dried over Na$_2$SO$_4$, concentrated. The mixture was not purified and used to next step directly. Tert-butyl N-[1'-[6-[3-chloro-2-(dimethylcarbamoyl)-7,7-difluoro-6,8-dihydro-4H-pyrazolo[1,5-a][1,4]diazepin-5-yl]-5-cyano-2-methylsulfinyl-pyrimidin-4-yl]-3-cyano-spiro[5,6-dihydrocyclopenta[b]thiophene-4,3'-azetidine]-2-yl]carbamate (91k, 30 mg) was obtained as a white solid. LCMS calcld for $C_{31}H_{34}ClF_2N_{10}O_4S_2(M+H)^+$ m/z=747.2, found: 747.1.

Step 12. Preparation of tert-butyl N-[1'-[6-[3-chloro-2-(dimethylcarbamoyl)-7,7-difluoro-6,8-dihydro-4H-pyrazolo[1,5-a][1,4]diazepin-5-yl]-5-cyano-2-[[(2R,8S)-2-fluoro-1,2,3,5,6,7-hexahydropyrrolizin-8-yl]methoxy]pyrimidin-4-yl]-3-cyano-spiro[5,6-dihydrocyclopenta[b]thiophene-4,3'-azetidine]-2-yl]carbamate (91l) To a solution of tert-butyl N-[1'-[6-[3-chloro-2-(dimethylcarbamoyl)-7,7-difluoro-6,8-dihydro-4H-pyrazolo[1,5-a][1,4]diazepin-5-yl]-5-cyano-2-methylsulfanyl-pyrimidin-4-yl]-3-cyano-spiro[5,6-dihydrocyclopenta[b]thiophene-4,3'-azetidine]-2-yl]carbamate (91k, 80 mg, 0.0 mmol) in THF (1 mL) was added [(2R,8S)-2-fluoro-1,2,3,5,6,7-hexahydropyrrolizin-8-yl]methanol (6.39 mg, 0.04 mmol) at 0° C., The mixture was added LiHDMS (0.04 mL, 0.04 mmol) at 0° C. for 1 h. The mixture was quenched with aqueous NH$_4$Cl and extracted with EtOAc (3×5 mL), dried over Na$_2$SO$_4$ and concentrated. The mixture was purified by silica gel chromatography (eluting with MeOH in DCM from 0% to 10%). The mixture of tert-butyl N-[1'-[6-[3-chloro-2-(dimethylcarbamoyl)-7,7-difluoro-6,8-dihydro-4H-pyrazolo[1,5-a][1,4]diazepin-5-yl]-5-cyano-2-[[(2R,8S)-2-fluoro-1,2,3,5,6,7-hexahydropyrrolizin-8-yl]methoxy]pyrimidin-4-yl]-3-cyano-spiro[5,6-dihydrocyclopenta[b]thiophene-4,3'-azetidine]-2-yl]carbamate (911, 85 mg, 0.101 mmol, 94% yield) was obtained as a white solid. LCMS calcld for $C_{38}H_{44}ClF_3N_{11}O_4S$ (M+H)$^+$ m/z=842.3, found: 842.4.

Step 13. Preparation of 5-[6-(2-amino-3-cyano-spiro[5,6-dihydrocyclopenta[b]thiophene-4,3'-azetidine]-1'-yl)-5-cyano-2-[[(2R,8S)-2-fluoro-1,2,3,5,6,7-hexahydropyrrolizin-8-yl]methoxy]pyrimidin-4-yl]-3-chloro-7,7-difluoro-N,N-dimethyl-6,8-dihydro-4H-pyrazolo[1,5-a][1,4]diazepine-2-carboxamide; 2,2,2-trifluoroacetic acid (Compound 91)

To a solution of tert-butyl N-[1'-[6-[3-chloro-2-(dimethylcarbamoyl)-7,7-difluoro-6,8-dihydro-4H-pyrazolo[1,5-a][1,4]diazepin-5-yl]-5-cyano-2-[[(2R,8S)-2-fluoro-1,2,3,5,6,7-hexahydropyrrolizin-8-yl]methoxy]pyrimidin-4-yl]-3-cyano-spiro[5,6-dihydrocyclopenta[b]thiophene-4,3'-azetidine]-2-yl]carbamate (911, 65 mg, 0.08 mmol) in DCM (1 mL) was added TFA (0.2 mL, 2.61 mmol) at 25° C., The mixture was stirred at 25° C. for 1 h. The mixture was concentrated. The mixture was purified by prep-HPLC (eluting with CH$_3$CN (0.1%) in H$_2$O from 5% to 95%). The product of 5-[6-(2-amino-3-cyano-spiro[5,6-dihydrocyclopenta[b]thiophene-4,3'-azetidine]-1'-yl)-5-cyano-2-[[(2R,8S)-2-fluoro-1,2,3,5,6,7-hexahydropyrrolizin-8-yl]methoxy]pyrimidin-4-yl]-3-chloro-7,7-difluoro-N,N-dimethyl-6,8-dihydro-4H-pyrazolo[1,5-a][1,4]diazepine-2-carboxamide; 2,2,2-trifluoroacetic acid (Compound 91, 6.75 mg, 0.008 mmol, 10.19% yield) was obtained as a white solid. LCMS calcld for $C_{33}H_{36}ClF_3N_{11}O_2S$ (M+H)$^+$ m/z=742.2, found: 742.1. $^1$H NMR (400 MHz, CD$_3$OD) δ: 5.57 (d, J=52 Hz, 1H), 4.95 (s, 2H), 4.88-4.67 (m, 2H), 4.82-4.82 (m, 2H), 4.75-4.69 (m, 2H), 4.61-4.56 (m, 2H), 4.45 (s, 2H), 3.96-3.83 (m, 3H), 3.50-3.39 (m, 1H), 3.13-3.10 (m, 6H), 2.78-2.69 (m, 4H), 2.68-2.48 (m, 2H), 2.39-2.25 (m, 3H), 2.19-2.09 (m, 1H).

Compound 92. 2-amino-1'-[5-cyano-6-[(1R,5S)-3,8-diazabicyclo[3.2.1]octan-3-yl]-2-[[(2S)-1-(2,2,2-trifluoroethyl)azetidin-2-yl]methoxy]pyrimidin-4-yl]spiro[5,6-dihydrocyclopenta[b]thiophene-4,3'-azetidine]-3-carbonitrile

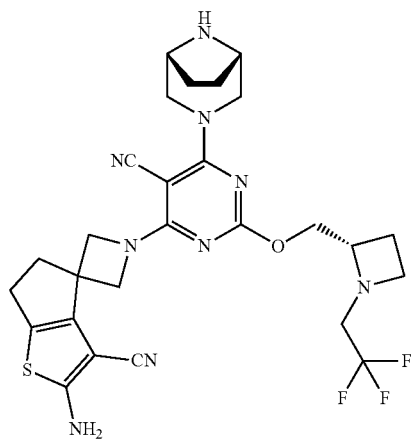

Compound 92 was prepared similarly to that of Ex. 3. LCMS calcld for $C_{27}H_{31}F_3N_9O$ S (M+H)$^+$ m/z=586.2, found: 586.3. $^1$H NMR (400 MHz, CD$_3$OD) δ 4.64-4.42 (m, 3H), 4.40-4.17 (m, 5H), 3.78-3.66 (m, 1H), 3.57-3.45 (m, 3H), 3.45-3.32 (m, 1H), 3.26 (m, 2H), 3.18-2.99 (m, 2H), 2.80-2.68 (m, 4H), 2.22-2.03 (m, 2H), 1.88-1.75 (m, 4H).

Compound 93. 5-[6-(2-amino-3-cyano-spiro[5,6-dihydrocyclopenta[b]thiophene-4,3'-azetidine]-1'-yl)-5-cyano-2-[(6-methylene-2,3,5,7-tetrahydro-1H-pyrrolizin-8-yl)methoxy]pyrimidin-4-yl]-3-chloro-N,N-dimethyl-4,6,7,8-tetrahydropyrazolo[1,5-a][1,4]diazepine-2-carboxamide

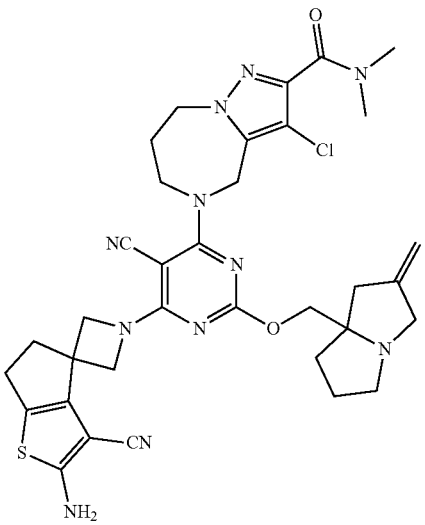 [SMILES: C=C1CN2CCCC2(COc2nc(N3CCCn4nc(C(=O)N(C)C)c(Cl)c4C3)c(C#N)c(N3CC4(CCc5sc(N)c(C#N)c54)C3)n2)C1]

Compound 93 was prepared similarly to that of Ex. 2. LCMS calculated for $C_{34}H_{39}ClN_{11}O_2S$ (M+H)$^+$ m/z=700.3; found: 700.0/702.0. $^1$H NMR (400 MHz, CD$_3$OD) δ 5.08 (s, 2H), 4.97 (s, 3H), 4.42-4.67 (m, 6H), 4.16 (m, 5H), 3.71 (d, J=14.8 Hz, 1H), 3.10-3.16 (m, 1H), 3.08 (s, 6H), 2.65-2.79 (m, 6H), 2.43 (d, J=15.6 Hz, 1H), 2.15-2.28 (m, 2H), 1.73-2.10 (m, 5H)

Compound 94. 2-amino-1'-[5-cyano-2-[(6-methylene-2,3,5,7-tetrahydro-1H-pyrrolizin-8-yl)methoxy]-6-[(1R,5S)-3,8-diazabicyclo[3.2.1]octan-3-yl]pyrimidin-4-yl]spiro[5,6-dihydrocyclopenta[b]thiophene-4,3'-azetidine]-3-carbonitrile

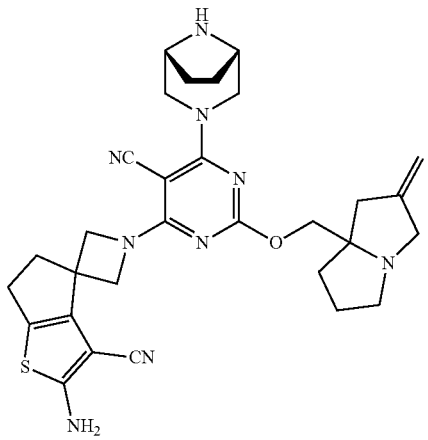

Compound 94 was prepared similarly to that of Ex. 3. LCMS calculated for $C_{30}H_{36}N_9O\ S$ (M+H)$^+$ m/z=570.3, found: 570.3. $^1$H NMR (400 MHz, CD$_3$OD) δ 4.96 (s, 2H), 4.43 (m, 6H), 4.02-4.11 (m, 2H), 3.65 (d, J=14.0 Hz, 1H), 3.53 (s, 2H), 3.18-3.30 (m, 3H), 3.05-3.13 (m, 1H), 2.60-2.82 (m, 6H), 2.41 (d, J=15.6 Hz, 1H), 1.72-2.11 (m, 8H).

Compound 95. 2-amino-1'-[5-cyano-6-[(1R,5S)-3,8-diazabicyclo[3.2.1]octan-3-yl]-2-[[1-[(1,1-dioxo-1,4-thiazinan-4-yl)methyl]cyclopropyl]methoxy]pyrimidin-4-yl]spiro[5,6-dihydrocyclopenta[b]thiophene-4,3'-azetidine]-3-carbonitrile

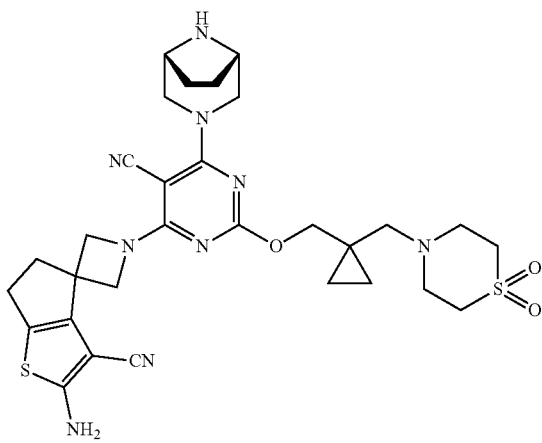

Compound 95 was prepared similarly to that of Ex. 3 as a TFA salt. LCMS calcld for $C_{30}H_{38}N_9O_3S_2$(M+H)$^+$ m/z=636.3, found: 636.1. $^1$H NMR (400 MHz, CD$_3$OD) δ 4.55-4.15 (m, 10H), 3.49-3.10 (m, 8H), 2.84-2.75 (m, 6H), 2.09 (s, 4H), 1.33-1.28 (d, 2H), 0.76 (s, 2H), 0.61 (s, 2H).

Compound 96. 5-[6-(2-amino-3-cyano-spiro[6,7-dihydro-5H-benzothiophene-4,3'-azetidine]-1'-yl)-5-cyano-2-[[1-[(dimethylamino)methyl]-2,2-difluorocyclopropyl]methoxy]pyrimidin-4-yl]-3-chloro-N,N-dimethyl-4,6,7,8-tetrahydropyrazolo[1,5-a][1,4]diazepine-2-carboxamide

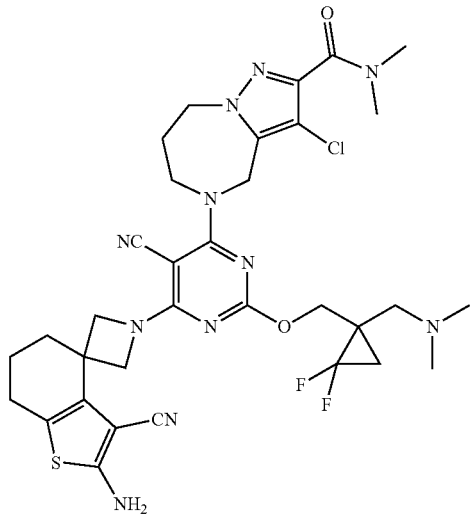 [SMILES: CN(C)CC1(COc2nc(N3CCCn4nc(C(=O)N(C)C)c(Cl)c4C3)c(C#N)c(N3CC4(CCCc5sc(N)c(C#N)c54)C3)n2)CC1(F)F]

Compound 96 was prepared similarly to that of Ex. 2. LCMS calculated for $C_{33}H_{39}ClF_2N_{11}O_2S$ (M+H)$^+$ m/z=726.3, found: 726.3/728.3. $^1$H NMR (400 MHz, CD$_3$OD) δ 5.11-5.26 (m, 1H), 5.01 (m, 1H), 4.59 (s, 6H), 4.47 (m, 4H), 4.36 (m, 1H), 3.08 (d, J=3.2 Hz, 6H), 2.75 (s, 1H), 2.49 (t, J=6.0 Hz, 2H), 2.31-2.41 (m, 1H), 2.20-2.28 (m, 8H), 2.08-2.14 (m, 2H), 1.76-1.85 (m, 2H), 1.53-1.62 (m, 1H), 1.27-1.39 (m, 2H).

Compound 97. 2-amino-1'-[5-cyano-2-[(2-methylpyrazol-3-yl)methoxy]-6-[(1R,5S)-3,8-diazabicyclo[3.2.1]octan-3-yl]pyrimidin-4-yl]spiro[5,6-dihydrocyclopenta[b]thiophene-4,3'-azetidine]-3-carbonitrile

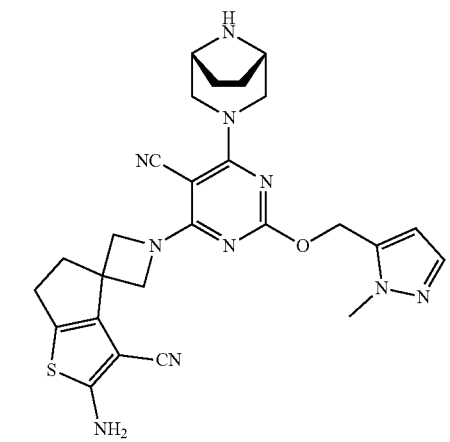

Compound 97 was prepared similarly to that of Ex. 3 as a TFA salt. LCMS calcld for $C_{26}H_{29}N_{10}OS$ (M+H)$^+$ m/z=529.2, found: 529.6. ¹H NMR (400 MHz, CD₃OD) δ 7.41 (d, J=1.8 Hz, 1H), 6.38 (d, J=1.8 Hz, 1H), 5.43 (s, 2H), 4.60 (m, 5H), 4.34 (s, 1H), 4.11 (m, 2H), 3.89 (m, 3H), 3.51 (s, 2H), 2.77 (dd, J=11.6, 8.0 Hz, 4H), 2.07 (s, 4H).

Compound 98. 2-amino-1'-[5-cyano-6-[(1R,5S)-3,8-diazabicyclo[3.2.1]octan-3-yl]-2-[[1-(1H-pyrazol-5-yl)cyclopropyl]methoxy]pyrimidin-4-yl]spiro[5,6-dihydrocyclopenta[b]thiophene-4,3'-azetidine]-3-carbonitrile

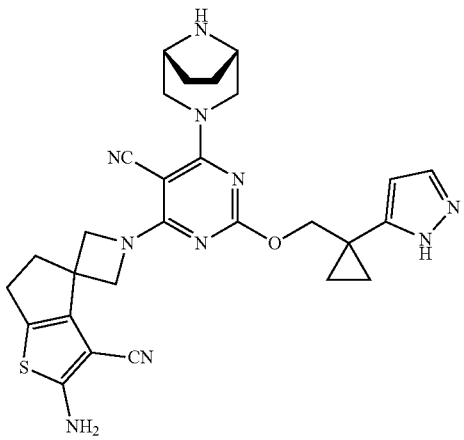

Compound 98 was prepared similarly to that of Ex. 3. LCMS calcld for C₂₈H₃₁N₁₀OS (M+H)⁺ m/z=555.2, found: 555.6. ¹H NMR (400 MHz, CD₃OD) δ 7.47 (s, 1H), 6.18 (s, 1H), 4.39 (m, 8H), 3.55 (s, 2H), 3.25 (m, 2H), 2.79-2.67 (m, 4H), 1.85-1.72 (m, 4H), 1.05 (s, 4H).

Compound 99. 2-amino-1'-[5-cyano-6-[(1R,5S)-3,8-diazabicyclo[3.2.1]octan-3-yl]-2-[[(2R,8S)-2-fluoro-1,2,3,5,6,7-hexahydropyrrolizin-8-yl]methoxy]pyrimidin-4-yl]spiro[4a,5,5a,6-tetrahydrocyclopropa[f]benzothiophene-4,3'-azetidine]-3-carbonitrile

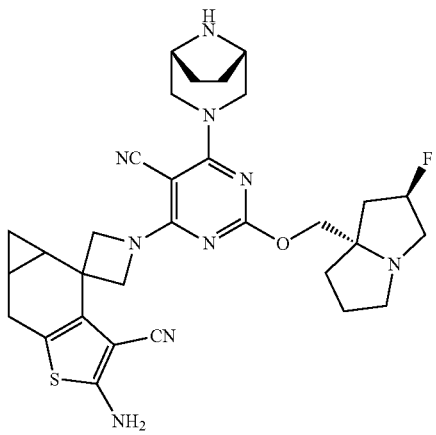 [SMILES: N#Cc1c(N2C[C@H]3CC[C@@H](C2)N3)nc(OC[C@@]23CCCN2C[C@H](F)C3)nc1N1CC2(C1)c1c(sc(N)c1C#N)CC1CC12]

Compound 99 was prepared similarly to that of Ex. 3 as a TFA salt using Intermediate 21. LCMS calcld for C₃₁H₃₇FN₉OS (M+H)⁺ m/z=602.3, found: 602.3. 1H NMR (400 MHz, CD₃OD) δ: 5.54 (d, J=52 Hz, 1H), 5.03-4.99 (in, 1H), 4.75-4.28 (in, 7H), 4.16 (s, 2H), 3.97-3.80 (in, 3H), 3.63-3.40 (m, 3H), 2.91-2.80 (m, 2H), 2.71-2.49 (m, 2H), 2.41-2.27 (m, 3H), 2.18-2.03 (m, 5H), 1.71-1.66 (m, 1H), 1.55-1.51 (m, 1H), 0.80-0.74 (m, 1H), 0.19-0.16 (m, 1H).

Compound 100. 2-amino-1'-[5-cyano-6-[(1R,5S)-3,8-diazabicyclo[3.2.1]octan-3-yl]-2-[[1-(morpholinomethyl)cyclopropyl]methoxy]pyrimidin-4-yl]spiro[6H-thieno[2,3-c]thiophene-4,3'-azetidine]-3-carbonitrile

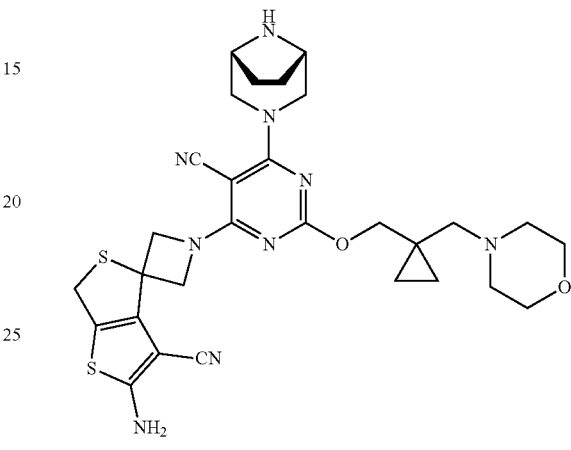

Compound 100 was prepared similarly to that of Ex. 3 as a formate salt using Intermediate 19.

LCMS calcld for C₂₉H₃₆N₉O₂S₂(M+H)⁺ m/z=606.2, found: 606.2. ¹H NMR (400 MHz, CD₃OD) δ 4.84-4.30 (m, 6H), 4.25 (s, 2H), 4.10 (s, 2H), 4.07 (s, 2H), 3.71 (s, 4H), 3.58-3.38 (m, 2H), 2.66 (s, 4H), 2.56 (s, 2H), 2.06 (s, 4H), 0.69 (s, 2H), 0.53 (s, 2H).

Compound 101. 2-amino-1'-[5-cyano-6-[(1R,5S)-3,8-diazabicyclo[3.2.1]octan-3-yl]-2-[[1-(morpholinomethyl)cyclopropyl]methoxy]pyrimidin-4-yl]-5-fluoro-spiro[5,6-dihydrocyclopenta[b]thiophene-4,3'-azetidine]-3-carbonitrile

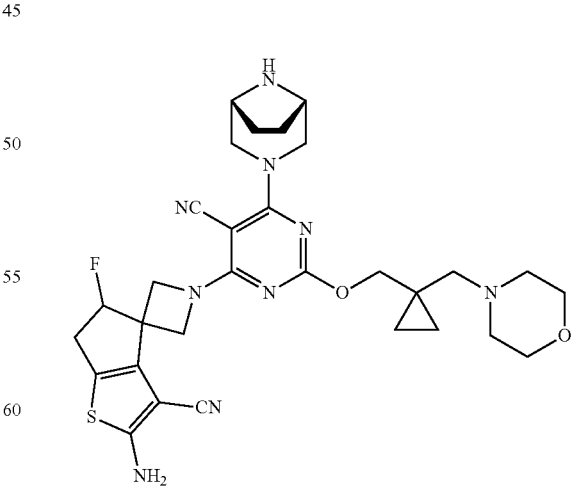

Compound 101 was prepared similarly to that of Ex. 3 using Intermediate 20. LCMS calculated for C₃₀H₃₇FN₉O₂S (M+H)⁺ m/z=606.6; found: 606.5. 1H NMR (400 MHz, CD$_3$OD) δ 5.60 (d, J=52.3 Hz, 1H), 4.27-4.55 (m, 6H), 4.24 (s, 2H), 3.66 (m, 4H), 3.54 (s, 2H), 3.14-3.29 (m, 3H), 2.89 (m, 1H), 2.47 (s, 4H), 2.37 (s, 2H), 1.75-1.85 (m, 4H), 0.64 (m, 2H), 0.44 (m, 2H).

Compound 102. 2-amino-1'-[2-[(4-bromo-1H-pyrazol-3-yl)methoxy]-5-cyano-6-[(1S,5R)-3,8-diazabicyclo[3.2.1]octan-3-yl]pyrimidin-4-yl]spiro[5,6-dihydrocyclopenta[b]thiophene-4,3'-azetidine]-3-carbonitrile

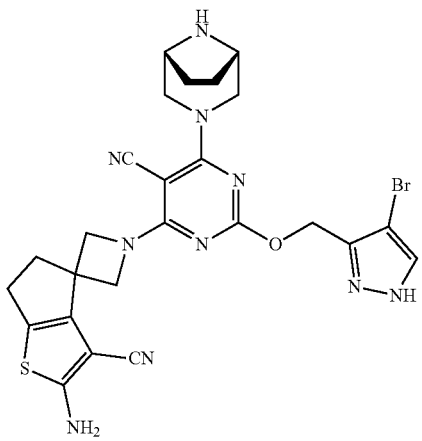

Compound 102 was prepared similarly to that of Ex. 3 as a TFA and formate salt. LCMS calcld for C$_{25}$H$_{26}$BrN$_{10}$OS (M+H)$^+$ m/z=593.2, found: 593.2. $^1$H NMR (400 MHz, CD$_3$OD) δ 8.53-8.45 (m, 1H), 7.79-7.60 (m, 1H), 5.34 (s, 2H), 4.74-4.18 (m, 6H), 4.15-3.98 (m, 2H), 3.60-3.38 (m, 2H), 2.82-2.69 (m, 4H), 2.03 (s, 4H).

Compound 103. 2-amino-1'-[5-cyano-6-[(1R,5S)-3,8-diazabicyclo[3.2.1]octan-3-yl]-2-(2H-triazol-4-ylmethoxy)pyrimidin-4-yl]spiro[5,6-dihydrocyclopenta[b]thiophene-4,3'-azetidine]-3-carbonitrile

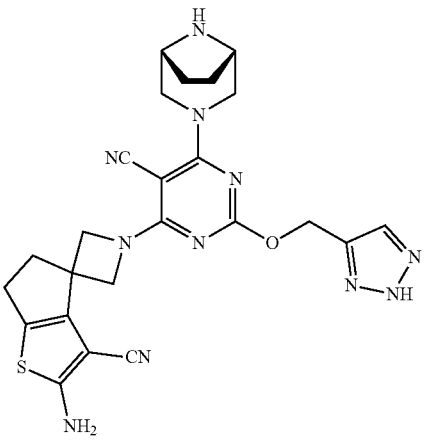

Compound 103 was prepared similarly to that of Ex. 3 as a formate salt. LCMS calcld for C$_{24}$H$_{26}$N$_{11}$OS (M+H)$^+$ m/z=516.5, found: 516.5. $^1$H NMR (DMSO-d$_6$, 400 MHz) δ 8.34 (s, 2H), 7.90 (s, 1H), 7.23 (s, 2H), 5.33 (s, 2H), 4.19 (d, J=12.0 Hz, 2H), 3.48 (s, 3H), 3.17 (d, J=12.0 Hz, 2H), 2.68 (s, 4H), 1.62-1.56 (m, 4H).

Compound 104. 2-amino-1'-[2-[(4-chloro-1H-pyrazol-3-yl)methoxy]-5-cyano-6-[(1R,5S)-3,8-diazabicyclo[3.2.1]octan-3-yl]pyrimidin-4-yl]spiro[5,6-dihydrocyclopenta[b]thiophene-4,3'-azetidine]-3-carbonitrile

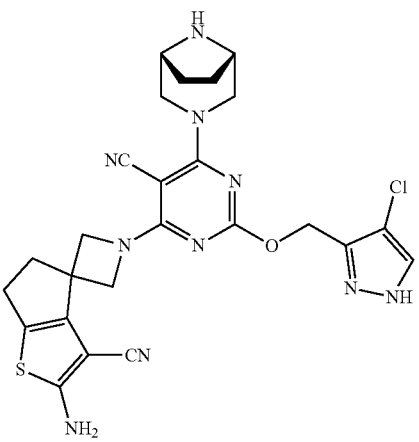

Compound 104 was prepared similarly to that of Ex. 3 as a TFA salt. LCMS calcld for C$_{25}$H$_{26}$ClN$_{10}$OS (M+H)$^+$ m/z=549.1, found: 549.2. $^1$H NMR (400 MHz, CD$_3$OD) δ 7.68 (s, 1H), 5.35 (s, 2H), 4.76-4.21 (m, 6H), 4.14 (s, 2H), 3.60-3.38 (m, 2H), 2.82-2.67 (m, 4H), 2.08 (s, 4H).

Compound 105. 2-amino-1'-[2-[(5-chloro-1H-pyrazol-3-yl)methoxy]-5-cyano-6-[(1R,5S)-3,8-diazabicyclo[3.2.1]octan-3-yl]pyrimidin-4-yl]spiro[5,6-dihydrocyclopenta[b]thiophene-4,3'-azetidine]-3-carbonitrile

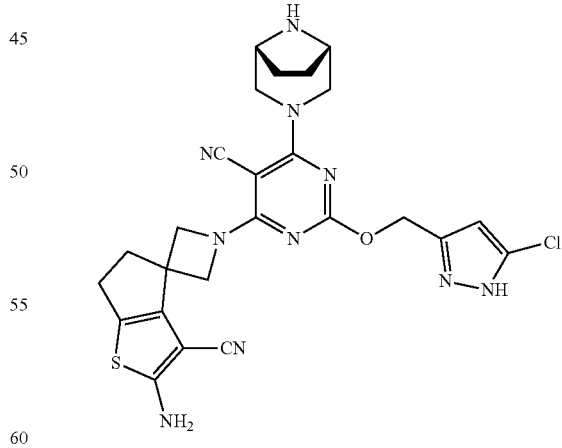

Compound 105 was prepared similarly to that of Ex. 3 as a TFA salt. LCMS calcld for C$_{25}$H$_{26}$ClN$_{10}$OS (M+H)$^+$ m/z=549.2, found: 549.3. $^1$H NMR (400 MHz, CD$_3$OD) δ 6.31 (s, 1H), 5.34 (s, 2H), 4.27 (s, 2H), 4.75-4.18 (m, 6H), 4.14 (s, 2H), 3.58-3.38 (m, 2H), 2.83-2.68 (m, 4H), 2.05 (s, 4H).

Compound 106. 2-amino-1'-[5-cyano-6-[(1R,5S)-3,8-diazabicyclo[3.2.1]octan-3-yl]-2-[[4-(trifluoromethyl)-1H-pyrazol-3-yl]methoxy]pyrimidin-4-yl]spiro[5,6-dihydrocyclopenta[b]thiophene-4,3'-azetidine]-3-carbonitrile

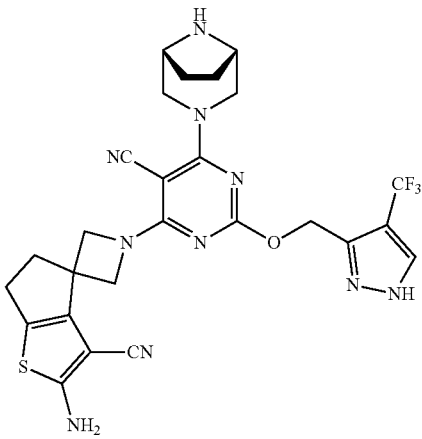

Compound 106 was prepared similarly to that of Ex. 3 as a TFA salt. LCMS calcld for $C_{26}H_{26}F_3N_{10}OS$ (M+H)$^+$ m/z=583.2, found: 583.2. $^1$H NMR (400 MHz, CD$_3$OD) δ 8.05 (s, 1H), 5.42 (s, 2H), 4.58 (s, 5H), 4.27 (s, 1H), 4.13 (s, 2H), 3.48 (s, 2H), 2.76 (dt, J=12.0, 6.8 Hz, 4H), 2.06 (s, 4H).

Compound 107. 2-amino-1'-[5-cyano-6-[(1R,5S)-3,8-diazabicyclo[3.2.1]octan-3-yl]-2-[(5-methyl-1H-1,2,4-triazol-3-yl)methoxy]pyrimidin-4-yl]spiro[5,6-dihydrocyclopenta[b]thiophene-4,3'-azetidine]-3-carbonitrile

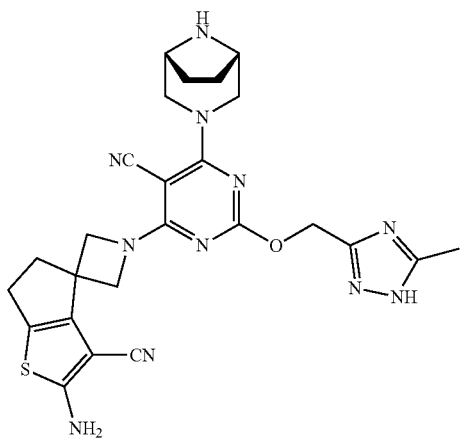

Compound 107 was prepared similarly to that of Ex. 3 as a TFA salt. LCMS calcld for $C_{25}H_{28}N_{11}OS$ (M+H)$^+$ m/z=530.3, found: 530.4. $^1$H NMR (400 MHz, CD$_3$OD) δ 5.35 (s, 2H), 4.75-4.18 (m, 6H), 4.17-4.09 (m, 2H), 3.56-3.42 (m, 2H), 2.85-2.66 (m, 4H), 2.43 (s, 3H), 2.12-1.97 (m, 4H).

Compound 108. 2-amino-1'-[5-cyano-6-[(1R,5S)-3,8-diazabicyclo[3.2.1]octan-3-yl]-2-[[4-(trifluoromethyl)-1H-pyrazol-3-yl]methoxy]pyrimidin-4-yl]spiro[5,6-dihydrocyclopenta[b]thiophene-4,3'-azetidine]-3-carbonitrile

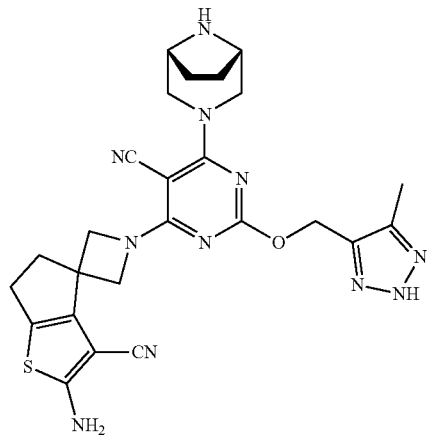

Compound 108 was prepared similarly to that of Ex. 3 as a TFA salt. LCMS calcld for $C_{25}H_{28}N_{11}OS$ (M+H)$^+$ m/z=530.6, found: 530.3. H NMR (400 MHz, CD$_3$OD) δ 5.43 (s, 2H), 4.74-4.20 (m, 6H), 4.14 (s, 2H), 3.61-3.37 (m, 2H), 2.85-2.66 (m, 4H), 2.36 (s, 3H), 2.07 (s, 4H).

Compound 109. 2-amino-1'-[5-cyano-6-[(1R,5S)-3,8-diazabicyclo[3.2.1]octan-3-yl]-2-[[4-(difluoromethyl)-1H-pyrazol-3-yl]methoxy]pyrimidin-4-yl]spiro[5,6-dihydrocyclopenta[b]thiophene-4,3'-azetidine]-3-carbonitrile

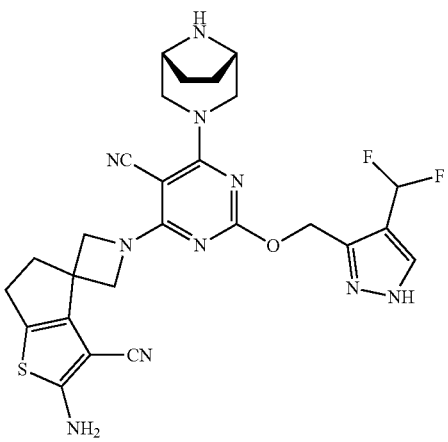

Compound 109 was prepared similarly to that of Ex. 3 as a TFA salt. LCMS calcld for $C_{26}H_{27}F_2N_{10}OS$ (M+H)$^+$ m/z=565.2, found: 565.2. $^1$H NMR (400 MHz, CD$_3$OD) δ 7.86 (s, 1H), 6.92 (t, J=55.9 Hz, 1H), 5.44 (s, 2H), 4.56 (s, 6H), 4.12 (s, 2H), 3.60-3.36 (m, 2H), 2.84-2.68 (m, 4H), 2.04 (s, 4H).

Compound 110. 2-amino-1'-[5-cyano-2-[[(2R,8S)-2-fluoro-1,2,3,5,6,7-hexahydropyrrolizin-8-yl]methoxy]-6-(1,4-oxazepan-4-yl)pyrimidin-4-yl]spiro[5,6-dihydrocyclopenta[b]thiophene-4,3'-azetidine]-3-carbonitrile

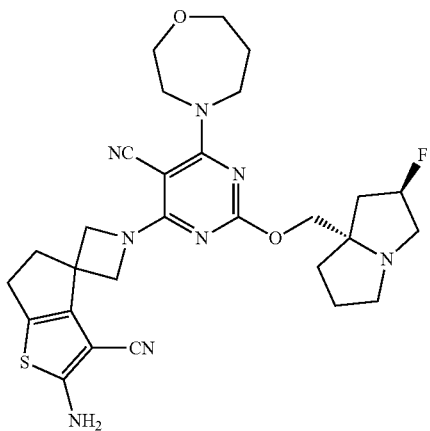 [SMILES: N#Cc1c(N2CCCOCC2)nc(OC[C@@]23CCCN2C[C@H](F)C3)nc1N1CC2(CCc3sc(N)c(C#N)c32)C1]

Compound 110 was prepared similarly to that of Ex. 3. LCMS calculated for $C_{28}H_{34}FN_8O_2S$ (M+H)$^+$ m/z=565.24; found: 565.3. $^1$H NMR (400 MHz, CD$_3$OD) δ 5.25 (d, J=53.6 Hz, 1H), 4.20-4.59 (m, 4H), 3.94-4.15 (m, 6H), 3.82-3.88 (m, 2H), 3.70-3.78 (m, 2H), 3.10-3.24 (m, 3H), 2.92-3.02 (m, 1H), 2.69-2.81 (m, 4H), 1.77-2.28 (m, 8H).

Compound 111. 2-amino-1'-[5-cyano-6-(3,5-dihydro-2H-pyrido[3,2-f][1,4]thiazepin-4-yl)-2-[[(2R,8S)-2-fluoro-1,2,3,5,6,7-hexahydropyrrolizin-8-yl]methoxy]pyrimidin-4-yl]spiro[5,6-dihydrocyclopenta[b]thiophene-4,3'-azetidine]-3-carbonitrile

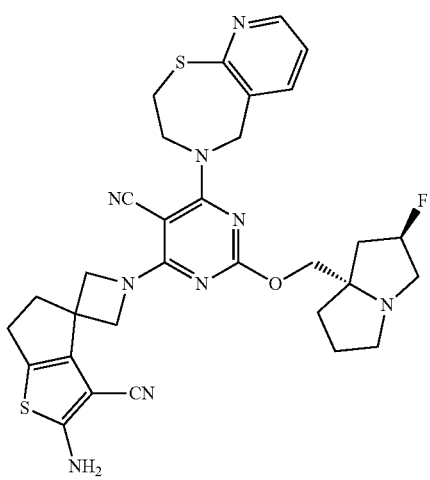 [SMILES: N#Cc1c(N2CCSc3ncccc3C2)nc(OC[C@@]23CCCN2C[C@H](F)C3)nc1N1CC2(CCc3sc(N)c(C#N)c32)C1]

Compound 111 was prepared similarly to that of Ex. 3 using intermediate 22. LCMS calculated for $C_{31}H_{33}FN_9OS_2$ (M+H)$^+$ m/z=630.22; found: 630.3. $^1$H NMR (400 MHz, DMSO) δ 8.23 (dd, J=4.7, 1.6 Hz, 1H), 7.70 (dd, J=7.6, 1.4 Hz, 1H), 7.22 (s, 2H), 7.13 (dd, J=7.6, 4.7 Hz, 1H), 5.21 (d, J=54.4 Hz, 1H), 4.88 (s, 2H), 4.42 (s, 2H), 4.18 (m, 3H), 3.65 (m, 2H), 3.45 (s, 2H), 3.03 (m, 2H), 2.93 (m, 1H), 2.82-2.74 (m, 1H), 2.66 (s, 4H), 1.98 (s, 1H), 1.94-1.87 (m, 1H), 1.86-1.75 (m, 2H), 1.68 (m, 2H).

Example 8: Nucleotide Exchange Assay

Ras proteins cycle between an active, GTP bound state, and an inactive GDP-bound state. This activity is tightly regulated by GTPase activating proteins (GAPs) and guanine nucleotide exchange factors (GEFs). GEFs, such as SOS1/2, activate Ras proteins by exchanging GDP for GTP, thus returning Ras to its active conformation (Simanshu, Nissley, & McCormick, 2017). Therefore, a small molecule that binds K-Ras in a manner that prevents SOS-mediated nucleotide exchange locks KRas in its inactive state. Homogenous time resolved fluorescence (HTRF) was used to detect SOS-mediated binding of a fluorescent GTP analog, GTP-DY-647P1 (Jena Biosciences NU-820-647P1) to GST-tagged KRAS-G12D (2-169, Reaction Biology, MSC-11-539) or to GST-tagged KRAS-G12V (2-169, Reaction Biology, MSC-11-540).

GST-tagged KRAS-G12D (2-169) and anti-GST MAb Tb Cryptate Gold (CisBio 61GSTTLB) were diluted into assay buffer (20 mM HEPES, pH 7.3, 150 mM NaCl, 5 mM MgCl2, 0.05% BSA 0.0025% NP40, 1 mM DTT) to prepare a 2.5× donor solution. 5× compound was added to the protein mixture and incubated for 1 h at RT. 2.5× acceptor solution containing SOSIcat (564-1049, Reaction Biology MSC-11-502) and GTP-DY-647P1 were then added to the donor KRAS mixture such that the final concentration of the reaction contained 5 nM GST-tagged KRAS-G12D (2-169), 20 nM SOScat, and 150 nM GTP. The reaction was monitored using at RT with the Envision multimode plate reader (Ex/Em 337/665, 620 nM) up to 90 minutes at 5 minute intervals. To monitor KRAS-G12V Sos-mediated nucleotide exchange, 80 nM SOS was added to reaction instead of 20 nM. All other components were the same as previously described. Data was blanked to reactions without SOS1 and % inhibition was calculated such that DMSO only=0% and blank=100%. Curve fitting was done using a 4 parameter fit. Reported IC$_{50}$ values were extracted at 30 min and 90 min for the KRAS-G12D and KRAS-G12V assays, respectively.

Curve fitting was done using a 4 parameter fit. NEA KRAS G12D IC$_{50}$ (uM) values of selected compounds are depicted in Table 2 with compounds having a value <0.01 uM as ++++; >0.01 uM to 0.1 uM as +++; >0.1 uM to 1 uM as ++; >1 uM to 20 uM as +; and >20 uM as NA.

Example 9: Protein Constructs for Protein-Protein Interaction

TABLE 1

Assay, Protein construct, and protein construct sequences. Table discloses SEQ ID NOS 1-5, respectively, in order of appearance.

| Assay | Protein Construct | Protein Construct Sequence | SEQ ID No |
|---|---|---|---|
| PPI | Biotinylated Avi-KRAS-G12D (1-169) | SGLNDIFEAQKIEWHEMTEYKLVVVGADGVGK SALTIQLIQNHFVDEYDPTIEDSYRKQVVIDGET CLLDILDTAGQEEYSAMRDQYMRTGEGFLCVF AINNTKSFEDIHHYREQIKRVKDSEDVPMVLVG NKCDLPSRTVDTKQAQDLARSYGIPFIETSAKTR QGVDDAFYTLVREIRKHKEK | 1 |
| PPI | Biotinylated Avi-KRAS-G12V (1-169) | SGLNDIFEAQKIEWHEMTEYKLVVVGAVGVGK SALTIQLIQNHFVDEYDPTIEDSYRKQVVIDGET CLLDILDTAGQEEYSAMRDQYMRTGEGFLCVF AINNTKSFEDIHHYREQIKRVKDSEDVPMVLVG NKCDLPSRTVDTKQAQDLARSYGIPFIETSAKTR QGVDDAFYTLVREIRKHKEK | 2 |
| PPI | Biotinylated Avi-KRAS wt (1-169) | SGLNDIFEAQKIEWHEMTEYKLVVVGAGGVGK SALTIQLIQNHFVDEYDPTIEDSYRKQVVIDGET CLLDILDTAGQEEYSAMRDQYMRTGEGFLCVF AINNTKSFEDIHHYREQIKRVKDSEDVPMVLVG NKCDLPSRTVDTKQAQDLARSYGIPFIETSAKTR QGVDDAFYTLVREIRKHKEK | 3 |
| PPI | Biotinylated Avi-NRAS (1-169) | SGLNDIFEAQKIEWHEMTEYKLVVVGAGGVGK SALTIQLIQNHFVDEYDPTIEDSYRKQVVIDGET CLLDILDTAGQEEYSAMRDQYMRTGEGFLCVF AINNSKSFADINLYREQIKRVKDSDDVPMVLVG NKCDLPTRTVDTKQAHELAKSYGIPFIETSAKTR QGVEDAFYTLVREIRQYRMK | 4 |
| PPI | His8-RAF1 RBD (52-131) | SHHHHHHHHSKTSNTIRVFLPNKQRTVVNVRN GMSLHDCLMKALKVRGLQPECCAVFRLLHEHK GKKARLDWNTDAASLIGEELQVDFL | 5 |

Example 10. Recombinant Protein Production

Biotinylated KRAS wt and KRAS G12DNV proteins were expressed and purified in conditions similar to those previously reported (Tran, et al., 2021) (Zhang, et al., 2020). Briefly, KRAS (1-169) proteins were expressed in *E. coli* at 18° C. with an upstream TEV cleavage site (ENLFYQS (SEQ ID NO: 6)) followed an Avi tag sequence (GLN-DIFEAQKIEWHE (SEQ ID NO: 7)). KRAS expression constructs contained both a His6 (SEQ ID NO: 8) and maltose-binding protein (MBP) tags at the N-terminus for Ni-NTA column purification prior to overnight TEV cleavage and MBP column purification. The avi-tagged NRAS expression construct contained both a His6 tag (SEQ ID NO: 8) and SUMO cleavage sige at the N-terminus for Ni-NTA column purification followed by His-ULPi digestion overnight. All avi-tagged RAS proteins were dialyzed into buffer containing ATP, biotin, and BirA followed by purification over a second Ni-NTA column and then run over a size exclusion HiLoad™ 26/600 Superdex™ column in 20 mM HEPES, pH 7.5, 300 mM NaCl, 5 mM MgCl$_2$, and 1 mM TCEP. Fractions containing the protein of interest were pooled, concentrated, and confirmed by intact mass spectrometry. To prepare 'GTP' loaded KRAS and NRAS, biotinylated KRAS or NRAS was nucleotide exchanged from GDP-bound protein to GppNHp-bound (Jena Biosciences, NU-401-50) protein in the presence of alkaline phosphatase and excess GppNHp as previously described and the resulting nucleotide content was confirmed by HPLC reverse phase analytical chromatography (Donohue, et al., 2019) (Tran, et al., 2021).

His-tagged RAF1 (52-131) was similarly expressed in *E. coli* at 18° C. overnight with an upstream TEV cleavage site. His-tagged RAF1 expression construct contained both a His6 (SEQ ID NO: 8) and MBP tags at the N-terminus for Ni-NTA column purification followed by MBP-tagged TEV digestion overnight. RAF1 protein samples were further purified over a MBP column followed by a Ni-NTA column and a second MBP column. The fractions containing the protein of interest were pooled, concentrated, and further purified over a HiLoad™ 16/600 Superdex™ 75 pg size exclusion column into 20 mM HEPES, pH8.0, 200 mM NaCl, 5 mM TCEP.

Example 11: Protein-Protein Interaction (PPI) Assay

When RAS proteins are in the active GTP-bound conformation, they bind the effector protein RAF1 at the N-terminus Ras-binding domain (RBD, residues 52-131) (Tran, et al., 2021). Homogenous time resolved fluorescence (HTRF) was used to monitor the interaction between wt or mutant KRAS and RAF1 or wt NRAS and RAFT. Compounds were assayed in the presence of KRAS G12D/V and RAF1 versus wt KRAS to assess activity against mutant and w.t. KRAS. Similarly, compounds were then assayed in the presence of w.t. NRAS and RAF1 to assess RAS isoform selectivity. In all assay formats, His-tagged RAF1 protein was incubated with the HTRF donor, anti-6His ("6His" disclosed as SEQ ID NO: 8) Tb Cryptate gold (Cisbio 61DB10RDF), and biotinylated RAS proteins were incubated with the HTRF acceptor, streptavidin-d2 (CisBio 610SADLA). The intensity of the fluorescence signal emitted is proportional to binding between the two proteins. The donor solution was prepared by mixing 16 nM His-tagged RAF1 in protein dilution buffer with 1:100 anti-6His ("6His" disclosed as SEQ ID NO: 8) Tb cryptate in PPI-Terbium detection buffer. 16 nM biotinylated RAS protein was diluted into protein dilution buffer (50 mM Tris-HCl pH 7.5, 150 mM NaCl, 0.1 mM MgCl2, 1 mM TCEP, 0.005% Tween20) and mixed with 1:2000 Streptavidin-d2 diluted in PPI-Terbium detection buffer (CisBio 61DBTORDF). 50× compound in DMSO was mixed with 16 nM KRAS-acceptor solution and incubated for 30 minutes at room temperature. After compound pre-incubation with KRAS, the RAF1 donor solution was added to the KRAS-acceptor solution and incubated for 1 hour at room temperature. The fluorescence signal emitted was monitored at 665 nm and 615 nm using an Envision multimode plate reader. The HTRF ratio (665/615) was calculated and normalized to 0% inhibition in the absence of compound and 100% inhibition in the presence of untagged RAF1 protein. PPI KRAS G12D/RAF1, KRAS G12V/RAF1, w.t.KRAS/RAF1 and NRAS/RAF1 $IC_{50}$ (uM) values of selected compounds are depicted in Table 3 with compounds having a value <0.1 uM as ++++; >0.1 uM to 1 uM as +++; >1 uM to 10 uM as ++; >10 uM to 100 uM as +; and >100 uM as NA.

Compounds described herein are active against KRAS G12 mutant and other alleles representative by PPI-G12D, PPI-G12V and PPI-w.t.KRAS potency for broad activity against mutant KRAS and wtKRAS amplification driven malignancies. Compounds described herein are selective for the KRAS isoform representative by lack of activity in the PPI-NRAS assay.

Example 12. pERK Inhibition Cellular HTRF Assay in AGS Cell Lines (Method A)

The Phospho-ERK cellular HTRF assay measures ERK protein phosphorylated at Thr202/Tyr204 as a readout of MAPK pathway activation (Cisbio 64ERKPEH). AGS cells (ATCC CRL-1739) are cultured in the complete medium containing 10% fetal bovine serum and 1× Penicillin/Streptomycin at 37° C. in a humid atmosphere of 5% $CO_2$ in the air (AGS cells: RPMI 1640 medium).

On day 1, the cells are plated in tissue-culture treated 96-well plates at the specified densities and allowed to attach for overnight (AGS: 30,000 cells/well). On day 2, the cells are treated with the serially diluted compound solutions in a final concentration of 0.5% DMSO. After the treatment for the specified time (AGS cells: 3 hours), the supernatant is removed, and the cells are lysed by the lysis buffer supplied with the kit. Then, the cell lysates are treated with the detection reagents overnight at 4° C. in darkness. On day 3, the fluorescence intensities at the wavelengths 665 and 620 nm are measured by the Envision plate reader (Perkin Elmer). The data are processed and fitted to a 4-parameter logistic model for $IC_{50}$ calculations (GraphPad Prism 9).

Example 13. pERK in Cell Western (ICW) Assay (Method B)

pERK ICW is a high throughput screening assay to evaluate the cellular potency of mutant KRAS small molecule inhibitors. KRAS mutant cell lines AGS and GP2D ($KRAS^{G12D}$) were purchased from ATCC and maintained respectively in RPMI and DMEM medium supplemented with 10% fetal bovine serum and Penicillin/Streptomycin.

Cells grown in exponential phase were trypsinized, resuspended in fresh media, and viable cells were counted using a cell counter with Trypan Blue (BioRad TC20). Cells were seeded into 384-well plate (Greiner 781091) at density of 5,000 cells/well for AGS and 10,000 cells/well for GP2D and allowed to grow overnight in a 37° C. $CO_2$ incubator. The next day, compounds were dispensed into wells with a ½ log, 10-point serial dilution and top concentration of 10 pM using Tecan D300e dispenser and incubated for 3 hours in a 37° C. $CO_2$ incubator. Cells were then fixed with paraformaldehyde (Electron Microscopy Sciences, 15710, 4% final concentration) for 30 min, permeabilized with wash buffer (1×PBS+0.1% Triton X-100) for 30 min and blocked with Odyssey blocking buffer (Li—COR 927-70001) for 1 hour, all at room temperature (RT). Phospho-ERK antibody (CST 4370L) was diluted 1:500 in Odyssey blocking+0.2% Tween 20 and incubated with cells overnight at 4° C. The next day, plates were washed 5× with wash buffer, incubated with IRDye 800 CW, Goat anti-Rabbit secondary antibody (Li—COR 926-32211, 1:500) and DRAQ5 (CST 4084L, 1:5,000) diluted in in Odyssey blocking+0.2% Tween 20 for 1 hour, washed 5×, and imaged on an Odyssey CLx imaging system.

For data analysis, signal intensities from 800 (phosphor-ERK) and 700 (DRAQ5) channels were extracted, and phospho-ERK signals were normalized to DRAQ5 signals for each well and percent of DMSO control values were computed. Data were then imported into Graphpad Prism to compute half-maximal inhibitory concentrations ($IC_{50}$) using a 4-parameter variable slope model. Z-factor for each plate was computed from signals derived from wells treated with either DMSO or 5 pM of Trametinib. AGS pERK ICW (Method B) $IC_{50}$ (uM) values of selected compounds are depicted in Table 2 with compounds having a value 0.001 uM to 0.01 uM as ++++; >0.01 uM to 0.1 uM as +++; >0.1 uM to 1 uM as ++; 1 uM to 10 uM as + and >10 uM as NA.

Table 2 includes NEA KRAS G12D $IC_{50}$ (uM) values (<0.01 uM as ++++; >0.01 uM to 0.1 uM as +++; >0.1 uM to 1 uM as ++; >1 uM to 20 uM as +; and >20 uM as NA), PPI KRAS G12D/RAF1 $IC_{50}$ (uM) values (<0.1 uM as ++++; >0.1 uM to 1 uM as +++; >1 uM to 10 uM as ++; >10 uM to 100 uM as +; and >100 uM as NA), AGS pERK HTRF (Method A) $IC_{50}$ (uM) values (<0.01 uM as ++++; >0.01 uM to 0.1 uM as +++; 0.1 uM to 1 uM as ++; 1 uM to 20 uM as + and >20 uM as NA), and AGS pERK ICW (Method B) $IC_{50}$ (uM) values (0.001 uM to 0.01 uM as ++++; >0.01 uM to 0.1 uM as +++; >0.1 uM to 1 uM as ++; 1 uM to 10 uM as + and >10 uM as NA) of selected compounds. ND indicates not determined.

TABLE 2

$IC_{50}$ (uM) values for various assays

| cpd# | NEA-G12D (uM) | PPI-G12D (uM) | pERK-AGS (uM) Method B |
|---|---|---|---|
| 1 | ++ | + | ND |
| 2 | ++++ | +++ | +++ |
| 3 | ++++ | + | ND |

Table 3 includes KRASG12V/RAF1, wtKRAS/RAF1 and wtNRAS/RAF1 PPI $IC_{50}$ (uM) values of selected compounds; with compounds having a value <0.1 uM as ++++; 0.1 uM to 1 uM as +++; >1 uM to 10 uM as ++; >10 uM to 100 uM as +; and >100 uM as NA.

TABLE 3

IC$_{50}$ (uM) values for KRASG12V/RAF1, wtKRAS/RAF1 and wtNRAS/RAF1 PPI

| cpd# | PPI-G12V (uM) | PPI-w.t.KRAS (uM) | PPI-w.t.NRAS (uM) |
|---|---|---|---|
| 2 | ++ | ++ | NA |
| 3 | + | ND | NA |

Table 4 includes NEA KRAS G12D IC$_{50}$ (uM) values (<0.01 uM as ++++; >0.01 uM to 0.1 uM as +++; >0.1 uM to 1 uM as ++; >1 uM to 20 uM as +; and >20 uM as NA), PPI KRAS G12D/RAF1 C$_{50}$ (uM) values (<0.1 uM as ++++; >0.1 uM to 1 uM as +++; >1 uM to 10 uM as ++; >10 uM to 100 uM as +; and >100 uM as NA), AGS and GP2D pERK ICW IC$_{50}$ (uM) values (0.001 uM to 0.01 uM as ++++; >0.01 uM to 0.1 uM as +++; >0.1 uM to 1 uM as ++; 1 uM to 10 uM as +; and >10 uM as NA) of selected compounds. ND indicates not determined.

TABLE 4

| # | NEA G12D | PPI G12D | ICW-AGS | ICW-GP2D |
|---|---|---|---|---|
| 1 | ++ | + | ND | ND |
| 2 | ++++ | +++ | +++ | ++++ |
| 3 | ++++ | ++ | +++ | ++++ |
| 4 | ++++ | ++++ | ++++ | ++++ |
| 5 | ++++ | ++ | +++ | ++++ |
| 6 | ++ | + | ND | ND |
| 7 | ++++ | +++ | + | ++ |
| 8 | ++++ | ++ | +++ | ++++ |
| 9 | ++++ | ++ | ++ | +++ |
| 10 | ++++ | ++ | +++ | +++ |
| 11 | ++++ | +++ | + | + |
| 12 | ++++ | +++ | + | + |
| 13 | ++++ | ++ | +++ | ++++ |
| 14 | ++++ | +++ | +++ | ++++ |
| 15 | ++++ | +++ | +++ | +++ |
| 16 | ++++ | + | ++ | ++ |
| 17 | ++++ | ++ | ++ | +++ |
| 18 | ++++ | +++ | ++ | +++ |
| 19 | +++ | ++ | + | ++ |
| 20 | ++++ | ++ | ND | ND |
| 21 | ++++ | ++ | ++ | +++ |
| 22 | ++++ | +++ | +++ | +++ |
| 23 | ++++ | ++ | ++ | +++ |
| 24 | +++ | + | ++ | ++ |
| 25 | ++++ | +++ | +++ | ++++ |
| 26 | ++++ | + | + | ++ |
| 27 | +++ | ++ | ND | ++ |
| 28 | +++ | +++ | ND | ND |
| 29 | +++ | + | + | ++ |
| 30 | ++++ | + | ++ | +++ |
| 31 | +++ | ++ | ND | ND |
| 32 | ++++ | + | ++ | +++ |
| 33 | +++ | ++ | + | ++ |
| 34 | ++++ | +++ | +++ | ++++ |
| 35 | + | NA | ND | ND |
| 36 | + | NA | ND | ND |
| 37 | NA | NA | ND | ND |
| 38 | +++ | ++ | ND | ND |
| 39 | ++ | NA | ND | ND |
| 40 | +++ | ++ | ND | ++ |
| 41 | ++++ | +++ | +++ | ++++ |
| 42 | ++++ | ++ | ++ | ++ |
| 43 | +++ | ++ | ND | ++ |
| 44 | + | NA | ND | ND |
| 45 | ++++ | +++ | +++ | ++++ |
| 46 | ++++ | ++ | ++ | +++ |
| 47 | ++++ | + | ++ | +++ |
| 48 | +++ | + | + | ++ |
| 49 | +++ | + | ND | ++ |
| 50 | + | NA | ND | ND |
| 51 | +++ | ++ | ND | ND |
| 52 | ++++ | ++ | ++ | ++++ |
| 53 | ++ | NA | ND | ND |
| 54 | ++ | +++ | ND | ND |
| 55 | ++ | + | ND | ND |
| 56 | ++++ | +++ | ND | ND |
| 57 | + | + | ND | ND |
| 58 | ++++ | ++ | ND | ND |
| 59 | ++ | + | ND | ND |
| 60 | ++++ | ++ | ND | ND |
| 61 | +++ | +++ | ND | ND |
| 62 | ++++ | + | +++ | +++ |
| 63 | +++ | + | ND | ND |
| 64 | ++++ | ++ | ND | ND |
| 65 | + | + | ND | ND |
| 66 | ++ | + | ND | ND |
| 67 | ++ | + | ND | ND |
| 68 | ++++ | ++ | ND | ND |
| 69 | ++++ | +++ | +++ | ++++ |
| 70 | ++++ | +++ | +++ | +++ |
| 71 | ++++ | ++ | ND | ++ |
| 72 | ++++ | +++ | ND | ND |
| 73 | ++++ | +++ | ND | ++++ |
| 74 | +++ | + | ND | + |
| 74.1 | ++++ | ++++ | ++++ | ++++ |
| 74.2 | +++ | + | ND | + |
| 75 | ++++ | +++ | ND | +++ |
| 76 | ++++ | +++ | ND | +++ |
| 77 | ++++ | + | ND | ND |
| 78 | +++ | NA | ND | ND |
| 79 | ++++ | +++ | +++ | +++ |
| 80 | ++++ | +++ | +++ | ++++ |
| 81 | ++++ | ++ | ++ | +++ |
| 82 | ++ | + | ND | ND |
| 83 | ++++ | +++ | ND | ND |
| 84 | ++++ | +++ | ND | ND |
| 85 | ++++ | + | ++ | +++ |
| 86 | ++++ | ++++ | +++ | ++++ |
| 87 | ++++ | ++ | +++ | ++++ |
| 88 | +++ | + | + | + |
| 89 | ++++ | +++ | +++ | +++ |
| 90 | +++ | + | ND | ND |
| 91 | ++++ | +++ | +++ | +++ |
| 92 | +++ | + | ND | + |
| 93 | ++++ | +++ | ND | ++++ |
| 94 | ++++ | ++++ | ND | ++++ |
| 95 | ++++ | ++ | ND | ND |
| 96 | ++++ | ++ | ND | +++ |
| 97 | ++++ | + | ND | ++ |
| 98 | ++++ | ++ | ND | + |
| 99 | ++++ | +++ | ND | ++++ |
| 100 | ++++ | ++++ | ND | ++++ |
| 101 | ++++ | +++ | ND | ++++ |
| 102 | ++++ | + | ND | ND |
| 103 | +++ | + | ND | ND |
| 104 | ++++ | + | ND | ND |
| 105 | ++++ | + | ND | ND |
| 106 | +++ | + | ND | ND |
| 107 | +++ | + | ND | ND |
| 108 | +++ | + | ND | + |
| 109 | +++ | ND | ND | ND |
| 110 | +++ | ND | ND | ND |
| 111 | +++ | ND | ND | ND |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

SEQUENCE LISTING

```
Sequence total quantity: 8
SEQ ID NO: 1                moltype = AA   length = 185
FEATURE                     Location/Qualifiers
source                      1..185
                            mol_type = protein
                            organism = synthetic construct
SEQUENCE: 1
SGLNDIFEAQ KIEWHEMTEY KLVVVGADGV GKSALTIQLI QNHFVDEYDP TIEDSYRKQV   60
VIDGETCLLD ILDTAGQEEY SAMRDQYMRT GEGFLCVFAI NNTKSFEDIH HYREQIKRVK  120
DSEDVPMVLV GNKCDLPSRT VDTKQAQDLA RSYGIPFIET SAKTRQGVDD AFYTLVREIR  180
KHKEK                                                              185

SEQ ID NO: 2                moltype = AA   length = 185
FEATURE                     Location/Qualifiers
source                      1..185
                            mol_type = protein
                            organism = synthetic construct
SEQUENCE: 2
SGLNDIFEAQ KIEWHEMTEY KLVVVGAVGV GKSALTIQLI QNHFVDEYDP TIEDSYRKQV   60
VIDGETCLLD ILDTAGQEEY SAMRDQYMRT GEGFLCVFAI NNTKSFEDIH HYREQIKRVK  120
DSEDVPMVLV GNKCDLPSRT VDTKQAQDLA RSYGIPFIET SAKTRQGVDD AFYTLVREIR  180
KHKEK                                                              185

SEQ ID NO: 3                moltype = AA   length = 185
FEATURE                     Location/Qualifiers
source                      1..185
                            mol_type = protein
                            organism = synthetic construct
SEQUENCE: 3
SGLNDIFEAQ KIEWHEMTEY KLVVVGAGGV GKSALTIQLI QNHFVDEYDP TIEDSYRKQV   60
VIDGETCLLD ILDTAGQEEY SAMRDQYMRT GEGFLCVFAI NNTKSFEDIH HYREQIKRVK  120
DSEDVPMVLV GNKCDLPSRT VDTKQAQDLA RSYGIPFIET SAKTRQGVDD AFYTLVREIR  180
KHKEK                                                              185

SEQ ID NO: 4                moltype = AA   length = 185
FEATURE                     Location/Qualifiers
source                      1..185
                            mol_type = protein
                            organism = synthetic construct
SEQUENCE: 4
SGLNDIFEAQ KIEWHEMTEY KLVVVGAGGV GKSALTIQLI QNHFVDEYDP TIEDSYRKQV   60
VIDGETCLLD ILDTAGQEEY SAMRDQYMRT GEGFLCVFAI NNSKSFADIN LYREQIKRVK  120
DSDDVPMVLV GNKCDLPTRT VDTKQAHELA KSYGIPFIET SAKTRQGVED AFYTLVREIR  180
QYRMK                                                              185

SEQ ID NO: 5                moltype = AA   length = 89
FEATURE                     Location/Qualifiers
source                      1..89
                            mol_type = protein
                            organism = synthetic construct
SEQUENCE: 5
SHHHHHHHHS KTSNTIRVFL PNKQRTVVNV RNGMSLHDCL MKALKVRGLQ PECCAVFRLL   60
HEHKGKKARL DWNTDAASLI GEELQVDFL                                     89

SEQ ID NO: 6                moltype = AA   length = 7
FEATURE                     Location/Qualifiers
source                      1..7
                            mol_type = protein
                            organism = synthetic construct
SEQUENCE: 6
ENLFYQS                                                              7

SEQ ID NO: 7                moltype = AA   length = 15
FEATURE                     Location/Qualifiers
source                      1..15
                            mol_type = protein
                            organism = synthetic construct
SEQUENCE: 7
GLNDIFEAQK IEWHE                                                    15

SEQ ID NO: 8                moltype = AA   length = 6
FEATURE                     Location/Qualifiers
source                      1..6
                            mol_type = protein
                            organism = synthetic construct
SEQUENCE: 8
HHHHHH                                                               6
```

What is claimed is:

1. A compound of Formula (I):

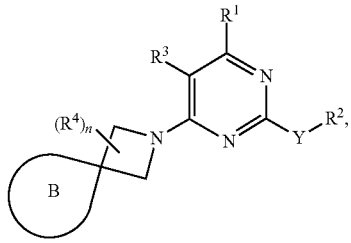

Formula (I)

or a pharmaceutically acceptable salt thereof wherein:

B is selected from a 7- to 15-membered heterocycle and $C_7$-$C_{15}$ carbocycle, wherein the 7- to 15-membered heterocycle and $C_7$-$C_{15}$ carbocycle are each optionally substituted with one or more substituents independently selected from halogen, —CN, —NO$_2$, =O, —N(R$^{21}$)$_2$, —B(OR$^{21}$)$_2$, —OR$^{21}$, —SR$^{21}$, —S(O)$_2$(R$^{21}$), —S(O)$_2$N(R$^{21}$)$_2$, —NR$^{21}$S(O)$_2$R$^{21}$, —C(O)N(R$^{21}$)$_2$, —C(O)NR$^{21}$OR$^{21}$, —N(R$^{21}$)C(O)R$^{21}$, —N(R$^{21}$)C(O)N(R$^{21}$)$_2$, —N(R$^{21}$)C(O)OR$^{21}$, —C(O)R$^{21}$, C(O)OR$^{21}$, —OC(O)R$^{21}$, —OC(O)N(R$^{21}$)$_2$, $C_{1-6}$ alkyl-N(R$^{20}$)$_2$, $C_{1-6}$ aminoalkyl, $C_{1-6}$ alkoxy, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, $C_3$-$C_{12}$ carbocycle and 5- to 12-membered heterocycle;

R$^1$ is selected from hydrogen and 5- to 15-membered heterocycle, wherein the 5- to 15-membered heterocycle is optionally substituted with one or more substituents independently selected from halogen, —B(OR$^{20}$)$_2$, —OR$^{20}$, —SR$^{20}$, —S(O)$_2$(R$^{20}$), —S(O)$_2$N(R$^{20}$)$_2$, —S(O)N(R$^{20}$)$_2$, —S(O)R$^{20}$ (=NR$^{20}$), —NR$^{20}$S(O)$_2$R$^{20}$, —C(O)N(R$^{20}$)$_2$, —C(=NR$^{20}$)N(R$^{20}$)$_2$, —C$_{1-6}$ alkyl(=NOR$^{20}$), —C(O)NR$^{20}$OR$^{20}$, —N(R$^{20}$)C(O)R$^{20}$, —N(R$^{20}$)C(O)N(R$^{20}$)$_2$, —N(R$^{20}$)C(O)OR$^{20}$, —N(R$^{20}$)$_2$, —C(O)R$^{20}$, —C(O)OR$^{20}$, —OC(O)R$^{20}$, —OC(O)N(R$^{20}$)$_2$, —NO$_2$, =O, =N(R$^{20}$), =NO(R$^{20}$), —CN, —NHCN, $C_{1-6}$ alkyl-N(R$^{20}$)$_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl-SO$_2$R$^{20}$, $C_{1-6}$ alkoxyalkyl, $C_{1-6}$ alkyl, $C_{2-6}$ alkenyl, $C_{2-6}$ alkynyl, $C_3$-$C_{12}$ carbocycle and 5- to 12-membered heterocycle, wherein the $C_3$-$C_{12}$ carbocycle and 5- to 12-membered heterocycle are each optionally substituted independently with one or more R$^{1*}$;

each R$^{1*}$ is independently selected from halogen, —B(OR$^{20}$)$_2$, —OR$^{20}$, —SR$^{20}$, —S(O)$_2$(R$^{20}$), —S(O)$_2$N(R$^{20}$)$_2$, —S(O)N(R$^{20}$)$_2$, —S(O)R$^{20}$ (=NR$^{20}$), —NR$^{20}$S(O)$_2$R$^{20}$, —C(O)N(R$^{20}$)$_2$, —C(O)NR$^{20}$OR$^{20}$, —N(R$^{20}$)C(O)R$^{20}$, —N(R$^{20}$)C(O)N(R$^{20}$)$_2$, —N(R$^{20}$)C(O)OR$^{20}$, —N(R$^{20}$)$_2$, —C(O)R$^{20}$, —C(O)OR$^{20}$, —OC(O)R$^{20}$, —OC(O)N(R$^{20}$)$_2$, —NO$_2$, =O, =N(R$^{20}$), =NO(R$^{20}$), —CN, —NHCN, $C_{1-6}$ alkyl-N(R$^{20}$)$_2$, $C_{1-6}$ aminoalkyl, $C_{1-6}$ alkoxy, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, and $C_3$-$C_{12}$ carbocycle;

Y is —O—;

R$^2$ is selected from heterocycle, -L-heterocycle, -L-N(R$^{23}$)$_2$, and -L-aryl, wherein the heterocycle, and the heterocycle portion of -L-heterocycle are each optionally substituted with one or more R$^6$, and wherein the aryl of the -L-aryl is optionally substituted with one or more R$^7$;

R$^3$ is selected from hydrogen, halogen, —CN, —NO$_2$, —N(R$^{20}$)$_2$, —OR$^{20}$, —SR$^{20}$, —S(O)$_2$(R$^{20}$), —S(O)$_2$N(R$^{20}$)$_2$, —S(O)N(R$^{20}$)$_2$, —S(O)R$^{20}$ (=NR$^{20}$), —NR$^{20}$S(O)$_2$R$^{20}$, —C(O)N(R$^{20}$)$_2$, —N(R$^{20}$)C(O)R$^{20}$, —N(R$^{20}$)C(O)N(R$^{20}$)$_2$, —N(R$^{20}$)C(O)OR$^{20}$, —C(O)R$^{20}$, —C(O)OR$^{20}$, —OC(O)R$^{20}$, —OC(O)N(R$^{20}$)$_2$, $C_{1-6}$ alkyl-N(R$^{20}$)$_2$, $C_{1-6}$ aminoalkyl, $C_{1-6}$ alkoxy, $C_{1-6}$ alkoxyalkyl, $C_{1-6}$ hydroxyalkyl, $C_{1-6}$ cyanoalkyl, $C_{1-6}$ haloalkyl, $C_{1-6}$ alkyl, $C_{2-6}$ alkenyl, $C_{2-6}$ alkynyl, $C_3$-$C_{12}$ carbocycle and 5- to 12-membered heterocycle;

each R$^4$ is independently selected from halogen, —NO$_2$, —O, =S, —CN, $C_{1-6}$ alkyl, $C_{2-6}$ alkynyl, $C_{1-6}$ alkyl-N(R$^{20}$)$_2$, $C_{1-6}$ aminoalkyl, $C_{1-6}$ alkoxy, $C_{1-6}$ cyanoalkyl, $C_{1-6}$ hydroxyalkyl, and $C_{1-6}$ haloalkyl;

n is selected from 0, 1, 2, 3, and 4;

each R$^5$ is independently selected from hydrogen and $C_1$-$C_6$ alkyl;

each R$^6$ is independently selected from halogen, hydroxy, $C_1$-$C_3$ hydroxyalkyl, $C_1$-$C_3$ alkyl, oxo, $C_1$-$C_3$ haloalkyl, $C_1$-$C_3$ alkoxy, cyano, =CH$_2$, =NO—$C_1$-$C_3$ alkyl, $C_1$-$C_3$ aminoalkyl, —N(R$^5$) S(O)$_2$(R$^5$), -Q-phenyl, -Q-phenylSO$_2$F, —NHC(O)phenyl, —NHC(O)phenylSO$_2$F, $C_1$-$C_3$ alkyl substituted pyrazolyl, —C$_1$-C$_3$ alkyl-N(R$^5$)$_2$, —C(O)N(R$^5$)$_2$, —C$_1$-C$_3$ alkyl-N(R$^5$)$_2$, —C(O)N(R$^5$)$_2$, tert-butyldimethylsilyloxyCH$_2$—, —N(R$^5$)$_2$, (C$_1$-C$_3$ alkoxy) C$_1$-C$_3$ alkyl-, (C$_1$-C$_3$ alkyl) C(=O), oxo, (C$_1$-C$_3$ haloalkyl) C(=O)—, —SO$_2$F, (C$_1$-C$_3$ alkoxy) C$_1$-C$_3$ alkoxy, —CH$_2$OC(O)N(R$^5$)$_2$, —CH$_2$NHC(O)OC$_1$-C$_6$ alkyl, —CH$_2$NHC(O)N(R$^5$)$_2$, —CH$_2$NHC(O) C$_1$-C$_6$ alkyl, —CH$_2$ (pyrazolyl), —CH$_2$NHSO$_2$C$_1$-C$_6$ alkyl, —CH$_2$OC(O)heterocycle, —OC(O)N(R$^5$)$_2$, —OC(O)NH(C$_1$-C$_3$ alkyl)O(C$_1$-C$_3$ alkyl), —OC(O)NH(C$_1$-C$_3$ alkyl)O(C$_1$-C$_3$ alkyl)phenyl(C$_1$-C$_3$ alkyl)N(CH$_3$)$_2$, —OC(O)NH(C$_1$-C$_3$ alkyl)O(C$_1$-C$_3$ alkyl)phenyl, —OC(O)heterocycle, —O—C$_1$-C$_3$ alkyl, —S(O)$_2$(R$^{20}$), —S(O)$_2$N(R$^{20}$)$_2$, —S(O)N(R$^{20}$)$_2$, —S(O)R$^{20}$ (=NR$^{20}$), —NR$^{20}$S(O)$_2$R$^{20}$, and —CH$_2$heterocycle, wherein the phenyl of —NHC(O)phenyl and —OC(O)NH(C$_1$-C$_3$ alkyl) (C$_1$-C$_3$ alkyl)phenyl are optionally substituted with one or more substituents selected from —C(O)H and OH, and wherein the alkyl of —O—C$_1$-C$_3$ alkyl is optionally substituted with substituents selected from heterocycle, oxo and hydroxy; and wherein the heterocycle of —CH$_2$heterocyclyl is optionally substituted with oxo;

each Q is selected from a bond, S, and O;

each R$^7$ is independently selected from halogen, hydroxy, HC(=O)—, $C_1$-$C_4$ alkyl, $C_1$-$C_4$ alkoxy, $C_1$-$C_4$ haloalkyl, $C_1$-$C_4$ hydroxyalkyl, —$C_1$-$C_3$ alkyl-N(R$^5$)$_2$, —C(O)N(R$^5$)$_2$, and —N(R$^5$)$_2$;

each L is independently selected from a $C_1$-$C_4$ alkylene optionally substituted with one or more substituents independently selected from halogen, hydroxy, $C_{1-6}$ alkoxy, $C_1$-$C_4$ hydroxyalkyl, $C_1$-$C_4$ alkyl, $C_3$-$C_6$ carbocycle, and 3- to 8-membered heterocycle, wherein the $C_3$-$C_6$ carbocycle and 3- to 8-membered heterocycle are each optionally substituted with one or more substituents independently selected from halogen, —OH, —NO$_2$, —O, =S, —CN, $C_{1-6}$ alkyl-N(R$^{20}$)$_2$, $C_{1-6}$ aminoalkyl, $C_{1-6}$ alkoxy, $C_{1-6}$ hydroxyalkyl, $C_{1-6}$ haloalkyl; and wherein optionally two substituents on the same carbon atom of L come together to form a $C_3$-$C_6$ carbocycle or 3- to 8-membered heterocycle, wherein the $C_3$-$C_6$ carbocycle and 3- to 8-membered heterocycle are each optionally substituted with one or more substituents independently selected from halogen, —OH, —NO₂, =O, =S, —CN, $C_{1-6}$ alkyl-N$(R^{20})_2$, $C_{1-6}$ aminoalkyl, $C_{1-6}$ alkoxy, $C_{1-6}$ hydroxyalkyl, and $C_{1-6}$ haloalkyl;

each $R^{20}$ is independently selected from hydrogen; and $C_{1-6}$ alkyl, $C_{2-6}$ alkenyl, $C_{2-6}$ alkynyl, $C_{3-12}$ carbocycle, and 3- to 12-membered heterocycle, each of which is optionally substituted with one or more substituents independently selected from halogen, —OH, —CN, —NO₂, —NH₂, —N($C_{1-6}$ alkyl)₂, $C_{1-10}$ alkyl, —$C_{1-10}$ haloalkyl, —O—$C_{1-10}$ alkyl, oxo, $C_{3-12}$ carbocycle, and 3- to 12-membered heterocycle;

each $R^{21}$ is independently selected from hydrogen; and $C_{1-6}$ alkyl, $C_{2-6}$ alkenyl, $C_{2-6}$ alkynyl, $C_{3-12}$ carbocycle, and 3- to 12-membered heterocycle, each of which is optionally substituted with one or more substituents independently selected from halogen, —OH, —CN, —NO₂, —NH₂, —N($C_{1-6}$ alkyl)₂, $C_{1-10}$ alkyl, —$C_{1-10}$ haloalkyl, —O—$C_{1-10}$ alkyl, oxo, $C_{3-12}$ carbocycle, and 3- to 12-membered heterocycle; and each $R^{23}$ is independently selected from hydrogen; and $C_{1-6}$ alkyl, $C_{2-6}$ alkenyl, $C_{2-6}$ alkynyl, $C_{3-12}$ carbocycle, and 3- to 12-membered heterocycle, each of which is optionally substituted with one or more substituents independently selected from halogen, —OH, —CN, —NO₂, —NH₂, —N($C_{1-6}$ alkyl)₂, $C_{1-10}$ alkyl, —$C_{1-10}$ haloalkyl, —O—$C_{1-10}$ alkyl, oxo, $C_{3-12}$ carbocycle, and 3- to 12-membered heterocycle.

2. The compound or salt of claim 1, wherein B is selected from an optionally substituted 7- to 11-membered fused heterocycle, wherein B has at least one sulfur atom.

3. The compound or salt of claim 2, wherein B is selected from

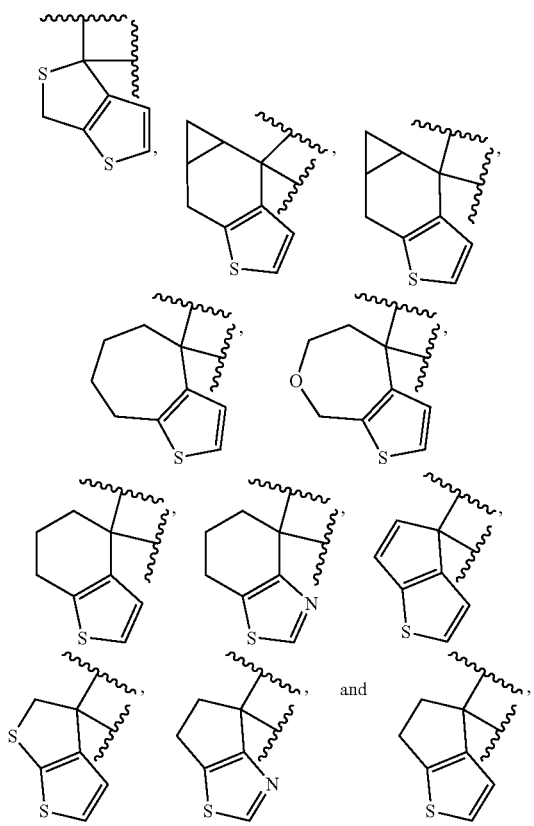

each of which is optionally substituted with one or more optional substituents independently selected at each occurrence from halogen, $C_1$-$C_3$ alkyl, —NH₂, and —CN.

4. The compound or salt of claim 1, wherein B is selected from

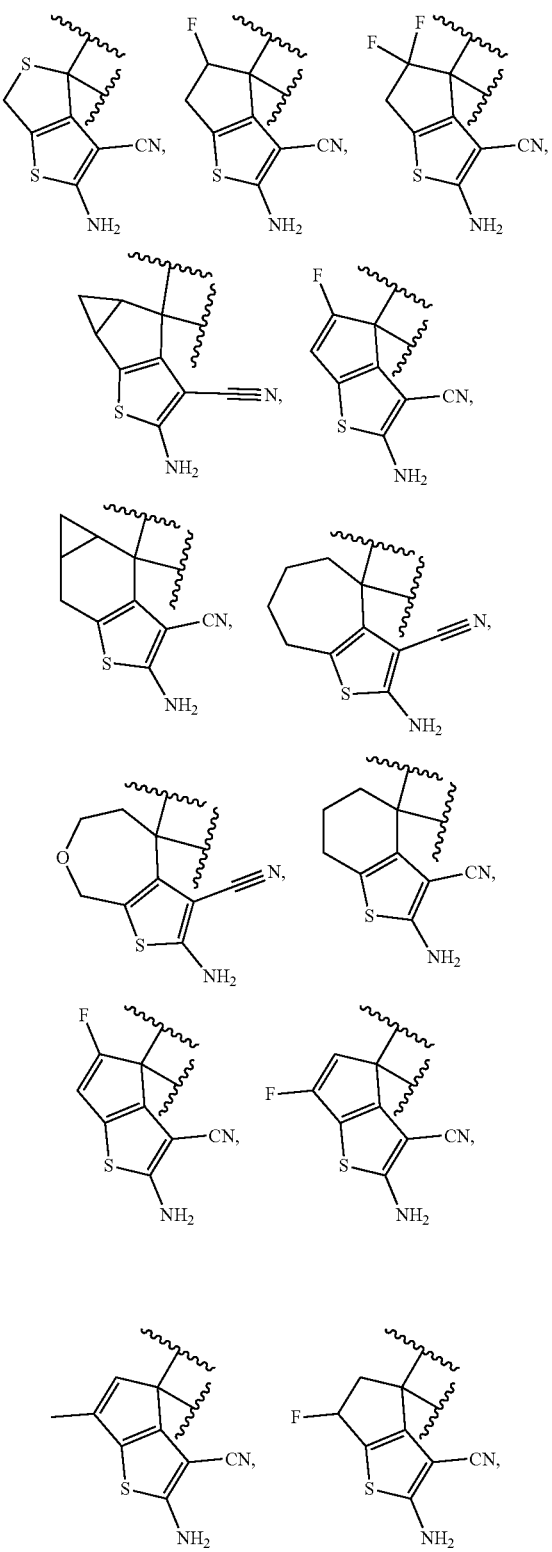

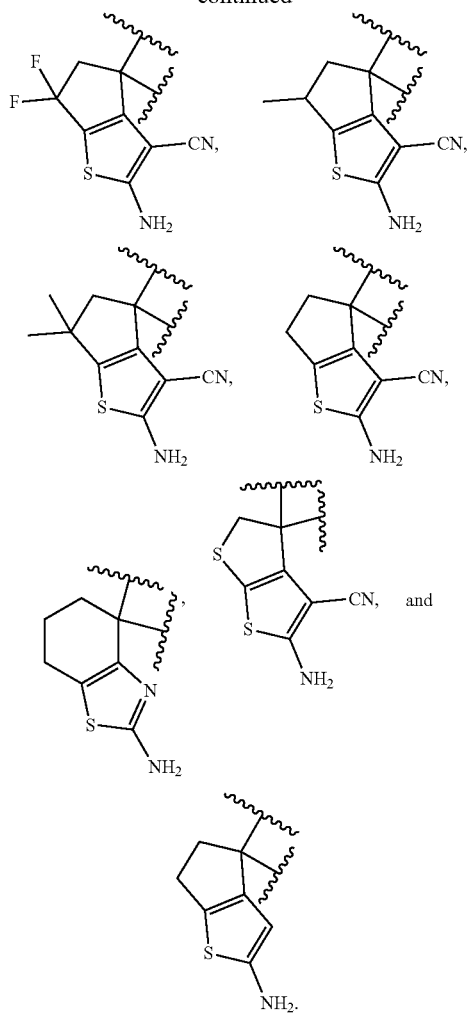

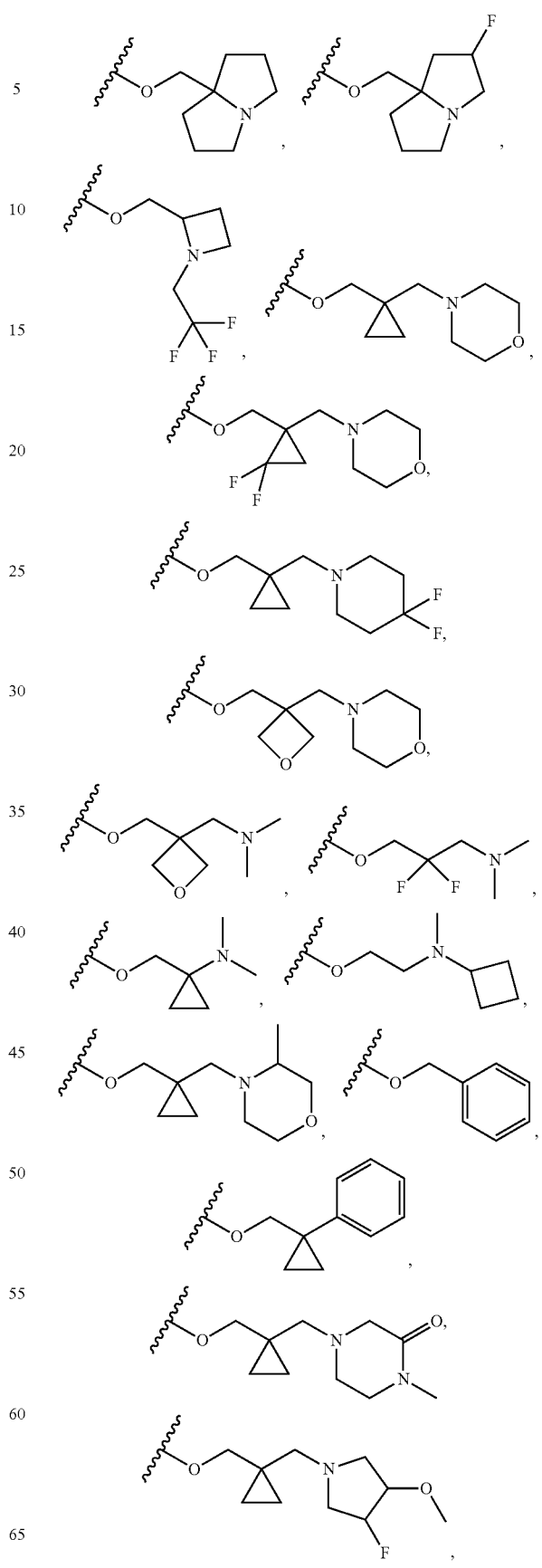

5. The compound or salt of claim 1, wherein $R^3$ is selected from hydrogen, halogen, —CN, —NO$_2$, —S(O)$_2$(R$^{20}$), —S(O)$_2$N(R$^{20}$)$_2$, —S(O)N(R$^{20}$)$_2$, —S(O)R$^{20}$ (=NR$^{20}$), —NR$^{20}$S(O)$_2$R$^{20}$, —C(O)N(R$^{20}$)$_2$, —N(R$^{20}$)C(O)R$^{20}$, —N(R$^{20}$)C(O)N(R$^{20}$)$_2$, —N(R$^{20}$)C(O)OR$^{20}$, —C(O)R$^{20}$, —C(O)OR$^{20}$, —C$_{1-6}$ alkyl-N(R$^{20}$)$_2$, C$_{1-6}$ aminoalkyl, C$_{1-6}$ alkoxy, C$_{1-6}$ alkoxyalkyl, C$_{1-6}$ hydroxyalkyl, C$_{1-6}$ cyanoalkyl, C$_{1-6}$ haloalkyl, C$_{1-6}$ alkyl, C$_{2-6}$ alkenyl, and C$_{2-6}$ alkynyl.

6. The compound or salt of claim 5, wherein $R^3$ is selected from hydrogen, fluorine, and —CN.

7. The compound or salt of claim 1, wherein each L is independently selected from an optionally substituted C$_1$-C$_4$ alkylene; and wherein optionally two substituents on the same carbon atom of L come together to form a C$_3$-C$_6$ carbocycle or 3- to 8-membered heterocycle, wherein the C$_3$-C$_6$ carbocycle and 3- to 8-membered heterocycle are each optionally substituted with one or more substituents selected from halogen, —OH, —NO$_2$, =O, =S, —CN, C$_{1-6}$ aminoalkyl, C$_{1-6}$ alkoxy, C$_{1-6}$ hydroxyalkyl, and C$_{1-6}$ haloalkyl.

8. The compound or salt of claim 1, wherein Y—R$^2$ is selected from

377
-continued
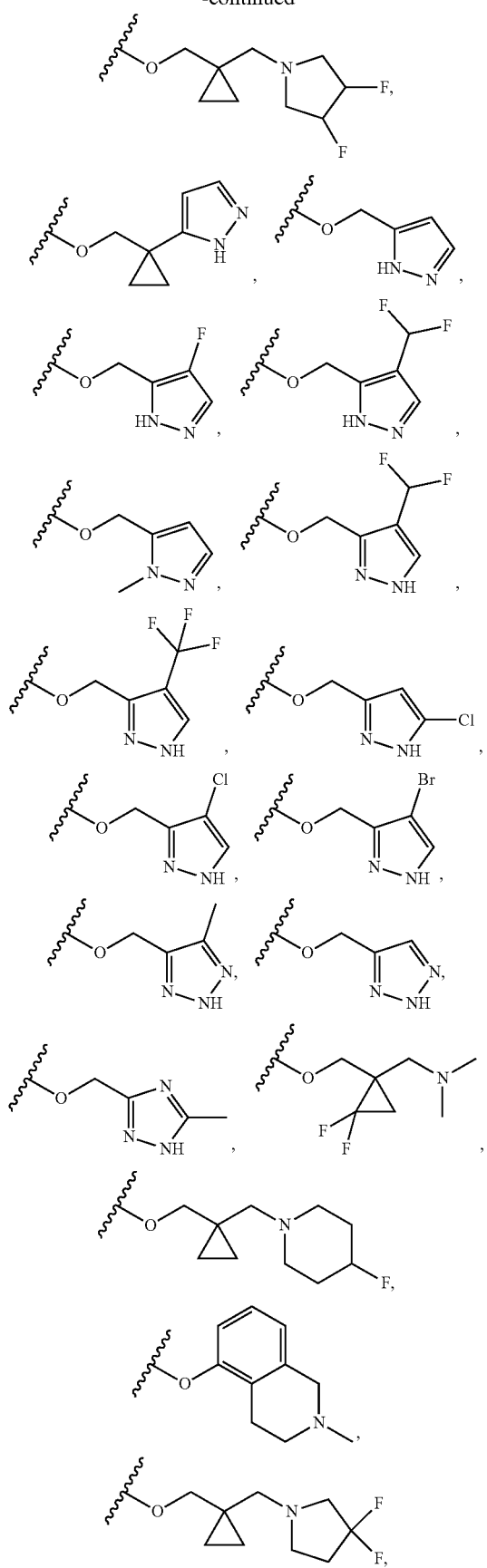
378
-continued
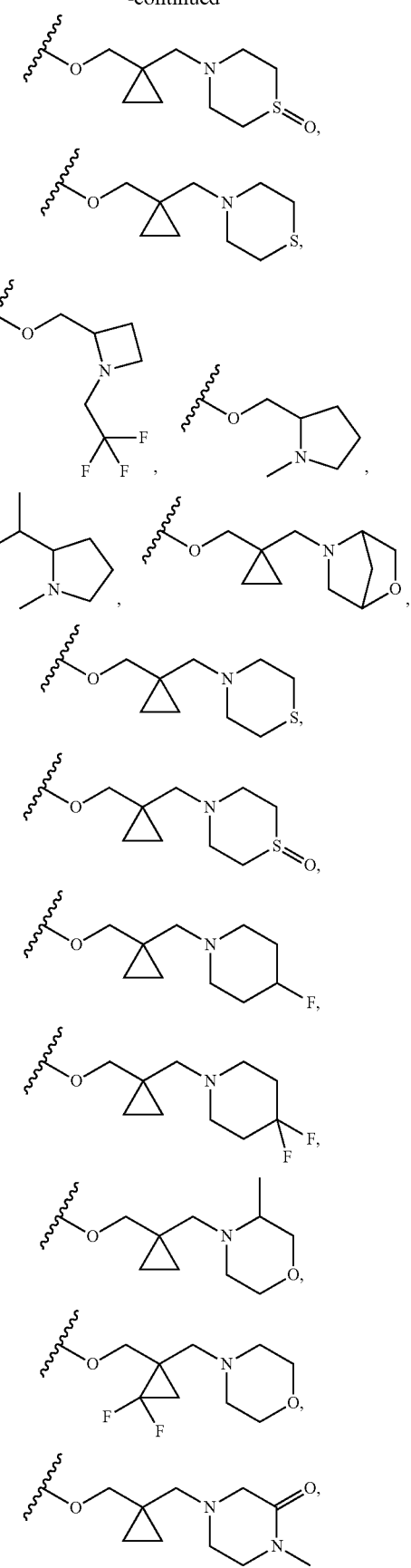

379
-continued
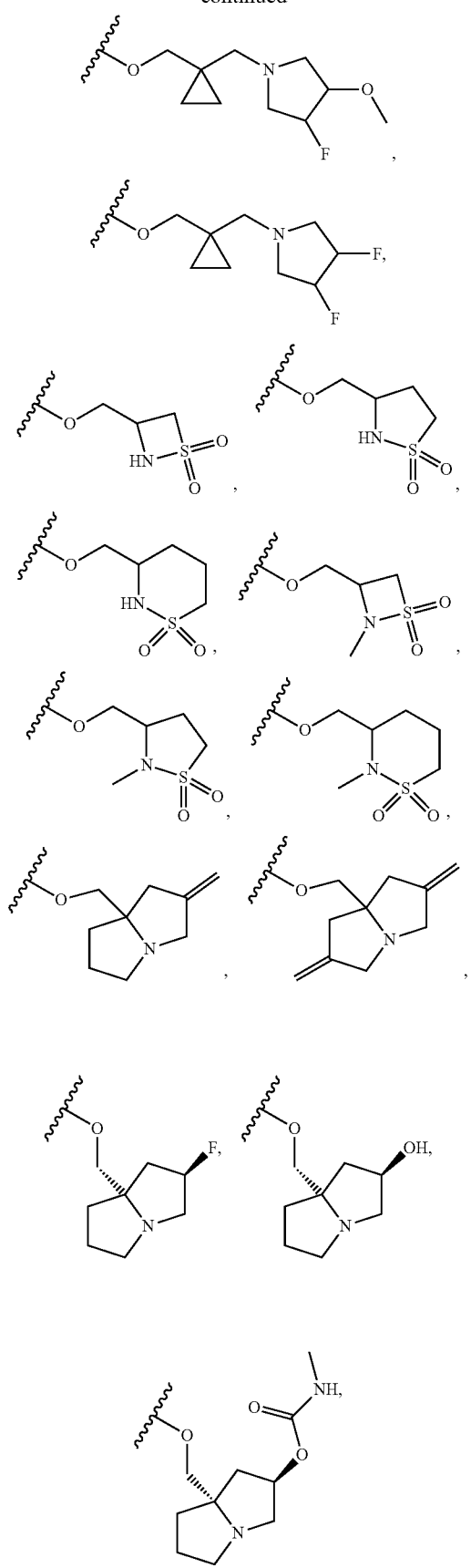
380
-continued
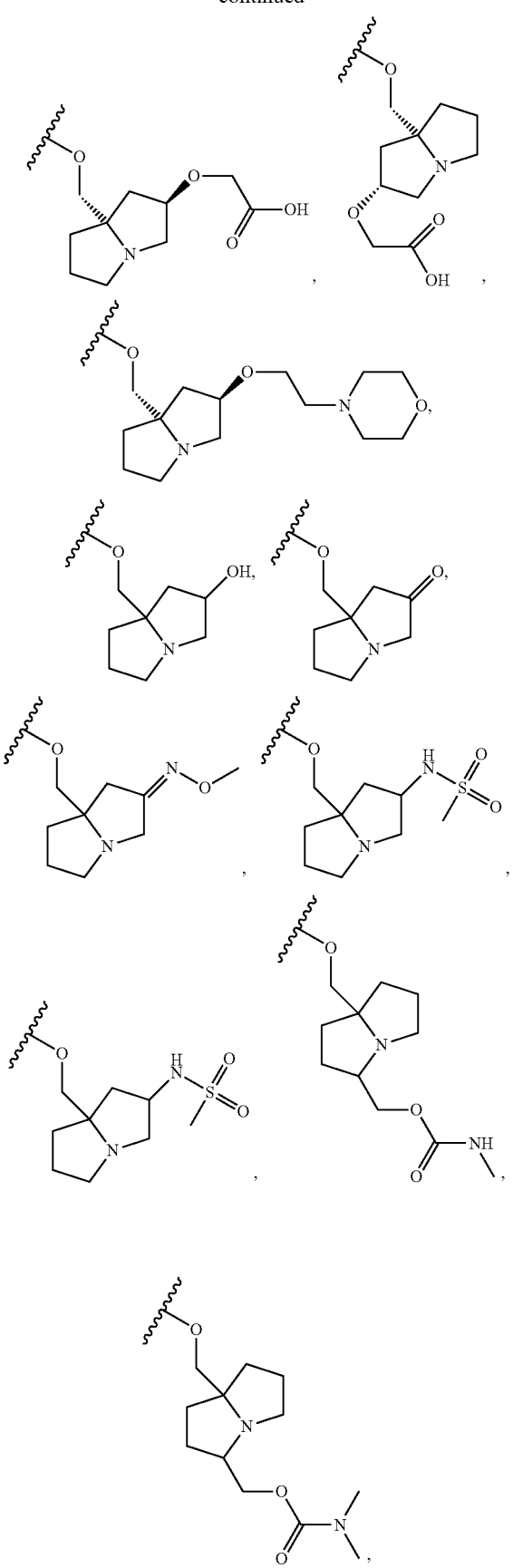

381
-continued

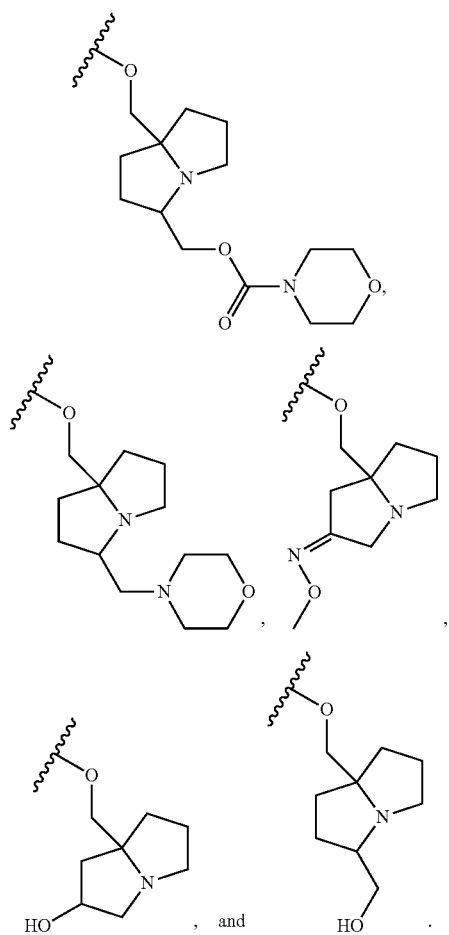

9. The compound or salt of claim 1, wherein Y—R² is selected from

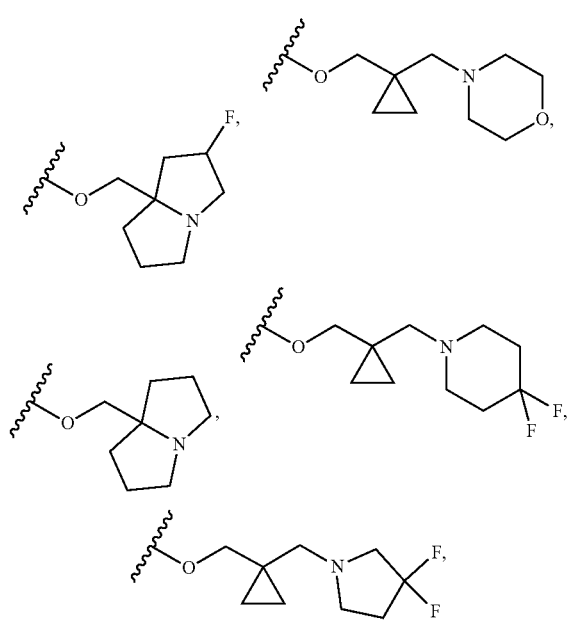

382
-continued

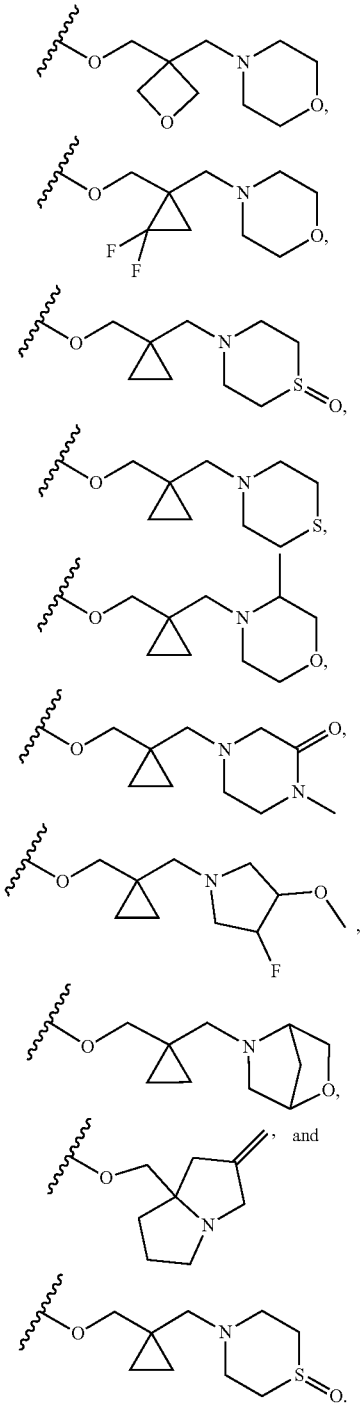

10. The compound or salt of claim 1, wherein R¹ is selected from 8- to 10-membered heterocycle, wherein the 8- to 10-membered heterocycle is optionally substituted with one or more substituents independently selected from halogen, —OR²⁰, —S(O)₂(R²⁰), —C(O)N(R²⁰)₂, —C₁₋₆ alkyl (=NOR²⁰), —C(O)R²⁰, =O, —CN, —NHCN, C₁₋₆ alkyl-N(R²⁰)₂, C₁₋₆ aminoalkyl, C₁₋₆ alkoxy, C₁₋₆ hydroxyalkyl, C₁₋₆ cyanoalkyl, C₁₋₆ haloalkyl, C₁₋₆ alkyl-SO₂R²⁰, C₁₋₆ alkoxyalkyl, C₁₋₆ alkyl, C₂₋₆ alkynyl, and 5- to 12-membered heterocycle, wherein the 5- to 12-membered heterocycle are each optionally substituted independently with one or more R¹*, and wherein each R¹* is independently selected from halogen, —OR²⁰, —N(R²⁰)₂, —NO₂, =O, =N(R²⁰), =NO(R²⁰), —CN, —NHCN, C₁₋₆ alkyl-N(R²⁰)₂, C₁₋₆ aminoalkyl, C₁₋₆ alkoxy, C₁₋₆ hydroxyalkyl, C₁₋₆ cyanoalkyl, C₁₋₆ haloalkyl, and C₁₋₆ alkyl.

11. The compound or salt of claim 10, wherein R¹ is

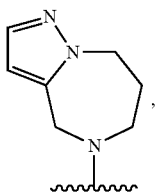 [SMILES: *N1CCCn2nccc2C1]

optionally substituted with one or more substituents independently selected from halogen, —S(O)₂(R²⁰), —C(O)N(R²⁰)₂, —C₁₋₆ alkyl(=NOR²⁰), —C(O)R²⁰, =O, and 5- to 9-membered heterocycle, wherein the 5- to -membered heterocycle are each optionally substituted independently with one or more R¹*.

12. The compound or salt of claim 1, wherein R¹ is selected from

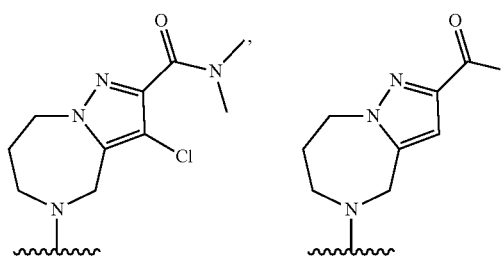

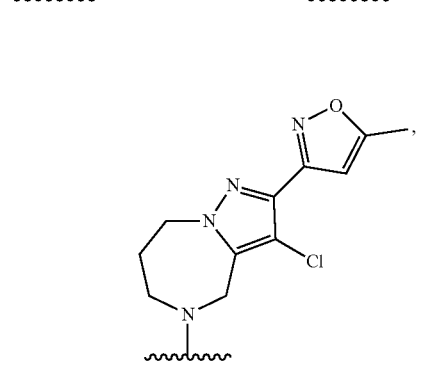

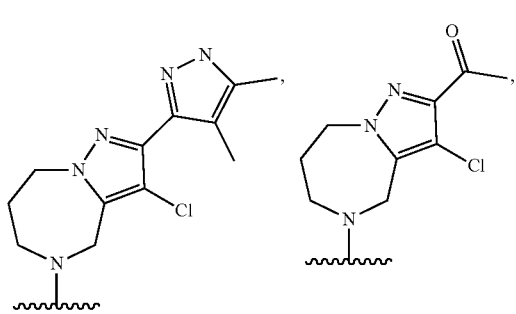

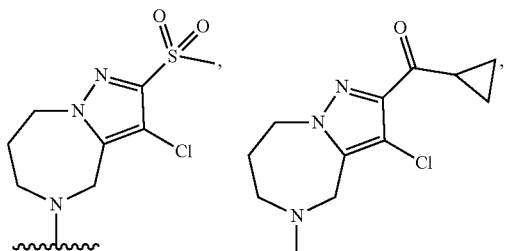

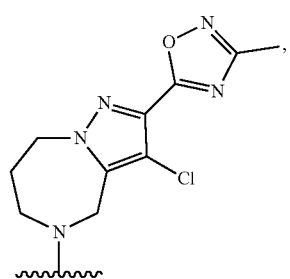

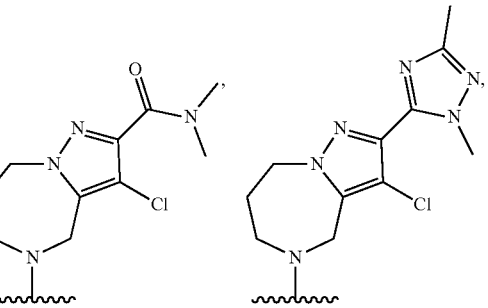

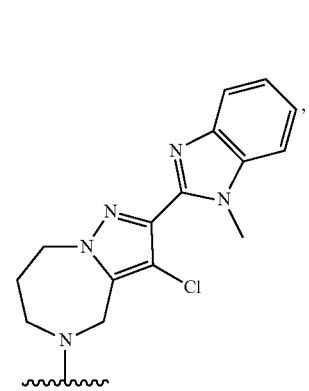

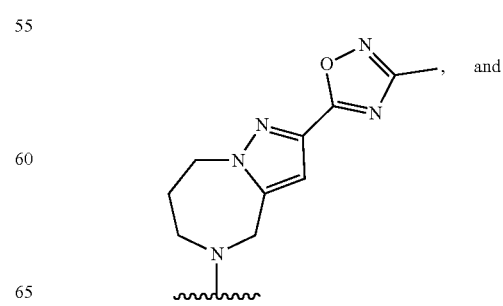

-continued
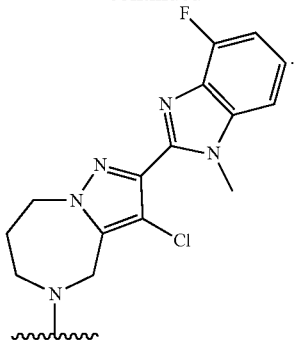
13. The compound or salt of claim 1, wherein R¹ is selected from
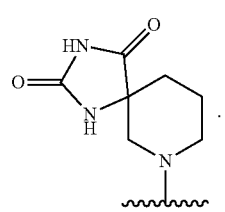
14. The compound or salt of claim 1, wherein R¹ is
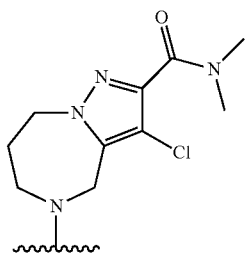
15. The compound or salt of claim 1, wherein R¹ is
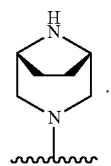
16. The compound or salt of claim 1, wherein R¹ is
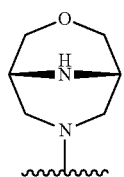
17. The compound or salt of claim 1, wherein the compound is selected from
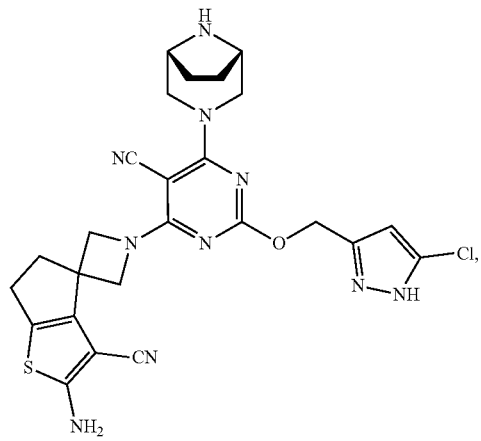
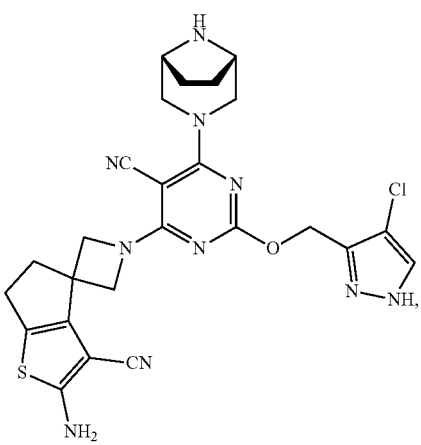
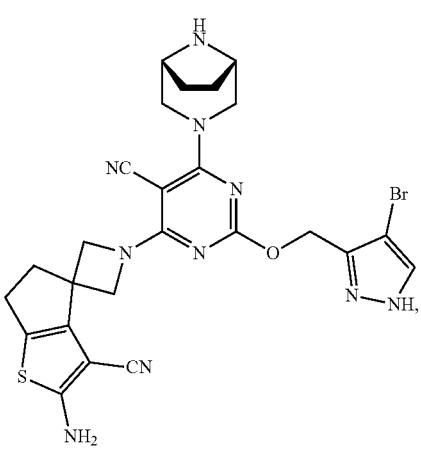

387
-continued
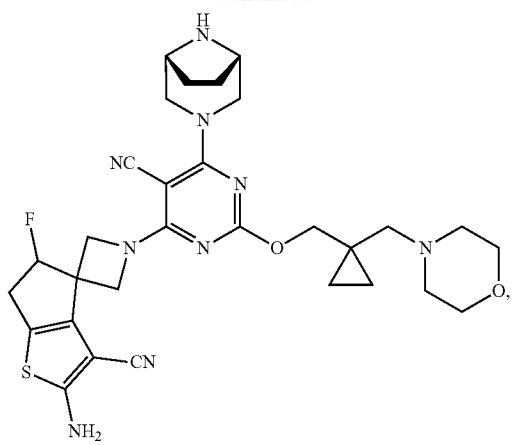
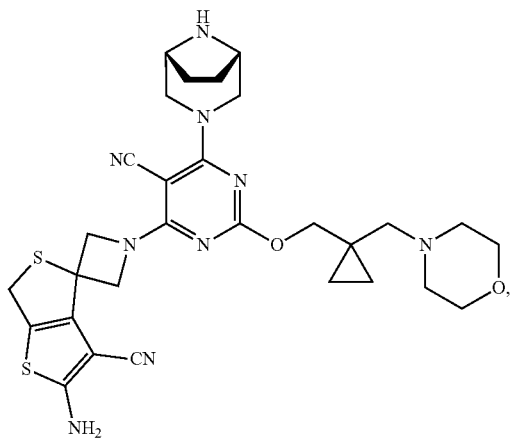
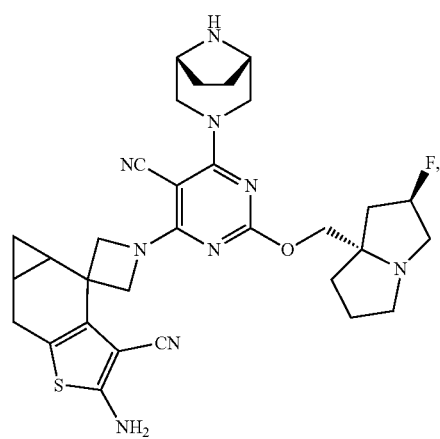
388
-continued
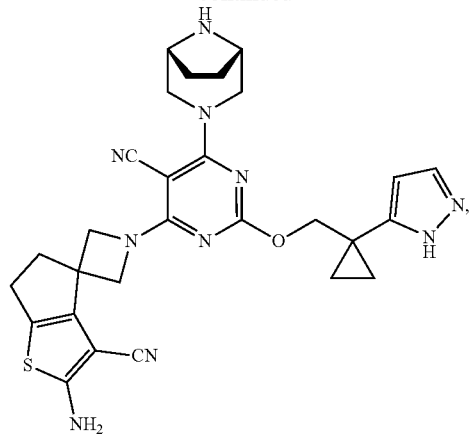
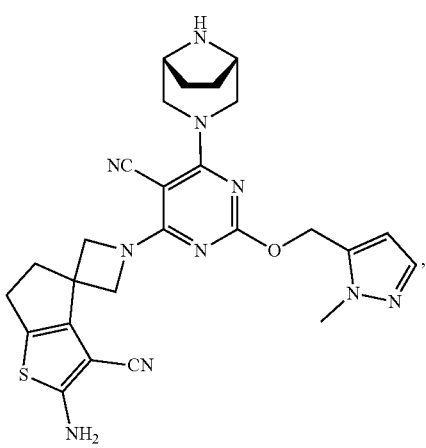
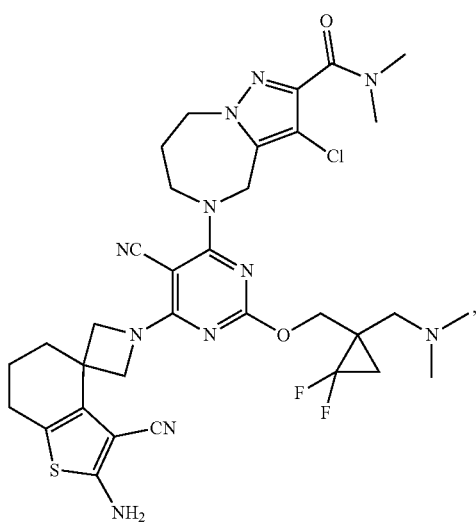

389
-continued
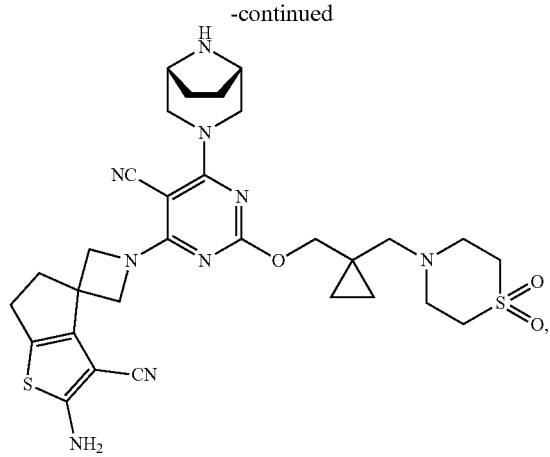
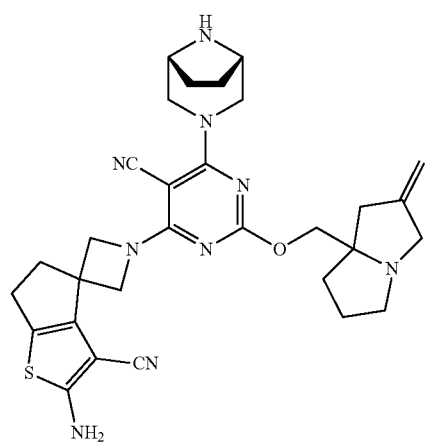
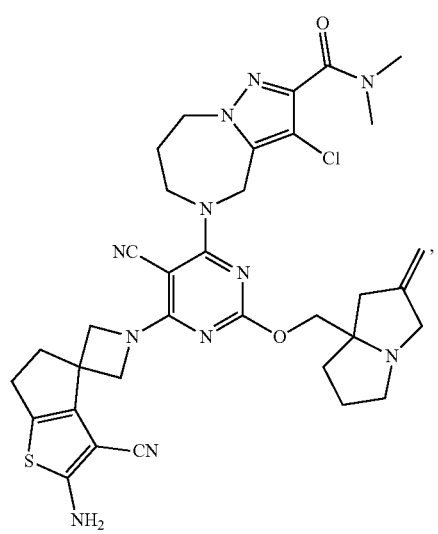
390
-continued
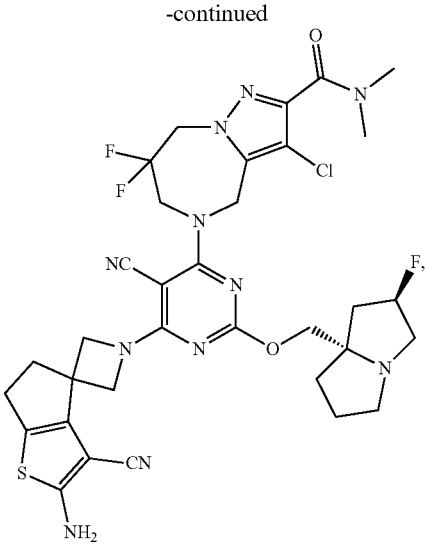
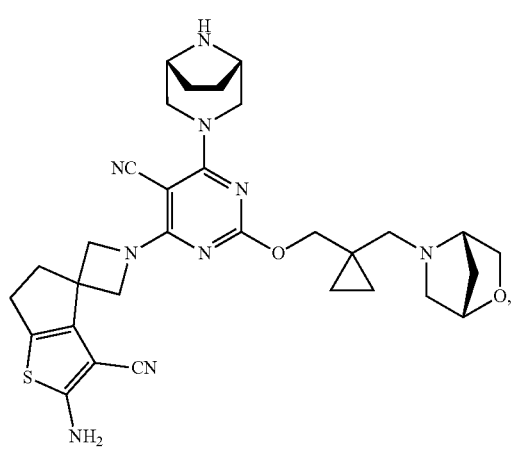
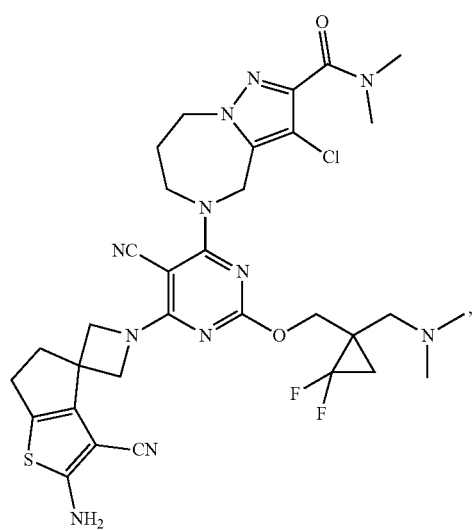

391
-continued
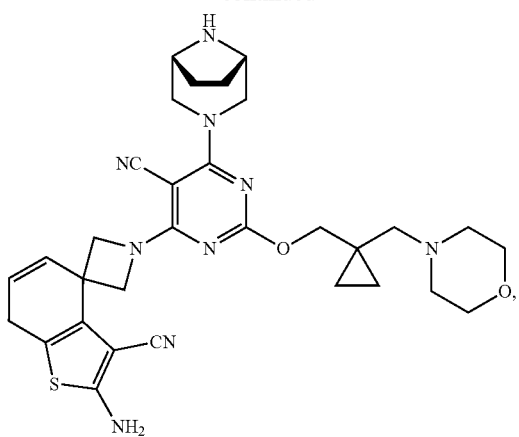
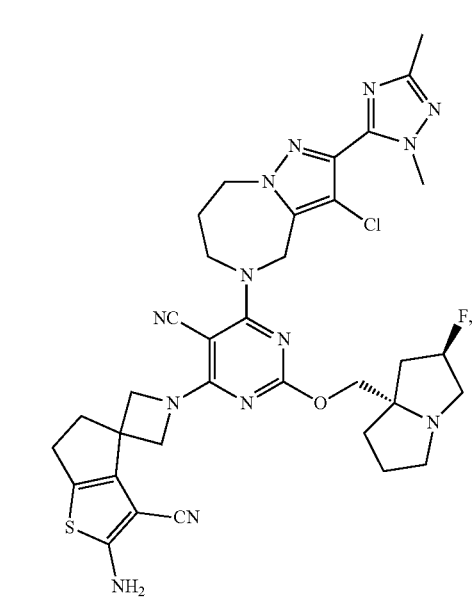
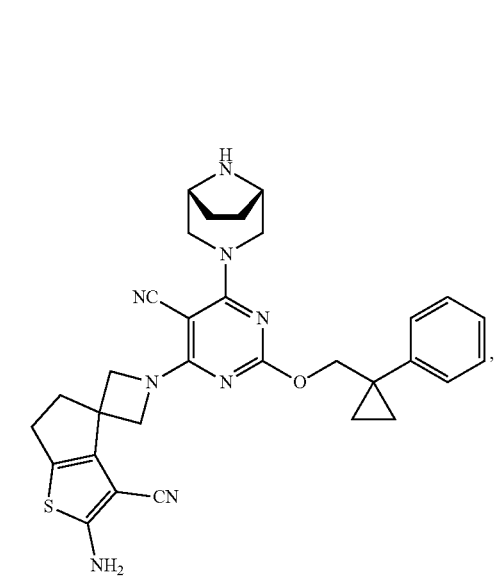
392
-continued
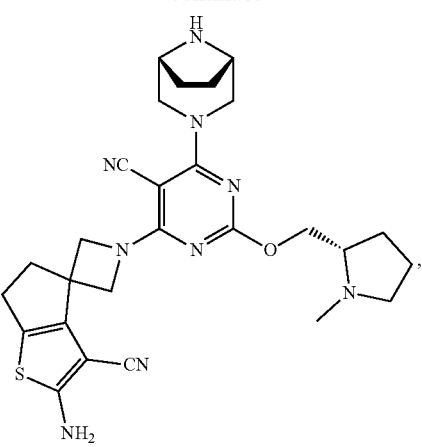
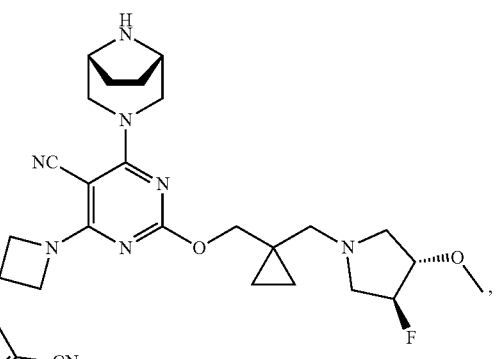
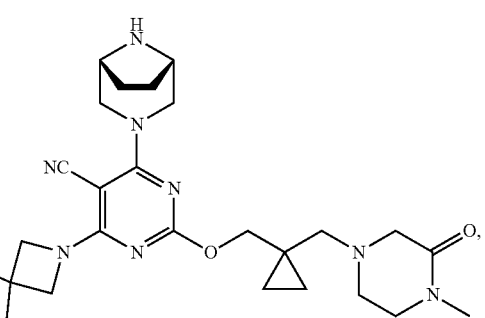

393
-continued
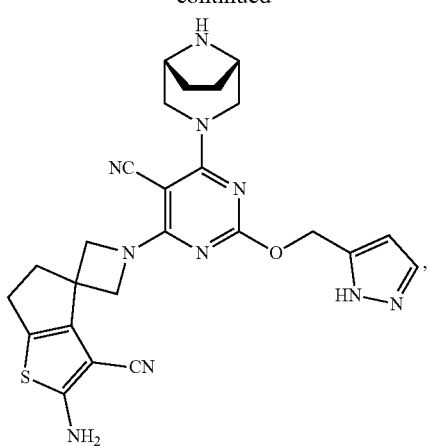
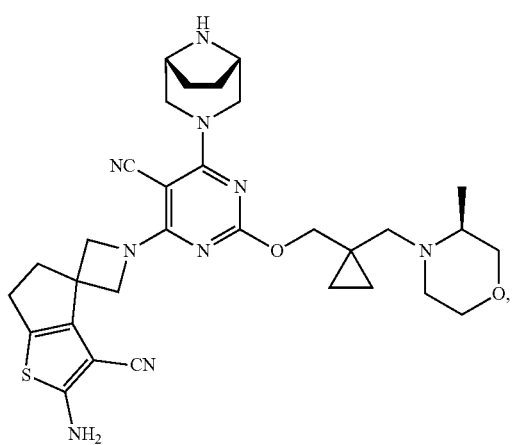
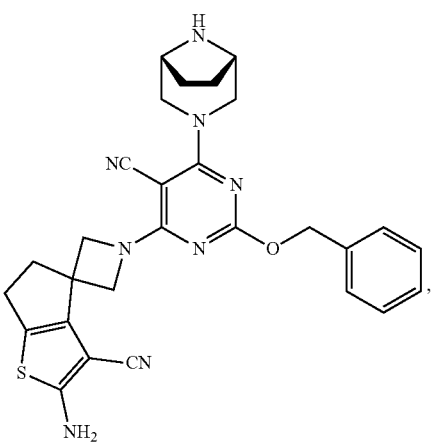
394
-continued
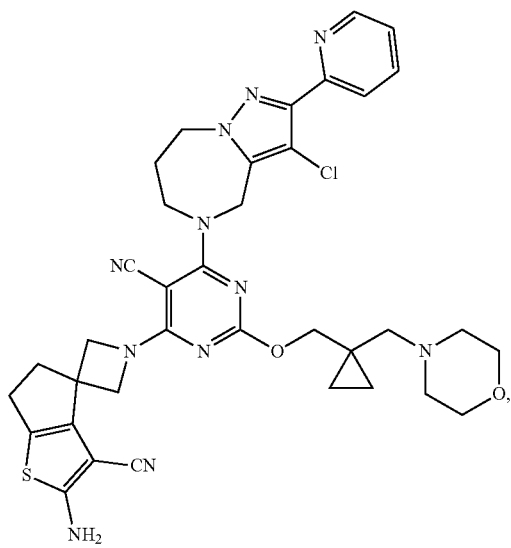
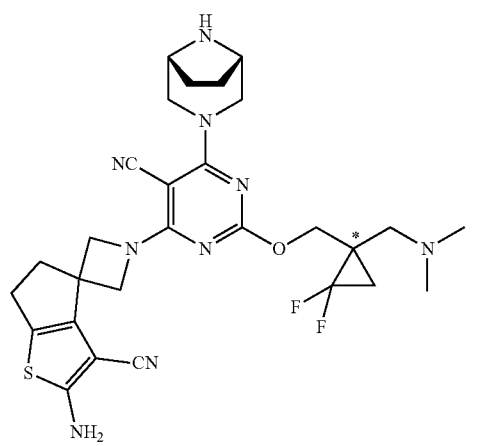
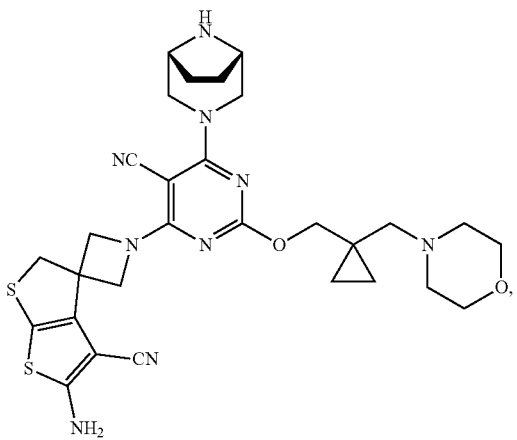

395
-continued
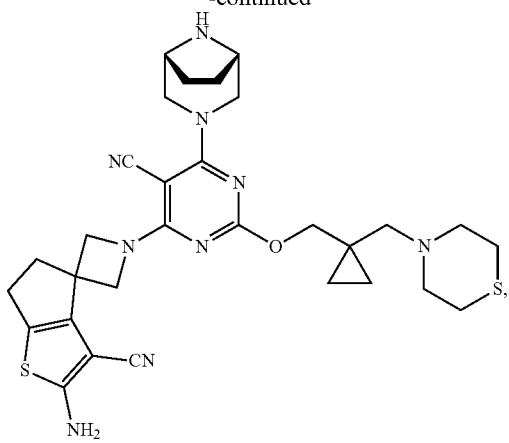
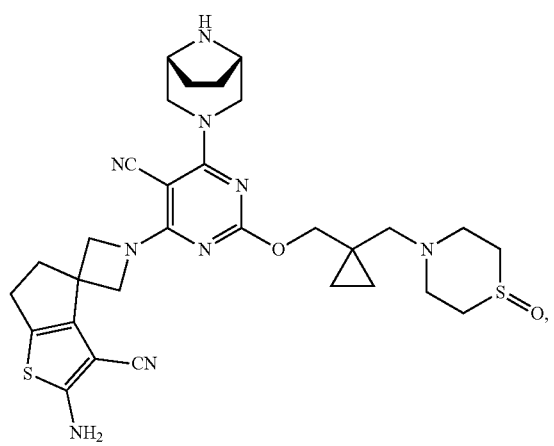
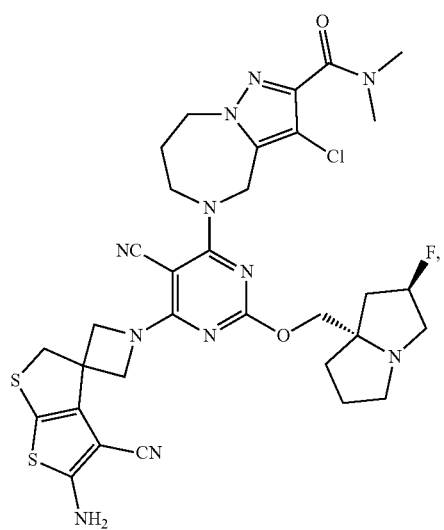
396
-continued
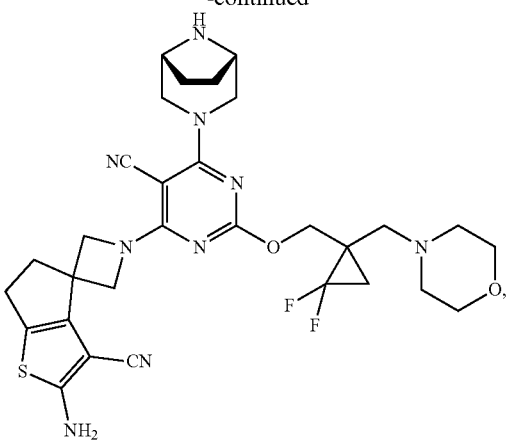
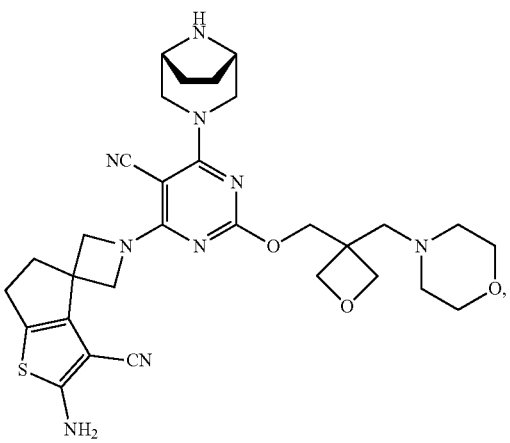
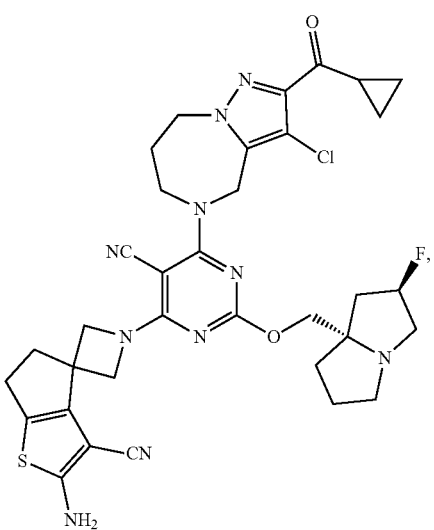

397
-continued
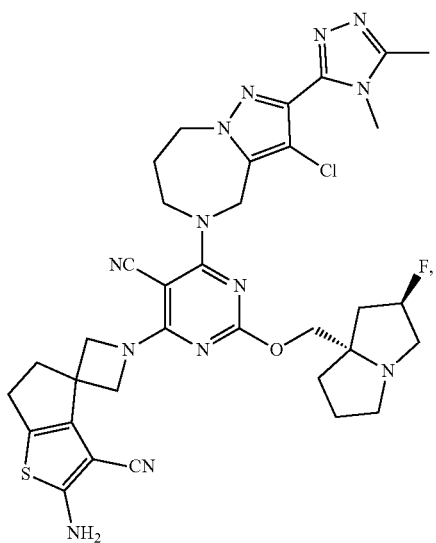
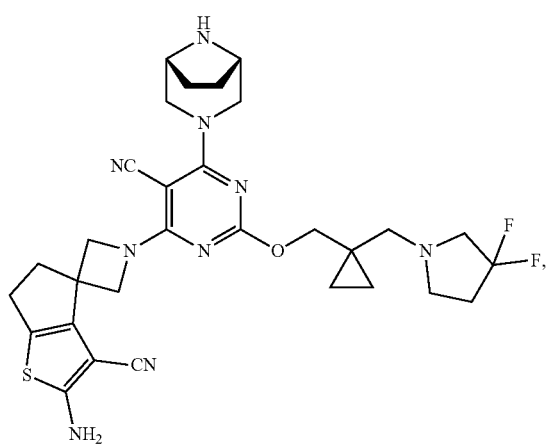
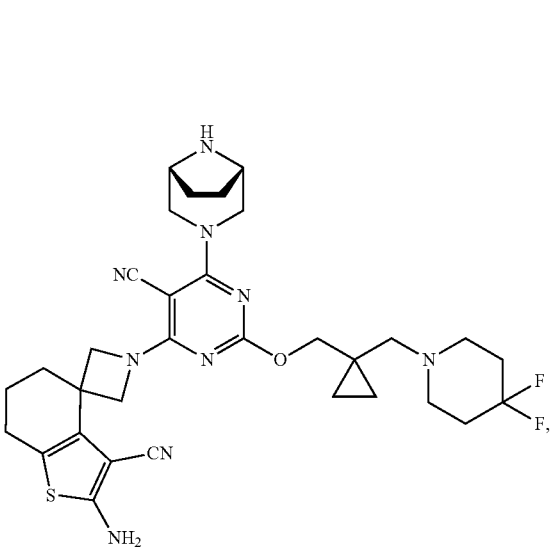
398
-continued
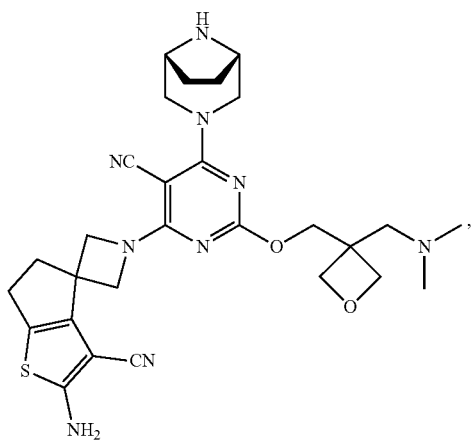
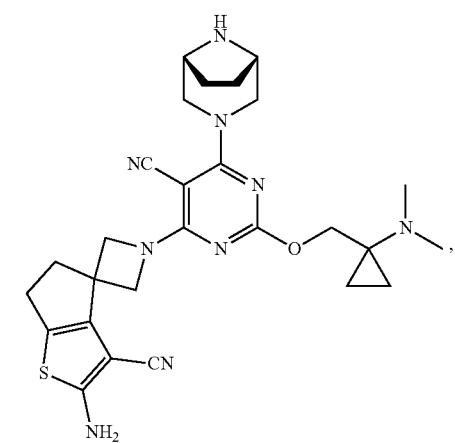
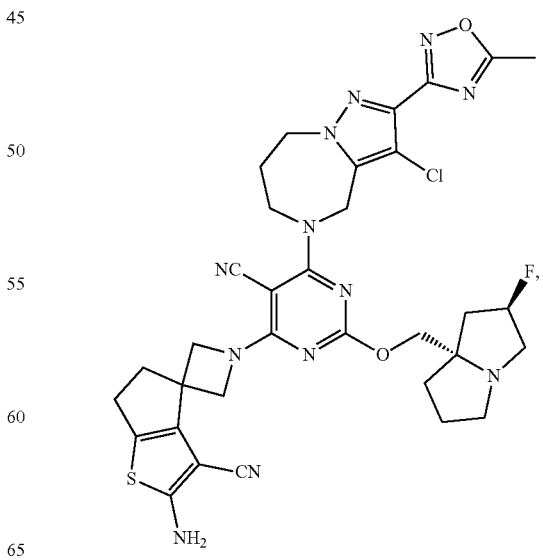

399
-continued
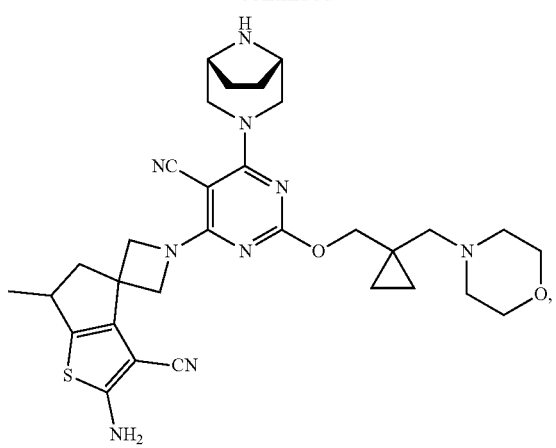
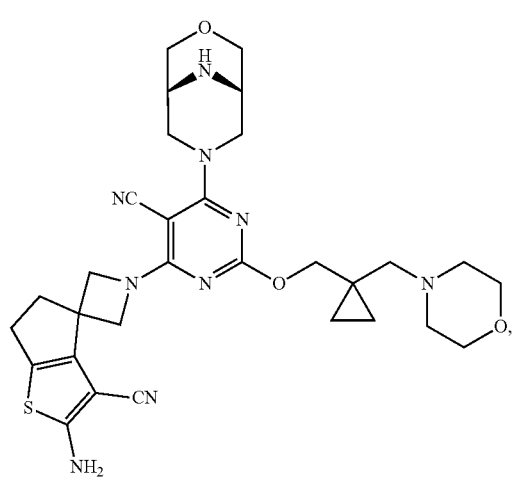
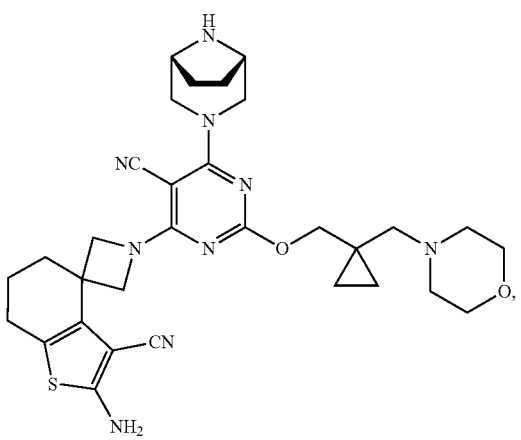
400
-continued
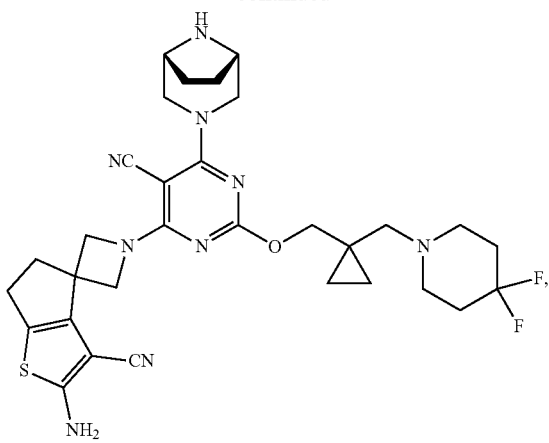
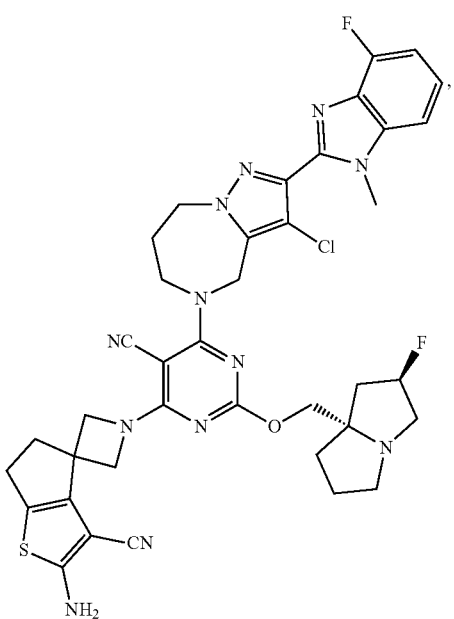
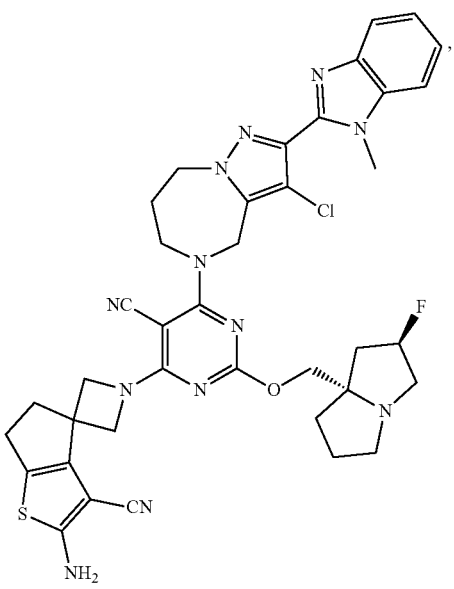

401
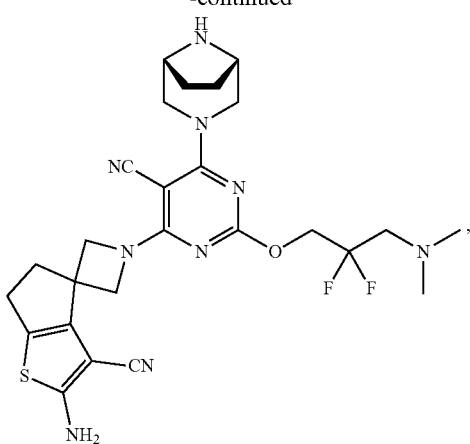
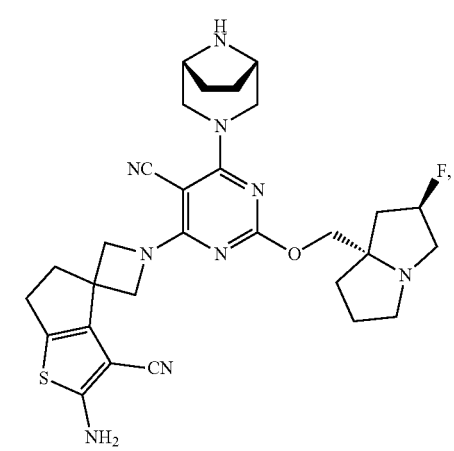
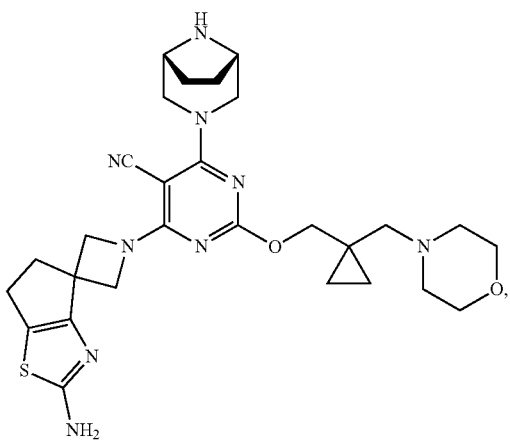
402
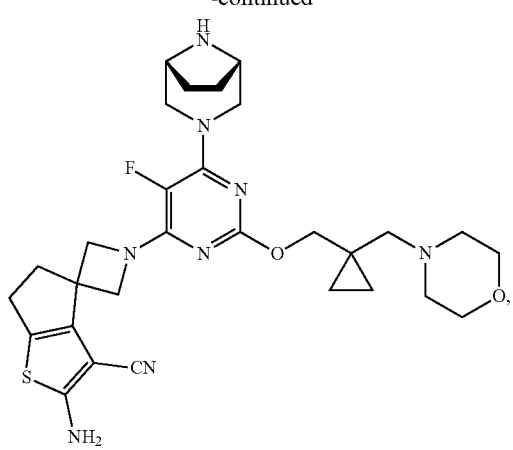
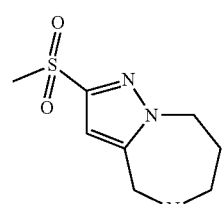
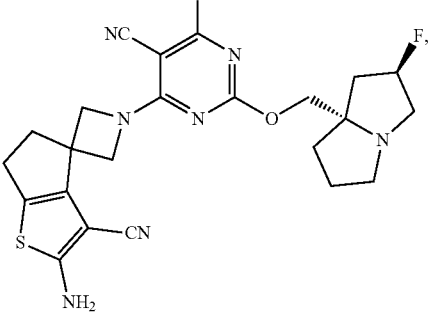
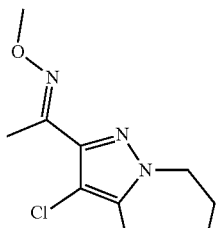
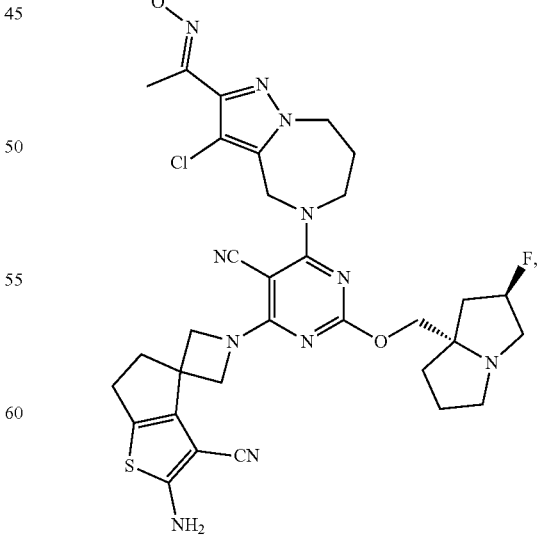

403
-continued
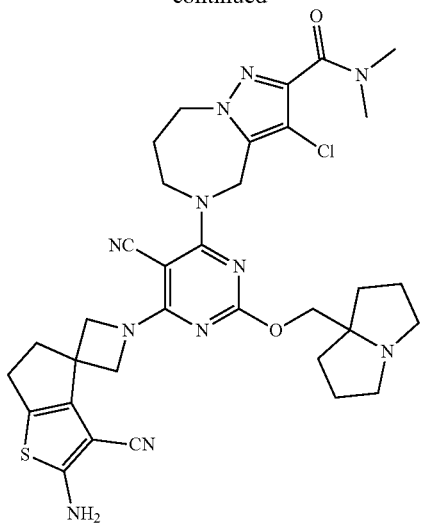
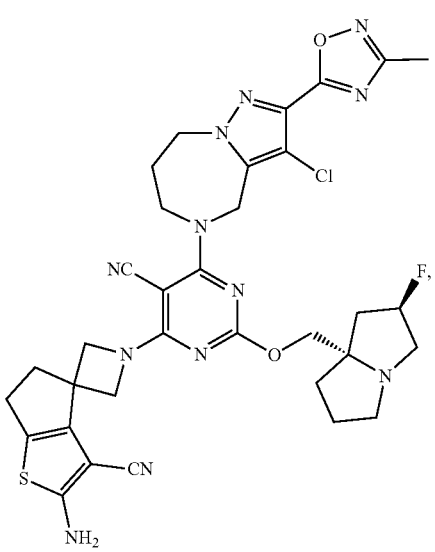
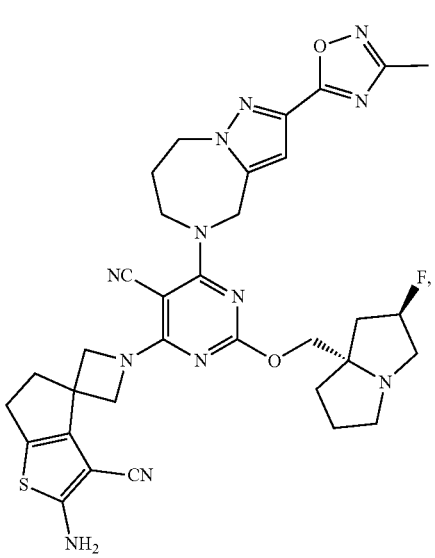
404
-continued
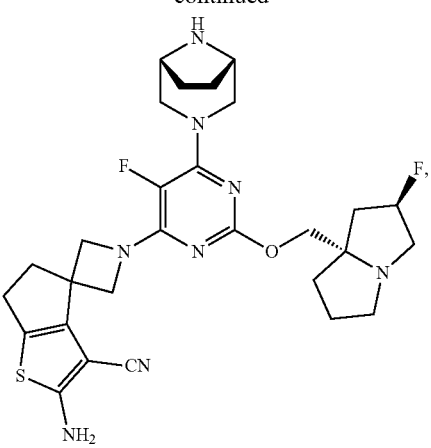
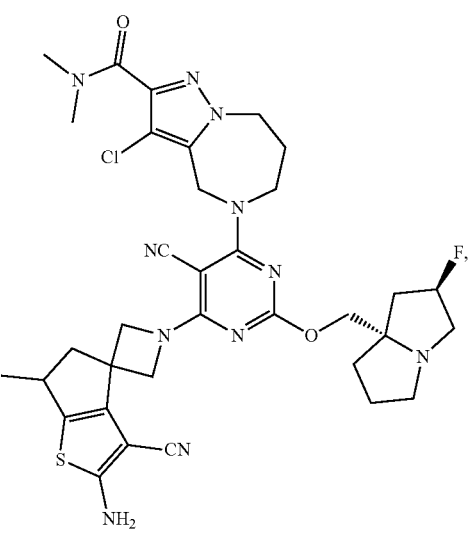
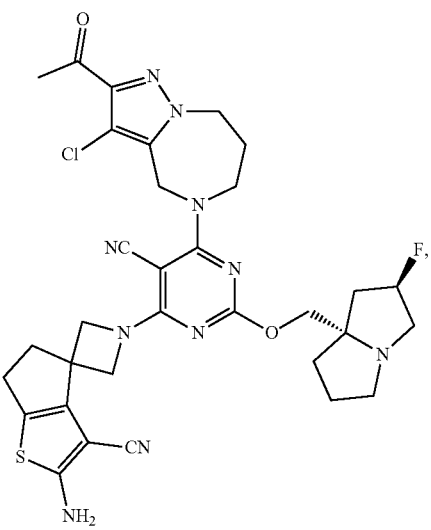

405
-continued
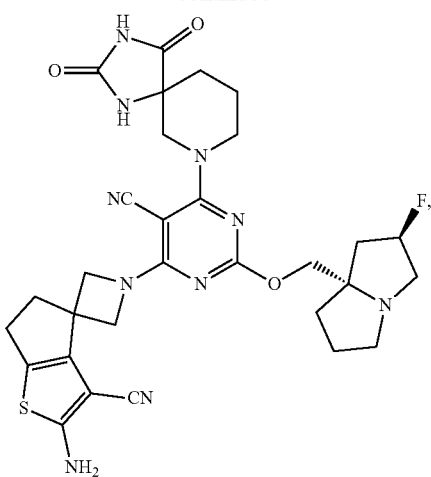
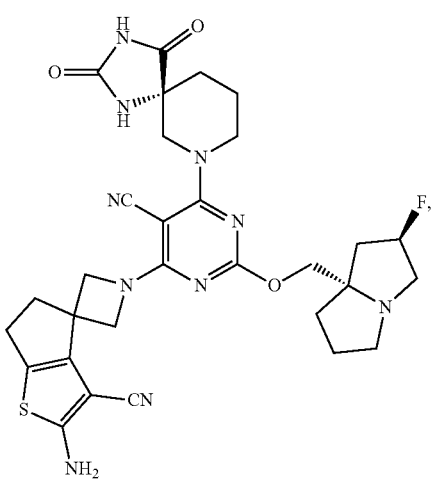
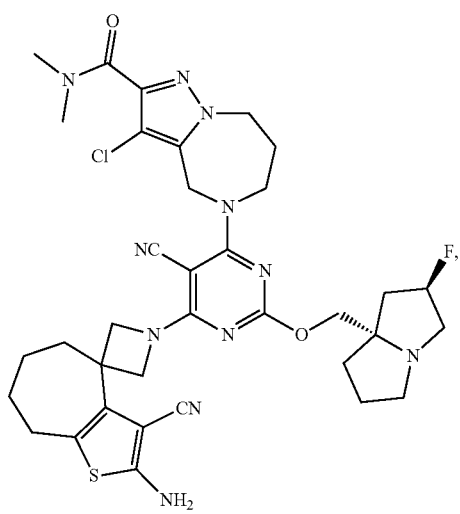
406
-continued
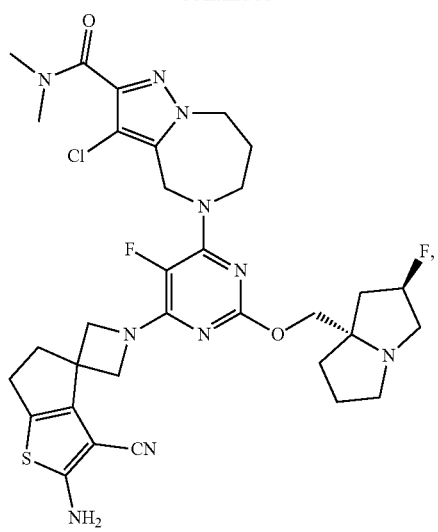 [SMILES: CN(C)C(=O)c1nn2c(c1Cl)CN(c1nc(OC[C@@]34CCCN3C[C@H](F)C4)nc(N3CC4(CCc5sc(N)c(C#N)c54)C3)c1C#N)CCC2]
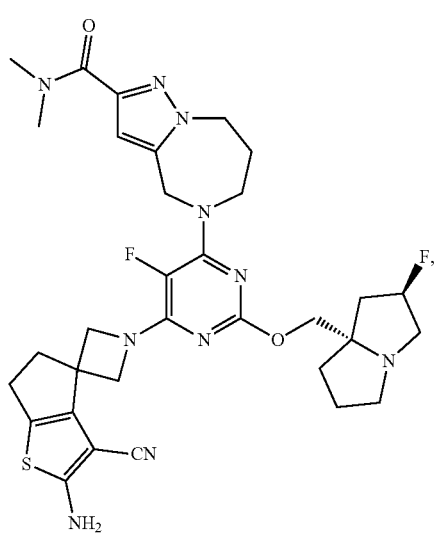
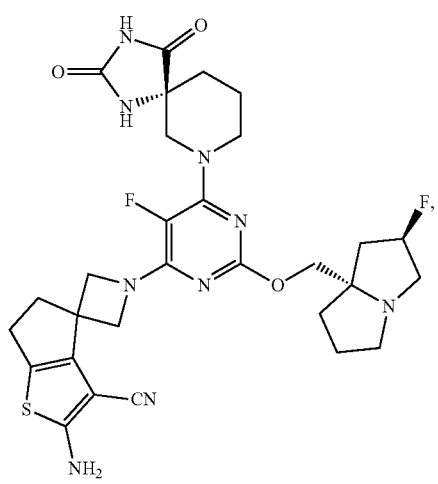

407
-continued
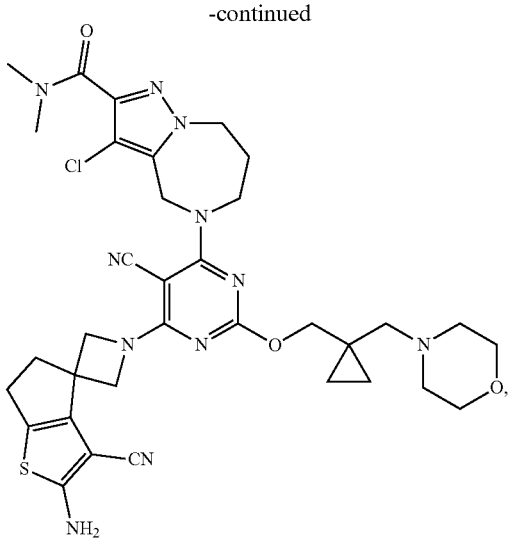
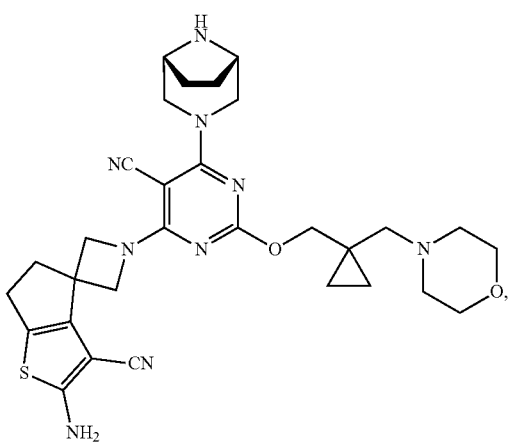
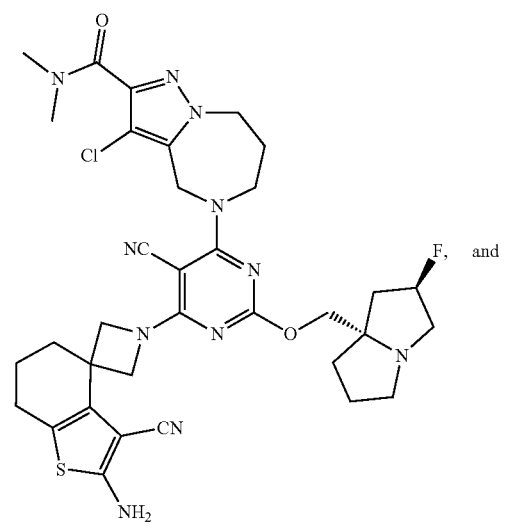
408
-continued
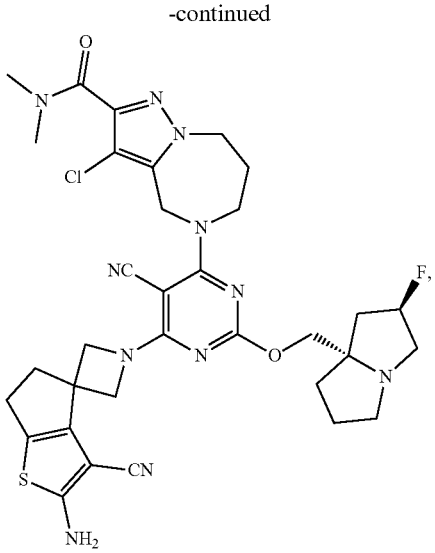
or a pharmaceutically salt of any one thereof.
18. A pharmaceutical composition comprising the compound or salt of claim 1, or a compound selected from
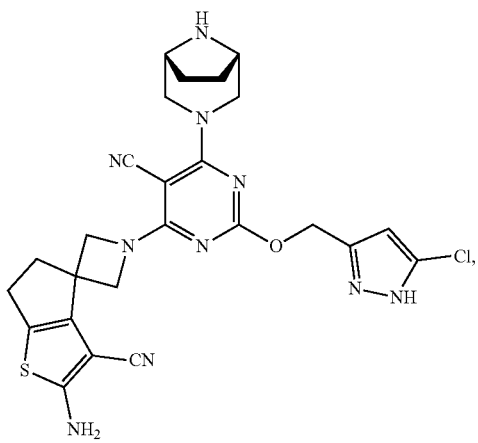
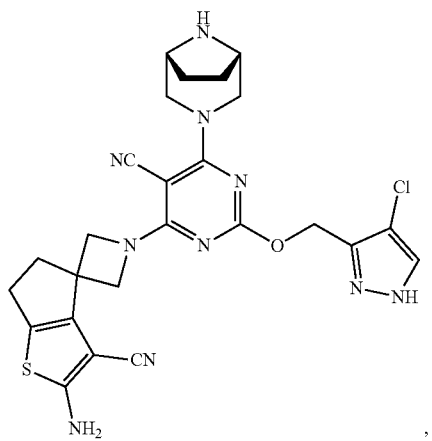
,

409
-continued
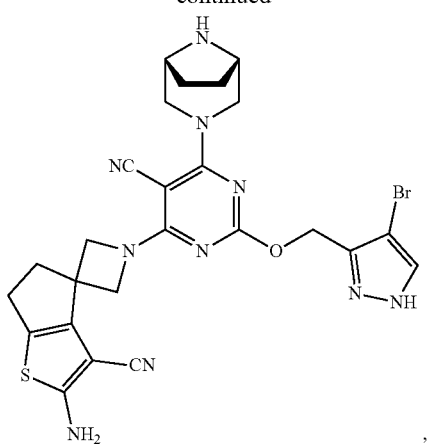
,
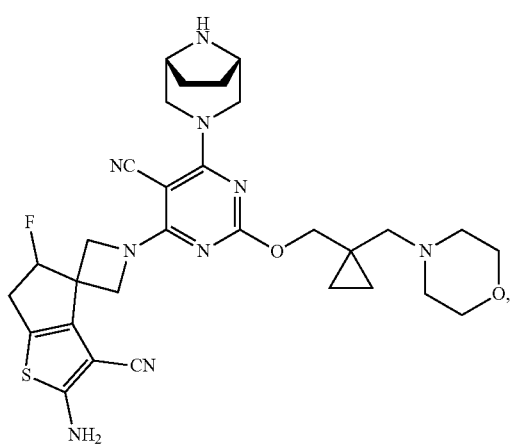
,
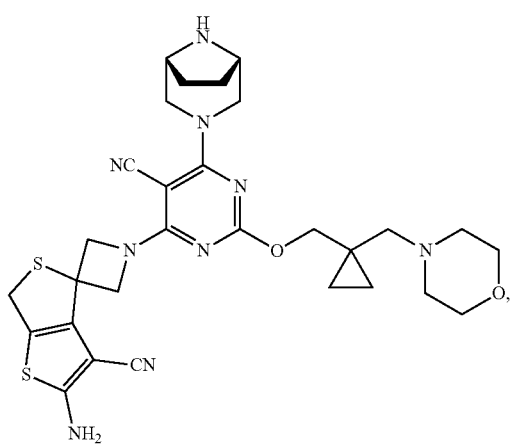
,
410
-continued
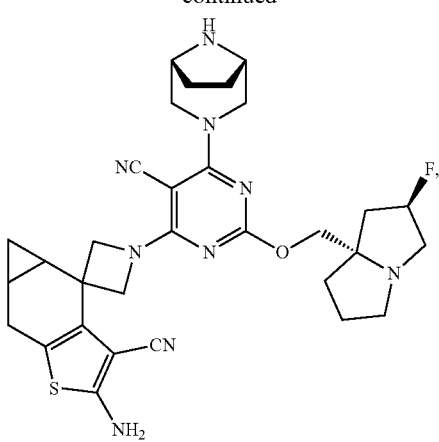
,
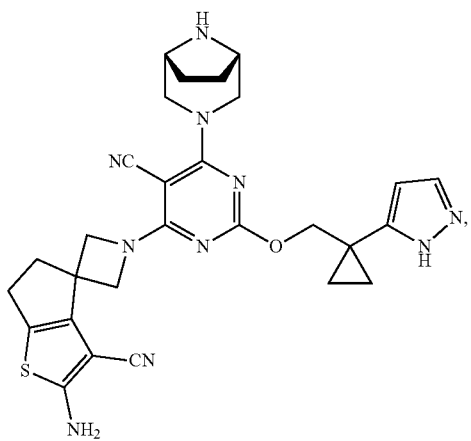
,
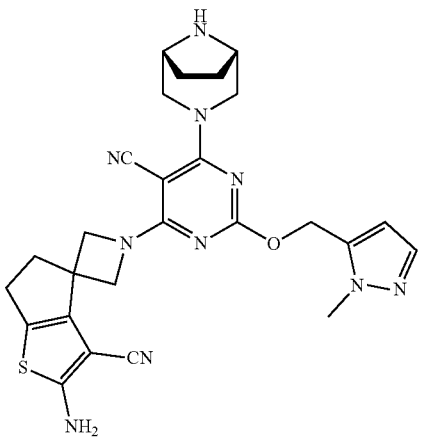
, 411
-continued
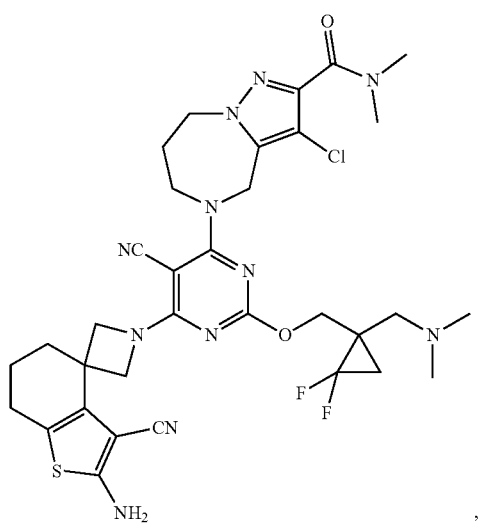
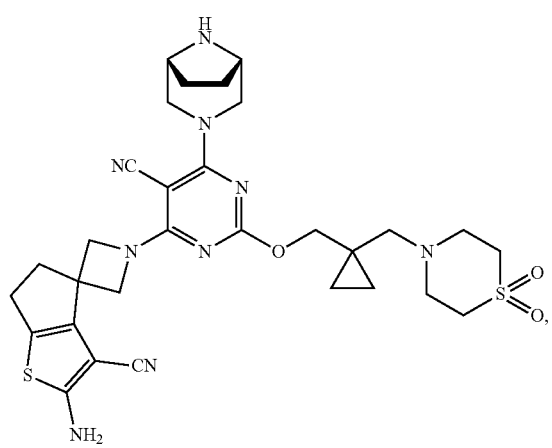
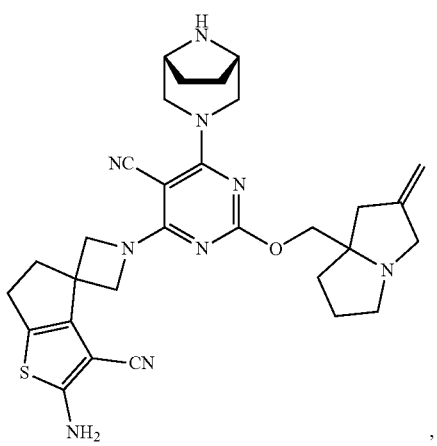
412
-continued
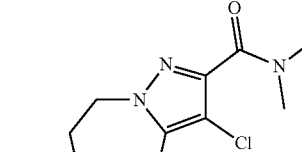
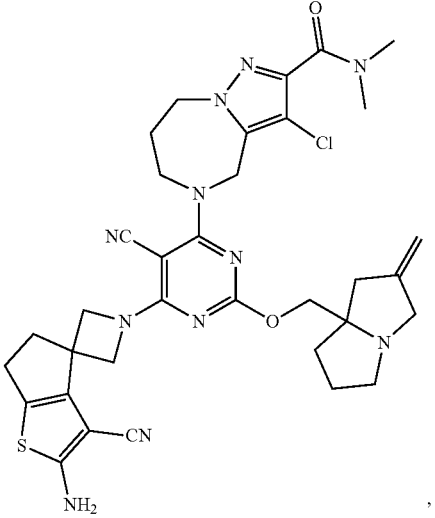
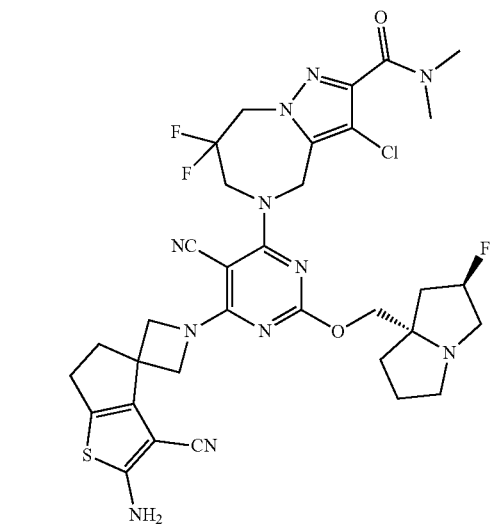
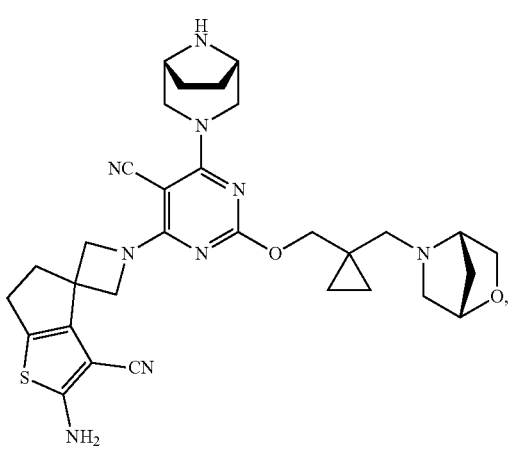

413
-continued
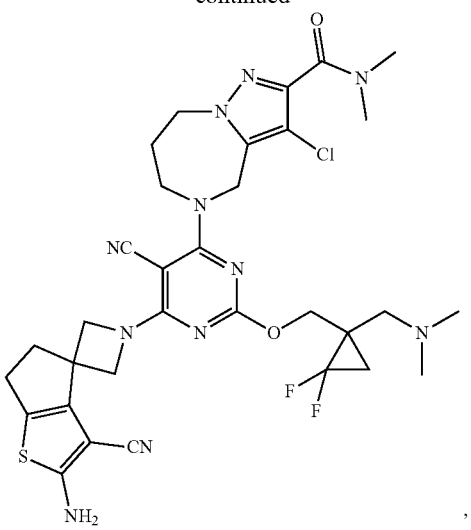
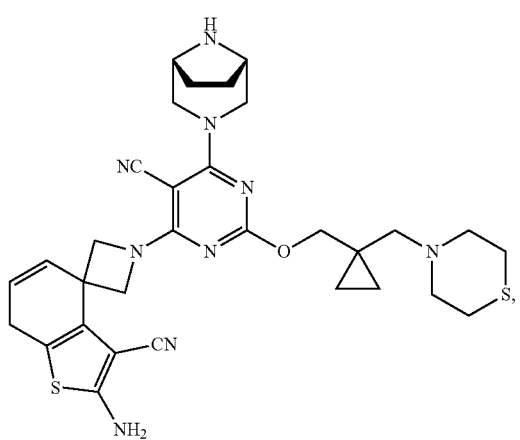
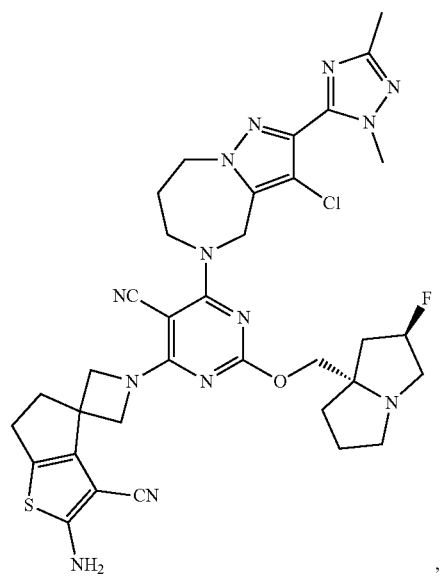
414
-continued
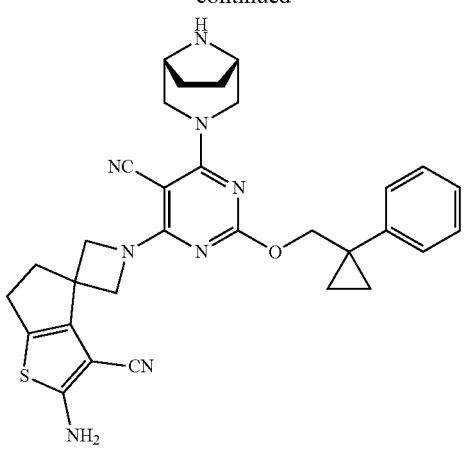
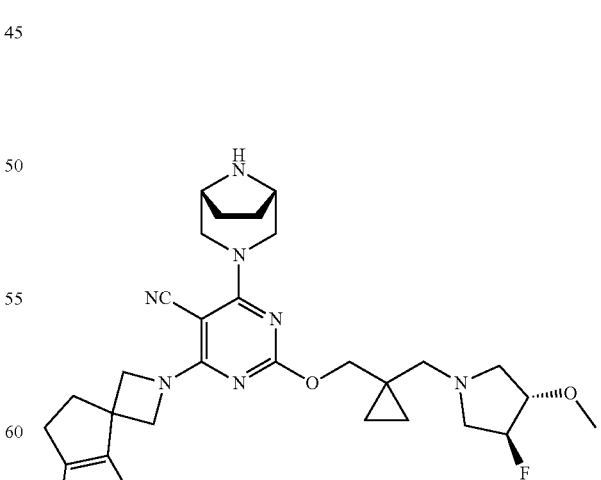

415
-continued
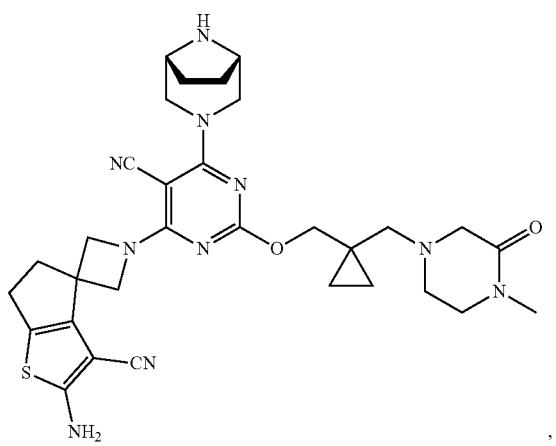
,
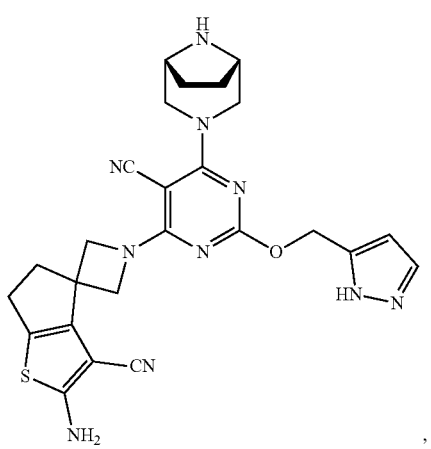
,
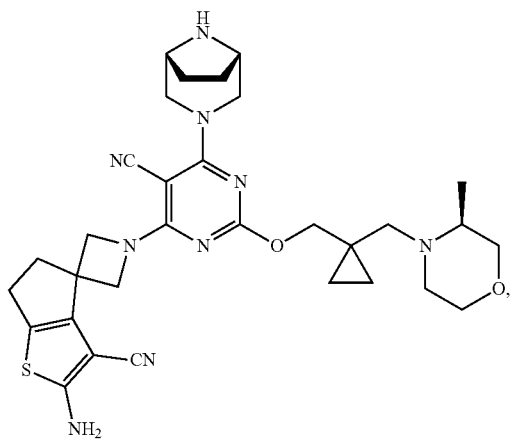
,
416
-continued
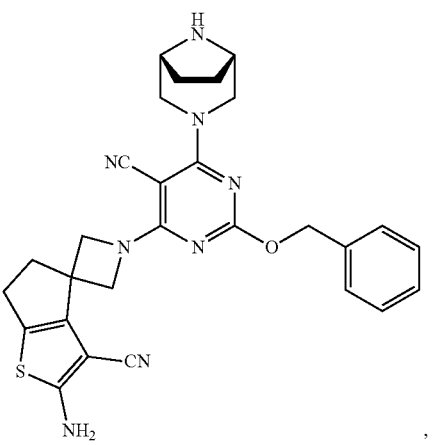
,
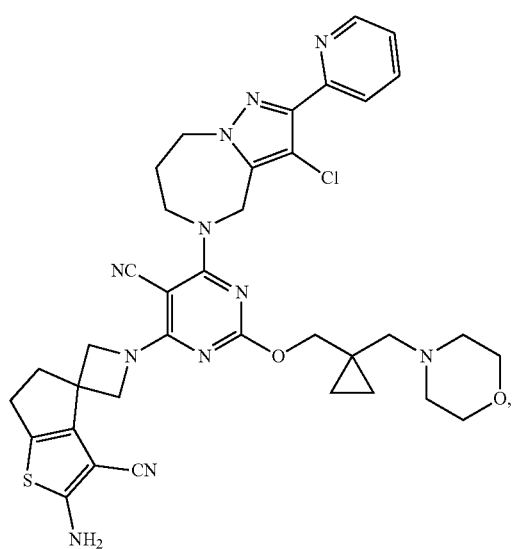
,
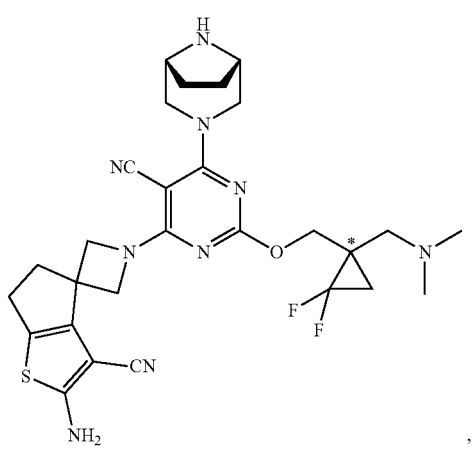
, 417
-continued
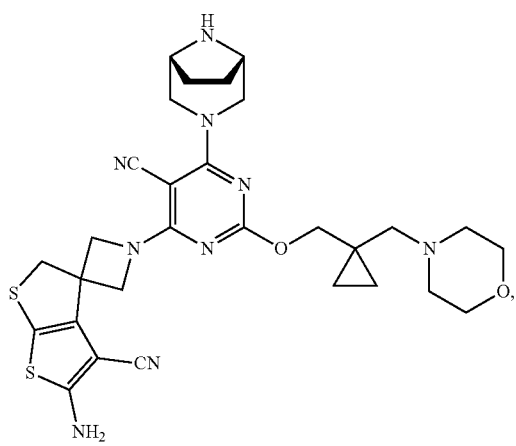
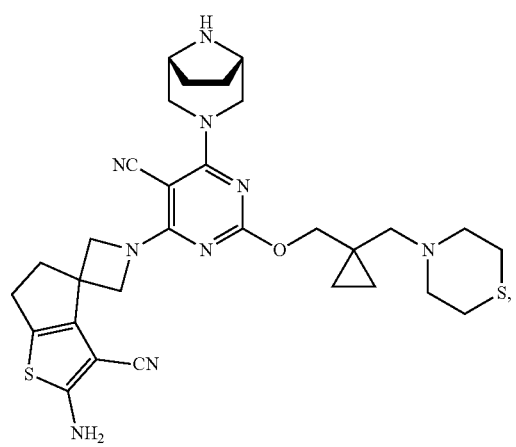
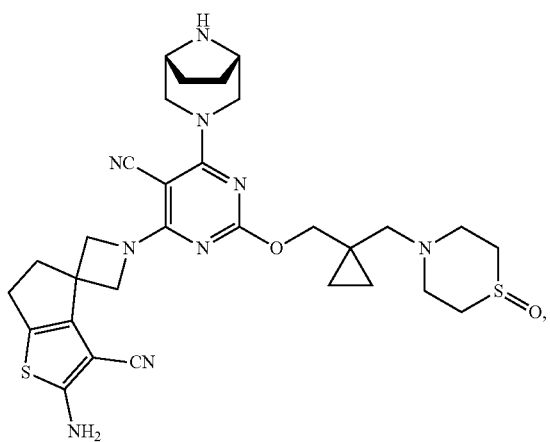
418
-continued
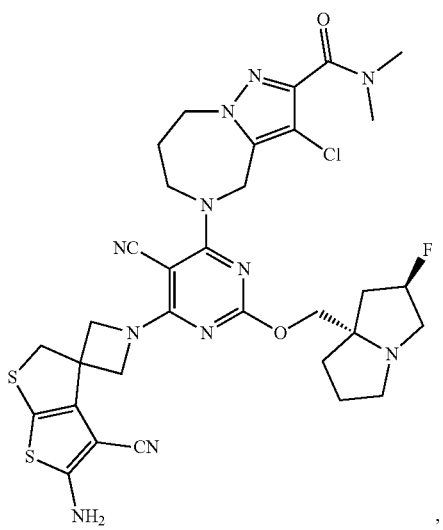
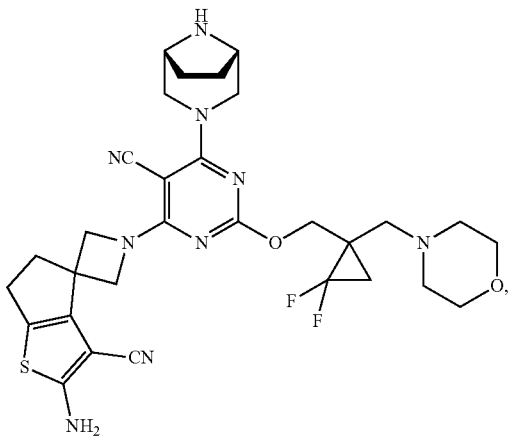
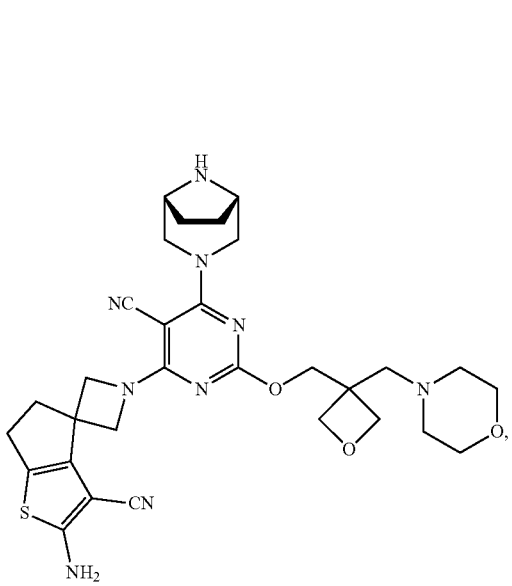

419
-continued
420
-continued
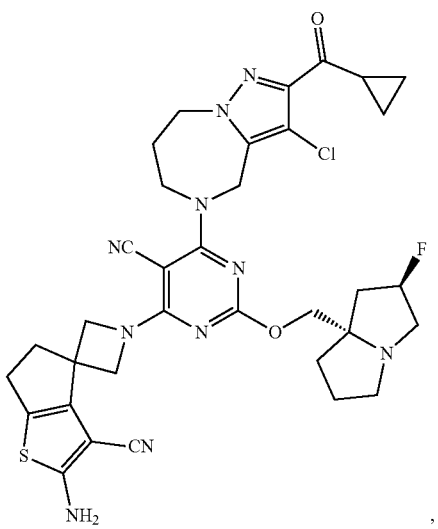
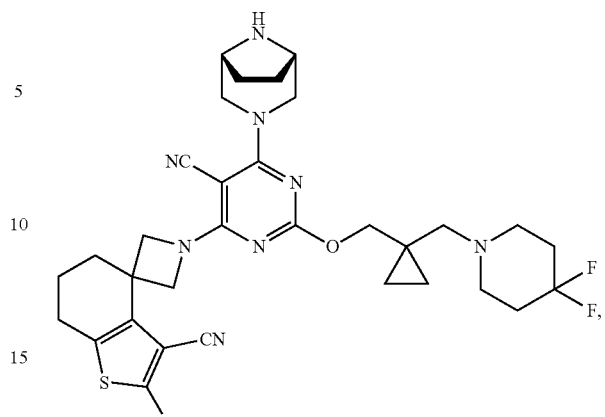
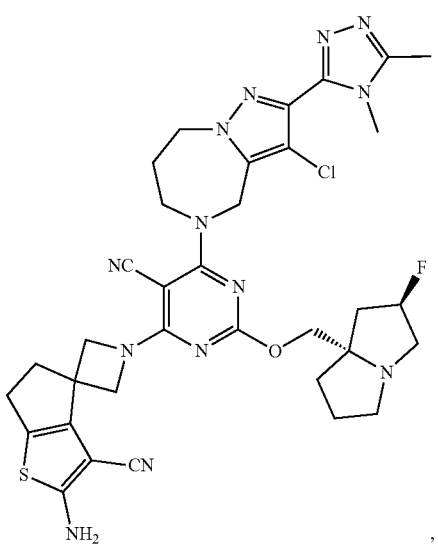
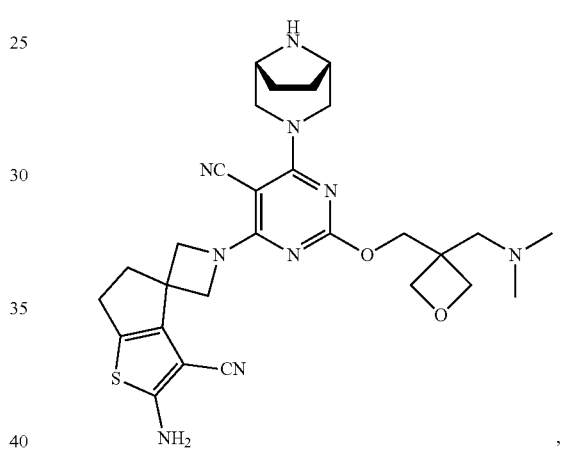
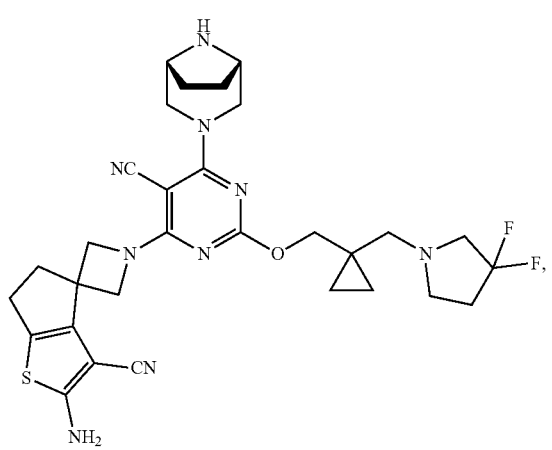
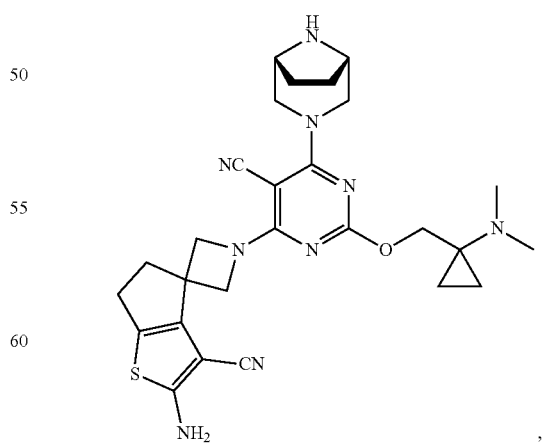

421
-continued
422
-continued
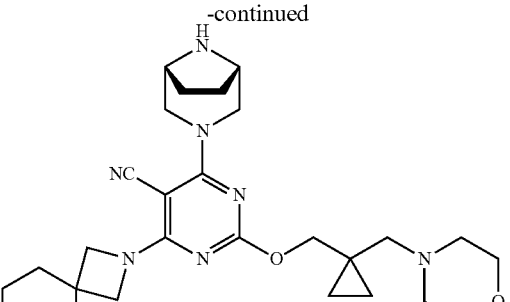
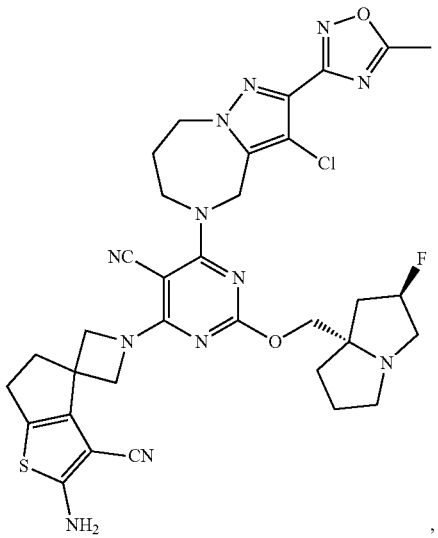
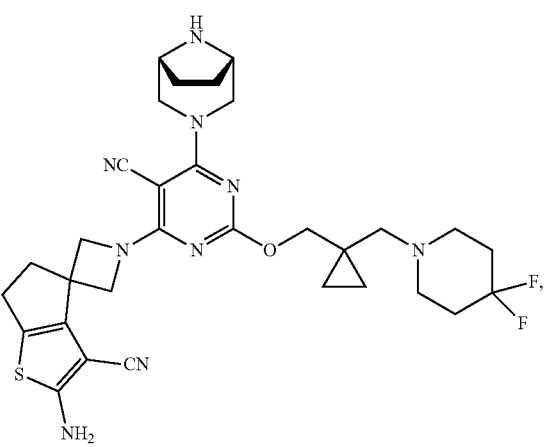
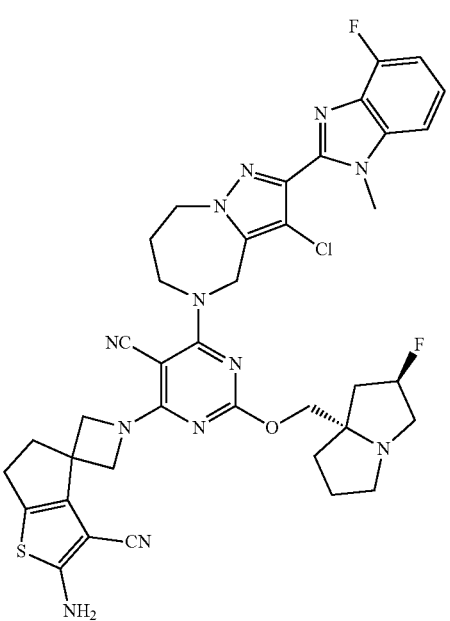

423
-continued
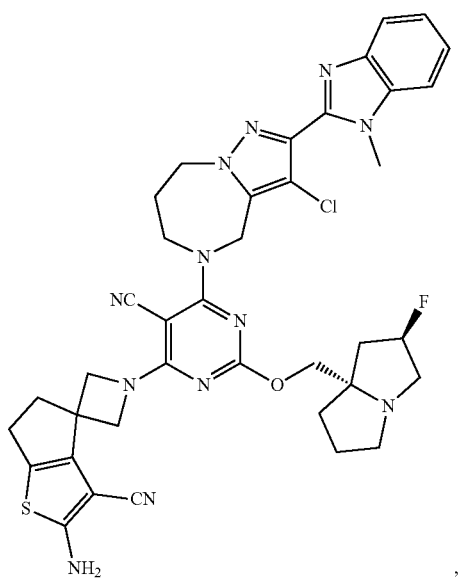
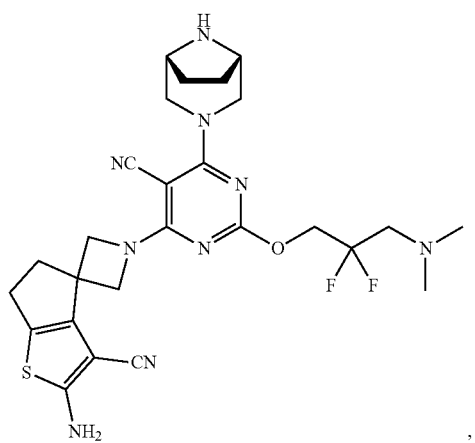
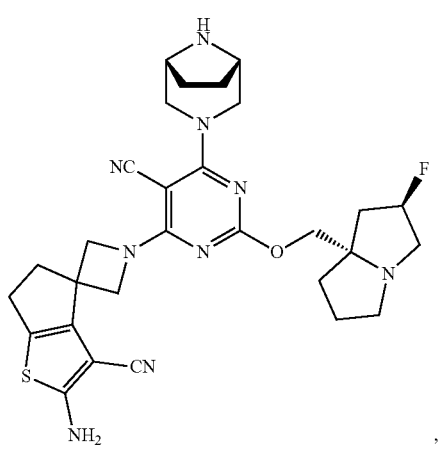
424
-continued
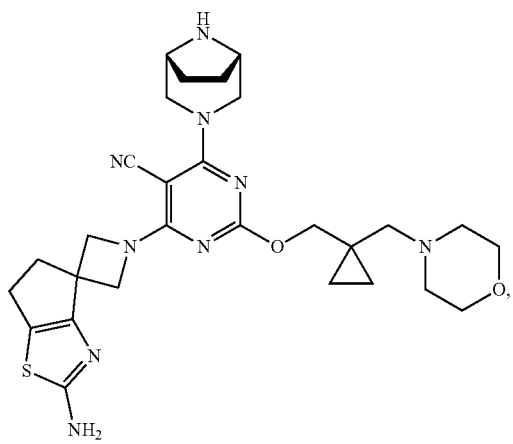
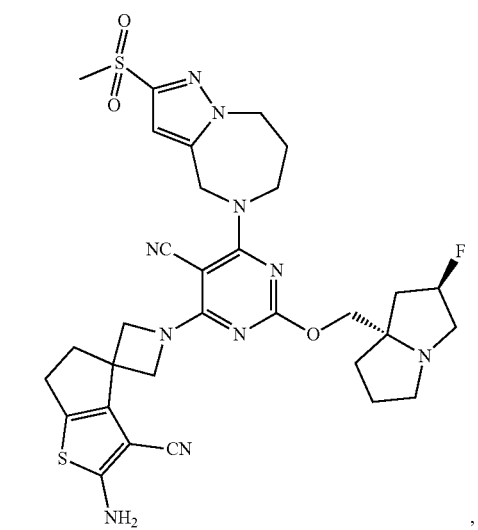

425
-continued
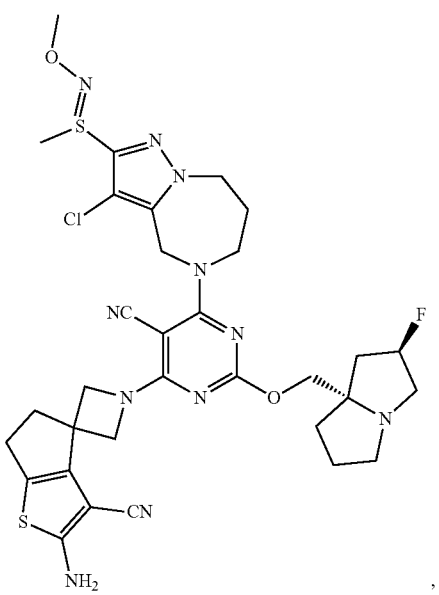
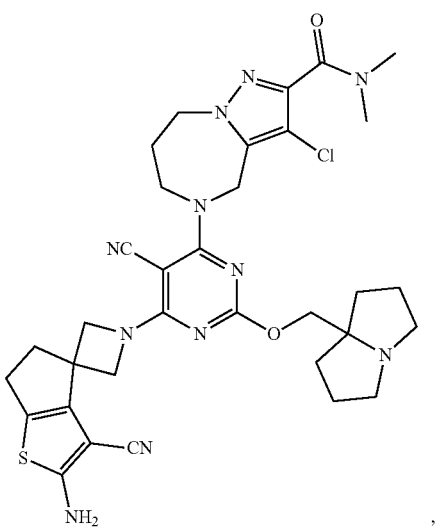
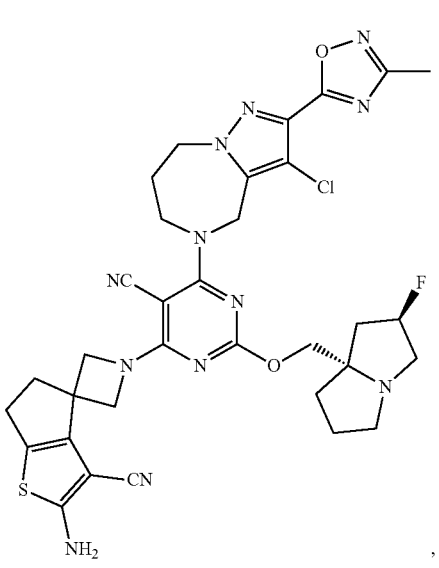
426
-continued
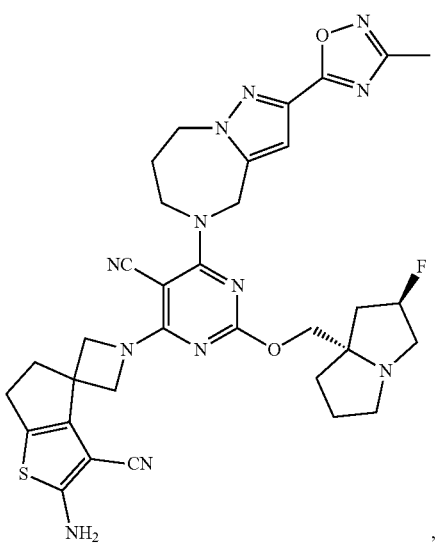
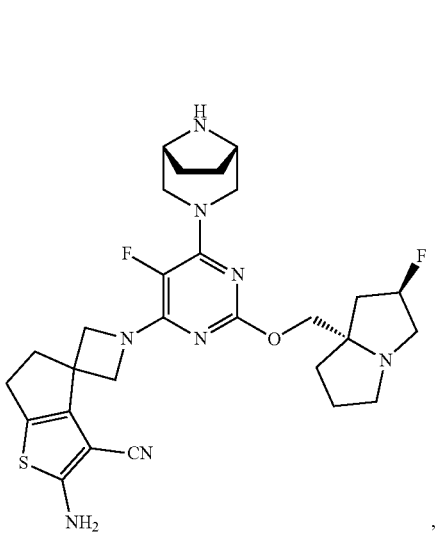
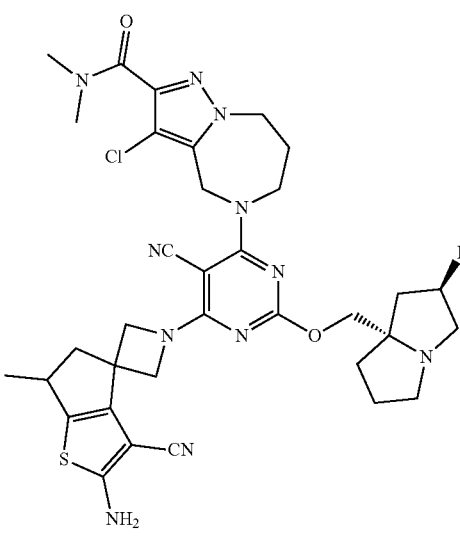

427
-continued
428
-continued
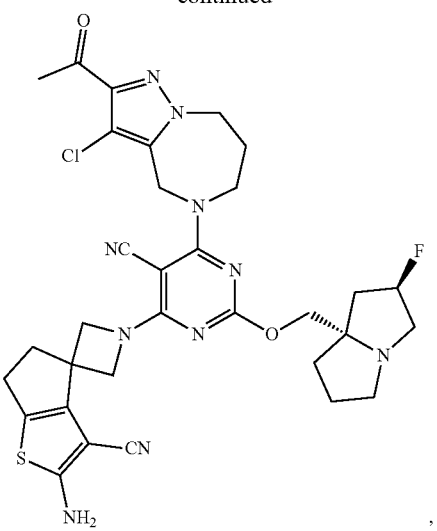
,
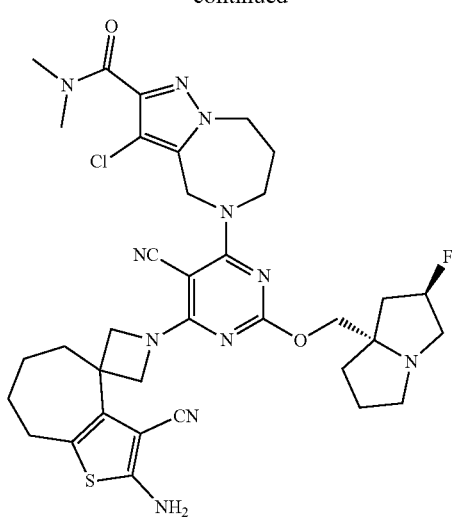
,
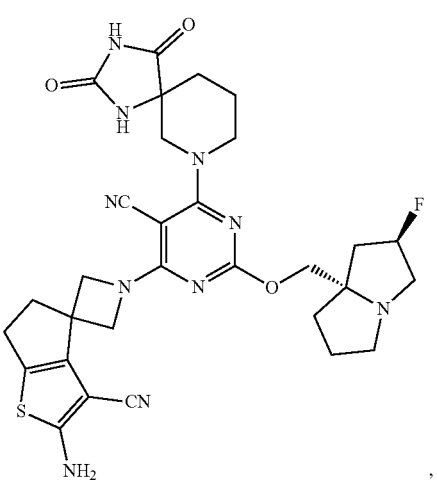
,
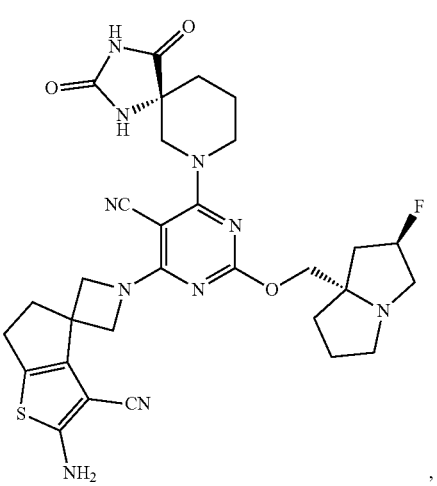
,

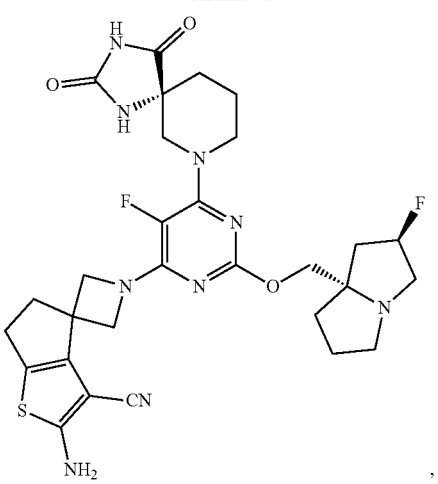
,
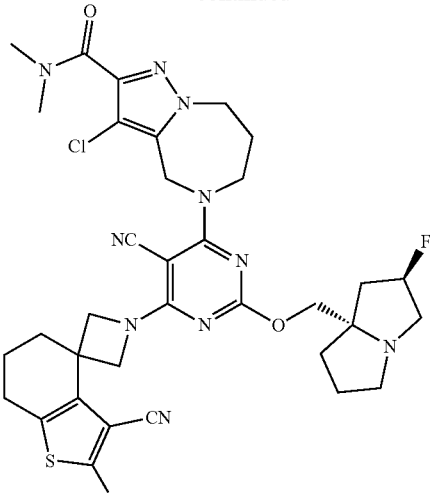
, and
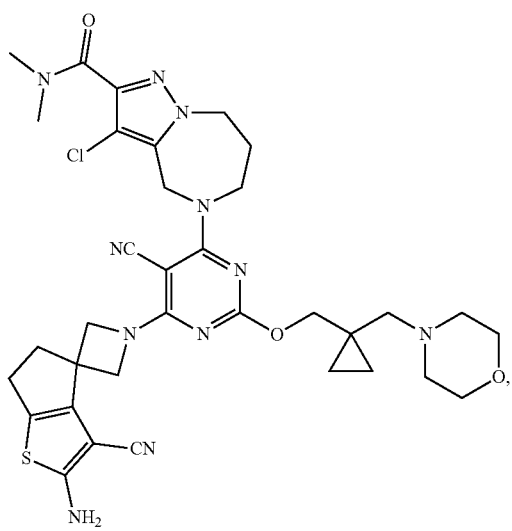
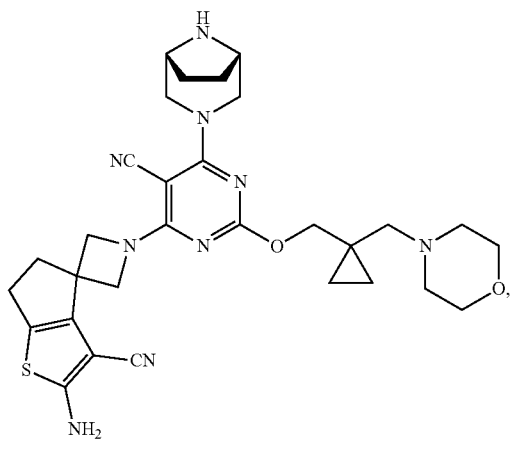
or a pharmaceutically salt of any one thereof; and
a pharmaceutically acceptable excipient.
19. A method of treating a disease or disorder, comprising administering to a subject in need thereof, the pharmaceutical composition of claim 18, or a compound or salt selected from
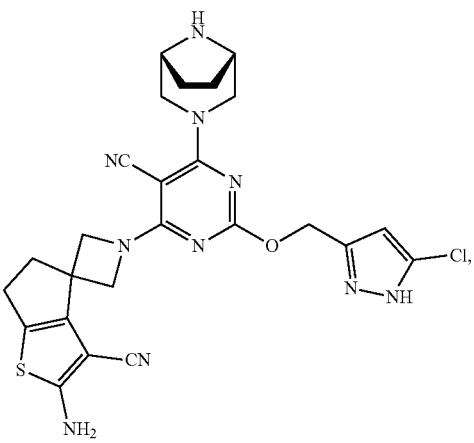

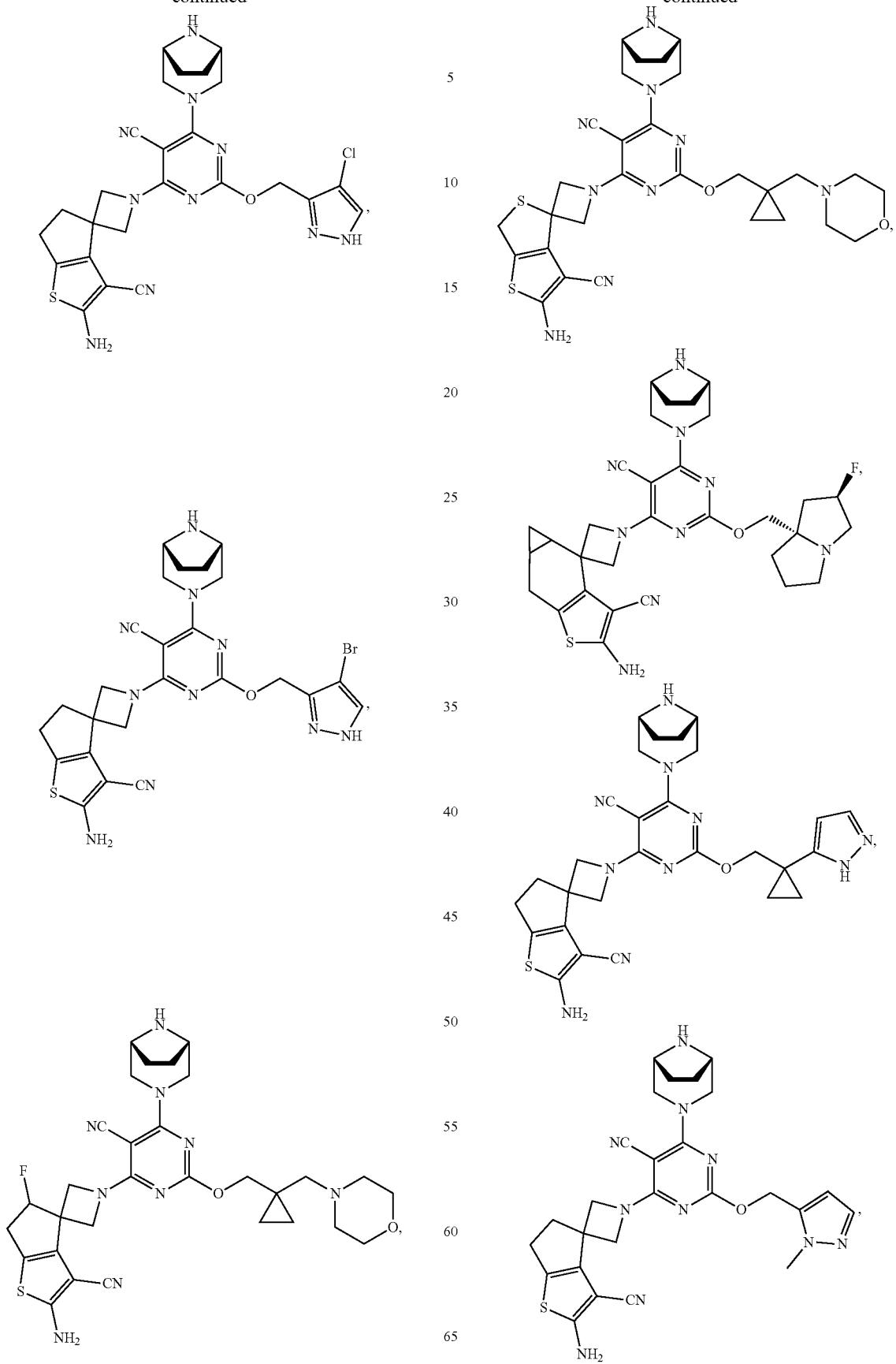

433 -continued
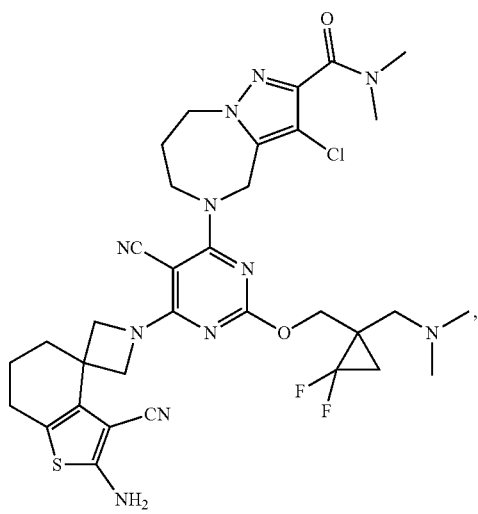
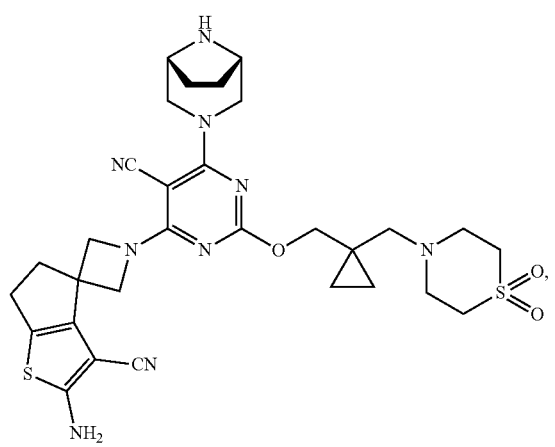
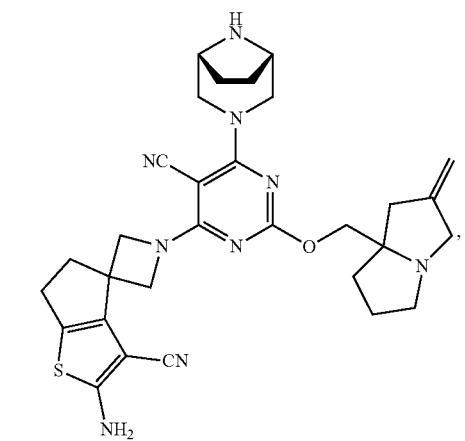
434 -continued
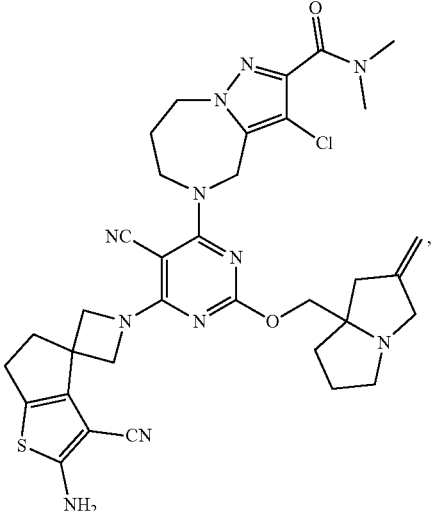
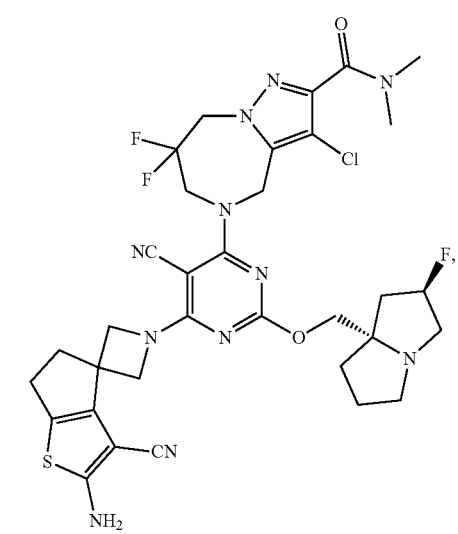
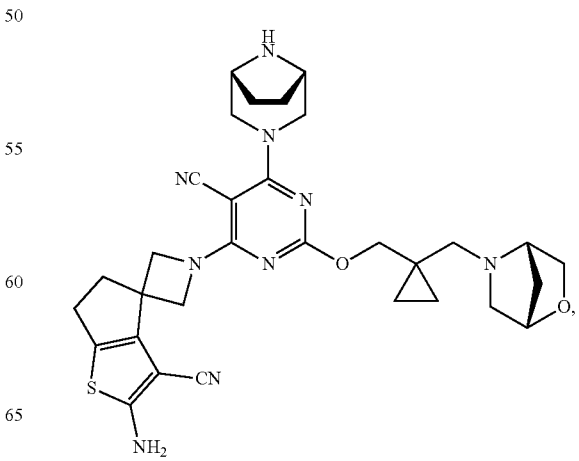

435
-continued
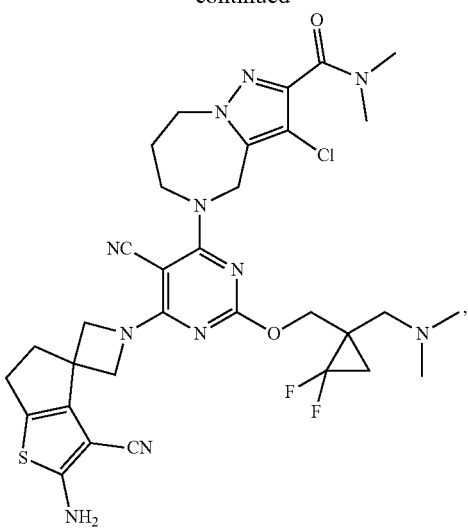
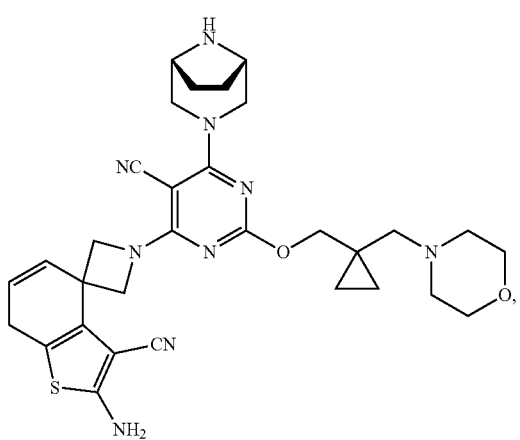
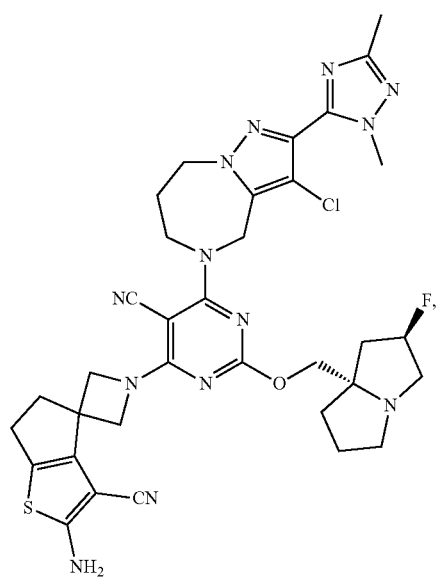
436
-continued
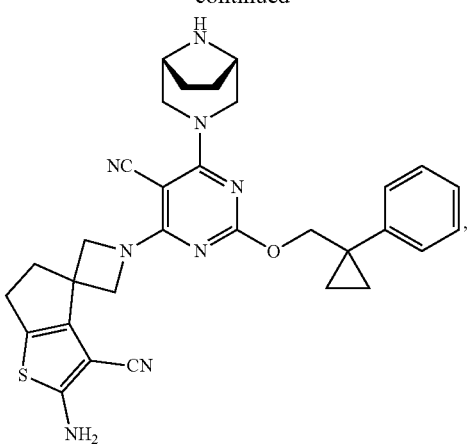
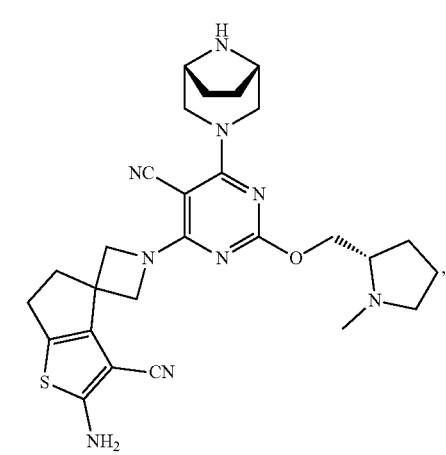
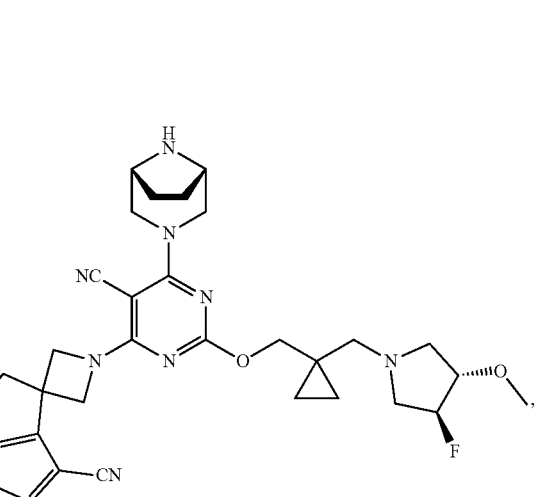

437
-continued
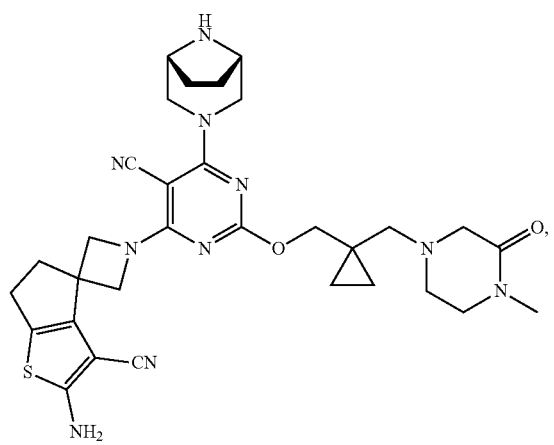
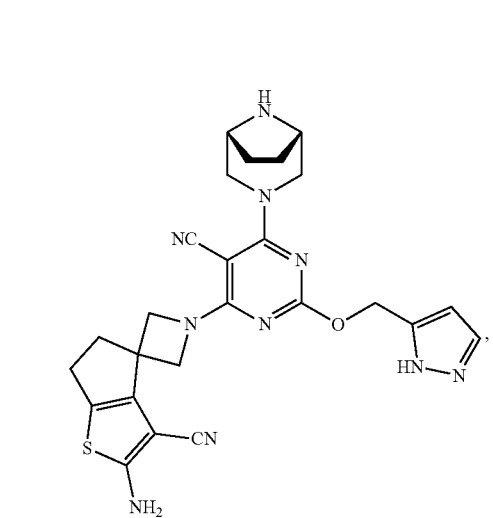
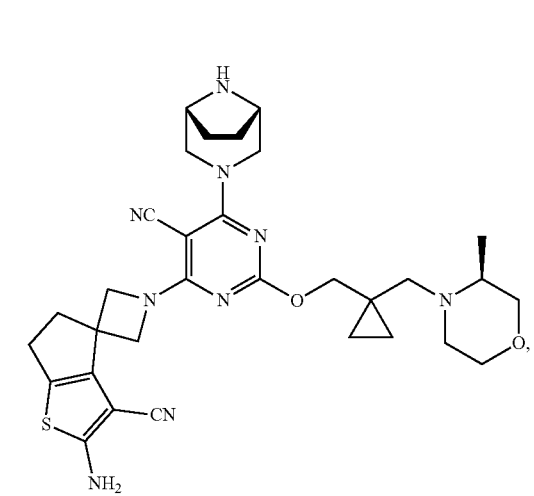
438
-continued
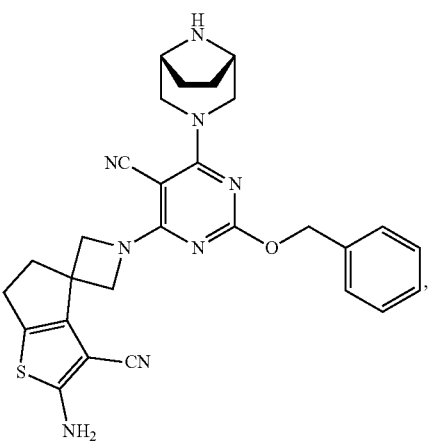
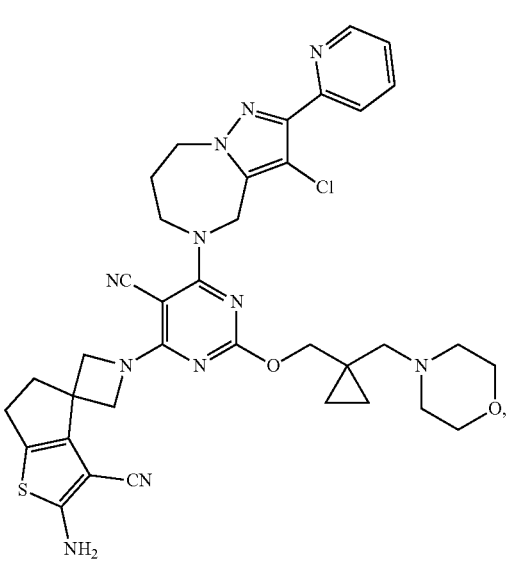
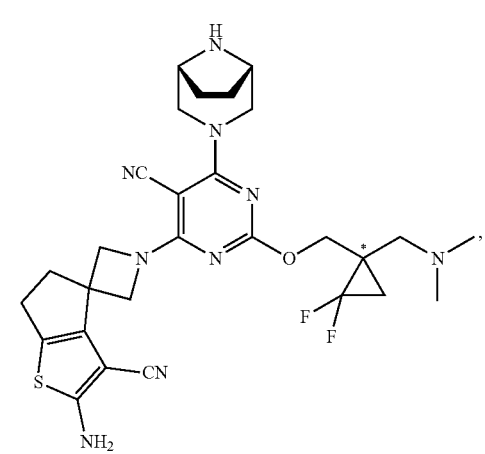

439
-continued
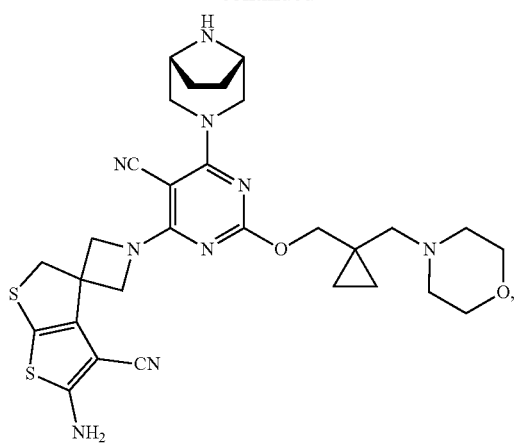
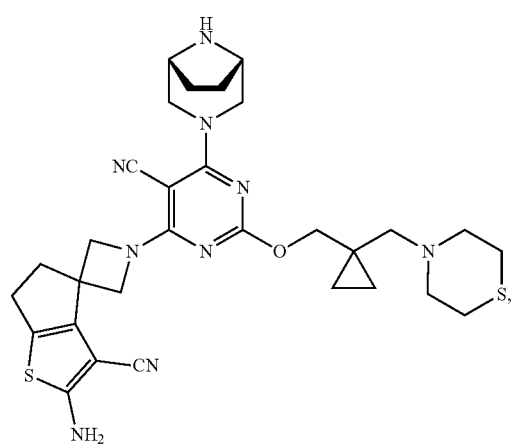
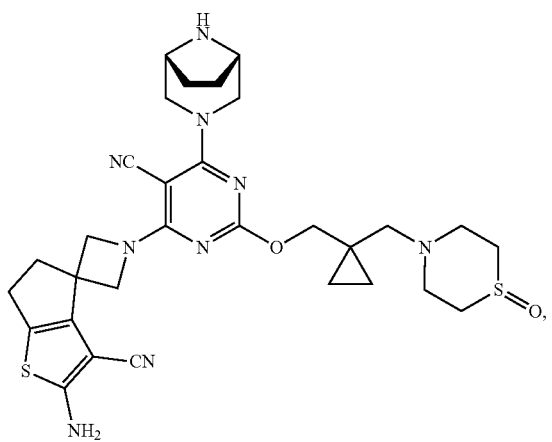
440
-continued
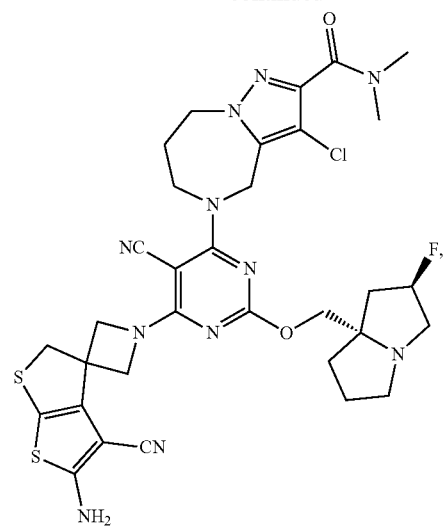
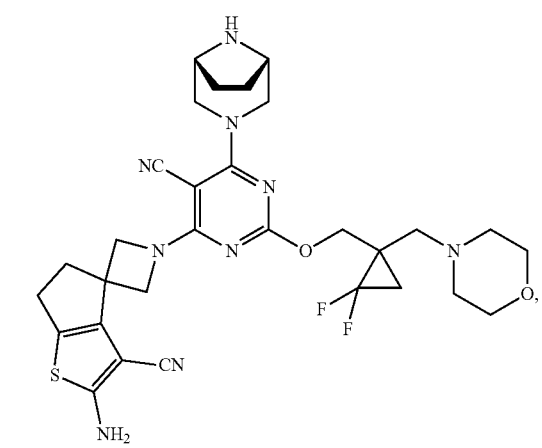
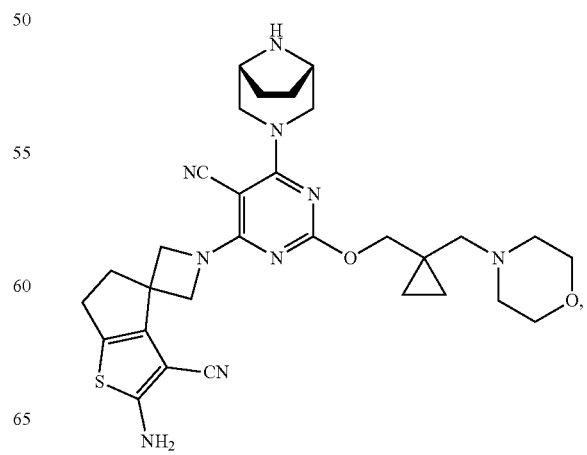

441
-continued
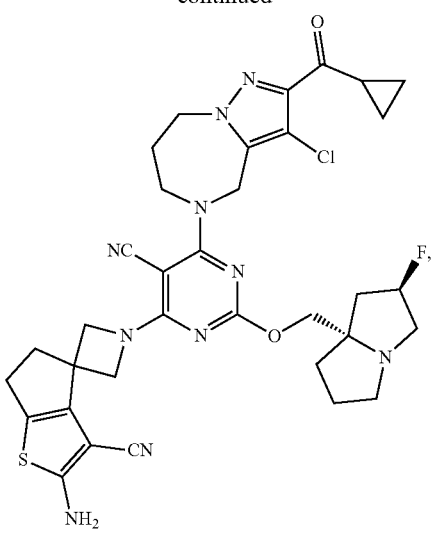
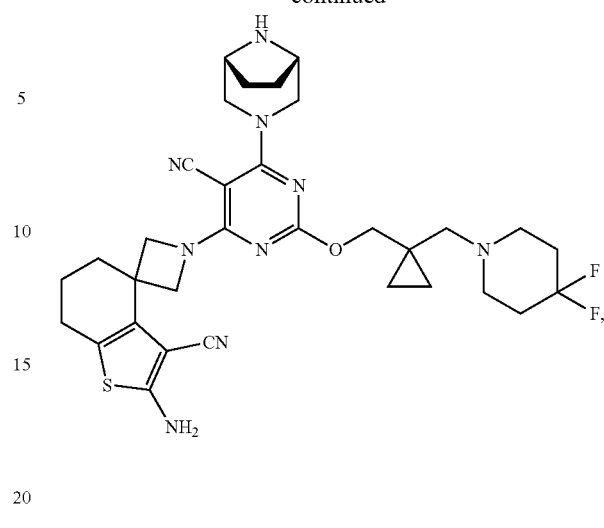
442
-continued
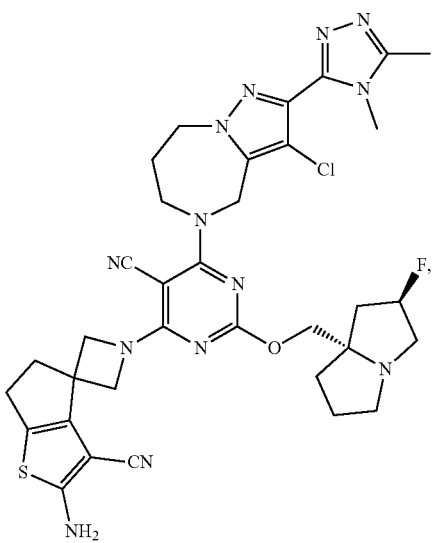
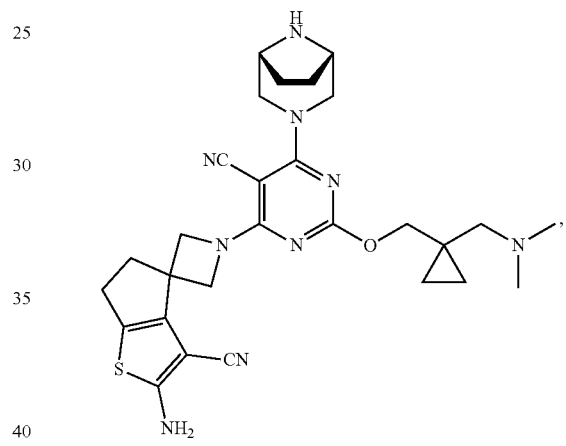
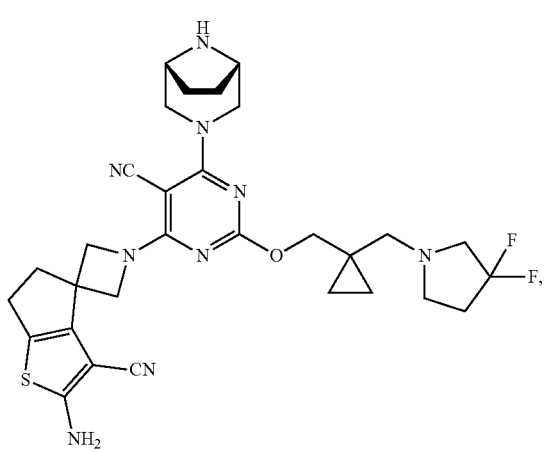
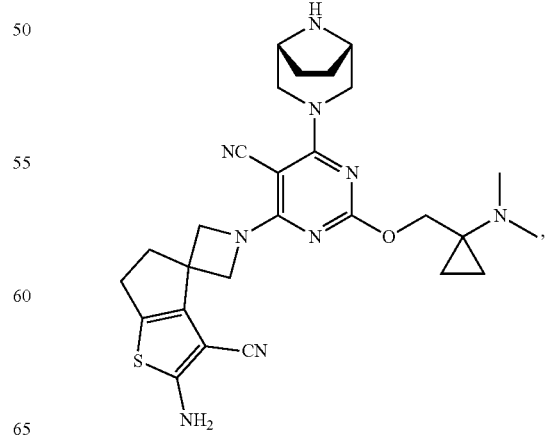

443
-continued
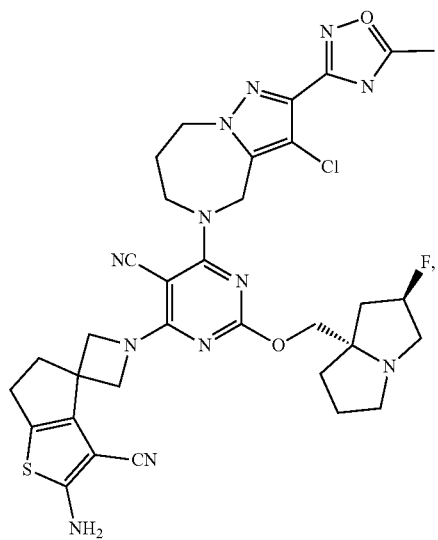
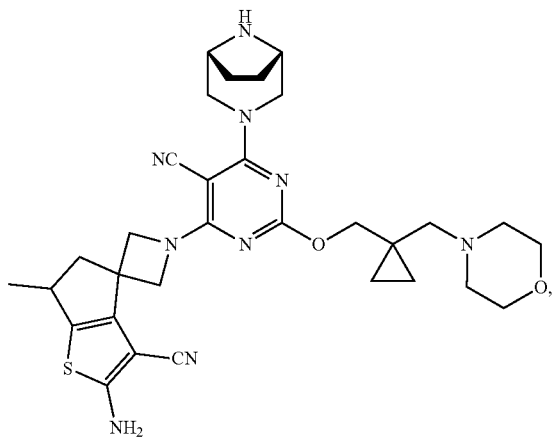
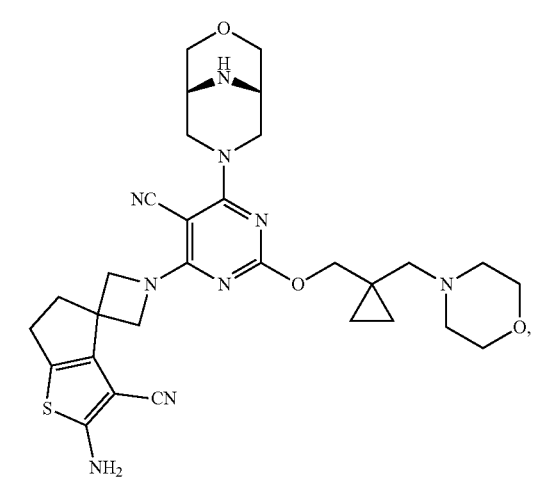
444
-continued
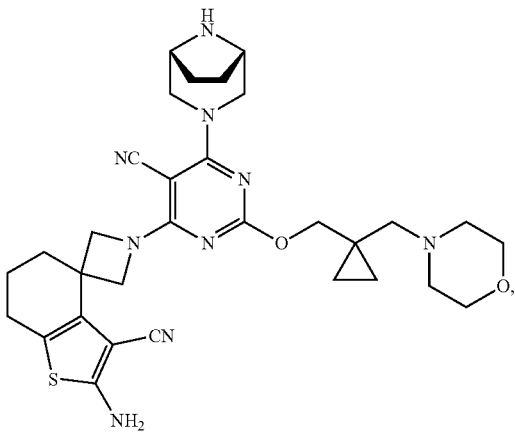
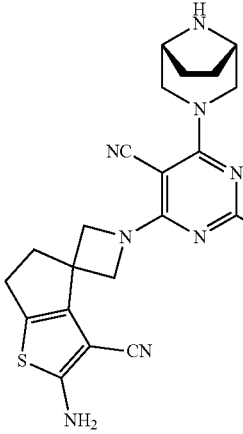
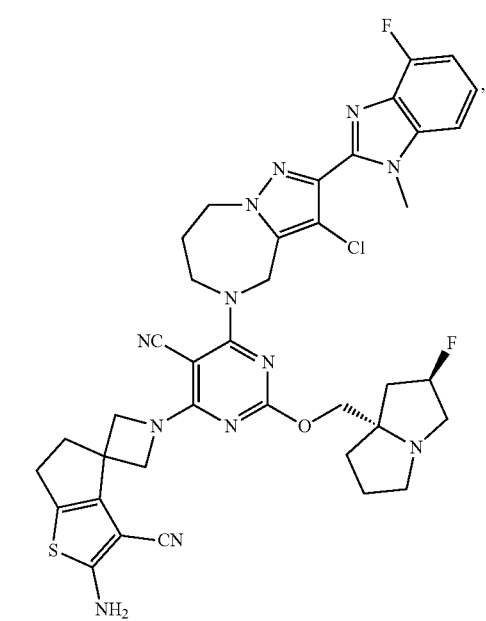

445
-continued
446
-continued
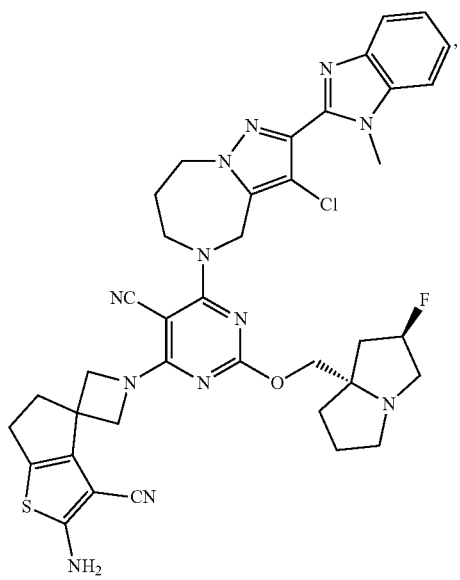
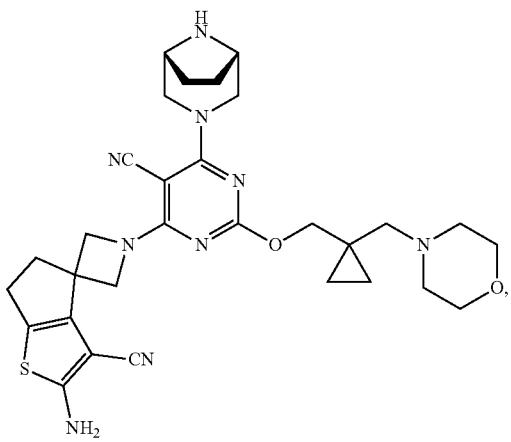
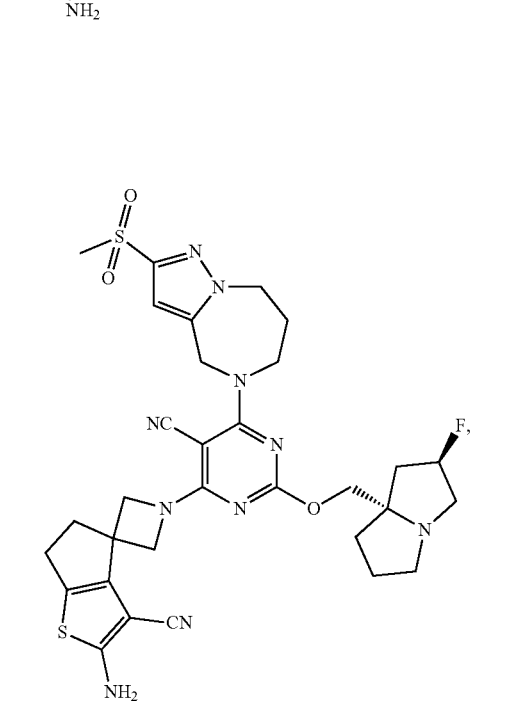

447
-continued
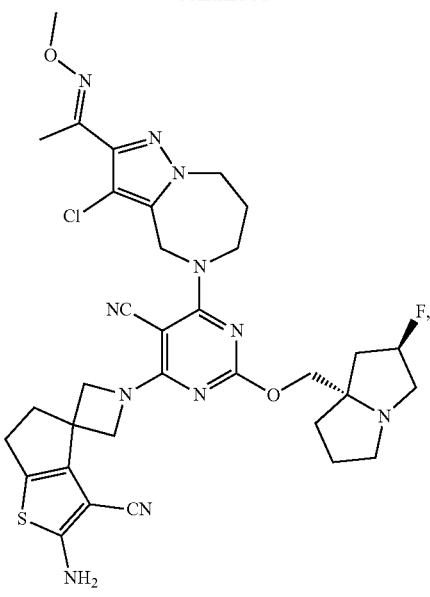
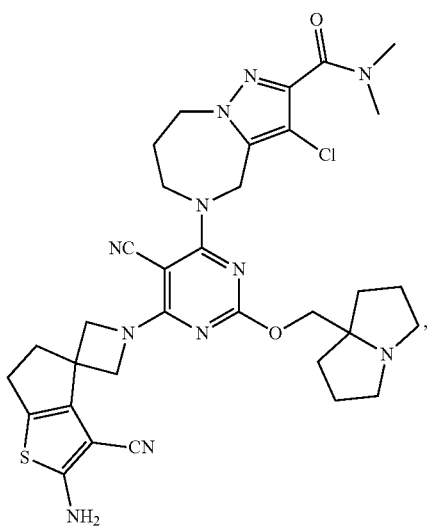
448
-continued
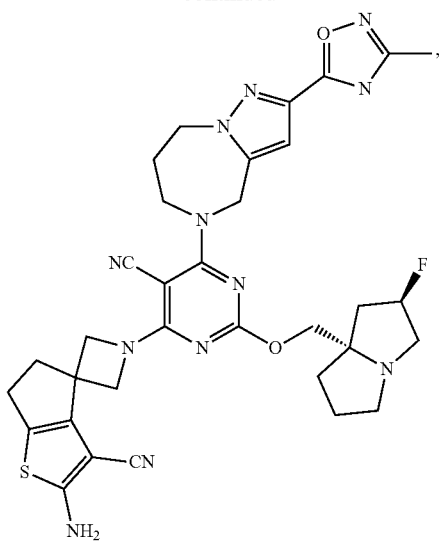
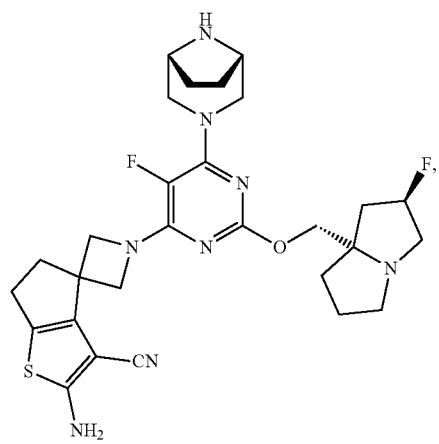
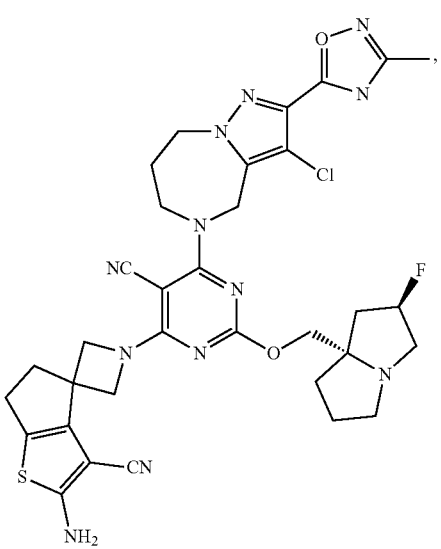
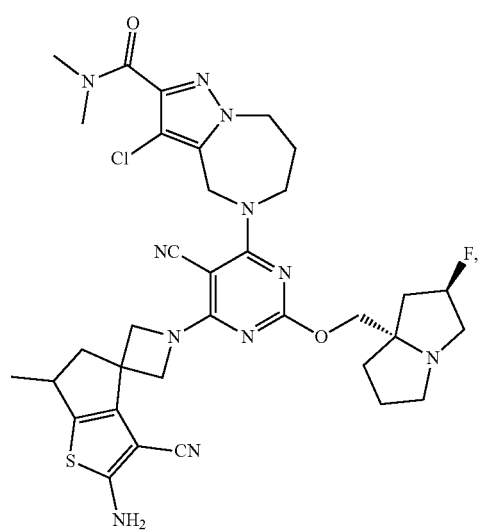

449
-continued
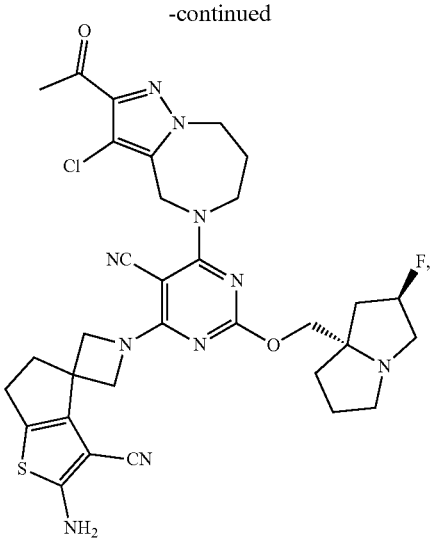
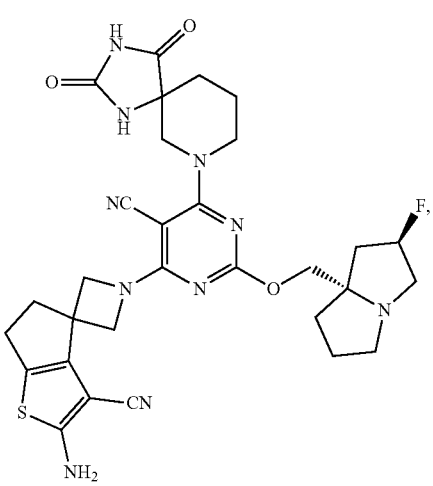
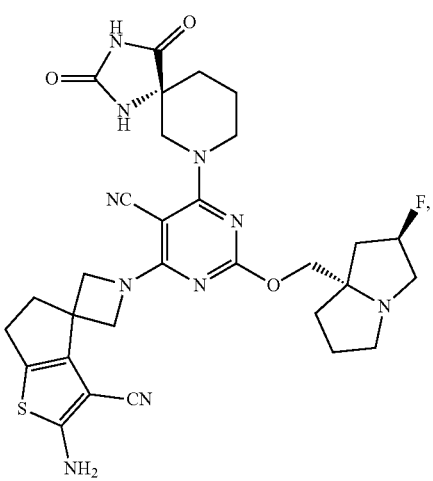
450
-continued
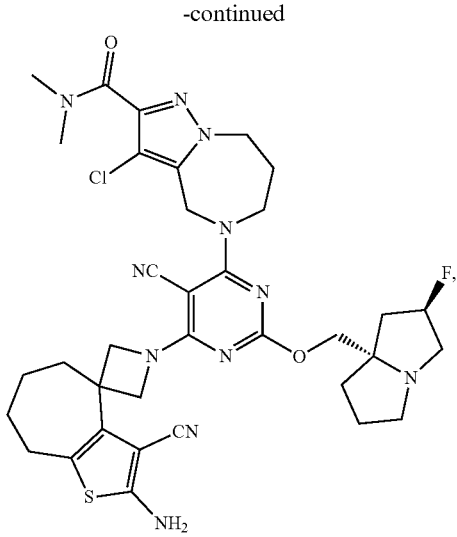
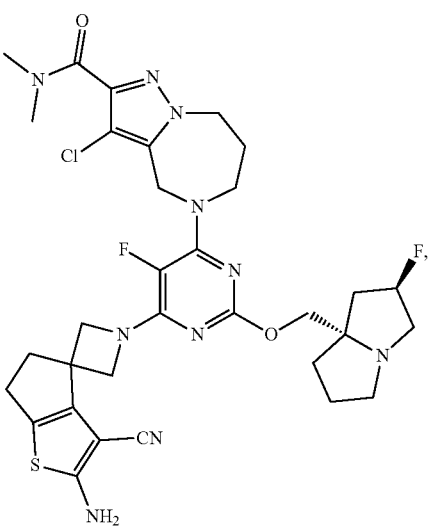
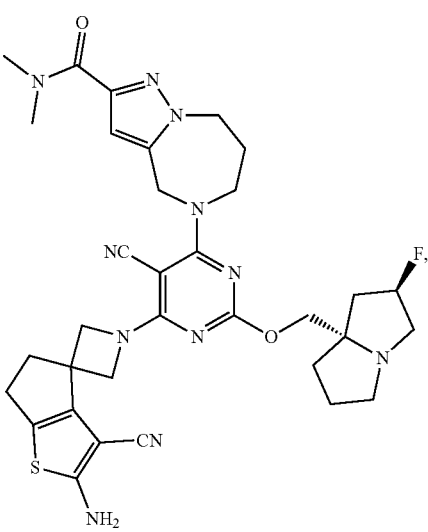

-continued

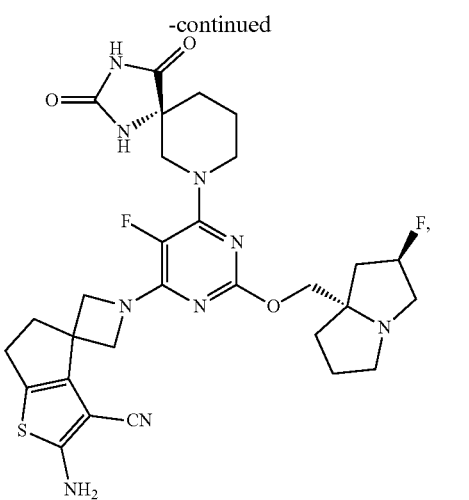

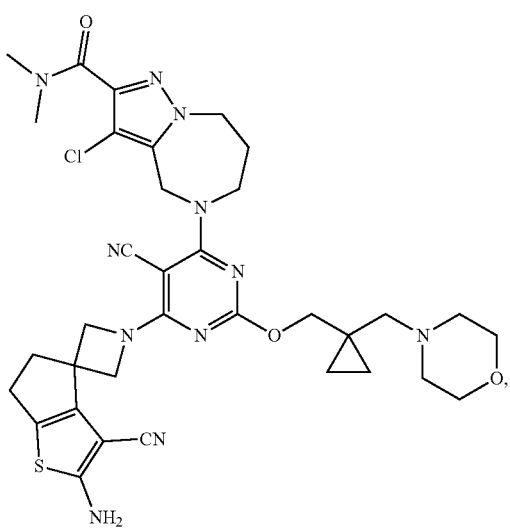

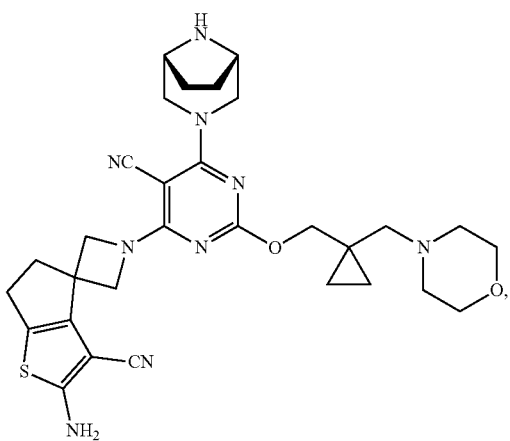

-continued

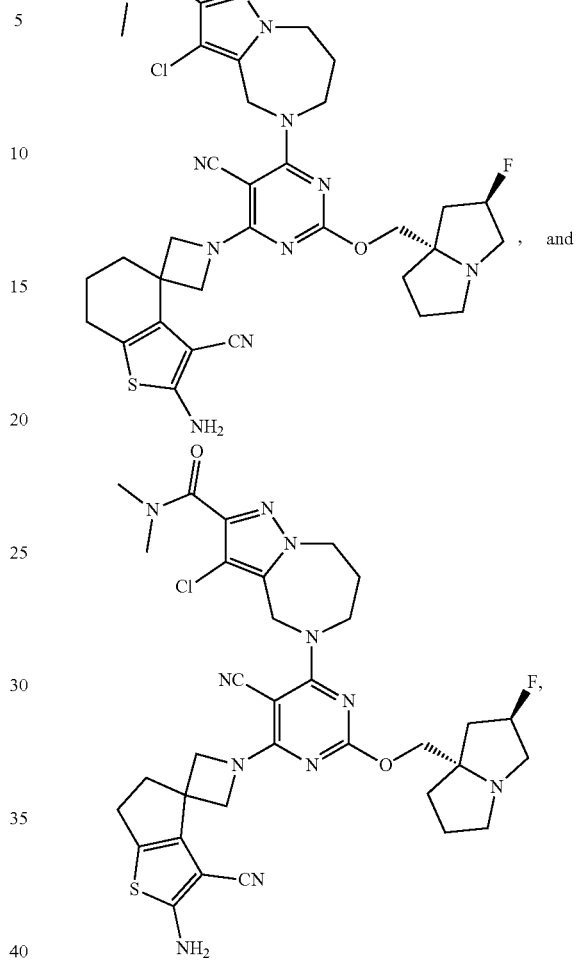

or a pharmaceutically acceptable salt of any one thereof.

20. The method of claim 19, wherein the disease or disorder is a KRas G12D or other G12 mutants-associated cancer.

21. The method of claim 19, wherein the disease or disorder is a cancer selected from:
Cardiac: sarcoma (angiosarcoma, fibrosarcoma, rhabdomyosarcoma, liposarcoma), myxoma, rhabdomyoma, fibroma, lipoma and teratoma;
Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma;
Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma);
Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma);

Liver: hepatoma (hepatocellular carcinoma), cholangiocarcinoma, hepatoblastoma, angiosarcoma, hepatocellular adenoma, hemangioma;

Biliary tract: gall bladder carcinoma, ampullary carcinoma, cholangiocarcinoma;

Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors;

Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma);

Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma);

Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma);

Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma.

22. The method of claim 19, wherein the disease or disorder is a cancer, wherein the cancer is non-small cell lung cancer, small cell lung cancer, colorectal cancer, rectal cancer or pancreatic cancer; or wherein the cancer is a tumor cancer.

* * * * *